US011484590B2

(12) United States Patent
Ciaramella et al.

(10) Patent No.: US 11,484,590 B2
(45) **Date of Patent: *Nov. 1, 2022**

(54) HUMAN CYTOMEGALOVIRUS RNA VACCINES

(71) Applicant: ModernaTX, Inc., Cambridge, MA (US)

(72) Inventors: Giuseppe Ciaramella, Sudbury, MA (US); Shinu John, Somerville, MA (US); Kambiz Mousavi, Acton, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/833,409

(22) Filed: Mar. 27, 2020

(65) Prior Publication Data

US 2020/0246453 A1 Aug. 6, 2020

Related U.S. Application Data

(63) Continuation of application No. 16/450,882, filed on Jun. 24, 2019, now Pat. No. 10,716,846, which is a continuation of application No. 16/006,526, filed on Jun. 12, 2018, now Pat. No. 10,383,937, which is a continuation of application No. 15/674,569, filed on Aug. 11, 2017, now Pat. No. 10,064,935, which is a continuation of application No. PCT/US2016/058310, filed on Oct. 21, 2016.

(60) Provisional application No. 62/247,614, filed on Oct. 28, 2015, provisional application No. 62/245,031, filed on Oct. 22, 2015, provisional application No. 62/245,166, filed on Oct. 22, 2015.

(51) Int. Cl.

| | |
|---|---|
| ***A61K 39/245*** | (2006.01) |
| ***A61K 39/12*** | (2006.01) |
| ***C12N 7/00*** | (2006.01) |
| ***C07K 14/005*** | (2006.01) |
| ***A61K 31/7105*** | (2006.01) |
| ***A61K 31/7115*** | (2006.01) |
| ***A61K 39/39*** | (2006.01) |
| ***A61K 39/00*** | (2006.01) |

(52) U.S. Cl.

CPC ........ *A61K 39/245* (2013.01); *A61K 31/7105* (2013.01); *A61K 31/7115* (2013.01); *A61K 39/12* (2013.01); *A61K 39/39* (2013.01); *C07K 14/005* (2013.01); *C12N 7/00* (2013.01); *A61K 2039/53* (2013.01); *A61K 2039/55* (2013.01); *A61K 2039/55511* (2013.01); *A61K 2039/55555* (2013.01); *A61K 2039/55566* (2013.01); *A61K 2039/575* (2013.01); *C07K 2319/02* (2013.01); *C12N 2710/16122* (2013.01); *C12N 2710/16134* (2013.01); *C12N 2710/16151* (2013.01); *C12N 2710/16171* (2013.01)

(58) Field of Classification Search

CPC .............. A61K 39/245; A61K 31/7105; A61K 31/7115; A61K 39/12; A61K 39/39; A61K 2039/53; A61K 2039/55; A61K 2039/55511; A61K 2039/55555; A61K 2039/55566; A61K 2039/575; C07K 14/005; C07K 2319/02; C12N 7/00; C12N 2710/16122; C12N 2710/16134; C12N 2710/16151; C12N 2710/16171; A61P 31/14; A61P 31/22; A61P 37/04

See application file for complete search history.

(56) References Cited

U.S. PATENT DOCUMENTS

| | | | |
|---|---|---|---|
| 3,906,092 | A | 9/1975 | Hilleman et al. |
| 6,074,645 | A | 6/2000 | Diamond et al. |
| 6,162,620 | A | 12/2000 | Smith et al. |
| 6,207,161 | B1 | 3/2001 | Pande et al. |
| 6,448,389 | B1 | 9/2002 | Gonczol et al. |
| 6,500,419 | B1 | 12/2002 | Hone et al. |
| 6,514,948 | B1 | 2/2003 | Raz et al. |
| 6,713,070 | B1 | 3/2004 | Plachter et al. |
| 6,843,992 | B2 | 1/2005 | Diamond et al. |
| 7,001,890 | B1 | 2/2006 | Wagner et al. |
| 7,204,990 | B1 | 4/2007 | Kemble et al. |
| 7,387,782 | B2 | 6/2008 | Zaia et al. |
| 7,410,795 | B2 | 8/2008 | Hermanson et al. |
| 7,419,674 | B2 | 9/2008 | Chulay et al. |
| 8,173,362 | B2 | 5/2012 | Shenk et al. |
| 8,217,016 | B2 | 7/2012 | Hoerr et al. |
| 8,425,898 | B2 | 4/2013 | Sampson et al. |
| 8,673,317 | B2 | 3/2014 | Hermanson et al. |

(Continued)

FOREIGN PATENT DOCUMENTS

| | | | |
|---|---|---|---|
| AU | 2015210364 | A1 | 3/2017 |
| CA | 2473135 | | 6/2003 |
| EP | 1026253 | | 8/2000 |
| EP | 1083232 | | 2/2005 |
| EP | 1905844 | A2 | 2/2008 |

(Continued)

OTHER PUBLICATIONS

Hassett KJ, Benenato KE, Jacquinet E, et al. Optimization of Lipid Nanoparticles for Intramuscular Administration of mRNA Vaccines. Mol Ther Nucleic Acids. Apr. 15, 2019;15:1-11. doi: 10.1016/j.omtn.2019.01.013. Epub Feb. 7, 2019.*

(Continued)

*Primary Examiner* — Rachel B Gill

(74) *Attorney, Agent, or Firm* — Wolf, Greenfield & Sacks, P.C.

(57) ABSTRACT

The disclosure describes HCMV ribonucleic acid (RNA) vaccines, as well as methods of using the vaccines and compositions comprising the vaccines.

24 Claims, 32 Drawing Sheets

Specification includes a Sequence Listing.

(56) References Cited

U.S. PATENT DOCUMENTS

| | | | |
|---|---|---|---|
| 8,691,966 | B2 | 4/2014 | Kariko et al. |
| 8,710,200 | B2 | 4/2014 | Schrum et al. |
| 8,734,853 | B2 | 5/2014 | Sood et al. |
| 8,754,062 | B2 | 6/2014 | De Fougerolles et al. |
| 8,822,663 | B2 | 9/2014 | Schrum et al. |
| 8,999,380 | B2 | 4/2015 | Bancel et al. |
| 9,221,891 | B2 | 12/2015 | Bancel et al. |
| 9,243,041 | B2 | 1/2016 | Weiner et al. |
| 9,283,287 | B2 | 3/2016 | Bancel et al. |
| 9,303,079 | B2 | 4/2016 | Bancel et al. |
| 9,464,124 | B2 | 10/2016 | Bancel et al. |
| 9,486,517 | B2 | 11/2016 | Becke et al. |
| 9,512,456 | B2 | 12/2016 | Wang et al. |
| 9,533,047 | B2 | 1/2017 | de Fougerolles et al. |
| 9,597,380 | B2 | 3/2017 | Chakraborty et al. |
| 9,764,026 | B2 | 9/2017 | Sampson et al. |
| 9,803,199 | B2 | 10/2017 | Koizumi et al. |
| 9,868,691 | B2 | 1/2018 | Benenato et al. |
| 9,872,900 | B2 | 1/2018 | Ciaramella et al. |
| 10,022,435 | B2 | 7/2018 | Ciaramella et al. |
| 10,064,934 | B2 | 9/2018 | Ciaramella et al. |
| 10,064,935 | B2 | 9/2018 | Ciaramella et al. |
| 10,124,055 | B2 | 11/2018 | Ciaramella et al. |
| 10,207,010 | B2 | 2/2019 | Besin et al. |
| 10,232,055 | B2 | 3/2019 | Kariko et al. |
| 10,273,269 | B2 | 4/2019 | Ciaramella |
| 10,286,086 | B2 | 5/2019 | Roy et al. |
| 10,323,076 | B2 | 6/2019 | Ellsworth et al. |
| 10,385,088 | B2 | 8/2019 | Fraley et al. |
| 10,449,244 | B2 | 10/2019 | Ciaramella et al. |
| 10,465,190 | B1 | 11/2019 | Chen et al. |
| 10,493,143 | B2 | 12/2019 | Ciaramella et al. |
| 10,526,629 | B2 | 1/2020 | Rabideau et al. |
| 10,653,712 | B2 | 5/2020 | Hoge |
| 10,653,767 | B2 | 5/2020 | Ciaramella et al. |
| 10,695,419 | B2 | 6/2020 | Ciaramella et al. |
| 10,857,105 | B2 | 12/2020 | Benenato et al. |
| 10,925,958 | B2 | 2/2021 | Ciaramella |
| 11,045,540 | B2 | 6/2021 | Ciaramella |
| 11,103,578 | B2 | 8/2021 | Ciaramella et al. |
| 2003/0092653 | A1 | 5/2003 | Kisich et al. |
| 2005/0032730 | A1 | 2/2005 | Von Der Mulbe et al. |
| 2005/0059624 | A1 | 3/2005 | Hoerr et al. |
| 2005/0250723 | A1 | 11/2005 | Hoerr et al. |
| 2006/0172003 | A1 | 8/2006 | Meers et al. |
| 2007/0280929 | A1 | 12/2007 | Hoerr et al. |
| 2008/0025944 | A1 | 1/2008 | Hoerr et al. |
| 2008/0171711 | A1 | 7/2008 | Hoerr et al. |
| 2010/0112042 | A1 | 5/2010 | Polisky et al. |
| 2010/0130588 | A1 | 5/2010 | Yaworski et al. |
| 2010/0203076 | A1 | 8/2010 | Fotin-Mleczek et al. |
| 2010/0239608 | A1 | 9/2010 | Von Der Mulbe et al. |
| 2010/0291156 | A1 | 11/2010 | Barner et al. |
| 2010/0305196 | A1 | 12/2010 | Probst et al. |
| 2011/0250225 | A1 | 10/2011 | Fotin-Mleczek et al. |
| 2011/0256175 | A1* | 10/2011 | Hope ..................... A61K 47/22 424/204.1 |
| 2011/0269950 | A1 | 11/2011 | Von Der Mulbe et al. |
| 2012/0009221 | A1 | 1/2012 | Hoerr et al. |
| 2012/0101148 | A1 | 4/2012 | Aking et al. |
| 2012/0219573 | A1 | 8/2012 | Baumhof et al. |
| 2012/0263648 | A1 | 10/2012 | Shapiro et al. |
| 2013/0022538 | A1 | 1/2013 | Rossi |
| 2013/0102034 | A1 | 4/2013 | Schrum et al. |
| 2013/0121988 | A1 | 5/2013 | Hoerr et al. |
| 2013/0142818 | A1 | 6/2013 | Baumhof et al. |
| 2013/0158021 | A1 | 6/2013 | Dong et al. |
| 2013/0183355 | A1 | 7/2013 | Jain et al. |
| 2013/0195867 | A1 | 8/2013 | Hoerr et al. |
| 2013/0195967 | A1 | 8/2013 | Guild et al. |
| 2013/0195969 | A1 | 8/2013 | Geall et al. |
| 2013/0202684 | A1 | 8/2013 | Geall et al. |
| 2013/0236974 | A1 | 9/2013 | De Fougerolles |
| 2013/0243848 | A1 | 9/2013 | Lobovkina et al. |
| 2013/0245103 | A1 | 9/2013 | de Fougerolles et al. |
| 2013/0259923 | A1 | 10/2013 | Bancel et al. |
| 2013/0266640 | A1 | 10/2013 | de Fougerolles et al. |
| 2013/0295043 | A1 | 11/2013 | Kallen et al. |
| 2013/0336998 | A1 | 12/2013 | Kallen et al. |
| 2014/0037660 | A1 | 2/2014 | Folin-Mleczek et al. |
| 2014/0147432 | A1 | 5/2014 | Bancel et al. |
| 2014/0148502 | A1 | 5/2014 | Bancel et al. |
| 2014/0193482 | A1 | 7/2014 | Bancel et al. |
| 2014/0206752 | A1 | 7/2014 | Afeyan et al. |
| 2014/0206753 | A1 | 7/2014 | Guild et al. |
| 2014/0227346 | A1 | 8/2014 | Geall et al. |
| 2014/0271829 | A1 | 9/2014 | Lilja et al. |
| 2014/0308304 | A1 | 10/2014 | Manoharan et al. |
| 2014/0308308 | A1 | 10/2014 | Anderson et al. |
| 2014/0348863 | A1 | 11/2014 | Bianchi et al. |
| 2014/0378538 | A1 | 12/2014 | Bancel |
| 2015/0051268 | A1 | 2/2015 | Bancel et al. |
| 2015/0056253 | A1 | 2/2015 | Bancel et al. |
| 2015/0118183 | A1 | 4/2015 | Baumhof et al. |
| 2015/0141499 | A1 | 5/2015 | Bancel et al. |
| 2015/0307542 | A1 | 10/2015 | Roy et al. |
| 2015/0307850 | A1 | 10/2015 | Fu et al. |
| 2015/0315541 | A1 | 11/2015 | Bancel et al. |
| 2015/0322115 | A1 | 11/2015 | Wellnitz et al. |
| 2015/0335732 | A1 | 11/2015 | Sampson et al. |
| 2015/0359879 | A1 | 12/2015 | Wellnitz et al. |
| 2015/0376115 | A1* | 12/2015 | Ansell .................. C07C 227/16 514/785 |
| 2016/0024140 | A1 | 1/2016 | Issa et al. |
| 2016/0024141 | A1 | 1/2016 | Issa et al. |
| 2016/0151284 | A1 | 1/2016 | Heyes et al. |
| 2016/0032273 | A1 | 2/2016 | Shahrokh et al. |
| 2016/0038612 | A1 | 2/2016 | Hoge et al. |
| 2016/0159864 | A1 | 6/2016 | Carfi et al. |
| 2016/0213771 | A1 | 7/2016 | Sampson et al. |
| 2016/0243221 | A1 | 8/2016 | Hoge et al. |
| 2016/0271272 | A1 | 9/2016 | Bancel et al. |
| 2016/0296619 | A1 | 10/2016 | Orlinger et al. |
| 2016/0317647 | A1* | 11/2016 | Ciaramella ........ A61K 31/7105 |
| 2016/0331828 | A1 | 11/2016 | Ciaramella et al. |
| 2016/0376224 | A1 | 12/2016 | Du et al. |
| 2017/0043037 | A1 | 2/2017 | Kariko et al. |
| 2017/0065675 | A1 | 3/2017 | Bancel et al. |
| 2017/0119874 | A1 | 5/2017 | Lanzavecchia et al. |
| 2017/0143848 | A1 | 5/2017 | Calias et al. |
| 2017/0202979 | A1 | 7/2017 | Chakraborty et al. |
| 2017/0204152 | A1 | 7/2017 | Nelson et al. |
| 2017/0210697 | A1 | 7/2017 | Benenato et al. |
| 2017/0239371 | A1 | 8/2017 | Guild et al. |
| 2017/0130255 | A1 | 10/2017 | Wang et al. |
| 2017/0320916 | A1 | 11/2017 | Carfi et al. |
| 2017/0362278 | A1 | 12/2017 | Carfi et al. |
| 2018/0000953 | A1 | 1/2018 | Almarsson et al. |
| 2018/0002393 | A1 | 1/2018 | Bancel et al. |
| 2018/0237849 | A1 | 8/2018 | Thompson |
| 2018/0243225 | A1 | 8/2018 | Ciaramella |
| 2018/0243230 | A1 | 8/2018 | Smith |
| 2018/0256628 | A1 | 9/2018 | Hoge et al. |
| 2018/0271795 | A1 | 9/2018 | Martini et al. |
| 2018/0271970 | A1 | 9/2018 | Ciaramella et al. |
| 2018/0273467 | A1* | 9/2018 | Benenato ............. C07D 263/20 |
| 2018/0273977 | A1 | 9/2018 | Mousavi et al. |
| 2018/0274009 | A1 | 9/2018 | Marquardt et al. |
| 2018/0280496 | A1 | 10/2018 | Ciaramella et al. |
| 2018/0289792 | A1 | 10/2018 | Ciaramella et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0312549 | A1 | 11/2018 | Ciaramella |
| 2018/0318409 | A1 | 11/2018 | Valiante et al. |
| 2018/0363019 | A1 | 12/2018 | Hoge |
| 2018/0369374 | A1 | 12/2018 | Frederick et al. |
| 2018/0371047 | A1 | 12/2018 | Ticho et al. |
| 2019/0002890 | A1 | 1/2019 | Martini et al. |
| 2019/0008938 | A1 | 1/2019 | Ciaramella et al. |
| 2019/0085368 | A1 | 3/2019 | Bancel et al. |
| 2019/0099481 | A1 | 4/2019 | Ciaramella et al. |
| 2019/0175517 | A1 | 6/2019 | Martini et al. |
| 2019/0175727 | A1 | 6/2019 | Huang et al. |

(56) References Cited

U.S. PATENT DOCUMENTS

| | | | |
|---|---|---|---|
| 2019/0192646 | A1 | 6/2019 | Cohen et al. |
| 2019/0192653 | A1 | 6/2019 | Hoge et al. |
| 2019/0241633 | A1 | 8/2019 | Fotin-Mleczek et al. |
| 2019/0275170 | A1 | 9/2019 | Benenato et al. |
| 2019/0298657 | A1 | 10/2019 | Martini et al. |
| 2019/0298658 | A1 | 10/2019 | Benenato |
| 2019/0300906 | A1 | 10/2019 | Martini et al. |
| 2019/0309337 | A1 | 10/2019 | Rabideau et al. |
| 2019/0314292 | A1 | 10/2019 | Benenato et al. |
| 2019/0314493 | A1 | 10/2019 | Ciaramella et al. |
| 2019/0336452 | A1 | 11/2019 | Brader |
| 2019/0336595 | A1 | 11/2019 | Ciaramella |
| 2019/0351040 | A1 | 11/2019 | Valiante et al. |
| 2019/0382774 | A1 | 12/2019 | Hoge et al. |
| 2019/0390181 | A1 | 12/2019 | Benenato et al. |
| 2020/0030432 | A1 | 1/2020 | Ciaramella et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0129608 | A1 | 4/2020 | Ciaramella et al. |
| 2020/0129615 | A1 | 4/2020 | Ciaramella et al. |
| 2020/0163878 | A1 | 5/2020 | Baumhof et al. |
| 2020/0239869 | A1 | 7/2020 | Issa et al. |
| 2020/0254086 | A1 | 8/2020 | Hoge et al. |
| 2020/0282047 | A1 | 9/2020 | Ciaramella et al. |
| 2021/0023199 | A1 | 1/2021 | Kallen et al. |
| 2021/0030866 | A1 | 2/2021 | Kallen et al. |
| 2021/0046173 | A1 | 2/2021 | Ciaramella et al. |
| 2021/0163919 | A1 | 6/2021 | Issa et al. |
| 2021/0187097 | A1 | 6/2021 | Ciaramella et al. |
| 2021/0217484 | A1 | 7/2021 | Giessel et al. |
| 2021/0228707 | A1 | 7/2021 | Mektar et al. |
| 2021/0268086 | A1 | 9/2021 | Zhong et al. |
| 2021/0309976 | A1 | 10/2021 | Dousis et al. |
| 2022/0031631 | A1 | 2/2022 | Almarsson et al. |
| 2022/0047518 | A1 | 2/2022 | Hennessy et al. |
| 2022/0054653 | A1 | 2/2022 | Martini et al. |
| 2022/0062408 | A1 | 3/2022 | Kramarczyk et al. |

FOREIGN PATENT DOCUMENTS

| | | | | |
|---|---|---|---|---|
| EP | 2548960 | | 1/2013 | |
| EP | 3310384 | | 4/2018 | |
| WO | WO 1987/005326 | | 9/1987 | |
| WO | WO 1990/011092 | | 10/1990 | |
| WO | WO 1993/014778 | | 8/1993 | |
| WO | WO 1995/024485 | | 9/1995 | |
| WO | WO 1995/026204 | | 10/1995 | |
| WO | WO 1995/033835 | | 12/1995 | |
| WO | WO 1999/033982 | | 7/1999 | |
| WO | WO 2003/059381 | | 7/2003 | |
| WO | WO 2004/058166 | A2 | 7/2004 | |
| WO | WO 2004/076645 | A2 | 9/2004 | |
| WO | WO 2005/007689 | A1 | 1/2005 | |
| WO | WO 2005/009346 | | 2/2005 | |
| WO | WO 2005/034979 | A2 | 4/2005 | |
| WO | WO 2006/056027 | A1 | 6/2006 | |
| WO | WO 2006/071903 | | 7/2006 | |
| WO | WO 2006/095259 | | 9/2006 | |
| WO | WO 2007/051303 | A1 | 5/2007 | |
| WO | WO 2007/095976 | A2 | 8/2007 | |
| WO | WO 2007/146024 | A2 | 12/2007 | |
| WO | WO 2008/052770 | A2 | 5/2008 | |
| WO | WO 2009/030254 | A1 | 3/2009 | |
| WO | WO 2009/030481 | A1 | 3/2009 | |
| WO | WO 2009/095226 | | 8/2009 | |
| WO | WO 2009/127060 | A1 | 10/2009 | |
| WO | WO 2009/127230 | A1 | 10/2009 | |
| WO | WO 2010/037408 | A1 | 4/2010 | |
| WO | WO 2010/037539 | A1 | 4/2010 | |
| WO | WO 2010/042877 | A1 | 4/2010 | |
| WO | WO 2010/053572 | A2 | 5/2010 | |
| WO | WO 2010/054406 | A1 | 5/2010 | |
| WO | WO 2010/088927 | A1 | 8/2010 | |
| WO | WO 2011/005799 | A2 | 1/2011 | |
| WO | WO 2011/026641 | A9 | 3/2011 | |
| WO | WO 2011/068810 | A1 | 6/2011 | |
| WO | WO 2011/069529 | A1 | 6/2011 | |
| WO | WO 2011/069586 | A1 | 6/2011 | |
| WO | WO 2011/140627 | A1 | 11/2011 | |
| WO | WO 2011/144358 | A1 | 11/2011 | |
| WO | WO 2012/006376 | A2 | 1/2012 | |
| WO | WO 2012/019630 | A1 | 2/2012 | |
| WO | WO 2012/019780 | A1 | 2/2012 | |
| WO | WO 2012/034025 | A1 | 3/2012 | |
| WO | WO 2012/051211 | A2 | 4/2012 | |
| WO | WO 2012/106377 | A2 | 8/2012 | |
| WO | WO 2012/116714 | A1 | 9/2012 | |
| WO | WO 2012/116715 | A1 | 9/2012 | |
| WO | WO 2012/116810 | A1 | 9/2012 | |
| WO | WO 2012/116811 | A1 | 9/2012 | |
| WO | WO 2013/006838 | A1 | 1/2013 | |
| WO | WO 2013/006842 | A2 | 1/2013 | |
| WO | WO 2013/036465 | A2 | 3/2013 | |
| WO | WO 2013/055905 | A1 | 4/2013 | |
| WO | WO 2013/068847 | A2 | 5/2013 | |
| WO | WO 2013/090186 | A1 | 6/2013 | |
| WO | WO 2013/096812 | A1 | 6/2013 | |
| WO | WO 2013/102203 | A1 | 7/2013 | |
| WO | WO 2013/120629 | A1 | 8/2013 | |
| WO | WO 2013/151666 | A2 | 10/2013 | |
| WO | WO 2013/185069 | A1 | 12/2013 | |
| WO | WO 2014/005959 | A1 | 1/2014 | |
| WO | WO 2014/018117 | A1 | 1/2014 | |
| WO | WO-2014005959 | A1 * | 1/2014 | ............ A61K 39/12 |
| WO | WO 2014/068001 | A1 | 5/2014 | |
| WO | WO 2014/089239 | A1 | 6/2014 | |
| WO | WO 2014/089486 | A1 | 6/2014 | |
| WO | WO 2014/152027 | A1 | 9/2014 | |
| WO | WO 2014/152774 | A1 | 9/2014 | |
| WO | WO 2014/152940 | A1 | 9/2014 | |
| WO | WO 2014/160243 | A1 | 10/2014 | |
| WO | WO 2014/172045 | A1 | 10/2014 | |
| WO | WO 2014/182661 | A2 | 11/2014 | |
| WO | WO 2015/005253 | A1 | 1/2015 | |
| WO | WO 2015/024668 | A2 | 2/2015 | |
| WO | WO 2015/061467 | A1 | 4/2015 | |
| WO | WO 2015/089340 | A1 | 6/2015 | |
| WO | WO 2015/095340 | A1 | 6/2015 | |
| WO | WO 2015/095346 | A1 | 6/2015 | |
| WO | WO 2015/110659 | A1 | 7/2015 | |
| WO | WO 2015/161926 | A1 | 10/2015 | |
| WO | WO 2015/082570 | A1 | 11/2015 | |
| WO | WO 2015/165480 | A1 | 11/2015 | |
| WO | WO 2015/170287 | A1 | 11/2015 | |
| WO | WO 2015/181142 | A1 | 12/2015 | |
| WO | WO 2015/199952 | A1 | 12/2015 | |
| WO | WO 2016/004318 | A1 | 1/2016 | |
| WO | WO 2016/037053 | A1 | 3/2016 | |
| WO | WO 2016/067239 | A1 | 5/2016 | |
| WO | WO 2016/092460 | A2 | 6/2016 | |
| WO | WO 2016/116904 | A1 | 7/2016 | |
| WO | WO 2016/116905 | A1 | 7/2016 | |
| WO | WO 2016/130693 | A1 | 8/2016 | |
| WO | WO 2016/133881 | A1 | 8/2016 | |
| WO | WO 2016/164762 | A1 | 10/2016 | |
| WO | WO 2016/184822 | A1 | 11/2016 | |
| WO | WO 2016/201377 | A1 | 12/2016 | |
| WO | WO 2016/203025 | A1 | 12/2016 | |
| WO | WO 2017/015457 | A1 | 1/2017 | |
| WO | WO 2017/019935 | A1 | 2/2017 | |
| WO | WO 2017/020026 | A1 | 2/2017 | |
| WO | WO 2017/062513 | A1 | 4/2017 | |
| WO | WO 2017/066789 | A1 | 4/2017 | |
| WO | WO 2017/070601 | A1 | 4/2017 | |
| WO | WO 2017/075531 | A1 | 5/2017 | |
| WO | WO 2017/127750 | A1 | 7/2017 | |
| WO | WO 2017/201333 | A1 | 11/2017 | |

(56) References Cited

FOREIGN PATENT DOCUMENTS

| | | |
|---|---|---|
| WO | WO 2017/201340 A1 | 11/2017 |
| WO | WO 2017/201342 A1 | 11/2017 |
| WO | WO 2017/201347 A1 | 11/2017 |
| WO | WO 2017/201349 A1 | 11/2017 |
| WO | WO 2017/208191 A1 | 12/2017 |
| WO | WO 2018/075980 A1 | 4/2018 |
| WO | WO 2018/078053 A1 | 5/2018 |
| WO | WO 2018/081459 A1 | 5/2018 |
| WO | WO 2018/089851 A1 | 5/2018 |
| WO | WO 2018/107088 A1 | 6/2018 |
| WO | WO 2018/111967 A1 | 6/2018 |
| WO | WO 2018/144082 A1 | 8/2018 |
| WO | WO 2018/144778 A1 | 8/2018 |
| WO | WO 2018/157009 A1 | 8/2018 |
| WO | WO 2018/170245 A1 | 9/2018 |
| WO | WO 2018/170256 A1 | 9/2018 |
| WO | WO 2018/170260 A1 | 9/2018 |
| WO | WO 2018/170270 A1 | 9/2018 |
| WO | WO 2018/170347 A1 | 9/2018 |
| WO | WO 2018/175783 A1 | 9/2018 |
| WO | WO 2018/187590 A2 | 10/2018 |
| WO | WO 2018/200737 A1 | 11/2018 |
| WO | WO 2018/232355 A1 | 12/2018 |
| WO | WO 2018/232357 A1 | 12/2018 |
| WO | WO 2019/036670 A1 | 2/2019 |
| WO | WO 2019/036682 A1 | 2/2019 |
| WO | WO 2019/036683 A1 | 2/2019 |
| WO | WO 2019/036685 A1 | 2/2019 |
| WO | WO 2019/103993 A1 | 5/2019 |
| WO | WO 2019/148101 A1 | 8/2019 |
| WO | WO 2020/006242 A1 | 1/2020 |
| WO | WO 2020/056370 A1 | 3/2020 |
| WO | WO 2020/061284 A1 | 3/2020 |
| WO | WO 2020/061295 A1 | 3/2020 |
| WO | WO 2020/061367 A1 | 3/2020 |
| WO | WO 2020/097291 A1 | 5/2020 |
| WO | WO 2020/172239 A1 | 8/2020 |
| WO | WO 2020/185811 A1 | 9/2020 |
| WO | WO 2020/190750 A1 | 9/2020 |
| WO | WO 2020/243561 A1 | 12/2020 |
| WO | WO 2021/030533 A1 | 2/2021 |
| WO | WO 2021/050864 A1 | 3/2021 |
| WO | WO 2021/055811 A1 | 3/2021 |
| WO | WO 2021/155243 A1 | 8/2021 |
| WO | WO 2021/159040 A2 | 8/2021 |
| WO | WO 2021/159130 A2 | 8/2021 |
| WO | WO 2021/211343 A1 | 10/2021 |
| WO | WO 2021/222304 A1 | 11/2021 |
| WO | WO 2021/231929 A1 | 11/2021 |
| WO | WO 2021/231963 A1 | 11/2021 |
| WO | WO 2021/237084 A1 | 11/2021 |
| WO | WO 2021/247817 A1 | 12/2021 |
| WO | WO 2022/067010 A1 | 3/2022 |

OTHER PUBLICATIONS

John S, Yuzhakov O, Woods A, Deterling J, Hassett K, Shaw CA, Ciaramella G. Multi-antigenic human cytomegalovirus mRNA vaccines that elicit potent humoral and cell-mediated immunity. Vaccine. Mar. 14, 2018;36(12):1689-1699. doi: 10.1016/j.vaccine.2018. 01.029. Epub Feb. 15, 2018.*
Chen S, Tam YYC, Lin PJC, Sung MMH, Tam YK, Cullis PR. Influence of particle size on the in vivo potency of lipid nanoparticle formulations of siRNA. J Control Release. Aug. 10, 2016;235:236-244. doi: 10.1016/j.jconrel.2016.05.059. Epub May 26, 2016.*
Xue HY, et al. Curr Pharm Des. 2015;21(22):3140-7.*
Ernsting MJ, et al. J Control Release. Dec. 28, 2013;172(3):782-94. Epub Sep. 25, 2013.*
Gerna G, Lilleri D. Human cytomegalovirus (HCMV) infection/reinfection: development of a protective HCMV vaccine. New Microbiol. Jan. 2019;42(1):1-20. Epub Jan. 21, 2019. Review.*
Szebeni J, et. al. Biochem Biophys Res Commun. Dec. 18, 2015;468(3):490-7. Epub Jul. 14, 2015. Review.*
Szebeni J. Mol Immunol. Oct. 2014;61(2):163-73. Epub Aug. 12, 2014.*
Szebeni J, et. al. Adv Drug Deliv Rev. Sep. 16, 2011;63(12):1020-30. Epub Jul. 14, 2011.*
Leroueil PR, et al. Nano Lett. Feb. 2008;8(2):420-4. Epub Jan. 25, 2008.*
Kallen KJ, Theß A. A development that may evolve into a revolution in medicine: mRNA as the basis for novel, nucleotide-based vaccines and drugs. Ther Adv Vaccines. Jan. 2014;2(1):10-31.*
Davison AJ. Human herpesvirus 5 strain Merlin, complete genome. GenBank: AY446894.2, Dep. Jul. 2, 2013.*
Yi Zhao, Leaf Huang. Chapter Two: Lipid Nanoparticles for Gene Delivery. Book: Advances in Genetics. Author: Yi Zhao, Leaf Huang. Publisher: Elsevier Date: 2014 Copyright © 2014 Elsevier Inc. All rights reserved. https://doi.org/10.1016/B978-0-12-800148-6.00002-X.*
Petsch B, Schnee M, Vogel AB, Lange E, Hoffmann B, Voss D, Schlake T, Thess A, Kallen KJ, Stitz L, Kramps T. Protective efficacy of in vitro synthesized, specific mRNA vaccines against influenza A virus infection. Nat Biotechnol. Dec. 2012;30(12):1210-6. Epub Nov. 25, 2012.*
Ramamoorth M, Narvekar A. Non viral vectors in gene therapy—an overview. J Clin Diagn Res. Jan. 2015;9(1):GE01-6. doi: 10.7860/JCDR/2015/10443.5394. Epub Jan. 1, 2015.*
McVoy MA. Cytomegalovirus vaccines. Clin Infect Dis. Dec. 2013;57 Suppl 4(Suppl 4):S196-9. (Year: 2013).*
U.S. Appl. No. 15/753,297, filed Feb. 17, 2018, Thompson.
PCT/US2016/058310, Feb. 28, 2017, International Search Report and Written Opinion.
International Search Report and Written Opinion for Application No. PCT/US2016/058310, dated Feb. 28, 2017.
[No Author Listed], "Messenger RNA", Internet: Wikipedia. Jun. 19, 2013, XP002699196, Retrieved from the Internet: URL: http://en.wikipedia.org/wiki/Messenger RNA.
Anderson et al., Stability of mRNA/cationic lipid lipoplexes in human and rat cerebrospinal fluid: methods and evidence for nonviral mRNA gene delivery to the central nervous system. Hum Gene Ther. Feb. 10, 2003;14(3):191-202.
Andries et al., N(1)-methylpseudouridine-incorporated mRNA outperforms pseudouridine-incorporated mRNA by providing enhanced protein expression and reduced immunogenicity in mammalian cell lines and mice. J Control Release. Nov. 10, 2015;217:337-44. doi: 10.1016/j.jconrel.2015.08.051. Epub Sep. 3, 2015.
Archer, S.J., Induction of a T-cell specific antigen on bone marrow lymphocytes with thymus RNA. Immunology. Jan. 1978;34(1):123-9.
Ashley, D.M. et al., Bone marrow-generated dendritic cells pulsed with tumor extracts or tumor RNA induce antitumor immunity against central nervous system tumors. J Exp Med. Oct. 6, 1997; 186(7): 1177-82.
Bettinger, T. et al., Peptide-mediated RNA delivery: a novel approach for enhanced transfection of primary and post-mitotic cells. Nucleic Acids Res. Sep. 15, 2001;29(18):3882-91.
Bogers et al., Potent immune responses in rhesus macaques induced by nonviral delivery of a self-amplifying RNA vaccine expressing HIV type 1 envelope with a cationic nanoemulsion.J Infect Dis. Mar. 15, 2015;211(6):947-55. doi: 10.1093/infdis/jiu522. Epub Sep. 18, 2014.
Bonehill, A., et al., Single-step antigen loading and activation of dendritic cells by mRNA electroporation for the purpose of therapeutic vaccination in melanoma patients. Clin Cancer Res. May 2009; 15(10): 3366-3375.
Bowie et al., Deciphering the message in protein sequences: tolerance to amino acid substitutions. Science. Mar. 16, 1990;247(4948): 1306-10.
Brito et al., A cationic nanoemulsion for the delivery of next-generation RNA vaccines. Mol Ther. Dec. 2014;22(12):2118-29. doi: 10.1038/mt.2014.133. Epub Jul. 16, 2014.
Brito et al., Self-amplifying mRNA vaccines. Adv Genet. 2015;89:179-233. doi: 10.1016/bs.adgen.2014.10.005. Epub Dec. 4, 2014.

(56) References Cited

OTHER PUBLICATIONS

Chiuppesi et al., Vaccine-Derived Neutralizing Antibodies to the Human Cytomegalovirus gH/gL Pentamer Potently Block Primary Cytotrophoblast Infection. J Virol. Dec. 2015;89(23):11884-98. doi: 10.1128/JVI.01701-15. Epub Sep. 16, 2015.
Conry, R.M. et al., Characterization of a messenger RNA polynucleotide vaccine vector. Cancer Res. Apr. 1, 1995 ;55 (7):1397-1400.
Cosman et al., ULBPs, Novel MHC Class I-Related Molecules, Bind to CMV Glycoprotein UL 16 and Stimulate NK Cytotoxicity through the NKG2D Receptor, Immunity, 2001, vol. 14, No vol. pp. 123-133.
Dahlman et al., In vivo endothelial siRNA delivery using polymeric nanoparticles with low molecular weight, Nature Nanotechnology, 2014, No vol.#, pp. 1-8.
Davison. UL 128 [Human herpesvirus 5]. GenBank: AAR31335. Dep. Dec. 20, 2003.
Deering et al., Nucleic Acid Vaccines: Prospects for Non-Viral Delivery of mRNA Vaccines, Expert Opinion, 2014, vol. 11, No. 6, pp. 1-15.
Diken et al., Current Developments in Actively Personalized Cancer Vaccination with a Focus on RNA as the Drug Format. Prog Tumor Res. 2015;42:44-54. doi: 10.1159/000437184. Epub Sep. 4, 2015 Review.
Durbin et al., RNAs Containing Modified Nucleotides Fail to Trigger RIG-I Conformational Changes for Innate Immune Signaling. mBio. Sep. 20, 2016;7(5):e00833-16. doi: 10.1128/mBio.00833-16.
Ernsting et al., Factors controlling the pharmacokinetics, biodistribution and intratumoral penetration of nanoparticles. J Control Release. Dec. 28, 2013;172(3):782-94. doi: 10.1016/j.jconrel.2013.09.013. Epub Sep. 25, 2013.
Ewert et al., Cationic liposome-nucleic acid complexes for gene delivery and silencing: pathways and mechanisms for plasmid DNA and siRNA. Top Curr Chem. 2010;296:191-226.
Fleeton et al., Self-replicative RNA vaccines elicit protection against influenza A virus, respiratory syncytial virus, and a tickborne encephalitis virus. J Infect Dis. May 1, 2001;183(9):1395-8. Epub Mar. 30, 2001.
Geall et al., Nonviral delivery of self-amplifying RNA vaccines. Proc Natl Acad Sci U S A. Sep. 4, 2012;109(36):14604-9. doi: 10.1073/pnas.1209367109. Epub Aug. 20, 2012.
Genini et al., Serum Antibody Response to the gH/gL/pUL128-131 Five-Protein Complex of Human Cytomegalovirus (HCMV) in Primary and Reactivated HCMV Infections. J Clin Virol. Oct. 2011;52(2):113-8. doi: 10.1016/j.jcv.2011.06.018. Epub Aug. 4, 2011.
Gilboa, E. et al., Cancer immunotherapy with mRNA-transfected dendritic cells. Immunol Rev. Jun. 2004;199:251-63.
Gjetting et al., In vitro and in vivo effects of polyethylene glycol (PEG)-modifted lipid in DOTAP/cholesterol-mediated gene transfection. Int J Nanomedicine. Aug. 9, 2010;5:371-83.
Hadinoto et al., Lipid-polymer Hybrid Nanoparticles as a New Generation Therapeutic Delivery Platform: A Review. Eur J Pharm Biopharm. Nov. 2013;85(3 Pt A):427-43. doi: 10.1016/j.ejpb.2013.07.002. Epub Jul. 17, 2013.
Hajj et al., Tools for translation: non-viral materials for therapeutic mRNA delivery. Nat Rev Mat. Sep. 2017;2:17056.
Hassett et al., Optimization of Lipid Nanoparticles for Intramuscular Administration of mRNA Vaccines. Mol Ther Nucleic Acids. Apr. 15, 2019;15:I-II. Epub Feb. 7, 2019
Hecker, J.G. et al., Non-Viral DNA and mRNA Gene Delivery to the CNS Pre-Operatively for Neuroprotection and Following Neurotrauma. Molecular Therapy. 2004; 9, S258-S258.
Hecker, Nonviral, cationic lipid-mediated delivery of mRNA. Methods Mol Biol. 2013;969:73-88. doi: 10.1007/978-1-62703-260-5_5.
Heiser, A. et al., Induction of polyclonal prostate cancer-specific CTL using dendritic cells transfected with amplified tumor RNA. J Immunol. Mar. 1, 2001; 166(5):2953-60.
Hoerr, I. et al., In vivo application of RNA leads to induction of specific cytotoxic T lymphocytes and antibodies. EurJ Immunol. Jan. 2000;30(1):1-7.
Hoerr, I. et al., Stabilized Messenger RNA (RNActiveTM) as a Tool for Innovative Gene Delivery. Tissue Engineering. Apr. 2007; 13(4): 865-925.
Hoerr, More than a messenger: A new class of drugs-mRNA-based therapeutics. Genetic Engineering & Biotechnology News. Jun. 18, 2013. http://www.genengnews.com/gen-articles/more-than-a-messenger-a-new-class-of-drugs-mrna-based-therapeutics/4916/ [last accessed Mar. 25, 2016].
Holtkamp, S. et al., Modification of antigen-encoding RNA increases stability, translational efficacy, and T-cell stimulatory capacity of dendritic cells. Blood. Dec. 15, 2006;108(13):4009-17.
Jirikowski, G.F., et al., Reversal of diabetes insipidus in Brattleboro Rats: Intrahypothalamic injection of vasopressin mRNA. Science. Feb. 1992; 255(5047): 996-998.
John et al., Multi-antigenic human cytomegalovirus mRNA vaccines that elicit potent humoral and cell-mediated immunity. Vaccine. Mar. 14, 2018;36(12):1689-1699. doi:10.1016/j.vaccine.2018.01.029. Epub Feb. 15, 2018.
Kallen et al., A development that may evolve into a revolution in medicine: mRNA as the basis for novel, nucleotide-based vaccines and drugs. Ther Adv Vaccines. Jan. 2014;2(1):10-31. doi: 10.1177/2051013613508729.
Kallen et al., A novel, disruptive vaccination technology: self-adjuvanted RNActive(®) vaccines. Hum Vaccin Immunother. Oct. 2013;9(10):2263-76. doi: 10.4161/hv.25181. Epub Jun. 4, 2013. Review.
Kanapathipillai, et al., Nanoparticle targeting of anti-cancer drugs that alter intracellular signaling or influence the tumor microenvironment, Adv. Drug Deliv. Rev. (2014), , pp. 1-12.
Kariko, K., et al., Generating the optimal mRNA for therapy: HPLC purification eliminates immune activation and improves translation of nucleoside-modified, protein-encoding mRNA, Nucleic Acids Research, Oxford University Press, GB, vol. 39, No. 21, Sep. 2, 2011 (Sep. 2, 2011), e142. doi: 10.1093/nar/gkr695. Epub Sep. 2, 2011.
Kauffman et al., Efficacy and immunogenicity of unmodified and pseudouridine-modified mRNA delivered systemically with lipid nanoparticles in vivo. Biomaterials. Dec. 2016; 109:78-87. doi: 10.1016/j.biomaterials.2016.09.006. Epub Sep. 25, 2016.
Kisich et al., Antimycobacterial agent based on mRNA encoding human beta-defensin 2 enables primary macrophages to restrict growth of *Mycobacterium tuberculosis*.Infect Immun. Apr. 2001;69(4):2692-9.
Kowalski et al., Delivering the Messenger: Advances in Technologies for Therapeutic mRNA Delivery. Mol Ther. Apr. 10, 2019;27(4):710-728. doi: 10.1016/j.ymthe.2019.02.012.
Kozielski, Kristen L. et al., Bioreducible Cationic Polymer-Based Nanoparticles for Efficient and Environmentally Triggered Cytoplasmic siRNA Delivery to Primary Human Brain Cancer Cells, ACS Nano, 2014, vol. 8, ‘ No. 4 ’, pp. 3232-3241.
Kreiter, S., et al., Intranodal vaccination with naked antigen-encoding RNA elicits potent prophylactic and therapeutic antitumoral immunity. Cancer Res. 2010; 70: 9031-9040.
Kreiter, S., et al., Tumor vaccination using messenger RNA: prospects of a future therapy. Curr Opinion in Immun. Jun. 2011; 23(3): 399-406.
Kuhn, A.N., et al., mRNA as a versatile tool for exogenous protein expression. Current Gene Therapy. Oct. 2012; 12 (5): 347-361.
Leitner, W.W. et al., DNA and RNA-based vaccines: principles, progress and prospects. Vaccine. Dec. 10, 1999; 18 (9-10):765-77.
Leroueil et al., Wide varieties of cationic nanoparticles induce defects in supported lipid bilayers. Nano Lett. Feb. 2008;8(2):420-4. doi: 10.1021/n10722929. Epub Jan. 25, 2008.
Li, L. et al., Overcoming obstacles to develop effective and safe siRNA therapeutics. Expert Opin Biol Ther. May 2009; 9(5): 609-19.
Lin et al., Lipid-based nanoparticles in the systemic delivery of siRNA. Nanomedicine (Lond). Jan. 2014;9(1): 105-20. doi: 10.2217/nnm.13.192.

(56) References Cited

OTHER PUBLICATIONS

Lorenzi, J.C., et al., Intranasal vaccination with messenger RNA as a new approach in gene therapy: Use against tuberculosis. BMC Biotechnol. Oct. 2010; 10(77): 1-11.
Magini et al., Self-Amplifying mRNA Vaccines Expressing Multiple Conserved Influenza Antigens Confer Protection against Homologous and Heterosubtypic Viral Challenge. PLoS One. Aug. 15, 2016;11(8):e0161193. doi: 10.1371/journal.pone.0161193. eCollection 2016.
Maier et al., Biodegradable Lipids Enabling Rapidly Eliminated Lipid Nanoparticles for Systemic Delivery of RNAi Therapeutics. Mol Ther. Aug. 2013; 21(8): 1570-1578.
Martinon, F. et al., Induction of virus-specific cytotoxic T lymphocytes in vivo by liposome-entrapped mRNA. EurJ Immunol. Jul. 1993;23(7):1719-22.
Mcvoy, Cytomegalovirus vaccines. Clin Infect Dis. Dec. 2013;57 Suppl 4:S196-9. doi: 10.1093/cid/cit587.
Midoux et al., Lipid-based mRNA vaccine delivery systems. Expert Rev Vaccines. Feb. 2015;14(2):221-34. doi: 10.1586/14760584.2015.986104. Epub Dec. 26, 2014. Review.
Mitchell, DA et al., RNA transfected dendritic cells as cancer vaccines. Curr Opin Mal Ther. Apr. 2000;2(2):176-81.
Mitchell, DA et al., RNA-transfected dendritic cells in cancer immunotherapy. J Clin Invest. Nov. 2000;106 (9): 1065-9.
Mockey et al., mRNA-based cancer vaccine: prevention of B16 melanoma progression and metastasis by systemic injection of MART1 mRNA histidylated lipopolyplexes, Cancer Gene Therapy, 2007, 14, pp. 802-814.
Muller, M.R. et al., Transfection of dendritic cells with RNA induces CD4- and COB-mediated T cell immunity against breast carcinomas and reveals the immunodominance of presented T cell epitopes. J Immunol. Jun. 15, 2003; 170 (12):5892-6.
Pardi et al., Expression Kinetics of Nucleoside-Modified mRNA Delivered in Lipid Nanoparticles to Mice by Various Routes. J Control Release. Nov. 10, 2015;217:345-51. doi: 10.1016/j.jconrel.2015.08.007. Epub Aug. 8, 2015.
Pardi et al., Nucleoside-modified mRNA vaccines induce potent T follicular helper and germinal center B cell responses. J Exp Med. Jun. 4, 2018;215(6):1571-1588. doi: 10.1084/jem.20171450. Epub May 8, 2018.
Pass et al., Vaccine prevention of maternal cytomegalovirus infection. N Engl J Med. Mar. 19, 2009;360(12):1191-9. doi: 10.1056/NEJMoa0804749.
Petsch et al., Protective efficacy of in vitro synthesized, specific mRNA vaccines against influenza A virus infection. Nat Biotechnol. Dec. 2012;30(12):1210-6. doi: 10.1038/nbt.2436. Epub Nov. 25, 2012.
Phua et al., Messenger RNA (mRNA) nanoparticle tumour vaccination. Nanoscale. Jul. 21, 2014;6(14):7715-29. doi: 10.1039/c4nr01346h. Review.
Poveda et al., Establishing Preferred Product Characterization for the Evaluation of RNA Vaccine Antigens. Vaccines (Basel). Sep. 27, 2019;7(4):131. doi: 10.3390/vaccines7040131.
Pulford, B., et al., Liposome-siRNA-peptide complexes cross the blood-brain barrier and significantly decrease PrP'C on neuronal cells and PrP'RES in infected cell cultures. PLoS ONE. 201 O; 5(6): el 1085.
Rabinovich, P.M., et al., Synthetic messenger RNA as a tool for gene therapy. Hum. Gene Ther. Oct. 2006; 17: 1027-1035.
Reap et al., Cellular and humoral immune responses to alphavirus replicon vaccines expressing cytomegalovirus pp65, IE1, and gB proteins. Clin Vaccine Immunol. Jun. 2007;14(6):748-55. Epub Apr. 18, 2007.
Reichmuth et al., mRNA Vaccine Delivery Using Lipid Nanoparticles. Ther Deliv. 2016;7(5):319-34. doi: 10.4155/tde-2016-0006.
Rittig et al., Intradermal vaccinations with RNA coding for TAA generate CD8+ and CD4+ immune responses and induce clinical benefit in vaccinated patients. Mol Ther. May 2011;19(5):990-9. doi: 10.1038/mt.2010.289. Epub Dec. 28, 2010.
Sabnis et al., A Novel Amino Lipid Series for mRNA Delivery: Improved Endosomal Escape and Sustained Pharmacology and Safety in Non-human Primates. Mol Ther. Jun. 6, 2018;26(6):1509-1519. doi: 10.1016/j.ymthe.2018.03.010. Epub Mar. 14, 2018.
Sahin et al., mRNA-based therapeutics—developing a new class of drugs. Nat Rev Drug Discov. Oct. 2014;13(10):759-80. doi: 10.1038/nrd4278. Epub Sep. 19, 2014.
Schleiss et al., Additive Protection against Congenital Cytomegalovirus Conferred by Combined Glycoprotein B/pp65 Vaccination Using a Lymphocytic Choriomeningitis Virus Vector. Clin Vaccine Immunol. Jan. 5, 2017;24(1). pii: e00300-16. doi: 10.1128/CVI.00300-16. Print Jan. 2017.
Schmitt, W.E. et al., In vitro induction of a bladder cancer-specific T-cell response by mRNA-transfected dendritic cells. J Cancer Res Clin Oncol. 2001 ;127(3):203-6.
Schott, J.W., et al., Viral and non-viral approaches for transient delivery of mRNA and proteins. Current Gene Ther. 2011; 11 (5): 382-398.
Segura, J., et al., Monitoring gene therapy by external imaging of mRNA: Pilot study on murine erythropoietin. Ther Drug Monit. Oct. 2007; 29(5): 612-8.
Sirin et al. AB-Bind: Antibody binding mutational database for computational affinity predictions. Protein Sci. Feb. 2016;25(2):393-409. doi: 10.1002/pro.2829. Epub Nov. 6, 2015.
Smits, E., et al., RNA-based gene transfer for adult stem cells and T cells. Leukemia. 2004; 18: 1898-1902.
Sohn, R.L., et al., In-vivo particle mediated delivery of mRNA to mammalian tissues: ballistic and biological effects. Wound Rep and Regen. Jul.-Aug. 2001; 287-296.
Stanton et al., Human herpesvirus 5 transgenic strain Merlin, complete genome. GenBank: GU179001. Dep. Dec. 13, 2009.
Strong, V.T. et al., Incorporation of beta-globin untranslated regions into a Sindbis virus vector for augmentation of heterologous mRNA expression. Gene Ther. Jun. 1997;4(6):624-7.
Sullenger, BA et al., Emerging clinical applications of RNA. Nature. Jul. 11, 2002;418(6894):252-8.
Sun et al., Human herpesvirus 5 isolate D-947 UL131A, UL130, and UL128 genes, complete cds. GenBank: GU568344. Dep. Apr. 20, 2010.
Szebeni et al., Activation of complement by therapeutic liposomes and other lipid excipient-based therapeutic products: prediction and prevention. Adv Drug Deliv Rev. Sep. 16, 2011;63(12):1020-30. doi: 10.1016/j.addr.2011.06.017. Epub Jul. 14, 2011.
Szebeni et al., Complement activation as a bioequivalence issue relevant to the development of generic liposomes and other nanoparticulate drugs. Biochem Biophys Res Commun. Dec. 18, 2015;468(3):490-7. doi: 10.1016/j.bbrc.2015.06.177. Epub Jul. 14, 2015.
Szebeni, Complement activation-related pseudoallergy: a stress reaction in blood triggered by nanomedicines and biologicals. Mol Immunol. Oct. 2014;61(2):163-73. doi: 10.1016/j.molimm.2014.06.038. Epub Aug. 12, 2014.
Tavernier, G., et al., mRNA as gene therapeutic: How to control protein expression. J. of Controlled Release. Mar. 2011; 150(3): 238-247.
Teufel, R. et al., Human peripheral blood mononuclear cells transfected with messenger RNA stimulate antigen-specific cytotoxic T-lymphocytes in vitro. Cell Mol Life Sci. Aug. 2005;62(15):1755-62.
Thess et al., Sequence-engineered mRNA Without Chemical Nucleoside Modifications Enables an Effective Protein Therapy in Large Animals. Mol Ther. Sep. 2015;23(9):1456-64. doi: 10.1038/mt.2015.103. Epub Jun. 8, 2015.
Torrecilla et al., Lipid Nanoparticles as Carriers for RNAi Against Viral Infections: Current Status and Future Perspectives. Biomed Res Int. 2014;2014:161794. doi: 10.1155/2014/161794. Epub Aug. 12, 2014.
Tripathy et al., Long-term expression of erythropoietin in the systemic circulation of mice after intramuscular injection of a plasmid DNA vector, Proc. Natl. Acad. Sci. USA 93, 1996, p. 10876-10880.
Uzgun, S., et al., PEGylation improves nanoparticle formation and transfection efficiency of messenger RNA. Pharm Res. Sep. 2011; 28(9); 2223-2232.

(56) References Cited

OTHER PUBLICATIONS

Van Den Bosch et al., Simultaneous activation of Viral Antigen-specific Memory CD4+ and CDS+ T-cells using mRNA—electroporated CD40-activaled autologous B-cells. J Immunother. Sep./Oct. 2006; 29, 512-23.
Vici et al., Immunologic treatments for precancerous lesions and uterine cervical cancer. J Exp Clin Cancer Res. Mar. 26, 2014;33:29. doi: 10.1186/1756-9966-33-29.
Wang et al., Systemic delivery of modified mRNA encoding herpes simplex virus 1 thymidine kinase for targeted cancer gene therapy. Mol Ther. Feb. 2013;21(2):358-67. doi: 10.1038/mt.2012.250. Epub Dec. 11, 2012.
Wen et al., Human cytomegalovirus gH/gL/UL128/UL130/UL131A complex elicits potently neutralizing antibodies in mice. Vaccine. Jun. 24, 2014;32(30):3796-804. doi: 10.1016/j.vaccine.2014.05.004. Epub May 14, 2014.
Winkler et al., Changing the antigen binding specificity by single point mutations of an anti-p24 (HIV-1) antibody. J Immunol. Oct. 15, 2000;165(8):4505-14.
Wong et al., An mRNA vaccine for influenza. Nat Biotechnol. Dec. 2012;30(12):1202-4. doi: 10.1038/nbt.2439.
Wussow et al., Human cytomegalovirus vaccine based on the envelope gH/gL pentamer complex. PLoS Pathog. Nov. 20, 2014;10(11):e1004524. doi: 10.1371/journal.ppat.1004524. eCollection Nov. 2014.
Xue et al., Lipid-Based Nanocarriers for RNA Delivery. Curr Pharm Des. 2015;21(22):3140-7.
Yamamoto et al., Current prospects for mRNA gene delivery, European Journal of Pharmaceutics and Biopharmaceutics 71 (2009) 484-489.
YP_0181566. Davison et al., Human betaherpesvirus 5 (HHV-5; HCMB). Dep. Sep. 27, 2002, Updated Jul. 2, 2013.
YP_018555. Davison et al., Human betaherpesvirus 5 (HHV-5; HCMB). Dep. Sep. 27, 2002, Updated Jul. 2, 2013.
YP_018565. Davison et al., Human betaherpesvirus 5 (HHV-5; HCMB). Dep. Sep. 27, 2002, Updated Jul. 2, 2013.
YP_081514. Davison et al., Human betaherpesvirus 5 (HHV-5; HCMB). Dep. Sep. 27, 2002, Updated Jul. 2, 2013.
YP_081523. Davison et al., Human betaherpesvirus 5 (HHV-5; HCMB). Dep. Sep. 27, 2002, Updated Jul. 2, 2013.
Zhou, W.Z. et al., RNA melanoma vaccine: induction of antitumor immunity by human glycoprotein 100 mRNA immunization. Hum Gene Ther. Nov. 1999 1;10(16):2719-24.
Zou et al., Lipid-mediated delivery of RNA is more efficient than delivery of DNA in non-dividing cells. Int J Pharm. Apr. 15, 2010;389(1-2):232-43. doi: 10.1016/j.ijpharm.2010.01.019. Epub Jan. 18, 2010.
U.S. Appl. No. 90/014,395, filed Oct. 24, 2019, Ciaramella et al.
U.S. Appl. No. 15/748,782, filed Jan. 30, 2018, Mousavi et al.
U.S. Appl. No. 16/853,973, filed Apr. 21, 2020, Ciaramella et al.
U.S. Appl. No. 16/850,519, filed Apr. 16, 2020, Ciaramella et al.
U.S. Appl. No. 15/746,286, filed Jan. 19, 2018, Ciaramella et al.
U.S. Appl. No. 16/599,661, filed Oct. 11, 2019, Besin et al.
U.S. Appl. No. 16/333,330, filed Mar. 14, 2019, Hoge et al.
U.S. Appl. No. 16/864,566, filed May 1, 2020, Ciaramella et al.
U.S. Appl. No. 16/880,829, filed May 21, 2020, Ciaramella et al.
U.S. Appl. No. 16/348,943, filed May 10, 2019, Ciaramella.
U.S. Appl. No. 16/467,142, filed Jun. 6, 2019, Ciaramella et al.
U.S. Appl. No. 16/657,122, filed Oct. 18, 2019, Rabideau et al.
U.S. Appl. No. 16/494,162, filed Sep. 13, 2019, Ciaramella.
U.S. Appl. No. 16/848,318, filed Apr. 14, 2020, Ciaramella et al.
U.S. Appl. No. 16/608,451, filed Oct. 25, 2019, Ciaramella et al.
U.S. Appl. No. 17/000,215, filed Aug. 21, 2020, Stewart-Jones et al.
[No Author Listed], Clinical Trial NCT03382405. "Safety, Reactogenicity, and Immunogenicity of Cytomegalovirus Vaccines mRNA-1647 and mRNA-1443 in Healthy Adults." First posted Dec. 22, 2017. Retrieved online Nov. 13, 2020 from https://www.clinical trials.gov/ct2/show/study/NCT03382405?term=modernatx&draw=3 &rank=14.
Cullis et al., Lipid Nanoparticle Systems for Enabling Gene Therapies. Mol Ther. Jul. 5, 2017;25(7):1467-1475. doi: 10.1016/j.ymthe.2017.03.013. Epub Apr. 13, 2017.
Hartmann et al., Handbook of RNA Biochemistry, Second Edition, "Part I RNA Synthesis and Detection." 2014. p. 1-27.
Kumar et al., Shielding of Lipid Nanoparticles for siRNA Delivery: Impact on Physicochemical Properties, Cytokine Induction, and Efficacy. Mol Ther Nucleic Acids. Nov. 18, 2014;3(11):e210. doi: 10.1038/mtna.2014.61.
Kurimoto et al., PEG-OligoRNA Hybridization of mRNA for Developing Sterically Stable Lipid Nanoparticles toward In Vivo Administration. Molecules. Apr. 3, 2019;24(7): 1303.
Wussow et al., Neutralization of Human Cytomegalovirus Entry into Fibroblasts and Epithelial Cells. Vaccines (Basel). Oct. 31, 2017;5(4):39. doi: 10.3390/vaccines5040039.
Kauffman et al., Materials for non-viral intracellular delivery of messenger RNA therapeutics. J Control Release. Oct. 28, 2016;240:227-234. doi: 10.1016/j.jconrel.2015.12.032. Epub Dec. 21, 2015.
Mcvoy et al., A cytomegalovirus DNA vaccine induces antibodies that block viral entry into fibroblasts and epithelial cells. Vaccine . Dec. 16, 2015;33(51):7328-7336. doi: 10.1016/j.vaccine.2015.10.078. Epub Oct. 24, 2015.
Oberli et al., Lipid Nanoparticle Assisted mRNA Delivery for Potent Cancer Immunotherapy. Nano Lett. Mar. 8, 2017;17(3):1326-1335. doi: 10.1021/acs.nanolett.6b03329. Epub Dec. 5, 2016.
Pardi et al., mRNA vaccines—a new era in vaccinology. Nat Rev Drug Discov. Apr. 2018;17(4):261-279. doi: 10.1038/nrd.2017.243. Epub Jan. 12, 2018.
Schlake et al., Developing mRNA-vaccine technologies. RNA Biol. Nov. 2012;9(11):1319-30. doi: 10.4161/rna.22269. Epub Oct. 12, 2012.
Zhao et al., Nanoparticle vaccines. Vaccine. Jan. 9, 2014;32(3):327-37. doi: 10.1016/j.vaccine.2013.11.069. Epub Dec. 2, 2013.
U.S. Appl. No. 16/036,318, filed Jul. 16, 2018, Ciaramella et al.
U.S. Appl. No. 16/144,394, filed Sep. 27, 2018, Ciaramella et al.
U.S. Appl. No. 17/204,801, filed Mar. 17, 2021, Ciaramella et al.
U.S. Appl. No. 17/683,171, filed Feb. 28, 2022, Ciaramella et al.
U.S. Appl. No. 15/748,773, filed Jan. 30, 2018, Ciaramella et al.
U.S. Appl. No. 17/554,182, filed Dec. 17, 2021, Ciaramella et al.
U.S. Appl. No. 15/753,293, filed Feb. 17, 2018, Smith.
U.S. Appl. No. 15/767,587, filed Apr. 11, 2018, Ciaramella.
U.S. Appl. No. 15/767,600, filed Apr. 11, 2018, Ciaramella et al.
U.S. Appl. No. 15/769,710, filed Apr. 19, 2018, Ciaramella et al.
U.S. Appl. No. 15/767,609, filed Apr. 11, 2018, Ciaramella et al.
U.S. Appl. No. 15/767,613, filed Apr. 11, 2018, Ciaramella et al.
U.S. Appl. No. 15/767,618, filed Apr. 11, 2018, Ciaramella et al.
U.S. Appl. No. 17/590,479, filed Feb. 1, 2022, Ciaramella et al.
U.S. Appl. No. 16/897,859, filed Jun. 10, 2020, Ciaramella et al.
U.S. Appl. No. 16/898,268, filed Jun. 10, 2020, Ciaramella et al.
U.S. Appl. No. 17/583,674, filed Jan. 25, 2022, Besin et al.
U.S. Appl. No. 17/523,034, filed Nov. 10, 2021, Hoge et al.
U.S. Appl. No. 17/523,060, filed Nov. 10, 2021, Hoge et al.
U.S. Appl. No. 17/548,172, filed Dec. 10, 2021, Ciaramella et al.
U.S. Appl. No. 16/897,734, filed Jun. 10, 2020, Ciaramella et al.
U.S. Appl. No. 16/468,838, filed Jun. 12, 2019, Miracco.
U.S. Appl. No. 16/001,765, filed Jun. 6, 2018, Marquardt et al.
U.S. Appl. No. 17/127,949, filed Dec. 18, 2020, Ciaramella.
U.S. Appl. No. 17/385,655, filed Jul. 26, 2021, Ciaramella et al.
U.S. Appl. No. 16/603,111, filed Oct. 4, 2019, Brito et al.
U.S. Appl. No. 16/482,844, filed Aug. 1, 2019, Valiante et al.
U.S. Appl. No. 16/496,135, filed Sep. 20, 2019, Narayanan et al.
U.S. Appl. No. 16/483,012, filed Aug. 1, 2019, Mauger et al.
U.S. Appl. No. 17/350,662, filed Jun. 17, 2021, Rabideau et al.
U.S. Appl. No. 16/362,366, filed Mar. 22, 2019, Ciaramella.
U.S. Appl. No. 16/493,986, filed Sep. 13, 2019, Ciaramella et al.
U.S. Appl. No. 16/494,130, filed Sep. 13, 2019, Ciaramella et al.
U.S. Appl. No. 16/494,103, filed Sep. 13, 2019, Ciaramella et al.
U.S. Appl. No. 17/245,973, filed Apr. 30, 2021, Ciaramella.
U.S. Appl. No. 16/494,988, filed Sep. 17, 2019, Ciaramella et al.
U.S. Appl. No. 17/155,592, filed Jan. 22, 2021, Ciaramella et al.
U.S. Appl. No. 16/639,265, filed Feb. 14, 2020, Issa et al.
U.S. Appl. No. 16/639,305, filed Feb. 14, 2020, Issa et al.
U.S. Appl. No. 16/765,285, filed May 19, 2020, Ciaramella et al.

(56) References Cited

OTHER PUBLICATIONS

U.S. Appl. No. 16/302,607, filed Nov. 16, 2018, Benenato et al.
U.S. Appl. No. 16/623,069, filed Dec. 16, 2019, Hoge et al.
U.S. Appl. No. 16/639,403, filed Feb. 14, 2020, Hoge et al.
U.S. Appl. No. 17/531,211, filed Nov. 19, 2021, Ciaramella et al.
U.S. Appl. No. 16/965,589, filed Jul. 28, 2020, Ciaramella et al.
U.S. Appl. No. 17/255,949, filed Dec. 23, 2020, Zhong et al.
U.S. Appl. No. 17/277,423, filed Mar. 18, 2021, Almarsson et al.
U.S. Appl. No. 17/277,452, filed Mar. 18, 2021, Hennessy et al.
U.S. Appl. No. 17/276,112, filed Mar. 12, 2021, Martini et al.
U.S. Appl. No. 17/438,049, filed Sep. 10, 2021, Elich et al.
U.S. Appl. No. 17/634,939, filed Feb. 11, 2022, Shamashkin et al.
U.S. Appl. No. 17/291,947, filed May 6, 2021, Ashburn et al.
U.S. Appl. No. 17/439,198, filed Sep. 14, 2021, Lusso et al.
U.S. Appl. No. 17/325,883, filed May 20, 2021, Dousis et al.
U.S. Appl. No. 16/788,182, filed Feb. 11, 2020, Panther et al.
U.S. Appl. No. 16/794,318, filed Feb. 19, 2020, Mauger et al.
U.S. Appl. No. 17/761,420, filed Mar. 17, 2022, Amato et al.
U.S. Appl. No. 17/145,164, filed Jan. 8, 2021, Giessel et al.
U.S. Appl. No. 17/615,202, filed Nov. 30, 2021, Hopson.
U.S. Appl. No. 17/641,967, filed Mar. 10, 2022, John et al.
U.S. Appl. No. 17/411,896, filed Aug. 25, 2021, Kramarczyk et al.
U.S. Appl. No. 17/000,201, filed Aug. 21, 2020, Stewart-Jones et al.
U.S. Appl. No. 17/000,215, filed Aug. 21, 2020, Metkar et al.
U.S. Appl. No. 17/518,542, filed Nov. 3, 2021, Metkar et al.
U.S. Appl. No. 17/572,465, filed Jan. 10, 2022, Nachbagauer et al.
[No Author Listed], Moderna Announces Additional Positive Phase 1 Data from Cytomegalovirus (CMV) Vaccine (mRNA-1647) and First Participant Dosed in Phase 2 Study', Jan. 9, 2020, retrieved from the internet on Sep. 28, 2021 from businesswire.com/news/home/20200109005801/en/Moderna-Announces-Additional-Positive-Phase-1-Data-from-Cytomegalovirus-CMV-Vaccine-mRNA-1647-and-First-Participant-Dosed-in-Phase-2-Study. 4 pages.
[No Author Listed], Moderna Announces First Participant Dosed in Phase 3 Pivotal Registration Study of Its mRNA Cytomegalovirus (CMV) Vaccine. Oct. 26, 2021, retrieved from the internet on Apr. 7, 2022 from https://investors.modernatx.com/news/news-details/2021/Moderna-Announces-First-Participant-Dosed-in-Phase-3-Pivotal-Registration-Study-of-Its-mRNA-Cytomegalovirus-CMV-Vaccine-Oct. 26, 2021/default.aspx. 2 pages.
[No Author Listed], Moderna Announces Positive Interim Results from Phase 1 Cytomegalovirus (CMV) Vaccine (mRNA-1647) Study and Progress Toward Phase 2 and Pivotal Trials, Sep. 12, 2019, retrieved from the internet on Sep. 28, 2021 from investors.modernatx.com/news-releases/news-release-details/moderna-announces-positive-interim-results-phase-1. 4 pages.
Cross, Without these lipid shells, there would be no mRNA vaccines for COVID-19. Chem Eng News. Mar. 6, 2021; 99(8). 4 pages.
Maruggi et al., mRNA as a Transformative Technology for Vaccine Development to Control Infectious Diseases. Mol Ther. Apr. 10, 2019;27(4):757-772. doi: 10.1016/j.ymthe.2019.01.020. Epub Feb. 7, 2019.
Michel et al., Cationic Nanoliposomes Meet mRNA: Efficient Delivery of Modified mRNA Using Hemocompatible and Stable Vectors for Therapeutic Applications. Mol Ther Nucleic Acids. Sep. 15, 2017;8:459-468. doi: 10.1016/j.omtn.2017.07.013. Epub Jul. 25, 2017.
Patel et al., Naturally-occurring cholesterol analogues in lipid nanoparticles induce polymorphic shape and enhance intracellular delivery of mRNA. Nat Commun. Feb. 20, 2020;11(1):983. doi: 10.1038/s41467-020-14527-2.
Shin et al., Recent Advances in RNA Therapeutics and RNA Delivery Systems Based on Nanoparticles. Adv. Therap., Nov. 2018;1(7):1800065. Review.
Terada et al., Characterization of Lipid Nanoparticles Containing Ionizable Cationic Lipids Using Design-of-Experiments Approach. Langmuir. Jan. 26, 2021;37(3):1120-1128. doi: 10.1021/acs.langmuir.0c03039. Epub Jan. 13, 2021.
Wang et al., Chapter 3: Lipid Nanoparticles for the Delivery of Nucleic Acids. Book: Nanoparticulate Drug Delivery Systems: Strategies, Technologies, and Applications. 2013. 29 pages.
Zeng et al., Formulation and Delivery Technologies for mRNA Vaccines. Curr Top Microbiol Immunol. Jun. 2, 2020; 10.1007/82 2020 217. doi: 10.1007/82 2020 217.

* cited by examiner

Adapted from Macagno et al., Journal of Virology, 2010.

| # doses | 1 | 2 | 2 | 2 | 1 | 2 |
|---|---|---|---|---|---|---|
| Pentamer dose (µg) | 10 | 1 | - | - | 10 | - |
| gB dose (µg) | - | - | 10 | 10 | 2 | - |
| Formulation | Pentamer pre-mix ( Equimolar) | | gB | gB / MF59 | gB+ Penta (Equal conc) | Empty |

A ● day 20 (3wk PD1)
B ● day 41 (3wk PD2)
C ● day 182 (~20 wk PD3)

* Clinical dose hCMVgH-2A-gL (ORF-gH-Furin-Linker-P2A-gL)
Furin: CCGCGCCAAGAGGAGC (SEQ ID NO:74)
Linker: GGAAGCGGA
P2A peptide: GCTACTAACTTCAGCCTGCTGAAGCAGGCTGGAGACGTGGAGGAGAACCCTGGACCT (SEQ ID NO:75)
5'-UTR: bold
3'-UTR: underline hCMVgH-2A-gL (ORF-gH-Furin-Linker-P2A-gL)

TCAAGCTTTTGGACCCTCGTACAGAAGCTAATACGACTCACTATAGGGAAATAAGAGAGAAAAGAAGAGTAAGAAGA
AATATAAGAGCCACCATGCGGCCAGGCCTCCCCTCCTACCTCATCATCCTCGCCGTCTGTCTCTTCAGCCACCTACT
TTCGTCACGATATGGCGCAGAAGCCGTATCCGAACCGCTGGACAAAGCGTTTCACCTACTGCTCAACACCTACGGGA
GACCCATCCGCTTCCTGCGTGAAAATACCACCCAGTGTACCTACAACAGCAGCCTCCGTAACAGCACGGTCGTCAGG
GAAAACGCCATCAGTTTCAACTTTTTCCAAAGCTATAATCAATACTATGTATTCCATATGCCTCGATGTCTTTTTGC
GGGTCCTCTGGCGGAGCAGTTTCTGAACCAGGTAGATCTGACCGAAACCCTGGAAAGATACCAACAGAGACTTAACA
CTTACGCGCTGGTATCCAAAGACCTGGCCAGCTACCGATCTTTTTCGCAGCAGCTAAAGGCACAAGACAGCCTAGGT
GAACAGCCCACCACTGTGCCACCGCCCATTGACCTGTCAATACCTCACGTTTGGATGCCACCGCAAACCACTCCACA
CGGCTGGACAGAATCACATACCACCTCAGGACTACACCGACCACACTTTAACCAGACCTGTATCCTCTTTGATGGAC
ACGATCTACTATTCAGCACCGTCACACCTTGTTTGCACCAAGGCTTTTACCTCATCGACGAACTACGTTACGTTAAA
ATAACACTGACCGAGGACTTCTTCGTAGTTACGGTGTCCATAGACGACGACACACCCATGCTGCTTATCTTCGGCCA
TCTTCCACGCGTACTTTTCAAAGCGCCCTATCAACGCGACAACTTTATACTACGACAAACTGAAAAACACGAGCTCC
TGGTGCTAGTTAAGAAAGATCAACTGAACCGTCACTCTTATCTCAAAGACCCGGACTTTCTTGACGCCGCACTTGAC
TTCAACTACCTAGACCTCAGCGCACTACTACGTAACAGCTTTCACCGTTACGCCGTGGATGTACTCAAGAGCGGTCG
ATGTCAGATGCTGGACCGCCGCACGGTAGAAATGGCCTTCGCCTACGCATTAGCACTGTTCGCAGCAGCCCGACAAG
AAGAGGCCGGCGCCCAAGTCTCCGTCCCACGGGCCCTAGACCGCCAGGCCGCACTCTTACAAATACAAGAATTTATG
ATCACCTGCCTCTCACAAACACCACCACGCACCACGTTGCTGCTGTATCCCACGGCCGTGGACCTGGCCAAACGAGC
CCTTTGGACACCGAATCAGATCACCGACATCACCAGCCTCGTACGCCTGGTCTACATACTCTCTAAACAGAATCAGC
AACATCTCATCCCCCAATGGGCACTACGACAGATCGCCGACTTTGCCCTAAAACTACACAAAACGCACCTGGCCTCT
TTTCTTTCAGCCTTCGCACGCCAAGAACTCTACCTCATGGGCAGCCTCGTCCACTCCATGCTGGTACATACGACGGA
GAGACGCGAAATCTTCATCGTAGAAACGGGCCTCTGTTCATTGGCCGAGCTATCACACTTTACGCAGTTGTTAGCTC
ATCCACACCACGAATACCTCAGCGACCTGTACACACCCTGTTCCAGTAGCGGGCGACGCGATCACTCGCTCGAACGC
CTCACGCGTCTCTTCCCCGATGCCACCGTCCCCGCTACCGTTCCCGCCGCCCTCTCCATCCTATCTACCATGCAACC
AAGCACGCTGGAAACCTTCCCCGACCTGTTTTGCTTGCCGCTCGGCGAATCCTTCTCCGCGCTGACCGTCTCCGAAC
ACGTCAGTTATATCGTAACAAACCAGTACCTGATCAAAGGTATCTCCTACCCTGTCTCCACCACCGTCGTAGGCCAG
AGCCTCATCATCACCCAGACGGACAGTCAAACTAAATGCGAACTGACGCGCAACATGCATACCACACACAGCATCAC
AGTGGCGCTCAACATTTCGCTAGAAAACTGCGCCTTTTGCCAAAGCGCCCTGCTAGAATACGACGACACGCAAGGCG
TCATCAACATCATGTACATGCACGACTCGGACGACGTCCTTTTCGCCCTGGATCCCTACAACGAAGTGGTGGTCTCA
TCTCCGCGAACTCACTACCTCATGCTTTTGAAAAACGGTACGGTACTAGAAGTAACTGACGTCGTCGTGGACGCCAC
CGACAGTCGTCTCCTCATGATGTCCGTCTACGCGCTATCGGCCATCATCGGCATCTATCTGCTCTACCGCATGCTCA
AGACATGCCGCGCCAAGAGGAGCGGAAGCGGAGCTACTAACTTCAGCCTGCTGAAGCAGGCTGGAGACGTGGAGGAG
AACCCTGGACCTATGTGCCGCCGCCCGGATTGCGGCTTCTCTTTCTCACCTGGACCGGTGATACTGCTGTGGTGTTG
CCTTCTGCTGCCCATTGTTTCCTCAGCCGCCGTCAGCGTCGCTCCTACCGCCGCCGAGAAAGTCCCCGCGGAGTGCC
CCGAACTAACGCGCCGATGCTTGTTGGGTGAGGTGTTTGAGGGTGACAAGTATGAAAGTTGGCTGCGCCCGTTGGTG
AATGTTACCGGGCGCGATGGCCCGCTATCGCAACTTATCCGTTACCGTCCCGTTACGCCGGAGGCCGCCAACTCCGT
GCTGTTGGACGAGGCTTTCCTGGACACTCTGGCCCTGCTGTACAACAATCCGGATCAATTGCGGGCCCTGCTGACGC
TGTTGAGCTCGGACACAGCGCCGCGCTGGATGACGGTGATGCGCGGCTACAGCGAGTGCGGCGATGGCTCGCCGGCC
GTGTACACGTGCGTGGACGACCTGTGCCGCGGCTACGACCTCACGCGACTGTCATACGGGCGCAGCATCTTCACGGA
ACACGTGTTAGGCTTCGAGCTGGTGCCACCGTCTCTCTTTAACGTGGTGGTGGCCATACGCAACGAAGCCACGCGTA
CCAACCGCGCCGTGCGTCTGCCCGTGAGCACCGCTGCCGCGCCCGAGGGCATCACGCTCTTTTACGGCCTGTACAAC
GCAGTGAAGGAATTCTGCCTGCGTCACCAGCTGGACCCGCCGCTGCTACGCCACCTAGATAAATACTACGCCGGACT
GCCGCCCGAGCTGAAGCAGACGCGCGTCAACCTGCCGGCTCACTCGCGCTATGGCCCTCAAGCAGTGGATGCTCGCT
GATAATAGGCTGGAGCCTCGGTGGCCATGCTTCTTGCCCCTTGGGCCTCCCCCCAGCCCCTCCTCCCCTTCCTGCAC
CCGTACCCCCGTGGTCTTTGAATAAAGTCTGAGTGGGCGGC (SEQ ID NO: 29)

Fig. 25A hCMVgH-2A-gL (ORF-gH-Furin-Linker-P2A-gL)

UCAAGCUUUUGGACCCUCGUACAGAAGCUAAUACGACUCACUAUAGGGAAAUAAGAGAGAAAAGAAGAGUAAGA
AGAAAUAUAAGAGCCACCAUGCGGCCAGGCCUCCCCUCCUACCUCAUCAUCCUCGCCGUCUGUCUCUUCAGCCA
CCUACUUUCGUCACGAUAUGGCGCAGAAGCCGUAUCCGAACCGCUGGACAAAGCGUUUCACCUACUGCUCAACA
CCUACGGGAGACCCAUCCGCUUCCUGCGUGAAAAUACCACCCAGUGUACCUACAACAGCAGCCUCCGUAACAGC
ACGGUCGUCAGGGAAAACGCCAUCAGUUUCAACUUUUUCCAAAGCUAUAAUCAAUACUAUGUAUUCCAUAUGCC
UCGAUGUCUUUUUGCGGGUCCUCUGGCGGAGCAGUUUCUGAACCAGGUAGAUCUGACCGAAACCCUGGAAAGAU
ACCAACAGAGACUUAACACUUACGCGCUGGUAUCCAAAGACCUGGCCAGCUACCGAUCUUUUUCGCAGCAGCUA
AAGGCACAAGACAGCCUAGGUGAACAGCCCACCACUGUGCCACCGCCCAUUGACCUGUCAAUACCUCACGUUUG
GAUGCCACCGCAAACCACUCCACACGGCUGGACAGAAUCACAUACCACCUCAGGACUACACCGACCACACUUUA
ACCAGACCUGUAUCCUCUUUGAUGGACACGAUCUACUAUUCAGCACCGUCACACCUUGUUUGCACCAAGGCUUU
UACCUCAUCGACGAACUACGUUACGUUAAAAUAACACUGACCGAGGACUUCUUCGUAGUUACGGUGUCCAUAGA
CGACGACACACCCAUGCUGCUUAUCUUCGGCCAUCUUCCACGCGUACUUUUCAAAGCGCCCUAUCAACGCGACA
ACUUUAUACUACGACAAACUGAAAAACACGAGCUCCUGGUGCUAGUUAAGAAAGAUCAACUGAACCGUCACUCU
UAUCUCAAAGACCCGGACUUUCUUGACGCCGCACUUGACUUCAACUACCUAGACCUCAGCGCACUACUACGUAA
CAGCUUUCACCGUUACGCCGUGGAUGUACUCAAGAGCGGUCGAUGUCAGAUGCUGGACCGCCGCACGGUAGAAA
UGGCCUUCGCCUACGCAUUAGCACUGUUCGCAGCAGCCCGACAAGAAGAGGCCGGCGCCCAAGUCUCCGUCCCA
CGGGCCCUAGACCGCCAGGCCGCACUCUUACAAAUACAAGAAUUUAUGAUCACCUGCCUCUCACAAACACCACC
ACGCACCACGUUGCUGCUGUAUCCCACGGCCGUGGACCUGGCCAAACGAGCCCUUUGGACACCGAAUCAGAUCA
CCGACAUCACCAGCCUCGUACGCCUGGUCUACAUACUCUCUAAACAGAAUCAGCAACAUCUCAUCCCCCAAUGG
GCACUACGACAGAUCGCCGACUUUGCCCUAAAACUACACAAAACGCACCUGGCCUCUUUUCUUUCAGCCUUCGC
ACGCCAAGAACUCUACCUCAUGGGCAGCCUCGUCCACUCCAUGCUGGUACAUACGACGGAGAGACGCGAAAUCU
UCAUCGUAGAAACGGGCCUCUGUUCAUUGGCCGAGCUAUCACACUUUACGCAGUUGUUAGCUCAUCCACACCAC
GAAUACCUCAGCGACCUGUACACACCCUGUUCCAGUAGCGGGCGACGCGAUCACUCGCUCGAACGCCUCACGCG
UCUCUUCCCCGAUGCCACCGUCCCCGCUACCGUUCCCGCCGCCCUCUCCAUCCUAUCUACCAUGCAACCAAGCA
CGCUGGAAACCUUCCCCGACCUGUUUUGCUUGCCGCUCGGCGAAUCCUUCUCCGCGCUGACCGUCUCCGAACAC
GUCAGUUAUAUCGUAACAAACCAGUACCUGAUCAAAGGUAUCUCCUACCCUGUCUCCACCACCGUCGUAGGCCA
GAGCCUCAUCAUCACCCAGACGGACAGUCAAACUAAAUGCGAACUGACGCGCAACAUGCAUACCACACACAGCA
UCACAGUGGCGCUCAACAUUUCGCUAGAAAACUGCGCCUUUUGCCAAAGCGCCCUGCUAGAAUACGACGACACG
CAAGGCGUCAUCAACAUCAUGUACAUGCACGACUCGGACGACGUCCUUUUCGCCCUGGAUCCCUACAACGAAGU
GGUGGUCUCAUCUCCGCGAACUCACUACCUCAUGCUUUUGAAAAACGGUACGGUACUAGAAGUAACUGACGUCG
UCGUGGACGCCACCGACAGUCGUCUCCUCAUGAUGUCCGUCUACGCGCUAUCGGCCAUCAUCGGCAUCUAUCUG
CUCUACCGCAUGCUCAAGACAUGCCGCGCCAAGAGGAGCGGAAGCGGAGCUACUAACUUCAGCCUGCUGAAGCA
GGCUGGAGACGUGGAGGAGAACCCUGGACCUAUGUGCCGCCGCCCGGAUUGCGGCUUCUCUUUCUCACCUGGAC
CGGUGAUACUGCUGUGGUGUUGCCUUCUGCUGCCCAUUGUUUCCUCAGCCGCCGUCAGCGUCGCUCCUACCGCC
GCCGAGAAAGUCCCCGCGGAGUGCCCCGAACUAACGCGCCGAUGCUUGUUGGGUGAGGUGUUUGAGGGUGACAA
GUAUGAAAGUUGGCUGCGCCCGUUGGUGAAUGUUACCGGGCGCGAUGGCCCGCUAUCGCAACUUAUCCGUUACC
GUCCCGUUACGCCGGAGGCCGCCAACUCCGUGCUGUUGGACGAGGCUUUCCUGGACACUCUGGCCCUGCUGUAC
AACAAUCCGGAUCAAUUGCGGGCCCUGCUGACGCUGUUGAGCUCGGACACAGCGCCGCGCUGGAUGACGGUGAU
GCGCGGCUACAGCGAGUGCGGCGAUGGCUCGCCGGCCGUGUACACGUGCGUGGACGACCUGUGCCGCGGCUACG
ACCUCACGCGACUGUCAUACGGGCGCAGCAUCUUCACGGAACACGUGUUAGGCUUCGAGCUGGUGCCACCGUCU
CUCUUUAACGUGGUGGUGGCCAUACGCAACGAAGCCACGCGUACCAACCGCGCCGUGCGUCUGCCCGUGAGCAC
CGCUGCCGCGCCCGAGGGCAUCACGCUCUUUUACGGCCUGUACAACGCAGUGAAGGAAUUCUGCCUGCGUCACC
AGCUGGACCCGCCGCUGCUACGCCACCUAGAUAAAUACUACGCCGGACUGCCGCCCGAGCUGAAGCAGACGCGC
GUCAACCUGCCGGCUCACUCGCGCUAUGGCCCUCAAGCAGUGGAUGCUCGCUGAUAAUAGGCUGGAGCCUCGGU
GGCCAUGCUUCUUGCCCCUUGGGCCUCCCCCCAGCCCCUCCUCCCCUUCCUGCACCCGUACCCCCGUGGUCUUU
GAAUAAAGUCUGAGUGGGCGGC (SEQ ID NO: 105)

Fig. 25B hCMVUL128-2A-UL131 (ORF- UL128- Furin-Linker-P2A-UL130 Furin-Linker-F2A-UL131A)
Furin: CCGCGCCAAGAGGAGC (SEQ ID NO:74)
Linker: GGAAGCGGA
P2A peptide:
GCTACTAACTTCAGCCTGCTGAAGCAGGCTGGAGACGTGGAGGAGAACCCTGGACCT (SEQ ID NO:75)
F2A peptide:
GTGAAACAGACTTTGAATTTTGACCTTCTCAAGTTGGCGGGAGACGTGGAGTCCAACCCTGGACCT (SEQ ID NO:76)
5'-UTR: bold
3'-UTR: underline
hCMVUL128-2A-UL131 (ORF- UL128- Furin-Linker-P2A-UL130 Furin-Linker-F2A-UL131A)
TCAAGCTTTTGGACCCTCGTACAGAAGCTAATACGACTCACTATAGGGAAATAAGAGAGAAAAGAAG
AGTAAGAAGAAATATAAGAGCCACCATGAGTCCCAAAGATCTGACGCCGTTCTTGACGGCGTTGTGG
CTGCTATTGGGTCACAGCCGCGTGCCGCGGGTGCGCGCAGAAGAATGTTGCGAATTCATAAACGTCA
ACCACCCGCCGGAACGCTGTTACGATTTCAAAATGTGCAATCGCTTCACCGTCGCGCTGCGGTGTCC
GGACGGCGAAGTCTGCTACAGTCCCGAGAAAACGGCTGAGATTCGCGGGATCGTCACCACCATGACC
CATTCATTGACACGCCAGGTCGTACACAACAAACTGACGAGCTGCAACTACAATCCGTTATACCTCG
AAGCTGACGGGCGAATACGCTGCGGCAAAGTAAACGACAAGGCGCAGTACCTGCTGGGCGCCGCTGG
CAGCGTTCCCTATCGATGGATCAATCTGGAATACGACAAGATAACCCGGATCGTGGGCCTGGATCAG
TACCTGGAGAGCGTTAAGAAACACAAACGGCTGGATGTGTGCCGCGCTAAAATGGGCTATATGCTGC
AGCGCGCCAAGAGGAGCGGAAGCGGAGCTACTAACTTCAGCCTGCTGAAGCAGGCTGGAGACGTGGA
GGAGAACCCTGGACCTATGCTGCGGCTTCTGCTTCGTCACCACTTTCACTGCCTGCTTCTGTGCGCG
GTTTGGGCAACGCCCTGTCTGGCGTCTCCGTGGTCGACGCTAACAGCAAACCAGAATCCGTCCCCGC
CATGGTCTAAACTGACGTATTCCAAACCGCATGACGCGGCGACGTTTTACTGTCCTTTTCTCTATCC
CTCGCCCCCACGATCCCCCTTGCAATTCTCGGGGTTCCAGCGGGTATCAACGGGTCCCGAGTGTCGC
AACGAGACCCTGTATCTGCTGTACAACCGGGAAGGCCAGACCTTGGTGGAGAGAAGCTCCACCTGGG
TGAAAAAGGTGATCTGGTACCTGAGCGGTCGGAACCAAACCATCCTCCAACGGATGCCCCGAACGGC
TTCGAAACCGAGCGACGGAAACGTGCAGATCAGCGTGGAAGACGCCAAGATTTTTGGAGCGCACATG
GTGCCCAAGCAGACCAAGCTGCTACGCTTCGTCGTCAACGATGGCACACGTTATCAGATGTGTGTGA
TGAAGCTGGAGAGCTGGGCTCACGTCTTCCGGGACTACAGCGTGTCTTTTCAGGTGCGATTGACGTT
CACCGAGGCCAATAACCAGACTTACACCTTCTGCACCCATCCCAATCTCATCGTTCGCGCCAAGAGG
AGCGGAAGCGGAGTGAAACAGACTTTGAATTTTGACCTTCTCAAGTTGGCGGGAGACGTGGAGTCCA
ACCCTGGACCTATGCGGCTGTGTCGGGTGTGGCTGTCTGTTTGTCTGTGCGCCGTGGTGCTGGGTCA
GTGCCAGCGGGAAACCGCGGAAAAAAACGATTATTACCGAGTACCGCATTACTGGGACGCGTGCTCT
CGCGCGCTGCCCGACCAAACCCGTTACAAGTATGTGGAACAGCTCGTGGACCTCACGTTGAACTACC
ACTACGATGCGAGCCACGGCTTGGACAACTTTGACGTGCTCAAGAGAATCAACGTGACCGAGGTGTC
GTTGCTCATCAGCGACTTTAGACGTCAGAACCGTCGCGGCGGCACCAACAAAAGGACCACGTTCAAC
GCCGCCGGTTCGCTGGCGCCACACGCCCGGAGCCTCGAGTTCAGCGTGCGGCTCTTTGCCAACTGAT
AATAGGCTGGAGCCTCGGTGGCCATGCTTCTTGCCCCTTGGGCCTCCCCCCAGCCCCTCCTCCCCTT
CCTGCACCCGTACCCCCGTGGTCTTTGAATAAAGTCTGAGTGGGCGGC (SEQ ID NO: 30)

Fig. 25C hCMVUL128-2A-UL131 (ORF- UL128- Furin-Linker-P2A-UL130 Furin-Linker-F2A-UL131A)

UCAAGCUUUUGGACCCUCGUACAGAAGCUAAUACGACUCACUAUAGGGAAAUAAGAGAGAAAAG
AAGAGUAAGAAGAAAUAUAAGAGCCACCAUGAGUCCCAAAGAUCUGACGCCGUUCUUGACGGCG
UUGUGGCUGCUAUUGGGUCACAGCCGCGUGCCGCGGGUGCGCGCAGAAGAAUGUUGCGAAUUCA
UAAACGUCAACCACCCGCCGGAACGCUGUUACGAUUUCAAAAUGUGCAAUCGCUUCACCGUCGC
GCUGCGGUGUCCGGACGGCGAAGUCUGCUACAGUCCCGAGAAAACGGCUGAGAUUCGCGGGAUC
GUCACCACCAUGACCCAUUCAUUGACACGCCAGGUCGUACACAACAAACUGACGAGCUGCAACU
ACAAUCCGUUAUACCUCGAAGCUGACGGGCGAAUACGCUGCGGCAAAGUAAACGACAAGGCGCA
GUACCUGCUGGGCGCCGCUGGCAGCGUUCCCUAUCGAUGGAUCAAUCUGGAAUACGACAAGAUA
ACCCGGAUCGUGGGCCUGGAUCAGUACCUGGAGAGCGUUAAGAAACACAAACGGCUGGAUGUGU
GCCGCGCUAAAAUGGGCUAUAUGCUGCAGCGCGCCAAGAGGAGCGGAAGCGGAGCUACUAACUU
CAGCCUGCUGAAGCAGGCUGGAGACGUGGAGGAGAACCCUGGACCUAUGCUGCGGCUUCUGCUU
CGUCACCACUUUCACUGCCUGCUUCUGUGCGCGGUUUGGGCAACGCCCUGUCUGGCGUCUCCGU
GGUCGACGCUAACAGCAAACCAGAAUCCGUCCCCGCCAUGGUCUAAACUGACGUAUUCCAAACC
GCAUGACGCGGCGACGUUUUACUGUCCUUUUCUCUAUCCCUCGCCCCCACGAUCCCCCUUGCAA
UUCUCGGGGUUCCAGCGGGUAUCAACGGGUCCCGAGUGUCGCAACGAGACCCUGUAUCUGCUGU
ACAACCGGGAAGGCCAGACCUUGGUGGAGAGAAGCUCCACCUGGGUGAAAAAGGUGAUCUGGUA
CCUGAGCGGUCGGAACCAAACCAUCCUCCAACGGAUGCCCCGAACGGCUUCGAAACCGAGCGAC
GGAAACGUGCAGAUCAGCGUGGAAGACGCCAAGAUUUUUGGAGCGCACAUGGUGCCCAAGCAGA
CCAAGCUGCUACGCUUCGUCGUCAACGAUGGCACACGUUAUCAGAUGUGUGUGAUGAAGCUGGA
GAGCUGGGCUCACGUCUUCCGGGACUACAGCGUGUCUUUUCAGGUGCGAUUGACGUUCACCGAG
GCCAAUAACCAGACUUACACCUUCUGCACCCAUCCCAAUCUCAUCGUUCGCGCCAAGAGGAGCG
GAAGCGGAGUGAAACAGACUUUGAAUUUUGACCUUCUCAAGUUGGCGGGAGACGUGGAGUCCAA
CCCUGGACCUAUGCGGCUGUGUCGGGUGUGGCUGUCUGUUUGUCUGUGCGCCGUGGUGCUGGGU
CAGUGCCAGCGGGAAACCGCGGAAAAAAACGAUUAUUACCGAGUACCGCAUUACUGGGACGCGU
GCUCUCGCGCGCUGCCCGACCAAACCCGUUACAAGUAUGUGGAACAGCUCGUGGACCUCACGUU
GAACUACCACUACGAUGCGAGCCACGGCUUGGACAACUUUGACGUGCUCAAGAGAAUCAACGUG
ACCGAGGUGUCGUUGCUCAUCAGCGACUUUAGACGUCAGAACCGUCGCGGCGGCACCAACAAAA
GGACCACGUUCAACGCCGCCGGUUCGCUGGCGCCACACGCCCGGAGCCUCGAGUUCAGCGUGCG
GCUCUUUGCCAACUGAUAAUAGGCUGGAGCCUCGGUGGCCAUGCUUCUUGCCCCUUGGGCCUCC
CCCCAGCCCCUCCUCCCCUUCCUGCACCCGUACCCCCGUGGUCUUUGAAUAAAGUCUGAGUGGG
CGGC (SEQ ID NO: 106)

Fig. 25D hCMVgH-gL-UL128-UL130-UL131A 2a

Furin-CCGCGCCAAGAGGAGC (SEQ ID NO:74)
Linker-GGAAGCGGA
P2A peptide-GCTACTAACTTCAGCCTGCTGAAGCAGGCTGGAGACGTGGAGGAGAACCCTGGACCT (SEQ ID NO:75)
F2A peptide-
GTGAAACAGACTTTGAATTTTGACCTTCTCAAGTTGGCGGGAGACGTGGAGTCCAACCCTGGACCT (SEQ ID NO:76)
E2A peptide-
CAGTGTACTAATTATGCTCTCTTGAAATTGGCTGGAGATGTTGAGAGCAACCCTGGACCT (SEQ ID NO:77)
T2A-GAGGGCAGAGGAAGTCTGCTAACATGCGGTGACGTCGAGGAGAATCCTGGACCT (SEQ ID NO:78)
ORF- gH- Furin-Linker-P2A-gL Furin-Linker-F2A-UL128- Furin-Linker-E2A-UL130-Furin-Linker-T2A-UL131A

TCAAGCTTTTGGACCCTCGTACAGAAGCTAATACGACTCACTATAGGGAAATAAGAGAGAAAAGAAGAGT
AAGAAGAAATATAAGAGCCACCATGCGGCCAGGCCTCCCCTCCTACCTCATCATCCTCGCCGTCTGTCTC
TTCAGCCACCTACTTTCGTCACGATATGGCGCAGAAGCCGTATCCGAACCGCTGGACAAAGCGTTTCACC
TACTGCTCAACACCTACGGGAGACCCATCCGCTTCCTGCGTGAAAATACCACCCAGTGTACCTACAACAG
CAGCCTCCGTAACAGCACGGTCGTCAGGGAAAACGCCATCAGTTTCAACTTTTTCCAAAGCTATAATCAA
TACTATGTATTCCATATGCCTCGATGTCTTTTTGCGGGTCCTCTGGCGGAGCAGTTTCTGAACCAGGTAG
ATCTGACCGAAACCCTGGAAAGATACCAACAGAGACTTAACACTTACGCGCTGGTATCCAAAGACCTGGC
CAGCTACCGATCTTTTTCGCAGCAGCTAAAGGCACAAGACAGCCTAGGTGAACAGCCCACCACTGTGCCA
CCGCCCATTGACCTGTCAATACCTCACGTTTGGATGCCACCGCAAACCACTCCACACGGCTGGACAGAAT
CACATACCACCTCAGGACTACACCGACCACACTTTAACCAGACCTGTATCCTCTTTGATGGACACGATCT
ACTATTCAGCACCGTCACACCTTGTTTGCACCAAGGCTTTTACCTCATCGACGAACTACGTTACGTTAAA
ATAACACTGACCGAGGACTTCTTCGTAGTTACGGTGTCCATAGACGACGACACACCCATGCTGCTTATCT
TCGGCCATCTTCCACGCGTACTTTTCAAAGCGCCCTATCAACGCGACAACTTTATACTACGACAAACTGA
AAAACACGAGCTCCTGGTGCTAGTTAAGAAAGATCAACTGAACCGTCACTCTTATCTCAAAGACCCGGAC
TTTCTTGACGCCGCACTTGACTTCAACTACCTAGACCTCAGCGCACTACTACGTAACAGCTTTCACCGTT
ACGCCGTGGATGTACTCAAGAGCGGTCGATGTCAGATGCTGGACCGCCGCACGGTAGAAATGGCCTTCGC
CTACGCATTAGCACTGTTCGCAGCAGCCCGACAAGAAGAGGCCGGCGCCCAAGTCTCCGTCCCACGGGCC
CTAGACCGCCAGGCCGCACTCTTACAAATACAAGAATTTATGATCACCTGCCTCTCACAAACACCACCAC
GCACCACGTTGCTGCTGTATCCCACGGCCGTGGACCTGGCCAAACGAGCCCTTTGGACACCGAATCAGAT
CACCGACATCACCAGCCTCGTACGCCTGGTCTACATACTCTCTAAACAGAATCAGCAACATCTCATCCCC
CAATGGGCACTACGACAGATCGCCGACTTTGCCCTAAAACTACACAAAACGCACCTGGCCTCTTTTCTTT
CAGCCTTCGCACGCCAAGAACTCTACCTCATGGGCAGCCTCGTCCACTCCATGCTGGTACATACGACGGA
GAGACGCGAAATCTTCATCGTAGAAACGGGCCTCTGTTCATTGGCCGAGCTATCACACTTTACGCAGTTG
TTAGCTCATCCACACCACGAATACCTCAGCGACCTGTACACACCCTGTTCCAGTAGCGGGCGACGCGATC
ACTCGCTCGAACGCCTCACGCGTCTCTTCCCCGATGCCACCGTCCCCGCTACCGTTCCCGCCGCCCTCTC
CATCCTATCTACCATGCAACCAAGCACGCTGGAAACCTTCCCCGACCTGTTTTGCTTGCCGCTCGGCGAA
TCCTTCTCCGCGCTGACCGTCTCCGAACACGTCAGTTATATCGTAACAAACCAGTACCTGATCAAAGGTA
TCTCCTACCCTGTCTCCACCACCGTCGTAGGCCAGAGCCTCATCATCACCCAGACGGACAGTCAAACTAA
ATGCGAACTGACGCGCAACATGCATACCACACACAGCATCACAGTGGCGCTCAACATTTCGCTAGAAAAC

Fig. 25E

TGCGCCTTTTGCCAAAGCGCCCTGCTAGAATACGACGACACGCAAGGCGTCATCAACATCATGTACATGC
ACGACTCGGACGACGTCCTTTTCGCCCTGGATCCCTACAACGAAGTGGTGGTCTCATCTCCGCGAACTCA
CTACCTCATGCTTTTGAAAAACGGTACGGTACTAGAAGTAACTGACGTCGTCGTGGACGCCACCGACAGT
CGTCTCCTCATGATGTCCGTCTACGCGCTATCGGCCATCATCGGCATCTATCTGCTCTACCGCATGCTCA
AGACATGCCGCGCCAAGAGGAGCGGAAGCGGAGCTACTAACTTCAGCCTGCTGAAGCAGGCTGGAGACGT
GGAGGAGAACCCTGGACCTATGTGCCGCCGCCCGGATTGCGGCTTCTCTTTCTCACCTGGACCGGTGATA
CTGCTGTGGTGTTGCCTTCTGCTGCCCATTGTTTCCTCAGCCGCCGTCAGCGTCGCTCCTACCGCCGCCG
AGAAAGTCCCCGCGGAGTGCCCCGAACTAACGCGCCGATGCTTGTTGGGTGAGGTGTTTGAGGGTGACAA
GTATGAAAGTTGGCTGCGCCCGTTGGTGAATGTTACCGGGCGCGATGGCCCGCTATCGCAACTTATCCGT
TACCGTCCCGTTACGCCGGAGGCCGCCAACTCCGTGCTGTTGGACGAGGCTTTCCTGGACACTCTGGCCC
TGCTGTACAACAATCCGGATCAATTGCGGGCCCTGCTGACGCTGTTGAGCTCGGACACAGCGCCGCGCTG
GATGACGGTGATGCGCGGCTACAGCGAGTGCGGCGATGGCTCGCCGGCCGTGTACACGTGCGTGGACGAC
CTGTGCCGCGGCTACGACCTCACGCGACTGTCATACGGGCGCAGCATCTTCACGGAACACGTGTTAGGCT
TCGAGCTGGTGCCACCGTCTCTCTTTAACGTGGTGGTGGCCATACGCAACGAAGCCACGCGTACCAACCG
CGCCGTGCGTCTGCCCGTGAGCACCGCTGCCGCGCCCGAGGGCATCACGCTCTTTTACGGCCTGTACAAC
GCAGTGAAGGAATTCTGCCTGCGTCACCAGCTGGACCCGCCGCTGCTACGCCACCTAGATAAATACTACG
CCGGACTGCCGCCCGAGCTGAAGCAGACGCGCGTCAACCTGCCGGCTCACTCGCGCTATGGCCCTCAAGC
AGTGGATGCTCGCCGCGCCAAGAGGAGCGGAAGCGGAGTGAAACAGACTTTGAATTTTGACCTTCTCAAG
TTGGCGGGAGACGTGGAGTCCAACCCTGGACCTATGAGTCCCAAAGATCTGACGCCGTTCTTGACGGCGT
TGTGGCTGCTATTGGGTCACAGCCGCGTGCCGCGGGTGCGCGCAGAAGAATGTTGCGAATTCATAAACGT
CAACCACCCGCCGGAACGCTGTTACGATTTCAAAATGTGCAATCGCTTCACCGTCGCGCTGCGGTGTCCG
GACGGCGAAGTCTGCTACAGTCCCGAGAAAACGGCTGAGATTCGCGGGATCGTCACCACCATGACCCATT
CATTGACACGCCAGGTCGTACACAACAAACTGACGAGCTGCAACTACAATCCGTTATACCTCGAAGCTGA
CGGGCGAATACGCTGCGGCAAAGTAAACGACAAGGCGCAGTACCTGCTGGGCGCCGCTGGCAGCGTTCCC
TATCGATGGATCAATCTGGAATACGACAAGATAACCCGGATCGTGGGCCTGGATCAGTACCTGGAGAGCG
TTAAGAAACACAAACGGCTGGATGTGTGCCGCGCTAAAATGGGCTATATGCTGCAGCGCGCCAAGAGGAG
CGGAAGCGGACAGTGTACTAATTATGCTCTCTTGAAATTGGCTGGAGATGTTGAGAGCAACCCTGGACCT
ATGCTGCGGCTTCTGCTTCGTCACCACTTTCACTGCCTGCTTCTGTGCGCGGTTTGGGCAACGCCCTGTC
TGGCGTCTCCGTGGTCGACGCTAACAGCAAACCAGAATCCGTCCCCGCCATGGTCTAAACTGACGTATTC
CAAACCGCATGACGCGGCGACGTTTTACTGTCCTTTTCTCTATCCCTCGCCCCCACGATCCCCCTTGCAA
TTCTCGGGGTTCCAGCGGGTATCAACGGGTCCCGAGTGTCGCAACGAGACCCTGTATCTGCTGTACAACC
GGGAAGGCCAGACCTTGGTGGAGAGAAGCTCCACCTGGGTGAAAAAGGTGATCTGGTACCTGAGCGGTCG
GAACCAAACCATCCTCCAACGGATGCCCCGAACGGCTTCGAAACCGAGCGACGGAAACGTGCAGATCAGC
GTGGAAGACGCCAAGATTTTTGGAGCGCACATGGTGCCCAAGCAGACCAAGCTGCTACGCTTCGTCGTCA
ACGATGGCACACGTTATCAGATGTGTGTGATGAAGCTGGAGAGCTGGGCTCACGTCTTCCGGGACTACAG
CGTGTCTTTTCAGGTGCGATTGACGTTCACCGAGGCCAATAACCAGACTTACACCTTCTGCACCCATCCC
AATCTCATCGTTCGCGCCAAGAGGAGCGGAAGCGGAGAGGGCAGAGGAAGTCTGCTAACATGCGGTGACG
TCGAGGAGAATCCTGGACCTATGCGGCTGTGTCGGGTGTGGCTGTCTGTTTGTCTGTGCGCCGTGGTGCT
GGGTCAGTGCCAGCGGGAAACCGCGGAAAAAAACGATTATTACCGAGTACCGCATTACTGGGACGCGTGC
TCTCGCGCGCTGCCCGACCAAACCCGTTACAAGTATGTGGAACAGCTCGTGGACCTCACGTTGAACTACC
ACTACGATGCGAGCCACGGCTTGGACAACTTTGACGTGCTCAAGAGAATCAACGTGACCGAGGTGTCGTT
GCTCATCAGCGACTTTAGACGTCAGAACCGTCGCGGCGGCACCAACAAAAGGACCACGTTCAACGCCGCC
GGTTCGCTGGCGCCACACGCCCGGAGCCTCGAGTTCAGCGTGCGGCTCTTTGCCAACTGATAATAGGCTG
GAGCCTCGGTGGCCATGCTTCTTGCCCCTTGGGCCTCCCCCCAGCCCCTCCTCCCCTTCCTGCACCCGTA
CCCCCGTGGTCTTTGAATAAAGTCTGAGTGGGCGGC (SEQ ID NO: 31)

Fig. 25F

ORF- gH- Furin-Linker-P2A-gL Furin-Linker-F2A-UL128- Furin-Linker-E2A-UL130-Furin-Linker-T2A-UL131A

UCAAGCUUUUGGACCCUCGUACAGAAGCUAAUACGACUCACUAUAGGGAAAUAAGAGAGAAAAGAAG
AGUAAGAAGAAAUAUAAGAGCCACCAUGCGGCCAGGCCUCCCCUCCUACCUCAUCAUCCUCGCCGUC
UGUCUCUUCAGCCACCUACUUUCGUCACGAUAUGGCGCAGAAGCCGUAUCCGAACCGCUGGACAAAG
CGUUUCACCUACUGCUCAACACCUACGGGAGACCCAUCCGCUUCCUGCGUGAAAAUACCACCCAGUG
UACCUACAACAGCAGCCUCCGUAACAGCACGGUCGUCAGGGAAAACGCCAUCAGUUUCAACUUUUUC
CAAAGCUAUAAUCAAUACUAUGUAUUCCAUAUGCCUCGAUGUCUUUUUGCGGGUCCUCUGGCGGAGC
AGUUUCUGAACCAGGUAGAUCUGACCGAAACCCUGGAAAGAUACCAACAGAGACUUAACACUUACGC
GCUGGUAUCCAAAGACCUGGCCAGCUACCGAUCUUUUUCGCAGCAGCUAAAGGCACAAGACAGCCUA
GGUGAACAGCCCACCACUGUGCCACCGCCCAUUGACCUGUCAAUACCUCACGUUUGGAUGCCACCGC
AAACCACUCCACACGGCUGGACAGAAUCACAUACCACCUCAGGACUACACCGACCACACUUUAACCA
GACCUGUAUCCUCUUUGAUGGACACGAUCUACUAUUCAGCACCGUCACACCUUGUUUGCACCAAGGC
UUUUACCUCAUCGACGAACUACGUUACGUUAAAAUAACACUGACCGAGGACUUCUUCGUAGUUACGG
UGUCCAUAGACGACGACACACCCAUGCUGCUUAUCUUCGGCCAUCUUCCACGCGUACUUUUCAAAGC
GCCCUAUCAACGCGACAACUUUAUACUACGACAAACUGAAAAACACGAGCUCCUGGUGCUAGUUAAG
AAAGAUCAACUGAACCGUCACUCUUAUCUCAAAGACCCGGACUUUCUUGACGCCGCACUUGACUUCA
ACUACCUAGACCUCAGCGCACUACUACGUAACAGCUUUCACCGUUACGCCGUGGAUGUACUCAAGAG
CGGUCGAUGUCAGAUGCUGGACCGCCGCACGGUAGAAAUGGCCUUCGCCUACGCAUUAGCACUGUUC
GCAGCAGCCCGACAAGAAGAGGCCGGCGCCCAAGUCUCCGUCCCACGGGCCCUAGACCGCCAGGCCG
CACUCUUACAAAUACAAGAAUUUAUGAUCACCUGCCUCUCACAAACACCACCACGCACCACGUUGCU
GCUGUAUCCCACGGCCGUGGACCUGGCCAAACGAGCCCUUUGGACACCGAAUCAGAUCACCGACAUC
ACCAGCCUCGUACGCCUGGUCUACAUACUCUCUAAACAGAAUCAGCAACAUCUCAUCCCCCAAUGGG
CACUACGACAGAUCGCCGACUUUGCCCUAAAACUACACAAAACGCACCUGGCCUCUUUUCUUUCAGC
CUUCGCACGCCAAGAACUCUACCUCAUGGGCAGCCUCGUCCACUCCAUGCUGGUACAUACGACGGAG
AGACGCGAAAUCUUCAUCGUAGAAACGGGCCUCUGUUCAUUGGCCGAGCUAUCACACUUUACGCAGU
UGUUAGCUCAUCCACACCACGAAUACCUCAGCGACCUGUACACACCCUGUUCCAGUAGCGGGCGACG
CGAUCACUCGCUCGAACGCCUCACGCGUCUCUUCCCCGAUGCCACCGUCCCCGCUACCGUUCCCGCC
GCCCUCUCCAUCCUAUCUACCAUGCAACCAAGCACGCUGGAAACCUUCCCCGACCUGUUUUGCUUGC
CGCUCGGCGAAUCCUUCUCCGCGCUGACCGUCUCCGAACACGUCAGUUAUAUCGUAACAAACCAGUA
CCUGAUCAAAGGUAUCUCCUACCCUGUCUCCACCACCGUCGUAGGCCAGAGCCUCAUCAUCACCCAG
ACGGACAGUCAAACUAAAUGCGAACUGACGCGCAACAUGCAUACCACACACAGCAUCACAGUGGCGC
UCAACAUUUCGCUAGAAAACUGCGCCUUUUGCCAAAGCGCCCUGCUAGAAUACGACGACACGCAAGG
CGUCAUCAACAUCAUGUACAUGCACGACUCGGACGACGUCCUUUUCGCCCUGGAUCCCUACAACGAA
GUGGUGGUCUCAUCUCCGCGAACUCACUACCUCAUGCUUUUGAAAAACGGUACGGUACUAGAAGUAA
CUGACGUCGUCGUGGACGCCACCGACAGUCGUCUCCUCAUGAUGUCCGUCUACGCGCUAUCGGCCAU
CAUCGGCAUCUAUCUGCUCUACCGCAUGCUCAAGACAUGCCGCGCCAAGAGGAGCGGAAGCGGAGCU
ACUAACUUCAGCCUGCUGAAGCAGGCUGGAGACGUGGAGGAGAACCCUGGACCUAUGUGCCGCCGCC
CGGAUUGCGGCUUCUCUUUCUCACCUGGACCGGUGAUACUGCUGUGGUGUUGCCUUCUGCUGCCCAU
UGUUUCCUCAGCCGCCGUCAGCGUCGCUCCUACCGCCGCCGAGAAAGUCCCCGCGGAGUGCCCCGAA
CUAACGCGCCGAUGCUUGUUGGGUGAGGUGUUUGAGGGUGACAAGUAUGAAAGUUGGCUGCGCCCGU
UGGUGAAUGUUACCGGGCGCGAUGGCCCGCUAUCGCAACUUAUCCGUUACCGUCCCGUUACGCCGGA
GGCCGCCAACUCCGUGCUGUUGGACGAGGCUUUCCUGGACACUCUGGCCCUGCUGUACAACAAUCCG

Fig. 25G

GAUCAAUUGCGGGCCCUGCUGACGCUGUUGAGCUCGGACACAGCGCCGCGCUGGAUGACGGUGAUGC
GCGGCUACAGCGAGUGCGGCGAUGGCUCGCCGGCCGUGUACACGUGCGUGGACGACCUGUGCCGCGG
CUACGACCUCACGCGACUGUCAUACGGGCGCAGCAUCUUCACGGAACACGUGUUAGGCUUCGAGCUG
GUGCCACCGUCUCUCUUUAACGUGGUGGUGGCCAUACGCAACGAAGCCACGCGUACCAACCGCGCCG
UGCGUCUGCCCGUGAGCACCGCUGCCGCGCCCGAGGGCAUCACGCUCUUUUACGGCCUGUACAACGC
AGUGAAGGAAUUCUGCCUGCGUCACCAGCUGGACCCGCCGCUGCUACGCCACCUAGAUAAAUACUAC
GCCGGACUGCCGCCCGAGCUGAAGCAGACGCGCGUCAACCUGCCGGCUCACUCGCGCUAUGGCCCUC
AAGCAGUGGAUGCUCGCCGCGCCAAGAGGAGCGGAAGCGGAGUGAAACAGACUUUGAAUUUUGACCU
UCUCAAGUUGGCGGGAGACGUGGAGUCCAACCCUGGACCUAUGAGUCCCAAAGAUCUGACGCCGUUC
UUGACGGCGUUGUGGCUGCUAUUGGGUCACAGCCGCGUGCCGCGGGUGCGCGCAGAAGAAUGUUGCG
AAUUCAUAAACGUCAACCACCCGCCGGAACGCUGUUACGAUUUCAAAAUGUGCAAUCGCUUCACCGU
CGCGCUGCGGUGUCCGGACGGCGAAGUCUGCUACAGUCCCGAGAAAACGGCUGAGAUUCGCGGGAUC
GUCACCACCAUGACCCAUUCAUUGACACGCCAGGUCGUACACAACAAACUGACGAGCUGCAACUACA
AUCCGUUAUACCUCGAAGCUGACGGGCGAAUACGCUGCGGCAAAGUAAACGACAAGGCGCAGUACCU
GCUGGGCGCCGCUGGCAGCGUUCCCUAUCGAUGGAUCAAUCUGGAAUACGACAAGAUAACCCGGAUC
GUGGGCCUGGAUCAGUACCUGGAGAGCGUUAAGAAACACAAACGGCUGGAUGUGUGCCGCGCUAAAA
UGGGCUAUAUGCUGCAGCGCGCCAAGAGGAGCGGAAGCGGACAGUGUACUAAUUAUGCUCUCUUGAA
AUUGGCUGGAGAUGUUGAGAGCAACCCUGGACCUAUGCUGCGGCUUCUGCUUCGUCACCACUUUCAC
UGCCUGCUUCUGUGCGCGGUUUGGGCAACGCCCUGUCUGGCGUCUCCGUGGUCGACGCUAACAGCAA
ACCAGAAUCCGUCCCCGCCAUGGUCUAAACUGACGUAUUCCAAACCGCAUGACGCGGCGACGUUUUA
CUGUCCUUUUCUCUAUCCCUCGCCCCCACGAUCCCCCUUGCAAUUCUCGGGGUUCCAGCGGGUAUCA
ACGGGUCCCGAGUGUCGCAACGAGACCCUGUAUCUGCUGUACAACCGGGAAGGCCAGACCUUGGUGG
AGAGAAGCUCCACCUGGGUGAAAAAGGUGAUCUGGUACCUGAGCGGUCGGAACCAAACCAUCCUCCA
ACGGAUGCCCCGAACGGCUUCGAAACCGAGCGACGGAAACGUGCAGAUCAGCGUGGAAGACGCCAAG
AUUUUUGGAGCGCACAUGGUGCCCAAGCAGACCAAGCUGCUACGCUUCGUCGUCAACGAUGGCACAC
GUUAUCAGAUGUGUGUGAUGAAGCUGGAGAGCUGGGCUCACGUCUUCCGGGACUACAGCGUGUCUUU
UCAGGUGCGAUUGACGUUCACCGAGGCCAAUAACCAGACUUACACCUUCUGCACCCAUCCCAAUCUC
AUCGUUCGCGCCAAGAGGAGCGGAAGCGGAGAGGGCAGAGGAAGUCUGCUAACAUGCGGUGACGUCG
AGGAGAAUCCUGGACCUAUGCGGCUGUGUCGGGUGUGGCUGUCUGUUUGUCUGUGCGCCGUGGUGCU
GGGUCAGUGCCAGCGGGAAACCGCGGAAAAAAACGAUUAUUACCGAGUACCGCAUUACUGGGACGCG
UGCUCUCGCGCGCUGCCCGACCAAACCCGUUACAAGUAUGUGGAACAGCUCGUGGACCUCACGUUGA
ACUACCACUACGAUGCGAGCCACGGCUUGGACAACUUUGACGUGCUCAAGAGAAUCAACGUGACCGA
GGUGUCGUUGCUCAUCAGCGACUUUAGACGUCAGAACCGUCGCGGCGGCACCAACAAAAGGACCACG
UUCAACGCCGCCGGUUCGCUGGCGCCACACGCCCGGAGCCUCGAGUUCAGCGUGCGGCUCUUUGCCA
ACUGAUAAUAGGCUGGAGCCUCGGUGGCCAUGCUUCUUGCCCCUUGGGCCUCCCCCCAGCCCCUCCU
CCCCUUCCUGCACCCGUACCCCCGUGGUCUUUGAAUAAAGUCUGAGUGGGCGGC (SEQ ID NO:
107)

Fig. 25H

SEQUENCE LISTING

```
<160> NUMBER OF SEQ ID NOS: 115

<210> SEQ ID NO 1
<211> LENGTH: 2437
<212> TYPE: DNA
<213> ORGANISM: Human Cytomegalovirus

<400> SEQUENCE: 1

tcaagctttt ggaccctcgt acagaagcta atacgactca ctatagggaa ataagagaga     60

aaagaagagt aagaagaaat ataagagcca ccatgcggcc aggcctcccc tcctacctca    120

tcatcctcgc cgtctgtctc ttcagccacc tactttcgtc acgatatggc gcagaagccg    180

tatccgaacc gctggacaaa gcgtttcacc tactgctcaa cacctacggg agacccatcc    240

gcttcctgcg tgaaaatacc acccagtgta cctacaacag cagcctccgt aacagcacgg    300

tcgtcaggga aaacgccatc agtttcaact tttccaaag ctataatcaa tactatgtat    360

tccatatgcc tcgatgtctt tttgcgggtc ctctggcgga gcagtttctg aaccaggtag    420

atctgaccga aaccctggaa agataccaac agagacttaa cacttacgcg ctggtatcca    480

aagacctggc cagctaccga tctttttcgc agcagctaaa ggcacaagac agcctaggtg    540

aacagcccac cactgtgcca ccgcccattg acctgtcaat acctcacgtt tggatgccac    600

cgcaaaccac tccacacggc tggacagaat cacataccac ctcaggacta caccgaccac    660

actttaacca gacctgtatc ctctttgatg gacacgatct actattcagc accgtcacac    720

cttgtttgca ccaaggcttt tacctcatcg acgaactacg ttacgttaaa ataacactga    780

ccgaggactt cttcgtagtt acggtgtcca tagacgacga cacacccatg ctgcttatct    840

tcggccatct tccacgcgta cttttcaaag cgccctatca acgcgacaac tttatactac    900
```

gacaaactga aaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040
gccaaagcgc cctgctagaa tacgacgaca cgcaaggcgt catcaacatc atgtacatgc 2100
acgactcgga cgacgtcctt ttcgccctgg atccctacaa cgaagtggtg gtctcatctc 2160
cgcgaactca ctacctcatg cttttgaaaa acggtacggt actagaagta actgacgtcg 2220
tcgtggacgc caccgacagt cgtctcctca tgatgtccgt ctacgcgcta tcggccatca 2280
tcggcatcta tctgctctac cgcatgctca agacatgctg ataataggct ggagcctcgg 2340
tggccatgct tcttgcccct tgggcctccc cccagcccct cctccccttc ctgcacccgt 2400
acccccgtgg tctttgaata aagtctgagt gggcggc 2437

<210> SEQ ID NO 2
<211> LENGTH: 2464
<212> TYPE: DNA
<213> ORGANISM: Artificial Sequence
<220> FEATURE:
<223> OTHER INFORMATION: Synthetic Polynucleotide

<400> SEQUENCE: 2
tcaagctttt ggaccctcgt acagaagcta atacgactca ctatagggaa ataagagaga 60
aaagaagagt aagaagaaat ataagagcca ccatgcggcc aggcctcccc tcctacctca 120
tcatcctcgc cgtctgtctc ttcagccacc tactttcgtc acgatatggc gcagaagccg 180
tatccgaacc gctggacaaa gcgtttcacc tactgctcaa cacctacggg agacccatcc 240
gcttcctgcg tgaaaatacc acccagtgta cctacaacag cagcctccgt aacagcacgg 300
tcgtcaggga aaacgccatc agtttcaact tttccaaag ctataatcaa tactatgtat 360
tccatatgcc tcgatgtctt tttgcgggtc ctctggcgga gcagtttctg aaccaggtag 420
atctgaccga aaccctggaa agataccaac agagacttaa cacttacgcg ctggtatcca 480

| | |
|---|---|
| aagacctggc cagctaccga tctttttcgc agcagctaaa ggcacaagac agcctaggtg | 540 |
| aacagcccac cactgtgcca ccgcccattg acctgtcaat acctcacgtt tggatgccac | 600 |
| cgcaaaccac tccacacggc tggacagaat cacataccac ctcaggacta caccgaccac | 660 |
| actttaacca gacctgtatc ctctttgatg gacacgatct actattcagc accgtcacac | 720 |
| cttgtttgca ccaaggcttt tacctcatcg acgaactacg ttacgttaaa ataacactga | 780 |
| ccgaggactt cttcgtagtt acggtgtcca tagacgacga cacacccatg ctgcttatct | 840 |
| tcggccatct tccacgcgta cttttcaaag cgccctatca acgcgacaac tttatactac | 900 |
| gacaaactga aaaacacgag ctcctggtgc tagttaagaa agatcaactg aaccgtcact | 960 |
| cttatctcaa agacccggac tttcttgacg ccgcacttga cttcaactac ctagacctca | 1020 |
| gcgcactact acgtaacagc tttcaccgtt acgccgtgga tgtactcaag agcggtcgat | 1080 |
| gtcagatgct ggaccgccgc acggtagaaa tggccttcgc ctacgcatta gcactgttcg | 1140 |
| cagcagcccg acaagaagag gccggcgccc aagtctccgt cccacgggcc ctagaccgcc | 1200 |
| aggccgcact cttacaaata caagaattta tgatcacctg cctctcacaa acaccaccac | 1260 |
| gcaccacgtt gctgctgtat cccacggccg tggacctggc caaacgagcc ctttggacac | 1320 |
| cgaatcagat caccgacatc accagcctcg tacgcctggt ctacatactc tctaaacaga | 1380 |
| atcagcaaca tctcatcccc caatgggcac tacgacagat cgccgacttt gccctaaaac | 1440 |
| tacacaaaac gcacctggcc tcttttcttt cagccttcgc acgccaagaa ctctacctca | 1500 |
| tgggcagcct cgtccactcc atgctggtac atacgacgga gagacgcgaa atcttcatcg | 1560 |
| tagaaacggg cctctgttca ttggccgagc tatcacactt tacgcagttg ttagctcatc | 1620 |
| cacaccacga atacctcagc gacctgtaca caccctgttc cagtagcggg cgacgcgatc | 1680 |
| actcgctcga acgcctcacg cgtctcttcc ccgatgccac cgtccccgct accgttcccg | 1740 |
| ccgccctctc catcctatct accatgcaac caagcacgct ggaaaccttc cccgacctgt | 1800 |
| tttgcttgcc gctcggcgaa tccttctccg cgctgaccgt ctccgaacac gtcagttata | 1860 |
| tcgtaacaaa ccagtacctg atcaaaggta tctcctaccc tgtctccacc accgtcgtag | 1920 |
| gccagagcct catcatcacc cagacggaca gtcaaactaa atgcgaactg acgcgcaaca | 1980 |
| tgcataccac acacagcatc acagtggcgc tcaacatttc gctagaaaac tgcgcctttt | 2040 |
| gccaaagcgc cctgctagaa tacgacgaca cgcaaggcgt catcaacatc atgtacatgc | 2100 |
| acgactcgga cgacgtcctt ttcgccctgg atccctacaa cgaagtggtg gtctcatctc | 2160 |
| cgcgaactca ctacctcatg cttttgaaaa acggtacggt actagaagta actgacgtcg | 2220 |
| tcgtggacgc caccgacagt cgtctcctca tgatgtccgt ctacgcgcta tcggccatca | 2280 |
| tcggcatcta tctgctctac cgcatgctca agacatgcga ttacaaggac gatgacgata | 2340 |
| agtgatgata ataggctgga gcctcggtgg ccatgcttct tgccccttgg gcctcccccc | 2400 |
| agcccctcct ccccttcctg cacccgtacc cccgtggtct ttgaataaag tctgagtggg | 2460 |
| cggc | 2464 |

<210> SEQ ID NO 3
<211> LENGTH: 1045
<212> TYPE: DNA
<213> ORGANISM: Human Cytomegalovirus

<400> SEQUENCE: 3

| | |
|---|---|
| tcaagctttt ggaccctcgt acagaagcta atacgactca ctatagggaa ataagagaga | 60 |
| aaagaagagt aagaagaaat ataagagcca ccatgtgccg ccgcccggat tgcggcttct | 120 |

ctttctcacc tggaccggtg atactgctgt ggtgttgcct tctgctgccc attgtttcct 180
cagccgccgt cagcgtcgct cctaccgccg ccgagaaagt ccccgcggag tgccccgaac 240
taacgcgccg atgcttgttg ggtgaggtgt ttgagggtga caagtatgaa agttggctgc 300
gcccgttggt gaatgttacc gggcgcgatg gcccgctatc gcaacttatc cgttaccgtc 360
ccgttacgcc ggaggccgcc aactccgtgc tgttggacga ggctttcctg gacactctgg 420
ccctgctgta caacaatccg gatcaattgc gggccctgct gacgctgttg agctcggaca 480
cagcgccgcg ctggatgacg gtgatgcgcg gctacagcga gtgcggcgat ggctcgccgg 540
ccgtgtacac gtgcgtggac gacctgtgcc gcggctacga cctcacgcga ctgtcatacg 600
ggcgcagcat cttcacggaa cacgtgttag gcttcgagct ggtgccaccg tctctcttta 660
acgtggtggt ggccatacgc aacgaagcca cgcgtaccaa ccgcgccgtg cgtctgcccg 720
tgagcaccgc tgccgcgccc gagggcatca cgctctttta cggcctgtac aacgcagtga 780
aggaattctg cctgcgtcac cagctggacc cgccgctgct acgccaccta gataaatact 840
acgccggact gccgcccgag ctgaagcaga cgcgcgtcaa cctgccggct cactcgcgct 900
atggccctca agcagtggat gctcgctgat aataggctgg agcctcggtg gccatgcttc 960
ttgccccttg ggcctccccc cagcccctcc tccccttcct gcacccgtac ccccgtggtc 1020
tttgaataaa gtctgagtgg gcggc 1045

<210> SEQ ID NO 4
<211> LENGTH: 1072
<212> TYPE: DNA
<213> ORGANISM: Artificial Sequence
<220> FEATURE:
<223> OTHER INFORMATION: Synthetic Polynucleotide

<400> SEQUENCE: 4
tcaagctttt ggaccctcgt acagaagcta atacgactca ctatagggaa ataagagaga 60
aaagaagagt aagaagaaat ataagagcca ccatgtgccg ccgcccggat tgcggcttct 120
ctttctcacc tggaccggtg atactgctgt ggtgttgcct tctgctgccc attgtttcct 180
cagccgccgt cagcgtcgct cctaccgccg ccgagaaagt ccccgcggag tgccccgaac 240
taacgcgccg atgcttgttg ggtgaggtgt ttgagggtga caagtatgaa agttggctgc 300
gcccgttggt gaatgttacc gggcgcgatg gcccgctatc gcaacttatc cgttaccgtc 360
ccgttacgcc ggaggccgcc aactccgtgc tgttggacga ggctttcctg gacactctgg 420
ccctgctgta caacaatccg gatcaattgc gggccctgct gacgctgttg agctcggaca 480
cagcgccgcg ctggatgacg gtgatgcgcg gctacagcga gtgcggcgat ggctcgccgg 540
ccgtgtacac gtgcgtggac gacctgtgcc gcggctacga cctcacgcga ctgtcatacg 600
ggcgcagcat cttcacggaa cacgtgttag gcttcgagct ggtgccaccg tctctcttta 660
acgtggtggt ggccatacgc aacgaagcca cgcgtaccaa ccgcgccgtg cgtctgcccg 720
tgagcaccgc tgccgcgccc gagggcatca cgctctttta cggcctgtac aacgcagtga 780
aggaattctg cctgcgtcac cagctggacc cgccgctgct acgccaccta gataaatact 840
acgccggact gccgcccgag ctgaagcaga cgcgcgtcaa cctgccggct cactcgcgct 900
atggccctca agcagtggat gctcgcgatt acaaggacga tgacgataag tgatgataat 960
aggctggagc ctcggtggcc atgcttcttg ccccttgggc ctccccccag cccctcctcc 1020
ccttcctgca cccgtacccc cgtggtcttt gaataaagtc tgagtgggcg gc 1072

<210> SEQ ID NO 5
<211> LENGTH: 2932
<212> TYPE: DNA
<213> ORGANISM: Human Cytomegalovirus

<400> SEQUENCE: 5
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctccttttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260
actgcgtacg tgatgaggct ataaataagt tacagcagat tttcaatact tcatacaatc 1320
aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560
cgttgcgcgg ttacatcaac cgggcgctgg cgcaaatcgc agaagcctgg tgtgtggatc 1620
aacggcgcac cctagaggtc ttcaaggaac tcagcaagat caacccgtca gccattctct 1680
cggccattta caacaaaccg attgccgcgc gtttcatggg tgatgtcttg ggcctggcca 1740
gctgcgtgac catcaaccaa accagcgtca aggtgctgcg tgatatgaac gtgaaggagt 1800
cgccaggacg ctgctactca cgacccgtgg tcatctttaa tttcgccaac agctcgtacg 1860
tgcagtacgg tcaactgggc gaggacaacg aaatcctgtt gggcaaccac cgcactgagg 1920
aatgtcagct tcccagcctc aagatcttca tcgccgggaa ctcggcctac gagtacgtgg 1980
actacctctt caaacgcatg attgacctca gcagtatctc caccgtcgac agcatgatcg 2040
ccctggatat cgacccgctg gaaaataccg acttcagggt actggaactt tactcgcaga 2100
aagagctgcg ttccagcaac gtttttgacc tcgaagagat catgcgcgaa ttcaactcgt 2160
acaagcagcg ggtaaagtac gtggaggaca aggtagtcga cccgctaccg ccctacctca 2220
agggtctgga cgacctcatg agcggcctgg gcgccgcggg aaaggccgtt ggcgtagcca 2280
ttggggccgt gggtggcgcg gtggcctccg tggtcgaagg cgttgccacc ttcctcaaaa 2340 acccccttcgg agcgttcacc atcatcctcg tggccatagc tgtagtcatt atcacttatt 2400
tgatctatac tcgacagcgg cgtttgtgca cgcagccgct gcagaacctc tttccctatc 2460
tggtgtccgc cgacgggacc accgtgacgt cgggcagcac caaagacacg tcgttacagg 2520
ctccgccttc ctacgaggaa agtgtttata attctggtcg caaaggaccg ggaccaccgt 2580
cgtctgatgc atccacggcg gctccgcctt acaccaacga gcaggcttac cagatgcttc 2640
tggccctggc ccgtctggac gcagagcagc gagcgcagca gaacggtaca gattctttgg 2700
acggacggac tggcacgcag gacaagggac agaagcccaa cctactagac cgactgcgac 2760
atcgcaaaaa cggctaccga cacttgaaag actctgacga agaagagaac gtctgataat 2820
aggctggagc ctcggtggcc atgcttcttg ccccttgggc ctccccccag cccctcctcc 2880
ccttcctgca cccgtacccc cgtggtcttt gaataaagtc tgagtgggcg gc 2932

<210> SEQ ID NO 6
<211> LENGTH: 2956
<212> TYPE: DNA
<213> ORGANISM: Artificial Sequence
<220> FEATURE:
<223> OTHER INFORMATION: Synthetic Polynucleotide

<400> SEQUENCE: 6
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctcctttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260

```
actgcgtacg tgatgaggct ataaataagt tacagcagat tttcaatact tcatacaatc   1320
aaacatatga aaaatatgga aacgtgtccg tctttgaaac cactggtggt ttggtagtgt   1380
tctggcaagg tatcaagcaa aaatctctgg tggaactcga acgtttggcc aaccgctcca   1440
gtctgaatct tactcataat agaaccaaaa gaagtacaga tggcaacaat gcaactcatt   1500
tatccaacat ggaatcggtg cacaatctgg tctacgccca gctgcagttc acctatgaca   1560
cgttgcgcgg ttacatcaac cgggcgctgg cgcaaatcgc agaagcctgg tgtgtggatc   1620
aacggcgcac cctagaggtc ttcaaggaac tcagcaagat caacccgtca gccattctct   1680
cggccattta caacaaaccg attgccgcgc gtttcatggg tgatgtcttg ggcctggcca   1740
gctgcgtgac catcaaccaa accagcgtca aggtgctgcg tgatatgaac gtgaaggagt   1800
cgccaggacg ctgctactca cgacccgtgg tcatctttaa tttcgccaac agctcgtacg   1860
tgcagtacgg tcaactgggc gaggacaacg aaatcctgtt gggcaaccac cgcactgagg   1920
aatgtcagct tcccagcctc aagatcttca tcgccgggaa ctcggcctac gagtacgtgg   1980
actacctctt caaacgcatg attgacctca gcagtatctc caccgtcgac agcatgatcg   2040
ccctggatat cgacccgctg gaaaataccg acttcagggt actggaactt tactcgcaga   2100
aagagctgcg ttccagcaac gtttttgacc tcgaagagat catgcgcgaa ttcaactcgt   2160
acaagcagcg ggtaaagtac gtggaggaca aggtagtcga cccgctaccg ccctacctca   2220
agggtctgga cgacctcatg agcggcctgg gcgccgcggg aaaggccgtt ggcgtagcca   2280
ttggggccgt gggtggcgcg gtggcctccg tggtcgaagg cgttgccacc ttcctcaaaa   2340
accccttcgg agcgttcacc atcatcctcg tggccatagc tgtagtcatt atcacttatt   2400
tgatctatac tcgacagcgg cgtttgtgca cgcagccgct gcagaacctc tttccctatc   2460
tggtgtccgc cgacgggacc accgtgacgt cgggcagcac caaagacacg tcgttacagg   2520
ctccgccttc ctacgaggaa agtgtttata attctggtcg caaaggaccg ggaccaccgt   2580
cgtctgatgc atccacggcg gctccgcctt acaccaacga gcaggcttac cagatgcttc   2640
tggccctggc ccgtctggac gcagagcagc gagcgcagca gaacggtaca gattctttgg   2700
acggacggac tggcacgcag gacaagggac agaagcccaa cctactagac cgactgcgac   2760
atcgcaaaaa cggctaccga cacttgaaag actctgacga agaagagaac gtcgattaca   2820
aggacgatga cgataagtga taataggctg gagcctcggt ggccatgctt cttgcccctt   2880
gggcctcccc ccagcccctc ctccccttcc tgcacccgta cccccgtggt ctttgaataa   2940
agtctgagtg ggcggc                                                   2956
```

<210> SEQ ID NO 7
<211> LENGTH: 2356
<212> TYPE: DNA
<213> ORGANISM: Human Cytomegalovirus

<400> SEQUENCE: 7

```
tcaagctttt ggaccctcgt acagaagcta atacgactca ctatagggaa ataagagaga     60
aaagaagagt aagaagaaat ataagagcca ccatgcggcc aggcctcccc tcctacctca    120
tcatcctcgc cgtctgtctc ttcagccacc tactttcgtc acgatatggc gcagaagccg    180
tatccgaacc gctggacaaa gcgtttcacc tactgctcaa cacctacggg agacccatcc    240
gcttcctgcg tgaaaatacc acccagtgta cctacaacag cagcctccgt aacagcacgg    300
tcgtcaggga aaacgccatc agtttcaact ttttccaaag ctataatcaa tactatgtat    360
tccatatgcc tcgatgtctt tttgcgggtc ctctggcgga gcagtttctg aaccaggtag    420
```

atctgaccga aaccctggaa agataccaac agagacttaa cacttacgcg ctggtatcca 480
aagacctggc cagctaccga tctttttcgc agcagctaaa ggcacaagac agcctaggtg 540
aacagcccac cactgtgcca ccgcccattg acctgtcaat acctcacgtt tggatgccac 600
cgcaaaccac tccacacggc tggacagaat cacataccac ctcaggacta caccgaccac 660
actttaacca gacctgtatc ctctttgatg gacacgatct actattcagc accgtcacac 720
cttgtttgca ccaaggcttt tacctcatcg acgaactacg ttacgttaaa ataacactga 780
ccgaggactt cttcgtagtt acggtgtcca tagacgacga cacacccatg ctgcttatct 840
tcggccatct tccacgcgta cttttcaaag cgccctatca acgcgacaac tttatactac 900
gacaaactga aaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040
gccaaagcgc cctgctagaa tacgacgaca cgcaaggcgt catcaacatc atgtacatgc 2100
acgactcgga cgacgtcctt ttcgccctgg atccctacaa cgaagtggtg gtctcatctc 2160
cgcgaactca ctacctcatg cttttgaaaa acggtacggt actagaagta actgacgtcg 2220
tcgtggacgc caccgactga taataggctg gagcctcggt ggccatgctt cttgcccctt 2280
gggcctcccc ccagcccctc ctccccttcc tgcacccgta cccccgtggt ctttgaataa 2340
agtctgagtg ggcggc 2356

<210> SEQ ID NO 8
<211> LENGTH: 2383
<212> TYPE: DNA
<213> ORGANISM: Artificial Sequence
<220> FEATURE:
<223> OTHER INFORMATION: Synthetic Polynucleotide

<400> SEQUENCE: 8
tcaagctttt ggaccctcgt acagaagcta atacgactca ctatagggaa ataagagaga 60

-continued

```
aaagaagagt aagaagaaat ataagagcca ccatgcggcc aggcctcccc tcctacctca    120
tcatcctcgc cgtctgtctc ttcagccacc tactttcgtc acgatatggc gcagaagccg    180
tatccgaacc gctggacaaa gcgtttcacc tactgctcaa cacctacggg agacccatcc    240
gcttcctgcg tgaaaatacc acccagtgta cctacaacag cagcctccgt aacagcacgg    300
tcgtcaggga aaacgccatc agtttcaact ttttccaaag ctataatcaa tactatgtat    360
tccatatgcc tcgatgtctt tttgcgggtc ctctggcgga gcagtttctg aaccaggtag    420
atctgaccga aaccctggaa agataccaac agagacttaa cacttacgcg ctggtatcca    480
aagacctggc cagctaccga tctttttcgc agcagctaaa ggcacaagac agcctaggtg    540
aacagcccac cactgtgcca ccgcccattg acctgtcaat acctcacgtt tggatgccac    600
cgcaaaccac tccacacggc tggacagaat cacataccac ctcaggacta caccgaccac    660
actttaacca gacctgtatc ctctttgatg gacacgatct actattcagc accgtcacac    720
cttgtttgca ccaaggcttt tacctcatcg acgaactacg ttacgttaaa ataacactga    780
ccgaggactt cttcgtagtt acggtgtcca tagacgacga cacacccatg ctgcttatct    840
tcggccatct tccacgcgta cttttcaaag cgccctatca acgcgacaac tttatactac    900
gacaaactga aaaacacgag ctcctggtgc tagttaagaa agatcaactg aaccgtcact    960
cttatctcaa agacccggac tttcttgacg ccgcacttga cttcaactac ctagacctca   1020
gcgcactact acgtaacagc tttcaccgtt acgccgtgga tgtactcaag agcggtcgat   1080
gtcagatgct ggaccgccgc acggtagaaa tggccttcgc ctacgcatta gcactgttcg   1140
cagcagcccg acaagaagag gccggcgccc aagtctccgt cccacgggcc ctagaccgcc   1200
aggccgcact cttacaaata caagaattta tgatcacctg cctctcacaa acaccaccac   1260
gcaccacgtt gctgctgtat cccacggccg tggacctggc caaacgagcc ctttggacac   1320
cgaatcagat caccgacatc accagcctcg tacgcctggt ctacatactc tctaaacaga   1380
atcagcaaca tctcatcccc caatgggcac tacgacagat cgccgacttt gccctaaaac   1440
tacacaaaac gcacctggcc tctttttcttt cagccttcgc acgccaagaa ctctacctca   1500
tgggcagcct cgtccactcc atgctggtac atacgacgga gagacgcgaa atcttcatcg   1560
tagaaacggg cctctgttca ttggccgagc tatcacactt tacgcagttg ttagctcatc   1620
cacaccacga atacctcagc gacctgtaca caccctgttc cagtagcggg cgacgcgatc   1680
actcgctcga acgcctcacg cgtctcttcc ccgatgccac cgtccccgct accgttcccg   1740
ccgccctctc catcctatct accatgcaac caagcacgct ggaaaccttc cccgacctgt   1800
tttgcttgcc gctcggcgaa tccttctccg cgctgaccgt ctccgaacac gtcagttata   1860
tcgtaacaaa ccagtacctg atcaaaggta tctcctaccc tgtctccacc accgtcgtag   1920
gccagagcct catcatcacc cagacggaca gtcaaactaa atgcgaactg acgcgcaaca   1980
tgcataccac acacagcatc acagtggcgc tcaacatttc gctagaaaac tgcgcctttt   2040
gccaaagcgc cctgctagaa tacgacgaca cgcaaggcgt catcaacatc atgtacatgc   2100
acgactcgga cgacgtcctt ttcgccctgg atccctacaa cgaagtggtg gtctcatctc   2160
cgcgaactca ctacctcatg cttttgaaaa acggtacggt actagaagta actgacgtcg   2220
tcgtggacgc caccgacgat tacaaggacg atgacgataa gtgatgataa taggctggag   2280
cctcggtggc catgcttctt gccccttggg cctcccccca gcccctcctc cccttcctgc   2340
acccgtaccc ccgtggtctt tgaataaagt ctgagtgggc ggc                     2383
```

<210> SEQ ID NO 9
<211> LENGTH: 2377
<212> TYPE: DNA
<213> ORGANISM: Artificial Sequence
<220> FEATURE:
<223> OTHER INFORMATION: Synthetic Polynucleotide

<400> SEQUENCE: 9
tcaagctttt ggaccctcgt acagaagcta atacgactca ctatagggaa ataagagaga 60
aaagaagagt aagaagaaat ataagagcca ccatgcggcc aggcctcccc tcctacctca 120
tcatcctcgc cgtctgtctc ttcagccacc tactttcgtc acgatatggc gcagaagccg 180
tatccgaacc gctggacaaa gcgtttcacc tactgctcaa cacctacggg agacccatcc 240
gcttcctgcg tgaaaatacc acccagtgta cctacaacag cagcctccgt aacagcacgg 300
tcgtcaggga aaacgccatc agtttcaact ttttccaaag ctataatcaa tactatgtat 360
tccatatgcc tcgatgtctt tttgcgggtc ctctggcgga gcagtttctg aaccaggtag 420
atctgaccga aaccctggaa agataccaac agagacttaa cacttacgcg ctggtatcca 480
aagacctggc cagctaccga tctttttcgc agcagctaaa ggcacaagac agcctaggtg 540
aacagcccac cactgtgcca ccgcccattg acctgtcaat acctcacgtt tggatgccac 600
cgcaaaccac tccacacggc tggacagaat cacataccac ctcaggacta caccgaccac 660
actttaacca gacctgtatc ctctttgatg gacacgatct actattcagc accgtcacac 720
cttgtttgca ccaaggcttt tacctcatcg acgaactacg ttacgttaaa ataacactga 780
ccgaggactt cttcgtagtt acggtgtcca tagacgacga cacacccatg ctgcttatct 840
tcggccatct tccacgcgta cttttcaaag cgccctatca acgcgacaac tttatactac 900
gacaaactga aaaacacgag ctcctggtgc tagttaagaa agatcaactg aaccgtcact 960
cttatctcaa agacccggac tttcttgacg ccgcacttga cttcaactac ctagacctca 1020
gcgcactact acgtaacagc tttcaccgtt acgccgtgga tgtactcaag agcggtcgat 1080
gtcagatgct ggaccgccgc acggtagaaa tggccttcgc ctacgcatta gcactgttcg 1140
cagcagcccg acaagaagag gccggcgccc aagtctccgt cccacgggcc ctagaccgcc 1200
aggccgcact cttacaaata caagaattta tgatcacctg cctctcacaa acaccaccac 1260
gcaccacgtt gctgctgtat cccacggccg tggacctggc caaacgagcc ctttggacac 1320
cgaatcagat caccgacatc accagcctcg tacgcctggt ctacatactc tctaaacaga 1380
atcagcaaca tctcatcccc caatgggcac tacgacagat cgccgacttt gccctaaaac 1440
tacacaaaac gcacctggcc tcttttcttt cagccttcgc acgccaagaa ctctacctca 1500
tgggcagcct cgtccactcc atgctggtac atacgacgga gagacgcgaa atcttcatcg 1560
tagaaacggg cctctgttca ttggccgagc tatcacactt tacgcagttg ttagctcatc 1620
cacaccacga atacctcagc gacctgtaca caccctgttc cagtagcggg cgacgcgatc 1680
actcgctcga acgcctcacg cgtctcttcc ccgatgccac cgtccccgct accgttcccg 1740
ccgccctctc catcctatct accatgcaac caagcacgct ggaaaccttc cccgacctgt 1800
tttgcttgcc gctcggcgaa tccttctccg cgctgaccgt ctccgaacac gtcagttata 1860
tcgtaacaaa ccagtacctg atcaaaggta tctcctaccc tgtctccacc accgtcgtag 1920
gccagagcct catcatcacc cagacggaca gtcaaactaa atgcgaactg acgcgcaaca 1980
tgcataccac acacagcatc acagtggcgc tcaacatttc gctagaaaac tgcgcctttt 2040
gccaaagcgc cctgctagaa tacgacgaca cgcaaggcgt catcaacatc atgtacatgc 2100
acgactcgga cgacgtcctt ttcgccctgg atccctacaa cgaagtggtg gtctcatctc 2160
cgcgaactca ctacctcatg cttttgaaaa acggtacggt actagaagta actgacgtcg 2220
tcgtggacgc caccgaccac catcaccacc atcactgatg ataataggct ggagcctcgg 2280
tggccatgct tcttgcccct tgggcctccc cccagcccct cctccccttc ctgcacccgt 2340
acccccgtgg tctttgaata aagtctgagt gggcggc 2377

<210> SEQ ID NO 10
<211> LENGTH: 2287
<212> TYPE: DNA
<213> ORGANISM: Human Cytomegalovirus

<400> SEQUENCE: 10
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctcctttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260
actgcgtacg tgatgaggct ataaataagt tacagcagat tttcaatact tcatacaatc 1320
aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560
cgttgcgcgg ttacatcaac cgggcgctgg cgcaaatcgc agaagcctgg tgtgtggatc 1620
aacggcgcac cctagaggtc ttcaaggaac tcagcaagat caacccgtca gccattctct 1680
cggccattta caacaaaccg attgccgcgc gtttcatggg tgatgtcttg ggcctggcca 1740
gctgcgtgac catcaaccaa accagcgtca aggtgctgcg tgatatgaac gtgaaggagt 1800
cgccaggacg ctgctactca cgacccgtgg tcatctttaa tttcgccaac agctcgtacg 1860
tgcagtacgg tcaactgggc gaggacaacg aaatcctgtt gggcaaccac cgcactgagg 1920
aatgtcagct tcccagcctc aagatcttca tcgccgggaa ctcggcctac gagtacgtgg 1980
actacctctt caaacgcatg attgacctca gcagtatctc caccgtcgac agcatgatcg 2040
ccctggatat cgacccgctg gaaaataccg acttcagggt actggaactt tactcgcaga 2100
aagagctgcg ttccagcaac gtttttgacc tcgaagagat catgcgcgaa ttcaactcgt 2160
acaagcagtg ataataggct ggagcctcgg tggccatgct tcttgcccct tgggcctccc 2220
cccagcccct cctccccttc ctgcacccgt acccccgtgg tctttgaata aagtctgagt 2280
gggcggc 2287

<210> SEQ ID NO 11
<211> LENGTH: 2311
<212> TYPE: DNA
<213> ORGANISM: Artificial Sequence
<220> FEATURE:
<223> OTHER INFORMATION: Synthetic Polynucleotide

<400> SEQUENCE: 11
tcaagctttt ggaccctcgt acagaagcta atacgactca ctatagggaa ataagagaga 60
aaagaagagt aagaagaaat ataagagcca ccatggaatc caggatctgg tgcctggtag 120
tctgcgttaa cttgtgtatc gtctgtctgg gtgctgcggt ttcctcatct tctactcgtg 180
gaacttctgc tactcacagt caccattcct ctcatacgac gtctgctgct cactctcgat 240
ccggttcagt ctctcaacgc gtaacttctt cccaaacggt cagccatggt gttaacgaga 300
ccatctacaa cactaccctc aagtacggag atgtggtggg ggtcaatacc accaagtacc 360
cctatcgcgt gtgttctatg gcccagggta cggatcttat tcgctttgaa cgtaatatcg 420
tctgcacctc gatgaagccc atcaatgaag acctggacga gggcatcatg gtggtctaca 480
aacgcaacat cgtcgcgcac acctttaagg tacgagtcta ccagaaggtt ttgacgtttc 540
gtcgtagcta cgcttacatc cacaccactt atctgctggg cagcaacacg gaatacgtgg 600
cgcctcctat gtgggagatt catcatatca acagccacag tcagtgctac agttcctaca 660
gccgcgttat agcaggcacg gttttcgtgg cttatcatag ggacagctat gaaaacaaaa 720
ccatgcaatt aatgcccgac gattattcca acacccacag tacccgttac gtgacggtca 780
aggatcaatg gcacagccgc ggcagcacct ggctctatcg tgagacctgt aatctgaatt 840
gtatggtgac catcactact gcgcgctcca aatatcctta tcattttttc gccacttcca 900
cgggtgacgt ggttgacatt tctcctttct acaacggaac caatcgcaat gccagctact 960
ttggagaaaa cgccgacaag tttttcattt ttccgaacta cactatcgtc tccgactttg 1020
gaagaccgaa ttctgcgtta gagacccaca ggttggtggc ttttcttgaa cgtgcggact 1080
cggtgatctc ctgggatata caggacgaaa agaatgtcac ttgtcaactc actttctggg 1140
aagcctcgga acgcaccatt cgttccgaag ccgaggactc gtatcacttt tcttctgcca 1200
aaatgaccgc cactttctta tctaagaagc aagaggtgaa catgtccgac tctgcgctgg 1260
actgcgtacg tgatgaggct ataaataagt tacagcagat tttcaatact tcatacaatc 1320
aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560

```
cgttgcgcgg ttacatcaac cgggcgctgg cgcaaatcgc agaagcctgg tgtgtggatc   1620

aacggcgcac cctagaggtc ttcaaggaac tcagcaagat caacccgtca gccattctct   1680

cggccattta caacaaaccg attgccgcgc gtttcatggg tgatgtcttg ggcctggcca   1740

gctgcgtgac catcaaccaa accagcgtca aggtgctgcg tgatatgaac gtgaaggagt   1800

cgccaggacg ctgctactca cgacccgtgg tcatctttaa tttcgccaac agctcgtacg   1860

tgcagtacgg tcaactgggc gaggacaacg aaatcctgtt gggcaaccac cgcactgagg   1920

aatgtcagct tcccagcctc aagatcttca tcgccgggaa ctcggcctac gagtacgtgg   1980

actacctctt caaacgcatg attgacctca gcagtatctc caccgtcgac agcatgatcg   2040

ccctggatat cgacccgctg gaaaataccg acttcagggt actggaactt tactcgcaga   2100

aagagctgcg ttccagcaac gtttttgacc tcgaagagat catgcgcgaa ttcaactcgt   2160

acaagcagga ttacaaggac gatgacgata agtgataata ggctggagcc tcggtggcca   2220

tgcttcttgc cccttgggcc tccccccagc ccctcctccc cttcctgcac ccgtaccccc   2280

gtggtctttg aataaagtct gagtgggcgg c                                  2311
```

<210> SEQ ID NO 12
<211> LENGTH: 2305
<212> TYPE: DNA
<213> ORGANISM: Artificial Sequence
<220> FEATURE:
<223> OTHER INFORMATION: Synthetic Polynucleotide

<400> SEQUENCE: 12

```
tcaagctttt ggaccctcgt acagaagcta atacgactca ctatagggaa ataagagaga     60

aaagaagagt aagaagaaat ataagagcca ccatggaatc caggatctgg tgcctggtag    120

tctgcgttaa cttgtgtatc gtctgtctgg gtgctgcggt ttcctcatct tctactcgtg    180

gaacttctgc tactcacagt caccattcct ctcatacgac gtctgctgct cactctcgat    240

ccggttcagt ctctcaacgc gtaacttctt cccaaacggt cagccatggt gttaacgaga    300

ccatctacaa cactaccctc aagtacggag atgtggtggg ggtcaatacc accaagtacc    360

cctatcgcgt gtgttctatg gcccagggta cggatcttat tcgctttgaa cgtaatatcg    420

tctgcacctc gatgaagccc atcaatgaag acctggacga gggcatcatg gtggtctaca    480

aacgcaacat cgtcgcgcac acctttaagg tacgagtcta ccagaaggtt ttgacgtttc    540

gtcgtagcta cgcttacatc cacaccactt atctgctggg cagcaacacg gaatacgtgg    600

cgcctcctat gtgggagatt catcatatca acagccacag tcagtgctac agttcctaca    660

gccgcgttat agcaggcacg gttttcgtgg cttatcatag ggacagctat gaaaacaaaa    720

ccatgcaatt aatgcccgac gattattcca acacccacag tacccgttac gtgacggtca    780

aggatcaatg gcacagccgc ggcagcacct ggctctatcg tgagacctgt aatctgaatt    840

gtatggtgac catcactact gcgcgctcca aatatcctta tcattttttc gccacttcca    900

cgggtgacgt ggttgacatt tctcctttct acaacggaac caatcgcaat gccagctact    960

ttggagaaaa cgccgacaag tttttcattt ttccgaacta cactatcgtc tccgactttg   1020

gaagaccgaa ttctgcgtta gagacccaca ggttggtggc ttttcttgaa cgtgcggact   1080

cggtgatctc ctgggatata caggacgaaa agaatgtcac ttgtcaactc actttctggg   1140

aagcctcgga acgcaccatt cgttccgaag ccgaggactc gtatcacttt tcttctgcca   1200

aaatgaccgc cactttctta tctaagaagc aagaggtgaa catgtccgac tctgcgctgg   1260

actgcgtacg tgatgaggct ataaataagt tacagcagat tttcaatact tcatacaatc   1320
```

aaacatatga aaaatatgga aacgtgtccg tctttgaaac cactggtggt ttggtagtgt 1380
tctggcaagg tatcaagcaa aaatctctgg tggaactcga acgtttggcc aaccgctcca 1440
gtctgaatct tactcataat agaaccaaaa gaagtacaga tggcaacaat gcaactcatt 1500
tatccaacat ggaatcggtg cacaatctgg tctacgccca gctgcagttc acctatgaca 1560
cgttgcgcgg ttacatcaac cgggcgctgg cgcaaatcgc agaagcctgg tgtgtggatc 1620
aacggcgcac cctagaggtc ttcaaggaac tcagcaagat caacccgtca gccattctct 1680
cggccattta caacaaaccg attgccgcgc gtttcatggg tgatgtcttg ggcctggcca 1740
gctgcgtgac catcaaccaa accagcgtca aggtgctgcg tgatatgaac gtgaaggagt 1800
cgccaggacg ctgctactca cgacccgtgg tcatctttaa tttcgccaac agctcgtacg 1860
tgcagtacgg tcaactgggc gaggacaacg aaatcctgtt gggcaaccac cgcactgagg 1920
aatgtcagct tcccagcctc aagatcttca tcgccgggaa ctcggcctac gagtacgtgg 1980
actacctctt caaacgcatg attgacctca gcagtatctc caccgtcgac agcatgatcg 2040
ccctggatat cgacccgctg gaaaataccg acttcagggt actggaactt tactcgcaga 2100
aagagctgcg ttccagcaac gtttttgacc tcgaagagat catgcgcgaa ttcaactcgt 2160
acaagcagca ccatcaccac catcactgat aataggctgg agcctcggtg gccatgcttc 2220
ttgccccttg ggcctccccc cagcccctcc tccccttcct gcacccgtac ccccgtggtc 2280
tttgaataaa gtctgagtgg gcggc 2305

<210> SEQ ID NO 13
<211> LENGTH: 724
<212> TYPE: DNA
<213> ORGANISM: Human Cytomegalovirus

<400> SEQUENCE: 13
tcaagctttt ggaccctcgt acagaagcta atacgactca ctatagggaa ataagagaga 60
aaagaagagt aagaagaaat ataagagcca ccatgagtcc caaagatctg acgccgttct 120
tgacggcgtt gtggctgcta ttgggtcaca gccgcgtgcc gcgggtgcgc gcagaagaat 180
gttgcgaatt cataaacgtc aaccacccgc cggaacgctg ttacgatttc aaaatgtgca 240
atcgcttcac cgtcgcgctg cggtgtccgg acggcgaagt ctgctacagt cccgagaaaa 300
cggctgagat tcgcgggatc gtcaccacca tgacccattc attgacacgc caggtcgtac 360
acaacaaact gacgagctgc aactacaatc cgttatacct cgaagctgac gggcgaatac 420
gctgcggcaa agtaaacgac aaggcgcagt acctgctggg cgccgctggc agcgttccct 480
atcgatggat caatctggaa tacgacaaga taacccggat cgtgggcctg gatcagtacc 540
tggagagcgt taagaaacac aaacggctgg atgtgtgccg cgctaaaatg ggctatatgc 600
tgcagtgata ataggctgga gcctcggtgg ccatgcttct tgccccttgg gcctcccccc 660
agcccctcct ccccttcctg cacccgtacc cccgtggtct ttgaataaag tctgagtggg 720
cggc 724

<210> SEQ ID NO 14
<211> LENGTH: 748
<212> TYPE: DNA
<213> ORGANISM: Artificial Sequence
<220> FEATURE:
<223> OTHER INFORMATION: Synthetic Polynucleotide

<400> SEQUENCE: 14

```
tcaagctttt ggaccctcgt acagaagcta atacgactca ctatagggaa ataagagaga     60

aaagaagagt aagaagaaat ataagagcca ccatgagtcc caaagatctg acgccgttct    120

tgacggcgtt gtggctgcta ttgggtcaca gccgcgtgcc gcgggtgcgc gcagaagaat    180

gttgcgaatt cataaacgtc aaccacccgc cggaacgctg ttacgatttc aaaatgtgca    240

atcgcttcac cgtcgcgctg cggtgtccgg acggcgaagt ctgctacagt cccgagaaaa    300

cggctgagat tcgcgggatc gtcaccacca tgacccattc attgacacgc caggtcgtac    360

acaacaaact gacgagctgc aactacaatc cgttatacct cgaagctgac gggcgaatac    420

gctgcggcaa agtaaacgac aaggcgcagt acctgctggg cgccgctggc agcgttccct    480

atcgatggat caatctggaa tacgacaaga taacccggat cgtgggcctg gatcagtacc    540

tggagagcgt taagaaacac aaacggctgg atgtgtgccg cgctaaaatg ggctatatgc    600

tgcaggatta caaggacgat gacgataagt gataataggc tggagcctcg gtggccatgc    660

ttcttgcccc ttgggcctcc ccccagcccc tcctcccctt cctgcacccg tacccccgtg    720

gtctttgaat aaagtctgag tgggcggc                                       748
```

<210> SEQ ID NO 15
<211> LENGTH: 853
<212> TYPE: DNA
<213> ORGANISM: Human Cytomegalovirus

<400> SEQUENCE: 15

```
tcaagctttt ggaccctcgt acagaagcta atacgactca ctatagggaa ataagagaga     60

aaagaagagt aagaagaaat ataagagcca ccatgctgcg gcttctgctt cgtcaccact    120

ttcactgcct gcttctgtgc gcggtttggg caacgccctg tctggcgtct ccgtggtcga    180

cgctaacagc aaaccagaat ccgtccccgc catggtctaa actgacgtat tccaaaccgc    240

atgacgcggc gacgttttac tgtccttttc tctatccctc gcccccacga tccccccttgc    300

aattctcggg gttccagcgg gtatcaacgg gtcccgagtg tcgcaacgag accctgtatc    360

tgctgtacaa ccgggaaggc cagaccttgg tggagagaag ctccacctgg gtgaaaaagg    420

tgatctggta cctgagcggt cggaaccaaa ccatcctcca acggatgccc cgaacggctt    480

cgaaaccgag cgacggaaac gtgcagatca gcgtggaaga cgccaagatt tttggagcgc    540

acatggtgcc caagcagacc aagctgctac gcttcgtcgt caacgatggc acacgttatc    600

agatgtgtgt gatgaagctg gagagctggg ctcacgtctt ccgggactac agcgtgtctt    660

ttcaggtgcg attgacgttc accgaggcca ataaccagac ttacaccttc tgcacccatc    720

ccaatctcat cgtttgataa taggctggag cctcggtggc catgcttctt gccccttggg    780

cctcccccca gcccctcctc cccttcctgc acccgtaccc ccgtggtctt tgaataaagt    840

ctgagtgggc ggc                                                       853
```

<210> SEQ ID NO 16
<211> LENGTH: 880
<212> TYPE: DNA
<213> ORGANISM: Artificial Sequence
<220> FEATURE:
<223> OTHER INFORMATION: Synthetic Polynucleotide

<400> SEQUENCE: 16

```
tcaagctttt ggaccctcgt acagaagcta atacgactca ctatagggaa ataagagaga     60

aaagaagagt aagaagaaat ataagagcca ccatgctgcg gcttctgctt cgtcaccact    120

ttcactgcct gcttctgtgc gcggtttggg caacgccctg tctggcgtct ccgtggtcga    180
```

cgctaacagc aaaccagaat ccgtccccgc catggtctaa actgacgtat tccaaaccgc 240
atgacgcggc gacgttttac tgtccttttc tctatccctc gcccccacga tccccccttgc 300 aattctcggg gttccagcgg gtatcaacgg gtcccgagtg tcgcaacgag accctgtatc 360
tgctgtacaa ccgggaaggc cagaccttgg tggagagaag ctccacctgg gtgaaaaagg 420
tgatctggta cctgagcggt cggaaccaaa ccatcctcca acggatgccc cgaacggctt 480
cgaaaccgag cgacggaaac gtgcagatca gcgtggaaga cgccaagatt tttggagcgc 540
acatggtgcc caagcagacc aagctgctac gcttcgtcgt caacgatggc acacgttatc 600
agatgtgtgt gatgaagctg gagagctggg ctcacgtctt ccgggactac agcgtgtctt 660
ttcaggtgcg attgacgttc accgaggcca ataaccagac ttacaccttc tgcacccatc 720
ccaatctcat cgttgattac aaggacgatg acgataagtg atgataatag gctggagcct 780
cggtggccat gcttcttgcc ccttgggcct ccccccagcc cctcctcccc ttcctgcacc 840
cgtacccccg tggtctttga ataaagtctg agtgggcggc 880

<210> SEQ ID NO 17
<211> LENGTH: 598
<212> TYPE: DNA
<213> ORGANISM: Human Cytomegalovirus

<400> SEQUENCE: 17
tcaagctttt ggaccctcgt acagaagcta atacgactca ctatagggaa ataagagaga 60
aaagaagagt aagaagaaat ataagagcca ccatgcggct gtgtcgggtg tggctgtctg 120
tttgtctgtg cgccgtggtg ctgggtcagt gccagcggga aaccgcggaa aaaaacgatt 180
attaccgagt accgcattac tgggacgcgt gctctcgcgc gctgcccgac caaacccgtt 240
acaagtatgt ggaacagctc gtggacctca cgttgaacta ccactacgat gcgagccacg 300
gcttggacaa ctttgacgtg ctcaagagaa tcaacgtgac cgaggtgtcg ttgctcatca 360
gcgactttag acgtcagaac cgtcgcggcg gcaccaacaa aaggaccacg ttcaacgccg 420
ccggttcgct ggcgccacac gcccggagcc tcgagttcag cgtgcggctc tttgccaact 480
gataataggc tggagcctcg gtggccatgc ttcttgcccc ttgggcctcc ccccagcccc 540
tcctcccctt cctgcacccg tacccccgtg gtctttgaat aaagtctgag tgggcggc 598

<210> SEQ ID NO 18
<211> LENGTH: 625
<212> TYPE: DNA
<213> ORGANISM: Artificial Sequence
<220> FEATURE:
<223> OTHER INFORMATION: Synthetic Polynucleotide

<400> SEQUENCE: 18
tcaagctttt ggaccctcgt acagaagcta atacgactca ctatagggaa ataagagaga 60
aaagaagagt aagaagaaat ataagagcca ccatgcggct gtgtcgggtg tggctgtctg 120
tttgtctgtg cgccgtggtg ctgggtcagt gccagcggga aaccgcggaa aaaaacgatt 180
attaccgagt accgcattac tgggacgcgt gctctcgcgc gctgcccgac caaacccgtt 240
acaagtatgt ggaacagctc gtggacctca cgttgaacta ccactacgat gcgagccacg 300
gcttggacaa ctttgacgtg ctcaagagaa tcaacgtgac cgaggtgtcg ttgctcatca 360
gcgactttag acgtcagaac cgtcgcggcg gcaccaacaa aaggaccacg ttcaacgccg 420
ccggttcgct ggcgccacac gcccggagcc tcgagttcag cgtgcggctc tttgccaacg 480
attacaagga cgatgacgat aagtgatgat aataggctgg agcctcggtg gccatgcttc 540
ttgccccttg ggcctccccc cagcccctcc tccccttcct gcacccgtac ccccgtggtc 600
tttgaataaa gtctgagtgg gcggc 625

<210> SEQ ID NO 19
<211> LENGTH: 2434
<212> TYPE: DNA
<213> ORGANISM: Artificial Sequence
<220> FEATURE:
<223> OTHER INFORMATION: Synthetic Polynucleotide

<400> SEQUENCE: 19
tcaagctttt ggaccctcgt acagaagcta atacgactca ctatagggac agacgagaga 60
gaagcacgcc aattctgcct gcttaagcca tgcggccagg cctcccctcc tacctcatca 120
tcctcgccgt ctgtctcttc agccacctac tttcgtcacg atatggcgca gaagccgtat 180
ccgaaccgct ggacaaagcg tttcacctac tgctcaacac ctacgggaga cccatccgct 240
tcctgcgtga aaataccacc cagtgtacct acaacagcag cctccgtaac agcacggtcg 300
tcagggaaaa cgccatcagt ttcaactttt tccaaagcta taatcaatac tatgtattcc 360
atatgcctcg atgtcttttt gcgggtcctc tggcggagca gtttctgaac caggtagatc 420
tgaccgaaac cctggaaaga taccaacaga gacttaacac ttacgcgctg gtatccaaag 480
acctggccag ctaccgatct tttcgcagc agctaaaggc acaagacagc ctaggtgaac 540
agcccaccac tgtgccaccg cccattgacc tgtcaatacc tcacgtttgg atgccaccgc 600
aaaccactcc acacggctgg acagaatcac ataccacctc aggactacac cgaccacact 660
ttaaccagac ctgtatcctc tttgatggac acgatctact attcagcacc gtcacacctt 720
gtttgcacca aggcttttac ctcatcgacg aactacgtta cgttaaaata acactgaccg 780
aggacttctt cgtagttacg gtgtccatag acgacgacac acccatgctg cttatcttcg 840
gccatcttcc acgcgtactt ttcaaagcgc cctatcaacg cgacaacttt atactacgac 900
aaactgaaaa acacgagctc ctggtgctag ttaagaaaga tcaactgaac cgtcactctt 960
atctcaaaga cccggacttt cttgacgccg cacttgactt caactaccta gacctcagcg 1020
cactactacg taacagcttt caccgttacg ccgtggatgt actcaagagc ggtcgatgtc 1080
agatgctgga ccgccgcacg gtagaaatgg ccttcgccta cgcattagca ctgttcgcag 1140
cagcccgaca agaagaggcc ggcgcccaag tctccgtccc acgggcccta gaccgccagg 1200
ccgcactctt acaaatacaa gaatttatga tcacctgcct ctcacaaaca ccaccacgca 1260
ccacgttgct gctgtatccc acggccgtgg acctggccaa acgagccctt tggacaccga 1320
atcagatcac cgacatcacc agcctcgtac gcctggtcta catactctct aaacagaatc 1380
agcaacatct catcccccaa tgggcactac gacagatcgc cgactttgcc ctaaaactac 1440
acaaaacgca cctggcctct ttctttcag ccttcgcacg ccaagaactc tacctcatgg 1500
gcagcctcgt ccactccatg ctggtacata cgacggagag acgcgaaatc ttcatcgtag 1560
aaacgggcct ctgttcattg gccgagctat cacactttac gcagttgtta gctcatccac 1620
accacgaata cctcagcgac ctgtacacac cctgttccag tagcgggcga cgcgatcact 1680
cgctcgaacg cctcacgcgt ctcttccccg atgccaccgt ccccgctacc gttcccgccg 1740
ccctctccat cctatctacc atgcaaccaa gcacgctgga aaccttcccc gacctgtttt 1800
gcttgccgct cggcgaatcc ttctccgcgc tgaccgtctc cgaacacgtc agttatatcg 1860
taacaaacca gtacctgatc aaaggtatct cctaccctgt ctccaccacc gtcgtaggcc 1920
agagcctcat catcacccag acggacagtc aaactaaatg cgaactgacg cgcaacatgc 1980
ataccacaca cagcatcaca gtggcgctca acatttcgct agaaaactgc gccttttgcc 2040
aaagcgccct gctagaatac gacgacacgc aaggcgtcat caacatcatg tacatgcacg 2100
actcggacga cgtccttttc gccctggatc cctacaacga agtggtggtc tcatctccgc 2160
gaactcacta cctcatgctt ttgaaaaacg gtacggtact agaagtaact gacgtcgtcg 2220
tggacgccac cgacagtcgt ctcctcatga tgtccgtcta cgcgctatcg gccatcatcg 2280
gcatctatct gctctaccgc atgctcaaga catgctgata ataggctgga gcctcggtgg 2340
ccatgcttct tgccccttgg gcctcccccc agcccctcct ccccttcctg cacccgtacc 2400
cccgtggtct ttgaataaag tctgagtggg cggc 2434

<210> SEQ ID NO 20
<211> LENGTH: 1044
<212> TYPE: DNA
<213> ORGANISM: Artificial Sequence
<220> FEATURE:
<223> OTHER INFORMATION: Synthetic Polynucleotide

<400> SEQUENCE: 20
tcaagctttt ggaccctcgt acagaagcta atacgactca ctatagggct taagcaggca 60
gaattggccc ttagcctgta ccagccgaac catgtgccgc cgcccggatt gcggcttctc 120
tttctcacct ggaccggtga tactgctgtg gtgttgcctt ctgctgccca ttgtttcctc 180
agccgccgtc agcgtcgctc ctaccgccgc cgagaaagtc cccgcggagt gccccgaact 240
aacgcgccga tgcttgttgg gtgaggtgtt tgagggtgac aagtatgaaa gttggctgcg 300
cccgttggtg aatgttaccg ggcgcgatgg cccgctatcg caacttatcc gttaccgtcc 360
cgttacgccg gaggccgcca actccgtgct gttggacgag gctttcctgg acactctggc 420
cctgctgtac aacaatccgg atcaattgcg ggccctgctg acgctgttga gctcggacac 480
agcgccgcgc tggatgacgg tgatgcgcgg ctacagcgag tgcggcgatg gctcgccggc 540
cgtgtacacg tgcgtggacg acctgtgccg cggctacgac ctcacgcgac tgtcatacgg 600
gcgcagcatc ttcacggaac acgtgttagg cttcgagctg gtgccaccgt ctctctttaa 660
cgtggtggtg gccatacgca acgaagccac gcgtaccaac cgcgccgtgc gtctgcccgt 720
gagcaccgct gccgcgcccg agggcatcac gctcttttac ggcctgtaca acgcagtgaa 780
ggaattctgc ctgcgtcacc agctggaccc gccgctgcta cgccacctag ataaatacta 840
cgccggactg ccgcccgagc tgaagcagac gcgcgtcaac ctgccggctc actcgcgcta 900
tggccctcaa gcagtggatg ctcgctgata ataggctgga gcctcggtgg ccatgcttct 960
tgccccttgg gcctcccccc agcccctcct ccccttcctg cacccgtacc cccgtggtct 1020
ttgaataaag tctgagtggg cggc 1044

<210> SEQ ID NO 21
<211> LENGTH: 1045
<212> TYPE: DNA
<213> ORGANISM: Artificial Sequence
<220> FEATURE:
<223> OTHER INFORMATION: Synthetic Polynucleotide

<400> SEQUENCE: 21
tcaagctttt ggaccctcgt acagaagcta atacgactca ctatagggtg gctcttatat 60
ttcttcttac tcttcttttc tctcttattt ccatgtgccg ccgcccggat tgcggcttct 120

```
ctttctcacc tggaccggtg atactgctgt ggtgttgcct tctgctgccc attgtttcct    180

cagccgccgt cagcgtcgct cctaccgccg ccgagaaagt ccccgcggag tgccccgaac    240

taacgcgccg atgcttgttg ggtgaggtgt ttgagggtga caagtatgaa agttggctgc    300

gcccgttggt gaatgttacc gggcgcgatg gcccgctatc gcaacttatc cgttaccgtc    360

ccgttacgcc ggaggccgcc aactccgtgc tgttggacga ggctttcctg gacactctgg    420

ccctgctgta caacaatccg gatcaattgc gggccctgct gacgctgttg agctcggaca    480

cagcgccgcg ctggatgacg gtgatgcgcg gctacagcga gtgcggcgat ggctcgccgg    540

ccgtgtacac gtgcgtggac gacctgtgcc gcggctacga cctcacgcga ctgtcatacg    600

ggcgcagcat cttcacggaa cacgtgttag gcttcgagct ggtgccaccg tctctcttta    660

acgtggtggt ggccatacgc aacgaagcca cgcgtaccaa ccgcgccgtg cgtctgcccg    720

tgagcaccgc tgccgcgccc gagggcatca cgctctttta cggcctgtac aacgcagtga    780

aggaattctg cctgcgtcac cagctggacc cgccgctgct acgccaccta gataaatact    840

acgccggact gccgcccgag ctgaagcaga cgcgcgtcaa cctgccggct cactcgcgct    900

atggccctca agcagtggat gctcgctgat aataggctgg agcctcggtg gccatgcttc    960

ttgccccttg ggcctccccc cagcccctcc tccccttcct gcacccgtac ccccgtggtc   1020

tttgaataaa gtctgagtgg gcggc                                         1045
```

<210> SEQ ID NO 22
<211> LENGTH: 722
<212> TYPE: DNA
<213> ORGANISM: Artificial Sequence
<220> FEATURE:
<223> OTHER INFORMATION: Synthetic Polynucleotide

<400> SEQUENCE: 22

```
tcaagctttt ggaccctcgt acagaagcta atacgactca ctatagggtt cggctggtac     60

aggctaacca gaagacagat aagagcctcc atgagtccca aagatctgac gccgttcttg    120

acggcgttgt ggctgctatt gggtcacagc cgcgtgccgc gggtgcgcgc agaagaatgt    180

tgcgaattca taaacgtcaa ccacccgccg gaacgctgtt acgatttcaa aatgtgcaat    240

cgcttcaccg tcgcgctgcg gtgtccggac ggcgaagtct gctacagtcc cgagaaaacg    300

gctgagattc gcgggatcgt caccaccatg acccattcat tgacacgcca ggtcgtacac    360

aacaaactga cgagctgcaa ctacaatccg ttatacctcg aagctgacgg gcgaatacgc    420

tgcggcaaag taaacgacaa ggcgcagtac ctgctgggcg ccgctggcag cgttccctat    480

cgatggatca atctggaata cgacaagata acccggatcg tgggcctgga tcagtacctg    540

gagagcgtta agaaacacaa acggctggat gtgtgccgcg ctaaaatggg ctatatgctg    600

cagtgataat aggctggagc ctcggtggcc atgcttcttg ccccttgggc ctccccccag    660

cccctcctcc ccttcctgca cccgtacccc cgtggtcttt gaataaagtc tgagtgggcg    720

gc                                                                   722
```

<210> SEQ ID NO 23
<211> LENGTH: 854
<212> TYPE: DNA
<213> ORGANISM: Artificial Sequence
<220> FEATURE:
<223> OTHER INFORMATION: Synthetic Polynucleotide

<400> SEQUENCE: 23

```
tcaagctttt ggaccctcgt acagaagcta atacgactca ctatagggag gctcttatct     60
```

gtcttctcag tccgaattcg aagtacggct accatgctgc ggcttctgct tcgtcaccac 120
tttcactgcc tgcttctgtg cgcggtttgg gcaacgccct gtctggcgtc tccgtggtcg 180
acgctaacag caaaccagaa tccgtccccg ccatggtcta aactgacgta ttccaaaccg 240
catgacgcgg cgacgtttta ctgtcctttt ctctatccct cgcccccacg atccccccttg 300 caattctcgg ggttccagcg ggtatcaacg ggtcccgagt gtcgcaacga gaccctgtat 360
ctgctgtaca accgggaagg ccagaccttg gtggagagaa gctccacctg ggtgaaaaag 420
gtgatctggt acctgagcgg tcggaaccaa accatcctcc aacggatgcc ccgaacggct 480
tcgaaaccga gcgacggaaa cgtgcagatc agcgtggaag acgccaagat ttttggagcg 540
cacatggtgc ccaagcagac caagctgcta cgcttcgtcg tcaacgatgg cacacgttat 600
cagatgtgtg tgatgaagct ggagagctgg gctcacgtct tccgggacta cagcgtgtct 660
tttcaggtgc gattgacgtt caccgaggcc aataaccaga cttacacctt ctgcacccat 720
cccaatctca tcgtttgata ataggctgga gcctcggtgg ccatgcttct tgccccttgg 780
gcctcccccc agcccctcct ccccttcctg cacccgtacc cccgtggtct ttgaataaag 840
tctgagtggg cggc 854

<210> SEQ ID NO 24
<211> LENGTH: 853
<212> TYPE: DNA
<213> ORGANISM: Artificial Sequence
<220> FEATURE:
<223> OTHER INFORMATION: Synthetic Polynucleotide

<400> SEQUENCE: 24
tcaagctttt ggaccctcgt acagaagcta atacgactca ctatagggtg gctcttatat 60
ttcttcttag tccgaattcg aagtacggct acatgctgcg gcttctgctt cgtcaccact 120
ttcactgcct gcttctgtgc gcggtttggg caacgccctg tctggcgtct ccgtggtcga 180
cgctaacagc aaaccagaat ccgtccccgc catggtctaa actgacgtat tccaaaccgc 240
atgacgcggc gacgttttac tgtccttttc tctatccctc gcccccacga tcccccttgc 300
aattctcggg gttccagcgg gtatcaacgg gtcccgagtg tcgcaacgag accctgtatc 360
tgctgtacaa ccgggaaggc cagaccttgg tggagagaag ctccacctgg gtgaaaaagg 420
tgatctggta cctgagcggt cggaaccaaa ccatcctcca acggatgccc cgaacggctt 480
cgaaaccgag cgacggaaac gtgcagatca gcgtggaaga cgccaagatt tttggagcgc 540
acatggtgcc caagcagacc aagctgctac gcttcgtcgt caacgatggc acacgttatc 600
agatgtgtgt gatgaagctg gagagctggg ctcacgtctt ccgggactac agcgtgtctt 660
ttcaggtgcg attgacgttc accgaggcca ataaccagac ttacaccttc tgcacccatc 720
ccaatctcat cgtttgataa taggctggag cctcggtggc catgcttctt gccccttggg 780
cctcccccca gcccctcctc cccttcctgc acccgtaccc ccgtggtctt tgaataaagt 840
ctgagtgggc ggc 853

<210> SEQ ID NO 25
<211> LENGTH: 597
<212> TYPE: DNA
<213> ORGANISM: Artificial Sequence
<220> FEATURE:
<223> OTHER INFORMATION: Synthetic Polynucleotide

<400> SEQUENCE: 25

-continued

```
tcaagctttt ggaccctcgt acagaagcta atacgactca ctatagggta gccgtacttc     60

gaattcggac aagcttctct ctcgtctgtc catgcggctg tgtcgggtgt ggctgtctgt    120

ttgtctgtgc gccgtggtgc tgggtcagtg ccagcgggaa accgcggaaa aaaacgatta    180

ttaccgagta ccgcattact gggacgcgtg ctctcgcgcg ctgcccgacc aaacccgtta    240

caagtatgtg gaacagctcg tggacctcac gttgaactac cactacgatg cgagccacgg    300

cttggacaac tttgacgtgc tcaagagaat caacgtgacc gaggtgtcgt tgctcatcag    360

cgactttaga cgtcagaacc gtcgcggcgg caccaacaaa aggaccacgt tcaacgccgc    420

cggttcgctg gcgccacacg cccggagcct cgagttcagc gtgcggctct ttgccaactg    480

ataataggct ggagcctcgg tggccatgct tcttgcccct tgggcctccc cccagcccct    540

cctccccttc ctgcacccgt acccccgtgg tctttgaata aagtctgagt gggcggc       597
```

<210> SEQ ID NO 26
<211> LENGTH: 597
<212> TYPE: DNA
<213> ORGANISM: Artificial Sequence
<220> FEATURE:
<223> OTHER INFORMATION: Synthetic Polynucleotide

<400> SEQUENCE: 26

```
tcaagctttt ggaccctcgt acagaagcta atacgactca ctatagggta gccgtacttc     60

gaattcggac tttcttttct ctcttatttc catgcggctg tgtcgggtgt ggctgtctgt    120

ttgtctgtgc gccgtggtgc tgggtcagtg ccagcgggaa accgcggaaa aaaacgatta    180

ttaccgagta ccgcattact gggacgcgtg ctctcgcgcg ctgcccgacc aaacccgtta    240

caagtatgtg gaacagctcg tggacctcac gttgaactac cactacgatg cgagccacgg    300

cttggacaac tttgacgtgc tcaagagaat caacgtgacc gaggtgtcgt tgctcatcag    360

cgactttaga cgtcagaacc gtcgcggcgg caccaacaaa aggaccacgt tcaacgccgc    420

cggttcgctg gcgccacacg cccggagcct cgagttcagc gtgcggctct ttgccaactg    480

ataataggct ggagcctcgg tggccatgct tcttgcccct tgggcctccc cccagcccct    540

cctccccttc ctgcacccgt acccccgtgg tctttgaata aagtctgagt gggcggc       597
```

<210> SEQ ID NO 27
<211> LENGTH: 3364
<212> TYPE: DNA
<213> ORGANISM: Artificial Sequence
<220> FEATURE:
<223> OTHER INFORMATION: Synthetic Polynucleotide

<400> SEQUENCE: 27

```
tcaagctttt ggaccctcgt acagaagcta atacgactca ctatagggaa ataagagaga     60

aaagaagagt aagaagaaat ataagagcca ccatggagtc gcgcggtcgc cgttgtcccg    120

aaatgatatc cgtactgggt cccatttcgg ggcacgtgct gaaagccgtg tttagtcgcg    180

gcgatacgcc ggtgctgccg cacgagacgc gactcctgca gacgggtatc cacgtacgcg    240

tgagccagcc ctcgctgatc ctggtgtcgc agtacacgcc cgactcgacg ccatgccacc    300

gcggcgacaa tcagctgcag gtgcagcaca cgtactttac gggcagcgag gtggagaacg    360

tgtcggtcaa cgtgcacaac cccacgggcc gaagcatctg ccccagccaa gagcccatgt    420

cgatctatgt gtacgcgctg ccgctcaaga tgctgaacat ccccagcatc aacgtgcacc    480

actacccgtc ggcggccgag cgcaaacacc gacacctgcc cgtagccgac gctgttattc    540

acgcgtcggg caagcagatg tggcaggcgc gtctcacggt ctcgggactg gcctggacgc    600
```

-continued

```
gtcagcagaa ccagtggaaa gagcccgacg tctactacac gtcagcgttc gtgtttccca    660
ccaaggacgt ggcactgcgg cacgtggtgt gcgcgcacga gctggtttgc tccatggaga    720
acacgcgcgc aaccaagatg caggtgatag gtgaccagta cgtcaaggtg tacctggagt    780
ccttctgcga ggacgtgccc tccggcaagc tctttatgca cgtcacgctg ggctctgacg    840
tggaagagga cctaacgatg acccgcaacc cgcaaccctt catgcgcccc cacgagcgca    900
acggctttac ggtgttgtgt cccaaaaata tgataatcaa accgggcaag atctcgcaca    960
tcatgctgga tgtggctttt acctcacacg agcattttgg gctgctgtgt cccaagagca   1020
tcccgggcct gagcatctca ggtaacctgt tgatgaacgg gcagcaaatc ttcctggagg   1080
tacaagcgat acgcgagacc gtggaactgc gtcagtacga tcccgtggct gcgctcttct   1140
ttttcgatat cgacttgttg ctgcagcgcg ggcctcagta cagcgagcac cccaccttca   1200
ccagccagta tcgcatccag ggcaagcttg agtaccgaca cacctgggac cggcacgacg   1260
agggtgccgc ccagggcgac gacgacgtct ggaccagcgg atcggactcc gacgaagaac   1320
tcgtaaccac cgagcgtaag acgccccgcg tcaccggcgg cggcgccatg gcgagcgcct   1380
ccacttccgc gggccgcaaa cgcaaatcag catcctcggc gacggcgtgc acggcgggcg   1440
ttatgacacg cggccgcctt aaggccgagt ccaccgtcgc gcccgaagag gacaccgacg   1500
aggattccga caacgaaatc cacaatccgg ccgtgttcac ctggccgccc tggcaggccg   1560
gcatcctggc ccgcaacctg gtgcccatgg tggctacggt tcagggtcag aatctgaagt   1620
accaggagtt cttctgggac gccaacgaca tctaccgcat cttcgccgaa ttggaaggcg   1680
tatggcagcc cgctgcgcaa cccaaacgtc gccgccaccg gcaagacgcc ttgcccgggc   1740
catgcatcgc ctcgacgccc aaaaagcacc gaggtgagtc ctctgccaag agaaagatgg   1800
accctgataa tcctgacgag ggcccttcct ccaaggtgcc acggcccgag acacccgtga   1860
ccaaggccac gacgttcctg cagactatgt taaggaagga ggttaacagt cagctgagcc   1920
tgggagaccc gctgttccca gaattggccg aagaatccct caaaaccttt gaacaagtga   1980
ccgaggattg caacgagaac cccgaaaaag atgtcctgac agaactcgtc aaacagatta   2040
aggttcgagt ggacatggtg cggcatagaa tcaaggagca catgctgaaa aaatataccc   2100
agacggaaga aaaattcact ggcgccttta atatgatggg aggatgtttg cagaatgcct   2160
tagatatctt agataaggtt catgagcctt tcgaggacat gaagtgtatt gggctaacta   2220
tgcagagcat gtatgagaac tacattgtac ctgaggataa gcgggagatg tggatggctt   2280
gtattaagga gctgcatgat gtgagcaagg gcgccgctaa caagttgggg ggtgcactgc   2340
aggctaaggc ccgtgctaaa aaggatgaac ttaggagaaa gatgatgtat atgtgctaca   2400
ggaatataga gttctttacc aagaactcag ccttccctaa gaccaccaat ggctgcagtc   2460
aggccatggc ggcattgcag aacttgcctc agtgctctcc tgatgagatt atgtcttatg   2520
cccagaaaat ctttaagatt ttggatgagg agagagacaa ggtgctcacg cacattgatc   2580
acatatttat ggatatcctc actacatgtg tggaaacaat gtgtaatgag tacaaggtca   2640
ctagtgacgc ttgtatgatg accatgtacg ggggcatctc tctcttaagt gagttctgtc   2700
gggtgctgtg ctgctatgtc ttagaggaga ctagtgtgat gctggccaag cggcctctga   2760
taaccaagcc tgaggttatc agtgtaatga agcgccgcat tgaggagatc tgcatgaagg   2820
tctttgccca gtacattctg gggggccgatc ctttgagagt ctgctctcct agtgtggatg   2880
acctacgggc catcgccgag gagtcagatg aggaagaggc tattgtagcc tacactttgg   2940
```

ccaccgctgg tgccagctcc tctgattctc tggtgtcacc tccagagtcc cctgtacccg 3000
cgactatccc tctgtcctca gtaattgtgg ctgagaacag tgatcaggaa gaaagtgaac 3060
agagtgatga ggaacaggag gagggtgctc aggaggagcg ggaggacact gtgtctgtca 3120
agtctgagcc agtgtctgag atagaggaag ttgcctcaga ggaagaggag gatggtgctg 3180
aggaacccac cgcctctgga ggcaagagca cccaccctat ggtgactaga agcaaggctg 3240
accagtgata ataggctgga gcctcggtgg ccatgcttct tgccccttgg gcctcccccc 3300
agcccctcct ccccttcctg cacccgtacc cccgtggtct ttgaataaag tctgagtggg 3360
cggc 3364

<210> SEQ ID NO 28
<211> LENGTH: 3388
<212> TYPE: DNA
<213> ORGANISM: Artificial Sequence
<220> FEATURE:
<223> OTHER INFORMATION: Synthetic Polynucleotide

<400> SEQUENCE: 28
tcaagctttt ggaccctcgt acagaagcta atacgactca ctatagggaa ataagagaga 60
aaagaagagt aagaagaaat ataagagcca ccatggagtc gcgcggtcgc cgttgtcccg 120
aaatgatatc cgtactgggt cccatttcgg ggcacgtgct gaaagccgtg tttagtcgcg 180
gcgatacgcc ggtgctgccg cacgagacgc gactcctgca gacgggtatc cacgtacgcg 240
tgagccagcc ctcgctgatc ctggtgtcgc agtacacgcc cgactcgacg ccatgccacc 300
gcggcgacaa tcagctgcag gtgcagcaca cgtactttac gggcagcgag gtggagaacg 360
tgtcggtcaa cgtgcacaac cccacgggcc gaagcatctg ccccagccaa gagcccatgt 420
cgatctatgt gtacgcgctg ccgctcaaga tgctgaacat ccccagcatc aacgtgcacc 480
actacccgtc ggcggccgag cgcaaacacc gacacctgcc cgtagccgac gctgttattc 540
acgcgtcggg caagcagatg tggcaggcgc gtctcacggt ctcgggactg gcctggacgc 600
gtcagcagaa ccagtggaaa gagcccgacg tctactacac gtcagcgttc gtgtttccca 660
ccaaggacgt ggcactgcgg cacgtggtgt gcgcgcacga gctggtttgc tccatggaga 720
acacgcgcgc aaccaagatg caggtgatag gtgaccagta cgtcaaggtg tacctggagt 780
ccttctgcga ggacgtgccc tccggcaagc tctttatgca cgtcacgctg ggctctgacg 840
tggaagagga cctaacgatg acccgcaacc cgcaaccctt catgcgcccc cacgagcgca 900
acggctttac ggtgttgtgt cccaaaaata tgataatcaa accgggcaag atctcgcaca 960
tcatgctgga tgtggctttt acctcacacg agcattttgg gctgctgtgt cccaagagca 1020
tcccgggcct gagcatctca ggtaacctgt tgatgaacgg gcagcaaatc ttcctggagg 1080
tacaagcgat acgcgagacc gtggaactgc gtcagtacga tcccgtggct gcgctcttct 1140
ttttcgatat cgacttgttg ctgcagcgcg ggcctcagta cagcgagcac cccaccttca 1200
ccagccagta tcgcatccag ggcaagcttg agtaccgaca cacctgggac cggcacgacg 1260
agggtgccgc ccagggcgac gacgacgtct ggaccagcgg atcggactcc gacgaagaac 1320
tcgtaaccac cgagcgtaag acgccccgcg tcaccggcgg cggcgccatg gcgagcgcct 1380
ccacttccgc gggccgcaaa cgcaaatcag catcctcggc gacggcgtgc acggcgggcg 1440
ttatgacacg cggccgcctt aaggccgagt ccaccgtcgc gcccgaagag gacaccgacg 1500
aggattccga caacgaaatc cacaatccgg ccgtgttcac ctggccgccc tggcaggccg 1560
gcatcctggc ccgcaacctg gtgcccatgg tggctacggt tcagggtcag aatctgaagt 1620

```
accaggagtt cttctgggac gccaacgaca tctaccgcat cttcgccgaa ttggaaggcg   1680

tatggcagcc cgctgcgcaa cccaaacgtc gccgccaccg gcaagacgcc ttgcccgggc   1740

catgcatcgc ctcgacgccc aaaaagcacc gaggtgagtc ctctgccaag agaaagatgg   1800

accctgataa tcctgacgag ggcccttcct ccaaggtgcc acggcccgag acacccgtga   1860

ccaaggccac gacgttcctg cagactatgt taaggaagga ggttaacagt cagctgagcc   1920

tgggagaccc gctgttccca gaattggccg aagaatccct caaaaccttt gaacaagtga   1980

ccgaggattg caacgagaac cccgaaaaag atgtcctgac agaactcgtc aaacagatta   2040

aggttcgagt ggacatggtg cggcatagaa tcaaggagca catgctgaaa aaatataccc   2100

agacggaaga aaaattcact ggcgccttta atatgatggg aggatgtttg cagaatgcct   2160

tagatatctt agataaggtt catgagcctt tcgaggacat gaagtgtatt gggctaacta   2220

tgcagagcat gtatgagaac tacattgtac ctgaggataa gcgggagatg tggatggctt   2280

gtattaagga gctgcatgat gtgagcaagg gcgccgctaa caagttgggg ggtgcactgc   2340

aggctaaggc ccgtgctaaa aaggatgaac ttaggagaaa gatgatgtat atgtgctaca   2400

ggaatataga gttctttacc aagaactcag ccttccctaa gaccaccaat ggctgcagtc   2460

aggccatggc ggcattgcag aacttgcctc agtgctctcc tgatgagatt atgtcttatg   2520

cccagaaaat ctttaagatt ttggatgagg agagagacaa ggtgctcacg cacattgatc   2580

acatatttat ggatatcctc actacatgtg tggaaacaat gtgtaatgag tacaaggtca   2640

ctagtgacgc ttgtatgatg accatgtacg ggggcatctc tctcttaagt gagttctgtc   2700

gggtgctgtg ctgctatgtc ttagaggaga ctagtgtgat gctggccaag cggcctctga   2760

taaccaagcc tgaggttatc agtgtaatga agcgccgcat tgaggagatc tgcatgaagg   2820

tctttgccca gtacattctg gggcgccgatc ctttgagagt ctgctctcct agtgtggatg   2880

acctacgggc catcgccgag gagtcagatg aggaagaggc tattgtagcc tacactttgg   2940

ccaccgctgg tgccagctcc tctgattctc tggtgtcacc tccagagtcc cctgtacccg   3000

cgactatccc tctgtcctca gtaattgtgg ctgagaacag tgatcaggaa gaaagtgaac   3060

agagtgatga ggaacaggag gagggtgctc aggaggagcg ggaggacact gtgtctgtca   3120

agtctgagcc agtgtctgag atagaggaag ttgcctcaga ggaagaggag gatggtgctg   3180

aggaacccac cgcctctgga ggcaagagca cccaccctat ggtgactaga agcaaggctg   3240

accaggatta caaggacgat gacgataagt gataataggc tggagcctcg gtggccatgc   3300

ttcttgcccc ttgggcctcc ccccagcccc tcctcccctt cctgcacccg tacccccgtg   3360

gtctttgaat aaagtctgag tgggcggc                                       3388
```

<210> SEQ ID NO 29
<211> LENGTH: 3352
<212> TYPE: DNA
<213> ORGANISM: Artificial Sequence
<220> FEATURE:
<223> OTHER INFORMATION: Synthetic Polynucleotide

<400> SEQUENCE: 29

```
tcaagctttt ggaccctcgt acagaagcta atacgactca ctatagggaa ataagagaga     60

aaagaagagt aagaagaaat ataagagcca ccatgcggcc aggcctcccc tcctacctca    120

tcatcctcgc cgtctgtctc ttcagccacc tactttcgtc acgatatggc gcagaagccg    180

tatccgaacc gctggacaaa gcgtttcacc tactgctcaa cacctacggg agacccatcc    240
```

-continued

```
gcttcctgcg tgaaaatacc acccagtgta cctacaacag cagcctccgt aacagcacgg    300
tcgtcaggga aaacgccatc agtttcaact ttttccaaag ctataatcaa tactatgtat    360
tccatatgcc tcgatgtctt tttgcgggtc ctctggcgga gcagtttctg aaccaggtag    420
atctgaccga aaccctggaa agataccaac agagacttaa cacttacgcg ctggtatcca    480
aagacctggc cagctaccga tctttttcgc agcagctaaa ggcacaagac agcctaggtg    540
aacagcccac cactgtgcca ccgcccattg acctgtcaat acctcacgtt tggatgccac    600
cgcaaaccac tccacacggc tggacagaat cacataccac ctcaggacta caccgaccac    660
actttaacca gacctgtatc ctctttgatg gacacgatct actattcagc accgtcacac    720
cttgtttgca ccaaggcttt tacctcatcg acgaactacg ttacgttaaa ataacactga    780
ccgaggactt cttcgtagtt acggtgtcca tagacgacga cacacccatg ctgcttatct    840
tcggccatct tccacgcgta cttttcaaag cgccctatca acgcgacaac tttatactac    900
gacaaactga aaaacacgag ctcctggtgc tagttaagaa agatcaactg aaccgtcact    960
cttatctcaa agacccggac tttcttgacg ccgcacttga cttcaactac ctagacctca   1020
gcgcactact acgtaacagc tttcaccgtt acgccgtgga tgtactcaag agcggtcgat   1080
gtcagatgct ggaccgccgc acggtagaaa tggccttcgc ctacgcatta gcactgttcg   1140
cagcagcccg acaagaagag gccggcgccc aagtctccgt cccacgggcc ctagaccgcc   1200
aggccgcact cttacaaata caagaattta tgatcacctg cctctcacaa acaccaccac   1260
gcaccacgtt gctgctgtat cccacggccg tggacctggc caaacgagcc ctttggacac   1320
cgaatcagat caccgacatc accagcctcg tacgcctggt ctacatactc tctaaacaga   1380
atcagcaaca tctcatcccc caatgggcac tacgacagat cgccgacttt gccctaaaac   1440
tacacaaaac gcacctggcc tcttttcttt cagccttcgc acgccaagaa ctctacctca   1500
tgggcagcct cgtccactcc atgctggtac atacgacgga gagacgcgaa atcttcatcg   1560
tagaaacggg cctctgttca ttggccgagc tatcacactt tacgcagttg ttagctcatc   1620
cacaccacga atacctcagc gacctgtaca caccctgttc cagtagcggg cgacgcgatc   1680
actcgctcga acgcctcacg cgtctcttcc ccgatgccac cgtccccgct accgttcccg   1740
ccgccctctc catcctatct accatgcaac caagcacgct ggaaaccttc cccgacctgt   1800
tttgcttgcc gctcggcgaa tccttctccg cgctgaccgt ctccgaacac gtcagttata   1860
tcgtaacaaa ccagtacctg atcaaaggta tctcctaccc tgtctccacc accgtcgtag   1920
gccagagcct catcatcacc cagacggaca gtcaaactaa atgcgaactg acgcgcaaca   1980
tgcataccac acacagcatc acagtggcgc tcaacatttc gctagaaaac tgcgcctttt   2040
gccaaagcgc cctgctagaa tacgacgaca cgcaaggcgt catcaacatc atgtacatgc   2100
acgactcgga cgacgtcctt ttcgccctgg atccctacaa cgaagtggtg gtctcatctc   2160
cgcgaactca ctacctcatg cttttgaaaa acggtacggt actagaagta actgacgtcg   2220
tcgtggacgc caccgacagt cgtctcctca tgatgtccgt ctacgcgcta tcggccatca   2280
tcggcatcta tctgctctac cgcatgctca agacatgccg cgccaagagg agcggaagcg   2340
gagctactaa cttcagcctg ctgaagcagg ctggagacgt ggaggagaac cctggaccta   2400
tgtgccgccg cccggattgc ggcttctctt tctcacctgg accggtgata ctgctgtggt   2460
gttgccttct gctgcccatt gtttcctcag ccgccgtcag cgtcgctcct accgccgccg   2520
agaaagtccc cgcggagtgc cccgaactaa cgcgccgatg cttgttgggt gaggtgtttg   2580
agggtgacaa gtatgaaagt tggctgcgcc cgttggtgaa tgttaccggg cgcgatggcc   2640
```

cgctatcgca acttatccgt taccgtcccg ttacgccgga ggccgccaac tccgtgctgt 2700
tggacgaggc tttcctggac actctggccc tgctgtacaa caatccggat caattgcggg 2760
ccctgctgac gctgttgagc tcggacacag cgccgcgctg gatgacggtg atgcgcggct 2820
acagcgagtg cggcgatggc tcgccggccg tgtacacgtg cgtggacgac ctgtgccgcg 2880
gctacgacct cacgcgactg tcatacgggc gcagcatctt cacggaacac gtgttaggct 2940
tcgagctggt gccaccgtct ctctttaacg tggtggtggc catacgcaac gaagccacgc 3000
gtaccaaccg cgccgtgcgt ctgcccgtga gcaccgctgc cgcgcccgag ggcatcacgc 3060
tcttttacgg cctgtacaac gcagtgaagg aattctgcct gcgtcaccag ctggacccgc 3120
cgctgctacg ccacctagat aaatactacg ccggactgcc gcccgagctg aagcagacgc 3180
gcgtcaacct gccggctcac tcgcgctatg gccctcaagc agtggatgct cgctgataat 3240
aggctggagc ctcggtggcc atgcttcttg ccccttgggc ctccccccag cccctcctcc 3300
ccttcctgca cccgtacccc cgtggtcttt gaataaagtc tgagtgggcg gc 3352

<210> SEQ ID NO 30
<211> LENGTH: 1924
<212> TYPE: DNA
<213> ORGANISM: Artificial Sequence
<220> FEATURE:
<223> OTHER INFORMATION: Synthetic Polynucleotide

<400> SEQUENCE: 30
tcaagctttt ggaccctcgt acagaagcta atacgactca ctatagggaa ataagagaga 60
aaagaagagt aagaagaaat ataagagcca ccatgagtcc caaagatctg acgccgttct 120
tgacggcgtt gtggctgcta ttgggtcaca gccgcgtgcc gcgggtgcgc gcagaagaat 180
gttgcgaatt cataaacgtc aaccacccgc cggaacgctg ttacgatttc aaaatgtgca 240
atcgcttcac cgtcgcgctg cggtgtccgg acggcgaagt ctgctacagt cccgagaaaa 300
cggctgagat tcgcgggatc gtcaccacca tgacccattc attgacacgc caggtcgtac 360
acaacaaact gacgagctgc aactacaatc cgttatacct cgaagctgac gggcgaatac 420
gctgcggcaa agtaaacgac aaggcgcagt acctgctggg cgccgctggc agcgttccct 480
atcgatggat caatctggaa tacgacaaga taacccggat cgtgggcctg gatcagtacc 540
tggagagcgt taagaaacac aaacggctgg atgtgtgccg cgctaaaatg ggctatatgc 600
tgcagcgcgc caagaggagc ggaagcggag ctactaactt cagcctgctg aagcaggctg 660
gagacgtgga ggagaaccct ggacctatgc tgcggcttct gcttcgtcac cactttcact 720
gcctgcttct gtgcgcggtt tgggcaacgc cctgtctggc gtctccgtgg tcgacgctaa 780
cagcaaacca gaatccgtcc ccgccatggt ctaaactgac gtattccaaa ccgcatgacg 840
cggcgacgtt ttactgtcct tttctctatc cctcgccccc acgatccccc ttgcaattct 900
cggggttcca gcgggtatca acgggtcccg agtgtcgcaa cgagaccctg tatctgctgt 960
acaaccggga aggccagacc ttggtggaga gaagctccac ctgggtgaaa aaggtgatct 1020
ggtacctgag cggtcggaac caaaccatcc tccaacggat gccccgaacg gcttcgaaac 1080
cgagcgacgg aaacgtgcag atcagcgtgg aagacgccaa gatttttgga gcgcacatgg 1140
tgcccaagca gaccaagctg ctacgcttcg tcgtcaacga tggcacacgt tatcagatgt 1200
gtgtgatgaa gctggagagc tgggctcacg tcttccggga ctacagcgtg tcttttcagg 1260
tgcgattgac gttcaccgag gccaataacc agacttacac cttctgcacc catcccaatc 1320

```
tcatcgttcg cgccaagagg agcggaagcg gagtgaaaca gactttgaat tttgaccttc   1380

tcaagttggc gggagacgtg gagtccaacc ctggacctat gcggctgtgt cgggtgtggc   1440

tgtctgtttg tctgtgcgcc gtggtgctgg gtcagtgcca gcgggaaacc gcggaaaaaa   1500

acgattatta ccgagtaccg cattactggg acgcgtgctc tcgcgcgctg cccgaccaaa   1560

cccgttacaa gtatgtggaa cagctcgtgg acctcacgtt gaactaccac tacgatgcga   1620

gccacggctt ggacaacttt gacgtgctca agagaatcaa cgtgaccgag gtgtcgttgc   1680

tcatcagcga ctttagacgt cagaaccgtc gcggcggcac caacaaaagg accacgttca   1740

acgccgccgg ttcgctggcg ccacacgccc ggagcctcga gttcagcgtg cggctctttg   1800

ccaactgata ataggctgga gcctcggtgg ccatgcttct tgccccttgg gcctcccccc   1860

agcccctcct ccccttcctg cacccgtacc cccgtggtct ttgaataaag tctgagtggg   1920

cggc                                                                1924
```

<210> SEQ ID NO 31
<211> LENGTH: 5146
<212> TYPE: DNA
<213> ORGANISM: Artificial Sequence
<220> FEATURE:
<223> OTHER INFORMATION: Synthetic Polynucleotide

<400> SEQUENCE: 31

```
tcaagctttt ggaccctcgt acagaagcta atacgactca ctatagggaa ataagagaga     60

aaagaagagt aagaagaaat ataagagcca ccatgcggcc aggcctcccc tcctacctca    120

tcatcctcgc cgtctgtctc ttcagccacc tactttcgtc acgatatggc gcagaagccg    180

tatccgaacc gctggacaaa gcgtttcacc tactgctcaa cacctacggg agacccatcc    240

gcttcctgcg tgaaaatacc acccagtgta cctacaacag cagcctccgt aacagcacgg    300

tcgtcaggga aaacgccatc agtttcaact tttccaaag ctataatcaa tactatgtat    360

tccatatgcc tcgatgtctt tttgcgggtc ctctggcgga gcagtttctg aaccaggtag    420

atctgaccga aaccctggaa agataccaac agagacttaa cacttacgcg ctggtatcca    480

aagacctggc cagctaccga tctttttcgc agcagctaaa ggcacaagac agcctaggtg    540

aacagcccac cactgtgcca ccgcccattg acctgtcaat acctcacgtt tggatgccac    600

cgcaaaccac tccacacggc tggacagaat cacataccac ctcaggacta caccgaccac    660

actttaacca gacctgtatc ctctttgatg gacacgatct actattcagc accgtcacac    720

cttgtttgca ccaaggcttt tacctcatcg acgaactacg ttacgttaaa ataacactga    780

ccgaggactt cttcgtagtt acggtgtcca tagacgacga cacacccatg ctgcttatct    840

tcggccatct tccacgcgta cttttcaaag cgccctatca acgcgacaac tttatactac    900

gacaaactga aaaacacgag ctcctggtgc tagttaagaa agatcaactg aaccgtcact    960

cttatctcaa agacccggac tttcttgacg ccgcacttga cttcaactac ctagacctca   1020

gcgcactact acgtaacagc tttcaccgtt acgccgtgga tgtactcaag agcggtcgat   1080

gtcagatgct ggaccgccgc acggtagaaa tggccttcgc ctacgcatta gcactgttcg   1140

cagcagcccg acaagaagag gccggcgccc aagtctccgt cccacgggcc ctagaccgcc   1200

aggccgcact cttacaaata caagaattta tgatcacctg cctctcacaa acaccaccac   1260

gcaccacgtt gctgctgtat cccacggccg tggacctggc caaacgagcc ctttggacac   1320

cgaatcagat caccgacatc accagcctcg tacgcctggt ctacatactc tctaaacaga   1380

atcagcaaca tctcatcccc caatgggcac tacgacagat cgccgacttt gccctaaaac   1440
```

```
tacacaaaac gcacctggcc tcttttcttt cagccttcgc acgccaagaa ctctacctca   1500
tgggcagcct cgtccactcc atgctggtac atacgacgga gagacgcgaa atcttcatcg   1560
tagaaacggg cctctgttca ttggccgagc tatcacactt tacgcagttg ttagctcatc   1620
cacaccacga atacctcagc gacctgtaca caccctgttc cagtagcggg cgacgcgatc   1680
actcgctcga acgcctcacg cgtctcttcc ccgatgccac cgtccccgct accgttcccg   1740
ccgccctctc catcctatct accatgcaac caagcacgct ggaaaccttc cccgacctgt   1800
tttgcttgcc gctcggcgaa tccttctccg cgctgaccgt ctccgaacac gtcagttata   1860
tcgtaacaaa ccagtacctg atcaaaggta tctcctaccc tgtctccacc accgtcgtag   1920
gccagagcct catcatcacc cagacggaca gtcaaactaa atgcgaactg acgcgcaaca   1980
tgcataccac acacagcatc acagtggcgc tcaacatttc gctagaaaac tgcgcctttt   2040
gccaaagcgc cctgctagaa tacgacgaca cgcaaggcgt catcaacatc atgtacatgc   2100
acgactcgga cgacgtcctt ttcgccctgg atccctacaa cgaagtggtg gtctcatctc   2160
cgcgaactca ctacctcatg cttttgaaaa acggtacggt actagaagta actgacgtcg   2220
tcgtggacgc caccgacagt cgtctcctca tgatgtccgt ctacgcgcta tcggccatca   2280
tcggcatcta tctgctctac cgcatgctca agacatgccg cgccaagagg agcggaagcg   2340
gagctactaa cttcagcctg ctgaagcagg ctggagacgt ggaggagaac cctggaccta   2400
tgtgccgccg cccggattgc ggcttctctt tctcacctgg accggtgata ctgctgtggt   2460
gttgccttct gctgcccatt gtttcctcag ccgccgtcag cgtcgctcct accgccgccg   2520
agaaagtccc cgcggagtgc cccgaactaa cgcgccgatg cttgttgggt gaggtgtttg   2580
agggtgacaa gtatgaaagt tggctgcgcc cgttggtgaa tgttaccggg cgcgatggcc   2640
cgctatcgca acttatccgt taccgtcccg ttacgccgga ggccgccaac tccgtgctgt   2700
tggacgaggc tttcctggac actctggccc tgctgtacaa caatccggat caattgcggg   2760
ccctgctgac gctgttgagc tcggacacag cgccgcgctg gatgacggtg atgcgcggct   2820
acagcgagtg cggcgatggc tcgccggccg tgtacacgtg cgtggacgac ctgtgccgcg   2880
gctacgacct cacgcgactg tcatacgggc gcagcatctt cacggaacac gtgttaggct   2940
tcgagctggt gccaccgtct ctctttaacg tggtggtggc catacgcaac gaagccacgc   3000
gtaccaaccg cgccgtgcgt ctgcccgtga gcaccgctgc cgcgcccgag ggcatcacgc   3060
tcttttacgg cctgtacaac gcagtgaagg aattctgcct gcgtcaccag ctggacccgc   3120
cgctgctacg ccacctagat aaatactacg ccggactgcc gcccgagctg aagcagacgc   3180
gcgtcaacct gccggctcac tcgcgctatg gccctcaagc agtggatgct cgccgcgcca   3240
agaggagcgg aagcggagtg aaacagactt tgaattttga ccttctcaag ttggcgggag   3300
acgtggagtc caaccctgga cctatgagtc ccaaagatct gacgccgttc ttgacggcgt   3360
tgtggctgct attgggtcac agccgcgtgc cgcgggtgcg cgcagaagaa tgttgcgaat   3420
tcataaacgt caaccacccg ccggaacgct gttacgattt caaaatgtgc aatcgcttca   3480
ccgtcgcgct gcggtgtccg gacggcgaag tctgctacag tcccgagaaa acggctgaga   3540
ttcgcgggat cgtcaccacc atgacccatt cattgacacg ccaggtcgta cacaacaaac   3600
tgacgagctg caactacaat ccgttatacc tcgaagctga cgggcgaata cgctgcggca   3660
aagtaaacga caaggcgcag tacctgctgg gcgccgctgg cagcgttccc tatcgatgga   3720
tcaatctgga atacgacaag ataacccgga tcgtgggcct ggatcagtac ctggagagcg   3780
```

ttaagaaaca caaacggctg gatgtgtgcc gcgctaaaat gggctatatg ctgcagcgcg 3840
ccaagaggag cggaagcgga cagtgtacta attatgctct cttgaaattg gctggagatg 3900
ttgagagcaa ccctggacct atgctgcggc ttctgcttcg tcaccacttt cactgcctgc 3960
ttctgtgcgc ggtttgggca acgccctgtc tggcgtctcc gtggtcgacg ctaacagcaa 4020
accagaatcc gtccccgcca tggtctaaac tgacgtattc caaaccgcat gacgcggcga 4080
cgttttactg tccttttctc tatccctcgc ccccacgatc cccccttgcaa ttctcggggt 4140 tccagcgggt atcaacgggt cccgagtgtc gcaacgagac cctgtatctg ctgtacaacc 4200
gggaaggcca gaccttggtg gagagaagct ccacctgggt gaaaaaggtg atctggtacc 4260
tgagcggtcg gaaccaaacc atcctccaac ggatgccccg aacggcttcg aaaccgagcg 4320
acggaaacgt gcagatcagc gtggaagacg ccaagatttt tggagcgcac atggtgccca 4380
agcagaccaa gctgctacgc ttcgtcgtca acgatggcac acgttatcag atgtgtgtga 4440
tgaagctgga gagctgggct cacgtcttcc gggactacag cgtgtctttt caggtgcgat 4500
tgacgttcac cgaggccaat aaccagactt acaccttctg cacccatccc aatctcatcg 4560
ttcgcgccaa gaggagcgga agcggagagg gcagaggaag tctgctaaca tgcggtgacg 4620
tcgaggagaa tcctggacct atgcggctgt gtcgggtgtg gctgtctgtt tgtctgtgcg 4680
ccgtggtgct gggtcagtgc cagcgggaaa ccgcggaaaa aaacgattat taccgagtac 4740
cgcattactg ggacgcgtgc tctcgcgcgc tgcccgacca aacccgttac aagtatgtgg 4800
aacagctcgt ggacctcacg ttgaactacc actacgatgc gagccacggc ttggacaact 4860
ttgacgtgct caagagaatc aacgtgaccg aggtgtcgtt gctcatcagc gactttagac 4920
gtcagaaccg tcgcggcggc accaacaaaa ggaccacgtt caacgccgcc ggttcgctgg 4980
cgccacacgc ccggagcctc gagttcagcg tgcggctctt tgccaactga taataggctg 5040
gagcctcggt ggccatgctt cttgcccctt gggcctcccc ccagcccctc ctccccttcc 5100
tgcacccgta cccccgtggt ctttgaataa agtctgagtg ggcggc 5146

<210> SEQ ID NO 32
<211> LENGTH: 742
<212> TYPE: PRT
<213> ORGANISM: Human Cytomegalovirus

<400> SEQUENCE: 32

Met Arg Pro Gly Leu Pro Ser Tyr Leu Ile Ile Leu Ala Val Cys Leu
1 5 10 15

Phe Ser His Leu Leu Ser Ser Arg Tyr Gly Ala Glu Ala Val Ser Glu
20 25 30

Pro Leu Asp Lys Ala Phe His Leu Leu Leu Asn Thr Tyr Gly Arg Pro
35 40 45

Ile Arg Phe Leu Arg Glu Asn Thr Thr Gln Cys Thr Tyr Asn Ser Ser
50 55 60

Leu Arg Asn Ser Thr Val Val Arg Glu Asn Ala Ile Ser Phe Asn Phe
65 70 75 80

Phe Gln Ser Tyr Asn Gln Tyr Tyr Val Phe His Met Pro Arg Cys Leu
85 90 95

Phe Ala Gly Pro Leu Ala Glu Gln Phe Leu Asn Gln Val Asp Leu Thr
100 105 110

Glu Thr Leu Glu Arg Tyr Gln Gln Arg Leu Asn Thr Tyr Ala Leu Val
115 120 125

Ser Lys Asp Leu Ala Ser Tyr Arg Ser Phe Ser Gln Gln Leu Lys Ala

```
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480

Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560
```

Ser Thr Leu Glu Thr Phe Pro Asp Leu Phe Cys Leu Pro Leu Gly Glu
565 570 575

Ser Phe Ser Ala Leu Thr Val Ser Glu His Val Ser Tyr Ile Val Thr
580 585 590

Asn Gln Tyr Leu Ile Lys Gly Ile Ser Tyr Pro Val Ser Thr Thr Val
595 600 605

Val Gly Gln Ser Leu Ile Ile Thr Gln Thr Asp Ser Gln Thr Lys Cys
610 615 620

Glu Leu Thr Arg Asn Met His Thr Thr His Ser Ile Thr Val Ala Leu
625 630 635 640

Asn Ile Ser Leu Glu Asn Cys Ala Phe Cys Gln Ser Ala Leu Leu Glu
645 650 655

Tyr Asp Asp Thr Gln Gly Val Ile Asn Ile Met Tyr Met His Asp Ser
660 665 670

Asp Asp Val Leu Phe Ala Leu Asp Pro Tyr Asn Glu Val Val Val Ser
675 680 685

Ser Pro Arg Thr His Tyr Leu Met Leu Leu Lys Asn Gly Thr Val Leu
690 695 700

Glu Val Thr Asp Val Val Val Asp Ala Thr Asp Ser Arg Leu Leu Met
705 710 715 720

Met Ser Val Tyr Ala Leu Ser Ala Ile Ile Gly Ile Tyr Leu Leu Tyr
725 730 735

Arg Met Leu Lys Thr Cys
740

<210> SEQ ID NO 33
<211> LENGTH: 310
<212> TYPE: PRT
<213> ORGANISM: Human Cytomegalovirus

<400> SEQUENCE: 33

Met Pro Ala Thr Asp Thr Asn Ser Thr His Thr Thr Pro Leu His Pro
1 5 10 15

Glu Asn Gln His Thr Leu Pro Leu His His Ser Thr Thr Gln Pro His
20 25 30

Val Gln Thr Ser Asp Lys His Ala Asp Lys Gln His Arg Thr Gln Met
35 40 45

Glu Leu Asp Ala Ala Asp Tyr Ala Ala Cys Ala Gln Ala Arg Gln His
50 55 60

Leu Tyr Gly Gln Thr Gln Pro Gln Pro His Ala Tyr Pro Asn Ala Asn
65 70 75 80

Pro Gln Glu Ser Ala His Phe Cys Thr Glu Asn Gln His Gln Leu Thr
85 90 95

Asn Leu Leu His Asn Ile Gly Glu Gly Ala Ala Leu Gly Tyr Pro Val
100 105 110

Pro Arg Ala Glu Ile Arg Arg Gly Gly Gly Asp Trp Ala Asp Ser Ala
115 120 125

Ser Asp Phe Asp Ala Asp Cys Trp Cys Met Trp Gly Arg Phe Gly Thr
130 135 140

Met Gly Arg Gln Pro Val Val Thr Leu Leu Leu Ala Arg Gln Arg Asp
145 150 155 160

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val

```
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 34
<211> LENGTH: 310
<212> TYPE: PRT
<213> ORGANISM: Human Cytomegalovirus

<400> SEQUENCE: 34

Met Pro Ala Thr Asp Thr Asn Ser Thr His Thr Thr Pro Leu His Pro
1               5                   10                  15

Glu Asp Gln His Thr Leu Pro Leu Gln His Asn Thr Thr Gln Pro His
            20                  25                  30

Val Gln Thr Ser Asp Lys Pro Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Cys Thr Asp Asn Gln His Arg Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Val Ser Thr Ser Pro Arg Pro Lys Ala Pro Gln Pro Thr Thr Ser
225                 230                 235                 240
```

```
Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 35
<211> LENGTH: 466
<212> TYPE: PRT
<213> ORGANISM: Human Cytomegalovirus

<400> SEQUENCE: 35

Met Gly Arg Lys Glu Met Met Val Arg Asp Val Pro Lys Met Val Phe
1               5                   10                  15

Leu Ile Ser Ile Ser Phe Leu Leu Val Ser Phe Ile Asn Cys Lys Val
            20                  25                  30

Met Ser Lys Ala Leu Tyr Asn Arg Pro Trp Arg Gly Leu Val Leu Ser
        35                  40                  45

Lys Ile Gly Lys Tyr Lys Leu Asp Gln Leu Lys Leu Glu Ile Leu Arg
    50                  55                  60

Gln Leu Glu Thr Thr Ile Ser Thr Lys Tyr Asn Val Ser Lys Gln Pro
65                  70                  75                  80

Val Lys Asn Leu Thr Met Asn Met Thr Glu Phe Pro Gln Tyr Tyr Ile
                85                  90                  95

Leu Ala Gly Pro Ile Gln Asn Tyr Ser Ile Thr Tyr Leu Trp Phe Asp
            100                 105                 110

Phe Tyr Ser Thr Gln Leu Arg Lys Pro Ala Lys Tyr Val Tyr Ser Gln
        115                 120                 125

Tyr Asn His Thr Ala Lys Thr Ile Thr Phe Arg Pro Pro Pro Cys Gly
    130                 135                 140

Thr Val Pro Ser Met Thr Cys Leu Ser Glu Met Leu Asn Val Ser Lys
145                 150                 155                 160

Arg Asn Asp Thr Gly Glu Gln Gly Cys Gly Asn Phe Thr Thr Phe Asn
                165                 170                 175

Pro Met Phe Phe Asn Val Pro Arg Trp Asn Thr Lys Leu Tyr Val Gly
            180                 185                 190

Pro Thr Lys Val Asn Val Asp Ser Gln Thr Ile Tyr Phe Leu Gly Leu
        195                 200                 205

Thr Ala Leu Leu Leu Arg Tyr Ala Gln Arg Asn Cys Thr His Ser Phe
    210                 215                 220

Tyr Leu Val Asn Ala Met Ser Arg Asn Leu Phe Arg Val Pro Lys Tyr
225                 230                 235                 240

Ile Asn Gly Thr Lys Leu Lys Asn Thr Met Arg Lys Leu Lys Arg Lys
                245                 250                 255

Gln Ala Pro Val Lys Glu Gln Phe Glu Lys Lys Ala Lys Lys Thr Gln
            260                 265                 270

Ser Thr Thr Thr Pro Tyr Phe Ser Tyr Thr Thr Ser Ala Ala Leu Asn
        275                 280                 285

Val Thr Thr Asn Val Thr Tyr Ser Ile Thr Thr Ala Ala Arg Arg Val
    290                 295                 300
```

```
Ser Thr Ser Thr Ile Ala Tyr Arg Pro Asp Ser Ser Phe Met Lys Ser
305                 310                 315                 320

Ile Met Ala Thr Gln Leu Arg Asp Leu Ala Thr Trp Val Tyr Thr Thr
                325                 330                 335

Leu Arg Tyr Arg Gln Asn Pro Phe Cys Glu Pro Ser Arg Asn Arg Thr
            340                 345                 350

Ala Val Ser Glu Phe Met Lys Asn Thr His Val Leu Ile Arg Asn Glu
        355                 360                 365

Thr Pro Tyr Thr Ile Tyr Gly Thr Leu Asp Met Ser Ser Leu Tyr Tyr
    370                 375                 380

Asn Glu Thr Met Phe Val Glu Asn Lys Thr Ala Ser Asp Ser Asn Lys
385                 390                 395                 400

Thr Thr Pro Thr Ser Pro Ser Met Gly Phe Gln Arg Thr Phe Ile Asp
                405                 410                 415

Pro Leu Trp Asp Tyr Leu Asp Ser Leu Leu Phe Leu Asp Glu Ile Arg
            420                 425                 430

Asn Phe Ser Leu Arg Ser Pro Thr Tyr Val Asn Leu Thr Pro Pro Glu
        435                 440                 445

His Arg Arg Ala Val Asn Leu Ser Thr Leu Asn Ser Leu Trp Trp Trp
    450                 455                 460

Leu Gln
465


<210> SEQ ID NO 36
<211> LENGTH: 135
<212> TYPE: PRT
<213> ORGANISM: Human Cytomegalovirus

<400> SEQUENCE: 36

Met Glu Cys Asn Thr Leu Val Leu Gly Leu Leu Val Leu Ser Val Val
1               5                   10                  15

Ala Ser Ser Asn Asn Thr Ser Thr Ala Ser Thr Pro Arg Pro Ser Ser
            20                  25                  30

Ser Thr His Ala Ser Thr Thr Val Lys Ala Thr Thr Val Ala Thr Thr
        35                  40                  45

Ser Thr Thr Thr Ala Thr Ser Thr Ser Ser Thr Thr Ser Ala Lys Pro
    50                  55                  60

Gly Phe Thr Thr His Asp Pro Asn Val Met Arg Pro His Ala His Asn
65                  70                  75                  80

Asp Phe Tyr Asn Ala His Cys Thr Ser His Met Tyr Glu Leu Ser Leu
                85                  90                  95

Ser Ser Phe Ala Ala Trp Trp Thr Met Leu Asn Ala Leu Ile Leu Met
            100                 105                 110

Gly Ala Phe Cys Ile Val Leu Arg His Cys Cys Phe Gln Asn Phe Thr
        115                 120                 125

Ala Thr Thr Thr Lys Gly Tyr
    130                 135


<210> SEQ ID NO 37
<211> LENGTH: 372
<212> TYPE: PRT
<213> ORGANISM: Human Cytomegalovirus

<400> SEQUENCE: 37

Met Ala Pro Ser His Val Asp Lys Val Asn Thr Arg Thr Trp Ser Ala
1               5                   10                  15
```

```
Ser Ile Val Phe Met Val Leu Thr Phe Val Asn Val Ser Val His Leu
            20                  25                  30

Val Leu Ser Asn Phe Pro His Leu Gly Tyr Pro Cys Val Tyr Tyr His
        35                  40                  45

Val Val Asp Phe Glu Arg Leu Asn Met Ser Ala Tyr Asn Val Met His
    50                  55                  60

Leu His Thr Pro Met Leu Phe Leu Asp Ser Val Gln Leu Val Cys Tyr
65                  70                  75                  80

Ala Val Phe Met Gln Leu Val Phe Leu Ala Val Thr Ile Tyr Tyr Leu
                85                  90                  95

Val Cys Trp Ile Lys Ile Ser Met Arg Lys Asp Lys Gly Met Ser Leu
            100                 105                 110

Asn Gln Ser Thr Arg Asp Ile Ser Tyr Met Gly Asp Ser Leu Thr Ala
        115                 120                 125

Phe Leu Phe Ile Leu Ser Met Asp Thr Phe Gln Leu Phe Thr Leu Thr
    130                 135                 140

Met Ser Phe Arg Leu Pro Ser Met Ile Ala Phe Met Ala Ala Val His
145                 150                 155                 160

Phe Phe Cys Leu Thr Ile Phe Asn Val Ser Met Val Thr Gln Tyr Arg
                165                 170                 175

Ser Tyr Lys Arg Ser Leu Phe Phe Phe Ser Arg Leu His Pro Lys Leu
            180                 185                 190

Lys Gly Thr Val Gln Phe Arg Thr Leu Ile Val Asn Leu Val Glu Val
        195                 200                 205

Ala Leu Gly Phe Asn Thr Thr Val Val Ala Met Ala Leu Cys Tyr Gly
    210                 215                 220

Phe Gly Asn Asn Phe Phe Val Arg Thr Gly His Met Val Leu Ala Val
225                 230                 235                 240

Phe Val Val Tyr Ala Ile Ile Ser Ile Ile Tyr Phe Leu Leu Ile Glu
                245                 250                 255

Ala Val Phe Phe Gln Tyr Val Lys Val Gln Phe Gly Tyr His Leu Gly
            260                 265                 270

Ala Phe Phe Gly Leu Cys Gly Leu Ile Tyr Pro Ile Val Gln Tyr Asp
        275                 280                 285

Thr Phe Leu Ser Asn Glu Tyr Arg Thr Gly Ile Ser Trp Ser Phe Gly
    290                 295                 300

Met Leu Phe Phe Ile Trp Ala Met Phe Thr Thr Cys Arg Ala Val Arg
305                 310                 315                 320

Tyr Phe Arg Gly Arg Gly Ser Gly Ser Val Lys Tyr Gln Ala Leu Ala
                325                 330                 335

Thr Ala Ser Gly Glu Glu Val Ala Val Leu Ser His His Asp Ser Leu
            340                 345                 350

Glu Ser Arg Arg Leu Arg Glu Glu Glu Asp Asp Asp Asp Asp Glu Asp
        355                 360                 365

Phe Glu Asp Ala
    370


<210> SEQ ID NO 38
<211> LENGTH: 171
<212> TYPE: PRT
<213> ORGANISM: Human Cytomegalovirus

<400> SEQUENCE: 38

Met Ser Pro Lys Asp Leu Thr Pro Phe Leu Thr Ala Leu Trp Leu Leu
```

```
1               5                   10                  15

Leu Gly His Ser Arg Val Leu Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170


<210> SEQ ID NO 39
<211> LENGTH: 171
<212> TYPE: PRT
<213> ORGANISM: Human Cytomegalovirus

<400> SEQUENCE: 39

Met Ser Pro Lys Asp Leu Thr Pro Phe Leu Thr Ala Leu Trp Leu Leu
1               5                   10                  15

Leu Gly His Ser Arg Val Leu Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170


<210> SEQ ID NO 40
<211> LENGTH: 304
<212> TYPE: PRT
<213> ORGANISM: Human Cytomegalovirus
```

<400> SEQUENCE: 40

Met Pro Ala Thr Asp Thr Asn Ser Thr His Thr Thr Pro Leu His Pro
1               5                   10                  15

Glu His His His Ser Thr Thr Gln Pro His Ala Gln Thr Ser Asp Lys
            20                  25                  30

His Ala Asp Lys Gln His Arg Thr Gln Met Glu Leu Asp Ala Ala Asp
        35                  40                  45

Tyr Ala Ala Cys Ala Gln Ala Arg Gln His Leu Tyr Gly Gln Thr Gln
    50                  55                  60

Pro Gln Leu His Ala Tyr Pro Asn Ala Asn Pro Gln Glu Ser Ala His
65                  70                  75                  80

Phe Cys Thr Glu Asn Gln His Gln Leu Thr Asn Leu Leu His Asn Ile
                85                  90                  95

Gly Glu Gly Ala Ala Leu Gly Tyr Pro Val Pro Arg Ala Glu Ile Arg
            100                 105                 110

Arg Gly Gly Gly Asp Trp Ala Asp Ser Ala Ser Asp Phe Asp Ala Asp
        115                 120                 125

Cys Trp Cys Met Trp Gly Arg Phe Gly Thr Met Gly Arg Gln Pro Val
    130                 135                 140

Val Thr Leu Leu Leu Ala Arg Gln Arg Asp Gly Leu Ala Asp Trp Asn
145                 150                 155                 160

Val Val Arg Cys Arg Gly Thr Gly Phe Arg Ala His Asp Ser Glu Asp
                165                 170                 175

Gly Val Ser Val Trp Arg Gln His Leu Val Phe Leu Leu Gly Gly His
            180                 185                 190

Gly Arg Arg Val Gln Leu Glu Arg Pro Ser Ala Gly Glu Ala Gln Ala
        195                 200                 205

Arg Gly Leu Leu Pro Arg Ile Arg Ile Thr Pro Ile Ser Thr Ser Pro
    210                 215                 220

Arg Pro Lys Pro Pro Gln Pro Thr Thr Ser Thr Ala Ser His Pro His
225                 230                 235                 240

Ala Thr Ala Arg Pro Asp His Thr Leu Phe Pro Val Pro Ser Thr Pro
                245                 250                 255

Ser Ala Thr Val His Asn Pro Arg Asn Tyr Ala Val Gln Leu His Ala
            260                 265                 270

Glu Thr Thr Arg Thr Trp Arg Trp Ala Arg Arg Gly Glu Arg Gly Ala
        275                 280                 285

Trp Met Pro Ala Glu Thr Phe Thr Cys Pro Lys Asp Lys Arg Pro Trp
    290                 295                 300

<210> SEQ ID NO 41
<211> LENGTH: 310
<212> TYPE: PRT
<213> ORGANISM: Human Cytomegalovirus

<400> SEQUENCE: 41

Met Pro Ala Thr Asp Thr Asn Ser Thr His Thr Thr Pro Leu His Pro
1               5                   10                  15

Glu Asp Gln His Thr Leu Pro Leu His His Ser Thr Thr Gln Pro His
            20                  25                  30

Val Gln Thr Ser Asp Lys His Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65 70 75 80

Pro Gln Glu Ser Ala His Phe Arg Thr Glu Asn Gln His Gln Leu Thr
85 90 95

Asn Leu Leu His Asn Ile Gly Glu Gly Ala Ala Leu Gly Tyr Pro Val
100 105 110

Pro Arg Ala Glu Ile Arg Arg Gly Gly Gly Asp Trp Ala Asp Ser Ala
115 120 125

Ser Asp Phe Asp Ala Asp Cys Trp Cys Met Trp Gly Arg Phe Gly Thr
130 135 140

Met Gly Arg Gln Pro Val Val Thr Leu Leu Leu Ala Arg Gln Arg Asp
145 150 155 160

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val
180 185 190

Phe Leu Leu Gly Gly His Gly Arg Arg Val Gln Leu Glu Arg Pro Ser
195 200 205

Ala Gly Glu Ala Gln Ala Arg Gly Leu Leu Pro Arg Ile Arg Ile Thr
210 215 220

Pro Ile Ser Thr Ser Pro Arg Pro Lys Pro Pro Gln Pro Thr Thr Ser
225 230 235 240

Thr Ala Ser His Pro His Ala Thr Ala Arg Pro Asp His Thr Leu Phe
245 250 255

Pro Val Pro Ser Thr Pro Ser Ala Thr Val His Asn Pro Arg Asn Tyr
260 265 270

Ala Val Gln Leu His Ala Glu Thr Thr Arg Thr Trp Arg Trp Ala Arg
275 280 285

Arg Gly Glu Arg Gly Ala Trp Met Pro Ala Glu Thr Phe Thr Cys Pro
290 295 300

Lys Asp Lys Arg Pro Trp
305 310

<210> SEQ ID NO 42
<211> LENGTH: 129
<212> TYPE: PRT
<213> ORGANISM: Human Cytomegalovirus

<400> SEQUENCE: 42

Met Arg Leu Cys Arg Val Trp Leu Ser Val Cys Leu Cys Ala Val Val
1 5 10 15

Leu Gly Gln Cys Gln Arg Glu Thr Ala Glu Lys Asn Asp Tyr Tyr Arg
20 25 30

Val Pro His Tyr Trp Asp Ala Cys Ser Arg Ala Leu Pro Asp Gln Thr
35 40 45

Arg Tyr Lys Tyr Val Glu Gln Leu Val Asp Leu Thr Leu Asn Tyr His
50 55 60

Tyr Asp Ala Ser His Gly Leu Asp Asn Phe Asp Val Leu Lys Arg Ile
65 70 75 80

Asn Val Thr Glu Val Ser Leu Leu Ile Ser Asp Phe Arg Arg Gln Asn
85 90 95

Arg Arg Gly Gly Thr Asn Lys Arg Thr Thr Phe Asn Ala Ala Gly Ser
100 105 110

Leu Ala Pro His Ala Arg Ser Leu Glu Phe Ser Val Arg Leu Phe Ala
115 120 125

Asn

<210> SEQ ID NO 43
<211> LENGTH: 129
<212> TYPE: PRT
<213> ORGANISM: Human Cytomegalovirus

<400> SEQUENCE: 43

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn

<210> SEQ ID NO 44
<211> LENGTH: 310
<212> TYPE: PRT
<213> ORGANISM: Human Cytomegalovirus

<400> SEQUENCE: 44

Met Pro Ala Thr Asp Thr Asn Ser Thr His Thr Thr Pro Leu His Pro
1               5                   10                  15

Glu Asp Gln His Thr Leu Pro Leu His His Ser Thr Thr Gln Pro His
            20                  25                  30

Val Gln Thr Ser Asp Lys His Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Arg Thr Glu Asn Gln His Gln Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val

```
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 45
<211> LENGTH: 310
<212> TYPE: PRT
<213> ORGANISM: Human Cytomegalovirus

<400> SEQUENCE: 45

Met Pro Ala Thr Asp Thr Asn Ser Thr His Thr Thr Pro Leu His Pro
1               5                   10                  15

Glu Asp Gln His Thr Leu Pro Leu His His Ser Thr Thr Gln Pro His
            20                  25                  30

Val Gln Thr Ser Asp Lys His Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Arg Thr Glu Asn Gln His Gln Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Ile Ser Thr Ser Pro Arg Pro Lys Pro Pro Gln Pro Thr Thr Ser
225                 230                 235                 240
```

-continued

```
Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300

Lys Asp Lys Arg Pro Trp
305                 310


<210> SEQ ID NO 46
<211> LENGTH: 310
<212> TYPE: PRT
<213> ORGANISM: Human Cytomegalovirus

<400> SEQUENCE: 46

Met Pro Ala Thr Asp Thr Asn Ser Thr His Thr Thr Pro Leu His Pro
1               5                   10                  15

Glu Asp Gln His Thr Leu Pro Leu Gln His Asn Thr Thr Gln Pro His
            20                  25                  30

Val Gln Thr Ser Asp Lys Pro Ala Asp Lys Gln His Arg Thr Gln Met
        35                  40                  45

Glu Leu Asp Ala Ala Asp Tyr Ala Ala Cys Ala Gln Ala Arg Gln His
    50                  55                  60

Leu Tyr Gly Gln Thr Gln Pro Gln Leu His Ala Tyr Pro Asn Ala Asn
65                  70                  75                  80

Pro Gln Glu Ser Ala His Phe Cys Thr Asp Asn Gln His Arg Leu Thr
                85                  90                  95

Asn Leu Leu His Asn Ile Gly Glu Gly Ala Ala Leu Gly Tyr Pro Val
            100                 105                 110

Pro Arg Ala Glu Ile Arg Arg Gly Gly Gly Asp Trp Ala Asp Ser Ala
        115                 120                 125

Ser Asp Phe Asp Ala Asp Cys Trp Cys Met Trp Gly Arg Phe Gly Thr
    130                 135                 140

Met Gly Arg Gln Pro Val Val Thr Leu Leu Leu Ala Arg Gln Arg Asp
145                 150                 155                 160

Gly Leu Ala Asp Trp Asn Val Val Arg Cys Arg Gly Thr Gly Phe Arg
                165                 170                 175

Ala His Asp Ser Glu Asp Gly Val Ser Val Trp Arg Gln His Leu Val
            180                 185                 190

Phe Leu Leu Gly Gly His Gly Arg Arg Val Gln Leu Glu Arg Pro Ser
        195                 200                 205

Ala Gly Glu Ala Gln Ala Arg Gly Leu Leu Pro Arg Ile Arg Ile Thr
    210                 215                 220

Pro Val Ser Thr Ser Pro Arg Pro Lys Ala Pro Gln Pro Thr Thr Ser
225                 230                 235                 240

Thr Ala Ser His Pro His Ala Thr Ala Arg Pro Asp His Thr Leu Phe
                245                 250                 255

Pro Val Pro Ser Thr Pro Ser Ala Thr Val His Asn Pro Arg Asn Tyr
            260                 265                 270

Ala Val Gln Leu His Ala Glu Thr Thr Arg Thr Trp Arg Trp Ala Arg
        275                 280                 285

Arg Gly Glu Arg Gly Ala Trp Met Pro Ala Glu Thr Phe Thr Cys Pro
    290                 295                 300
```

Lys Asp Lys Arg Pro Trp
305 310

<210> SEQ ID NO 47
<211> LENGTH: 310
<212> TYPE: PRT
<213> ORGANISM: Human Cytomegalovirus

<400> SEQUENCE: 47

Met Pro Ala Thr Asp Thr Asn Ser Thr His Thr Thr Pro Leu His Pro
1 5 10 15

Glu Asp Gln His Thr Leu Pro Leu His His Ser Thr Thr Gln Pro His
20 25 30

Val Gln Thr Ser Asp Lys His Ala Asp Lys Gln His Arg Thr Gln Met
35 40 45

Glu Leu Asp Ala Ala Asp Tyr Ala Ala Cys Ala Gln Ala Arg Gln His
50 55 60

Leu Tyr Gly Gln Thr Gln Pro Gln Leu His Ala Tyr Pro Asn Ala Asn
65 70 75 80

Pro Gln Glu Ser Ala His Phe Arg Thr Glu Asn Gln His Gln Leu Thr
85 90 95

Asn Leu Leu His Asn Ile Gly Glu Gly Ala Ala Leu Gly Tyr Pro Val
100 105 110

Pro Arg Ala Glu Ile Arg Arg Gly Gly Gly Asp Trp Ala Asp Ser Ala
115 120 125

Ser Asp Phe Asp Ala Asp Cys Trp Cys Met Trp Gly Arg Phe Gly Thr
130 135 140

Met Gly Arg Gln Pro Val Val Thr Leu Leu Leu Ala Arg Gln Arg Asp
145 150 155 160

Gly Leu Ala Asp Trp Asn Val Val Arg Cys Arg Gly Thr Gly Phe Arg
165 170 175

Ala His Asp Ser Glu Asp Gly Val Ser Val Trp Arg Gln His Leu Val
180 185 190

Phe Leu Leu Gly Gly His Gly Arg Arg Val Gln Leu Glu Arg Pro Ser
195 200 205

Ala Gly Glu Ala Gln Ala Arg Gly Leu Leu Pro Arg Ile Arg Ile Thr
210 215 220

Pro Ile Ser Thr Ser Pro Arg Pro Lys Pro Pro Gln Pro Thr Thr Ser
225 230 235 240

Thr Ala Ser His Pro His Ala Thr Ala Arg Pro Asp His Thr Leu Phe
245 250 255

Pro Val Pro Ser Thr Pro Ser Ala Thr Val His Asn Pro Arg Asn Tyr
260 265 270

Ala Val Gln Leu His Ala Glu Thr Thr Arg Thr Trp Arg Trp Ala Arg
275 280 285

Arg Gly Glu Arg Gly Ala Trp Met Pro Ala Glu Thr Phe Thr Cys Pro
290 295 300

Lys Asp Lys Arg Pro Trp
305 310

<210> SEQ ID NO 48
<211> LENGTH: 760
<212> TYPE: PRT
<213> ORGANISM: Artificial Sequence
<220> FEATURE:
<223> OTHER INFORMATION: Synthetic Polypeptide

<400> SEQUENCE: 48

Ser Ser Phe Trp Thr Leu Val Gln Lys Leu Ile Arg Leu Thr Ile Gly
1 5 10 15

Lys Glu Arg Lys Glu Glu Glu Glu Ile Glu Pro Pro Cys Gly Gln Ala
20 25 30

Ser Pro Pro Thr Ser Ser Ser Ser Pro Ser Val Ser Ser Ala Thr Tyr
35 40 45

Phe Arg His Asp Met Ala Gln Lys Pro Tyr Pro Asn Arg Trp Thr Lys
50 55 60

Arg Phe Thr Tyr Cys Ser Thr Pro Thr Gly Asp Pro Ser Ala Ser Cys
65 70 75 80

Val Lys Ile Pro Pro Ser Val Pro Thr Thr Ala Ala Ser Val Thr Ala
85 90 95

Arg Ser Ser Gly Lys Thr Pro Ser Val Ser Thr Phe Ser Lys Ala Ile
100 105 110

Ile Asn Thr Met Tyr Ser Ile Cys Leu Asp Val Phe Leu Arg Val Leu
115 120 125

Trp Arg Ser Ser Phe Thr Arg Ile Pro Lys Pro Trp Lys Asp Thr Asn
130 135 140

Arg Asp Leu Thr Leu Thr Arg Trp Tyr Pro Lys Thr Trp Pro Ala Thr
145 150 155 160

Asp Leu Phe Arg Ser Ser Arg His Lys Thr Ala Val Asn Ser Pro Pro
165 170 175

Leu Cys His Arg Pro Leu Thr Cys Gln Tyr Leu Thr Phe Gly Cys His
180 185 190

Arg Lys Pro Leu His Thr Ala Gly Gln Asn His Ile Pro Pro Gln Asp
195 200 205

Tyr Thr Asp His Thr Leu Thr Arg Pro Val Ser Ser Leu Met Asp Thr
210 215 220

Ile Tyr Tyr Ser Ala Pro Ser His Leu Val Cys Thr Lys Ala Phe Thr
225 230 235 240

Ser Ser Thr Asn Tyr Val Thr Leu Lys His Pro Arg Thr Ser Ser Leu
245 250 255

Arg Cys Pro Thr Thr Thr His Pro Cys Cys Leu Ser Ser Ala Ile Phe
260 265 270

His Ala Tyr Phe Ser Lys Arg Pro Ile Asn Ala Thr Thr Leu Tyr Tyr
275 280 285

Asp Lys Leu Lys Asn Thr Ser Ser Trp Cys Leu Arg Lys Ile Asn Val
290 295 300

Thr Leu Ile Ser Lys Thr Arg Thr Phe Leu Thr Pro His Leu Thr Ser
305 310 315 320

Thr Thr Thr Ser Ala His Tyr Tyr Val Thr Ala Phe Thr Val Thr Pro
325 330 335

Trp Met Tyr Ser Arg Ala Val Asp Val Arg Cys Trp Thr Ala Ala Arg
340 345 350

Lys Trp Pro Ser Pro Thr His His Cys Ser Gln Gln Pro Asp Lys Lys
355 360 365

Arg Pro Ala Pro Lys Ser Pro Ser His Gly Pro Thr Ala Arg Pro His
370 375 380

Ser Tyr Lys Tyr Lys Asn Leu Ser Pro Ala Ser His Lys His His His
385 390 395 400

Ala Pro Arg Cys Cys Cys Ile Pro Arg Pro Trp Thr Trp Pro Asn Glu

```
                405                 410                 415

Pro Phe Gly His Arg Ile Arg Ser Pro Thr Ser Pro Ala Ser Tyr Ala
            420                 425                 430

Trp Ser Thr Tyr Ser Leu Asn Arg Ile Ser Asn Ile Ser Ser Pro Asn
        435                 440                 445

Gly His Tyr Asp Arg Ser Pro Thr Leu Pro Asn Tyr Thr Lys Arg Thr
    450                 455                 460

Trp Pro Leu Phe Phe Gln Pro Ser His Ala Lys Asn Ser Thr Ser Trp
465                 470                 475                 480

Ala Ala Ser Ser Thr Pro Cys Trp Tyr Ile Arg Arg Arg Asp Ala Lys
                485                 490                 495

Ser Ser Ser Lys Arg Ala Ser Val His Trp Pro Ser Tyr His Thr Leu
            500                 505                 510

Arg Ser Cys Leu Ile His Thr Thr Asn Thr Ser Ala Thr Cys Thr His
        515                 520                 525

Pro Val Pro Val Ala Gly Asp Ala Ile Thr Arg Ser Asn Ala Ser Arg
    530                 535                 540

Val Ser Ser Pro Met Pro Pro Ser Pro Leu Pro Phe Pro Pro Pro Ser
545                 550                 555                 560

Pro Ser Tyr Leu Pro Cys Asn Gln Ala Arg Trp Lys Pro Ser Pro Thr
                565                 570                 575

Cys Phe Ala Cys Arg Ser Ala Asn Pro Ser Pro Arg Pro Ser Pro Asn
            580                 585                 590

Thr Ser Val Ile Ser Gln Thr Ser Thr Ser Lys Val Ser Pro Thr Leu
        595                 600                 605

Ser Pro Pro Pro Ser Ala Arg Ala Ser Ser Ser Pro Arg Arg Thr Val
    610                 615                 620

Lys Leu Asn Ala Asn Arg Ala Thr Cys Ile Pro His Thr Ala Ser Gln
625                 630                 635                 640

Trp Arg Ser Thr Phe Arg Lys Thr Ala Pro Phe Ala Lys Ala Pro Cys
                645                 650                 655

Asn Thr Thr Thr Arg Lys Ala Ser Ser Thr Ser Cys Thr Cys Thr Thr
            660                 665                 670

Arg Thr Thr Ser Phe Ser Pro Trp Ile Pro Thr Thr Lys Trp Trp Ser
        675                 680                 685

His Leu Arg Glu Leu Thr Thr Ser Cys Phe Lys Thr Val Arg Tyr Lys
    690                 695                 700

Leu Thr Ser Ser Trp Thr Pro Pro Thr Ile Thr Arg Thr Met Thr Ile
705                 710                 715                 720

Ser Asp Asp Asn Arg Leu Glu Pro Arg Trp Pro Cys Phe Leu Pro Leu
                725                 730                 735

Gly Pro Pro Pro Ser Pro Ser Ser Pro Ser Cys Thr Arg Thr Pro Val
            740                 745                 750

Val Phe Glu Ser Leu Ser Gly Arg
        755                 760


<210> SEQ ID NO 49
<211> LENGTH: 759
<212> TYPE: PRT
<213> ORGANISM: Artificial Sequence
<220> FEATURE:
<223> OTHER INFORMATION: Synthetic Polypeptide

<400> SEQUENCE: 49

Ser Ser Phe Trp Thr Leu Val Gln Lys Leu Ile Arg Leu Thr Ile Gly
```

-continued

```
1               5                   10                  15

Lys Glu Arg Lys Glu Glu Glu Glu Ile Glu Pro Pro Cys Gly Gln Ala
            20                  25                  30

Ser Pro Pro Thr Ser Ser Ser Ser Pro Ser Val Ser Ser Ala Thr Tyr
        35                  40                  45

Phe Arg His Asp Met Ala Gln Lys Pro Tyr Pro Asn Arg Trp Thr Lys
    50                  55                  60

Arg Phe Thr Tyr Cys Ser Thr Pro Thr Gly Asp Pro Ser Ala Ser Cys
65                  70                  75                  80

Val Lys Ile Pro Pro Ser Val Pro Thr Thr Ala Ala Ser Val Thr Ala
                85                  90                  95

Arg Ser Ser Gly Lys Thr Pro Ser Val Ser Thr Phe Ser Lys Ala Ile
            100                 105                 110

Ile Asn Thr Met Tyr Ser Ile Cys Leu Asp Val Phe Leu Arg Val Leu
        115                 120                 125

Trp Arg Ser Ser Phe Thr Arg Ile Pro Lys Pro Trp Lys Asp Thr Asn
    130                 135                 140

Arg Asp Leu Thr Leu Thr Arg Trp Tyr Pro Lys Thr Trp Pro Ala Thr
145                 150                 155                 160

Asp Leu Phe Arg Ser Ser Arg His Lys Thr Ala Val Asn Ser Pro Pro
                165                 170                 175

Leu Cys His Arg Pro Leu Thr Cys Gln Tyr Leu Thr Phe Gly Cys His
            180                 185                 190

Arg Lys Pro Leu His Thr Ala Gly Gln Asn His Ile Pro Pro Gln Asp
        195                 200                 205

Tyr Thr Asp His Thr Leu Thr Arg Pro Val Ser Ser Leu Met Asp Thr
    210                 215                 220

Ile Tyr Tyr Ser Ala Pro Ser His Leu Val Cys Thr Lys Ala Phe Thr
225                 230                 235                 240

Ser Ser Thr Asn Tyr Val Thr Leu Lys His Pro Arg Thr Ser Ser Leu
                245                 250                 255

Arg Cys Pro Thr Thr Thr His Pro Cys Cys Leu Ser Ser Ala Ile Phe
            260                 265                 270

His Ala Tyr Phe Ser Lys Arg Pro Ile Asn Ala Thr Thr Leu Tyr Tyr
        275                 280                 285

Asp Lys Leu Lys Asn Thr Ser Ser Trp Cys Leu Arg Lys Ile Asn Thr
    290                 295                 300

Val Thr Leu Ile Ser Lys Thr Arg Thr Phe Leu Thr Pro His Leu Thr
305                 310                 315                 320

Ser Thr Thr Thr Ser Ala His Tyr Tyr Val Thr Ala Phe Thr Val Thr
                325                 330                 335

Pro Trp Met Tyr Ser Arg Ala Val Asp Val Arg Cys Trp Thr Ala Ala
            340                 345                 350

Arg Lys Trp Pro Ser Pro Thr His His Cys Ser Gln Gln Pro Asp Lys
        355                 360                 365

Lys Arg Pro Ala Pro Lys Ser Pro Ser His Gly Pro Thr Ala Arg Pro
    370                 375                 380

His Ser Tyr Lys Tyr Lys Asn Leu Ser Pro Ala Ser His Lys His His
385                 390                 395                 400

His Ala Pro Arg Cys Cys Cys Ile Pro Arg Pro Trp Thr Trp Pro Asn
                405                 410                 415

Glu Pro Phe Gly His Arg Ile Arg Ser Pro Thr Ser Pro Ala Ser Tyr
            420                 425                 430
```

```
Ala Trp Ser Thr Tyr Ser Leu Asn Arg Ile Ser Asn Ile Ser Ser Pro
        435                 440                 445

Asn Gly His Tyr Asp Arg Ser Pro Thr Leu Pro Asn Tyr Thr Lys Arg
    450                 455                 460

Thr Trp Pro Leu Phe Phe Gln Pro Ser His Ala Lys Asn Ser Thr Ser
465                 470                 475                 480

Trp Ala Ala Ser Ser Thr Pro Cys Trp Tyr Ile Arg Arg Arg Asp Ala
                485                 490                 495

Lys Ser Ser Ser Lys Arg Ala Ser Val His Trp Pro Ser Tyr His Thr
            500                 505                 510

Leu Arg Ser Cys Leu Ile His Thr Thr Asn Thr Ser Ala Thr Cys Thr
        515                 520                 525

His Pro Val Pro Val Ala Gly Asp Ala Ile Thr Arg Ser Asn Ala Ser
    530                 535                 540

Arg Val Ser Ser Pro Met Pro Pro Ser Pro Leu Pro Phe Pro Pro Pro
545                 550                 555                 560

Ser Pro Ser Tyr Leu Pro Cys Asn Gln Ala Arg Trp Lys Pro Ser Pro
                565                 570                 575

Thr Cys Phe Ala Cys Arg Ser Ala Asn Pro Ser Pro Arg Pro Ser Pro
            580                 585                 590

Asn Thr Ser Val Ile Ser Gln Thr Ser Thr Ser Lys Val Ser Pro Thr
        595                 600                 605

Leu Ser Pro Pro Pro Ser Ala Arg Ala Ser Ser Ser Pro Arg Arg Thr
    610                 615                 620

Val Lys Leu Asn Ala Asn Arg Ala Thr Cys Ile Pro His Thr Ala Ser
625                 630                 635                 640

Gln Trp Arg Ser Thr Phe Arg Lys Thr Ala Pro Phe Ala Lys Ala Pro
                645                 650                 655

Cys Asn Thr Thr Thr Arg Lys Ala Ser Ser Thr Ser Cys Thr Cys Thr
            660                 665                 670

Thr Arg Thr Thr Ser Phe Ser Pro Trp Ile Pro Thr Thr Lys Trp Trp
        675                 680                 685

Ser His Leu Arg Glu Leu Thr Thr Ser Cys Phe Lys Thr Val Arg Tyr
    690                 695                 700

Lys Leu Thr Ser Ser Trp Thr Pro Pro Thr Thr Ile Thr Thr Ile Thr
705                 710                 715                 720

Asp Asp Asn Arg Leu Glu Pro Arg Trp Pro Cys Phe Leu Pro Leu Gly
                725                 730                 735

Pro Pro Pro Ser Pro Ser Ser Pro Ser Cys Thr Arg Thr Pro Val Val
            740                 745                 750

Phe Glu Ser Leu Ser Gly Arg
        755


<210> SEQ ID NO 50
<211> LENGTH: 735
<212> TYPE: PRT
<213> ORGANISM: Artificial Sequence
<220> FEATURE:
<223> OTHER INFORMATION: Synthetic Polypeptide

<400> SEQUENCE: 50

Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Trp Asn Pro Gly
            20                  25                  30
```

```
Ser Gly Ala Trp Ala Leu Thr Cys Val Ser Ser Val Trp Val Leu Arg
        35                  40                  45

Phe Pro His Leu Leu Leu Val Glu Leu Leu Leu Leu Thr Val Thr Ile
    50                  55                  60

Pro Leu Ile Arg Arg Leu Leu Leu Thr Leu Asp Pro Val Gln Ser Leu
65                  70                  75                  80

Asn Ala Leu Leu Pro Lys Arg Ser Ala Met Val Leu Thr Arg Pro Ser
                85                  90                  95

Thr Thr Leu Pro Ser Ser Thr Glu Met Trp Trp Gly Ser Ile Pro Pro
            100                 105                 110

Ser Thr Pro Ile Ala Cys Val Leu Trp Pro Arg Val Arg Ile Leu Phe
        115                 120                 125

Ala Leu Asn Val Ile Ser Ser Ala Pro Arg Ser Pro Ser Met Lys Thr
    130                 135                 140

Trp Thr Arg Ala Ser Trp Trp Ser Thr Asn Ala Thr Ser Ser Arg Thr
145                 150                 155                 160

Pro Leu Arg Tyr Glu Ser Thr Arg Arg Phe Arg Phe Val Val Ala Thr
                165                 170                 175

Leu Thr Ser Thr Pro Leu Ile Cys Trp Ala Ala Thr Arg Asn Thr Trp
            180                 185                 190

Arg Leu Leu Cys Gly Arg Phe Ile Ile Ser Thr Ala Thr Val Ser Ala
        195                 200                 205

Thr Val Pro Thr Ala Ala Leu Gln Ala Arg Phe Ser Trp Leu Ile Ile
    210                 215                 220

Gly Thr Ala Met Lys Thr Lys Pro Cys Asn Cys Pro Thr Ile Ile Pro
225                 230                 235                 240

Thr Pro Thr Val Pro Val Thr Arg Ser Arg Ile Asn Gly Thr Ala Ala
                245                 250                 255

Ala Ala Pro Gly Ser Ile Val Arg Pro Val Ile Ile Val Trp Pro Ser
            260                 265                 270

Leu Leu Arg Ala Pro Asn Ile Leu Ile Ile Phe Ser Pro Leu Pro Arg
        275                 280                 285

Val Thr Trp Leu Thr Phe Leu Leu Ser Thr Thr Glu Pro Ile Ala Met
    290                 295                 300

Pro Ala Thr Leu Glu Lys Thr Pro Thr Ser Phe Ser Phe Phe Arg Thr
305                 310                 315                 320

Thr Leu Ser Ser Pro Thr Leu Glu Asp Arg Ile Leu Arg Arg Pro Thr
                325                 330                 335

Gly Trp Trp Leu Phe Leu Asn Val Arg Thr Arg Ser Pro Gly Ile Tyr
            340                 345                 350

Arg Thr Lys Arg Met Ser Leu Val Asn Ser Leu Ser Gly Lys Pro Arg
        355                 360                 365

Asn Ala Pro Phe Val Pro Lys Pro Arg Thr Arg Ile Thr Phe Leu Leu
    370                 375                 380

Pro Lys Pro Pro Leu Ser Tyr Leu Arg Ser Lys Arg Thr Cys Pro Thr
385                 390                 395                 400

Leu Arg Trp Thr Ala Tyr Val Met Arg Leu Ile Ser Tyr Ser Arg Phe
                405                 410                 415

Ser Ile Leu His Thr Ile Lys His Met Lys Asn Met Glu Thr Cys Pro
            420                 425                 430

Ser Leu Lys Pro Leu Val Val Trp Cys Ser Gly Lys Val Ser Ser Lys
        435                 440                 445
```

Asn Leu Trp Trp Asn Ser Asn Val Trp Pro Thr Ala Pro Val Ile Leu
    450                 455                 460

Leu Ile Ile Glu Pro Lys Glu Val Gln Met Ala Thr Met Gln Leu Ile
465                 470                 475                 480

Tyr Pro Thr Trp Asn Arg Cys Thr Ile Trp Ser Thr Pro Ser Cys Ser
                485                 490                 495

Ser Pro Met Thr Arg Cys Ala Val Thr Ser Thr Gly Arg Trp Arg Lys
            500                 505                 510

Ser Gln Lys Pro Gly Val Trp Ile Asn Gly Ala Pro Arg Ser Ser Arg
        515                 520                 525

Asn Ser Ala Arg Ser Thr Arg Gln Pro Phe Ser Arg Pro Phe Thr Thr
    530                 535                 540

Asn Arg Leu Pro Arg Val Ser Trp Val Met Ser Trp Ala Trp Pro Ala
545                 550                 555                 560

Ala Pro Ser Thr Lys Pro Ala Ser Arg Cys Cys Val Ile Thr Arg Ser
                565                 570                 575

Arg Gln Asp Ala Ala Thr His Asp Pro Trp Ser Ser Leu Ile Ser Pro
            580                 585                 590

Thr Ala Arg Thr Cys Ser Thr Val Asn Trp Ala Arg Thr Thr Lys Ser
        595                 600                 605

Cys Trp Ala Thr Thr Ala Leu Arg Asn Val Ser Phe Pro Ala Ser Arg
    610                 615                 620

Ser Ser Ser Pro Gly Thr Arg Pro Thr Ser Thr Trp Thr Thr Ser Ser
625                 630                 635                 640

Asn Ala Leu Thr Ser Ala Val Ser Pro Pro Ser Thr Ala Ser Pro Trp
                645                 650                 655

Ile Ser Thr Arg Trp Lys Ile Pro Thr Ser Gly Tyr Trp Asn Phe Thr
            660                 665                 670

Arg Arg Lys Ser Cys Val Pro Ala Thr Phe Leu Thr Ser Lys Arg Ser
        675                 680                 685

Cys Ala Asn Ser Thr Arg Thr Ser Ser Asp Asn Arg Leu Glu Pro Arg
    690                 695                 700

Trp Pro Cys Phe Leu Pro Leu Gly Pro Pro Pro Ser Pro Ser Ser Pro
705                 710                 715                 720

Ser Cys Thr Arg Thr Pro Val Val Phe Glu Ser Leu Ser Gly Arg
                725                 730                 735

<210> SEQ ID NO 51
<211> LENGTH: 744
<212> TYPE: PRT
<213> ORGANISM: Artificial Sequence
<220> FEATURE:
<223> OTHER INFORMATION: Synthetic Polypeptide

<400> SEQUENCE: 51

Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Trp Asn Pro Gly
            20                  25                  30

Ser Gly Ala Trp Ser Ala Leu Thr Cys Val Ser Ser Val Trp Val Leu
        35                  40                  45

Arg Phe Pro His Leu Leu Leu Val Glu Leu Leu Leu Leu Thr Val Thr
    50                  55                  60

Ile Pro Leu Ile Arg Arg Leu Leu Leu Thr Leu Asp Pro Val Gln Ser
65                  70                  75                  80

-continued

```
Leu Asn Ala Leu Leu Pro Lys Arg Ser Ala Met Val Leu Thr Arg Pro
                85                  90                  95

Ser Thr Thr Leu Pro Ser Ser Thr Glu Met Trp Trp Gly Ser Ile Pro
            100                 105                 110

Pro Ser Thr Pro Ile Ala Cys Val Leu Trp Pro Arg Val Arg Ile Leu
        115                 120                 125

Phe Ala Leu Asn Val Ile Ser Ser Ala Pro Arg Ser Pro Ser Met Lys
    130                 135                 140

Thr Trp Thr Arg Ala Ser Trp Trp Ser Thr Asn Ala Thr Ser Ser Arg
145                 150                 155                 160

Thr Pro Leu Arg Tyr Glu Ser Thr Arg Arg Phe Arg Phe Val Val Ala
                165                 170                 175

Thr Leu Thr Ser Thr Pro Leu Ile Cys Trp Ala Ala Thr Arg Asn Thr
            180                 185                 190

Trp Arg Leu Leu Cys Gly Arg Phe Ile Ile Ser Thr Ala Thr Val Ser
        195                 200                 205

Ala Thr Val Pro Thr Ala Ala Leu Gln Ala Arg Phe Ser Trp Leu Ile
    210                 215                 220

Ile Gly Thr Ala Met Lys Thr Lys Pro Cys Asn Cys Pro Thr Ile Ile
225                 230                 235                 240

Pro Thr Pro Thr Val Pro Val Thr Arg Ser Arg Ile Asn Gly Thr Ala
                245                 250                 255

Ala Ala Ala Pro Gly Ser Ile Val Arg Pro Val Ile Ile Val Trp Pro
            260                 265                 270

Ser Leu Leu Arg Ala Pro Asn Ile Leu Ile Ile Phe Ser Pro Leu Pro
        275                 280                 285

Arg Val Thr Trp Leu Thr Phe Leu Leu Ser Thr Thr Glu Pro Ile Ala
    290                 295                 300

Met Pro Ala Thr Leu Glu Lys Thr Pro Thr Ser Phe Ser Phe Phe Arg
305                 310                 315                 320

Thr Thr Leu Ser Ser Pro Thr Leu Glu Asp Arg Ile Leu Arg Arg Pro
                325                 330                 335

Thr Gly Trp Trp Leu Phe Leu Asn Val Arg Thr Arg Ser Pro Gly Ile
            340                 345                 350

Tyr Arg Thr Lys Arg Met Ser Leu Val Asn Ser Leu Ser Gly Lys Pro
        355                 360                 365

Arg Asn Ala Pro Phe Val Pro Lys Pro Arg Thr Arg Ile Thr Phe Leu
    370                 375                 380

Leu Pro Lys Pro Pro Leu Ser Tyr Leu Arg Ser Lys Arg Thr Cys Pro
385                 390                 395                 400

Thr Leu Arg Trp Thr Ala Tyr Val Met Arg Leu Ile Ser Tyr Ser Arg
                405                 410                 415

Phe Ser Ile Leu His Thr Ile Lys His Met Lys Asn Met Glu Thr Cys
            420                 425                 430

Pro Ser Leu Lys Pro Leu Val Val Trp Cys Ser Gly Lys Val Ser Ser
        435                 440                 445

Lys Asn Leu Trp Trp Asn Ser Asn Val Trp Pro Thr Ala Pro Val Ile
    450                 455                 460

Leu Leu Ile Ile Glu Pro Lys Glu Val Gln Met Ala Thr Met Gln Leu
465                 470                 475                 480

Ile Tyr Pro Thr Trp Asn Arg Cys Thr Ile Trp Ser Thr Pro Ser Cys
                485                 490                 495

Ser Ser Pro Met Thr Arg Cys Ala Val Thr Ser Thr Gly Arg Trp Arg
```

```
            500                 505                 510

Lys Ser Gln Lys Pro Gly Val Trp Ile Asn Gly Ala Pro Arg Ser Ser
        515                 520                 525

Arg Asn Ser Ala Arg Ser Thr Arg Gln Pro Phe Ser Arg Pro Phe Thr
    530                 535                 540

Thr Asn Arg Leu Pro Arg Val Ser Trp Val Met Ser Trp Ala Trp Pro
545                 550                 555                 560

Ala Ala Pro Ser Thr Lys Pro Ala Ser Arg Cys Cys Val Ile Thr Arg
                565                 570                 575

Ser Arg Gln Asp Ala Ala Thr His Asp Pro Trp Ser Ser Leu Ile Ser
            580                 585                 590

Pro Thr Ala Arg Thr Cys Ser Thr Val Asn Trp Ala Arg Thr Thr Lys
        595                 600                 605

Ser Cys Trp Ala Thr Thr Ala Leu Arg Asn Val Ser Phe Pro Ala Ser
    610                 615                 620

Arg Ser Ser Ser Pro Gly Thr Arg Pro Thr Ser Thr Trp Thr Thr Ser
625                 630                 635                 640

Ser Asn Ala Leu Thr Ser Ala Val Ser Pro Pro Ser Thr Ala Ser Pro
                645                 650                 655

Trp Ile Ser Thr Arg Trp Lys Ile Pro Thr Ser Gly Tyr Trp Asn Phe
            660                 665                 670

Thr Arg Arg Lys Ser Cys Val Pro Ala Thr Phe Leu Thr Ser Lys Arg
        675                 680                 685

Ser Cys Ala Asn Ser Thr Arg Thr Ser Arg Ile Thr Arg Thr Met Thr
    690                 695                 700

Ile Ser Asp Asn Arg Leu Glu Pro Arg Trp Pro Cys Phe Leu Pro Leu
705                 710                 715                 720

Gly Pro Pro Pro Ser Pro Ser Ser Pro Ser Cys Thr Arg Thr Pro Val
                725                 730                 735

Val Phe Glu Ser Leu Ser Gly Arg
            740


<210> SEQ ID NO 52
<211> LENGTH: 742
<212> TYPE: PRT
<213> ORGANISM: Artificial Sequence
<220> FEATURE:
<223> OTHER INFORMATION: Synthetic Polypeptide

<400> SEQUENCE: 52

Ser Ser Phe Trp Thr Leu Val Gln Lys Leu Ile Arg Leu Thr Ile Gly
1               5                   10                  15

Lys Glu Arg Lys Glu Glu Glu Glu Ile Glu Pro Pro Trp Asn Pro Gly
            20                  25                  30

Ser Gly Ala Trp Ser Ala Leu Thr Cys Val Ser Ser Val Trp Val Leu
        35                  40                  45

Arg Phe Pro His Leu Leu Leu Val Glu Leu Leu Leu Leu Thr Val Thr
    50                  55                  60

Ile Pro Leu Ile Arg Arg Leu Leu Leu Thr Leu Asp Pro Val Gln Ser
65                  70                  75                  80

Leu Asn Ala Leu Leu Pro Lys Arg Ser Ala Met Val Leu Thr Arg Pro
                85                  90                  95

Ser Thr Thr Leu Pro Ser Ser Thr Glu Met Trp Trp Gly Ser Ile Pro
            100                 105                 110

Pro Ser Thr Pro Ile Ala Cys Val Leu Trp Pro Arg Val Arg Ile Leu
```

```
        115                 120                 125

Phe Ala Leu Asn Val Ile Ser Ser Ala Pro Arg Ser Pro Ser Met Lys
    130                 135                 140

Thr Trp Thr Arg Ala Ser Trp Trp Ser Thr Asn Ala Thr Ser Ser Arg
145                 150                 155                 160

Thr Pro Leu Arg Tyr Glu Ser Thr Arg Arg Phe Arg Phe Val Val Ala
                165                 170                 175

Thr Leu Thr Ser Thr Pro Leu Ile Cys Trp Ala Ala Thr Arg Asn Thr
            180                 185                 190

Trp Arg Leu Leu Cys Gly Arg Phe Ile Ile Ser Thr Ala Thr Val Ser
        195                 200                 205

Ala Thr Val Pro Thr Ala Ala Leu Gln Ala Arg Phe Ser Trp Leu Ile
    210                 215                 220

Ile Gly Thr Ala Met Lys Thr Lys Pro Cys Asn Cys Pro Thr Ile Ile
225                 230                 235                 240

Pro Thr Pro Thr Val Pro Val Thr Arg Ser Arg Ile Asn Gly Thr Ala
                245                 250                 255

Ala Ala Ala Pro Gly Ser Ile Val Arg Pro Val Ile Ile Val Trp Pro
            260                 265                 270

Ser Leu Leu Arg Ala Pro Asn Ile Leu Ile Ile Phe Ser Pro Leu Pro
        275                 280                 285

Arg Val Thr Trp Leu Thr Phe Leu Leu Ser Thr Thr Glu Pro Ile Ala
    290                 295                 300

Met Pro Ala Thr Leu Glu Lys Thr Pro Thr Ser Phe Ser Phe Phe Arg
305                 310                 315                 320

Thr Thr Leu Ser Ser Pro Thr Leu Glu Asp Arg Ile Leu Arg Arg Pro
                325                 330                 335

Thr Gly Trp Trp Leu Phe Leu Asn Val Arg Thr Arg Ser Pro Gly Ile
            340                 345                 350

Tyr Arg Thr Lys Arg Met Ser Leu Val Asn Ser Leu Ser Gly Lys Pro
        355                 360                 365

Arg Asn Ala Pro Phe Val Pro Lys Pro Arg Thr Arg Ile Thr Phe Leu
    370                 375                 380

Leu Pro Lys Pro Pro Leu Ser Tyr Leu Arg Ser Lys Arg Thr Cys Pro
385                 390                 395                 400

Thr Leu Arg Trp Thr Ala Tyr Val Met Arg Leu Ile Ser Tyr Ser Arg
                405                 410                 415

Phe Ser Ile Leu His Thr Ile Lys His Met Lys Asn Met Glu Thr Cys
            420                 425                 430

Pro Ser Leu Lys Pro Leu Val Val Trp Cys Ser Gly Lys Val Ser Ser
        435                 440                 445

Lys Asn Leu Trp Trp Asn Ser Asn Val Trp Pro Thr Ala Pro Val Ile
    450                 455                 460

Leu Leu Ile Ile Glu Pro Lys Glu Val Gln Met Ala Thr Met Gln Leu
465                 470                 475                 480

Ile Tyr Pro Thr Trp Asn Arg Cys Thr Ile Trp Ser Thr Pro Ser Cys
                485                 490                 495

Ser Ser Pro Met Thr Arg Cys Ala Val Thr Ser Thr Gly Arg Trp Arg
            500                 505                 510

Lys Ser Gln Lys Pro Gly Val Trp Ile Asn Gly Ala Pro Arg Ser Ser
        515                 520                 525

Arg Asn Ser Ala Arg Ser Thr Arg Gln Pro Phe Ser Arg Pro Phe Thr
    530                 535                 540
```

Thr Asn Arg Leu Pro Arg Val Ser Trp Val Met Ser Trp Ala Trp Pro
545 550 555 560

Ala Ala Pro Ser Thr Lys Pro Ala Ser Arg Cys Cys Val Ile Thr Arg
565 570 575

Ser Arg Gln Asp Ala Ala Thr His Asp Pro Trp Ser Ser Leu Ile Ser
580 585 590

Pro Thr Ala Arg Thr Cys Ser Thr Val Asn Trp Ala Arg Thr Thr Lys
595 600 605

Ser Cys Trp Ala Thr Thr Ala Leu Arg Asn Val Ser Phe Pro Ala Ser
610 615 620

Arg Ser Ser Ser Pro Gly Thr Arg Pro Thr Ser Thr Trp Thr Thr Ser
625 630 635 640

Ser Asn Ala Leu Thr Ser Ala Val Ser Pro Pro Ser Thr Ala Ser Pro
645 650 655

Trp Ile Ser Thr Arg Trp Lys Ile Pro Thr Ser Gly Tyr Trp Asn Phe
660 665 670

Thr Arg Arg Lys Ser Cys Val Pro Ala Thr Phe Leu Thr Ser Lys Arg
675 680 685

Ser Cys Ala Asn Ser Thr Arg Thr Ser Ser Thr Ile Thr Thr Ile Thr
690 695 700

Asp Asn Arg Leu Glu Pro Arg Trp Pro Cys Phe Leu Pro Leu Gly Pro
705 710 715 720

Pro Pro Ser Pro Ser Ser Pro Ser Cys Thr Arg Thr Pro Val Val Phe
725 730 735

Glu Ser Leu Ser Gly Arg
740

<210> SEQ ID NO 53
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 53

Met Asp Trp Thr Trp Ile Leu Phe Leu Val Ala Ala Ala Thr Arg Val
1 5 10 15

His Ser

<210> SEQ ID NO 54
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 54

Met Glu Thr Pro Ala Gln Leu Leu Phe Leu Leu Leu Leu Trp Leu Pro
1 5 10 15

Asp Thr Thr Gly
20

<210> SEQ ID NO 55
<211> LENGTH: 278
<212> TYPE: PRT
<213> ORGANISM: Human Cytomegalovirus

<400> SEQUENCE: 55

Met Cys Arg Arg Pro Asp Cys Gly Phe Ser Phe Ser Pro Gly Pro Val
1 5 10 15

Ile Leu Leu Trp Cys Cys Leu Leu Leu Pro Ile Val Ser Ser Ala Ala
20 25 30

Val Ser Val Ala Pro Thr Ala Ala Glu Lys Val Pro Ala Glu Cys Pro
35 40 45

Glu Leu Thr Arg Arg Cys Leu Leu Gly Glu Val Phe Glu Gly Asp Lys
50 55 60

Tyr Glu Ser Trp Leu Arg Pro Leu Val Asn Val Thr Gly Arg Asp Gly
65 70 75 80

Pro Leu Ser Gln Leu Ile Arg Tyr Arg Pro Val Thr Pro Glu Ala Ala
85 90 95

Asn Ser Val Leu Leu Asp Glu Ala Phe Leu Asp Thr Leu Ala Leu Leu
100 105 110

Tyr Asn Asn Pro Asp Gln Leu Arg Ala Leu Leu Thr Leu Leu Ser Ser
115 120 125

Asp Thr Ala Pro Arg Trp Met Thr Val Met Arg Gly Tyr Ser Glu Cys
130 135 140

Gly Asp Gly Ser Pro Ala Val Tyr Thr Cys Val Asp Asp Leu Cys Arg
145 150 155 160

Gly Tyr Asp Leu Thr Arg Leu Ser Tyr Gly Arg Ser Ile Phe Thr Glu
165 170 175

His Val Leu Gly Phe Glu Leu Val Pro Pro Ser Leu Phe Asn Val Val
180 185 190

Val Ala Ile Arg Asn Glu Ala Thr Arg Thr Asn Arg Ala Val Arg Leu
195 200 205

Pro Val Ser Thr Ala Ala Ala Pro Glu Gly Ile Thr Leu Phe Tyr Gly
210 215 220

Leu Tyr Asn Ala Val Lys Glu Phe Cys Leu Arg His Gln Leu Asp Pro
225 230 235 240

Pro Leu Leu Arg His Leu Asp Lys Tyr Tyr Ala Gly Leu Pro Pro Glu
245 250 255

Leu Lys Gln Thr Arg Val Asn Leu Pro Ala His Ser Arg Tyr Gly Pro
260 265 270

Gln Ala Val Asp Ala Arg
275

<210> SEQ ID NO 56
<211> LENGTH: 907
<212> TYPE: PRT
<213> ORGANISM: Human Cytomegalovirus

<400> SEQUENCE: 56

Met Glu Ser Arg Ile Trp Cys Leu Val Val Cys Val Asn Leu Cys Ile
1 5 10 15

Val Cys Leu Gly Ala Ala Val Ser Ser Ser Ser Thr Arg Gly Thr Ser
20 25 30

Ala Thr His Ser His His Ser Ser His Thr Thr Ser Ala Ala His Ser
35 40 45

Arg Ser Gly Ser Val Ser Gln Arg Val Thr Ser Ser Gln Thr Val Ser
50 55 60

His Gly Val Asn Glu Thr Ile Tyr Asn Thr Thr Leu Lys Tyr Gly Asp
65 70 75 80

Val Val Gly Val Asn Thr Thr Lys Tyr Pro Tyr Arg Val Cys Ser Met
85 90 95

```
Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300

Ile Val Ser Asp Phe Gly Arg Pro Asn Ser Ala Leu Glu Thr His Arg
305                 310                 315                 320

Leu Val Ala Phe Leu Glu Arg Ala Asp Ser Val Ile Ser Trp Asp Ile
                325                 330                 335

Gln Asp Glu Lys Asn Val Thr Cys Gln Leu Thr Phe Trp Glu Ala Ser
            340                 345                 350

Glu Arg Thr Ile Arg Ser Glu Ala Glu Asp Ser Tyr His Phe Ser Ser
        355                 360                 365

Ala Lys Met Thr Ala Thr Phe Leu Ser Lys Lys Gln Glu Val Asn Met
    370                 375                 380

Ser Asp Ser Ala Leu Asp Cys Val Arg Asp Glu Ala Ile Asn Lys Leu
385                 390                 395                 400

Gln Gln Ile Phe Asn Thr Ser Tyr Asn Gln Thr Tyr Glu Lys Tyr Gly
                405                 410                 415

Asn Val Ser Val Phe Glu Thr Thr Gly Gly Leu Val Val Phe Trp Gln
            420                 425                 430

Gly Ile Lys Gln Lys Ser Leu Val Glu Leu Glu Arg Leu Ala Asn Arg
        435                 440                 445

Ser Ser Leu Asn Leu Thr His Asn Arg Thr Lys Arg Ser Thr Asp Gly
    450                 455                 460

Asn Asn Ala Thr His Leu Ser Asn Met Glu Ser Val His Asn Leu Val
465                 470                 475                 480

Tyr Ala Gln Leu Gln Phe Thr Tyr Asp Thr Leu Arg Gly Tyr Ile Asn
                485                 490                 495

Arg Ala Leu Ala Gln Ile Ala Glu Ala Trp Cys Val Asp Gln Arg Arg
            500                 505                 510
```

-continued

```
Thr Leu Glu Val Phe Lys Glu Leu Ser Lys Ile Asn Pro Ser Ala Ile
        515                 520                 525

Leu Ser Ala Ile Tyr Asn Lys Pro Ile Ala Ala Arg Phe Met Gly Asp
    530                 535                 540

Val Leu Gly Leu Ala Ser Cys Val Thr Ile Asn Gln Thr Ser Val Lys
545                 550                 555                 560

Val Leu Arg Asp Met Asn Val Lys Glu Ser Pro Gly Arg Cys Tyr Ser
                565                 570                 575

Arg Pro Val Val Ile Phe Asn Phe Ala Asn Ser Ser Tyr Val Gln Tyr
            580                 585                 590

Gly Gln Leu Gly Glu Asp Asn Glu Ile Leu Leu Gly Asn His Arg Thr
        595                 600                 605

Glu Glu Cys Gln Leu Pro Ser Leu Lys Ile Phe Ile Ala Gly Asn Ser
    610                 615                 620

Ala Tyr Glu Tyr Val Asp Tyr Leu Phe Lys Arg Met Ile Asp Leu Ser
625                 630                 635                 640

Ser Ile Ser Thr Val Asp Ser Met Ile Ala Leu Asp Ile Asp Pro Leu
                645                 650                 655

Glu Asn Thr Asp Phe Arg Val Leu Glu Leu Tyr Ser Gln Lys Glu Leu
            660                 665                 670

Arg Ser Ser Asn Val Phe Asp Leu Glu Glu Ile Met Arg Glu Phe Asn
        675                 680                 685

Ser Tyr Lys Gln Arg Val Lys Tyr Val Glu Asp Lys Val Val Asp Pro
    690                 695                 700

Leu Pro Pro Tyr Leu Lys Gly Leu Asp Asp Leu Met Ser Gly Leu Gly
705                 710                 715                 720

Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905
```

<210> SEQ ID NO 57
<211> LENGTH: 214
<212> TYPE: PRT

<213> ORGANISM: Human Cytomegalovirus

<400> SEQUENCE: 57

Met Leu Arg Leu Leu Leu Arg His His Phe His Cys Leu Leu Leu Cys
1 5 10 15

Ala Val Trp Ala Thr Pro Cys Leu Ala Ser Pro Trp Ser Thr Leu Thr
20 25 30

Ala Asn Gln Asn Pro Ser Pro Pro Trp Ser Lys Leu Thr Tyr Ser Lys
35 40 45

Pro His Asp Ala Ala Thr Phe Tyr Cys Pro Phe Leu Tyr Pro Ser Pro
50 55 60

Pro Arg Ser Pro Leu Gln Phe Ser Gly Phe Gln Arg Val Ser Thr Gly
65 70 75 80

Pro Glu Cys Arg Asn Glu Thr Leu Tyr Leu Leu Tyr Asn Arg Glu Gly
85 90 95

Gln Thr Leu Val Glu Arg Ser Ser Thr Trp Val Lys Lys Val Ile Trp
100 105 110

Tyr Leu Ser Gly Arg Asn Gln Thr Ile Leu Gln Arg Met Pro Arg Thr
115 120 125

Ala Ser Lys Pro Ser Asp Gly Asn Val Gln Ile Ser Val Glu Asp Ala
130 135 140

Lys Ile Phe Gly Ala His Met Val Pro Lys Gln Thr Lys Leu Leu Arg
145 150 155 160

Phe Val Val Asn Asp Gly Thr Arg Tyr Gln Met Cys Val Met Lys Leu
165 170 175

Glu Ser Trp Ala His Val Phe Arg Asp Tyr Ser Val Ser Phe Gln Val
180 185 190

Arg Leu Thr Phe Thr Glu Ala Asn Asn Gln Thr Tyr Thr Phe Cys Thr
195 200 205

His Pro Asn Leu Ile Val
210

<210> SEQ ID NO 58
<211> LENGTH: 2437
<212> TYPE: DNA
<213> ORGANISM: Artificial Sequence
<220> FEATURE:
<223> OTHER INFORMATION: Synthetic Polynucleotide

<400> SEQUENCE: 58
tcaagctttt ggaccctcgt acagaagcta atacgactca ctatagggaa ataagagaga 60
aaagaagagt aagaagaaat ataagagcca ccatgcggcc aggcctcccc tcctacctca 120
tcatcctcgc cgtctgtctc ttcagccacc tactttcgtc acgatatggc gcagaagccg 180
tatccgaacc gctggacaaa gcgtttcacc tactgctcaa cacctacggg agacccatcc 240
gcttcctgcg tgaaaatacc acccagtgta cctacaacag cagcctccgt aacagcacgg 300
tcgtcaggga aaacgccatc agtttcaact tcttccaaag ctataatcaa tactatgtat 360
tccatatgcc tcgatgtctc tttgcgggtc ctctggcgga gcagtttctg aaccaggtag 420
atctgaccga aaccctggaa agataccaac agagacttaa cacttacgcg ctggtatcca 480
aagacctggc cagctaccga tctttctcgc agcagctaaa ggcacaagac agcctaggtg 540
aacagcccac cactgtgcca ccgcccattg acctgtcaat acctcacgtt tggatgccac 600
cgcaaaccac tccacacggc tggacagaat cacataccac ctcaggacta caccgaccac 660
actttaacca gacctgtatc ctctttgatg gacacgatct actattcagc accgtcacac 720

```
cttgtttgca ccaaggcttt tacctcatcg acgaactacg ttacgttaaa ataacactga    780

ccgaggactt cttcgtagtt acggtgtcca tagacgacga cacacccatg ctgcttatct    840

tcggccatct tccacgcgta cttttcaaag cgccctatca acgcgacaac tttatactac    900

gacaaactga gaaacacgag ctcctggtgc tagttaagaa agatcaactg aaccgtcact    960

cttatctcaa agacccggac tttcttgacg ccgcacttga cttcaactac ctagacctca   1020

gcgcactact acgtaacagc tttcaccgtt acgccgtgga tgtactcaag agcggtcgat   1080

gtcagatgct ggaccgccgc acggtagaaa tggccttcgc ctacgcatta gcactgttcg   1140

cagcagcccg acaagaagag gccggcgccc aagtctccgt cccacgggcc ctagaccgcc   1200

aggccgcact cttacaaata caagaattta tgatcacctg cctctcacaa acaccaccac   1260

gcaccacgtt gctgctgtat cccacggccg tggacctggc caaacgagcc ctttggacac   1320

cgaatcagat caccgacatc accagcctcg tacgcctggt ctacatactc tctaaacaga   1380

atcagcaaca tctcatcccc caatgggcac tacgacagat cgccgacttt gccctaaaac   1440

tacacaaaac gcacctggcc tcttttcttt cagccttcgc acgccaagaa ctctacctca   1500

tgggcagcct cgtccactcc atgctggtac atacgacgga gagacgcgaa atcttcatcg   1560

tagaaacggg cctctgttca ttggccgagc tatcacactt tacgcagttg ttagctcatc   1620

cacaccacga atacctcagc gacctgtaca caccctgttc cagtagcggg cgacgcgatc   1680

actcgctcga acgcctcacg cgtctcttcc ccgatgccac cgtccccgct accgttcccg   1740

ccgccctctc catcctatct accatgcaac caagcacgct ggaaaccttc cccgacctgt   1800

tttgcttgcc gctcggcgaa tccttctccg cgctgaccgt ctccgaacac gtcagttata   1860

tcgtaacaaa ccagtacctg atcaaaggta tctcctaccc tgtctccacc accgtcgtag   1920

gccagagcct catcatcacc cagacggaca gtcaaactaa atgcgaactg acgcgcaaca   1980

tgcataccac acacagcatc acagtggcgc tcaacatttc gctagaaaac tgcgcctttt   2040

gccaaagcgc cctgctagaa tacgacgaca cgcaaggcgt catcaacatc atgtacatgc   2100

acgactcgga cgacgtcctt ttcgccctgg atccctacaa cgaagtggtg gtctcatctc   2160

cgcgaactca ctacctcatg cttttgaaga acggtacggt actagaagta actgacgtcg   2220

tcgtggacgc caccgacagt cgtctcctca tgatgtccgt ctacgcgcta tcggccatca   2280

tcggcatcta tctgctctac cgcatgctca agacatgctg ataataggct ggagcctcgg   2340

tggccatgct tcttgcccct tggcctccc cccagcccct cctccccttc ctgcacccgt    2400

acccccgtgg tctttgaata aagtctgagt gggcggc                            2437
```

```
<210> SEQ ID NO 59
<211> LENGTH: 742
<212> TYPE: PRT
<213> ORGANISM: Artificial Sequence
<220> FEATURE:
<223> OTHER INFORMATION: Synthetic Polypeptide

<400> SEQUENCE: 59

Met Arg Pro Gly Leu Pro Ser Tyr Leu Ile Ile Leu Ala Val Cys Leu
1               5                   10                  15

Phe Ser His Leu Leu Ser Ser Arg Tyr Gly Ala Glu Ala Val Ser Glu
            20                  25                  30

Pro Leu Asp Lys Ala Phe His Leu Leu Leu Asn Thr Tyr Gly Arg Pro
        35                  40                  45

Ile Arg Phe Leu Arg Glu Asn Thr Thr Gln Cys Thr Tyr Asn Ser Ser
```

```
    50                  55                  60

Leu Arg Asn Ser Thr Val Val Arg Glu Asn Ala Ile Ser Phe Asn Phe
65                  70                  75                  80

Phe Gln Ser Tyr Asn Gln Tyr Tyr Val Phe His Met Pro Arg Cys Leu
                85                  90                  95

Phe Ala Gly Pro Leu Ala Glu Gln Phe Leu Asn Gln Val Asp Leu Thr
            100                 105                 110

Glu Thr Leu Glu Arg Tyr Gln Gln Arg Leu Asn Thr Tyr Ala Leu Val
        115                 120                 125

Ser Lys Asp Leu Ala Ser Tyr Arg Ser Phe Ser Gln Gln Leu Lys Ala
    130                 135                 140

Gln Asp Ser Leu Gly Glu Gln Pro Thr Thr Val Pro Pro Pro Ile Asp
145                 150                 155                 160

Leu Ser Ile Pro His Val Trp Met Pro Pro Gln Thr Thr Pro His Gly
                165                 170                 175

Trp Thr Glu Ser His Thr Thr Ser Gly Leu His Arg Pro His Phe Asn
            180                 185                 190

Gln Thr Cys Ile Leu Phe Asp Gly His Asp Leu Leu Phe Ser Thr Val
        195                 200                 205

Thr Pro Cys Leu His Gln Gly Phe Tyr Leu Ile Asp Glu Leu Arg Tyr
    210                 215                 220

Val Lys Ile Thr Leu Thr Glu Asp Phe Phe Val Val Thr Val Ser Ile
225                 230                 235                 240

Asp Asp Asp Thr Pro Met Leu Leu Ile Phe Gly His Leu Pro Arg Val
                245                 250                 255

Leu Phe Lys Ala Pro Tyr Gln Arg Asp Asn Phe Ile Leu Arg Gln Thr
            260                 265                 270

Glu Lys His Glu Leu Leu Val Leu Val Lys Lys Asp Gln Leu Asn Arg
        275                 280                 285

His Ser Tyr Leu Lys Asp Pro Asp Phe Leu Asp Ala Ala Leu Asp Phe
    290                 295                 300

Asn Tyr Leu Asp Leu Ser Ala Leu Leu Arg Asn Ser Phe His Arg Tyr
305                 310                 315                 320

Ala Val Asp Val Leu Lys Ser Gly Arg Cys Gln Met Leu Asp Arg Arg
                325                 330                 335

Thr Val Glu Met Ala Phe Ala Tyr Ala Leu Ala Leu Phe Ala Ala Ala
            340                 345                 350

Arg Gln Glu Glu Ala Gly Ala Gln Val Ser Val Pro Arg Ala Leu Asp
        355                 360                 365

Arg Gln Ala Ala Leu Leu Gln Ile Gln Glu Phe Met Ile Thr Cys Leu
    370                 375                 380

Ser Gln Thr Pro Pro Arg Thr Thr Leu Leu Leu Tyr Pro Thr Ala Val
385                 390                 395                 400

Asp Leu Ala Lys Arg Ala Leu Trp Thr Pro Asn Gln Ile Thr Asp Ile
                405                 410                 415

Thr Ser Leu Val Arg Leu Val Tyr Ile Leu Ser Lys Gln Asn Gln Gln
            420                 425                 430

His Leu Ile Pro Gln Trp Ala Leu Arg Gln Ile Ala Asp Phe Ala Leu
        435                 440                 445

Lys Leu His Lys Thr His Leu Ala Ser Phe Leu Ser Ala Phe Ala Arg
    450                 455                 460

Gln Glu Leu Tyr Leu Met Gly Ser Leu Val His Ser Met Leu Val His
465                 470                 475                 480
```

```
Thr Thr Glu Arg Arg Glu Ile Phe Ile Val Glu Thr Gly Leu Cys Ser
                485                 490                 495

Leu Ala Glu Leu Ser His Phe Thr Gln Leu Leu Ala His Pro His His
            500                 505                 510

Glu Tyr Leu Ser Asp Leu Tyr Thr Pro Cys Ser Ser Ser Gly Arg Arg
        515                 520                 525

Asp His Ser Leu Glu Arg Leu Thr Arg Leu Phe Pro Asp Ala Thr Val
    530                 535                 540

Pro Ala Thr Val Pro Ala Ala Leu Ser Ile Leu Ser Thr Met Gln Pro
545                 550                 555                 560

Ser Thr Leu Glu Thr Phe Pro Asp Leu Phe Cys Leu Pro Leu Gly Glu
                565                 570                 575

Ser Phe Ser Ala Leu Thr Val Ser Glu His Val Ser Tyr Ile Val Thr
            580                 585                 590

Asn Gln Tyr Leu Ile Lys Gly Ile Ser Tyr Pro Val Ser Thr Thr Val
        595                 600                 605

Val Gly Gln Ser Leu Ile Ile Thr Gln Thr Asp Ser Gln Thr Lys Cys
    610                 615                 620

Glu Leu Thr Arg Asn Met His Thr Thr His Ser Ile Thr Val Ala Leu
625                 630                 635                 640

Asn Ile Ser Leu Glu Asn Cys Ala Phe Cys Gln Ser Ala Leu Leu Glu
                645                 650                 655

Tyr Asp Asp Thr Gln Gly Val Ile Asn Ile Met Tyr Met His Asp Ser
            660                 665                 670

Asp Asp Val Leu Phe Ala Leu Asp Pro Tyr Asn Glu Val Val Val Ser
        675                 680                 685

Ser Pro Arg Thr His Tyr Leu Met Leu Leu Lys Asn Gly Thr Val Leu
    690                 695                 700

Glu Val Thr Asp Val Val Val Asp Ala Thr Asp Ser Arg Leu Leu Met
705                 710                 715                 720

Met Ser Val Tyr Ala Leu Ser Ala Ile Ile Gly Ile Tyr Leu Leu Tyr
                725                 730                 735

Arg Met Leu Lys Thr Cys
            740
```

<210> SEQ ID NO 60
<211> LENGTH: 1045
<212> TYPE: DNA
<213> ORGANISM: Human Cytomegalovirus

<400> SEQUENCE: 60

```
tcaagctttt ggaccctcgt acagaagcta atacgactca ctatagggaa ataagagaga      60

aaagaagagt aagaagaaat ataagagcca ccatgtgccg ccgcccggat tgcggcttct     120

ctttctcacc tggaccggtg atactgctgt ggtgttgcct tctgctgccc attgtttcct     180

cagccgccgt cagcgtcgct cctaccgccg ccgagaaagt ccccgcggag tgccccgaac     240

taacgcgccg atgcttgttg ggtgaggtgt ttgagggtga caagtatgaa agttggctgc     300

gcccgttggt gaatgttacc gggcgcgatg gcccgctatc gcaacttatc cgttaccgtc     360

ccgttacgcc ggaggccgcc aactccgtgc tgttggacga ggctttcctg gacactctgg     420

ccctgctgta caacaatccg gatcaattgc gggccctgct gacgctgttg agctcggaca     480

cagcgccgcg ctggatgacg gtgatgcgcg gctacagcga gtgcggcgat ggctcgccgg     540

ccgtgtacac gtgcgtggac gacctgtgcc gcggctacga cctcacgcga ctgtcatacg     600
```

```
ggcgcagcat cttcacggaa cacgtgttag gcttcgagct ggtgccaccg tctctcttta    660

acgtggtggt ggccatacgc aacgaagcca cgcgtaccaa ccgcgccgtg cgtctgcccg    720

tgagcaccgc tgccgcgccc gagggcatca cgctctttta cggcctgtac aacgcagtga    780

aggaattctg cctgcgtcac cagctggacc cgccgctgct acgccaccta gataaatact    840

acgccggact gccgcccgag ctgaagcaga cgcgcgtcaa cctgccggct cactcgcgct    900

atggccctca agcagtggat gctcgctgat aataggctgg agcctcggtg gccatgcttc    960

ttgccccttg ggcctccccc cagcccctcc tccccttcct gcacccgtac ccccgtggtc   1020

tttgaataaa gtctgagtgg gcggc                                         1045


<210> SEQ ID NO 61
<211> LENGTH: 278
<212> TYPE: PRT
<213> ORGANISM: Human Cytomegalovirus

<400> SEQUENCE: 61

Met Cys Arg Arg Pro Asp Cys Gly Phe Ser Phe Ser Pro Gly Pro Val
1               5                   10                  15

Ile Leu Leu Trp Cys Cys Leu Leu Leu Pro Ile Val Ser Ser Ala Ala
            20                  25                  30

Val Ser Val Ala Pro Thr Ala Ala Glu Lys Val Pro Ala Glu Cys Pro
        35                  40                  45

Glu Leu Thr Arg Arg Cys Leu Leu Gly Glu Val Phe Glu Gly Asp Lys
    50                  55                  60

Tyr Glu Ser Trp Leu Arg Pro Leu Val Asn Val Thr Gly Arg Asp Gly
65                  70                  75                  80

Pro Leu Ser Gln Leu Ile Arg Tyr Arg Pro Val Thr Pro Glu Ala Ala
                85                  90                  95

Asn Ser Val Leu Leu Asp Glu Ala Phe Leu Asp Thr Leu Ala Leu Leu
            100                 105                 110

Tyr Asn Asn Pro Asp Gln Leu Arg Ala Leu Leu Thr Leu Leu Ser Ser
        115                 120                 125

Asp Thr Ala Pro Arg Trp Met Thr Val Met Arg Gly Tyr Ser Glu Cys
    130                 135                 140

Gly Asp Gly Ser Pro Ala Val Tyr Thr Cys Val Asp Asp Leu Cys Arg
145                 150                 155                 160

Gly Tyr Asp Leu Thr Arg Leu Ser Tyr Gly Arg Ser Ile Phe Thr Glu
                165                 170                 175

His Val Leu Gly Phe Glu Leu Val Pro Pro Ser Leu Phe Asn Val Val
            180                 185                 190

Val Ala Ile Arg Asn Glu Ala Thr Arg Thr Asn Arg Ala Val Arg Leu
        195                 200                 205

Pro Val Ser Thr Ala Ala Ala Pro Glu Gly Ile Thr Leu Phe Tyr Gly
    210                 215                 220

Leu Tyr Asn Ala Val Lys Glu Phe Cys Leu Arg His Gln Leu Asp Pro
225                 230                 235                 240

Pro Leu Leu Arg His Leu Asp Lys Tyr Tyr Ala Gly Leu Pro Pro Glu
                245                 250                 255

Leu Lys Gln Thr Arg Val Asn Leu Pro Ala His Ser Arg Tyr Gly Pro
            260                 265                 270

Gln Ala Val Asp Ala Arg
        275
```

-continued

<210> SEQ ID NO 62
<211> LENGTH: 724
<212> TYPE: DNA
<213> ORGANISM: Human Cytomegalovirus

<400> SEQUENCE: 62

```
tcaagctttt ggaccctcgt acagaagcta atacgactca ctatagggaa ataagagaga     60
aaagaagagt aagaagaaat ataagagcca ccatgagtcc caaagatctg acgccgttct    120
tgacggcgtt gtggctgcta ttgggtcaca gccgcgtgcc gcgggtgcgc gcagaagaat    180
gttgcgaatt cataaacgtc aaccacccgc cggaacgctg ttacgatttc aaaatgtgca    240
atcgcttcac cgtcgcgctg cggtgtccgg acggcgaagt ctgctacagt cccgagaaaa    300
cggctgagat tcgcgggatc gtcaccacca tgacccattc attgacacgc caggtcgtac    360
acaacaaact gacgagctgc aactacaatc cgttatacct cgaagctgac gggcgaatac    420
gctgcggcaa agtaaacgac aaggcgcagt acctgctggg cgccgctggc agcgttccct    480
atcgatggat caatctggaa tacgacaaga taacccggat cgtgggcctg gatcagtacc    540
tggagagcgt taagaaacac aaacggctgg atgtgtgccg cgctaaaatg ggctatatgc    600
tgcagtgata ataggctgga gcctcggtgg ccatgcttct tgccccttgg gcctcccccc    660
agcccctcct ccccttcctg cacccgtacc cccgtggtct ttgaataaag tctgagtggg    720
cggc                                                                 724
```

<210> SEQ ID NO 63
<211> LENGTH: 171
<212> TYPE: PRT
<213> ORGANISM: Human Cytomegalovirus

<400> SEQUENCE: 63

```
Met Ser Pro Lys Asp Leu Thr Pro Phe Leu Thr Ala Leu Trp Leu Leu
1               5                   10                  15

Leu Gly His Ser Arg Val Pro Arg Val Arg Ala Glu Glu Cys Cys Glu
            20                  25                  30

Phe Ile Asn Val Asn His Pro Pro Glu Arg Cys Tyr Asp Phe Lys Met
        35                  40                  45

Cys Asn Arg Phe Thr Val Ala Leu Arg Cys Pro Asp Gly Glu Val Cys
    50                  55                  60

Tyr Ser Pro Glu Lys Thr Ala Glu Ile Arg Gly Ile Val Thr Thr Met
65                  70                  75                  80

Thr His Ser Leu Thr Arg Gln Val Val His Asn Lys Leu Thr Ser Cys
                85                  90                  95

Asn Tyr Asn Pro Leu Tyr Leu Glu Ala Asp Gly Arg Ile Arg Cys Gly
            100                 105                 110

Lys Val Asn Asp Lys Ala Gln Tyr Leu Leu Gly Ala Ala Gly Ser Val
        115                 120                 125

Pro Tyr Arg Trp Ile Asn Leu Glu Tyr Asp Lys Ile Thr Arg Ile Val
    130                 135                 140

Gly Leu Asp Gln Tyr Leu Glu Ser Val Lys Lys His Lys Arg Leu Asp
145                 150                 155                 160

Val Cys Arg Ala Lys Met Gly Tyr Met Leu Gln
                165                 170
```

<210> SEQ ID NO 64
<211> LENGTH: 846
<212> TYPE: DNA

<213> ORGANISM: Human Cytomegalovirus

<400> SEQUENCE: 64
tcaagctttt ggaccctcgt acagaagcta atacgactca ctatagggaa ataagagaga 60
aaagaagagt aagaagaaat ataagagcca ccatgctgcg gcttctgctt cgtcaccact 120
ttcactgcct gcttctgtgc gcggtttggg caacgccctg tctggcgtct ccgtggtcga 180
cgctaacagc aaaccagaat ccgtccccgc catggtctaa actgacgtat tccaaaccgc 240
atgacgcggc gacgttttac tgtccttttc tctatccctc gcccccacga tccccccttgc 300 aattctcggg gttccagcgg gtatcaacgg gtcccgagtg tcgcaacgag accctgtatc 360
tgctgtacaa ccgggaaggc cagaccttgg tggagagaag ctccacctgg gtgaaaaagg 420
tgatctggta cctgagcggt cggaaccaaa ccatcctcca acggatgccc cgaacggctt 480
cgaaaccgag cgacggaaac gtgcagatca gcgtggaaga cgccaagatt tttggagcgc 540
acatggtgcc caagcgctgc tacgcttcgt cgtcaacgat ggcacacgtt atcagatgtg 600
tgtgatgaag ctggagagct gggctcacgt cttccgggac tacagcgtgt cttttcaggt 660
gcgattgacg ttcaccgagg ccaataacca gacttacacc ttctgcaccc atcccaatct 720
catcgtttga taataggctg gagcctcggt ggccatgctt cttgcccctt gggcctcccc 780
ccagcccctc ctccccttcc tgcacccgta cccccgtggt ctttgaataa agtctgagtg 840
ggcggc 846

<210> SEQ ID NO 65
<211> LENGTH: 214
<212> TYPE: PRT
<213> ORGANISM: Human Cytomegalovirus

<400> SEQUENCE: 65

Met Leu Arg Leu Leu Leu Arg His His Phe His Cys Leu Leu Leu Cys
1 5 10 15

Ala Val Trp Ala Thr Pro Cys Leu Ala Ser Pro Trp Ser Thr Leu Thr
20 25 30

Ala Asn Gln Asn Pro Ser Pro Pro Trp Ser Lys Leu Thr Tyr Ser Lys
35 40 45

Pro His Asp Ala Ala Thr Phe Tyr Cys Pro Phe Leu Tyr Pro Ser Pro
50 55 60

Pro Arg Ser Pro Leu Gln Phe Ser Gly Phe Gln Arg Val Ser Thr Gly
65 70 75 80

Pro Glu Cys Arg Asn Glu Thr Leu Tyr Leu Leu Tyr Asn Arg Glu Gly
85 90 95

Gln Thr Leu Val Glu Arg Ser Ser Thr Trp Val Lys Lys Val Ile Trp
100 105 110

Tyr Leu Ser Gly Arg Asn Gln Thr Ile Leu Gln Arg Met Pro Arg Thr
115 120 125

Ala Ser Lys Pro Ser Asp Gly Asn Val Gln Ile Ser Val Glu Asp Ala
130 135 140

Lys Ile Phe Gly Ala His Met Val Pro Lys Gln Thr Lys Leu Leu Arg
145 150 155 160

Phe Val Val Asn Asp Gly Thr Arg Tyr Gln Met Cys Val Met Lys Leu
165 170 175

Glu Ser Trp Ala His Val Phe Arg Asp Tyr Ser Val Ser Phe Gln Val
180 185 190

Arg Leu Thr Phe Thr Glu Ala Asn Asn Gln Thr Tyr Thr Phe Cys Thr

```
        195                 200                 205

His Pro Asn Leu Ile Val
    210


<210> SEQ ID NO 66
<211> LENGTH: 598
<212> TYPE: DNA
<213> ORGANISM: Human Cytomegalovirus

<400> SEQUENCE: 66

tcaagctttt ggaccctcgt acagaagcta atacgactca ctatagggaa ataagagaga     60

aaagaagagt aagaagaaat ataagagcca ccatgcggct gtgtcgggtg tggctgtctg    120

tttgtctgtg cgccgtggtg ctgggtcagt gccagcggga aaccgcggaa aagaacgatt    180

attaccgagt accgcattac tgggacgcgt gctctcgcgc gctgcccgac caaacccgtt    240

acaagtatgt ggaacagctc gtggacctca cgttgaacta ccactacgat gcgagccacg    300

gcttggacaa ctttgacgtg ctcaagagaa tcaacgtgac cgaggtgtcg ttgctcatca    360

gcgactttag acgtcagaac cgtcgcggcg gcaccaacaa aaggaccacg ttcaacgccg    420

ccggttcgct ggcgccacac gcccggagcc tcgagttcag cgtgcggctc tttgccaact    480

gataataggc tggagcctcg gtggccatgc ttcttgcccc ttgggcctcc ccccagcccc    540

tcctcccctt cctgcacccg tacccccgtg gtctttgaat aaagtctgag tgggcggc      598


<210> SEQ ID NO 67
<211> LENGTH: 129
<212> TYPE: PRT
<213> ORGANISM: Human Cytomegalovirus

<400> SEQUENCE: 67

Met Arg Leu Cys Arg Val Trp Leu Ser Val Cys Leu Cys Ala Val Val
1               5                   10                  15

Leu Gly Gln Cys Gln Arg Glu Thr Ala Glu Lys Asn Asp Tyr Tyr Arg
            20                  25                  30

Val Pro His Tyr Trp Asp Ala Cys Ser Arg Ala Leu Pro Asp Gln Thr
        35                  40                  45

Arg Tyr Lys Tyr Val Glu Gln Leu Val Asp Leu Thr Leu Asn Tyr His
    50                  55                  60

Tyr Asp Ala Ser His Gly Leu Asp Asn Phe Asp Val Leu Lys Arg Ile
65                  70                  75                  80

Asn Val Thr Glu Val Ser Leu Leu Ile Ser Asp Phe Arg Arg Gln Asn
                85                  90                  95

Arg Arg Gly Gly Thr Asn Lys Arg Thr Thr Phe Asn Ala Ala Gly Ser
            100                 105                 110

Leu Ala Pro His Ala Arg Ser Leu Glu Phe Ser Val Arg Leu Phe Ala
        115                 120                 125

Asn


<210> SEQ ID NO 68
<211> LENGTH: 2933
<212> TYPE: DNA
<213> ORGANISM: Human Cytomegalovirus

<400> SEQUENCE: 68

tcaagctttt ggaccctcgt acagaagcta atacgactca ctatagggaa ataagagaga     60

aaagaagagt aagaagaaat ataagagcca ccatggaatc caggatctgg tgcctggtag    120
```

```
tctgcgttaa cttgtgtatc gtctgtctgg gtgctgcggt ttcctcatct tctactcgtg    180
gaacttctgc tactcacagt caccattcct ctcatacgac gtctgctgct cactctcgat    240
ccggttcagt ctctcaacgc gtaacttctt cccaaacggt cagccatggt gttaacgaga    300
ccatctacaa cactaccctc aagtacggag atgtggtggg ggtcaatacc accaagtacc    360
cctatcgcgt gtgttctatg gcccagggta cggatcttat tcgctttgaa cgtaatatcg    420
tctgcacctc gatgaagccc atcaatgaag acctggacga gggcatcatg gtggtctaca    480
aacgcaacat cgtcgcgcac acctttaagg tacgagtcta ccagaaggtt ttgacgtttc    540
gtcgtagcta cgcttacatc cacaccactt atctgctggg cagcaacacg gaatacgtgg    600
cgcctcctat gtgggagatt catcatatca acagccacag tcagtgctac agttcctaca    660
gccgcgttat agcaggcacg gttttcgtgg cttatcatag ggacagctat gaaaacaaaa    720
ccatgcaatt aatgcccgac gattattcca acacccacag tacccgttac gtgacggtca    780
aggatcaatg gcacagccgc ggcagcacct ggctctatcg tgagacctgt aatctgaatt    840
gtatggtgac catcactact gcgcgctcca aatatcctta tcattttttc gccacttcca    900
cgggtgacgt ggttgacatt tctcctttct acaacggaac caatcgcaat gccagctact    960
ttggagaaaa cgccgacaag tttttcattt ttccgaacta cactatcgtc tccgactttg   1020
gaagaccgaa ttctgcgtta gagacccaca ggttggtggc ttttcttgaa cgtgcggact   1080
cggtgatctc ctgggatata caggacgaaa agaatgtcac ttgtcaactc actttctggg   1140
aagcctcgga acgcaccatt cgttccgaag ccgaggactc gtatcacttt tcttctgcca   1200
aaatgaccgc cactttctta tctaagaagc aagaggtgaa catgtccgac tctgcgctgg   1260
actgcgtacg tgatgaggct ataaataagt tacagcagat tttcaatact tcatacaatc   1320
aaacatatga aaaatatgga aacgtgtccg tctttgaaac cactggtggt ttggtagtgt   1380
tctggcaagg tatcaagcaa aaatctctgg tggaactcga acgtttggcc aaccgctcca   1440
gtctgaatct tactcataat agaaccaaaa gaagtacaga tggcaacaat gcaactcatt   1500
tatccaacat ggaatcggtg cacaatctgg tctacgccca gctgcagttc acctatgaca   1560
cgttgcgcgg ttacatcaac cgggcgctgg cgcaaatcgc agaagcctgg tgtgtggatc   1620
aacggcgcac cctagaggtc ttcaaggaac tcagcaagat caacccgtca gccattctct   1680
cggccattta caacaaaccg attgccgcgc gtttcatggg tgatgtcttg ggcctggcca   1740
gctgcgtgac catcaaccaa accagcgtca aggtgctgcg tgatatgaac gtgaaggagt   1800
cgccaggacg ctgctactca cgacccgtgg tcatctttaa tttcgccaac agctcgtacg   1860
tgcagtacgg tcaactgggc gaggacaacg aaatcctgtt gggcaaccac cgcactgagg   1920
aatgtcagct tcccagcctc aagatcttca tcgccgggaa ctcggcctac gagtacgtgg   1980
actacctctt caaacgcatg attgacctca gcagtatctc caccgtcgac agcatgatcg   2040
ccctggatat cgacccgctg gaaaataccg acttcagggt actggaactt tactcgcaga   2100
aagagctgcg ttccagcaac gtttttgacc tcgaagagat catgcgcgaa ttcaactcgt   2160
acaagcagcg ggtaaagtac gtggaggaca aggtagtcga cccgctaccg ccctacctca   2220
agggtctgga cgacctcatg agcggcctgg gcgccgcggg aaaggccgtt ggcgtagcca   2280
ttggggccgt gggtggcgcg gtggcctccg tggtcgaagg cgttgccacc ttcctcaaaa   2340
acccctccgg agcgttcacc atcatcctcg tggccatagc tgtagtcatt atcacttatt   2400
tgatctatac tcgacagcgg cgtttgtgca cgcagccgct gcagaacctc tttccctatc   2460
tggtgtccgc cgacgggacc accgtgacgt cgggcagcac caaagacacg tcgttacagg   2520
```

```
ctccgccttc ctacgaggaa agtgtttata attctggtcg caaaggaccg ggaccaccgt   2580

cgtctgatgc atccacggcg gctccgcctt acaccaacga gcaggcttac cagatgcttc   2640

tggccctggc ccgtctggac gcagagcagc gagcgcagca gaacggtaca gattctttgg   2700

acggacggac tggcacgcag gacaagggac agaagcccaa cctactagac cgactgcgac   2760

atcgcaaaaa cggctaccga cacttgaaag actctgacga agaagagaac gtcttgataa   2820

taggctggag cctcggtggc catgcttctt gccccttggg cctcccccca gcccctcctc   2880

cccttcctgc acccgtaccc ccgtggtctt tgaataaagt ctgagtgggc ggc          2933
```

<210> SEQ ID NO 69
<211> LENGTH: 907
<212> TYPE: PRT
<213> ORGANISM: Human Cytomegalovirus

<400> SEQUENCE: 69

```
Met Glu Ser Arg Ile Trp Cys Leu Val Val Cys Val Asn Leu Cys Ile
1               5                   10                  15

Val Cys Leu Gly Ala Ala Val Ser Ser Ser Ser Thr Arg Gly Thr Ser
            20                  25                  30

Ala Thr His Ser His His Ser Ser His Thr Thr Ser Ala Ala His Ser
        35                  40                  45

Arg Ser Gly Ser Val Ser Gln Arg Val Thr Ser Ser Gln Thr Val Ser
    50                  55                  60

His Gly Val Asn Glu Thr Ile Tyr Asn Thr Thr Leu Lys Tyr Gly Asp
65                  70                  75                  80

Val Val Gly Val Asn Thr Thr Lys Tyr Pro Tyr Arg Val Cys Ser Met
                85                  90                  95

Ala Gln Gly Thr Asp Leu Ile Arg Phe Glu Arg Asn Ile Val Cys Thr
            100                 105                 110

Ser Met Lys Pro Ile Asn Glu Asp Leu Asp Glu Gly Ile Met Val Val
        115                 120                 125

Tyr Lys Arg Asn Ile Val Ala His Thr Phe Lys Val Arg Val Tyr Gln
    130                 135                 140

Lys Val Leu Thr Phe Arg Arg Ser Tyr Ala Tyr Ile His Thr Thr Tyr
145                 150                 155                 160

Leu Leu Gly Ser Asn Thr Glu Tyr Val Ala Pro Pro Met Trp Glu Ile
                165                 170                 175

His His Ile Asn Ser His Ser Gln Cys Tyr Ser Ser Tyr Ser Arg Val
            180                 185                 190

Ile Ala Gly Thr Val Phe Val Ala Tyr His Arg Asp Ser Tyr Glu Asn
        195                 200                 205

Lys Thr Met Gln Leu Met Pro Asp Asp Tyr Ser Asn Thr His Ser Thr
    210                 215                 220

Arg Tyr Val Thr Val Lys Asp Gln Trp His Ser Arg Gly Ser Thr Trp
225                 230                 235                 240

Leu Tyr Arg Glu Thr Cys Asn Leu Asn Cys Met Val Thr Ile Thr Thr
                245                 250                 255

Ala Arg Ser Lys Tyr Pro Tyr His Phe Phe Ala Thr Ser Thr Gly Asp
            260                 265                 270

Val Val Asp Ile Ser Pro Phe Tyr Asn Gly Thr Asn Arg Asn Ala Ser
        275                 280                 285

Tyr Phe Gly Glu Asn Ala Asp Lys Phe Phe Ile Phe Pro Asn Tyr Thr
    290                 295                 300
```

Ile Val Ser Asp Phe Gly Arg Pro Asn Ser Ala Leu Glu Thr His Arg
305 310 315 320

Leu Val Ala Phe Leu Glu Arg Ala Asp Ser Val Ile Ser Trp Asp Ile
325 330 335

Gln Asp Glu Lys Asn Val Thr Cys Gln Leu Thr Phe Trp Glu Ala Ser
340 345 350

Glu Arg Thr Ile Arg Ser Glu Ala Glu Asp Ser Tyr His Phe Ser Ser
355 360 365

Ala Lys Met Thr Ala Thr Phe Leu Ser Lys Lys Gln Glu Val Asn Met
370 375 380

Ser Asp Ser Ala Leu Asp Cys Val Arg Asp Glu Ala Ile Asn Lys Leu
385 390 395 400

Gln Gln Ile Phe Asn Thr Ser Tyr Asn Gln Thr Tyr Glu Lys Tyr Gly
405 410 415

Asn Val Ser Val Phe Glu Thr Thr Gly Gly Leu Val Val Phe Trp Gln
420 425 430

Gly Ile Lys Gln Lys Ser Leu Val Glu Leu Glu Arg Leu Ala Asn Arg
435 440 445

Ser Ser Leu Asn Leu Thr His Asn Arg Thr Lys Arg Ser Thr Asp Gly
450 455 460

Asn Asn Ala Thr His Leu Ser Asn Met Glu Ser Val His Asn Leu Val
465 470 475 480

Tyr Ala Gln Leu Gln Phe Thr Tyr Asp Thr Leu Arg Gly Tyr Ile Asn
485 490 495

Arg Ala Leu Ala Gln Ile Ala Glu Ala Trp Cys Val Asp Gln Arg Arg
500 505 510

Thr Leu Glu Val Phe Lys Glu Leu Ser Lys Ile Asn Pro Ser Ala Ile
515 520 525

Leu Ser Ala Ile Tyr Asn Lys Pro Ile Ala Ala Arg Phe Met Gly Asp
530 535 540

Val Leu Gly Leu Ala Ser Cys Val Thr Ile Asn Gln Thr Ser Val Lys
545 550 555 560

Val Leu Arg Asp Met Asn Val Lys Glu Ser Pro Gly Arg Cys Tyr Ser
565 570 575

Arg Pro Val Val Ile Phe Asn Phe Ala Asn Ser Ser Tyr Val Gln Tyr
580 585 590

Gly Gln Leu Gly Glu Asp Asn Glu Ile Leu Leu Gly Asn His Arg Thr
595 600 605

Glu Glu Cys Gln Leu Pro Ser Leu Lys Ile Phe Ile Ala Gly Asn Ser
610 615 620

Ala Tyr Glu Tyr Val Asp Tyr Leu Phe Lys Arg Met Ile Asp Leu Ser
625 630 635 640

Ser Ile Ser Thr Val Asp Ser Met Ile Ala Leu Asp Ile Asp Pro Leu
645 650 655

Glu Asn Thr Asp Phe Arg Val Leu Glu Leu Tyr Ser Gln Lys Glu Leu
660 665 670

Arg Ser Ser Asn Val Phe Asp Leu Glu Glu Ile Met Arg Glu Phe Asn
675 680 685

Ser Tyr Lys Gln Arg Val Lys Tyr Val Glu Asp Lys Val Val Asp Pro
690 695 700

Leu Pro Pro Tyr Leu Lys Gly Leu Asp Asp Leu Met Ser Gly Leu Gly
705 710 715 720

```
Ala Ala Gly Lys Ala Val Gly Val Ala Ile Gly Ala Val Gly Gly Ala
                725                 730                 735

Val Ala Ser Val Val Glu Gly Val Ala Thr Phe Leu Lys Asn Pro Phe
            740                 745                 750

Gly Ala Phe Thr Ile Ile Leu Val Ala Ile Ala Val Val Ile Ile Thr
        755                 760                 765

Tyr Leu Ile Tyr Thr Arg Gln Arg Arg Leu Cys Thr Gln Pro Leu Gln
    770                 775                 780

Asn Leu Phe Pro Tyr Leu Val Ser Ala Asp Gly Thr Thr Val Thr Ser
785                 790                 795                 800

Gly Ser Thr Lys Asp Thr Ser Leu Gln Ala Pro Pro Ser Tyr Glu Glu
                805                 810                 815

Ser Val Tyr Asn Ser Gly Arg Lys Gly Pro Gly Pro Pro Ser Ser Asp
            820                 825                 830

Ala Ser Thr Ala Ala Pro Pro Tyr Thr Asn Glu Gln Ala Tyr Gln Met
        835                 840                 845

Leu Leu Ala Leu Ala Arg Leu Asp Ala Glu Gln Arg Ala Gln Gln Asn
    850                 855                 860

Gly Thr Asp Ser Leu Asp Gly Arg Thr Gly Thr Gln Asp Lys Gly Gln
865                 870                 875                 880

Lys Pro Asn Leu Leu Asp Arg Leu Arg His Arg Lys Asn Gly Tyr Arg
                885                 890                 895

His Leu Lys Asp Ser Asp Glu Glu Glu Asn Val
            900                 905


<210> SEQ ID NO 70
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 70

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 71
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 71

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 72
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 72

Gly Ser Gly Gln Cys Thr Asn Tyr Ala Leu Leu Lys Leu Ala Gly Asp
```

```
1               5                   10                  15

Val Glu Ser Asn Pro Gly Pro
            20


<210> SEQ ID NO 73
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 73

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25


<210> SEQ ID NO 74
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 74

ccgcgccaag aggagc                                                   16


<210> SEQ ID NO 75
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 75

gctactaact tcagcctgct gaagcaggct ggagacgtgg aggagaaccc tggacct      57


<210> SEQ ID NO 76
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 76

gtgaaacaga ctttgaattt tgaccttctc aagttggcgg gagacgtgga gtccaaccct   60

ggacct                                                              66


<210> SEQ ID NO 77
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 77

cagtgtacta attatgctct cttgaaattg gctggagatg ttgagagcaa ccctggacct   60


<210> SEQ ID NO 78
<211> LENGTH: 54
<212> TYPE: DNA
<213> ORGANISM: Artificial Sequence
<220> FEATURE:
<223> OTHER INFORMATION: Synthetic Polynucleotide
```

<400> SEQUENCE: 78
gagggcagag gaagtctgct aacatgcggt gacgtcgagg agaatcctgg acct 54

<210> SEQ ID NO 79
<211> LENGTH: 2437
<212> TYPE: RNA
<213> ORGANISM: Human Cytomegalovirus

<400> SEQUENCE: 79
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040

```
gccaaagcgc ccugcuagaa uacgacgaca cgcaaggcgu caucaacauc auguacaugc   2100

acgacucgga cgacguccuu uucgcccugg aucccuacaa cgaaguggug gucucaucuc   2160

cgcgaacuca cuaccucaug cuuuugaaaa acgguacggu acuagaagua acugacgucg   2220

ucguggacgc caccgacagu cgucuccuca ugauguccgu cuacgcgcua ucggccauca   2280

ucggcaucua ucugcucuac cgcaugcuca agacaugcug auaauaggcu ggagccucgg   2340

uggccaugcu ucuugccccu ugggccuccc cccagccccu ccucccuuc cugcacccgu   2400

acccccgugg ucuuugaaua aagucugagu gggcggc                            2437
```

<210> SEQ ID NO 80
<211> LENGTH: 2464
<212> TYPE: RNA
<213> ORGANISM: Artificial Sequence
<220> FEATURE:
<223> OTHER INFORMATION: Synthetic Polynucleotide

<400> SEQUENCE: 80

```
ucaagcuuuu ggacccucgu acagaagcua auacgacuca cuauagggaa auaagagaga     60

aaagaagagu aagaagaaau auaagagcca ccaugcggcc aggccucccc uccuaccuca    120

ucauccucgc cgucugucuc uucagccacc uacuuucguc acgauauggc gcagaagccg    180

uauccgaacc gcuggacaaa gcguuucacc uacugcucaa caccuacggg agacccaucc    240

gcuuccugcg ugaaaauacc acccagugua ccuacaacag cagccuccgu aacagcacgg    300

ucgucaggga aaacgccauc aguuucaacu uuuuccaaag cuauaaucaa uacuauguau    360

uccauaugcc ucgaugucuu uuugcggguc cucuggcgga gcaguuucug aaccagguag    420

aucugaccga aacccuggaa agauaccaac agagacuuaa cacuuacgcg cugguaucca    480

aagaccuggc cagcuaccga ucuuuuucgc agcagcuaaa ggcacaagac agccuaggug    540

aacagcccac cacugugcca ccgcccauug accugucaau accucacguu uggaugccac    600

cgcaaaccac uccacacggc uggacagaau cacauaccac cucaggacua caccgaccac    660

acuuuaacca gaccuguauc cucuuugaug gacacgaucu acuauucagc accgucacac    720

cuuguuugca ccaaggcuuu uaccucaucg acgaacuacg uuacguuaaa auaacacuga    780

ccgaggacuu cuucguaguu acggugucca uagacgacga cacacccaug cugcuuaucu    840

ucggccaucu uccacgcgua cuuuucaaag cgcccuauca acgcgacaac uuuauacuac    900

gacaaacuga aaaacacgag cuccuggugc uaguuaagaa agaucaacug aaccgucacu    960

cuuaucucaa agacccggac uuucuugacg ccgcacuuga cuucaacuac cuagaccuca   1020

gcgcacuacu acguaacagc uuucaccguu acgccgugga uguacucaag agcggucgau   1080

gucagaugcu ggaccgccgc acgguagaaa uggccuucgc cuacgcauua gcacuguucg   1140

cagcagcccg acaagaagag gccggcgccc aagucuccgu cccacgggcc cuagaccgcc   1200

aggccgcacu cuuacaaaua caagaauuua ugaucaccug ccucucacaa acaccaccac   1260

gcaccacguu gcugcuguau cccacggccg uggaccuggc caaacgagcc cuuuggacac   1320

cgaaucagau caccgacauc accagccucg uacgccuggu cuacauacuc ucuaaacaga   1380

aucagcaaca ucucaucccc caaugggcac uacgacagau cgccgacuuu gcccuaaaac   1440

uacacaaaac gcaccuggcc ucuuuucuuu cagccuucgc acgccaagaa cucuaccuca   1500

ugggcagccu cguccacucc augcugguac auacgacgga gagacgcgaa aucuucaucg   1560

uagaaacggg ccucuguuca uuggccgagc uaucacacuu uacgcaguug uuagcucauc   1620
```

cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacagu cgucuccuca ugauguccgu cuacgcgcua ucggccauca 2280
ucggcaucua ucugcucuac cgcaugcuca agacaugcga uuacaaggac gaugacgaua 2340
agugaugaua auaggcugga gccucggugg ccaugcuucu ugccccuugg gccucccccc 2400
agccccuccu ccccuuccug cacccguacc cccguggucu uugaauaaag ucugaguggg 2460
cggc 2464

<210> SEQ ID NO 81
<211> LENGTH: 1045
<212> TYPE: RNA
<213> ORGANISM: Human Cytomegalovirus

<400> SEQUENCE: 81
ucaagcuuuu ggacccucgu acagaagcua auacgacuca cuauagggaa auaagagaga 60
aaagaagagu aagaagaaau auaagagcca ccaugugccg ccgcccggau ugcggcuucu 120
cuuucucacc uggaccggug auacugcugu gguguugccu ucugcugccc auuguuuccu 180
cagccgccgu cagcgucgcu ccuaccgccg ccgagaaagu ccccgcggag ugccccgaac 240
uaacgcgccg augcuuguug ggugaggugu uugaggguga caaguaugaa aguuggcugc 300
gcccguuggu gaauguuacc gggcgcgaug gcccgcuauc gcaacuuauc cguuaccguc 360
ccguuacgcc ggaggccgcc aacuccgugc uguuggacga ggcuuuccug gacacucugg 420
cccugcugua caacaauccg gaucaauugc gggcccugcu gacgcuguug agcucggaca 480
cagcgccgcg cuggaugacg gugaugcgcg gcuacagcga gugcggcgau ggcucgccgg 540
ccguguacac gugcguggac gaccugugcc gcggcuacga ccucacgcga cugucauacg 600
ggcgcagcau cuucacggaa cacguguuag gcuucgagcu ggugccaccg ucucucuuua 660
acgugguggu ggccauacgc aacgaagcca cgcguaccaa ccgcgccgug cgucugcccg 720
ugagcaccgc ugccgcgccc gagggcauca cgcucuuuua cggccuguac aacgcaguga 780
aggaauucug ccugcgucac cagcuggacc cgccgcugcu acgccaccua gauaaauacu 840
acgccggacu gccgcccgag cugaagcaga cgcgcgucaa ccugccggcu cacucgcgcu 900
auggcccuca agcaguggau gcucgcugau aauaggcugg agccucggug gccaugcuuc 960
uugccccuug ggccuccccc cagccccucc uccccuuccu gcacccguac cccguggucu 1020
uuugaauaaa gucugagugg gcggc 1045

<210> SEQ ID NO 82
<211> LENGTH: 1072
<212> TYPE: RNA
<213> ORGANISM: Artificial Sequence
<220> FEATURE:
<223> OTHER INFORMATION: Synthetic Polynucleotide

<400> SEQUENCE: 82
ucaagcuuuu ggacccucgu acagaagcua auacgacuca cuauagggaa auaagagaga 60
aaagaagagu aagaagaaau auaagagcca ccaugugccg ccgcccggau ugcggcuucu 120
cuuucucacc uggaccggug auacugcugu gguguugccu ucugcugccc auuguuuccu 180
cagccgccgu cagcgucgcu ccuaccgccg ccgagaaagu ccccgcggag ugccccgaac 240
uaacgcgccg augcuuguug ggugaggugu uugaggguga caaguaugaa aguuggcugc 300
gcccguuggu gaauguuacc gggcgcgaug gcccgcuauc gcaacuuauc cguuaccguc 360
ccguuacgcc ggaggccgcc aacuccgugc uguuggacga ggcuuuccug gacacucugg 420
cccugcugua caacaauccg gaucaauugc gggcccugcu gacgcuguug agcucggaca 480
cagcgccgcg cuggaugacg gugaugcgcg gcuacagcga gugcggcgau ggcucgccgg 540
ccguguacac gugcguggac gaccugugcc gcggcuacga ccucacgcga cugucauacg 600
ggcgcagcau cuucacggaa cacguguuag gcuucgagcu ggugccaccg ucucucuuua 660
acgugguggu ggccauacgc aacgaagcca cgcguaccaa ccgcgccgug cgucugcccg 720
ugagcaccgc ugccgcgccc gagggcauca cgcucuuuua cggccuguac aacgcaguga 780
aggaauucug ccugcgucac cagcuggacc cgccgcugcu acgccaccua gauaaauacu 840
acgccggacu gccgcccgag cugaagcaga cgcgcgucaa ccugccggcu cacucgcgcu 900
auggcccuca agcaguggau gcucgcgauu acaaggacga ugacgauaag ugaugauaau 960
aggcuggagc cucgguggcc augcuucuug ccccuugggc cucccccag ccccuccucc 1020 ccuuccugca cccguacccc cgguggucuuu gaauaaaguc ugagugggcg gc 1072

<210> SEQ ID NO 83
<211> LENGTH: 2932
<212> TYPE: RNA
<213> ORGANISM: Human Cytomegalovirus

<400> SEQUENCE: 83
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguugguggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaauaagu uacagcagau uuucaauacu ucauacaauc 1320
aaacauauga aaaauaugga aacguguccg ucuuugaaac cacuggugu uugguagugu 1380 ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg ugugugggauc 1620 aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagcg gguaaaguac guggaggaca agguagucga cccgcuaccg cccuaccuca 2220
agggucugga cgaccucaug agcggccugg gcgccgcggg aaaggccguu ggcguagcca 2280
uuggggccgu ggguggcgcg guggccuccg uggucgaagg cguugccacc uuccucaaaa 2340
accccuucgg agcguucacc aucauccucg uggccauagc uguagucauu aucacuuauu 2400
ugaucuauac ucgacagcgg cguuugugca cgcagccgcu gcagaaccuc uuucccuauc 2460 uggguguccgc cgacgggacc accgugacgu cgggcagcac caaagacacg ucguuacagg 2520
cuccgccuuc cuacgaggaa aguguuuaua auucuggucg caaaggaccg ggaccaccgu 2580
cgucugaugc auccacggcg gcuccgccuu acaccaacga gcaggcuuac cagaugcuuc 2640
uggcccuggc ccgucuggac gcagagcagc gagcgcagca gaacgguaca gauucuuugg 2700
acggacggac uggcacgcag gacaagggac agaagcccaa ccuacuagac cgacugcgac 2760
aucgcaaaaa cggcuaccga cacuugaaag acucugacga agaagagaac gucugauaau 2820
aggcuggagc cucgguggcc augcuucuug ccccuugggc cuccccccag ccccuccucc 2880
ccuuccugca cccguacccc cguggucuuu gaauaaaguc ugagugggcg gc 2932

<210> SEQ ID NO 84
<211> LENGTH: 2956
<212> TYPE: RNA
<213> ORGANISM: Artificial Sequence
<220> FEATURE:
<223> OTHER INFORMATION: Synthetic Polynucleotide

<400> SEQUENCE: 84
ucaagcuuuu ggacccucgu acagaagcua auacgacuca cuauagggaa auaagagaga 60

-continued

```
aaagaagagu aagaagaaau auaagagcca ccauggaauc caggaucugg ugccugguag    120
ucugcguuaa cuuguguauc gucugucugg gugcugcggu uuccucaucu ucuacucgug    180
gaacuucugc uacucacagu caccauuccu cucauacgac gucugcugcu cacucucgau    240
ccgguucagu cucucaacgc guaacuucuu cccaaacggu cagccauggu guuaacgaga    300
ccaucuacaa cacuacccuc aaguacggag auguggugg ggucaauacc accaaguacc    360
ccuaucgcgu guguucuaug gcccagggua cggaucuuau ucgcuuugaa cguaauaucg    420
ucugcaccuc gaugaagccc aucaaugaag accuggacga gggcaucaug guggucuaca    480
aacgcaacau cgucgcgcac accuuuaagg uacgagucua ccagaagguu uugacguuuc    540
gucguagcua cgcuuacauc cacaccacuu aucugcuggg cagcaacacg gaauacgugg    600
cgccuccuau gugggagauu caucauauca acagccacag ucagugcuac aguuccuaca    660
gccgcguuau agcaggcacg guuuucgugg cuuaucauag ggacagcuau gaaaacaaaa    720
ccaugcaauu aaugcccgac gauuauucca acacccacag uacccguuac gugacgguca    780
aggaucaaug gcacagccgc ggcagcaccu ggcucuaucg ugagaccugu aaucugaauu    840
guauggugac caucacuacu gcgcgcucca aauauccuua ucauuuuuuc gccacuucca    900
cgggugacgu gguugacauu ucuccuuucu acaacggaac caaucgcaau gccagcuacu    960
uuggagaaaa cgccgacaag uuuuucauuu uuccgaacua cacuaucguc uccgacuuug   1020
gaagaccgaa uucugcguua gagacccaca gguugguggc uuuucuugaa cgugcggacu   1080
cggugaucuc cugggauaua caggacgaaa agaaugucac uugucaacuc acuuucuggg   1140
aagccucgga acgcaccauu cguuccgaag ccgaggacuc guaucacuuu ucuucugcca   1200
aaaugaccgc cacuuucuua ucuaagaagc aagaggugaa cauguccgac ucugcgcugg   1260
acugcguacg ugaugaggcu auaaauaagu uacagcagau uucaauacu ucauacaauc    1320
aaacauauga aaaauaugga aacguguccg ucuuugaaac cacuggugu uugguagugu    1380
ucuggcaagg uaucaagcaa aaaucucugg uggaacucga acguuuggcc aaccgcucca   1440
gucugaaucu uacucauaau agaaccaaaa gaaguacaga uggcaacaau gcaacucauu   1500
uauccaacau ggaaucggug cacaaucugg ucuacgccca gcugcaguuc accuaugaca   1560
cguugcgcgg uuacaucaac cgggcgcugg cgcaaaucgc agaagccugg ugugugggauc  1620
aacggcgcac ccuagagguc uucaaggaac ucagcaagau caacccguca gccauucucu   1680
cggccauuua caacaaaccg auugccgcgc guuucauggg ugaugucuug ggccuggcca   1740
gcugcgugac caucaaccaa accagcguca aggugcugcg ugauaugaac gugaaggagu   1800
cgccaggacg cugcuacuca cgacccgugg ucaucuuuaa uuucgccaac agcucguacg   1860
ugcaguacgg ucaacugggc gaggacaacg aaauccuguu gggcaaccac cgcacugagg   1920
aaugucagcu ucccagccuc aagaucuuca ucgccgggaa cucggccuac gaguacgugg   1980
acuaccucuu caaacgcaug auugaccuca gcaguaucuc caccgucgac agcaugaucg   2040
cccuggauau cgacccgcug gaaaauaccg acuucagggu acuggaacuu uacucgcaga   2100
aagagcugcg uuccagcaac guuuuugacc ucgaagagau caugcgcgaa uucaacucgu   2160
acaagcagcg gguaaaguac guggaggaca agguagucga cccgcuaccg cccuaccuca   2220
agggucugga cgaccucaug agcggccugg gcgccgcggg aaaggccguu ggcguagcca   2280
uuggggccgu gggugggcgcg guggccuccg uggucgaagg cguugccacc uuccucaaaa  2340
accccuucgg agcguucacc aucauccucg uggccauagc uguagucauu aucacuuauu   2400
```

ugaucuauac ucgacagcgg cguuugugca cgcagccgcu gcagaaccuc uuucccuauc 2460 uggugucgc cgacgggacc accgugacgu cgggcagcac caaagacacg ucguuacagg 2520
cuccgccuuc cuacgaggaa aguguuuaua auucuggucg caaaggaccg ggaccaccgu 2580
cgucugaugc auccacggcg gcuccgccuu acaccaacga gcaggcuuac cagaugcuuc 2640
uggcccuggc ccgucuggac gcagagcagc gagcgcagca gaacgguaca gauucuuugg 2700
acggacggac uggcacgcag gacaagggac agaagcccaa ccuacuagac cgacugcgac 2760
aucgcaaaaa cggcuaccga cacuugaaag acucugacga agaagagaac gucgauuaca 2820
aggacgauga cgauaaguga uaauaggcug gagccucggu ggccaugcuu cuugcccuu 2880 gggccucccc ccagccccuc cuccccuucc ugcacccgua cccccguggu cuuugaauaa 2940
agucugagug ggcggc 2956

<210> SEQ ID NO 85
<211> LENGTH: 2356
<212> TYPE: RNA
<213> ORGANISM: Human Cytomegalovirus

<400> SEQUENCE: 85
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cgucccccgcu accguucccg 1740 ccgcccucuc cauccuaucu accaugcaac caagcacgcu ggaaaccuuc cccgaccugu 1800
uuugcuugcc gcucggcgaa ucccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacuga uaauaggcug gagccucggu ggccaugcuu cuugccccuu 2280
gggccucccc ccagccccuc cuccccuucc ugcacccgua cccccguggu cuuugaauaa 2340
agucugagug ggcggc 2356

<210> SEQ ID NO 86
<211> LENGTH: 2383
<212> TYPE: RNA
<213> ORGANISM: Artificial Sequence
<220> FEATURE:
<223> OTHER INFORMATION: Synthetic Polynucleotide

<400> SEQUENCE: 86
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacgau uacaaggacg augacgauaa gugaugauaa uaggcuggag 2280
ccucgguggc caugcuucuu gccccuuggg ccucccccca gccccuccuc cccuuccugc 2340
acccguaccc ccguggucuu ugaauaaagu cugagugggc ggc 2383

<210> SEQ ID NO 87
<211> LENGTH: 2377
<212> TYPE: RNA
<213> ORGANISM: Artificial Sequence
<220> FEATURE:
<223> OTHER INFORMATION: Synthetic Polynucleotide

<400> SEQUENCE: 87
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgaccac caucaccacc aucacugaug auaauaggcu ggagccucgg 2280
uggccaugcu ucuugccccu ugggccuccc cccagccccu ccuccccuuc cugcacccgu 2340
acccccgugg ucuuugaaua aagucugagu gggcggc 2377

<210> SEQ ID NO 88
<211> LENGTH: 2287
<212> TYPE: RNA
<213> ORGANISM: Human Cytomegalovirus

<400> SEQUENCE: 88
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguugguggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaauaagu uacagcagau uuucaauacu ucauacaauc 1320
aaacauauga aaaauaugga aacguguccg ucuuugaaac cacuggugu uugguagugu 1380 ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg uguguggauc 1620
aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagug auaaauaggcu ggagccucgg uggccaugcu ucuugccccu ugggccuccc 2220
cccagccccu ccuccccuuc cugcacccgu accccccgugg ucuuugaaua aagucugagu 2280
gggcggc 2287

<210> SEQ ID NO 89
<211> LENGTH: 2311
<212> TYPE: RNA
<213> ORGANISM: Artificial Sequence
<220> FEATURE:
<223> OTHER INFORMATION: Synthetic Polynucleotide

<400> SEQUENCE: 89
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag augugguggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguuggugge uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaaauaagu uacagcagau uuucaauacu ucauacaauc 1320
aaacauauga aaaauaugga aacguguccg ucuuugaaac cacuggugu uugguagugu 1380 ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg uguguggauc 1620
aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160
acaagcagga uuacaaggac gaugacgaua agugauaaua ggcuggagcc ucgguggcca 2220
ugcuucuugc cccuugggcc uccccccagc cccuccuccc cuuccugcac ccguaccccc 2280
guggucuuug aauaaagucu gagugggcgg c 2311

<210> SEQ ID NO 90
<211> LENGTH: 2305
<212> TYPE: RNA
<213> ORGANISM: Artificial Sequence
<220> FEATURE:
<223> OTHER INFORMATION: Synthetic Polynucleotide

<400> SEQUENCE: 90
ucaagcuuuu ggacccucgu acagaagcua auacgacuca cuauagggaa auaagagaga 60

-continued

```
aaagaagagu aagaagaaau auaagagcca ccauggaauc caggaucugg ugccugguag    120
ucugcguuaa cuuguguauc gucugucugg gugcugcggu uuccucaucu ucuacucgug    180
gaacuucugc uacucacagu caccauuccu cucauacgac gucugcugcu cacucucgau    240
ccgguucagu cucucaacgc guaacuucuu cccaaacggu cagccauggu guuaacgaga    300
ccaucuacaa cacuacccuc aaguacggag auguggúggg ggucaauacc accaaguacc    360
ccuaucgcgu guguucuaug gcccagggua cggaucuuau ucgcuuugaa cguaauaucg    420
ucugcaccuc gaugaagccc aucaaugaag accuggacga gggcaucaug guggucuaca    480
aacgcaacau cgucgcgcac accuuuaagg uacgagucua ccagaagguu uugacguuuc    540
gucguagcua cgcuuacauc cacaccacuu aucugcuggg cagcaacacg gaauacgugg    600
cgccuccuau gugggagauu caucauauca acagccacag ucagugcuac aguuccuaca    660
gccgcguuau agcaggcacg guuuucgugg cuuaucauag ggacagcuau gaaaacaaaa    720
ccaugcaauu aaugcccgac gauuauucca acacccacag uacccguuac gugacgguca    780
aggaucaaug gcacagccgc ggcagcaccu ggcucuaucg ugagaccugu aaucugaauu    840
guauggugac caucacuacu gcgcgcucca aauauccuua ucauuuuuuc gccacuucca    900
cgggugacgu gguugacauu ucuccuuucu acaacggaac caaucgcaau gccagcuacu    960
uuggagaaaa cgccgacaag uuuuucauuu uuccgaacua cacuaucguc uccgacuuug   1020
gaagaccgaa uucugcguua gagacccaca gguugguggc uuuucuugaa cgugcggacu   1080
cggugaucuc cugggauaua caggacgaaa agaaugucac uugucaacuc acuuucuggg   1140
aagccucgga acgcaccauu cguuccgaag ccgaggacuc guaucacuuu ucuucugcca   1200
aaaugaccgc cacuuucuua ucuaagaagc aagaggugaa cauguccgac ucugcgcugg   1260
acugcguacg ugaugaggcu auaaauaagu uacagcagau uuucaauacu ucauacaauc   1320
aaacauauga aaaauaugga aacguguccg ucuuugaaac cacugguggu uugguagugu   1380
ucuggcaagg uaucaagcaa aaaucucugg uggaacucga acguuuggcc aaccgcucca   1440
gucugaaucu uacucauaau agaaccaaaa gaaguacaga uggcaacaau gcaacucauu   1500
uauccaacau ggaaucggug cacaaucugg ucuacgccca gcugcaguuc accuaugaca   1560
cguugcgcgg uuacaucaac cgggcgcugg cgcaaaucgc agaagccugg uguguggauc   1620
aacggcgcac ccuagagguc uucaaggaac ucagcaagau caacccguca gccauucucu   1680
cggccauuua caacaaaccg auugccgcgc guuucauggg ugaugucuug ggccuggcca   1740
gcugcgugac caucaaccaa accagcguca aggugcugcg ugauaugaac gugaaggagu   1800
cgccaggacg cugcuacuca cgacccgugg ucaucuuuaa uuucgccaac agcucguacg   1860
ugcaguacgg ucaacugggc gaggacaacg aaauccuguu gggcaaccac cgcacugagg   1920
aaugucagcu ucccagccuc aagaucuuca ucgccgggaa cucggccuac gaguacgugg   1980
acuaccucuu caaacgcaug auugaccuca gcaguaucuc caccgucgac agcaugaucg   2040
cccuggauau cgacccgcug gaaaauaccg acuucagggu acuggaacuu uacucgcaga   2100
aagagcugcg uuccagcaac guuuuugacc ucgaagagau caugcgcgaa uucaacucgu   2160
acaagcagca ccaucaccac caucacugau aauaggcugg agccucggug gccaugcuuc   2220
uugccccuug ggccuccccc cagccccucc uccccuuccu gcacccguac cccguggguc   2280
uuugaauaaa gucugagugg gcggc                                         2305
```

<210> SEQ ID NO 91
<211> LENGTH: 724

<212> TYPE: RNA
<213> ORGANISM: Human Cytomegalovirus

<400> SEQUENCE: 91
ucaagcuuuu ggacccucgu acagaagcua auacgacuca cuauagggaa auaagagaga 60
aaagaagagu aagaagaaau auaagagcca ccaugagucc caaagaucug acgccguucu 120
ugacggcguu guggcugcua uugggucaca gccgcgugcc gcgggugcgc gcagaagaau 180
guugcgaauu cauaaacguc aaccacccgc cggaacgcug uuacgauuuc aaaaugugca 240
aucgcuucac cgucgcgcug cggguguccgg acggcgaagu cugcuacagu cccgagaaaa 300
cggcugagau ucgcgggauc gucaccacca ugacccauuc auugacacgc caggucguac 360
acaacaaacu gacgagcugc aacuacaauc cguuauaccu cgaagcugac gggcgaauac 420
gcugcggcaa aguaaacgac aaggcgcagu accugcuggg cgccgcuggc agcguucccu 480
aucgauggau caaucuggaa uacgacaaga uaacccggau cgugggccug gaucaguacc 540
uggagagcgu uaagaaacac aaacggcugg augugugccg cgcuaaaaug ggcuauaugc 600
ugcagugaua auaggcugga gccucggugg ccaugcuucu ugccccuugg gccuccccc 660 agccccuccu ccccuuccug cacccguacc cccguggucu uugaauaaag ucugaguggg 720
cggc 724

<210> SEQ ID NO 92
<211> LENGTH: 748
<212> TYPE: RNA
<213> ORGANISM: Artificial Sequence
<220> FEATURE:
<223> OTHER INFORMATION: Synthetic Polynucleotide

<400> SEQUENCE: 92
ucaagcuuuu ggacccucgu acagaagcua auacgacuca cuauagggaa auaagagaga 60
aaagaagagu aagaagaaau auaagagcca ccaugagucc caaagaucug acgccguucu 120
ugacggcguu guggcugcua uugggucaca gccgcgugcc gcgggugcgc gcagaagaau 180
guugcgaauu cauaaacguc aaccacccgc cggaacgcug uuacgauuuc aaaaugugca 240
aucgcuucac cgucgcgcug cggguguccgg acggcgaagu cugcuacagu cccgagaaaa 300
cggcugagau ucgcgggauc gucaccacca ugacccauuc auugacacgc caggucguac 360
acaacaaacu gacgagcugc aacuacaauc cguuauaccu cgaagcugac gggcgaauac 420
gcugcggcaa aguaaacgac aaggcgcagu accugcuggg cgccgcuggc agcguucccu 480
aucgauggau caaucuggaa uacgacaaga uaacccggau cgugggccug gaucaguacc 540
uggagagcgu uaagaaacac aaacggcugg augugugccg cgcuaaaaug ggcuauaugc 600
ugcaggauua caaggacgau gacgauaagu gauaauaggc uggagccucg guggccaugc 660
uucuugcccc uugggccucc ccccagcccc uccuccccuu ccugcacccg uacccccgug 720
gucuuugaau aaagucugag ugggcggc 748

<210> SEQ ID NO 93
<211> LENGTH: 853
<212> TYPE: RNA
<213> ORGANISM: Human Cytomegalovirus

<400> SEQUENCE: 93
ucaagcuuuu ggacccucgu acagaagcua auacgacuca cuauagggaa auaagagaga 60
aaagaagagu aagaagaaau auaagagcca ccaugcugcg gcuucugcuu cgucaccacu 120
uucacugccu gcuucugugc gcgguuuggg caacgcccug ucuggcgucu ccguggucga 180
cgcuaacagc aaaccagaau ccguccccgc cauggucuaa acugacguau uccaaaccgc 240
augacgcggc gacguuuuac uguccuuuuc ucuaucccuc gcccccacga ucccccuugc 300
aauucucggg guuccagcgg guaucaacgg gucccgagug ucgcaacgag acccuguauc 360
ugcuguacaa ccgggaaggc cagaccuugg uggagagaag cuccaccugg gugaaaaagg 420
ugaucuggua ccugagcggu cggaaccaaa ccauccucca acggaugccc cgaacggcuu 480
cgaaaccgag cgacggaaac gugcagauca gcguggaaga cgccaagauu uuuggagcgc 540
acauggugcc caagcagacc aagcugcuac gcuucgucgu caacgauggc acacguuauc 600 agauguguguu gaugaagcug gagagcuggg cucacgucuu ccgggacuac agcgugucuu 660
uucaggugcg auugacguuc accgaggcca auaaccagac uuacaccuuc ugcacccauc 720
ccaaucucau cguuugauaa uaggcuggag ccucgguggc caugcuucuu gccccuuggg 780
ccucccccca gccccuccuc cccuuccugc acccguaccc ccguggucuu ugaauaaagu 840
cugagugggc ggc 853

<210> SEQ ID NO 94
<211> LENGTH: 880
<212> TYPE: RNA
<213> ORGANISM: Artificial Sequence
<220> FEATURE:
<223> OTHER INFORMATION: Synthetic Polynucleotide

<400> SEQUENCE: 94
ucaagcuuuu ggacccucgu acagaagcua auacgacuca cuauagggaa auaagagaga 60
aaagaagagu aagaagaaau auaagagcca ccaugcugcg gcuucugcuu cgucaccacu 120
uucacugccu gcuucugugc gcgguuuggg caacgcccug ucuggcgucu ccguggucga 180
cgcuaacagc aaaccagaau ccguccccgc cauggucuaa acugacguau uccaaaccgc 240
augacgcggc gacguuuuac uguccuuuuc ucuaucccuc gcccccacga ucccccuugc 300
aauucucggg guuccagcgg guaucaacgg gucccgagug ucgcaacgag acccuguauc 360
ugcuguacaa ccgggaaggc cagaccuugg uggagagaag cuccaccugg gugaaaaagg 420
ugaucuggua ccugagcggu cggaaccaaa ccauccucca acggaugccc cgaacggcuu 480
cgaaaccgag cgacggaaac gugcagauca gcguggaaga cgccaagauu uuuggagcgc 540
acauggugcc caagcagacc aagcugcuac gcuucgucgu caacgauggc acacguuauc 600
agaugugugu gaugaagcug gagagcuggg cucacgucuu ccgggacuac agcgugucuu 660
uucaggugcg auugacguuc accgaggcca auaaccagac uuacaccuuc ugcacccauc 720
ccaaucucau cguugauuac aaggacgaug acgauaagug augauaauag gcuggagccu 780
cgguggccau gcuucuugcc ccuugggccu ccccccagcc ccuccucccc uuccugcacc 840
cguacccccg uggucuuuga auaaagucug agugggcggc 880

<210> SEQ ID NO 95
<211> LENGTH: 598
<212> TYPE: RNA
<213> ORGANISM: Human Cytomegalovirus

<400> SEQUENCE: 95
ucaagcuuuu ggacccucgu acagaagcua auacgacuca cuauagggaa auaagagaga 60
aaagaagagu aagaagaaau auaagagcca ccaugcggcu gugucgggug uggcugucug 120
uuugucugug cgccguggug cugggucagu gccagcggga aaccgcggaa aaaaacgauu 180
auuaccgagu accgcauuac ugggacgcgu gcucucgcgc gcugcccgac caaacccguu 240
acaaguaugu ggaacagcuc guggaccuca cguugaacua ccacuacgau gcgagccacg 300
gcuuggacaa cuuugacgug cucaagagaa ucaacgugac cgaggugucg uugcucauca 360
gcgacuuuag acgucagaac cgucgcggcg gcaccaacaa aaggaccacg uucaacgccg 420
ccgguucgcu ggcgccacac gcccggagcc ucgaguucag cgugcggcuc uuugccaacu 480
gauaauaggc uggagccucg guggccaugc uucuugcccc uugggccucc ccccagcccc 540
uccuccccuu ccugcacccg uacccccgug gucuuugaau aaagucugag ugggcggc 598

<210> SEQ ID NO 96
<211> LENGTH: 625
<212> TYPE: RNA
<213> ORGANISM: Artificial Sequence
<220> FEATURE:
<223> OTHER INFORMATION: Synthetic Polynucleotide

<400> SEQUENCE: 96
ucaagcuuuu ggacccucgu acagaagcua auacgacuca cuauagggaa auaagagaga 60
aaagaagagu aagaagaaau auaagagcca ccaugcggcu gugucgggug uggcugucug 120
uuugucugug cgccguggug cugggucagu gccagcggga aaccgcggaa aaaaacgauu 180
auuaccgagu accgcauuac ugggacgcgu gcucucgcgc gcugcccgac caaacccguu 240
acaaguaugu ggaacagcuc guggaccuca cguugaacua ccacuacgau gcgagccacg 300
gcuuggacaa cuuugacgug cucaagagaa ucaacgugac cgaggugucg uugcucauca 360
gcgacuuuag acgucagaac cgucgcggcg gcaccaacaa aaggaccacg uucaacgccg 420
ccgguucgcu ggcgccacac gcccggagcc ucgaguucag cgugcggcuc uuugccaacg 480
auuacaagga cgaugacgau aagugaugau aauaggcugg agccucggug gccaugcuuc 540
uugccccuug ggccuccccc cagccccucc uccccuuccu gcacccguac ccccguggucc 600 uuugaauaaa gucugagugg gcggc 625

<210> SEQ ID NO 97
<211> LENGTH: 2434
<212> TYPE: RNA
<213> ORGANISM: Artificial Sequence
<220> FEATURE:
<223> OTHER INFORMATION: Synthetic Polynucleotide

<400> SEQUENCE: 97
ucaagcuuuu ggacccucgu acagaagcua auacgacuca cuauagggac agacgagaga 60
gaagcacgcc aauucugccu gcuuaagcca ugcggccagg ccucccccucc uaccucauca 120 uccucgccgu cugucucuuc agccaccuac uuucgucacg auauggcgca gaagccguau 180
ccgaaccgcu ggacaaagcg uuucaccuac ugcucaacac cuacgggaga cccauccgcu 240
uccugcguga aaauaccacc caguguaccu acaacagcag ccuccguaac agcacggucg 300
ucagggaaaa cgccaucagu uucaacuuuu uccaaagcua uaaucaauac uauguauucc 360
auaugccucg augucuuuuu gcggguccuc uggcggagca guuucugaac cagguagauc 420
ugaccgaaac ccuggaaaga uaccaacaga gacuuaacac uuacgcgcug guauccaaag 480
accuggccag cuaccgaucu uuuucgcagc agcuaaaggc acaagacagc cuaggugaac 540
agcccaccac ugugccaccg cccauugacc ugucaauacc ucacguuugg augccaccgc 600
aaaccacucc acacggcugg acagaaucac auaccaccuc aggacuacac cgaccacacu 660
uuaaccagac cuguauccuc uuugauggac acgaucuacu auucagcacc gucacaccuu 720
guuugcacca aggcuuuuac cucaucgacg aacuacguua cguuaaaaua acacugaccg 780
aggacuucuu cguaguuacg guguccauag acgacgacac acccaugcug cuuaucuucg 840
gccaucuucc acgcguacuu uucaaagcgc ccuaucaacg cgacaacuuu auacuacgac 900
aaacugaaaa acacgagcuc cuggugcuag uuaagaaaga ucaacugaac cgucacucuu 960
aucucaaaga cccggacuuu cuugacgccg cacuugacuu caacuaccua gaccucagcg 1020
cacuacuacg uaacagcuuu caccguuacg ccguggaugu acucaagagc ggucgauguc 1080
agaugcugga ccgccgcacg guagaaaugg ccuucgccua cgcauuagca cuguucgcag 1140
cagcccgaca agaagaggcc ggcgcccaag ucuccguccc acgggcccua gaccgccagg 1200
ccgcacucuu acaaauacaa gaauuuauga ucaccugccu cucacaaaca ccaccacgca 1260
ccacguugcu gcuguauccc acggccgugg accuggccaa acgagcccuu uggacaccga 1320
aucagaucac cgacaucacc agccucguac gccuggucua cauacucucu aaacagaauc 1380
agcaacaucu caucccccaa ugggcacuac gacagaucgc cgacuuugcc cuaaaacuac 1440
acaaaacgca ccuggccucu uuucuuucag ccuucgcacg ccaagaacuc uaccucaugg 1500
gcagccucgu ccacuccaug cugguacaua cgacggagag acgcgaaauc uucaucguag 1560
aaacgggccu cuguucauug gccgagcuau cacacuuuac gcaguuguua gcucauccac 1620
accacgaaua ccucagcgac cuguacacac ccuguuccag uagcgggcga cgcgaucacu 1680
cgcucgaacg ccucacgcgu cucuuccccg augccaccgu ccccgcuacc guucccgccg 1740
cccucuccau ccuaucuacc augcaaccaa gcacgcugga aaccuucccc gaccuguuuu 1800
gcuugccgcu cggcgaaucc uucuccgcgc ugaccgucuc cgaacacguc aguuauaucg 1860
uaacaaacca guaccugauc aaagguaucu ccuacccugu cuccaccacc gucguaggcc 1920
agagccucau caucacccag acggacaguc aaacuaaaug cgaacugacg cgcaacaugc 1980
auaccacaca cagcaucaca guggcgcuca acauuucgcu agaaaacugc gccuuuugcc 2040
aaagcgcccu gcuagaauac gacgacacgc aaggcgucau caacaucaug uacaugcacg 2100
acucggacga cguccuuuuc gcccuggauc ccuacaacga aguggugguc ucaucuccgc 2160
gaacucacua ccucaugcuu uugaaaaacg guacgguacu agaaguaacu gacgucgucg 2220
uggacgccac cgacagucgu cuccucauga uguccgucua cgcgcuaucg gccaucaucg 2280
gcaucuaucu gcucuaccgc augcucaaga caugcugaua auaggcugga gccucggugg 2340
ccaugcuucu ugccccuugg gccucccccc agccccuccu ccccuuccug cacccguacc 2400
cccguggucu uugaauaaag ucugaguggg cggc 2434

<210> SEQ ID NO 98
<211> LENGTH: 1044
<212> TYPE: RNA
<213> ORGANISM: Artificial Sequence
<220> FEATURE:
<223> OTHER INFORMATION: Synthetic Polynucleotide

<400> SEQUENCE: 98
ucaagcuuuu ggacccucgu acagaagcua auacgacuca cuauagggcu uaagcaggca 60
gaauuggccc uuagccugua ccagccgaac caugugccgc cgcccggauu gcggcuucuc 120
uuucucaccu ggaccgguga uacugcugug guguugccuu cugcugccca uuguuuccuc 180
agccgccguc agcgucgcuc cuaccgccgc cgagaaaguc cccgcggagu gccccgaacu 240
aacgcgccga ugcuuguugg gugaggugau ugagggugac aaguaugaaa guuggcugcg 300
cccguuggug aauguuaccg ggcgcgaugg cccgcuaucg caacuuaucc guuaccgucc 360
cguuacgccg gaggccgcca acuccgugcu guuggacgag gcuuuccugg acacucuggc 420
ccugcuguac aacaauccgg aucaauugcg ggcccugcug acgcuguuga gcucggacac 480
agcgccgcgc uggaugacgg ugaugcgcgg cuacagcgag ugcggcgaug gcucgccggc 540
cguguacacg ugcguggacg accugugccg cggcuacgac cucacgcgac ugucauacgg 600
gcgcagcauc uucacggaac acguguuagg cuucgagcug gugccaccgu cucucuuuaa 660
cgugguggug gccauacgca acgaagccac gcguaccaac cgcgccgugc gucugcccgu 720
gagcaccgcu gccgcgcccg agggcaucac gcucuuuuac ggccuguaca acgcagugaa 780
ggaauucugc cugcgucacc agcuggaccc gccgcugcua cgccaccuag auaaauacua 840
cgccggacug ccgcccgagc ugaagcagac gcgcgucaac cugccggcuc acucgcgcua 900
uggcccucaa gcaguggaug cucgcugaua auaggcugga gccucggugg ccaugcuucu 960
ugccccuugg gccucccccc agccccuccu ccccuuccug cacccguacc cccguggucu 1020
uugaauaaag ucugaguggg cggc 1044

<210> SEQ ID NO 99
<211> LENGTH: 722
<212> TYPE: RNA
<213> ORGANISM: Artificial Sequence
<220> FEATURE:
<223> OTHER INFORMATION: Synthetic Polynucleotide

<400> SEQUENCE: 99
ucaagcuuuu ggacccucgu acagaagcua auacgacuca cuauaggguu cggcugguac 60
aggcuaacca gaagacagau aagagccucc augaguccca aagaucugac gccguucuug 120
acggcguugu ggcugcuauu gggucacagc cgcgugccgc gggugcgcgc agaagaaugu 180
ugcgaauuca uaaacgucaa ccacccgccg gaacgcuguu acgauuucaa aaugugcaau 240
cgcuucaccg ucgcgcugcg guguccggac ggcgaagucu gcuacagucc cgagaaaacg 300
gcugagauuc gcgggaucgu caccaccaug acccauucau ugacacgcca ggucguacac 360
aacaaacuga cgagcugcaa cuacaauccg uuauaccucg aagcugacgg gcgaauacgc 420
ugcggcaaag uaaacgacaa ggcgcaguac cugcugggcg ccgcuggcag cguucccuau 480
cgauggauca aucuggaaua cgacaagaua acccggaucg ugggccugga ucaguaccug 540
gagagcguua agaaacacaa acggcuggau gugugccgcg cuaaaauggg cuauaugcug 600
cagugauaau aggcuggagc cucgguggcc augcuucuug ccccuugggc cucccccag 660 ccccuccucc ccuuccugca cccguacccc cguggucuuu gaauaaaguc ugagugggcg 720
gc 722

<210> SEQ ID NO 100
<211> LENGTH: 854
<212> TYPE: RNA
<213> ORGANISM: Artificial Sequence
<220> FEATURE:
<223> OTHER INFORMATION: Synthetic Polynucleotide

<400> SEQUENCE: 100
ucaagcuuuu ggacccucgu acagaagcua auacgacuca cuauagggag gcucuuaucu 60
gucuucucag uccgaauucg aaguacggcu accaugcugc ggcuucugcu ucgucaccac 120
uuucacugcc ugcuucugug cgcgguuugg gcaacgcccu gucuggcguc uccguggucg 180

-continued

```
acgcuaacag caaaccagaa uccgucccccg ccauggucua aacugacgua uuccaaaccg    240
caugacgcgg cgacguuuua cuguccuuuu cucuaucccu cgcccccacg aucccccuug    300
caauucucgg gguuccagcg gguaucaacg ggucccgagu gucgcaacga gacccuguau    360
cugcuguaca accgggaagg ccagaccuug guggagagaa gcuccaccug ggugaaaaag    420
gugaucuggu accugagcgg ucggaaccaa accauccucc aacggaugcc ccgaacggcu    480
ucgaaaccga gcgacggaaa cgugcagauc agcguggaag acgccaagau uuuuggagcg    540
cacauggugc ccaagcagac caagcugcua cgcuucgucg ucaacgaugg cacacguuau    600
cagaugugug ugaugaagcu ggagagcugg gcucacgucu uccgggacua cagcgugucu    660
uuucaggugc gauugacguu caccgaggcc aauaaccaga cuuacaccuu cugcacccau    720
cccaaucuca ucguuugaua auaggcugga gccucggugg ccaugcuucu ugccccuugg    780
gccucccccc agccccuccu ccccuuccug cacccguacc cccguggucu uugaauaaag    840
ucugaguggg cggc                                                       854
```

```
<210> SEQ ID NO 101
<211> LENGTH: 597
<212> TYPE: RNA
<213> ORGANISM: Artificial Sequence
<220> FEATURE:
<223> OTHER INFORMATION: Synthetic Polynucleotide

<400> SEQUENCE: 101

ucaagcuuuu ggacccucgu acagaagcua auacgacuca cuauagggua gccguacuuc     60
gaauucggac aagcuucucu cucgucuguc caugcggcug ugucgggugu ggcugucugu    120
uugucugugc gccguggugc ugggucagug ccagcgggaa accgcggaaa aaaacgauua    180
uuaccgagua ccgcauuacu gggacgcgug cucucgcgcg cugcccgacc aaacccguua    240
caaguaugug gaacagcucg uggaccucac guugaacuac cacuacgaug cgagccacgg    300
cuuggacaac uuugacgugc ucaagagaau caacgugacc gaggugucgu ugcucaucag    360
cgacuuuaga cgucagaacc gucgcggcgg caccaacaaa aggaccacgu ucaacgccgc    420
cgguucgcug gcgccacacg cccggagccu cgaguucagc gugcggcucu uugccaacug    480
auaauaggcu ggagccucgg uggccaugcu ucuugccccu ugggccuccc cccagccccu    540
ccuccccuuc cugcacccgu acccccgugg ucuuugaaua aagucugagu gggcggc        597
```

```
<210> SEQ ID NO 102
<211> LENGTH: 597
<212> TYPE: RNA
<213> ORGANISM: Artificial Sequence
<220> FEATURE:
<223> OTHER INFORMATION: Synthetic Polynucleotide

<400> SEQUENCE: 102

ucaagcuuuu ggacccucgu acagaagcua auacgacuca cuauagggua gccguacuuc     60
gaauucggac uuucuuuucu cucuuauuuc caugcggcug ugucgggugu ggcugucugu    120
uugucugugc gccguggugc ugggucagug ccagcgggaa accgcggaaa aaaacgauua    180
uuaccgagua ccgcauuacu gggacgcgug cucucgcgcg cugcccgacc aaacccguua    240
caaguaugug gaacagcucg uggaccucac guugaacuac cacuacgaug cgagccacgg    300
cuuggacaac uuugacgugc ucaagagaau caacgugacc gaggugucgu ugcucaucag    360
cgacuuuaga cgucagaacc gucgcggcgg caccaacaaa aggaccacgu ucaacgccgc    420
cgguucgcug gcgccacacg cccggagccu cgaguucagc gugcggcucu uugccaacug    480
```

auaauaggcu ggagccucgg uggccaugcu ucuugccccu ugggccuccc cccagccccu 540 ccucccccuuc cugcacccgu accccccgugg ucuuugaaua aagucugagu gggcggc 597

<210> SEQ ID NO 103
<211> LENGTH: 3364
<212> TYPE: RNA
<213> ORGANISM: Artificial Sequence
<220> FEATURE:
<223> OTHER INFORMATION: Synthetic Polynucleotide

<400> SEQUENCE: 103
ucaagcuuuu ggacccucgu acagaagcua auacgacuca cuauagggaa auaagagaga 60
aaagaagagu aagaagaaau auaagagcca ccauggaguc gcgcggucgc cguuguccccg 120 aaaugauauc cguacugggu cccauuucgg ggcacgugcu gaaagccgug uuuagucgcg 180
gcgauacgcc ggugcugccg cacgagacgc gacuccugca gacggguauc cacguacgcg 240
ugagccagcc cucgcugauc cuggugucgc aguacacgcc cgacucgacg ccaugccacc 300
gcggcgacaa ucagcugcag gugcagcaca cguacuuuac gggcagcgag guggagaacg 360
ugucggucaa cgugcacaac ccacgggcc gaagcaucug ccccagccaa gagcccaugu 420
cgaucuaugu guacgcgcug ccgcucaaga ugcugaacau ccccagcauc aacgugcacc 480
acuacccguc ggcggccgag cgcaaacacc gacaccugcc cguagccgac gcuguuauuc 540
acgcgucggg caagcagaug uggcaggcgc gucucacggu cucgggacug gccuggacgc 600
gucagcagaa ccaguggaaa gagcccgacg ucuacuacac gucagcguuc guguuuccca 660
ccaaggacgu ggcacugcgg cacguggugu gcgcgcacga gcugguuugc uccauggaga 720
acacgcgcgc aaccaagaug caggugauag gugaccagua cgucaaggug uaccuggagu 780
ccuucugcga ggacgugccc uccggcaagc ucuuuaugca cgucacgcug ggcucugacg 840
uggaagagga ccuaacgaug acccgcaacc cgcaacccuu caugcgcccc cacgagcgca 900
acggcuuuac gguguugugu cccaaaaaua ugauaaucaa accgggcaag aucucgcaca 960
ucaugcugga uguggcuuuu accucacacg agcauuuugg gcugcugugu cccaagagca 1020
ucccgggccu gagcaucuca gguaaccugu ugaugaacgg gcagcaaauc uuccuggagg 1080
uacaagcgau acgcgagacc guggaacugc gucaguacga ucccguggcu gcgcucuucu 1140
uuuucgauau cgacuuguug cugcagcgcg ggccucagua cagcgagcac cccaccuuca 1200
ccagccagua ucgcauccag ggcaagcuug aguaccgaca caccugggac cggcacgacg 1260
agggugccgc ccagggcgac gacgacgucu ggaccagcgg aucggacucc gacgaagaac 1320
ucguaaccac cgagcguaag acgccccgcg ucaccggcgg cggcgccaug gcgagcgccu 1380
ccacuuccgc gggccgcaaa cgcaaaucag cauccucggc gacggcgugc acggcgggcg 1440
uuaugacacg cggccgccuu aaggccgagu ccaccgucgc gcccgaagag gacaccgacg 1500
aggauuccga caacgaaauc cacaauccgg ccguguucac cuggccgccc uggcaggccg 1560
gcauccuggc ccgcaaccug gugcccaugg uggcuacggu ucagggucag aaucugaagu 1620
accaggaguu cuucugggac gccaacgaca ucuaccgcau cuucgccgaa uuggaaggcg 1680
uauggcagcc cgcugcgcaa cccaaacguc gccgccaccg gcaagacgcc uugcccgggc 1740
caugcaucgc cucgacgccc aaaaagcacc gaggugaguc cucugccaag agaaagaugg 1800
acccugauaa uccugacgag ggcccuuccu ccaaggugcc acggcccgag acacccguga 1860
ccaaggccac gacguuccug cagacuaugu uaaggaagga gguuaacagu cagcugagcc 1920

-continued

```
ugggagaccc gcuguuccca gaauuggccg aagaaucccu caaaaccuuu gaacaaguga   1980

ccgaggauug caacgagaac cccgaaaaag auguccugac agaacucguc aaacagauua   2040

agguucgagu ggacauggug cggcauagaa ucaaggagca caugcugaaa aaauauaccc   2100

agacggaaga aaaauucacu ggcgccuuua auaugauggg aggauguuug cagaaugccu   2160

uagauaucuu agauaagguu caugagccuu ucgaggacau gaaguguauu gggcuaacua   2220

ugcagagcau guaugagaac uacauuguac cugaggauaa gcgggagaug uggauggcuu   2280

guauuaagga gcugcaugau gugagcaagg gcgccgcuaa caaguugggg ggugcacugc   2340

aggcuaaggc ccgugcuaaa aaggaugaac uuaggagaaa gaugauguau augugcuaca   2400

ggaauauaga guucuuuacc aagaacucag ccuucccuaa gaccaccaau ggcugcaguc   2460

aggccauggc ggcauugcag aacuugccuc agugcucucc ugaugagauu augucuuaug   2520

cccagaaaau cuuuaagauu uuggaugagg agagagacaa ggugcucacg cacauugauc   2580

acauauuuau ggauauccuc acuacaugug uggaaacaau guguaaugag uacaagguca   2640

cuagugacgc uuguaugaug accauguacg ggggcaucuc ucucuuaagu gaguucuguc   2700

gggugcugug cugcuauguc uuagaggaga cuagugugau gcuggccaag cggccucuga   2760

uaaccaagcc ugagguuauc aguguaauga agcgccgcau ugaggagauc ugcaugaagg   2820

ucuuugccca guacauucug gggcgcgauc cuuugagagu cugcucuccu aguguggaug   2880

accuacgggc caucgccgag gagucagaug aggaagaggc uauuguagcc uacacuuugg   2940

ccaccgcugg ugccagcucc ucugauucuc uggugucacc uccagagucc ccuguacccg   3000

cgacuauccc ucuguccuca guaauugugg cugagaacag ugaucaggaa gaaagugaac   3060

agagugauga ggaacaggag gagggugcuc aggaggagcg ggaggacacu gugucuguca   3120

agucugagcc agugucugag auagaggaag uugccucaga ggaagaggag gauggugcug   3180

aggaacccac cgccucugga ggcaagagca cccacccuau ggugacuaga agcaaggcug   3240

accagugaua auaggcugga gccucggugg ccaugcuucu ugccccuugg gccuccccccc   3300

agccccuccu ccccuuccug cacccguacc cccguggucu uugaauaaag ucugaguggg   3360

cggc                                                                 3364
```

<210> SEQ ID NO 104
<211> LENGTH: 3364
<212> TYPE: RNA
<213> ORGANISM: Artificial Sequence
<220> FEATURE:
<223> OTHER INFORMATION: Synthetic Polynucleotide

<400> SEQUENCE: 104

```
ucaagcuuuu ggacccucgu acagaagcua auacgacuca cuauagggaa auaagagaga     60

aaagaagagu aagaagaaau auaagagcca ccauggaguc gcgcggucgc cguugucccg    120

aaaugauauc cguacugggu cccauuucgg ggcacgugcu gaaagccgug uuuagucgcg    180

gcgauacgcc ggugcugccg cacgagacgc gacuccugca gacggguauc cacguacgcg    240

ugagccagcc cucgcugauc cuggugucgc aguacacgcc cgacucgacg ccaugccacc    300

gcggcgacaa ucagcugcag gugcagcaca cguacuuuac gggcagcgag guggagaacg    360

ugucggucaa cgugcacaac cccacgggcc gaagcaucug ccccagccaa gagcccaugu    420

cgaucuaugu guacgcgcug ccgcucaaga ugcugaacau ccccagcauc aacgugcacc    480

acuacccguc ggcggccgag cgcaaacacc gacaccugcc cguagccgac gcuguuauuc    540

acgcgucggg caagcagaug uggcaggcgc gucucacggu cucgggacug gccuggacgc    600
```

gucagcagaa ccaguggaaa gagcccgacg ucuacuacac gucagcguuc guguuuccca 660
ccaaggacgu ggcacugcgg cacgugguggu gcgcgcacga gcugguuugc uccauggaga 720
acacgcgcgc aaccaagaug caggugauag gugaccagua cgucaaggug uaccuggagu 780
ccuucugcga ggacgugccc uccggcaagc ucuuuaugca cgucacgcug ggcucugacg 840
uggaagagga ccuaacgaug acccgcaacc cgcaacccuu caugcgcccc cacgagcgca 900
acggcuuuac gguguugugu cccaaaaaua ugauaaucaa accgggcaag aucucgcaca 960
ucaugcugga uguggcuuuu accucacacg agcauuuugg gcugcugugu cccaagagca 1020
ucccgggccu gagcaucuca gguaaccugu ugaugaacgg gcagcaaauc uuccuggagg 1080
uacaagcgau acgcgagacc guggaacugc gucaguacga ucccguggcu gcgcucuucu 1140
uuuucgauau cgacuuguug cugcagcgcg ggccucagua cagcgagcac cccaccuuca 1200
ccagccagua ucgcauccag ggcaagcuug aguaccgaca caccugggac cggcacgacg 1260
agggugccgc ccagggcgac gacgacgucu ggaccagcgg aucggacucc gacgaagaac 1320
ucguaaccac cgagcguaag acgccccgcg ucaccggcgg cggcgccaug gcgagcgccu 1380
ccacuuccgc gggccgcaaa cgcaaaucag cauccucggc gacggcgugc acggcgggcg 1440
uuaugacacg cggccgccuu aaggccgagu ccaccgucgc gcccgaagag gacaccgacg 1500
aggauuccga caacgaaauc cacaauccgg ccguguucac cuggccgccc uggcaggccg 1560
gcauccuggc ccgcaaccug gugcccaugg uggcuacggu ucagggucag aaucugaagu 1620
accaggaguu cuucugggac gccaacgaca ucuaccgcau cuucgccgaa uuggaaggcg 1680
uauggcagcc cgcugcgcaa cccaaacguc gccgccaccg gcaagacgcc uugcccgggc 1740
caugcaucgc cucgacgccc aaaaagcacc gaggugaguc cucugccaag agaaagaugg 1800
acccugauaa uccugacgag ggcccuuccu ccaaggugcc acggcccgag acacccguga 1860
ccaaggccac gacguuccug cagacuaugu uaaggaagga gguuaacagu cagcugagcc 1920
ugggagaccc gcuguuccca gaauuggccg aagaaucccu caaaaccuuu gaacaaguga 1980
ccgaggauug caacgagaac cccgaaaaag auguccugac agaacucguc aaacagauua 2040
agguucgagu ggacauggug cggcauagaa ucaaggagca caugcugaaa aaauauaccc 2100
agacggaaga aaaauucacu ggcgccuuua auaugauggg aggauguuug cagaaugccu 2160
uagauaucuu agauaagguu caugagccuu ucgaggacau gaaguguauu gggcuaacua 2220
ugcagagcau guaugagaac uacauuguac cugaggauaa gcgggagaug uggauggcuu 2280
guauuaagga gcugcaugau gugagcaagg gcgccgcuaa caaguugggg ggugcacugc 2340
aggcuaaggc ccgugcuaaa aaggaugaac uuaggagaaa gaugauguau augugcuaca 2400
ggaauauaga guucuuuacc aagaacucag ccuucccuaa gaccaccaau ggcugcaguc 2460
aggccauggc ggcauugcag aacuugccuc agugcucucc ugaugagauu augucuuaug 2520
cccagaaaau cuuuaagauu uuggaugagg agagagacaa ggugcucacg cacauugauc 2580
acauauuuau ggauauccuc acuacaugug uggaaacaau guguaaugag uacaagguca 2640
cuagugacgc uuguaugaug accauguacg ggggcaucuc ucucuuaagu gaguucuguc 2700
gggugcugug cugcuauguc uuagaggaga cuagugugau gcuggccaag cggccucuga 2760
uaaccaagcc ugagguuauc aguguaauga agcgccgcau ugaggagauc ugcaugaagg 2820
ucuuugccca guacauucug gggggccgauc cuuugagagu cugcucuccu aguguggaug 2880
accuacgggc caucgccgag gagucagaug aggaagaggc uauuguagcc uacacuuugg 2940
ccaccgcugg ugccagcucc ucugauucuc uggugucacc uccagagucc ccuguacccg 3000
cgacuauccc ucuguccuca guaauugugg cugagaacag ugaucaggaa gaaagugaac 3060
agagugauga ggaacaggag gagggugcuc aggaggagcg ggaggacacu gugucuguca 3120
agucugagcc agugucugag auagaggaag uugccucaga ggaagaggag gauggugcug 3180
aggaacccac cgccucugga ggcaagagca cccacccuau ggugacuaga agcaaggcug 3240
accagugaua auaggcugga gccucggugg ccaugcuucu ugccccuugg gccucccccc 3300
agccccuccu ccccuuccug cacccguacc cccguggucu uugaauaaag ucugaguggg 3360
cggc 3364

<210> SEQ ID NO 105
<211> LENGTH: 3352
<212> TYPE: RNA
<213> ORGANISM: Artificial Sequence
<220> FEATURE:
<223> OTHER INFORMATION: Synthetic Polynucleotide

<400> SEQUENCE: 105
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacagu cgucuccuca ugauguccgu cuacgcgcua ucggccauca 2280
ucggcaucua ucugcucuac cgcaugcuca agacaugccg cgccaagagg agcggaagcg 2340
gagcuacuaa cuucagccug cugaagcagg cuggagacgu ggaggagaac ccuggaccua 2400
ugugccgccg cccggauugc ggcuucucuu ucucaccugg accggugaua cugcuguggu 2460
guugccuucu gcugcccauu guuuccucag ccgccgucag cgucgcuccu accgccgccg 2520
agaaaguccc cgcggagugc cccgaacuaa cgcgccgaug cuuguugggu gagguguuug 2580
agggugacaa guaugaaagu uggcugcgcc cguuggugaa uguuaccggg cgcgauggcc 2640
cgcuaucgca acuuauccgu uaccgucccg uuacgccgga ggccgccaac uccgugcugu 2700
uggacgaggc uuuccuggac acucuggccc ugcuguacaa caauccggau caauugcggg 2760
cccugcugac gcuguugagc ucggacacag cgccgcgcug gaugacggug augcgcggcu 2820
acagcgagug cggcgauggc ucgccggccg uguacacgug cguggacgac cugugccgcg 2880
gcuacgaccu cacgcgacug ucauacgggc gcagcaucuu cacggaacac guguuaggcu 2940
ucgagcuggu gccaccgucu cucuuuaacg ugguggugcc cauacgcaac gaagccacgc 3000
guaccaaccg cgccgugcgu cugcccguga gcaccgcugc cgcgcccgag ggcaucacgc 3060
ucuuuuacgg ccuguacaac gcagugaagg aauucugccu gcgucaccag cuggacccgc 3120
cgcugcuacg ccaccuagau aaauacuacg ccggacugcc gcccgagcug aagcagacgc 3180
gcgucaaccu gccggcucac ucgcgcuaug gcccucaagc aguggaugcu cgcugauaau 3240
aggcuggagc cucgguggcc augcuucuug ccccuuggc cuccccccag ccccuccucc 3300
ccuuccugca cccguacccc cguggucuuu gaauaaaguc ugagugggcg gc 3352

<210> SEQ ID NO 106
<211> LENGTH: 1924
<212> TYPE: RNA
<213> ORGANISM: Artificial Sequence
<220> FEATURE:
<223> OTHER INFORMATION: Synthetic Polynucleotide

<400> SEQUENCE: 106
ucaagcuuuu ggacccucgu acagaagcua auacgacuca cuauagggaa auaagagaga 60
aaagaagagu aagaagaaau auaagagcca ccaugagucc caaagaucug acgccguucu 120
ugacggcguu guggcugcua uugggucaca gccgcgugcc gcgggugcgc gcagaagaau 180
guugcgaauu cauaaacguc aaccacccgc cggaacgcug uuacgauuuc aaaaugugca 240
aucgcuucac cgucgcgcug cggugcuccgg acggcgaagu cugcuacagu cccgagaaaa 300
cggcugagau ucgcgggauc gucaccacca ugacccauuc auugacacgc caggucguac 360
acaacaaacu gacgagcugc aacuacaauc cguuauaccu cgaagcugac gggcgaauac 420
gcugcggcaa aguaaacgac aaggcgcagu accugcuggg cgcccgcuggc agcguucccu 480 aucgauggau caaucuggaa uacgacaaga uaacccggau cgugggccug gaucaguacc 540
uggagagcgu uaagaaacac aaacggcugg augugugccg cgcuaaaaug ggcuauaugc 600
ugcagcgcgc caagaggagc ggaagcggag cuacuaacuu cagccugcug aagcaggcug 660
gagacgugga ggagaacccu ggaccuaugc ugcggcuucu gcuucgucac cacuuucacu 720
gccugcuucu gugcgcgguu ugggcaacgc ccugucuggc gucuccgugg ucgacgcuaa 780
cagcaaacca gaauccgucc ccgccauggu cuaaacugac guauuccaaa ccgcaugacg 840
cggcgacguu uuacuguccu uuucucuauc ccucgccccc acgauccccc uugcaauucu 900
cggguuucca gcggguauca acgggucccg agugucgcaa cgagacccug uaucugcugu 960
acaaccggga aggccagacc uugguggaga gaagcuccac cugggugaaa aaggugaucu 1020
gguaccugag cggucggaac caaaccaucc uccaacggau gccccgaacg gcuucgaaac 1080
cgagcgacgg aaacgugcag aucagcgugg aagacgccaa gauuuugga gcgcacaugg 1140 ugcccaagca gaccaagcug cuacgcuucg ucgucaacga uggcacacgu uaucagaugu 1200
gugugaugaa gcuggagagc ugggcucacg ucuuccggga cuacagcgug ucuuuucagg 1260
ugcgauugac guucaccgag gccaauaacc agacuuacac cuucugcacc caucccaauc 1320
ucaucguucg cgccaagagg agcggaagcg gagugaaaca gacuuugaau uuugaccuuc 1380
ucaaguuggc gggagacgug gaguccaacc cuggaccuau gcggcugugu cgggugugc 1440 ugucuguuug ucugugcgcc guggugcugg gucagugcca gcgggaaacc gcggaaaaaa 1500
acgauuauua ccgaguaccg cauuacuggg acgcgugcuc ucgcgcgcug cccgaccaaa 1560
cccguuacaa guauguggaa cagcucgugg accucacguu gaacuaccac uacgaugcga 1620
gccacggcuu ggacaacuuu gacgugcuca agagaaucaa cgugaccgag gugucguugc 1680
ucaucagcga cuuuagacgu cagaaccguc gcggcggcac caacaaaagg accacguuca 1740
acgccgccgg uucgcuggcg ccacacgccc ggagccucga guucagcgug cggcucuuug 1800
ccaacugaua auaggcugga gccucggugg ccaugcuucu ugccccuugg gccuccccc 1860 agccccuccu ccccuuccug cacccguacc cccguggucu uugaauaaag ucugaguggg 1920
cggc 1924

<210> SEQ ID NO 107
<211> LENGTH: 5146
<212> TYPE: RNA
<213> ORGANISM: Artificial Sequence
<220> FEATURE:
<223> OTHER INFORMATION: Synthetic Polynucleotide

<400> SEQUENCE: 107
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu uuuuccaaag cuauaaucaa uacuauguau 360
uccauaugcc ucgaugucuu uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuuuucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga aaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cguccccgcu accguucccg 1740
ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040
gccaaagcgc ccugcuagaa uacgacgaca cgcaaggcgu caucaacauc auguacaugc 2100
acgacucgga cgacguccuu uucgcccugg aucccuacaa cgaaguggug gucucaucuc 2160
cgcgaacuca cuaccucaug cuuuugaaaa acgguacggu acuagaagua acugacgucg 2220
ucguggacgc caccgacagu cgucuccuca ugauguccgu cuacgcgcua ucggccauca 2280
ucggcaucua ucugcucuac cgcaugcuca agacaugccg cgccaagagg agcggaagcg 2340
gagcuacuaa cuucagccug cugaagcagg cuggagacgu ggaggagaac ccuggaccua 2400
ugugccgccg cccggauugc ggcuucucuu ucucaccugg accggugaua cugcuguggu 2460
guugccuucu gcugcccauu guuuccucag ccgccgucag cgucgcuccu accgccgccg 2520
agaaaguccc cgcggagugc cccgaacuaa cgcgccgaug cuuguugggu gagguguuug 2580
agggugacaa guaugaaagu uggcugcgcc cguuggugaa uguuaccggg cgcgauggcc 2640
cgcuaucgca acuuauccgu uaccgucccg uuacgccgga ggccgccaac uccgugcugu 2700
uggacgaggc uuuccuggac acucuggccc ugcuguacaa caauccggau caauugcggg 2760

-continued

```
cccugcugac gcuguugagc ucggacacag cgccgcgcug gaugacggug augcgcggcu   2820
acagcgagug cggcgauggc ucgccggccg uguacacgug cguggacgac cugugccgcg   2880
gcuacgaccu cacgcgacug ucauacgggc gcagcaucuu cacggaacac guguuaggcu   2940
ucgagcuggu gccaccgucu cucuuuaacg ugguggugc cauacgcaac gaagccacgc   3000
guaccaaccg cgccgugcgu cugcccguga gcaccgcugc cgcgcccgag ggcaucacgc   3060
ucuuuuacgg ccuguacaac gcagugaagg aauucugccu gcgucaccag cuggacccgc   3120
cgcugcuacg ccaccuagau aaauacuacg ccggacugcc gcccgagcug aagcagacgc   3180
gcgucaaccu gccggcucac ucgcgcuaug gcccucaagc aguggaugcu cgccgcgcca   3240
agaggagcgg aagcggagug aaacagacuu ugaauuuuga ccuucucaag uuggcgggag   3300
acguggaguc caacccugga ccuaugaguc ccaaagaucu gacgccguuc uugacggcgu   3360
uguggcugcu auugggucac agccgcgugc cgcgggugcg cgcagaagaa uguugcgaau   3420
ucauaaacgu caaccacccg ccggaacgcu guuacgauuu caaaaugugc aaucgcuuca   3480
ccgucgcgcu gcggguguccg gacggcgaag ucugcuacag ucccgagaaa acggcugaga   3540
uucgcgggau cgucaccacc augacccauu cauugacacg ccaggucgua cacaacaaac   3600
ugacgagcug caacuacaau ccguuauacc ucgaagcuga cgggcgaaua cgcugcggca   3660
aaguaaacga caaggcgcag uaccugcugg gcgccgcugg cagcguuccc uaucgaugga   3720
ucaaucugga auacgacaag auaacccgga ucgugggccu ggaucaguac cuggagagcg   3780
uuaagaaaca caaacggcug gaugugugcc gcgcuaaaau gggcuauaug cugcagcgcg   3840
ccaagaggag cggaagcgga caguguacua auuaugcucu cuugaaauug gcuggagaug   3900
uugagagcaa cccuggaccu augcugcggc uucugcuucg ucaccacuuu cacugccugc   3960
uucugugcgc gguuugggca acgcccuguc uggcgucucc gugguucgacg cuaacagcaa   4020
accagaaucc gucccgcca uggucuaaac ugacguauuc caaaccgcau gacgcggcga   4080
cguuuuacug uccuuuucuc uaucccucgc ccccacgauc ccccuugcaa uucucggggu   4140
uccagcgggu aucaacgggu cccgaguguc gcaacgagac ccuguaucug cuguacaacc   4200
gggaaggcca gaccuuggug gagagaagcu ccaccugggu gaaaaaggug aucugguacc   4260
ugagcggucg gaaccaaacc auccuccaac ggaugccccg aacggcuucg aaaccgagcg   4320
acggaaacgu gcagaucagc guggaagacg ccaagauuuu uggagcgcac auggugccca   4380
agcagaccaa gcugcuacgc uucgucguca acgauggcac acguuaucag auguguguga   4440
ugaagcugga gagcugggcu cacgucuucc gggacuacag cgugucuuuu caggugcgau   4500
ugacguucac cgaggccaau aaccagacuu acaccuucug cacccauccc aaucucaucg   4560
uucgcgccaa gaggagcgga agcggagagg gcagaggaag ucugcuaaca ugcggugacg   4620
ucgaggagaa uccuggaccu augcggcugu gucgggugug gcugucuguu ugucugugcg   4680
ccguggugcu gggucagugc cagcgggaaa ccgcggaaaa aaacgauuau uaccgaguac   4740
cgcauuacug ggacgcgugc ucucgcgcgc ugcccgacca aacccguuac aaguaugugg   4800
aacagcucgu ggaccucacg uugaacuacc acuacgaugc gagccacggc uuggacaacu   4860
uugacgugcu caagagaauc aacgugaccg aggugucguu gcucaucagc gacuuuagac   4920
gucagaaccg ucgcggcggc accaacaaaa ggaccacguu caacgccgcc gguucgcugg   4980
cgccacacgc ccggagccuc gaguucagcg ugcggcucuu ugccaacuga uaauaggcug   5040
gagccucggu ggccaugcuu cuugccccuu gggccucccc ccagccccuc cuccccuucc   5100
ugcacccgua cccccguggu cuuugaauaa agucugagug ggcggc                  5146
```

<210> SEQ ID NO 108
<211> LENGTH: 2437
<212> TYPE: RNA
<213> ORGANISM: Artificial Sequence
<220> FEATURE:
<223> OTHER INFORMATION: Synthetic Polynucleotide

<400> SEQUENCE: 108
ucaagcuuuu ggacccucgu acagaagcua auacgacuca cuauagggaa auaagagaga 60
aaagaagagu aagaagaaau auaagagcca ccaugcggcc aggccucccc uccuaccuca 120
ucauccucgc cgucugucuc uucagccacc uacuuucguc acgauauggc gcagaagccg 180
uauccgaacc gcuggacaaa gcguuucacc uacugcucaa caccuacggg agacccaucc 240
gcuuccugcg ugaaaauacc acccagugua ccuacaacag cagccuccgu aacagcacgg 300
ucgucaggga aaacgccauc aguuucaacu ucuuccaaag cuauaaucaa uacuauguau 360
uccauaugcc ucgaugucuc uuugcggguc cucuggcgga gcaguuucug aaccagguag 420
aucugaccga aacccuggaa agauaccaac agagacuuaa cacuuacgcg cugguaucca 480
aagaccuggc cagcuaccga ucuuucucgc agcagcuaaa ggcacaagac agccuaggug 540
aacagcccac cacugugcca ccgcccauug accugucaau accucacguu uggaugccac 600
cgcaaaccac uccacacggc uggacagaau cacauaccac cucaggacua caccgaccac 660
acuuuaacca gaccuguauc cucuuugaug gacacgaucu acuauucagc accgucacac 720
cuuguuugca ccaaggcuuu uaccucaucg acgaacuacg uuacguuaaa auaacacuga 780
ccgaggacuu cuucguaguu acggugucca uagacgacga cacacccaug cugcuuaucu 840
ucggccaucu uccacgcgua cuuuucaaag cgcccuauca acgcgacaac uuuauacuac 900
gacaaacuga gaaacacgag cuccuggugc uaguuaagaa agaucaacug aaccgucacu 960
cuuaucucaa agacccggac uuucuugacg ccgcacuuga cuucaacuac cuagaccuca 1020
gcgcacuacu acguaacagc uuucaccguu acgccgugga uguacucaag agcggucgau 1080
gucagaugcu ggaccgccgc acgguagaaa uggccuucgc cuacgcauua gcacuguucg 1140
cagcagcccg acaagaagag gccggcgccc aagucuccgu cccacgggcc cuagaccgcc 1200
aggccgcacu cuuacaaaua caagaauuua ugaucaccug ccucucacaa acaccaccac 1260
gcaccacguu gcugcuguau cccacggccg uggaccuggc caaacgagcc cuuuggacac 1320
cgaaucagau caccgacauc accagccucg uacgccuggu cuacauacuc ucuaaacaga 1380
aucagcaaca ucucaucccc caaugggcac uacgacagau cgccgacuuu gcccuaaaac 1440
uacacaaaac gcaccuggcc ucuuuucuuu cagccuucgc acgccaagaa cucuaccuca 1500
ugggcagccu cguccacucc augcugguac auacgacgga gagacgcgaa aucuucaucg 1560
uagaaacggg ccucuguuca uuggccgagc uaucacacuu uacgcaguug uuagcucauc 1620
cacaccacga auaccucagc gaccuguaca cacccuguuc caguagcggg cgacgcgauc 1680
acucgcucga acgccucacg cgucucuucc ccgaugccac cgucccccgcu accguucccg 1740 ccgcccucuc cauccuaucu accaugcaac caagcacgcu ggaaaccuuc cccgaccugu 1800
uuugcuugcc gcucggcgaa uccuucuccg cgcugaccgu cuccgaacac gucaguuaua 1860
ucguaacaaa ccaguaccug aucaaaggua ucuccuaccc ugucuccacc accgucguag 1920
gccagagccu caucaucacc cagacggaca gucaaacuaa augcgaacug acgcgcaaca 1980
ugcauaccac acacagcauc acaguggcgc ucaacauuuc gcuagaaaac ugcgccuuuu 2040

```
gccaaagcgc ccugcuagaa uacgacgaca cgcaaggcgu caucaacauc auguacaugc   2100

acgacucgga cgacguccuu uucgcccugg aucccuacaa cgaaguggug gucucaucuc   2160

cgcgaacuca cuaccucaug cuuuugaaga acgguacggu acuagaagua acugacgucg   2220

ucguggacgc caccgacagu cgucuccuca ugauguccgu cuacgcgcua ucggccauca   2280

ucggcaucua ucugcucuac cgcaugcuca agacaugcug auaauaggcu ggagccucgg   2340

uggccaugcu ucuugccccu ugggccuccc cccagccccu ccuccccuuc cugcacccgu   2400

acccccgugg ucuuugaaua aagucugagu gggcggc                            2437
```

<210> SEQ ID NO 109
<211> LENGTH: 1045
<212> TYPE: RNA
<213> ORGANISM: Human Cytomegalovirus

<400> SEQUENCE: 109

```
ucaagcuuuu ggacccucgu acagaagcua auacgacuca cuauagggaa auaagagaga     60

aaagaagagu aagaagaaau auaagagcca ccaugugccg ccgcccggau ugcggcuucu    120

cuuucucacc uggaccggug auacugcugu gguguugccu ucugcugccc auuguuuccu    180

cagccgccgu cagcgucgcu ccuaccgccg ccgagaaagu ccccgcggag ugccccgaac    240

uaacgcgccg augcuuguug ggugaggugu uugaggguga caaguaugaa aguuggcugc    300

gcccguuggu gaauguuacc gggcgcgaug gcccgcuauc gcaacuuauc cguuaccguc    360

ccguuacgcc ggaggccgcc aacuccgugc uguuggacga ggcuuuccug gacacucugg    420

cccugcugua caacaauccg gaucaauugc gggcccugcu gacgcuguug agcucggaca    480

cagcgccgcg cuggaugacg gugaugcgcg gcuacagcga gugcggcgau ggcucgccgg    540

ccguguacac gugcguggac gaccugugcc gcggcuacga ccucacgcga cugucauacg    600

ggcgcagcau cuucacggaa cacguguuag gcuucgagcu ggugccaccg ucucucuuua    660

acgugguggu ggccauacgc aacgaagcca cgcguaccaa ccgcgccgug cgucugcccg    720

ugagcaccgc ugccgcgccc gagggcauca cgcucuuuua cggccuguac aacgcaguga    780

aggaauucug ccugcgucac cagcuggacc cgccgcugcu acgccaccua gauaaauacu    840

acgccggacu gccgcccgag cugaagcaga cgcgcgucaa ccugccggcu cacucgcgcu    900

auggcccuca agcaguggau gcucgcugau aauaggcugg agccucggug gccaugcuuc    960

uugccccuug ggccuccccc cagccccucc uccccuuccu gcacccguac ccccgugguc   1020

uuugaauaaa gucugagugg gcggc                                         1045
```

<210> SEQ ID NO 110
<211> LENGTH: 724
<212> TYPE: RNA
<213> ORGANISM: Human Cytomegalovirus

<400> SEQUENCE: 110

```
ucaagcuuuu ggacccucgu acagaagcua auacgacuca cuauagggaa auaagagaga     60

aaagaagagu aagaagaaau auaagagcca ccaugagucc caaagaucug acgccguucu    120

ugacggcguu guggcugcua uugggucaca gccgcgugcc gcgggugcgc gcagaagaau    180

guugcgaauu cauaaacguc aaccacccgc cggaacgcug uuacgauuuc aaaaugugca    240

aucgcuucac cgucgcgcug cgguguccgg acggcgaagu cugcuacagu cccgagaaaa    300

cggcugagau ucgcgggauc gucaccacca ugacccauuc auugacacgc caggucguac    360

acaacaaacu gacgagcugc aacuacaauc cguuauaccu cgaagcugac gggcgaauac    420
```

gcugcggcaa aguaaacgac aaggcgcagu accugcuggg cgccgcuggc agcguucccu 480
aucgauggau caaucuggaa uacgacaaga uaacccggau cgugggccug gaucaguacc 540
uggagagcgu uaagaaacac aaacggcugg augugugccg cgcuaaaaug ggcuauaugc 600
ugcagugaua auaggcugga gccucggugg ccaugcuucu ugccccuugg gccucccccc 660
agccccuccu ccccuuccug cacccguacc cccguggucu uugaauaaag ucugaguggg 720
cggc 724

<210> SEQ ID NO 111
<211> LENGTH: 846
<212> TYPE: RNA
<213> ORGANISM: Human Cytomegalovirus

<400> SEQUENCE: 111
ucaagcuuuu ggacccucgu acagaagcua auacgacuca cuauagggaa auaagagaga 60
aaagaagagu aagaagaaau auaagagcca ccaugcugcg gcuucugcuu cgucaccacu 120
uucacugccu gcuucugugc gcgguuuggg caacgcccug ucuggcgucu ccguggucga 180
cgcuaacagc aaaccagaau ccguccccgc cauggucuaa acugacguau uccaaaccgc 240
augacgcggc gacguuuuac uguccuuuuc ucuaucccuc gcccccacga ucccccuugc 300
aauucucggg guuccagcgg guaucaacgg gucccgagug ucgcaacgag acccuguauc 360
ugcuguacaa ccgggaaggc cagaccuugg uggagagaag cuccaccugg gugaaaaagg 420
ugaucuggua ccugagcggu cggaaccaaa ccauccucca acggaugccc cgaacggcuu 480
cgaaaccgag cgacggaaac gugcagauca gcguggaaga cgccaagauu uuuggagcgc 540
acauggugcc caagcgcugc uacgcuucgu cgucaacgau ggcacacguu aucagaugug 600
ugugaugaag cuggagagcu gggcucacgu cuuccgggac uacagcgugu cuuuucaggu 660
gcgauugacg uucaccgagg ccaauaacca gacuuacacc uucugcaccc aucccaaucu 720
caucguuuga uaauaggcug gagccucggu ggccaugcuu cuugccccuu gggccucccc 780
ccagccccuc cuccccuucc ugcacccgua cccccguggu cuuugaauaa agucugagug 840
ggcggc 846

<210> SEQ ID NO 112
<211> LENGTH: 598
<212> TYPE: RNA
<213> ORGANISM: Human Cytomegalovirus

<400> SEQUENCE: 112
ucaagcuuuu ggacccucgu acagaagcua auacgacuca cuauagggaa auaagagaga 60
aaagaagagu aagaagaaau auaagagcca ccaugcggcu gugucgggug uggcugucug 120
uuugucugug cgccguggug cugggucagu gccagcggga aaccgcggaa aagaacgauu 180
auuaccgagu accgcauuac ugggacgcgu gcucucgcgc gcugcccgac caaacccguu 240
acaaguaugu ggaacagcuc guggaccuca cguugaacua ccacuacgau gcgagccacg 300
gcuuggacaa cuuugacgug cucaagagaa ucaacgugac cgaggugucg uugcucauca 360
gcgacuuuag acgucagaac cgucgcggcg gcaccaacaa aaggaccacg uucaacgccg 420
ccgguucgcu ggcgccacac gcccggagcc ucgaguucag cgugcggcuc uuugccaacu 480 gauaaauaggc uggagccucg guggccaugc uucuugcccc uugggccucc ccccagcccc 540
uccuccccuu ccugcacccg uacccccgug gucuuugaau aaagucugag ugggcggc 598

<210> SEQ ID NO 113
<211> LENGTH: 2933
<212> TYPE: RNA
<213> ORGANISM: Human Cytomegalovirus

<400> SEQUENCE: 113
ucaagcuuuu ggacccucgu acagaagcua auacgacuca cuauagggaa auaagagaga 60
aaagaagagu aagaagaaau auaagagcca ccauggaauc caggaucugg ugccugguag 120
ucugcguuaa cuuguguauc gucugucugg gugcugcggu uuccucaucu ucuacucgug 180
gaacuucugc uacucacagu caccauuccu cucauacgac gucugcugcu cacucucgau 240
ccgguucagu cucucaacgc guaacuucuu cccaaacggu cagccauggu guuaacgaga 300
ccaucuacaa cacuacccuc aaguacggag auguggugggg ggucaauacc accaaguacc 360
ccuaucgcgu guguucuaug gcccagggua cggaucuuau ucgcuuugaa cguaauaucg 420
ucugcaccuc gaugaagccc aucaaugaag accuggacga gggcaucaug guggucuaca 480
aacgcaacau cgucgcgcac accuuuaagg uacgagucua ccagaagguu uugacguuuc 540
gucguagcua cgcuuacauc cacaccacuu aucugcuggg cagcaacacg gaauacgugg 600
cgccuccuau gugggagauu caucauauca acagccacag ucagugcuac aguuccuaca 660
gccgcguuau agcaggcacg guuuucgugg cuuaucauag ggacagcuau gaaaacaaaa 720
ccaugcaauu aaugcccgac gauuauucca acacccacag uacccguuac gugacgguca 780
aggaucaaug gcacagccgc ggcagcaccu ggcucuaucg ugagaccugu aaucugaauu 840
guauggugac caucacuacu gcgcgcucca aauauccuua ucauuuuuuc gccacuucca 900
cgggugacgu gguugacauu ucuccuuucu acaacggaac caaucgcaau gccagcuacu 960
uuggagaaaa cgccgacaag uuuuucauuu uuccgaacua cacuaucguc uccgacuuug 1020
gaagaccgaa uucugcguua gagacccaca gguugguggc uuuucuugaa cgugcggacu 1080
cggugaucuc cugggauaua caggacgaaa agaaugucac uugucaacuc acuuucuggg 1140
aagccucgga acgcaccauu cguuccgaag ccgaggacuc guaucacuuu ucuucugcca 1200
aaaugaccgc cacuuucuua ucuaagaagc aagaggugaa cauguccgac ucugcgcugg 1260
acugcguacg ugaugaggcu auaaaauaagu uacagcagau uuucaauacu ucauacaauc 1320
aaacauauga aaaauaugga aacgugucg ucuuugaaac cacugguggu uugguagugu 1380
ucuggcaagg uaucaagcaa aaaucucugg uggaacucga acguuuggcc aaccgcucca 1440
gucugaaucu uacucauaau agaaccaaaa gaaguacaga uggcaacaau gcaacucauu 1500
uauccaacau ggaaucggug cacaaucugg ucuacgccca gcugcaguuc accuaugaca 1560
cguugcgcgg uuacaucaac cgggcgcugg cgcaaaucgc agaagccugg uguguggauc 1620
aacggcgcac ccuagagguc uucaaggaac ucagcaagau caacccguca gccauucucu 1680
cggccauuua caacaaaccg auugccgcgc guuucauggg ugaugucuug ggccuggcca 1740
gcugcgugac caucaaccaa accagcguca aggugcugcg ugauaugaac gugaaggagu 1800
cgccaggacg cugcuacuca cgacccgugg ucaucuuuaa uuucgccaac agcucguacg 1860
ugcaguacgg ucaacugggc gaggacaacg aaauccuguu gggcaaccac cgcacugagg 1920
aaugucagcu ucccagccuc aagaucuuca ucgccgggaa cucggccuac gaguacgugg 1980
acuaccucuu caaacgcaug auugaccuca gcaguaucuc caccgucgac agcaugaucg 2040
cccuggauau cgacccgcug gaaaauaccg acuucagggu acuggaacuu uacucgcaga 2100
aagagcugcg uuccagcaac guuuuugacc ucgaagagau caugcgcgaa uucaacucgu 2160

```
acaagcagcg gguaaaguac guggaggaca agguagucga cccgcuaccg cccuaccuca   2220

agggucugga cgaccucaug agcggccugg gcgccgcggg aaaggccguu ggcguagcca   2280

uuggggccgu ggguggcgcg guggccuccg uggucgaagg cguugccacc uuccucaaaa   2340

accccuucgg agcguucacc aucauccucg uggccauagc uguagucauu aucacuuauu   2400

ugaucuauac ucgacagcgg cguuugugca cgcagccgcu gcagaaccuc uuucccuauc   2460

ugguguccgc cgacgggacc accgugacgu cgggcagcac caaagacacg ucguuacagg   2520

cuccgccuuc cuacgaggaa aguguuuaua auucuggucg caaaggaccg ggaccaccgu   2580

cgucugaugc auccacggcg gcuccgccuu acaccaacga gcaggcuuac cagaugcuuc   2640

uggcccuggc ccgucuggac gcagagcagc gagcgcagca gaacgguaca gauucuuugg   2700

acggacggac uggcacgcag gacaagggac agaagcccaa ccuacuagac cgacugcgac   2760

aucgcaaaaa cggcuaccga cacuugaaag acucugacga agaagagaac gucuugauaa   2820

uaggcuggag ccucgguggc caugcuucuu gccccuuggg ccucccccca gccccuccuc   2880

cccuuccugc acccguaccc ccguggucuu ugaauaaagu cugagugggc ggc          2933
```

<210> SEQ ID NO 114
<211> LENGTH: 1045
<212> TYPE: RNA
<213> ORGANISM: Artificial Sequence
<220> FEATURE:
<223> OTHER INFORMATION: Synthetic Polynucleotide

<400> SEQUENCE: 114

```
ucaagcuuuu ggacccucgu acagaagcua auacgacuca cuauagggug gcucuuauau     60

uucuucuuac ucuucuuuuc ucucuuauuu ccaugugccg ccgcccggau ugcggcuucu    120

cuuucucacc uggaccggug auacugcugu gguguugccu ucugcugccc auuguuuccu    180

cagccgccgu cagcgucgcu ccuaccgccg ccgagaaagu ccccgcggag ugccccgaac    240

uaacgcgccg augcuuguug ggugaggugu uugaggguga caaguaugaa aguuggcugc    300

gcccguuggu gaauguuacc gggcgcgaug gcccgcuauc gcaacuuauc cguuaccguc    360

ccguuacgcc ggaggccgcc aacuccgugc uguuggacga ggcuuuccug gacacucugg    420

cccugcugua caacaauccg gaucaauugc gggcccugcu gacgcuguug agcucggaca    480

cagcgccgcg cuggaugacg gugaugcgcg gcuacagcga gugcggcgau ggcucgccgg    540

ccguguacac gugcguggac gaccugugcc gcggcuacga ccucacgcga cugucauacg    600

ggcgcagcau cuucacggaa cacguguuag gcuucgagcu ggugccaccg ucucucuuua    660

acgugguggu ggccauacgc aacgaagcca cgcguaccaa ccgcgccgug cgucugcccg    720

ugagcaccgc ugccgcgccc gagggcauca cgcucuuuua cggccuguac aacgcaguga    780

aggaauucug ccugcgucac cagcuggacc cgccgcugcu acgccaccua gauaaauacu    840

acgccggacu gccgcccgag cugaagcaga cgcgcgucaa ccugccggcu cacucgcgcu    900

auggcccuca agcaguggau gcucgcugau aauaggcugg agccucggug gccaugcuuc    960

uugccccuug ggccuccccc cagccccucc uccccuuccu gcacccguac ccccgugguc   1020

uuugaauaaa gucugagugg gcggc                                         1045
```

<210> SEQ ID NO 115
<211> LENGTH: 853
<212> TYPE: RNA
<213> ORGANISM: Artificial Sequence
<220> FEATURE:
<223> OTHER INFORMATION: Synthetic Polynucleotide -continued

<400> SEQUENCE: 115

```
ucaagcuuuu ggacccucgu acagaagcua auacgacuca cuauagggug gcucuuauau    60
uucuucuuag uccgaauucg aaguacggcu acaugcugcg gcuucugcuu cgucaccacu   120
uucacugccu gcuucugugc gcgguuuggg caacgcccug ucuggcgucu ccguggucga   180
cgcuaacagc aaaccagaau ccguccccgc cauggucuaa acugacguau uccaaaccgc   240
augacgcggc gacguuuuac uguccuuuuc ucuaucccuc gcccccacga ucccccuugc   300
aauucucggg guuccagcgg guaucaacgg gucccgagug ucgcaacgag acccuguauc   360
ugcuguacaa ccgggaaggc cagaccuugg uggagagaag cuccaccugg gugaaaaagg   420
ugaucuggua ccugagcggu cggaaccaaa ccauccucca acggaugccc cgaacggcuu   480
cgaaaccgag cgacggaaac gugcagauca gcguggaaga cgccaagauu uuuggagcgc   540
acauggugcc caagcagacc aagcugcuac gcuucgucgu caacgauggc acacguuauc   600
agaugugugu gaugaagcug gagagcuggg cucacgucuu ccgggacuac agcgugucuu   660
uucaggugcg auugacguuc accgaggcca auaaccagac uuacaccuuc ugcacccauc   720
ccaaucucau cguuugauaa uaggcuggag ccucgguggc caugcuucuu gccccuuggg   780
ccucccccca gccccuccuc cccuuccugc acccguaccc ccguggucuu ugaauaaagu   840
cugagugggc ggc                                                      853
```

HUMAN CYTOMEGALOVIRUS RNA VACCINES

RELATED APPLICATIONS

This application is a continuation of U.S. application Ser. No. 16/450,882 filed Jun. 24, 2019, which is a continuation of U.S. application Ser. No. 16/006,526, filed Jun. 12, 2018, which is a continuation of U.S. application Ser. No. 15/674,569, filed Aug. 11, 2017, which is a continuation of international application number PCT/US2016/058310, filed Oct. 21, 2016, entitled "HUMAN CYTOMEGALOVIRUS VACCINE," which was published under PCT Article 21(2) in English and which claims the benefit under 35 U.S.C. § 119(e) of U.S. provisional application No. 62/245,166, filed Oct. 22, 2015, entitled "HUMAN CYTOMEGALOVIRUS VACCINE," U.S. provisional application No. 62/247,614, filed Oct. 28, 2015, entitled "HUMAN CYTOMEGALOVIRUS VACCINE," and U.S. provisional application No. 62/245,031, filed Oct. 22, 2015, each of which is herein incorporated by reference in its entirety.

BACKGROUND

Human cytomegalovirus (HCMV) is a genus of viruses in the order Herpesvirales, in the family Herpesviridae, in the subfamily Betaherpesvirinae. There are currently eight species in this genus, which have been identified and classified for different mammals, including humans, monkeys, and rodents. The most studied genus is human cytomegalovirus, also known as human herpesvirus 5 (HHV-5), which is widely distributed in the human population. Diseases associated with HHV-5 include mononucleosis and pneumonias. All herpesviruses share a characteristic ability to remain latent within the body over long periods of time. Although they may be found throughout the body, CMV infections are frequently associated with the salivary glands in humans and other mammals. Other CMV viruses are found in several mammal species, but species isolated from animals differ from HCMV in terms of genomic structure, and have not been reported to cause human disease.

HCMV is endemic in most parts of the world. It is a ubiquitous large enveloped virus that infects 50 to 100% of the adult population worldwide. Although generally asymptomatic in immunocompetent hosts, HCMV infection is a major cause of morbidity and mortality in immunocompromised persons, such as infants following congenital or neonatal infections, transplant recipients, or AIDS patients.

Primary infection normally results in subclinical disease after which the virus becomes latent, retaining the capacity to reactivate at a later time. The virus is transmitted through body fluids, such as blood, saliva, urine, semen and breast milk. In particular, individuals with undeveloped or compromised immunity are highly sensitive to infection by HCMV. It is estimated that at least 60% of the US population has been exposed to CMV, with a prevalence of more than 90% in high-risk groups (e.g., unborn babies whose mothers become infected with CMV during the pregnancy or people with HIV).

In healthy individuals, HCMV typically causes an asymptomatic infection or produces mild, flulike symptoms. However, among two populations, HCMV is responsible for serious medical conditions. First, HCMV is a major cause of congenital defects in newborns infected in utero. Among congenitally infected newborns, 5-10% have major clinical symptoms at birth, such as microcephaly, intracranial calcifications, and hepatitis, as well as cytomegalic inclusion disease, which affects many tissues and organs including the central nervous system, liver, and retina and can lead to multi-organ failure and death. Other infants may be asymptomatic at birth, but later develop hearing loss or central nervous system abnormalities causing, in particular, poor intellectual performance and mental retardation. These pathologies are due in part to the ability of HCMV to enter and replicate in diverse cell types including epithelial cells, endothelial cells, smooth muscle cells, fibroblasts, neurons, and monocytes/macrophages.

The second population at risk are immunocompromised patients, such as those suffering from HIV infection and those undergoing transplantations. In this situation, the virus becomes an opportunistic pathogen and causes severe disease with high morbidity and mortality. The clinical disease causes a variety of symptoms including fever, pneumonia, hepatitis, encephalitis, myelitis, colitis, uveitis, retinitis, and neuropathy. Rarer manifestations of HCMV infections in immunocompetent individuals include Guillain-Barré syndrome, meningoencephalitis, pericarditis, myocarditis, thrombocytopenia, and hemolytic anemia. Moreover, HCMV infection increases the risk of organ graft loss through transplant vascular sclerosis and restenosis, and may increase atherosclerosis in transplant patients as well as in the general population. It is estimated that HCMV infection causes clinical disease in 75% of patients in the first year after transplantation.

There is currently no approved HCMV vaccine. Two candidate vaccines, Towne and gB/MF59, have completed phase II efficacy trials. The Towne vaccine appears protective against both infection and disease caused by challenge with pathogenic Toledo strain and also appears to be effective in preventing severe post-transplantation CMV disease. However, in a small phase II clinical trial, a low dose of Towne vaccine failed to show protection against infection of seronegative mothers who had children actively shedding CMV.

The gB/MF59 vaccine is a protein subunit vaccine comprised of a transmembrane-deleted version of HCMV gB protein, which induces high levels of fibroblast entry neutralizing antibodies in humans and has been shown to be safe and well tolerated in both adults and toddlers. A recent phase II double-blind placebo-controlled trial of the gB/MF59 vaccine revealed a 50% efficacy in inducing sterilizing immunity. As this vaccine induces potent antibody responses but very weak T-cell responses, the partial efficacy provided by the vaccine is thought to be primarily antibody-mediated. While this HCMV vaccine is the first to show any protective efficacy, its 50% protection falls short of the 80-90% desired for most vaccines.

In addition, antibody therapy has been used to control HCMV infection in immunocompromised individuals and to reduce the pathological consequences of maternal-fetal transmission, although such therapy is usually not sufficient to eradicate the virus. HCMV immunoglobulins (Igs) have been administered to transplant patients in association with immunosuppressive treatments for prophylaxis of HCMV disease with mixed results. Antibody therapy has also been used to control congenital infection and prevent disease in newborns. However, these products are plasma derivatives with relatively low potency and have to be administered by intravenous infusion at very high doses in order to deliver sufficient amounts of neutralizing antibodies.

HCMV is the leading viral cause of neurodevelopmental abnormality and other birth defects in children and the costs to society are substantial. Although antiviral therapy is available, the treatment with antiviral agents is imperfect and development of a CMV vaccine is the most promising strategy for preventing CMV infection. Given that the health and economic benefits of effective HCMV vaccines are significant, the US Institute of Medicine and US National Vaccine Program Office has categorized development of a CMV vaccine as a highest priority, but no candidate vaccine is under consideration for licensure.

SUMMARY

In view of the lack of HCMV vaccines, there is a significant need for a vaccine that would be safe and effective in all patient populations to prevent and/or to treat HCMV infection. In particular, there is a need for a vaccine that would be safe and effective for immunocompromised, at-risk pregnant women, and infant patients to prevent or to reduce the severity and/or duration of HCMV. Provided herein is a ribonucleic acid (RNA) vaccine that builds on the knowledge that RNA (e.g., messenger RNA (mRNA)) can safely direct the body's cellular machinery to produce nearly any protein of interest, from native proteins to antibodies and other entirely novel protein constructs that can have therapeutic activity inside and outside of cells. The HCMV RNA vaccines of the present disclosure may be used to induce a balanced immune response against human cytomegalovirus comprising both cellular and humoral immunity, without many of the risks associated with DNA or attenuated virus vaccination.

The RNA vaccines may be utilized in various settings depending on the prevalence of the infection or the degree or level of unmet medical need. The RNA vaccines may be utilized to treat and/or prevent a HCMV of various genotypes, strains, and isolates. The RNA vaccines have superior properties in that they produce much larger antibody titers and produce responses earlier than commercially available anti-viral therapeutic treatments. While not wishing to be bound by theory, it is believed that the RNA vaccines, as mRNA polynucleotides, are better designed to produce the appropriate protein conformation upon translation as the RNA vaccines co-opt natural cellular machinery. Unlike traditional vaccines which are manufactured ex vivo and may trigger unwanted cellular responses, the RNA vaccines are presented to the cellular system in a more native fashion.

Various human cytomegalovirus amino acid sequences encompasses by the present disclosure are provided in Tables 1, 2 and 6 below. RNA vaccines as provided herein may include at least one RNA polynucleotide encoding at least one of the HCMV proteins provided in Tables 1, 2 or 6, or a fragment, homolog (e.g., having at least 80%, 85%, 90%, 95%, 98% or 99% identity) or derivative thereof.

Some embodiments of the present disclosure provide HCMV vaccines that include at least one ribonucleic acid (RNA) polynucleotide having an open reading frame encoding at least one HCMV antigenic polypeptide or an immunogenic fragment or epitope thereof.

Some embodiments of the present disclosure provide HCMV vaccines that include at least one RNA polynucleotide having an open reading frame encoding two or more HCMV antigenic polypeptides or an immunogenic fragment or epitope thereof. Some embodiments of the present disclosure provide HCMV vaccines that include two or more RNA polynucleotides having an open reading frame encoding two or more HCMV antigenic polypeptides or immunogenic fragments or epitopes thereof. The one or more HCMV antigenic polypeptides may be encoded on a single RNA polynucleotide or may be encoded individually on multiple (e.g., two or more) RNA polynucleotides.

In some embodiments, an antigenic polypeptide is an HCMV glycoprotein. For example, a HCMV glycoprotein may be selected from HCMV gH, gL, gB, gO, gN, and gM and an immunogenic fragment or epitope thereof. In some embodiments, the antigenic polypeptide is a HCMV gH polypeptide. In some embodiments, the antigenic polypeptide is a HCMV gL polypeptide. In some embodiments, the antigenic polypeptide is a HCMV gB polypeptide. In some embodiments, the antigenic polypeptide is a HCMV gO polypeptide. In some embodiments, the antigenic polypeptide is a HCMV gN polypeptide. In some embodiments, the antigenic polypeptide is a HCMV gM polypeptide. In some embodiments, the HCMV glycoprotein is encoded by a nucleic acid sequence of SEQ ID NO: 1, SEQ ID NO:2, SEQ ID NO: 3, SEQ ID NO: 4, SEQ ID NO: 5, SEQ ID NO:6, SEQ ID NO:58, SEQ ID NO:60, SEQ ID NO:62, SEQ ID NO:64, SEQ ID NO:66, SEQ ID NO:68, SEQ ID NO:108, SEQ ID NO:109, SEQ ID NO:110, SEQ ID NO:111, SEQ ID NO: 112, or SEQ ID NO:113.

In some embodiments, the HCMV glycoprotein is a variant gH polypeptide, a variant gL polypeptide, or a variant gB polypeptide. In some embodiments, the variant HCMV gH, gL, or gB polypeptide is a truncated polypeptide lacking one or more of the following domain sequences: (1) the hydrophobic membrane proximal domain, (2) the transmembrane domain, and (3) the cytoplasmic domain. In some embodiments, the truncated HCMV gH, gL, or gB polypeptide lacks the hydrophobic membrane proximal domain, the transmembrane domain, and the cytoplasmic domain. In some embodiments, the truncated HCMV gH, gL, or gB polypeptide comprises only the ectodomain sequence. In some embodiments, the HCMV truncated glycoprotein is encoded by a nucleic acid sequence of SEQ ID NO: 7, SEQ ID NO:8, SEQ ID NO: 9, SEQ ID NO: 10, SEQ ID NO: 11, or SEQ ID NO:12.

In some embodiments, an antigenic polypeptide is an HCMV protein selected from UL83, UL123, UL128, UL130 and UL131A or an immunogenic fragment or epitope thereof. In some embodiments, the antigenic polypeptide is a HCMV UL83 polypeptide. In some embodiments, the antigenic polypeptide is a HCMV UL123 polypeptide. In some embodiments, the antigenic polypeptide is a HCMV UL128 polypeptide. In some embodiments, the antigenic polypeptide is a HCMV UL130 polypeptide. In some embodiments, the antigenic polypeptide is a HCMV UL131A polypeptide. In some embodiments, the HCMV protein is encoded by a nucleic acid sequence of SEQ ID NO: 13, SEQ ID NO:14, SEQ ID NO: 15, SEQ ID NO: 16, SEQ ID NO: 17, or SEQ ID NO:18.

In some embodiments, the antigenic polypeptide comprises two or more HCMV proteins, fragments, or epitopes thereof. In some embodiments, the antigenic polypeptide comprises two or more glycoproteins, fragments, or epitopes thereof. In some embodiments, the antigenic polypeptide comprises at least one HCMV glycoprotein, fragment or epitope thereof and at least one other HCMV protein, fragment or epitope thereof. In some embodiments, the two or more HCMV polypeptides are encoded by a single RNA polynucleotide. In some embodiments, the two or more HCMV polypeptides are encoded by two or more RNA polynucleotides, for example, each HCMV polypeptide is encoded by a separate RNA polynucleotide. In some embodiments, the two or more HCMV glycoproteins can be any combination of HCMV gH, gL, gB, gO, gN, and gM polypeptides or immunogenic fragments or epitopes thereof. In some embodiments, the two or more glycoproteins can be any combination of HCMV gB and one or more HCMV polypeptides selected from gH, gL, gO, gN, and gM polypeptides or immunogenic fragments or epitopes thereof. In some embodiments, the two or more glycoproteins can be any combination of HCMV gH and one or more HCMV polypeptides selected from gL, gO, gN, and gM polypeptides or immunogenic fragments or epitopes thereof. In some embodiments, the two or more glycoproteins can be any combination of HCMV gL and one or more HCMV polypeptides selected from gB, gH, gO, gN, and gM polypeptides or immunogenic fragments or epitopes thereof. In some embodiments, the two or more HCMV glycoproteins are gB and gH. In some embodiments, the two or more HCMV glycoproteins are gB and gL. In some embodiments, the two or more HCMV glycoproteins are gH and gL. In some embodiments, the two or more HCMV glycoproteins are gB, gL, and gH. In some embodiments, the two or more HCMV proteins can be any combination of HCMV UL83, UL123, UL128, UL130, and UL131A polypeptides or immunogenic fragments or epitopes thereof. In some embodiments, the two or more HCMV glycoproteins are UL123 and UL130. In some embodiments, the two or more HCMV glycoproteins are UL123 and 131A. In some embodiments, the two or more HCMV glycoproteins are UL130 and 131A. In some embodiments, the two or more HCMV glycoproteins are UL 128, UL130 and 131A. In some embodiments, the two or more HCMV proteins can be any combination of HCMV gB, gH, gL, gO, gM, gN, UL83, UL123, UL128, UL130, and UL131A polypeptides or immunogenic fragments or epitopes thereof. In some embodiments, the two or more glycoproteins can be any combination of HCMV gH and one or more HCMV polypeptides selected from gL, UL128, UL130, and UL131A polypeptides or immunogenic fragments or epitopes thereof. In some embodiments, the two or more glycoproteins can be any combination of HCMV gL and one or more HCMV polypeptides selected from gH, UL128, UL130, and UL131A polypeptides or immunogenic fragments or epitopes thereof. In some embodiments, the two or more HCMV glycoproteins are gL, gH, UL 128, UL130 and 131A. In any of these embodiments in which the vaccine comprises two or more HCMV proteins, the HCMV gH may be a variant gH, such as any of the variant HCMV gH glycoproteins disclosed herein, for example, any of the variant HCMV gH disclosed in the preceding paragraphs and in the Examples. In any of these embodiments in which the vaccine comprises two or more HCMV proteins, the HCMV gB may be a variant gB, such as any of the variant HCMV gB glycoproteins disclosed herein, for example, any of the variant HCMV gB disclosed in the preceding paragraphs and in the Examples. In any of these embodiments in which the vaccine comprises two or more HCMV gL proteins, the HCMV gL may be a variant gL, such as any of the variant HCMV gL glycoproteins disclosed herein, for example, any of the variant HCMV gL disclosed in the preceding paragraphs and in the Examples.

In certain embodiments in which the HCMV vaccine includes two or more RNA polynucleotides having an open reading frame encoding two or more HCMV antigenic polypeptides or an immunogenic fragment or epitope thereof (either encoded by a single RNA polynucleotide or encoded by two or more RNA polynucleotides, for example, each protein encoded by a separate RNA polynucleotide), the two or more HCMV proteins are a variant gB, for example, any of the variant gB polypeptides disclosed herein in the preceding paragraphs, and a HCMV protein selected from gH, gL, gO, gM, gN, UL128, UL130, and UL131A polypeptides or immunogenic fragments or epitopes thereof. In some embodiments, the two or more HCMV proteins are a variant gH, for example, any of the variant gH polypeptides disclosed herein in the preceding paragraphs, and a HCMV protein selected from gH, gL, gO, gM, gN, UL128, UL130, and UL131A polypeptides or immunogenic fragments or epitopes thereof. In some embodiments, the two or more HCMV proteins are a variant gH, for example, any of the variant gH polypeptides disclosed herein in the preceding paragraphs, and a HCMV protein selected from gH, gL, gO, gM, gN, UL128, UL130, and UL131A polypeptides or immunogenic fragments or epitopes thereof. In some embodiments in which the variant HCMV proteins are variant HCMV gB, variant HCMV gL, and variant HCMV gH, the variant HCMV polypeptide is a truncated polypeptide selected from the following truncated polypeptides: lacks the hydrophobic membrane proximal domain; lacks the transmembrane domain; lacks the cytoplasmic domain; lacks two or more of the hydrophobic membrane proximal, transmembrane, and cytoplasmic domains; and comprises only the ectodomain.

In some embodiments, the HCMV vaccine includes multimeric RNA polynucleotides having an open reading frame encoding at least one HCMV antigenic polypeptide or an immunogenic fragment or epitope thereof. Some embodiments of the present disclosure provide HCMV vaccines that include at least one ribonucleic acid (RNA) polynucleotide having an open reading frame encoding at least one HCMV antigenic polypeptide or an immunogenic fragment or epitope thereof, wherein the 5'UTR of the RNA polynucleotide comprises a patterned UTR. In some embodiments, the patterned UTR has a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level. In some embodiments, the 5'UTR of the RNA polynucleotide (e.g., a first nucleic acid) has regions of complementarity with a UTR of another RNA polynucleotide (a second nucleic acid). For example, UTR nucleotide sequences of two polynucleotides sought to be joined (e.g., in a multimeric molecule) can be modified to include a region of complementarity such that the two UTRs hybridize to form a multimeric molecule.

In some embodiments, the 5'UTR of an RNA polynucleotide encoding an HCMV antigenic polypeptide is modified to allow the formation of a multimeric sequence. In some embodiments, the 5'UTR of an RNA polynucleotide encoding an HCMV protein selected from UL128, UL130, UL131A1 is modified to allow the formation of a multimeric sequence. In some embodiments, the 5'UTR of an RNA polynucleotide encoding an HCMV glycoprotein is modified to allow the formation of a multimeric sequence. In some embodiments, the 5'UTR of an RNA polynucleotide encoding an HCMV glycoprotein selected from gH, gL, gB, gO, gM, and gN is modified to allow the formation of a multimeric sequence. In any of these embodiments, the multimer may be a dimer, a trimer, pentamer, hexamer, heptamer, octamer nonamer, or decamer. Thus, in some embodiments, the 5'UTR of an RNA polynucleotide encoding an HCMV protein selected from gH, gL, gB, gO, gM, gN, UL128, UL130, and UL131A1 is modified to allow the formation of a dimer. In some embodiments, the 5'UTR of an RNA polynucleotide encoding an HCMV protein selected from gH, gL, gB, gO, gM, gN, UL128, UL130, and UL131A1 is modified to allow the formation of a trimer. In some embodiments, the 5'UTR of an RNA polynucleotide encoding an HCMV protein selected from gH, gL, gB, gO, gM, gN, UL128, UL130, and UL131A1 is modified to allow the formation of a pentamer. Exemplary HCMV nucleic acids having modified 5'UTR sequence for the formation of a multimeric molecule (e.g., dimers, trimers, pentamers, etc) comprise SEQ ID Nos: 19-26.

In any of the above-described embodiments, the HCMV RNA polynucleotides may further comprise additional sequences, for example, one or more linker sequences or one or more sequence tags, such as FLAG-tag and histidine tag.

Some embodiments of the present disclosure provide HCMV vaccines that include at least one ribonucleic acid (RNA) polynucleotide having a single open reading frame encoding two or more (for example, two, three, four, five, or more) HCMV antigenic polypeptides or an immunogenic fragment or epitope thereof. Some embodiments of the present disclosure provide HCMV vaccines that include at least one ribonucleic acid (RNA) polynucleotide having more than one open reading frame, for example, two, three, four, five or more open reading frames encoding two, three, four, five or more HCMV antigenic polypeptides. In either of these embodiments, the at least one RNA polynucleotide may encode two or more HCMV antigenic polypeptides selected from gH, gB, gL, gO, gM, gN, UL83, UL123, UL128, UL130, UL131A, and fragments or epitopes thereof. In some embodiments, the at least one RNA polynucleotide encodes UL83 and UL123. In some embodiments, the at least one RNA polynucleotide encodes gH and gL. In some embodiments, the at least one RNA polynucleotide encodes UL128, UL130, and UL131A. In some embodiments, the at least one RNA polynucleotide encodes gH, gL, UL128, UL130, and UL131A. In some embodiments, in which the at least one RNA polynucleotide has a single open reading frame encoding two or more (for example, two, three, four, five, or more) HCMV antigenic polypeptides, the RNA polynucleotide further comprises additional sequence, for example, a linker sequence or a sequence that aids in the processing of the HCMV RNA transcripts or polypeptides, for example a cleavage site sequence. In some embodiments, the additional sequence may be a protease sequence, such as a furin sequence. In some embodiments, the additional sequence may be self-cleaving 2A peptide, such as a P2A, E2A, F2A, and T2A sequence. In some embodiments, the linker sequences and cleavage site sequences are interspersed between the sequences encoding HCMV polypeptides. In some embodiments, the RNA polynucleotide is encoded by SEQ ID NO: 27, SEQ ID NO: 28, SEQ ID NO: 29, SEQ ID NO: 30 or SEQ ID NO: 31.

In some embodiments, at least one RNA polynucleotide is encoded by at least one nucleic acid sequence selected from any of SEQ ID NOs: 1-31, 58, 60, 62, 64, 66, 68, and 108-113 and homologs having at least 80% (e.g., 85%, 90%, 95%, 98%, 99%) identity with a nucleic acid sequence selected from SEQ ID NOs:1-31, 58, 60, 62, 64, 66, 68, and 108-113. In some embodiments, at least one RNA polynucleotide is encoded by at least one nucleic acid sequence selected from any of SEQ ID NOs: 1-31, 58, 60, 62, 64, 66, 68, and 108-113 and homologs having at least 90% (90%, 91%, 92%, 93%, 94%, 95%, 96%, 97%, 98%, 99%, 99.8% or 99.9%) identity with a nucleic acid sequence selected from SEQ ID NO:1-31, 58, 60, 62, 64, 66, 68, and 108-113. In some embodiments, at least one RNA polynucleotide is encoded by at least one fragment of a nucleic acid sequence selected from any of SEQ ID NOs: 1-31, 58, 60, 62, 64, 66, 68, and 108-113 and homologs having at least 80% (e.g., 85%, 90%, 95%, 98%, 99%) identity with a nucleic acid sequence selected from SEQ ID NO:1-31, 58, 60, 62, 64, 66, 68, and 108-113. In some embodiments, at least one RNA polynucleotide is encoded by at least one nucleic acid sequence selected from any of the nucleic acid sequences disclosed herein and homologs having at least 80% (e.g., 85%, 90%, 95%, 96%, 97%, 98%, 99%) identity with any of the nucleic acid sequences disclosed herein.

In any of the above-described embodiments in the preceding paragraphs, the HCMV RNA polynucleotides may further comprise additional sequences, for example, one or more linker sequences or one or more sequence tags, such as FLAG-tag and histidine tag.

In some embodiments, at least one RNA polynucleotide encodes an antigenic polypeptide having at least 90% identity to the amino acid sequence of any of SEQ ID NOs: 32-52, 59, 61, 63, 65, 67, and 69. In some embodiments, at least one RNA polynucleotide encodes an antigenic polypeptide having at least 95% identity to the amino acid sequence of any of SEQ ID Nos: 32-52, 59, 61, 63, 65, 67, and 69. In some embodiments, at least one RNA polynucleotide encodes an antigenic polypeptide having at least 96% identity to the amino acid sequence of any of SEQ ID Nos:32-52, 59, 61, 63, 65, 67, and 69. In some embodiments, at least one RNA polynucleotide encodes an antigenic polypeptide having at least 97% identity to the amino acid sequence of any of SEQ ID Nos: 32-52, 59, 61, 63, 65, 67, and 69. In some embodiments, at least one RNA polynucleotide encodes an antigenic polypeptide having at least 98% identity to the amino acid sequence of SEQ ID Nos: 32-52, 59, 61, 63, 65, 67, and 69. In some embodiments, at least one RNA polynucleotide encodes an antigenic polypeptide having at least 99% identity to the amino acid sequence of SEQ ID Nos: 32-52, 59, 61, 63, 65, 67, and 69.

In some embodiments, the open reading from which the HCMV polypeptide is encoded is codon-optimized. In some embodiments, the at least one RNA polynucleotide encodes an antigenic protein of SEQ ID NO: 32, and wherein the RNA polynucleotide is codon optimized mRNA. In some embodiments, the at least one RNA polynucleotide encodes an antigenic protein of SEQ ID NO: 33, and wherein the RNA polynucleotide is codon optimized mRNA. In some embodiments, the at least one RNA polynucleotide encodes an antigenic protein of SEQ ID NO: 34, and wherein the RNA polynucleotide is codon optimized mRNA. In some embodiments, the at least one RNA polynucleotide encodes an antigenic protein of SEQ ID NO: 38, and wherein the RNA polynucleotide is codon optimized mRNA. In some embodiments, the at least one RNA polynucleotide encodes an antigenic protein of SEQ ID NO: 40, and wherein the RNA polynucleotide is codon optimized mRNA. In some embodiments, the at least one RNA polynucleotide encodes an antigenic protein of SEQ ID NO: 42, and wherein the RNA polynucleotide is codon optimized mRNA. In some embodiments, the at least one RNA polynucleotide encodes an antigenic protein of SEQ ID NO: 47, and wherein the RNA polynucleotide is codon optimized mRNA. In some embodiments, the at least one RNA polynucleotide encodes an antigenic protein of SEQ ID NO: 50, and wherein the RNA polynucleotide is codon optimized mRNA.

In some embodiments, the at least one RNA polynucleotide encodes an antigenic protein of SEQ ID NO: 32, and wherein the RNA polynucleotide has less than 80% identity to wild-type mRNA sequence. In some embodiments, the at least one RNA polynucleotide encodes an antigenic protein of SEQ ID NO: 32, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 33, and wherein the RNA polynucleotide has less than 80% identity to wild-type mRNA sequence. In some embodiments, the at least one RNA polynucleotide encodes an antigenic protein of SEQ ID NO: 33, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 34, and wherein the RNA polynucleotide has less than 80% identity to wild-type mRNA sequence. In some embodiments, the at least one RNA polynucleotide encodes an antigenic protein of SEQ ID NO: 34, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 38, and wherein the RNA polynucleotide has less than 80% identity to wild-type mRNA sequence. In some embodiments, the at least one RNA polynucleotide encodes an antigenic protein of SEQ ID NO: 38, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 40, and wherein the RNA polynucleotide has less than 80% identity to wild-type mRNA sequence. In some embodiments, the at least one RNA polynucleotide encodes an antigenic protein of SEQ ID NO: 40, and wherein the RNA polynucleotide has greater than 80% identity to wild-type mRNA sequence, but does not include wild-type mRNA sequence.

In some embodiments, the at least one RNA polynucleotide encodes an antigenic protein of SEQ ID NO: 42, and wherein the RNA polynucleotide has less than 80% identity to wild-type mRNA sequence. In some embodiments, the at least one RNA polynucleotide encodes an antigenic protein of SEQ ID NO: 42, and wherein the RNA polynucleotide has greater than 80% identity to wild-type mRNA sequence, but does not include wild-type mRNA sequence.

In some embodiments, the at least one RNA polynucleotide is encoded by a sequence selected from SEQ ID NO: 1-31 and includes at least one chemical modification.

In some embodiments, the HCMV vaccine is multivalent. In some embodiments, the RNA polynucleotide comprises a polynucleotide sequence derived from a virus strain or isolate selected from VR1814 VR6952, VR3480B1 (ganciclovir resistant), VR4760 (ganciclovir and foscarnet resistant), Towne, TB40/E, AD169, Merlin, and Toledo.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof and at least one 5' terminal cap. In some embodiments, a 5' terminal cap is 7mG(5')ppp(5')NlmpNp.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof, wherein the at least one ribonucleic acid (RNA) polynucleotide has at least one chemical modification. In some embodiments, the at least one ribonucleic acid (RNA) polynucleotide further comprises a second chemical modification. In some embodiments, the at least one ribonucleic acid (RNA) polynucleotide having at least one chemical modification has a 5' terminal cap. In some embodiments, the at least one chemical modification is selected from pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine.

Some embodiments of the present disclosure provide a HCMV vaccine that includes at least one ribonucleic acid (RNA) polynucleotide having an open reading frame encoding at least one HCMV antigenic polypeptide or an immunogenic fragment thereof, wherein at least 80% (e.g., 85%, 90%, 95%, 98%, 99%, 100%) of the uracil in the open reading frame have a chemical modification, optionally wherein the vaccine is formulated in a lipid nanoparticle. In some embodiments, 100% of the uracil in the open reading frame have a chemical modification. In some embodiments, a chemical modification is in the 5-position of the uracil. In some embodiments, a chemical modification is a N1-methyl pseudouridine. In some embodiments, a chemical modification is a N1-ethyl pseudouridine.

Some embodiments of the present disclosure provide a HCMV vaccine that is formulated within a cationic lipid nanoparticle. In some embodiments, the cationic lipid nanoparticle comprises a cationic lipid, a PEG-modified lipid, a sterol and a non-cationic lipid.

In some embodiments, a cationic lipid is an ionizable cationic lipid and the non-cationic lipid is a neutral lipid, and the sterol is a cholesterol. In some embodiments, a cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), di((Z)-non-2-en-1-yl) 9-((4-(dimethylamino)butanoyl)oxy)heptadecanedioate (L319), (12Z,15Z)—N,N-dimethyl-2-nonylhenicosa-12,15-dien-1-amine (L608), and N,N-dimethyl-1-[(1S,2R)-2-octylcyclopropyl]heptadecan-8-amine (L530).

In some embodiments, the lipid is (L608)

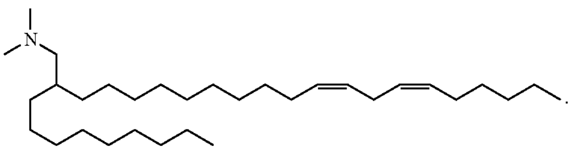

In some embodiments, the lipid is (L530)

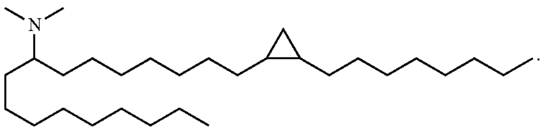

In some embodiments, the cationic lipid nanoparticle has a molar ratio of about 20-60% cationic lipid, about 5-25% non-cationic lipid, about 25-55% sterol, and about 0.5-15% PEG-modified lipid. In some embodiments, the nanoparticle has a polydiversity value of less than 0.4. In some embodiments, the nanoparticle has a net neutral charge at a neutral pH. In some embodiments, the nanoparticle has a mean diameter of 50-200 nm.

Some embodiments of the present disclosure provide methods of inducing an antigen specific immune response in a subject, comprising administering to the subject a HCMV RNA vaccine in an amount effective to produce an antigen specific immune response. In some embodiments, an antigen specific immune response comprises a T cell response or a B cell response. In some embodiments, an antigen specific immune response comprises a T cell response and a B cell response. In some embodiments, a method of producing an antigen specific immune response involves a single administration of the vaccine. In some embodiments, a method further includes administering to the subject a booster dose of the vaccine. In some embodiments, a vaccine is administered to the subject by intradermal or intramuscular injection.

Also provided herein are HCMV RNA vaccines for use in a method of inducing an antigen specific immune response in a subject, the method comprising administering the vaccine to the subject in an amount effective to produce an antigen specific immune response.

Further provided herein are uses of HCMV RNA vaccines in the manufacture of a medicament for use in a method of inducing an antigen specific immune response in a subject, the method comprising administering the vaccine to the subject in an amount effective to produce an antigen specific immune response.

Further provided herein are methods of preventing or treating HCMV infection comprising administering to a subject the vaccine of the present disclosure.

The HCMV vaccine disclosed herein may be formulated in an effective amount to produce an antigen specific immune response in a subject.

In some embodiments, an anti-HCMV antigenic polypeptide antibody titer produced in the subject is increased by at least 1 log relative to a control. In some embodiments, the anti-HCMV antigenic polypeptide antibody titer produced in the subject is increased by 1-3 log relative to a control. In some embodiments, an anti-HCMV antigenic polypeptide antibody titer produced in the subject is increased at least 2 times relative to a control. In some embodiments, the anti-HCMV antigenic polypeptide antibody titer produced in the subject is increased at least 5 times relative to a control. In some embodiments, the anti-HCMV antigenic polypeptide antibody titer produced in the subject is increased at least 10 times relative to a control. In some embodiments, the anti-HCMV antigenic polypeptide antibody titer produced in the subject is increased 2-10 times relative to a control.

In some embodiments, the control is an anti-HCMV antigenic polypeptide antibody titer produced in a subject who has not been administered HCMV vaccine.

In some embodiments, the control is an anti-HCMV antigenic polypeptide antibody titer produced in a subject who has been administered a live attenuated or inactivated HCMV vaccine.

In some embodiments, the control is an anti-HCMV antigenic polypeptide antibody titer produced in a subject who has been administered a recombinant or purified HCMV protein vaccine.

In some embodiments, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a total dose of 50-1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

Other aspects of the present disclosure provide methods of inducing an antigen specific immune response in a subject, including administering to a subject the HCMV vaccine disclosed herein in an effective amount to produce an antigen specific immune response in a subject.

In some embodiments, an anti-HCMV antigenic polypeptide antibody titer produced in the subject is increased by at least 1 log relative to a control. In some embodiments, an anti-HCMV antigenic polypeptide antibody titer produced in the subject is increased by 1-3 log relative to a control. In some embodiments, an anti-HCMV antigenic polypeptide antibody titer produced in the subject is increased at least 2 times relative to a control. In some embodiments, the anti-HCMV antigenic polypeptide antibody titer produced in the subject is increased at least 5 times relative to a control. In some embodiments, the anti-HCMV antigenic polypeptide antibody titer produced in the subject is increased at least 10 times relative to a control. In some embodiments, the anti-HCMV antigenic polypeptide antibody titer produced in the subject is increased 2-10 times relative to a control.

In some embodiments, the control is an anti-HCMV antigenic polypeptide antibody titer produced in a subject who has not been administered HCMV vaccine.

In some embodiments, the control is an anti-HCMV antigenic polypeptide antibody titer produced in a subject who has been administered a live attenuated or inactivated HCMV vaccine.

In some embodiments, the control is an anti-HCMV antigenic polypeptide antibody titer produced in a subject who has been administered a recombinant or purified HCMV protein vaccine.

In some embodiments, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant HCMV protein vaccine or a live attenuated HCMV vaccine.

In some embodiments, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a total dose of 50-1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

Other aspects of the present disclosure provide HCMV vaccines containing a signal peptide linked to a HCMV antigenic polypeptide.

In some embodiments, the HCMV antigenic polypeptide is a HCMV glycoprotein or an antigenic fragment thereof. In some embodiments, the HCMV antigenic polypeptide is a HCMV gB, gM, gN, gH, gL, gO, UL 83, UL123, UL128, UL130, or UL131A protein or an antigenic fragment or epitope thereof. In some embodiments, the HCMV glycoprotein is selected from HCMV gB, gM, gN, gH, gL, and gO.

In some embodiments, the HCMV glycoprotein is HCMV gH. In some embodiments, the HCMV glycoprotein is HCMV gL. In some embodiments, the HCMV glycoprotein is HCMV gB. In some embodiments, the HCMV protein is HCMV UL128. In some embodiments, the HCMV protein is HCMV UL130. In some embodiments, the HCMV protein is HCMV UL131A. In some embodiments, the HCMV protein is HCMV UL83. In some embodiments, the HCMV protein is HCMV UL123. In some embodiments, the HCMV glycoprotein is a variant HCMV gH polypeptide. In some embodiments, the HCMV glycoprotein is a variant HCMV gL polypeptide. In some embodiments, the HCMV glycoprotein is a variant HCMV gB polypeptide.

In some embodiments, the signal peptide is an IgE signal peptide. In some embodiments, the signal peptide is an IgE HC (Ig heavy chain epsilon-1) signal peptide. In some embodiments, the signal peptide has the amino acid sequence MDWTWILFLVAAATRVHS (SEQ ID NO: 53).

In some embodiments, the signal peptide is an IgGκ signal peptide. In some embodiments, the signal peptide has the amino acid sequence METPAQLLFLLLLWLPDTTG (SEQ ID NO: 54).

In some embodiments, the HCMV vaccine comprises at least one RNA polynucleotide encoding gH, gL, UL128, UL130, and UL131A, or antigenic fragments or epitopes thereof, and at least one RNA polynucleotide encoding gB, or an antigenic fragment or epitope thereof.

Further provided herein are uses of HCMV vaccines for prevention of congenital HCMV infection. Further provided herein are methods of administering HCMV vaccines to a women of child-bearing age.

Aspects of the invention relate to a human cytomegalovirus (HCMV) vaccine comprising: i) at least one RNA polynucleotide having one or more open reading frames encoding HCMV antigenic polypeptides gH, gL, UL128, UL130, and/or UL131A, or antigenic fragments or epitopes thereof; ii) an RNA polynucleotide having an open reading frame encoding HCMV antigenic polypeptide gB, or an antigenic fragment or epitope thereof; and iii) a pharmaceutically acceptable carrier or excipient.

In some embodiments, the HCMV vaccine comprises: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; and an RNA polynucleotide having an open reading frame encoding HCMV antigenic polypeptide UL131A, or an antigenic fragment or epitope thereof.

In some embodiments, at least one RNA polynucleotide has an open reading frame encoding two or more HCMV antigenic polypeptides, or antigenic fragments or epitopes thereof. In some embodiments, one or more of the open reading frames is codon-optimized. In some embodiments, at least one RNA polynucleotide is encoded by at least one nucleic acid sequence selected from SEQ ID NOs: 58, 60, 62, 64, 66, 68, and 108-113. In some embodiments, at least one of the RNA polynucleotides encodes an antigenic polypeptide having at least 90%, at least 95%, at least 96%, at least 97%, at least 98%, or at least 99% identity to any of the amino acid sequences of SEQ ID NOs: 59, 61, 63, 65, 67, and 69.

In some embodiments, at least one RNA polynucleotide encodes an antigenic protein of SEQ ID NO.: 59, wherein the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 61, wherein the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 63, and wherein the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 65, and wherein the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 67, and wherein the RNA polynucleotide has less than 80% identity to wild-type mRNA sequence or has greater than 80% identity to wild-type mRNA sequence, but does not include wild-type mRNA sequence. In some embodiments, at least one RNA polynucleotide encodes an antigenic protein of SEQ ID NO.: 69, and wherein the RNA polynucleotide has less than 80% identity to wild-type mRNA sequence or has greater than 80% identity to wild-type mRNA sequence, but does not include wild-type mRNA sequence.

In some embodiments, at least one RNA polynucleotide includes at least one chemical modification. In some embodiments, the vaccine is multivalent. In some embodiments, the RNA polynucleotide comprises a polynucleotide sequence derived from a virus strain or isolate selected from VR1814, VR6952, VR3480B1, VR4760, Towne, TB40/E, AD169, Merlin, and Toledo.

In some embodiments, the HCMV vaccine further comprises a second chemical modification. In some embodiments, the chemical modification is selected from the group consisting of pseudouridine, N1-methylpseudouridine, N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

In some embodiments, 80% of the uracil in the open reading frame have a chemical modification. In some embodiments, 100% of the uracil in the open reading frame have a chemical modification. In some embodiments, the chemical modification is in the 5-position of the uracil. In some embodiments, the chemical modification is N1-methylpseudouridine. In some embodiments, the chemical modification is N1-ethylpseudouridine.

In some embodiments, the vaccine is formulated within a cationic lipid nanoparticle. In some embodiments, the cationic lipid nanoparticle comprises a cationic lipid, a PEG-modified lipid, a sterol and a non-cationic lipid. In some embodiments, the cationic lipid is an ionizable cationic lipid and the non-cationic lipid is a neutral lipid, and the sterol is a cholesterol. In some embodiments, the cationic lipid is selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319). In some embodiments, the cationic lipid nanoparticle has a molar ratio of about 20-60% cationic lipid, about 5-25% non-cationic lipid, about 25-55% sterol, and about 0.5-15% PEG-modified lipid.

In some embodiments, the nanoparticle has a polydiversity value of less than 0.4. In some embodiments, the nanoparticle has a net neutral charge at a neutral pH. In some embodiments, the nanoparticle has a mean diameter of 50-200 nm.

Aspects of the invention relate to methods of inducing an antigen specific immune response in a subject, comprising administering any of the vaccines described herein to the subject in an effective amount to produce an antigen specific immune response. In some embodiments, the antigen specific immune response comprises a T cell response. In some embodiments, the antigen specific immune response comprises a B cell response. In some embodiments, the antigen specific immune response comprises a T cell response and a B cell response. In some embodiments, the method of producing an antigen specific immune response involves a single administration of the vaccine. In some embodiments, methods further comprise administering a booster dose of the vaccine. In some embodiments, the vaccine is administered to the subject by intradermal or intramuscular injection.

Aspects of the invention relate to HCMV vaccines as described herein for use in a method of inducing an antigen specific immune response in a subject, the method comprising administering the vaccine to the subject in an effective amount to produce an antigen specific immune response.

Aspects of the invention relate to the use of an HCMV vaccine described herein in the manufacture of a medicament for use in a method of inducing an antigen specific immune response in a subject, the method comprising administering the vaccine to the subject in an effective amount to produce an antigen specific immune response.

Aspects of the invention relate to methods of preventing or treating HCMV infection comprising administering to a subject a vaccine described herein.

Aspects of the invention relate to HCMV vaccines described herein formulated in an effective amount to produce an antigen specific immune response in a subject. In some embodiments, an anti-HCMV antigenic polypeptide antibody titer produced in the subject is increased by at least 1 log relative to a control, or by 1-3 log relative to a control. In some embodiments, an anti-HCMV antigenic polypeptide antibody titer produced in the subject is increased at least 2 times relative to a control, at least 5 times relative to a control, at least 10 times relative to a control, or 2-10 times relative to a control.

In some embodiments, the control is an anti-HCMV antigenic polypeptide antibody titer produced in a subject who has not been administered HCMV vaccine. In some embodiments, the control is an anti-HCMV antigenic polypeptide antibody titer produced in a subject who has been administered a live attenuated or inactivated HCMV vaccine. In some embodiments, the control is an anti-HCMV antigenic polypeptide antibody titer produced in a subject who has been administered a recombinant or purified HCMV protein vaccine. In some embodiments, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount is a total dose of 50-1000 μg. In some embodiments, the effective amount is a total dose of 100 μg. In some embodiments, the effective amount is a dose of 25 μg administered to the subject a total of two times. In some embodiments, the effective amount is a dose of 100 μg administered to the subject a total of two times. In some embodiments, the effective amount is a dose of 400 μg administered to the subject a total of two times. In some embodiments, the effective amount is a dose of 500 μg administered to the subject a total of two times.

In some embodiments of methods disclosed herein, an anti-HCMV antigenic polypeptide antibody is produced in the subject and wherein the titer of the anti-HCMV antigenic polypeptide antibody is increased by at least 1 log relative to a control. In some embodiments, the anti-HCMV antigenic polypeptide antibody titer produced in the subject is increased by 1-3 log relative to a control.

In some embodiments of methods disclosed herein, the anti-HCMV antigenic polypeptide antibody titer produced in the subject is increased at least 2 times relative to a control, at least 5 times relative to a control, at least 10 times relative to a control, or 2-10 times relative to a control.

In some embodiments of methods disclosed herein, the control is an anti-HCMV antigenic polypeptide antibody titer produced in a subject who has not been administered HCMV vaccine. In some embodiments of methods disclosed herein, the control is an anti-HCMV antigenic polypeptide antibody titer produced in a subject who has been administered a live attenuated or inactivated HCMV vaccine. In some embodiments of methods disclosed herein, the control is an anti-HCMV antigenic polypeptide antibody titer produced in a subject who has been administered a recombinant or purified HCMV protein vaccine.

In some embodiments of methods disclosed herein, the effective amount is a dose equivalent to an at least 2-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant HCMV protein vaccine or a live attenuated HCMV vaccine.

In some embodiments of methods disclosed herein, the effective amount is a dose equivalent to an at least 4-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to an at least 10-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to an at least 100-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to an at least 1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a dose equivalent to a 2-1000-fold reduction in the standard of care dose of a recombinant HCMV protein vaccine, and wherein an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments of methods disclosed herein, the effective amount is a total dose of 50-1000 μg. In some embodiments of methods disclosed herein, the effective amount is a total dose of 100 μg. In some embodiments of methods disclosed herein, the effective amount is a dose of 25 μg administered to the subject a total of two times. In some embodiments of methods disclosed herein, the effective amount is a dose of 100 μg administered to the subject a total of two times. In some embodiments of methods disclosed herein, the effective amount is a dose of 400 μg administered to the subject a total of two times. In some embodiments of methods disclosed herein, the effective amount is a dose of 500 μg administered to the subject a total of two times.

Aspects of the invention relate to an HCMV vaccine, comprising: i) HCMV antigenic polypeptides gH, gL, UL128, UL130, and/or UL131A, or antigenic fragments or epitopes thereof; and ii) HCMV antigenic polypeptide gB, or an antigenic fragment or epitope thereof; wherein one or more of the HCMV antigenic polypeptides comprises a signal sequence linked to the HCMV antigenic polypeptide.

In some embodiments, the signal peptide is an IgE signal peptide. In some embodiments, the signal peptide is an IgE HC (Ig heavy chain epsilon-1) signal peptide. In some embodiments, the signal peptide has the amino acid sequence MDWTWILFLVAAATRVHS (SEQ ID NO: 53). In some embodiments, the signal peptide is an IgGκ signal peptide. In some embodiments, the signal peptide has the amino acid sequence METPAQLLFLLLLWLPDTTG (SEQ ID NO: 54).

In some embodiments, the subject is a woman of child-bearing age.

Aspects of the invention relate to methods of preventing congenital HCMV infection comprising administering to a woman of child-bearing age a therapeutically effective amount of a human cytomegalovirus (HCMV) vaccine comprising: i) at least one RNA polynucleotide having one or more open reading frames encoding HCMV antigenic polypeptides gH, gL, UL128, UL130, and/or UL131A, or antigenic fragments or epitopes thereof; ii) an RNA polynucleotide having an open reading frame encoding HCMV antigenic polypeptide gB, or an antigenic fragment or epitope thereof; and iv) a pharmaceutically acceptable carrier or excipient.

In some embodiments of methods disclosed herein, the vaccine comprises: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; and an RNA polynucleotide having an open reading frame encoding UL131, or an antigenic fragment or epitope thereof.

In some embodiments the nucleic acid vaccines described herein are chemically modified. In other embodiments the nucleic acid vaccines are unmodified.

Yet other aspects provide compositions for and methods of vaccinating a subject comprising administering to the subject a nucleic acid vaccine comprising one or more RNA polynucleotides having an open reading frame encoding a first antigenic polypeptide, wherein the RNA polynucleotide does not include a stabilization element, and wherein an adjuvant is not coformulated or co-administered with the vaccine.

In other aspects the invention is a composition for or method of vaccinating a subject comprising administering to the subject a nucleic acid vaccine comprising one or more RNA polynucleotides having an open reading frame encoding a first antigenic polypeptide wherein a dosage of between 10 μg/kg and 400 μg/kg of the nucleic acid vaccine is administered to the subject. In some embodiments the dosage of the RNA polynucleotide is 1-5 μg, 5-10 μg, 10-15 μg, 15-20 μg, 10-25 μg, 20-25 μg, 20-50 μg, 30-50 μg, 40-50 μg, 40-60 μg, 60-80 μg, 60-100 μg, 50-100 μg, 80-120 μg, 40-120 μg, 40-150 μg, 50-150 μg, 50-200 μg, 80-200 μg, 100-200 μg, 120-250 μg, 150-250 μg, 180-280 μg, 200-300 μg, 50-300 μg, 80-300 μg, 100-300 μg, 40-300 μg, 50-350 μg, 100-350 μg, 200-350 μg, 300-350 μg, 320-400 μg, 40-380 μg, 40-100 μg, 100-400 μg, 200-400 μg, or 300-400 μg per dose. In some embodiments, the nucleic acid vaccine is administered to the subject by intradermal or intramuscular injection. In some embodiments, the nucleic acid vaccine is administered to the subject on day zero. In some embodiments, a second dose of the nucleic acid vaccine is administered to the subject on day twenty one.

In some embodiments, a dosage of 25 micrograms of the RNA polynucleotide is included in the nucleic acid vaccine administered to the subject. In some embodiments, a dosage of 100 micrograms of the RNA polynucleotide is included in the nucleic acid vaccine administered to the subject. In some embodiments, a dosage of 50 micrograms of the RNA polynucleotide is included in the nucleic acid vaccine administered to the subject. In some embodiments, a dosage of 75 micrograms of the RNA polynucleotide is included in the nucleic acid vaccine administered to the subject. In some embodiments, a dosage of 150 micrograms of the RNA polynucleotide is included in the nucleic acid vaccine administered to the subject. In some embodiments, a dosage of 400 micrograms of the RNA polynucleotide is included in the nucleic acid vaccine administered to the subject. In some embodiments, a dosage of 200 micrograms of the RNA polynucleotide is included in the nucleic acid vaccine administered to the subject. In some embodiments, the RNA polynucleotide accumulates at a 100 fold higher level in the local lymph node in comparison with the distal lymph node. In other embodiments the nucleic acid vaccine is chemically modified and in other embodiments the nucleic acid vaccine is not chemically modified.

Aspects of the invention provide a nucleic acid vaccine comprising one or more RNA polynucleotides having an open reading frame encoding a first antigenic polypeptide, wherein the RNA polynucleotide does not include a stabilization element, and a pharmaceutically acceptable carrier or excipient, wherein an adjuvant is not included in the vaccine. In some embodiments, the stabilization element is a histone stem-loop. In some embodiments, the stabilization element is a nucleic acid sequence having increased GC content relative to wild type sequence.

Aspects of the invention provide nucleic acid vaccines comprising one or more RNA polynucleotides having an open reading frame encoding a first antigenic polypeptide, wherein the RNA polynucleotide is present in the formulation for in vivo administration to a host, which confers an antibody titer superior to the criterion for seroprotection for the first antigen for an acceptable percentage of human subjects. In some embodiments, the antibody titer produced by the mRNA vaccines of the invention is a neutralizing antibody titer. In some embodiments the neutralizing antibody titer is greater than a protein vaccine. In other embodiments the neutralizing antibody titer produced by the mRNA vaccines of the invention is greater than an adjuvanted protein vaccine. In yet other embodiments the neutralizing antibody titer produced by the mRNA vaccines of the invention is 1,000-10,000, 1,200-10,000, 1,400-10,000, 1,500-10,000, 1,000-5,000, 1,000-4,000, 1,800-10,000, 2000-10,000, 2,000-5,000, 2,000-3,000, 2,000-4,000, 3,000-5,000, 3,000-4,000, or 2,000-2,500. A neutralization titer is typically expressed as the highest serum dilution required to achieve a 50% reduction in the number of plaques.

Also provided are nucleic acid vaccines comprising one or more RNA polynucleotides having an open reading frame encoding a first antigenic polypeptide, wherein the RNA polynucleotide is present in a formulation for in vivo administration to a host for eliciting a longer lasting high antibody titer than an antibody titer elicited by an mRNA vaccine having a stabilizing element or formulated with an adjuvant and encoding the first antigenic polypeptide. In some embodiments, the RNA polynucleotide is formulated to produce a neutralizing antibodies within one week of a single administration. In some embodiments, the adjuvant is selected from a cationic peptide and an immunostimulatory nucleic acid. In some embodiments, the cationic peptide is protamine.

Aspects provide nucleic acid vaccines comprising one or more RNA polynucleotides having an open reading frame comprising at least one chemical modification or optionally no nucleotide modification, the open reading frame encoding a first antigenic polypeptide, wherein the RNA polynucleotide is present in the formulation for in vivo administration to a host such that the level of antigen expression in the host significantly exceeds a level of antigen expression produced by an mRNA vaccine having a stabilizing element or formulated with an adjuvant and encoding the first antigenic polypeptide.

Other aspects provide nucleic acid vaccines comprising one or more RNA polynucleotides having an open reading frame comprising at least one chemical modification or optionally no nucleotide modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms. Aspects of the invention also provide a unit of use vaccine, comprising between 10 ug and 400 ug of one or more RNA polynucleotides having an open reading frame comprising at least one chemical modification or optionally no nucleotide modification, the open reading frame encoding a first antigenic polypeptide, and a pharmaceutically acceptable carrier or excipient, formulated for delivery to a human subject. In some embodiments, the vaccine further comprises a cationic lipid nanoparticle.

Aspects of the invention provide methods of creating, maintaining or restoring antigenic memory to a virus strain in an individual or population of individuals comprising administering to said individual or population an antigenic memory booster nucleic acid vaccine comprising (a) at least one RNA polynucleotide, said polynucleotide comprising at least one chemical modification or optionally no nucleotide modification and two or more codon-optimized open reading frames, said open reading frames encoding a set of reference antigenic polypeptides, and (b) optionally a pharmaceutically acceptable carrier or excipient. In some embodiments, the vaccine is administered to the individual via a route selected from the group consisting of intramuscular administration, intradermal administration and subcutaneous administration. In some embodiments, the administering step comprises contacting a muscle tissue of the subject with a device suitable for injection of the composition. In some embodiments, the administering step comprises contacting a muscle tissue of the subject with a device suitable for injection of the composition in combination with electroporation.

Aspects of the invention provide methods of vaccinating a subject comprising administering to the subject a single dosage of between 25 ug/kg and 400 ug/kg of a nucleic acid vaccine comprising one or more RNA polynucleotides having an open reading frame encoding a first antigenic polypeptide in an effective amount to vaccinate the subject. Other aspects provide nucleic acid vaccines comprising one or more RNA polynucleotides having an open reading frame comprising at least one chemical modification, the open reading frame encoding a first antigenic polypeptide, wherein the vaccine has at least 10 fold less RNA polynucleotide than is required for an unmodified mRNA vaccine to produce an equivalent antibody titer. In some embodiments, the RNA polynucleotide is present in a dosage of 25-100 micrograms.

Other aspects provide nucleic acid vaccines comprising an LNP formulated RNA polynucleotide having an open reading frame comprising no nucleotide modifications (unmodified), the open reading frame encoding a first antigenic polypeptide, wherein the vaccine has at least 10 fold less RNA polynucleotide than is required for an unmodified mRNA vaccine not formulated in a LNP to produce an equivalent antibody titer. In some embodiments, the RNA polynucleotide is present in a dosage of 25-100 micrograms.

The data presented in the Examples demonstrate significant enhanced immune responses using the formulations of the invention. Surprisingly, in contrast to prior art reports that it was preferable to use chemically unmodified mRNA formulated in a carrier for the production of vaccines, it is described herein that chemically modified mRNA-LNP vaccines require a much lower effective mRNA dose than unmodified mRNA, i.e., tenfold less than unmodified mRNA when formulated in carriers other than LNP. Both the chemically modified and unmodified RNA vaccines of the invention produce better immune responses than mRNA vaccines formulated in a different lipid carrier.

In other aspects the invention encompasses a method of treating an elderly subject age 60 years or older comprising administering to the subject a nucleic acid vaccine comprising one or more RNA polynucleotides having an open reading frame encoding an antigenic polypeptide in an effective amount to vaccinate the subject.
In other aspects the invention encompasses a method of treating a young subject age 17 years or younger comprising administering to the subject a nucleic acid vaccine comprising one or more RNA polynucleotides having an open reading frame encoding an antigenic polypeptide in an effective amount to vaccinate the subject.

In other aspects the invention encompasses a method of treating an adult subject comprising administering to the subject a nucleic acid vaccine comprising one or more RNA polynucleotides having an open reading frame encoding an antigenic polypeptide in an effective amount to vaccinate the subject.

In some aspects the invention is a method of vaccinating a subject with a combination vaccine including at least two nucleic acid sequences encoding antigens wherein the dosage for the vaccine is a combined therapeutic dosage wherein the dosage of each individual nucleic acid encoding an antigen is a sub therapeutic dosage. In some embodiments, the combined dosage is 25 micrograms of the RNA polynucleotide in the nucleic acid vaccine administered to the subject. In some embodiments, the combined dosage is 100 micrograms of the RNA polynucleotide in the nucleic acid vaccine administered to the subject. In some embodiments the combined dosage is 50 micrograms of the RNA polynucleotide in the nucleic acid vaccine administered to the subject. In some embodiments, the combined dosage is 75 micrograms of the RNA polynucleotide in the nucleic acid vaccine administered to the subject. In some embodiments, the combined dosage is 150 micrograms of the RNA polynucleotide in the nucleic acid vaccine administered to the subject. In some embodiments, the combined dosage is 400 micrograms of the RNA polynucleotide in the nucleic acid vaccine administered to the subject. In some embodiments, the sub therapeutic dosage of each individual nucleic acid encoding an antigen is 1, 2, 3, 4, 5, 6, 7, 8, 9, 10, 11, 12, 13, 14, 15, 16, 17, 18, 19, or 20 micrograms. In other embodiments the nucleic acid vaccine is chemically modified and in other embodiments the nucleic acid vaccine is not chemically modified.

In some embodiments, the RNA polynucleotide is one of SEQ ID NO: 1-6, 58, 60, 62, 64, 66. 68, and 108-113 and includes at least one chemical modification. In other embodiments the RNA polynucleotide is one of SEQ ID NO: 1-6, 58, 60, 62, 64, 66, 68, and 108-113 and does not include any nucleotide modifications, or is unmodified. In yet other embodiments the at least one RNA polynucleotide encodes an antigenic protein of any of SEQ ID NO: 7-12, 59, 61, 63, 65, 67, and 69 and includes at least one chemical modification. In other embodiments the RNA polynucleotide encodes an antigenic protein of any of SEQ ID NO: 7-12, 59, 61, 63, 65, 67, and 69 and does not include any nucleotide modifications, or is unmodified.

In preferred aspects, vaccines of the invention (e.g., LNP-encapsulated mRNA vaccines) produce prophylactically- and/or therapeutically—efficacious levels, concentrations and/or titers of antigen-specific antibodies in the blood or serum of a vaccinated subject. As defined herein, the term antibody titer refers to the amount of antigen-specific antibody produces in s subject, e.g., a human subject. In exemplary embodiments, antibody titer is expressed as the inverse of the greatest dilution (in a serial dilution) that still gives a positive result. In exemplary embodiments, antibody titer is determined or measured by enzyme-linked immunosorbent assay (ELISA). In exemplary embodiments, antibody titer is determined or measured by neutralization assay, e.g., by microneutralization assay. In certain aspects, antibody titer measurement is expressed as a ratio, such as 1:40, 1:100, etc.

In exemplary embodiments of the invention, an efficacious vaccine produces an antibody titer of greater than 1:40, greater that 1:100, greater than 1:400, greater than 1:1000, greater than 1:2000, greater than 1:3000, greater than 1:4000, greater than 1:500, greater than 1:6000, greater than 1:7500, greater than 1:10000. In exemplary embodiments, the antibody titer is produced or reached by 10 days following vaccination, by 20 days following vaccination, by 30 days following vaccination, by 40 days following vaccination, or by 50 or more days following vaccination. In exemplary embodiments, the titer is produced or reached following a single dose of vaccine administered to the subject. In other embodiments, the titer is produced or reached following multiple doses, e.g., following a first and a second dose (e.g., a booster dose.) In exemplary aspects of the invention, antigen-specific antibodies are measured in units of μg/ml or are measured in units of IU/L (International Units per liter) or mIU/ml (milli International Units per ml). In exemplary embodiments of the invention, an efficacious vaccine produces >0.5 μg/ml, >0.1 μg/ml, >0.2 μg/ml, >0.35 μg/ml, >0.5 μg/ml, >1 μg/ml, >2 μg/ml, >5 μg/ml or >10 μg/ml. In exemplary embodiments of the invention, an efficacious vaccine produces >10 mIU/ml, >20 mIU/ml, >50 mIU/ml, >100 mIU/ml, >200 mIU/ml, >500 mIU/ml or >1000 mIU/ml. In exemplary embodiments, the antibody level or concentration is produced or reached by 10 days following vaccination, by 20 days following vaccination, by 30 days following vaccination, by 40 days following vaccination, or by 50 or more days following vaccination. In exemplary embodiments, the level or concentration is produced or reached following a single dose of vaccine administered to the subject. In other embodiments, the level or concentration is produced or reached following multiple doses, e.g., following a first and a second dose (e.g., a booster dose.) In exemplary embodiments, antibody level or concentration is determined or measured by enzyme-linked immunosorbent assay (ELISA). In exemplary embodiments, antibody level or concentration is determined or measured by neutralization assay, e.g., by microneutralization assay.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 1A shows the gH/gL/gB complex that mediates the entry of hCMV into fibroblasts. FIG. 1B shows the pentameric complex containing gH/gL/UL128/UL130/UL131A. Such a pentameric complex mediates the entry of hCMV into epithelial cells, endothelial cells, monocytes, and dendritic cells. FIG. 1C, which is adapted from Macagno et al. (2010) *J. Virology* 84(2):1005-13 shows the hCMV pentameric complex (gH/gL/UL128/UL130/UL131A) further in complex with antibodies specific for the protein components of the pentameric complex: 8121 (anti-pentamer), 3G16 (anti-gH), 15D8 (anti-UL128), 7113 (anti-UL128/UL130/UL131A), and 10P3 (anti-gL).

FIG. 2A shows the surface expression of gH. FIG. 2B shows the surface expression of UL128/UL130/UL131A. FIG. 2C shows the surface expression of UL128. FIG. 2D shows the surface expression of the pentamer.

FIGS. 10A and 10C shows the results of a fluorescence-activated cell (FACS) sorting experiment detecting the surface expression of the pentameric complex using the 8121 (anti-pentamer) antibodies. Surface expression of the pentameric complex is indicated by the emerging fluorescent cell population. FIGS. 10B and 10D shows the quantification of the FACS experiment.

FIG. 18A depicts a graph showing anti-pentamer antibody titers. Equimolar and equal mass formulations of the pentameric mRNAs were compared and were found to be equally effective. FIG. 18B depicts a graph showing neutralizing titers measured on ARPE19 epithelial cells infected with hCMV strain VR1814. Equimolar and equal mass formulations of the pentameric mRNAs were compared and were found to be equally effective. Neutralizing titers were found to be approximately 25 fold higher than CytoGam®.

FIG. 19A shows that the depleting protein was either the pentamer or a gH/gL dimer. FIG. 19B and FIG. 19C depict graphs showing neutralization. FIG. 19B shows neutralization by sera from mice immunized with the pentamer or with a gH/gL dimer. FIG. 19C shows neutralization by CytoGam® combined with the pentamer or with a gH/gL.

FIGS. 25A-25H show hCMV concatemeric sequences for the hCMV vaccine.

DETAILED DESCRIPTION

Figure 1A:
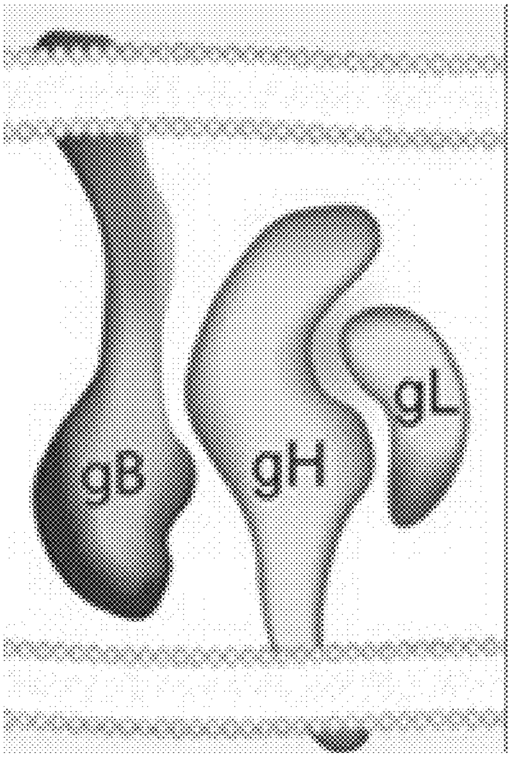
FIGS. 1A-1C depict different protein complexes formed by hCMV proteins. The tropism of hCMV is dictated by distinct protein complexes.

Embodiments of the present disclosure provide RNA (e.g., mRNA) vaccines that include polynucleotide encoding a human cytomegalovirus (HCMV) antigen. The human cytomegalovirus (HCMV) is a ubiquitous double-stranded DNA virus belonging to the Herpes virus family. HCMV is made up of a DNA core, an outer capsid and covered by a lipid membrane (envelope) which incorporates virus specific glycoproteins. The diameter is around 150-200 nm. Genomes are linear and non-segmented, around 200 kb in length. Viral replication is nuclear, and is lysogenic. Replication is dsDNA bidirectional replication.

HCMV can infect a wide range of mammalian cells, which correlates with its ability to infect most organs and tissues. Entry into the host cell is achieved by attachment of the viral glycoproteins to host cell receptors, which mediates endocytosis. HCMV displays a broad host cell range, with the ability to infect several cell types, such as endothelial cells, epithelial cells, smooth muscle cells, fibroblasts, leukocytes, and dendritic cells. This broad cellular tropism suggests that HCMV may bind a number of receptors or a common surface molecule.

HCMV envelopment is very complicated and comprises more than 20 glycoproteins which may be the reason for broad cellular tropism of HCMV. HCMV particles contain at least four major glycoprotein complexes, all of which are involved in HCMV infection, which requires initial interaction with the cell surface through binding to heparin sulfate proteoglycans and possibly other surface receptors.

The gCI complex is comprised of dimeric molecules of the glycoprotein gB. Each 160-kDa monomer is cleaved to generate a 116-kDa surface unit linked by disulfide bonds to a 55-kDa transmembrane component. Some antibodies immunospecific for gB inhibit the attachment of virions to cells, whereas others block the fusion of infected cells, suggesting that the gB protein might execute multiple functions at the start of infection. Studies have confirmed that glycoprotein B (gB) facilitates HCMV entry into cells by binding receptors and mediating membrane fusion. Several cellular membrane proteins interact with gB, which interactions likely facilitate entry and activate cellular signaling pathways.

The gCII complex is the most abundant of the glycoprotein complexes and is a heterodimer consisting of glycoproteins gM and gN. The complex binds to heparan sulfate proteoglycans, suggesting it might contribute to the initial interaction of the virion with the cell surface. It may also perform a structural role during virion assembly/envelopment, similar to the gM-gN complex found in some α-herpesviruses.

The gCIII complex is a trimer comprised of glycoproteins gH, gL, gO which are covalently linked by disulfide bonds. All known herpesviruses encode gH-gL heterodimers, which mediate fusion of the virion envelope with the cell membrane. Antibodies specific for human CMV gH do not affect virus attachment but block penetration and cell-to-cell transmission. A gO-deficient mutant of HCMV (strain AD169) shows a significant growth defect.

HCMV proteins UL128, UL130, and UL131A assemble with gH and gL proteins to form a heterologous pentameric complex, designated gH/gL/UL128-131A, found on the surface of the HCMV. Natural variants and deletion and mutational analyses have implicated proteins of the gH/gL/UL128-131A complex with the ability to infect certain cell types, including for example, endothelial cells, epithelial cells, and leukocytes.

HCMV enters cells by fusing its envelope with either the plasma membrane (fibroblasts) or the endosomal membrane (epithelial and endothelial cells). HCMV initiates cell entry by attaching to the cell surface heparan sulfate proteoglycans using envelope glycoprotein M (gM) or gB. This step is followed by interaction with cell surface receptors that trigger entry or initiate intracellular signaling. The entry receptor function is provided by gH/gL glycoprotein complexes. Different gH/gL complexes are known to facilitate entry into epithelial cells, endothelial cells, or fibroblasts.

For example, while entry into fibroblasts requires gH/gL heterodimer, entry into epithelial and endothelial cells requires the pentameric complex gH/gL/UL128/UL130/UL131 in addition to gH/gL. Thus, different gH/gL complexes engage distinct entry receptors on epithelial/endothelial cells and fibroblasts. Receptor engagement is followed by membrane fusion, a process mediated by gB and gH/gL. Early antibody studies have supported critical roles for both gB and gH/gL in HCMV entry. gB is essential for entry and cell spread. gB and gH/gL are necessary and sufficient for cell fusion and thus constitute the "core fusion machinery" of HCMV, which is conserved among other herpesviruses.

Thus, the four glycoprotein complexes play a crucial role in viral attachment, binding, fusion and entry into the host cell.

Studies involving the gH/gL/UL128-131A complex have shown that HCMV glycoproteins gB, gH, gL, gM, and gN, as well as UL128, UL130, and UL131A proteins, are antigenic and involved in the immunostimulatory response in a variety of cell types. Moreover, UL128, UL130, and UL131A genes are relatively conserved among HCMV isolates and therefore represent an attractive target for vaccination. Furthermore, recent studies have shown that antibodies to epitopes within the pentameric gH/gL/UL128-131 complex neutralize entry into endothelial, epithelial, and other cell types, thus blocking the ability of HCMV to infect several cell types.

HCMV envelope glycoprotein complexes (gCI, II, III, gH/gL/UL128-131A) represent major antigenic targets of antiviral immune responses. Embodiments of the present disclosure provide RNA (e.g., mRNA) vaccines that include polynucleotide encoding a HCMV antigen, in particular an HCMV antigen from one of the HCMV glycoprotein complexes. Embodiments of the present disclosure provide RNA (e.g., mRNA) vaccines that include at least one polynucleotide encoding at least one HCMV antigenic polypeptide. The HCMV RNA vaccines provided herein may be used to induce a balanced immune response, comprising both cellular and humoral immunity, without many of the risks associated with DNA vaccines and live attenuated vaccines.

The entire contents of International Application No. PCT/US2015/027400 (WO 2015/164674), entitled "Nucleic Acid Vaccines," is incorporated herein by reference. It has been discovered that the mRNA vaccines described herein are superior to current vaccines in several ways. First, the lipid nanoparticle (LNP) delivery is superior to other formulations including a protamine base approach described in the literature and no additional adjuvants are to be necessary. The use of LNPs enables the effective delivery of chemically modified or unmodified mRNA vaccines. Additionally it has been demonstrated herein that both modified and unmodified LNP formulated mRNA vaccines were superior to conventional vaccines by a significant degree. In some embodiments the mRNA vaccines of the invention are superior to conventional vaccines by a factor of at least 10 fold, 20 fold, 40 fold, 50 fold, 100 fold, 500 fold or 1,000 fold.

Although attempts have been made to produce functional RNA vaccines, including mRNA vaccines and self-replicating RNA vaccines, the therapeutic efficacy of these RNA vaccines have not yet been fully established. Quite surprisingly, the inventors have discovered, according to aspects of the invention a class of formulations for delivering mRNA vaccines in vivo that results in significantly enhanced, and in many respects synergistic, immune responses including enhanced antigen generation and functional antibody production with neutralization capability. These results can be achieved even when significantly lower doses of the mRNA are administered in comparison with mRNA doses used in other classes of lipid based formulations. The formulations of the invention have demonstrated significant unexpected in vivo immune responses sufficient to establish the efficacy of functional mRNA vaccines as prophylactic and therapeutic agents. Additionally, self-replicating RNA vaccines rely on viral replication pathways to deliver enough RNA to a cell to produce an immunogenic response. The formulations of the invention do not require viral replication to produce enough protein to result in a strong immune response. Thus, the mRNA of the invention are not self-replicating RNA and do not include components necessary for viral replication.

The invention involves, in some aspects, the surprising finding that lipid nanoparticle (LNP) formulations significantly enhance the effectiveness of mRNA vaccines, including chemically modified and unmodified mRNA vaccines. The efficacy of mRNA vaccines formulated in LNP was examined in vivo using several distinct antigens. The results presented herein demonstrate the unexpected superior efficacy of the mRNA vaccines formulated in LNP over other commercially available vaccines.

In addition to providing an enhanced immune response, the formulations of the invention generate a more rapid immune response with fewer doses of antigen than other vaccines tested. The mRNA-LNP formulations of the invention also produce quantitatively and qualitatively better immune responses than vaccines formulated in a different carriers. The data described herein demonstrate that the formulations of the invention produced significant unexpected improvements over existing antigen vaccines. Additionally, the mRNA-LNP formulations of the invention are superior to other vaccines even when the dose of mRNA is lower than other vaccines.

The LNP used in the studies described herein has been used previously to deliver siRNA in various animal models as well as in humans. In view of the observations made in association with the siRNA delivery of LNP formulations, the fact that LNP is useful in vaccines is quite surprising. It has been observed that therapeutic delivery of siRNA formulated in LNP causes an undesirable inflammatory response associated with a transient IgM response, typically leading to a reduction in antigen production and a compromised immune response. In contrast to the findings observed with siRNA, the LNP-mRNA formulations of the invention are demonstrated herein to generate enhanced IgG levels, sufficient for prophylactic and therapeutic methods rather than transient IgM responses.

Nucleic Acids/Polynucleotides

Human cytomegalovirus (HCMV) vaccines, as provided herein, comprise at least one (one or more) ribonucleic acid (RNA) polynucleotide having an open reading frame encoding at least one HCMV antigenic polypeptide. The term "nucleic acid," in its broadest sense, includes any compound and/or substance that comprises a polymer of nucleotides. These polymers are referred to as polynucleotides.

In some embodiments, at least one RNA polynucleotide of a HCMV vaccine is encoded by at least one nucleic acid sequence selected from any of SEQ ID NOs: 1-31, 58, 60, 62, 64, 66 and 68. In some embodiments, at least one RNA polynucleotide of a HCMV vaccine is encoded by at least one fragment of a nucleic acid sequence selected from any of SEQ ID NOs: 1-31, 58, 60, 62, 64, 66 and 68.

In some embodiments, an RNA vaccine comprises an RNA polynucleotide having an open reading frame encoded by SEQ ID NO:58, or an antigenic fragment or epitope thereof; an RNA polynucleotide having an open reading frame encoded by SEQ ID NO:60, or an antigenic fragment or epitope thereof; an RNA polynucleotide having an open reading frame encoded by SEQ ID NO:62, or an antigenic fragment or epitope thereof; an RNA polynucleotide having an open reading frame encoded by SEQ ID NO:64, or an antigenic fragment or epitope thereof; an RNA polynucleotide having an open reading frame encoded by SEQ ID NO:66, or an antigenic fragment or epitope thereof, and an RNA polynucleotide having an open reading frame encoded by SEQ ID NO:68, or an antigenic fragment or epitope thereof.

Nucleic acids (also referred to as polynucleotides) may be or may include, for example, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, polynucleotides of the present disclosure function as messenger RNA (mRNA). "Messenger RNA" (mRNA) refers to any polynucleotide that encodes a (at least one) polypeptide (a naturally-occurring, non-naturally-occurring, or modified polymer of amino acids) and can be translated to produce the encoded polypeptide in vitro, in vivo, in situ or ex vivo. In some preferred embodiments, an mRNA is translated in vivo. The skilled artisan will appreciate that, except where otherwise noted, polynucleotide sequences set forth in the instant application will recite "T"s in a representative DNA sequence but where the sequence represents RNA (e.g., mRNA), the "T"s would be substituted for "U"s. Thus, any of the RNA polynucleotides encoded by a DNA identified by a particular sequence identification number may also comprise the corresponding RNA (e.g., mRNA) sequence encoded by the DNA, where each "T" of the DNA sequence is substituted with "U."

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild-type mRNA in their functional and/or structural design features which serve to overcome existing problems of effective polypeptide expression using nucleic-acid based therapeutics.

Some embodiments of the present disclosure provide HCMV vaccines that include at least one ribonucleic acid (RNA) polynucleotide having an open reading frame encoding at least one HCMV antigenic polypeptide or an immunogenic fragment or epitope thereof. Some embodiments of the present disclosure provide HCMV vaccines that include at least one RNA polynucleotide having an open reading frame encoding two or more HCMV antigenic polypeptides or an immunogenic fragment or epitope thereof. Some embodiments of the present disclosure provide HCMV vaccines that include two or more RNA polynucleotides having an open reading frame encoding two or more HCMV antigenic polypeptides or immunogenic fragments or epitopes thereof. The one or more HCMV antigenic polypeptides may be encoded on a single RNA polynucleotide or may be encoded individually on multiple (e.g., two or more) RNA polynucleotides.

Some embodiments of the present disclosure provide HCMV vaccines that include at least one ribonucleic acid (RNA) polynucleotide having a single open reading frame encoding two or more (for example, two, three, four, five, or more) HCMV antigenic polypeptides or an immunogenic fragment or epitope thereof. Some embodiments of the present disclosure provide HCMV vaccines that include at least one ribonucleic acid (RNA) polynucleotide having more than one open reading frame, for example, two, three, four, five or more open reading frames encoding two, three, four, five or more HCMV antigenic polypeptides. In either of these embodiments, the at least one RNA polynucleotide may encode two or more HCMV antigenic polypeptides selected from gH, gB, gL, gO, gM, gN, UL83, UL123, UL128, UL130, UL131A, and fragments or epitopes thereof. In some embodiments, the at least one RNA polynucleotide encodes UL83 and UL123. In some embodiments, the at least one RNA polynucleotide encodes gH and gL. In some embodiments, the at least one RNA polynucleotide encodes UL128, UL130, and UL131A. In some embodiments, the at least one RNA polynucleotide encodes gH, gL, UL128, UL130, and UL131A.

In some embodiments, a vaccine comprises an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; an RNA polynucleotide having an open reading frame encoding HCMV antigenic polypeptide UL131A, or an antigenic fragment or epitope thereof; and an RNA polynucleotide having an open reading frame encoding HCMV antigenic polypeptide gB, or an antigenic fragment or epitope thereof.

In some embodiments, in which the at least one RNA polynucleotide has a single open reading frame encoding two or more (for example, two, three, four, five, or more) HCMV antigenic polypeptides, the RNA polynucleotide may further comprise additional sequence, for example, a linker sequence or a sequence that aids in the processing of the HCMV RNA transcripts or polypeptides, for example a cleavage site sequence. In some embodiments, the additional sequence may be a protease sequence, such as a furin sequence. Furin, also referred to as PACE (paired basic amino acid cleaving enzyme), is a calcium-dependent serine endoprotease that cleaves precursor proteins into biologically active products at paired basic amino acid processing sites. Some of its substrates include the following: proparathyroid hormone, transforming growth factor beta 1 precursor, proalbumin, pro-beta-secretase, membrane type-1 matrix metalloproteinase, beta subunit of pro-nerve growth factor, and von Willebrand factor. The envelope proteins of certain viruses must be cleaved by furin in order to become fully functional, while some viruses require furin processing during their entry into host cells. T cells require furin to maintain peripheral immune tolerance. In some embodiments, the additional sequence may be self-cleaving 2A peptide, such as a P2A, E2A, F2A, and T2A sequence. In some embodiments, the linker sequences and cleavage site sequences are interspersed between the sequences encoding HCMV polypeptides. 2A peptides are "self-cleaving" small peptides, approximately 18-22 amino acids in length. Ribosomes skip the synthesis of a glycyl-prolyl peptide bond at the C-terminus of a 2A peptide, resulting in the cleavage of the 2A peptide and its immediate downstream peptide. They are frequently used in biomedical research to allow for the simultaneous expression of more than one gene in cells using a single plasmid. There are a number of 2A peptides, including the following: foot-and-mouth disease virus (FMDV) 2A (F2A), equine rhinitis A virus (ERAV) 2A (E2A), porcine teschovirus-1 2A (P2A), and Thoseaasigna virus 2A (T2A). T2A has the highest cleavage efficiency (close to 100%), followed by E2A, P2A, and F2A. Amino acid sequences are the following: P2A:(GSG) ATNFSLLKQAGDVEENPGP (SEQ ID NO:70); T2A: (GSG)EGRGSLLTCGDVEENPGP (SEQ ID NO:71); E2A: (GSG)QCTNYALLKLAGDVESNPGP (SEQ ID NO:72); F2A: (GSG)VKQTLNFDLLKLAGDVESNPGP (SEQ ID NO:73). In some embodiments, the linker sequences and cleavage site sequences are interspersed between the sequences encoding HCMV polypeptides. In some embodiments, the RNA polynucleotide is encoded by SEQ ID NO: 27, SEQ ID NO: 28, SEQ ID NO: 29, SEQ ID NO: 30 or SEQ ID NO: 31.

In some embodiments, a RNA polynucleotide of a HCMV vaccine encodes 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antigenic polypeptides. In some embodiments, a RNA polynucleotide of a HCMV vaccine encodes at least 10, 20, 30, 40, 50, 60, 70, 80, 90 or 100 antigenic polypeptides. In some embodiments, a RNA polynucleotide of a HCMV vaccine encodes at least 100 or at least 200 antigenic polypeptides. In some embodiments, a RNA polynucleotide of a HCMV vaccine encodes 1-10, 5-15, 10-20, 15-25, 20-30, 25-35, 30-40, 35-45, 40-50, 1-50, 1-100, 2-50 or 2-100 antigenic polypeptides.

Polynucleotides of the present disclosure, in some embodiments, are codon optimized. Codon optimization methods are known in the art and may be used as provided herein. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g. glycosylation sites); add, remove or shuffle protein domains; insert or delete restriction sites; modify ribosome binding sites and mRNA degradation sites; adjust translational rates to allow the various domains of the protein to fold properly; or to reduce or eliminate problem secondary structures within the polynucleotide. Codon optimization tools, algorithms and services are known in the art—non-limiting examples include services from GeneArt (Life Technologies), DNA2.0 (Menlo Park Calif.) and/or proprietary methods. In some embodiments, the open reading frame (ORF) sequence is optimized using optimization algorithms.

In some embodiments, a codon optimized sequence shares less than 95% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 90% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 85% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 80% sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares less than 75% sequence identity to a naturally-occurring or wild-type sequence (e.g., a naturally-occurring or wild-type mRNA sequence encoding a polypeptide or protein of interest (e.g., an antigenic protein or polypeptide.

In some embodiments, a codon optimized sequence shares between 65% and 85% (e.g., between about 67% and about 85% or between about 67% and about 80%) sequence identity to a naturally-occurring or wild-type sequence (e.g., a naturally-occurring or wild-type mRNA sequence encoding a polypeptide or protein of interest (e.g., an antigenic protein or polypeptide. In some embodiments, a codon optimized sequence shares between 65% and 75 or about 80% sequence identity to a naturally-occurring or wild-type sequence (e.g., a naturally-occurring or wild-type mRNA sequence encoding a polypeptide or protein of interest (e.g., an antigenic protein or polypeptide.

The skilled artisan will appreciate that, except where otherwise noted, polynucleotide sequences set forth in the instant application will recite "T"s in a representative DNA sequence but where the sequence represents RNA, the "T"s would be substituted for "U"s.

Antigens/Antigenic Polypeptides

In some embodiments, an antigenic polypeptide is an HCMV glycoprotein. For example, a HCMV glycoprotein may be HCMV gB, gH, gL, gO, gN, or gM or an immunogenic fragment or epitope thereof. In some embodiments, the antigenic polypeptide is a HCMV gH polypeptide. In some embodiments, the antigenic polypeptide is a HCMV gL polypeptide. In some embodiments, the antigenic polypeptide is a HCMV gB polypeptide. In some embodiments, the antigenic polypeptide is a HCMV gO polypeptide. In some embodiments, the antigenic polypeptide is a HCMV gN polypeptide. In some embodiments, the antigenic polypeptide is a HCMV gM polypeptide. In some embodiments, the antigenic polypeptide is a HCMV gC polypeptide. In some embodiments, the antigenic polypeptide is a HCMV gN polypeptide. In some embodiments, the antigenic polypeptide is a HCMV gM polypeptide.

In some embodiments, an antigenic polypeptide is a HCMV protein selected from UL83, UL123, UL128, UL130, and UL131A or an immunogenic fragment or epitope thereof. In some embodiments, the antigenic polypeptide is a HCMV UL83 polypeptide. In some embodiments, the antigenic polypeptide is a HCMV UL123 polypeptide. In some embodiments, the antigenic polypeptide is a HCMV UL128 polypeptide. In some embodiments, the antigenic polypeptide is a HCMV UL130 polypeptide. In some embodiments, the antigenic polypeptide is a HCMV UL131A polypeptide.

In some embodiments, the antigenic HCMV polypeptide comprises two or more HCMV polypeptides. The two or more HCMV polypeptides can be encoded by a single RNA polynucleotide or can be encoded by two or more RNA polynucleotides, for example, each glycoprotein encoded by a separate RNA polynucleotide. In some embodiments, the two or more HCMV polypeptides can be any combination of HCMV gH, gL, gB, gO, gN, gM, UL83, UL123, UL128, UL130, and UL131A polypeptides or immunogenic fragments or epitopes thereof. In some embodiments, the two or more HCMV polypeptides can be any combination of HCMV gH and a polypeptide selected from gL, gB, gO, gN, gM, UL83, UL123, UL128, UL130, and UL131A polypeptides or immunogenic fragments or epitopes thereof. In some embodiments, the two or more HCMV polypeptides can be any combination of HCMV gB and a polypeptide selected from gH, gL, gO, gN, gM, UL83, UL123, UL128, UL130, and UL131A polypeptides or immunogenic fragments or epitopes thereof. In some embodiments, the two or more HCMV polypeptides can be any combination of HCMV gL and a polypeptide selected from gH, gB, gO, gN, gM, UL83, UL123, UL128, UL130, and UL131A polypeptides or immunogenic fragments or epitopes thereof. In some embodiments, the two or more HCMV polypeptides can be any combination of HCMV gH, gL and a polypeptide selected from gB, gO, gN, gM, UL83, UL123, UL128, UL130, and UL131A polypeptides or immunogenic fragments or epitopes thereof. In some embodiments, the two or more HCMV polypeptides can be any combination of HCMV gH, gL, and a glycoprotein selected from gB, gH, gK, gL, gC, gN, and gM polypeptides or immunogenic fragments or epitopes thereof. In some embodiments, the two or more HCMV polypeptides can be any combination of HCMV gH, gL, and a polypeptide selected from UL83, UL123, UL128, UL130, and UL131A polypeptides or immunogenic fragments or epitopes thereof. In some embodiments, the two or more HCMV polypeptides are UL128, UL130, and UL131A. In some embodiments, the two or more HCMV polypeptides are gH and gL. In some embodiments, the two or more HCMV polypeptides are gH, gL, UL128, UL130, and UL131A. In some embodiments, the two or more HCMV polypeptides are gB, gH, gL, UL128, UL130, and UL131A.

The present disclosure includes variant HCMV antigenic polypeptides. In some embodiments, the variant HCMV antigenic polypeptide is a variant HCMV gH polypeptide. In some embodiments, the variant HCMV antigenic polypeptide is a variant HCMV gL polypeptide. In some embodiments, the variant HCMV antigenic polypeptide is a variant HCMV gB polypeptide. The variant HCMV polypeptides are designed to expedite passage of the antigenic polypeptide through the ER/golgi, leading to increased surface expression of the antigen. In some embodiments, the variant HCMV polypeptides are truncated to delete one or more of the following domains: hydrophobic membrane proximal domain, transmembrane domain, and cytoplasmic domain. In some embodiments, the variant HCMV polypeptides are truncated to include only the ectodomain sequence. For example, the variant HCMV polypeptide can be a truncated HCMV gH polypeptide, truncated HCMV gB polypeptide, or truncated HCMV gL polypeptide comprising at least amino acids 1-124, including, for example, amino acids 1-124, 1-140, 1-160, 1-200, 1-250, 1-300, 1-350, 1-360, 1-400, 1-450, 1-500, 1-511, 1-550, and 1-561, as well as polypeptide fragments having fragment sizes within the recited size ranges.

In some embodiments, a HCMV antigenic polypeptide is longer than 25 amino acids and shorter than 50 amino acids. Thus, polypeptides include gene products, naturally occurring polypeptides, synthetic polypeptides, homologs, orthologs, paralogs, fragments and other equivalents, variants, and analogs of the foregoing. A polypeptide may be a single molecule or may be a multi-molecular complex such as a dimer, trimer or tetramer. Polypeptides may also comprise single chain or multichain polypeptides such as antibodies or insulin and may be associated or linked. Most commonly, disulfide linkages are found in multichain polypeptides. The term polypeptide may also apply to amino acid polymers in which at least one amino acid residue is an artificial chemical analogue of a corresponding naturally-occurring amino acid.

The term "polypeptide variant" refers to molecules which differ in their amino acid sequence from a native or reference sequence. The amino acid sequence variants may possess substitutions, deletions, and/or insertions at certain positions within the amino acid sequence, as compared to a native or reference sequence. Ordinarily, variants possess at least 50% identity to a native or reference sequence. In some embodiments, variants share at least 80%, or at least 90% identity with a native or reference sequence.

In some embodiments "variant mimics" are provided. As used herein, the term "variant mimic" is one which contains at least one amino acid that would mimic an activated sequence. For example, glutamate may serve as a mimic for phosphoro-threonine and/or phosphoro-serine. Alternatively, variant mimics may result in deactivation or in an inactivated product containing the mimic, for example, phenylalanine may act as an inactivating substitution for tyrosine; or alanine may act as an inactivating substitution for serine.

"Orthologs" refers to genes in different species that evolved from a common ancestral gene by speciation. Normally, orthologs retain the same function in the course of evolution. Identification of orthologs is critical for reliable prediction of gene function in newly sequenced genomes.

"Analogs" is meant to include polypeptide variants which differ by one or more amino acid alterations, for example, substitutions, additions or deletions of amino acid residues that still maintain one or more of the properties of the parent or starting polypeptide.

The present disclosure provides several types of compositions that are polynucleotide or polypeptide based, including variants and derivatives. These include, for example, substitutional, insertional, deletion and covalent variants and derivatives. The term "derivative" is used synonymously with the term "variant" but generally refers to a molecule that has been modified and/or changed in any way relative to a reference molecule or starting molecule.

As such, polynucleotides encoding peptides or polypeptides containing substitutions, insertions and/or additions, deletions and covalent modifications with respect to reference sequences, in particular the polypeptide sequences disclosed herein, are included within the scope of this disclosure. For example, sequence tags or amino acids, such as one or more lysines, can be added to peptide sequences (e.g., at the N-terminal or C-terminal ends). Sequence tags can be used for peptide detection, purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. Substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Features" when referring to polypeptide or polynucleotide are defined as distinct amino acid sequence-based or nucleotide-based components of a molecule respectively. Features of the polypeptides encoded by the polynucleotides include surface manifestations, local conformational shape, folds, loops, half-loops, domains, half-domains, sites, termini or any combination thereof.

As used herein when referring to polypeptides the term "domain" refers to a motif of a polypeptide having one or more identifiable structural or functional characteristics or properties (e.g., binding capacity, serving as a site for protein-protein interactions). As used herein when referring to polypeptides the terms "site" as it pertains to amino acid based embodiments is used synonymously with "amino acid residue" and "amino acid side chain." As used herein when referring to polynucleotides the terms "site" as it pertains to nucleotide based embodiments is used synonymously with "nucleotide." A site represents a position within a peptide or polypeptide or polynucleotide that may be modified, manipulated, altered, derivatized or varied within the polypeptide or polynucleotide based molecules.

As used herein the terms "termini" or "terminus" when referring to polypeptides or polynucleotides refers to an extremity of a polypeptide or polynucleotide respectively. Such extremity is not limited only to the first or final site of the polypeptide or polynucleotide but may include additional amino acids or nucleotides in the terminal regions. Polypeptide-based molecules may be characterized as having both an N-terminus (terminated by an amino acid with a free amino group (NH2)) and a C-terminus (terminated by an amino acid with a free carboxyl group (COOH)). Proteins are in some cases made up of multiple polypeptide chains brought together by disulfide bonds or by non-covalent forces (multimers, oligomers). These proteins have multiple N- and C-termini. Alternatively, the termini of the polypeptides may be modified such that they begin or end, as the case may be, with a non-polypeptide based moiety such as an organic conjugate.

As recognized by those skilled in the art, protein fragments, functional protein domains, and homologous proteins are also considered to be within the scope of polypeptides of interest. For example, provided herein is any protein fragment (meaning a polypeptide sequence at least one amino acid residue shorter than a reference polypeptide sequence but otherwise identical) of a reference protein 10, 20, 30, 40, 50, 60, 70, 80, 90, 100 or greater than 100 amino acids in length. In another example, any protein that includes a stretch of 20, 30, 40, 50, or 100 amino acids which are 40%, 50%, 60%, 70%, 80%, 90%, 95%, or 100% identical to any of the sequences described herein can be utilized in accordance with the disclosure. In some embodiments, a polypeptide includes 2, 3, 4, 5, 6, 7, 8, 9, 10, or more mutations as shown in any of the sequences provided or referenced herein.

Polypeptide or polynucleotide molecules of the present disclosure may share a certain degree of sequence similarity or identity with the reference molecules (e.g., reference polypeptides or reference polynucleotides), for example, with art-described molecules (e.g., engineered or designed molecules or wild-type molecules). The term "identity" as known in the art, refers to a relationship between the sequences of two or more polypeptides or polynucleotides, as determined by comparing the sequences. In the art, identity also means the degree of sequence relatedness between them as determined by the number of matches between strings of two or more amino acid residues or nucleic acid residues. Identity measures the percent of identical matches between the smaller of two or more sequences with gap alignments (if any) addressed by a particular mathematical model or computer program (e.g., "algorithms"). Identity of related peptides can be readily calculated by known methods. "% identity" as it applies to polypeptide or polynucleotide sequences is defined as the percentage of residues (amino acid residues or nucleic acid residues) in the candidate amino acid or nucleic acid sequence that are identical with the residues in the amino acid sequence or nucleic acid sequence of a second sequence after aligning the sequences and introducing gaps, if necessary, to achieve the maximum percent identity. Methods and computer programs for the alignment are well known in the art. It is understood that identity depends on a calculation of percent identity but may differ in value due to gaps and penalties introduced in the calculation. Generally, variants of a particular polynucleotide or polypeptide have at least 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that particular reference polynucleotide or polypeptide as determined by sequence alignment programs and parameters described herein and known to those skilled in the art. Such tools for alignment include those of the BLAST suite (Stephen F. Altschul, et al (1997), "Gapped BLAST and PSI-BLAST: a new generation of protein database search programs", Nucleic Acids Res. 25:3389-3402). Another popular local alignment technique is based on the Smith-Waterman algorithm (Smith, T. F. & Waterman, M. S. (1981) "Identification of common molecular subsequences." J. Mol. Biol. 147:195-197.) A general global alignment technique based on dynamic programming is the Needleman-Wunsch algorithm (Needleman, S. B. & Wunsch, C. D. (1970) "A general method applicable to the search for similarities in the amino acid sequences of two proteins." J. Mol. Biol. 48:443-453.). More recently a Fast Optimal Global Sequence Alignment Algorithm (FOGSAA) has been developed that purportedly produces global alignment of nucleotide and protein sequences faster than other optimal global alignment methods, including the Needleman-Wunsch algorithm. Other tools are described herein, specifically in the definition of "identity" below.

As used herein, the term "homology" refers to the overall relatedness between polymeric molecules, e.g. between nucleic acid molecules (e.g. DNA molecules and/or RNA molecules) and/or between polypeptide molecules. Polymeric molecules (e.g. nucleic acid molecules (e.g. DNA molecules and/or RNA molecules) and/or polypeptide molecules) that share a threshold level of similarity or identity determined by alignment of matching residues are termed homologous. Homology is a qualitative term that describes a relationship between molecules and can be based upon the quantitative similarity or identity. Similarity or identity is a quantitative term that defines the degree of sequence match between two compared sequences. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). Two polynucleotide sequences are considered homologous if the polypeptides they encode are at least 50%, 60%, 70%, 80%, 90%, 95%, or even 99% for at least one stretch of at least 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. Two protein sequences are considered homologous if the proteins are at least 50%, 60%, 70%, 80%, or 90% identical for at least one stretch of at least 20 amino acids.

Homology implies that the compared sequences diverged in evolution from a common origin. The term "homolog" refers to a first amino acid sequence or nucleic acid sequence (e.g., gene (DNA or RNA) or protein sequence) that is related to a second amino acid sequence or nucleic acid sequence by descent from a common ancestral sequence. The term "homolog" may apply to the relationship between genes and/or proteins separated by the event of speciation or to the relationship between genes and/or proteins separated by the event of genetic duplication. "Orthologs" are genes (or proteins) in different species that evolved from a common ancestral gene (or protein) by speciation. Typically, orthologs retain the same function in the course of evolution. "Paralogs" are genes (or proteins) related by duplication within a genome. Orthologs retain the same function in the course of evolution, whereas paralogs evolve new functions, even if these are related to the original one.

The term "identity" refers to the overall relatedness between polymeric molecules, for example, between polynucleotide molecules (e.g. DNA molecules and/or RNA molecules) and/or between polypeptide molecules. Calculation of the percent identity of two polynucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleic acid sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, Part I, Griffin, A. M., and Griffin, H. G., eds., Humana Press, New Jersey, 1994; and Sequence Analysis Primer, Gribskov, M. and Devereux, J., eds., M Stockton Press, New York, 1991; each of which is incorporated herein by reference. For example, the percent identity between two nucleic acid sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleic acid sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Altschul, S. F. et al., *J. Molec. Biol.,* 215, 403 (1990)).

In some embodiments, the polypeptides further comprise additional sequences or functional domains. For example, the HCMV polypeptides of the present disclosure may comprise one or more linker sequences. In some embodiments, the HCMV of the present invention may comprise a polypeptide tag, such as an affinity tag (chitin binding protein (CBP), maltose binding protein (MBP), glutathione-S-transferase (GST), SBP-tag, Strep-tag, AviTag, Calmodulin-tag); solubilization tag; chromatography tag (polyanionic amino acid tag, such as FLAG-tag); epitope tag (short peptide sequences that bind to high-affinity antibodies, such as V5-tag, Myc-tag, VSV-tag, Xpress tag, E-tag, S-tag, and HA-tag); fluorescence tag (e.g., GFP). In some embodiments, the HCMV of the present invention may comprise an amino acid tag, such as one or more lysines, histidines, or glutamates, which can be added to the polypeptide sequences (e.g., at the N-terminal or C-terminal ends). Lysines can be used to increase peptide solubility or to allow for biotinylation. Protein and amino acid tags are peptide sequences genetically grafted onto a recombinant protein. Sequence tags are attached to proteins for various purposes, such as peptide purification, identification, or localization, for use in various applications including, for example, affinity purification, protein array, western blotting, immunofluorescence, and immunoprecipitation. Such tags are subsequently removable by chemical agents or by enzymatic means, such as by specific proteolysis or intein splicing.

Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

Multiprotein and Multicomponent Vaccines

The present disclosure encompasses HCMV vaccines, e.g., vaccines against human cytomegalovirus, comprising multiple RNA (e.g., mRNA) polynucleotides, each encoding a single antigenic polypeptide, as well as HCMV vaccines comprising a single RNA polynucleotide encoding more than one antigenic polypeptide (e.g., as a fusion polypeptide). Thus, it should be understood that a vaccine composition comprising a RNA polynucleotide having an open reading frame encoding a first HCMV antigenic polypeptide and a RNA polynucleotide having an open reading frame encoding a second HCMV antigenic polypeptide encompasses (a) vaccines that comprise a first RNA polynucleotide encoding a first HCMV antigenic polypeptide and a second RNA polynucleotide encoding a second HCMV antigenic polypeptide, and (b) vaccines that comprise a single RNA polynucleotide encoding a first and second HCMV antigenic polypeptide (e.g., as a fusion polypeptide). HCMV RNA vaccines of the present disclosure, in some embodiments, comprise 2-10 (e.g., 2, 3, 4, 5, 6, 7, 8, 9 or 10), or more, RNA polynucleotides having an open reading frame, each of which encodes a different HCMV antigenic polypeptide (or a single RNA polynucleotide encoding 2-10, or more, different HCMV antigenic polypeptides). In some embodiments, an HCMV RNA vaccine comprises a RNA polynucleotide having an open reading frame encoding an HCMV glycoprotein. In some embodiments, an HCMV RNA vaccine comprises a RNA polynucleotide having an open reading frame encoding an HCMV glycoprotein B (gB), a RNA polynucleotide having an open reading frame encoding an HCMV glycoprotein M (gM), a RNA polynucleotide having an open reading frame encoding an HCMV glyprotein N (gN), a RNA polynucleotide having an open reading frame encoding an HCMV glycoprotein H (gH), a RNA polynucleotide having an open reading frame encoding an HCMV glycoprotein L (gL), and a RNA polynucleotide having an open reading frame encoding an HCMV glycoprotein 0 (gO). In some embodiments, an HCMV RNA vaccine comprises a RNA polynucleotide having an open reading frame encoding an HCMV gB protein. In some embodiments, an HCMV RNA vaccine comprises a RNA polynucleotide having an open reading frame encoding an HCMV UL128 protein. In some embodiments, an HCMV RNA vaccine comprises a RNA polynucleotide having an open reading frame encoding an HCMV UL130 protein. In some embodiments, an HCMV RNA vaccine comprises a RNA polynucleotide having an open reading frame encoding an HCMV UL131 protein. In some embodiments, an HCMV RNA vaccine comprises a RNA polynucleotide having an open reading frame encoding an HCMV gM and gN proteins. In some embodiments, an HCMV RNA vaccine comprises a RNA polynucleotide having an open reading frame encoding an HCMV gH, gL, and gO proteins. In some embodiments, an HCMV RNA vaccine comprises a RNA polynucleotide having an open reading frame encoding an HCMV gH, gL, UL128, UL130, and UL131A proteins. In some embodiments, an HCMV RNA vaccine comprises RNA polynucleotides having one or more open reading frames encoding an HCMV UL83, UL128, UL123, UL130, or UL131A protein. In some embodiments, the HCMV RNA vaccine further comprises a RNA polynucleotide having an open reading frame encoding one or more (e.g., 2, 3, 4, 5, 6 or 7) HCMV proteins.

In some embodiments, an HCMV RNA vaccine comprises RNA polynucleotides having one or more open reading frames encoding HCMV gH, gL, UL128, UL130, and UL131A proteins, or fragments thereof, and an HCMV gB protein, or fragment thereof.

In some embodiments, an HCMV RNA vaccine comprises an RNA polynucleotide having an open reading frame encoding a gH protein or a fragment thereof, an RNA polynucleotide having an open reading frame encoding a gL protein or a fragment thereof, an RNA polynucleotide having an open reading frame encoding a UL128 protein or a fragment thereof, an RNA polynucleotide having an open reading frame encoding a UL130 protein or a fragment thereof, an RNA polynucleotide having an open reading frame encoding a UL131A protein or a fragment thereof, and an an RNA polynucleotide having an open reading frame encoding a gB protein, or a fragment thereof.

In some embodiments, a RNA polynucleotide encodes an HCMV antigenic polypeptide fused to a signal peptide (e.g., SEQ ID NO: 53 or 54). The signal peptide may be fused at the N-terminus or the C-terminus of the antigenic polypeptide.

Signal Peptides

In some embodiments, antigenic polypeptides encoded by HCMV nucleic acids comprise a signal peptide. Signal peptides, comprising the N-terminal 15-60 amino acids of proteins, are typically needed for the translocation across the membrane on the secretory pathway and thus universally control the entry of most proteins both in eukaryotes and prokaryotes to the secretory pathway. Signal peptides generally include three regions: an N-terminal region of differing length, which usually comprises positively charged amino acids, a hydrophobic region, and a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. The signal peptide is not responsible for the final destination of the mature protein, however. Secretory proteins devoid of further address tags in their sequence are by default secreted to the external environment. Signal peptides are cleaved from precursor proteins by an endoplasmic reticulum (ER)-resident signal peptidase or they remain uncleaved and function as a membrane anchor. During recent years, a more advanced view of signal peptides has evolved, showing that the functions and immunodorminance of certain signal peptides are much more versatile than previously anticipated.

HCMV vaccines of the present disclosure may comprise, for example, RNA polynucleotides encoding an artificial signal peptide, wherein the signal peptide coding sequence is operably linked to and is in frame with the coding sequence of the HCMV antigenic polypeptide. Thus, HCMV vaccines of the present disclosure, in some embodiments, produce an antigenic polypeptide comprising a HCMV antigenic polypeptide fused to a signal peptide. In some embodiments, a signal peptide is fused to the N-terminus of the HCMV antigenic polypeptide. In some embodiments, a signal peptide is fused to the C-terminus of the HCMV antigenic polypeptide.

In some embodiments, the signal peptide fused to the HCMV antigenic polypeptide is an artificial signal peptide. In some embodiments, an artificial signal peptide fused to the HCMV antigenic polypeptide encoded by the HCMV RNA vaccine is obtained from an immunoglobulin protein, e.g., an IgE signal peptide or an IgG signal peptide. In some embodiments, a signal peptide fused to the HCMV antigenic polypeptide encoded by an HCMV mRNA vaccine is an Ig heavy chain epsilon-1 signal peptide (IgE HC SP) having the sequence of: MDWTWILFLVAAATRVHS (SEQ ID NO: 53). In some embodiments, a signal peptide fused to a HCMV antigenic polypeptide encoded by the HCMV RNA vaccine is an $IgG_k$ chain V-III region HAH signal peptide ($IgG_k$ SP) having the sequence of METPAQLLFLLLLWLPDTTG (SEQ ID NO: 54). In some embodiments, a signal peptide fused to the HCMV antigenic polypeptide encoded by an HCMV RNA vaccine has an amino acid sequence set forth in SEQ ID NO: 53 or SEQ ID NO: 54. The examples disclosed herein are not meant to be limiting and any signal peptide that is known in the art to facilitate targeting of a protein to ER for processing and/or targeting of a protein to the cell membrane may be used in accordance with the present disclosure.

A signal peptide may have a length of 15-60 amino acids. For example, a signal peptide may have a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids. In some embodiments, a signal peptide may have a length of 20-60, 25-60, 30-60, 35-60, 40-60, 45-60, 50-60, 55-60, 15-55, 20-55, 25-55, 30-55, 35-55, 40-55, 45-55, 50-55, 15-50, 20-50, 25-50, 30-50, 35-50, 40-50, 45-50, 15-45, 20-45, 25-45, 30-45, 35-45, 40-45, 15-40, 20-40, 25-40, 30-40, 35-40, 15-35, 20-35, 25-35, 30-35, 15-30, 20-30, 25-30, 15-25, 20-25, or 15-20 amino acids.

Non-limiting examples of HCMV antigenic polypeptides fused to signal peptides, which are encoded by the HCMV RNA vaccine of the present disclosure, may be found in Table 2, SEQ ID NOs: 32-52.

A signal peptide is typically cleaved from the nascent polypeptide at the cleavage junction during ER processing. The mature HCMV antigenic polypeptide produce by HCMV RNA vaccine of the present disclosure typically does not comprise a signal peptide.

Chemical Modifications

HCMV RNA vaccines of the present disclosure comprise, in some embodiments, at least one ribonucleic acid (RNA) polynucleotide having an open reading frame encoding at least one HCMV antigenic polypeptide, or an immunogenic fragment thereof, that comprises at least one chemical modification.

The terms "chemical modification" and "chemically modified" refer to modification with respect to adenosine (A), guanosine (G), uridine (U), thymidine (T) or cytidine (C) ribonucleosides or deoxyribnucleosides in at least one of their position, pattern, percent or population. Generally, these terms do not refer to the ribonucleotide modifications in naturally occurring 5'-terminal mRNA cap moieties. With respect to a polypeptide, the term "modification" refers to a modification relative to the canonical set 20 amino acids. Polypeptides, as provided herein, are also considered "modified" of they contain amino acid substitutions, insertions or a combination of substitutions and insertions.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Modifications of polynucleotides include, without limitation, those described herein. Polynucleotides (e.g., RNA polynucleotides, such as mRNA polynucleotides) may comprise modifications that are naturally-occurring, non-naturally-occurring or the polynucleotide may comprise a combination of naturally-occurring and non-naturally-occurring modifications. Polynucleotides may include any useful modification, for example, of a sugar, a nucleobase, or an internucleoside linkage (e.g., to a linking phosphate, to a phosphodiester linkage or to the phosphodiester backbone).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphodiester linkages, in which case the polynucleotides would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleotide inosine and adenine, cytosine or uracil. Any combination of base/sugar or linker may be incorporated into polynucleotides of the present disclosure.

Modifications of polynucleotides (e.g., RNA polynucleotides, such as mRNA polynucleotides) that are useful in the vaccines of the present disclosure include, but are not limited to the following: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6,N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2',2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-a-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl) cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueuosine;

galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseduouridine; 1-methyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uridine; N1-ethyl-pseudo-uridine; uridine 5-oxyacetic acid; uridine 5-oxyacetic acid methyl ester; 3-(3-Amino-3-carboxypropyl)-Uridine TP; 5-(iso-Pentenylaminomethyl)-2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2 (thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 2 (thio)pseudouracil; 2' deoxy uridine; 2' fluorouridine; 2-(thio)uracil; 2,4-(dithio) psuedouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl)uracil; 4 (thio)pseudouracil; 4-(thio)pseudouracil; 4-(thio)uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio) uracil; 5 (propynyl)uracil; 5 (trifluoromethyl)uracil; 5-(2-aminopropyl)uracil; 5-(alkyl)-2-(thio)pseudouracil; 5-(alkyl)-2,4 (dithio)pseudouracil; 5-(alkyl)-4 (thio) pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±) 1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3,4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonyl-benzyl)pseudouridine TP; 1-(4-Methoxybenzyl)pseudouridine TP; 1-(4-Methoxy-benzyl)pseudo-UTP; 1-(4-Methoxy-phenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6-tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; I-Vinylpseudouridine TP; 2,2'-anhydro-uridine TP; 2'-bromo-deoxyuridine TP; 2'-F-5-Methyl-2'-deoxy-UTP; 2'-OMe-5-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2(2-ethoxy)-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}] propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine;

N6-substituted purines; N-alkylated derivative; Napthalenyl; Nitrobenzimidazolyl; Nitroimidazolyl; Nitroindazolyl; Nitropyrazolyl; Nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of pseudouridine (ψ), N1-methylpseudouridine ($m^1\psi$), N1-ethylpseudouridine, 2-thiouridine, 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine and 2'-O-methyl uridine. In some embodiments, polynucleotides (e.g., RNA polynucleotides, such as mRNA polynucleotides) include a combination of at least two (e.g., 2, 3, 4 or more) of the aforementioned modified nucleobases.

In some embodiments, modified nucleobases in polynucleotides (e.g., RNA polynucleotides, such as mRNA polynucleotides) are selected from the group consisting of 1-methyl-pseudouridine ($m^1\psi$), 5-methoxy-uridine ($mo^5U$), 5-methyl-cytidine ($m^5C$), pseudouridine (ψ), α-thio-guanosine and α-thio-adenosine. In some embodiments, polynucleotides includes a combination of at least two (e.g., 2, 3, 4 or more) of the aforementioned modified nucleobases.

In some embodiments, polynucleotides (e.g., RNA polynucleotides, such as mRNA polynucleotides) comprise pseudouridine (ψ) and 5-methyl-cytidine ($m^5C$). In some embodiments, polynucleotides (e.g., RNA polynucleotides, such as mRNA polynucleotides) comprise 1-methyl-pseudouridine ($m^1\psi$). In some embodiments, polynucleotides (e.g., RNA polynucleotides, such as mRNA polynucleotides) comprise 1-methyl-pseudouridine ($m^1\psi$) and 5-methyl-cytidine ($m^5C$). In some embodiments, polynucleotides (e.g., RNA polynucleotides, such as mRNA polynucleotides) comprise 2-thiouridine ($s^2U$). In some embodiments, polynucleotides (e.g., RNA polynucleotides, such as mRNA polynucleotides) comprise 2-thiouridine and 5-methyl-cytidine ($m^5C$). In some embodiments, polynucleotides (e.g., RNA polynucleotides, such as mRNA polynucleotides) comprise methoxy-uridine ($mo^5U$). In some embodiments, polynucleotides (e.g., RNA polynucleotides, such as mRNA polynucleotides) comprise 5-methoxy-uridine ($mo^5U$) and 5-methyl-cytidine ($m^5C$). In some embodiments, polynucleotides (e.g., RNA polynucleotides, such as mRNA polynucleotides) comprise 2'-O-methyl uridine. In some embodiments polynucleotides (e.g., RNA polynucleotides, such as mRNA polynucleotides) comprise 2'-O-methyl uridine and 5-methyl-cytidine ($m^5C$). In some embodiments, polynucleotides (e.g., RNA polynucleotides, such as mRNA polynucleotides) comprise N6-methyl-adenosine ($m^6A$). In some embodiments, polynucleotides (e.g., RNA polynucleotides, such as mRNA polynucleotides) comprise N6-methyl-adenosine ($m^6A$) and 5-methyl-cytidine ($m^5C$).

In some embodiments, polynucleotides (e.g., RNA polynucleotides, such as mRNA polynucleotides) are uniformly modified (e.g., fully modified, modified throughout the entire sequence) for a particular modification. For example, a polynucleotide can be uniformly modified with 5-methyl-cytidine ($m^5C$), meaning that all cytosine residues in the mRNA sequence are replaced with 5-methyl-cytidine ($m^5C$). Similarly, a polynucleotide can be uniformly modified for any type of nucleoside residue present in the sequence by replacement with a modified residue such as those set forth above. Exemplary nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), and 2-thio-5-methyl-cytidine.

In some embodiments, a modified nucleobase is a modified uridine. Exemplary nucleobases and In some embodiments, a modified nucleobase is a modified cytosine. nucleosides having a modified uridine include 5-cyano uridine, and 4'-thio uridine.

In some embodiments, a modified nucleobase is a modified adenine. Exemplary nucleobases and nucleosides having a modified adenine include 7-deaza-adenine, 1-methyl-adenosine (ml A), 2-methyl-adenine (m2A), and N6-methyl-adenosine (m6A).

In some embodiments, a modified nucleobase is a modified guanine. Exemplary nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

The polynucleotides of the present disclosure may be partially or fully modified along the entire length of the molecule. For example, one or more or all or a given type of nucleotide (e.g., purine or pyrimidine, or any one or more or all of A, G, U, C) may be uniformly modified in a polynucleotide of the invention, or in a given predetermined sequence region thereof (e.g., in the mRNA including or excluding the polyA tail). In some embodiments, all nucleotides X in a polynucleotide of the present disclosure (or in a given sequence region thereof) are modified nucleotides, wherein X may any one of nucleotides A, G, U, C, or any one of the combinations A+G, A+U, A+C, G+U, G+C, U+C, A+G+U, A+G+C, G+U+C or A+G+C.

The polynucleotide may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The polynucleotides may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the polynucleotides may contain a modified pyrimidine such as a modified uracil or cytosine. In some embodiments, at least 5%, at least 10%, at least 25%, at least 50%, at least 80%, at least 90% or 100% of the uracil in the polynucleotide is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the polynucleotide is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

In some embodiments a codon optimized RNA may, for instance, be one in which the levels of G/C are enhanced. The G/C-content of nucleic acid molecules may influence the stability of the RNA. RNA having an increased amount of guanine (G) and/or cytosine (C) residues may be functionally more stable than nucleic acids containing a large amount of adenine (A) and thymine (T) or uracil (U) nucleotides. WO02/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid. The approach is limited to coding regions of the RNA.

Thus, in some embodiments, the RNA (e.g., mRNA) vaccines comprise a 5'UTR element, an optionally codon optimized open reading frame, and a 3'UTR element, a poly(A) sequence and/or a polyadenylation signal wherein the RNA is not chemically modified. In some embodiments, the modified nucleobase is a modified uracil. Exemplary nucleobases and nucleosides having a modified uracil include pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-amino-allyl-uridine, 5-halo-uridine (e.g., 5-iodo-uridineor 5-bromo-uridine), 3-methyl-uridine (m3U), 5-methoxy-uridine (mo5U), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (Tm5U), 1-taurinomethyl-pseudouridine, 5-taurinomethyl-2-thio-uridine(τm5s2U), 1-taurinomethyl-4-thio-pseudouridine, 5-methyl-uridine (m5U, i.e., having the nucleobase deoxythymine), 1-methyl-pseudouridine (m1ψ), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, N1-ethyl-pseudouridine 3-(3-amino-3-carboxypropyl)uridine (acp3U), 1-methyl-3-(3-amino-3-carboxypropyl)pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), and 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)] uridine.

In some embodiments, the modified nucleobase is a modified cytosine. Exemplary nucleobases and nucleosides having a modified cytosine include 5-aza-cytidine, 6-aza-cytidine, pseudoisocytidine, 3-methyl-cytidine (m3C), N4-acetyl-cytidine (ac4C), 5-formyl-cytidine (f5C), N4-methyl-cytidine (m4C), 5-methyl-cytidine (m5C), 5-halo-cytidine (e.g., 5-iodo-cytidine), 5-hydroxymethyl-cytidine (hm5C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k2C), α-thio-cytidine, 2'-O-methyl-cytidine (Cm), 5,2'-O-dimethyl-cytidine (m5Cm), N4-acetyl-2'-O-methyl-cytidine (ac4Cm), N4,2'-O-dimethyl-cytidine (m4Cm), 5-formyl-2'-O-methyl-cytidine (f5Cm), N4,N4,2'-O-trimethyl-cytidine (m42Cm), 1-thio-cytidine, 2'-F-ara-cytidine, 2'-F-cytidine, and 2'-OH-ara-cytidine.

In some embodiments, the modified nucleobase is a modified adenine. Exemplary nucleobases and nucleosides having a modified adenine include 2-amino-purine, 2, 6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenine, 7-deaza-8-aza-adenine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m1A), 2-methyl-adenine (m2A), N6-methyl-adenosine (m6A), 2-methylthio-N6-methyl-adenosine (ms2m6A), N6-isopentenyl-adenosine (i6A), 2-methylthio-N6-isopentenyl-adenosine (ms2i6A), N6-(cis-hydroxyisopentenyl)adenosine (io6A), 2-methylthio-N6-(cis-hydroxyisopentenyl) adenosine (ms2io6A), N6-glycinylcarbamoyl-adenosine (g6A), N6-threonylcarbamoyl-adenosine (t6A), N6-methyl-N6-threonylcarbamoyl-adenosine (m6t6A), 2-methylthio-N6-threonylcarbamoyl-adenosine (ms2g6A), N6,N6-dimethyl-adenosine (m62A), N6-hydroxynorvalylcarbamoyl-adenosine (hn6A), 2-methylthio-N6-hydroxynorvalylcarbamoyl-adenosine (ms2hn6A), N6-acetyl-adenosine (ac6A), 7-methyl-adenine, 2-methylthio-adenine, 2-methoxy-adenine, α-thio-adenosine, 2'-O-methyl-adenosine (Am), N6,2'-O-dimethyl-adenosine (m6Am), N6,N6,2'-O-trimethyl-adenosine (m62Am), 1,2'-O-dimethyl-adenosine (m1Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

In some embodiments, the modified nucleobase is a modified guanine. Exemplary nucleobases and nucleosides having a modified guanine include inosine (I), 1-methyl-inosine (m1I), wyosine (imG), methylwyosine (mimG), 4-demethyl-wyosine (imG-14), isowyosine (imG2), wybutosine (yW), peroxywybutosine (o2yW), hydroxywybutosine (OhyW), undermodified hydroxywybutosine (OhyW*), 7-deaza-guanosine, queuosine (Q), epoxyqueuosine (oQ), galactosyl-queuosine (galQ), mannosyl-queuosine (manQ), 7-cyano-7-deaza-guanosine (preQ0), 7-aminomethyl-7-deaza-guanosine (preQ1), archaeosine (G+), 7-deaza-8-aza-guanosine, 6-thio-guanosine, 6-thio-7-deaza-guanosine, 6-thio-7-deaza-8-aza-guanosine, 7-methyl-guanosine (m7G), 6-thio-7-methyl-guanosine, 7-methyl-inosine, 6-methoxy-guanosine, 1-methyl-guanosine (m1G), N2-methyl-guanosine (m2G), N2,N2-dimethyl-guanosine (m22G), N2,7-dimethyl-guanosine (m2,7G), N2, N2,7-dimethyl-guanosine (m2,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m2Gm), N2,N2-dimethyl-2'-O-methyl-guanosine (m22Gm), 1-methyl-2'-O-methyl-guanosine (m1Gm), N2,7-dimethyl-2'-O-methyl-guanosine (m2,7Gm), 2'-O-methyl-inosine (Im), 1,2'-O-dimethyl-inosine (m1Im), 2'-O-ribosylguanosine (phosphate) (Gr(p)), 1-thio-guanosine, 06-methyl-guanosine, 2'-F-ara-guanosine, and 2'-F-guanosine.

In Vitro Transcription of RNA (e.g., mRNA)

HCMV vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

A "5' untranslated region" (UTR) refers to a region of an mRNA that is directly upstream (i.e., 5') from the start codon (i.e., the first codon of an mRNA transcript translated by a ribosome) that does not encode a polypeptide.

A "3' untranslated region" (UTR) refers to a region of an mRNA that is directly downstream (i.e., 3') from the stop codon (i.e., the codon of an mRNA transcript that signals a termination of translation) that does not encode a polypeptide.

An "open reading frame" is a continuous stretch of DNA beginning with a start codon (e.g., methionine (ATG)), and ending with a stop codon (e.g., TAA, TAG or TGA) and encodes a polypeptide.

A "polyA tail" is a region of mRNA that is downstream, e.g., directly downstream (i.e., 3'), from the 3' UTR that contains multiple, consecutive adenosine monophosphates. A polyA tail may contain 10 to 300 adenosine monophosphates. For example, a polyA tail may contain 10, 20, 30, 40, 50, 60, 70, 80, 90, 100, 110, 120, 130, 140, 150, 160, 170, 180, 190, 200, 210, 220, 230, 240, 250, 260, 270, 280, 290 or 300 adenosine monophosphates. In some embodiments, a polyA tail contains 50 to 250 adenosine monophosphates. In a relevant biological setting (e.g., in cells, in vivo) the poly(A) tail functions to protect mRNA from enzymatic degradation, e.g., in the cytoplasm, and aids in transcription termination, export of the mRNA from the nucleus and translation.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

Methods of Treatment

Provided herein are compositions (e.g., pharmaceutical compositions), methods, kits and reagents for prevention and/or treatment of HCMV in humans and other mammals. HCMV RNA vaccines can be used as therapeutic or prophylactic agents. They may be used in medicine to prevent and/or treat infectious disease. In exemplary aspects, the HCMV RNA vaccines of the invention are used to provide prophylactic protection from human cytomegalovirus infection and may be particularly useful for prevention and/or treatment of immunocompromised and infant patients to prevent or to reduce the severity and/or duration of the clinical manifestation of the cytomegalovirus infection. In some embodiments, vaccines described herein reduce or prevent congenital transmission of HCMV from mother to child.

Broad Spectrum Vaccines

HCMV RNA (e.g., mRNA) vaccines can be used as therapeutic or prophylactic agents. It is envisioned that there may be situations where persons are at risk for infection with more than one betacoronovirus, for example, at risk for infection with HCMV. RNA (e.g., mRNA) therapeutic vaccines are particularly amenable to combination vaccination approaches due to a number of factors including, but not limited to, speed of manufacture, ability to rapidly tailor vaccines to accommodate perceived geographical threat, and the like. Moreover, because the vaccines utilize the human body to produce the antigenic protein, the vaccines are amenable to the production of larger, more complex antigenic proteins, allowing for proper folding, surface expression, antigen presentation, etc. in the human subject. To protect against more than one HCMV strain, a combination vaccine can be administered that includes RNA encoding at least one antigenic polypeptide of a first HCMV and further includes RNA encoding at least one antigenic polypeptide of a second HCMV. RNAs (mRNAs) can be co-formulated, for example, in a single LNP or can be formulated in separate LNPs destined for co-administration.

A method of eliciting an immune response in a subject against a HCMV is provided in aspects of the invention. The method involves administering to the subject a HCMV RNA vaccine comprising at least one RNA polynucleotide having an open reading frame encoding at least one HCMV antigenic polypeptide or an immunogenic fragment thereof, thereby inducing in the subject an immune response specific to HCMV antigenic polypeptide or an immunogenic fragment thereof, wherein anti-antigenic polypeptide antibody titer in the subject is increased following vaccination relative to anti-antigenic polypeptide antibody titer in a subject vaccinated with a prophylactically effective dose of a traditional vaccine against the HCMV. An "anti-antigenic polypeptide antibody" is a serum antibody the binds specifically to the antigenic polypeptide.

A prophylactically effective dose is a therapeutically effective dose that prevents infection with the virus at a clinically acceptable level. In some embodiments the therapeutically effective dose is a dose listed in a package insert for the vaccine. A traditional vaccine, as used herein, refers to a vaccine other than the mRNA vaccines of the invention. For instance, a traditional vaccine includes but is not limited to live microorganism vaccines, killed microorganism vaccines, subunit vaccines, protein antigen vaccines, DNA vaccines, etc. In exemplary embodiments, a traditional vaccine is a vaccine that has achieved regulatory approval and/or is registered by a national drug regulatory body, for example the Food and Drug Administration (FDA) in the United States or the European Medicines Agency (EMA).

In some embodiments the anti-antigenic polypeptide antibody titer in the subject is increased 1 log to 10 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 1 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 2 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 3 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 5 log following vaccination relative to anti-antigenic polypeptide antibody titer in a subject vaccinated with a prophylactically effective dose of a traditional vaccine against the HCMV.

In some embodiments the anti-antigenic polypeptide antibody titer in the subject is increased 10 log following vaccination relative to anti-antigenic polypeptide antibody titer in a subject vaccinated with a prophylactically effective dose of a traditional vaccine against the HCMV.

A method of eliciting an immune response in a subject against a HCMV is provided in other aspects of the invention. The method involves administering to the subject a HCMV RNA vaccine comprising at least one RNA polynucleotide having an open reading frame encoding at least one HCMV antigenic polypeptide or an immunogenic fragment thereof, thereby inducing in the subject an immune response specific to HCMV antigenic polypeptide or an immunogenic fragment thereof, wherein the immune response in the subject is equivalent to an immune response in a subject vaccinated with a traditional vaccine against the HCMV at 2 times to 100 times the dosage level relative to the RNA vaccine.

In some embodiments the immune response in the subject is equivalent to an immune response in a subject vaccinated with a traditional vaccine at twice the dosage level relative to the HCMV RNA vaccine.

In some embodiments the immune response in the subject is equivalent to an immune response in a subject vaccinated with a traditional vaccine at three times the dosage level relative to the HCMV RNA vaccine.

In some embodiments the immune response in the subject is equivalent to an immune response in a subject vaccinated with a traditional vaccine at 4 times the dosage level relative to the HCMV RNA vaccine.

In some embodiments the immune response in the subject is equivalent to an immune response in a subject vaccinated with a traditional vaccine at 5 times the dosage level relative to the HCMV RNA vaccine.

In some embodiments the immune response in the subject is equivalent to an immune response in a subject vaccinated with a traditional vaccine at 10 times the dosage level relative to the HCMV RNA vaccine.

In some embodiments the immune response in the subject is equivalent to an immune response in a subject vaccinated with a traditional vaccine at 50 times the dosage level relative to the HCMV RNA vaccine.

In some embodiments the immune response in the subject is equivalent to an immune response in a subject vaccinated with a traditional vaccine at 100 times the dosage level relative to the HCMV RNA vaccine.

In some embodiments the immune response in the subject is equivalent to an immune response in a subject vaccinated with a traditional vaccine at 10 times to 1000 times the dosage level relative to the HCMV RNA vaccine.

In some embodiments the immune response in the subject is equivalent to an immune response in a subject vaccinated with a traditional vaccine at 100 times to 1000 times the dosage level relative to the HCMV RNA vaccine.

In other embodiments the immune response is assessed by determining anti-antigenic polypeptide antibody titer in the subject.

In other aspects the invention is a method of eliciting an immune response in a subject against a HCMV by administering to the subject a HCMV RNA vaccine comprising at least one RNA polynucleotide having an open reading frame encoding at least one HCMV antigenic polypeptide or an immunogenic fragment thereof, thereby inducing in the subject an immune response specific to HCMV antigenic polypeptide or an immunogenic fragment thereof, wherein the immune response in the subject is induced 2 days to 10 weeks earlier relative to an immune response induced in a subject vaccinated with a prophylactically effective dose of a traditional vaccine against the HCMV. In some embodiments the immune response in the subject is induced in a subject vaccinated with a prophylactically effective dose of a traditional vaccine at 2 times to 100 times the dosage level relative to the RNA vaccine.

In some embodiments the immune response in the subject is induced 2 days earlier relative to an immune response induced in a subject vaccinated with a prophylactically effective dose of a traditional vaccine.

In some embodiments the immune response in the subject is induced 3 days earlier relative to an immune response induced in a subject vaccinated a prophylactically effective dose of a traditional vaccine.

In some embodiments the immune response in the subject is induced 1 week earlier relative to an immune response induced in a subject vaccinated with a prophylactically effective dose of a traditional vaccine.

In some embodiments the immune response in the subject is induced 2 weeks earlier relative to an immune response induced in a subject vaccinated with a prophylactically effective dose of a traditional vaccine.

In some embodiments the immune response in the subject is induced 3 weeks earlier relative to an immune response induced in a subject vaccinated with a prophylactically effective dose of a traditional vaccine.

In some embodiments the immune response in the subject is induced 5 weeks earlier relative to an immune response induced in a subject vaccinated with a prophylactically effective dose of a traditional vaccine.

In some embodiments the immune response in the subject is induced 10 weeks earlier relative to an immune response induced in a subject vaccinated with a prophylactically effective dose of a traditional vaccine.

A method of eliciting an immune response in a subject against a HCMV by administering to the subject a HCMV RNA vaccine having an open reading frame encoding a first antigenic polypeptide, wherein the RNA polynucleotide does not include a stabilization element, and wherein an adjuvant is not coformulated or co-administered with the vaccine is also provided herein.

Standard of Care for CMV Prevention and Treatment

A variety of approaches to preventing and/or treating CMV, including immunization strategies, have previously been pursued or are currently being pursued, some of which are summarized below. However, all of these approaches have drawbacks and limitations. (Schleiss et al. (2008), *Curr Top Microbiol Immunol.* 325:361-382).

Ganciclovir and Valganciclovir

In some embodiments, Ganciclovir or Valganciclovir is the standard of care therapy for treatment or prevention of CMV infections (Reusser P. et al. (2000); 130(4):101-12; Biron et al. (2006) *Antiviral Research* 71:154-163).

Ganciclovir (marketed as CYTOVENE® and ZIRGAN®) and Valganciclovir (a prodrug form of Ganciclovir marketed as VALCYTE®) are antiviral medications developed by Hoffmann-La Roche to treat CMV infection. They are analogues of 2'-deoxy-guanosine, which competitively inhibits dGTP incorporation into DNA and, in turn, viral replication (Sugawara M et al., *J Pharm Sci.* 2000; 89(6): 781-9). CYTOVENE-IV (ganciclovir sodium for injection) is FDA approved "for use only in the treatment of cytomegalovirus (CMV) retinitis in immunocompromised patients and for the prevention of CMV disease in transplant patients at risk for CMV disease." (FDA Label, 1/31/2006, page 1.)

The recommended dose regimen for CYTOVENE-IV for treatment of CMV retinitis for patients with normal renal function includes an induction phase of 5 mg/kg (administered intravenously over an hour) every 12 hours for 14-21 days, followed by a maintenance phase of 5 mg/kg (administered intravenously over an hour) once daily seven days a week or 6 mg/kg once daily five days a week. (Id., page 22.) For prevention of CMV in transplant patients with normal renal function, the recommended dose regimen includes 5 mg/kg (administered intravenously over an hour) every 12 hours for 7-14 days; then 5 mg/kg once daily seven days a week or 6 mg/kg once daily five days a week. (Id.)

In a study involving heart transplant patients, at 120 days post-transplant, the incidence of CMV in seropositive subjects was 9% in subjects receiving treatment compared to 46% in subjects receiving a placebo. (Biron et al. (2006) *Antiviral Research* 71:154-163, page 157.) In a study involving bone marrow transplant subjects, at 100 days post-transplant the incidence of CMV in treated subjects was 3% compared to 43% in subjects treated with a placebo. (Id.) One form of Ganciclovir that is marketed by Bausch and Lomb, ZIRGAN®, is in the form of an ophthalmic gel, which is FDA approved for treatment of acute herpetic keratitis (dendritic ulcers.) (FDA label, 9/15/2009, page 4; Wilhelmus K R et al., 2010, *Cochrane Database Syst Rev* 12: CD002898).

VALCYTE@ (valganciclovir hydrochloride) in tablet form is FDA approved in adult patients for treatment of CMV retinitis in patients with acquired immunodeficiency syndrome (AIDS) and prevention of CMV disease in kidney, heart, and kidney-pancreas transplant patients at high risk. (FDA label, 4/23/2015, page 1.) The dose regimen for VALCYTE® is shown in the following table, as depicted on the FDA label dated 4/23/2015:

TABLE 1

Dose regimen for VALCYTE ®
DOSAGE AND ADMINISTRATION

| | |
|---|---|
| **Adult Dosage (2.2)** | |
| Treatment of CMV retinitis | Induction: 900 mg (two 450 mg tablets) twice a day for 21 days<br>Maintenance: 900 mg (two 450 mg tablets) once a day |
| Prevention of CMV disease in heart or kidney-pancreas transplant patients | 900 mg (two 450 mg tablets) once a day within 10 days of transplantation until 100 days post-transplantation |
| Prevention of CMV disease in kidney transplant patients | 900 mg (two 450 mg tablets) once a day within 10 days of tansplantation until 200 days post-transplantation |
| **Pediatric Dosage (2.3)** | |
| Prevention of CMV disease in kidney transplant patients 4 months to 16 years of age | Dose once a day within 10 days of transplantation until 200 days post-transplantation according to dosage algorithm (note the calculation of creatinine clearance using a modified Schwartz formula in children) |
| Prevention of CMV disease in heart transplant patients 1 month to 16 years of age | Dose once a day within 10 days of transplantation until 100 days post-transplantation according to dosage algorithm (note the calculation of creatinine clearance using a modified Schwartz formula in children) |

An oral form of Ganciclovir was found to have low bioavailability. (Biron et al. (2006) *Antiviral Research* 71:154-163.) Valganciclovir was reported to have better bioavailability than Ganciclovir. (Pescovitz M D et al., *Antimicrob Agents Chemother.* 2000; 44(10):2811-5; Biron et al. (2006) *Antiviral Research* 71:154-163.)

Adverse side effects associated with Ganciclovir and Valganciclovir include: fever, rash, diarrhea, and hematologic effects (such as neutropenia, anemia, and thrombocytopenia), as well as potential reproductive toxicity. Ganciclovir was also found to affect fertility and to be carcinogenic and teratogenic in animal studies. (Biron et al. (2006) *Antiviral Research* 71:154-163.)

Phase 3 clinical trials involving treatment of CMV infection with Ganciclovir or Valganciclovir include trials associated with ClinicalTrials government database identifier numbers: NCT00000143, NCT00000136, NCT00000134, NCT00497796, NCT00227370, NCT00466817, and NCT00294515. Results of clinical trials involving Ganciclovir or Valganciclovir are summarized in Biron et al. (2006) *Antiviral Research* 71:154-163, incorporated by reference herein in its entirety.

Experimental Vaccines in Development for CMV

TransVax™ (also known as ASP0113 and VCL-CB01)

TransVax™ is a CMV vaccine being developed by Vical Incorporated and Astellas Pharma Inc. (Smith et al. (2013) Vaccines 1(4):398-414.) TransVax™ is a bivalent DNA vaccine containing plasmids encoding CMV pp65 and gB antigens formulated in CRL1005 poloxamer and benzalkonium. (Id.; Kharfan-Dabaja et al. (2012) *Lancet Infect Dis* 12:290-99). The pp65 antigen induces cytotoxic T cell response, conferring cellular immunity, while the gB antigen elicits both cellular immunity and antigen-specific antibody production. Accordingly, the vaccine is intended to induce both cellular and humoral immune responses. The pp65 and gB sequences are modified from wild type protein sequences through deletions and codon optimization, as described on pages 402-403 of Smith et al. (2013) Vaccines 1(4):398-414, incorporated by reference herein in its entirety.

TransVax™ has received orphan drug designation in the United States and Europe for hematopoietic stem cell transplantation (HSCT), e.g., bone marrow transplantation, and solid organ transplantation (SOT) patients.

In a Phase 1 clinical trial, 37.5% and 50% of $CMV^-$ subjects, who were dosed with 1 mg and 5 mg, respectively, of the vaccine, demonstrated antibody or T-cell responses. (Page 406 of Smith et al. (2013) V*accines* 1(4):398-414.) A Phase 2 clinical trial was conducted in patients undergoing allogenic haemopoietic stem cell transplantation (ClinicalTrials government database identifier number NCT00285259) (Kharfan-Dabaja et al. (2012) *Lancet Infect Dis* 12:290-99). Transplant patients received the experimental vaccine four times, including once before the transplantation. (Id., page 292.) The dose before transplantation was administered between 3-5 days before transplantation, while the doses after transplantation were administered between 21-42 days after transplantation, and at 84 and 196 days after transplantation. (Id.) Endpoints included assessment of safety and reduction in cytomegalovirus viraemia. (Id.) The incidence of cytomegalovirus viraemia was found to be lower in patients who received the vaccine compared to placebo (32.5% (vaccine group) compared to 61.8% (placebo); Table 2, on page 294 of Kharfan-Dabaja et al.). The vaccine was also reported to be well-tolerated and safe. (Id., page 295.) However, after vaccine treatment, rates of viraemia necessitation anti-viral treatment resembled those of placebo controls. (Id., page 296.)

TransVax™ is currently being tested in a Phase 3 clinical trial for treatment of hematopoietic cell transplant (HCT) patients, accorded ClinicalTrials government database identifier number NCT01877655. The endpoint for the trial is mortality and end organ disease (EOD) 1 year after transplant. The estimated enrollment is 500 and the vaccine is administered by intramuscular injection. TransVax™ is also currently being tested in a Phase 2 clinical trial in CMV-Seronegative kidney transplant recipients receiving an organ from a CMV-Seropositive donor, accorded ClinicalTrials government database identifier number NCT01974206. The primary outcome being measured in this trial is incidence of CMV viremia one year after first administration of the drug. The enrollment is 150 and the vaccine is administered by intramuscular injection. Subjects included in the trial also received ganciclovir or valganciclovir from within ten days up transplant through randomization.

Clinical trials involving TransVax™ are found at the ClinicalTrials government website with the following ClinicalTrials government database identifier numbers: NCT02103426, NCT01877655, NCT01974206, and NCT01903928.

US patents and published applications that are assigned to Vical Inc. and relate to CMV include: U.S. Pat. Nos. 8,673,317, 9,180,162, 8,278,093, 7,888,112, 7,410,795, which are incorporated by reference herein in their entireties.

Experimental Vaccines in Development by City of Hope/National Cancer Institute/Helocyte Several experimental CMV vaccines are being developed by City of Hope and its licensee Helocyte. US patents and published applications that are assigned to City of Hope and relate to CMV include: U.S. Pat. Nos. 7,387,782, 7,025,969, 6,133,433, 6,207,161, 6,074,645, 6,251,399, 6,727,093, 6,726,910, 6,843,992, 6,544,521, 6,951,651, 8,580,276, 7,163,685, 6,242,567, 6,835,383, 6,156,317, 6,562,345, US 2014-0065181 and US 2015-0216965, which are incorporated by reference herein in their entireties.

CMVPepVax

CMVPepVax is an experimental vaccine being developed by City of Hope Medical Center, National Cancer Institute, and Helocyte, Inc. The vaccine includes a pp65 T-cell epitope and a tetanus T-helper epitope in the form of a chimeric peptide, and also includes the adjuvant PF03512676. (Nakamura R et al., *Lancet Heamatology* (2016) February; 3(2):e87-98). CMVPepVax was tested in a Phase 1b clinical trial on CMV-seropositive patients who were undergoing haemopoietic stem-cell transplantation (HCT). (Id.) The vaccine was administered on days 28 and 56 through subcutaneous administration. (Id.) It was reported that patients receiving the vaccine showed improved relapse-free survival. (Id.) This clinical trial was accorded ClinicalTrials government database identifier number NCT01588015. CMVPepVax is currently being tested in a Phase 2 clinical trial to measure efficacy in reducing the frequency of Cytomegalovirus events in patients with hematologic malignancies undergoing donor stem cell transplant, accorded ClinicalTrials government database identifier number NCT02396134.

CMV-MVA Triplex

CMV-MVA-Triplex is an experimental CMV vaccine being developed by City of Hope Medical Center, National Cancer Institute, and Helocyte, Inc. (formerly DiaVax Biosciences). This vaccine consists of an inactivated Modified Vaccinia Ankara (MVA) viral vector that encodes the CMV antigens UL83 (pp65), UL123 (IE1) and UL122 (IE2). (NCI Drug Dictionary.)

CMV-MVA Triplex is currently being tested in a Phase 2 clinical trial investigating efficacy in reducing CMV complications in patients previously infected with CMV and undergoing donor hematopoietic cell transplant. This trial has been accorded ClinicalTrials government database identifier number NCT02506933. A Phase 1 clinical trial in healthy volunteers with or without previous exposure to CMV is also ongoing (ClinicalTrials government database identifier No. NCT01941056).

Pentamer

City of Hope and Helocyte, Inc. are also pursuing a pentameric vaccine using a Modified Vaccinia Ankara (MVA) viral vector that encodes the five CMV pentameric subunits. This vaccine is still in preclinical development. (Wussow et al. (2014) PLoS Pathog 10(11): e1004524. doi: 10.1371/journal.ppat.1004524).

gB/MF59

This experimental vaccine, originally developed in the 1990s combines the gB antigen with the MF59 adjuvant. (Pass et al. (2009) *J Clin Virol* 46(Suppl 4):S73-S76.) Several clinical trials that were conducted in the 1990s, sponsored by Chiron Corporation, indicated that the vaccine was safe. (Id., page 2.) Sanofi Pasteur later obtained the rights to this vaccine. (Id.)

A Phase 2 clinical trial was conducted in postpartum females starting in 1999 (with enrollment completed in 2006) using the endpoint of time to CMV infection. (Id., page 3.) Subjects were administered the vaccine at 0, 1, and 6 months. (Rieder et al. (2014) *Clin Microbiol Infect* 20 (Suppl. 5):95-102, page 98). Infection with CMV was diagnosed in 8% of vaccine-treated subjects compared to 14% of placebo-treated subjects, respectively (corresponding to 43% efficacy). Results indicated a 50% reduction in rate of CMV infection in subjects treated with the vaccine (3.3% in test subjects compared to 6.6% in placebo-treated subjects). (Id.; Pass et al. (2009) *J Clin Virol* 46(Suppl 4):S73-S76., page 4.). The 50% reduction in rate of CMV infection has been described as "lower than wished for from a clinical perspective." (Rieder et al. (2014) *Clin Microbiol Infect* 20 (Suppl. 5):95-102, page 98.)

A Phase 2 clinical trial has also been conducted with gB/MF59 in kidney and liver transplant patients. (Id., page 100.) It was reported that "high gB-antibody titres correlated with shorter duration of viraemia" and that "duration of viraemia and number of days of ganciclovir treatment were reduced." (Id.)

Clinical trials involving gB/MF59 are found at the ClinicalTrials government website with the following ClinicalTrials government database identifier numbers: NCT00133497, NCT00815165, and NCT00125502.

US 2009-0104227, assigned to Sanofi Pasteur SA, is incorporated by reference herein in its entirety.

gB/AS01

GlaxoSmithKline is developing an experimental vaccine that includes the gB antigen combined with the ASOI adjuvant. (McVoy (2013) *Clinical Infectious Diseases* 57(S4):S196-9, page S197.) This vaccine is referred to as GSK1492903A. Clinical trials involving GSK1492903A are found at the ClinicalTrials government website with the following ClinicalTrials government database identifier numbers: NCT00435396 and NCT01357915.

WO 2016/067239 and WO 2015/181142, filed by GlaxoSmithKline Biologicals SA, are incorporated by reference herein in their entireties.

Towne Vaccine

The CMV Towne vaccine is a live attenuated vaccine. (McVoy (2013) *Clinical Infectious Diseases* 57(S4):S196-9, page S197.) This vaccine was not successful in protecting against primary maternal infection, at least when administered at a low dose. (Id.) In a trial involving kidney transplant subjects, treatment with this vaccine resulted in reduction of severe disease, while only having a minimal impact on mild disease. (Plotkin et al. (1994) *Transplantation* 58(11):1176-8.)

Live attenuated vaccines in which sections of the Towne genome have been replaced with sequence from other "low-passage" strains have also been developed, referred to as "Towne-Toledo chimeras," which were found to be well-tolerated in a Phase 1 clinical trial. (McVoy (2013) *Clinical Infectious Diseases* 57(S4):S196-9, page S197; Heineman et al. (2006) *The Journal of Infectious Diseases* 193:1350-60.) Chimeric viral genomes including portions of the Towne genome are described in and incorporated by reference from U.S. Pat. No. 7,204,990, incorporated by reference herein in its entirety.

Another approach that is being explored involves co-administering the Towne vaccine with the adjuvant recombinant interleukin-12 (rhIL-12) (Jacobson et al. (2006) *Vaccine* 24:5311-9.)

CMV-CTL

CMV Targeted T-Cell Program (CMV-CTL) represents a cellular immunotherapy approach being developed by Atara Biotherapeutics.

A Phase 1 clinical trial used CMV pp65 or pp65/IE1 peptide mixes to pulse monocytes to expand CMV CTL and investigated the immunologic effects. (Bao et al. (2012) *J Immunother* 35(3):293-298). CMV specific immune responses were observed in approximately 70% of subjects receiving CTL. (Id., page 5.)

A Phase 2 clinical trial is currently ongoing, investigating third party donor derived CMVpp65 specific T-cells for the treatment of CMV infection or persistent CMV viremia after allogeneic hematopoietic stem cell transplantation. This trial was assigned ClinicalTrials government database identifier number NCT02136797. A second Phase 2 clinical trial is also ongoing, investigating primary transplant donor derived CMVpp65 specific T-cells for the treatment of CMV infection or persistent CMV viremia after allogeneic hematopoietic stem cell transplantation. This trial was assigned ClinicalTrials government database identifier number NCT01646645.

Monoclonal Abs

Novartis

CSJ148, being developed by Novartis, represents a combination of two monoclonal antibodies that target gB and the CMV pentameric complex. (Dole et al. (2016) *Antimicrob Agents Chemother. April* 22; 60(5):2881-7). The two antibodies are known as LJP538 and LJP539. (Id.) LJP538, LJP539, and CSJ148 were found to be safe when administered intravenously to healthy volunteers and revealed expected pharmacokinetics for IgG. (Id.) CSJ148 is currently in a Phase 2 clinical trial investigating efficacy and safety in stem cell transplant patients (ClinicalTrials government database identifier number NCT02268526).

Theraclone

TCN-202 is a fully human monoclonal antibody being developed by Theraclone for treatment of CMV infection. TCN-202 was found to be safe and well-tolerated in a Phase 1 clinical trial (ClinicalTrials government database identifier number NCT01594437). A Phase 2 study was initiated in 2013 to investigate efficacy in kidney transplant recipients. (Theraclone Press Release, Sep. 10, 2013.)

Brincidofovir

Brincidofovir (CMX001) is an experimental lipid-nucleotide conjugate being developed by Chimerix, Durham, N.C., for treatment of DNA viruses including CMV. Brincidofovir received Fast Track designation from the FDA for CMV.

Results from a Phase 3 clinical trial (called "SUPPRESS") investigating prevention of CMV in subjects undergoing hematopoietic cell transplantation (HCT) were announced in February, 2016. (Chimerix Press Release, Feb. 20, 2016.) It was reported that the trial failed to meet its primary endpoint of preventing CMV at week 24, although an anti-viral effect was observed during the treatment phase. (Id.) The trial involved 452 subjects undergoing HCT who were administered Brincidofovir twice a week for up to fourteen weeks. (Id.) It was speculated that increased use of immunosteroids, such as corticosteroids, for treatment of graft versus host disease (GVHD), after treatment with Brincidofovir, may have contributed to failure to reach the primary endpoint of the trial. (Id.) Other Phase 3 trials were terminated based on the results of the SUPPRESS trial, but Chimerix has indicated that they intend to pursue further Phase 2 trials in subjects undergoing kidney transplants. (Id.)

Information about clinical trials associated with Brincidofovir are found at the ClinicalTrials government website, including identifier numbers: NCT02087306, NCT02271347, NCT02167685, NCT02596997, NCT02439970, NCT00793598, NCT01769170, NCT00780182, NCT01241344, NCT00942305, NCT02420080, NCT02439957, NCT01143181, and NCT01610765.

V160

V160 is an experimental CMV vaccine being developed by Merck, which is based on the attenuated AD169 strain. V160 is currently being tested in a Phase 1 clinical trial evaluating a three dose regimen testing several formulations in healthy adults. This trial was assigned the ClinicalTrials government database identifier number NCT01986010.

Merck is also pursuing vaccines that target the CMV pentameric complex. (Loughney et al. (2015) jbc.M115.652230.) US patents and published applications assigned to Merck Sharp & Dohme Corp include: US 2014-0220062 and US 2015-0307850, which are incorporated by reference herein in their entireties.

Letermovir

Letermovir (AIC246) is an antiviral drug being developed by Merck for the treatment of CMV infections (Chemaly et al. (2014) *New England Journal of Medicine,* 370; 19, May 8, 2014, Verghese et al. (2013) *Drugs Future*. May; 38(5): 291-298). It was tested in a Phase IIb clinical trial investigating prevention of CMV in HSCT recipients, corresponding to ClinicalTrials government database identifier number NCT01063829, and was found to reduce the incidence of CMV infection in transplant subjects.

Redvax GmbH/Pfizer

A preclinical candidate tgrgeting CMV was developed by Redvax GmbH, which spun out from Redbiotec AG. This candidate is now being pursued by Pfizer Inc.

Patents and patent publications assigned to Redvax GmbH or Pfizer and related to CMV include: US 2015-0322115, WO 2015/170287, US 2015-0359879, and WO 2014/068001, incorporated by reference herein in their entireties.

Therapeutic and Prophylactic Compositions

Provided herein are compositions (e.g., pharmaceutical compositions), methods, kits and reagents for prevention, treatment or diagnosis of HCMV in humans. HCMV RNA vaccines can be used as therapeutic or prophylactic agents. They may be used in medicine to prevent and/or treat infectious disease. In some embodiments, the HCMV vaccines of the invention can be envisioned for use in the priming of immune effector cells, for example, to activate peripheral blood mononuclear cells (PBMCs) ex vivo, which are then infused (re-infused) into a subject.

In exemplary embodiments, a HCMV vaccine containing RNA polynucleotides as described herein can be administered to a subject (e.g., a mammalian subject, such as a human subject), and the RNA polynucleotides are translated in vivo to produce an antigenic polypeptide. In some embodiments, the subject is a woman of child-bearing age. In some embodiments, vaccines described herein reduce or prevent congenital transmission of HCMV from a mother to a child. (Pass et al. (2014) *J Ped Infect Dis* 3 (suppl 1): S2-S6.)

The HCMV RNA vaccines may be induced for translation of a polypeptide (e.g., antigen or immunogen) in a cell, tissue or organism. In exemplary embodiments, such translation occurs in vivo, although there can be envisioned embodiments where such translation occurs ex vivo, in culture or in vitro. In exemplary embodiments, the cell, tissue or organism is contacted with an effective amount of a composition containing a HCMV RNA vaccine that contains a polynucleotide that has at least one a translatable region encoding an antigenic polypeptide.

An "effective amount" of the HCMV RNA vaccine is provided based, at least in part, on the target tissue, target cell type, means of administration, physical characteristics of the polynucleotide (e.g., size, and extent of modified nucleosides) and other components of the HCMV RNA vaccine, and other determinants. In general, an effective amount of the HCMV RNA vaccine composition provides an induced or boosted immune response as a function of antigen production in the cell, preferably more efficient than a composition containing a corresponding unmodified polynucleotide encoding the same antigen or a peptide antigen. Increased antigen production may be demonstrated by increased cell transfection (the percentage of cells transfected with the RNA vaccine), increased protein translation from the polynucleotide, decreased nucleic acid degradation (as demonstrated, for example, by increased duration of protein translation from a modified polynucleotide), or altered antigen specific immune response of the host cell.

In some embodiments, RNA vaccines (including polynucleotides their encoded polypeptides) in accordance with the present disclosure may be used for treatment of HCMV. HCMV RNA vaccines may be administered prophylactically or therapeutically as part of an active immunization scheme to healthy individuals or early in infection during the incubation phase or during active infection after onset of symptoms. In some embodiments, the amount of RNA vaccines of the present disclosure provided to a cell, a tissue or a subject may be an amount effective for immune prophylaxis.

HCMV RNA vaccines may be administrated with other prophylactic or therapeutic compounds. As a non-limiting example, a prophylactic or therapeutic compound may be an adjuvant or a booster. As used herein, when referring to a prophylactic composition, such as a vaccine, the term "booster" refers to an extra administration of the prophylactic (vaccine) composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, 45 years, 50 years, 55 years, 60 years, 65 years, 70 years, 75 years, 80 years, 85 years, 90 years, 95 years or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months or 1 year.

In some embodiments, HCMV RNA vaccines may be administered intramuscularly or intradermally, similarly to the administration of inactivated vaccines known in the art. The HCMV RNA vaccines may be utilized in various settings depending on the prevalence of the infection or the degree or level of unmet medical need. As a non-limiting example, the RNA vaccines may be utilized to treat and/or prevent a variety of infectious disease. RNA vaccines have superior properties in that they produce much larger antibody titers and produce responses early than commercially available anti-virals.

Provided herein are pharmaceutical compositions including HCMV RNA vaccines and RNA vaccine compositions and/or complexes optionally in combination with one or more pharmaceutically acceptable excipients.

HCMV RNA vaccines may be formulated or administered alone or in conjunction with one or more other components. For instance, HCMV RNA vaccines (vaccine compositions) may comprise other components including, but not limited to, adjuvants. In some embodiments, HCMV RNA vaccines do not include an adjuvant (they are adjuvant free).

HCMV RNA vaccines may be formulated or administered in combination with one or more pharmaceutically-acceptable excipients. In some embodiments, vaccine compositions comprise at least one additional active substances, such as, for example, a therapeutically-active substance, a prophylactically-active substance, or a combination of both. Vaccine compositions may be sterile, pyrogen-free or both sterile and pyrogen-free. General considerations in the formulation and/or manufacture of pharmaceutical agents, such as vaccine compositions, may be found, for example, in Remington: The Science and Practice of Pharmacy 21st ed., Lippincott Williams & Wilkins, 2005 (incorporated herein by reference in its entirety).

In some embodiments, HCMV RNA vaccines are administered to humans, human patients or subjects. For the purposes of the present disclosure, the phrase "active ingredient" generally refers to the RNA vaccines or the polynucleotides contained therein, for example, RNA polynucleotides (e.g., mRNA polynucleotides) encoding antigenic polypeptides. Formulations of the vaccine compositions described herein may be prepared by any method known or hereafter developed in the art of pharmacology. In general, such preparatory methods include the step of bringing the active ingredient (e.g., mRNA polynucleotide) into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

HCMV RNA vaccines can be formulated using one or more excipients to: (1) increase stability; (2) increase cell transfection; (3) permit the sustained or delayed release (e.g., from a depot formulation); (4) alter the biodistribution (e.g., target to specific tissues or cell types); (5) increase the translation of encoded protein in vivo; and/or (6) alter the release profile of encoded protein (antigen) in vivo. In addition to traditional excipients such as any and all solvents, dispersion media, diluents, or other liquid vehicles, dispersion or suspension aids, surface active agents, isotonic agents, thickening or emulsifying agents, preservatives, excipients can include, without limitation, lipidoids, liposomes, lipid nanoparticles, polymers, lipoplexes, core-shell nanoparticles, peptides, proteins, cells transfected with HCMV RNA vaccines (e.g., for transplantation into a subject), hyaluronidase, nanoparticle mimics and combinations thereof.

Stabilizing Elements

Naturally-occurring eukaryotic mRNA molecules have been found to contain stabilizing elements, including, but not limited to untranslated regions (UTR) at their 5'-end (5'UTR) and/or at their 3'-end (3'UTR), in addition to other structural features, such as a 5'-cap structure or a 3'-poly(A) tail. Both the 5'UTR and the 3'UTR are typically transcribed from the genomic DNA and are elements of the premature mRNA. Characteristic structural features of mature mRNA, such as the 5'-cap and the 3'-poly(A) tail are usually added to the transcribed (premature) mRNA during mRNA processing. The 3'-poly(A) tail is typically a stretch of adenine nucleotides added to the 3'-end of the transcribed mRNA. It can comprise up to about 400 adenine nucleotides. In some embodiments the length of the 3'-poly(A) tail may be an essential element with respect to the stability of the individual mRNA.

In some embodiments the RNA vaccine may include one or more stabilizing elements. Stabilizing elements may include for instance a histone stem-loop. A stem-loop binding protein (SLBP), a 32 kDa protein has been identified. It is associated with the histone stem-loop at the 3-end of the histone messages in both the nucleus and the cytoplasm. Its expression level is regulated by the cell cycle; it is peaks during the S-phase, when histone mRNA levels are also elevated. The protein has been shown to be essential for efficient 3-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA vaccines include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

In some embodiments, the RNA vaccine does not comprise a histone downstream element (HDE). "Histone downstream element" (HDE) includes a purine-rich polynucleotide stretch of approximately 15 to 20 nucleotides 3' of naturally occurring stem-loops, representing the binding site for the U7 snRNA, which is involved in processing of histone pre-mRNA into mature histone mRNA. Ideally, the inventive nucleic acid does not include an intron.

In some embodiments, the RNA vaccine may or may not contain a enhancer and/or promoter sequence, which may be modified or unmodified or which may be activated or inactivated. In some embodiments, the histone stem-loop is generally derived from histone genes, and includes an intramolecular base pairing of two neighbored partially or entirely reverse complementary sequences separated by a spacer, consisting of a short sequence, which forms the loop of the structure. The unpaired loop region is typically unable to base pair with either of the stem loop elements. It occurs more often in RNA, as is a key component of many RNA secondary structures, but may be present in single-stranded DNA as well. Stability of the stem-loop structure generally depends on the length, number of mismatches or bulges, and base composition of the paired region. In some embodiments, wobble base pairing (non-Watson-Crick base pairing) may result. In some embodiments, the at least one histone stem-loop sequence comprises a length of 15 to 45 nucleotides.

In other embodiments the RNA vaccine may have one or more AU-rich sequences removed. These sequences, sometimes referred to as AURES are destabilizing sequences found in the 3'UTR. The AURES may be removed from the RNA vaccines. Alternatively the AURES may remain in the RNA vaccine.

Nanoparticle Formulations

In some embodiments, HCMV RNA vaccines are formulated in a nanoparticle. In some embodiments, HCMV RNA vaccines are formulated in a lipid nanoparticle. In some embodiments, HCMV RNA vaccines are formulated in a lipid-polycation complex, referred to as a cationic lipid nanoparticle. The formation of the lipid nanoparticle may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In some embodiments, HCMV RNA vaccines are formulated in a lipid nanoparticle that includes a non-cationic lipid such as, but not limited to, cholesterol or dioleoyl phosphatidylethanolamine (DOPE).

A lipid nanoparticle formulation may be influenced by, but not limited to, the selection of the cationic lipid component, the degree of cationic lipid saturation, the nature of the PEGylation, ratio of all components and biophysical parameters such as size. In one example by Semple et al. (*Nature Biotech.* 2010 28:172-176; herein incorporated by reference in its entirety), the lipid nanoparticle formulation is composed of 57.1% cationic lipid, 7.1% dipalmitoylphosphatidylcholine, 34.3% cholesterol, and 1.4% PEG-c-DMA. As another example, changing the composition of the cationic lipid can more effectively deliver siRNA to various antigen presenting cells (Basha et al. *Mol Ther.* 2011 19:2186-2200; herein incorporated by reference in its entirety).

In some embodiments, lipid nanoparticle formulations may comprise 35 to 45% cationic lipid, 40% to 50% cationic lipid, 50% to 60% cationic lipid and/or 55% to 65% cationic lipid. In some embodiments, the ratio of lipid to RNA (e.g., mRNA) in lipid nanoparticles may be 5:1 to 20:1, 10:1 to 25:1, 15:1 to 30:1 and/or at least 30:1.

In some embodiments, the ratio of PEG in the lipid nanoparticle formulations may be increased or decreased and/or the carbon chain length of the PEG lipid may be modified from C14 to C18 to alter the pharmacokinetics and/or biodistribution of the lipid nanoparticle formulations. As a non-limiting example, lipid nanoparticle formulations may contain 0.5% to 3.0%, 1.0% to 3.5%, 1.5% to 4.0%, 2.0% to 4.5%, 2.5% to 5.0% and/or 3.0% to 6.0% of the lipid molar ratio of PEG-c-DOMG (R-3-[(ω-methoxy-poly(ethyleneglycol)2000)carbamoyl)]-1,2-dimyristyloxypropyl-3-amine) (also referred to herein as PEG-DOMG) as compared to the cationic lipid, DSPC and cholesterol. In some embodiments, the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, a HCMV RNA vaccine formulation is a nanoparticle that comprises at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In some embodiments, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl)$^9$-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, a lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl)$^9$-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of 20-60% cationic lipid: 5-25% neutral lipid: 25-55% sterol; 0.5-15% PEG-lipid.

In some embodiments, a lipid nanoparticle formulation includes 25% to 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., 35 to 65%, 45 to 65%, 60%, 57.5%, 50% or 40% on a molar basis.

In some embodiments, a lipid nanoparticle formulation includes 0.5% to 15% on a molar basis of the neutral lipid, e.g., 3 to 12%, 5 to 10% or 15%, 10%, or 7.5% on a molar basis. Examples of neutral lipids include, without limitation, DSPC, POPC, DPPC, DOPE and SM. In some embodiments, the formulation includes 5% to 50% on a molar basis of the sterol (e.g., 15 to 45%, 20 to 40%, 40%, 38.5%, 35%, or 31% on a molar basis. A non-limiting example of a sterol is cholesterol. In some embodiments, a lipid nanoparticle formulation includes 0.5% to 20% on a molar basis of the PEG or PEG-modified lipid (e.g., 0.5 to 10%, 0.5 to 5%, 1.5%, 0.5%, 1.5%, 3.5%, or 5% on a molar basis. In some embodiments, a PEG or PEG modified lipid comprises a PEG molecule of an average molecular weight of 2,000 Da. In some embodiments, a PEG or PEG modified lipid comprises a PEG molecule of an average molecular weight of less than 2,000, for example around 1,500 Da, around 1,000 Da, or around 500 Da. Non-limiting examples of PEG-modified lipids include PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in its entirety).

In some embodiments, lipid nanoparticle formulations include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, lipid nanoparticle formulations include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, lipid nanoparticle formulations include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, lipid nanoparticle formulations include 60% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.5% of the neutral lipid, 31% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 38.5% of the sterol, and 1.5% of the PEG or PEG-modified lipid on a molar basis.

In some embodiments, lipid nanoparticle formulations include 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 10% of the neutral lipid, 35% of the sterol, 4.5% or 5% of the PEG or PEG-modified lipid, and 0.5% of the targeting lipid on a molar basis.

In some embodiments, lipid nanoparticle formulations include 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 15% of the neutral lipid, 40% of the sterol, and 5% of the PEG or PEG-modified lipid on a molar basis.

In some embodiments, lipid nanoparticle formulations include 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 7.1% of the neutral lipid, 34.3% of the sterol, and 1.4% of the PEG or PEG-modified lipid on a molar basis.

In some embodiments, lipid nanoparticle formulations include 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), 7.5% of the neutral lipid, 31.5% of the sterol, and 3.5% of the PEG or PEG-modified lipid on a molar basis.

In some embodiments, lipid nanoparticle formulations consists essentially of a lipid mixture in molar ratios of 20-70% cationic lipid: 5-45% neutral lipid: 20-55% cholesterol: 0.5-15% PEG-modified lipid. In some embodiments, lipid nanoparticle formulations consists essentially of a lipid mixture in a molar ratio of 20-60% cationic lipid: 5-25% neutral lipid: 25-55% cholesterol: 0.5-15% PEG-modified lipid.

In some embodiments, the molar lipid ratio is 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Non-limiting examples of lipid nanoparticle compositions and methods of making them are described, for example, in Semple et al. (2010) *Nat. Biotechnol.* 28:172-176; Jayarama et al. (2012), *Angew. Chem. Int. Ed.,* 51: 8529-8533; and Maier et al. (2013) *Molecular Therapy* 21, 1570-1578 (the contents of each of which are incorporated herein by reference in their entirety).

In some embodiments, lipid nanoparticle formulations may comprise a cationic lipid, a PEG lipid and a structural lipid and optionally comprise a non-cationic lipid. As a non-limiting example, a lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, a lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise 40-60% of cationic lipid, 5-15% of a non-cationic lipid, 1-2% of a PEG lipid and 30-50% of a structural lipid. As another non-limiting example, the lipid nanoparticle may comprise 50% cationic lipid, 10% non-cationic lipid, 1.5% PEG lipid and 38.5% structural lipid. As yet another non-limiting example, the lipid nanoparticle may comprise 55% cationic lipid, 10% non-cationic lipid, 2.5% PEG lipid and 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise 50% of the cationic lipid DLin-KC2-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DOMG and 38.5% of the structural lipid cholesterol. As a non-limiting example, the lipid nanoparticle comprise 50% of the cationic lipid DLin-MC3-DMA, 10% of the non-cationic lipid DSPC, 1.5% of the PEG lipid PEG-DMG and 38.5% of the structural lipid cholesterol. As yet another non-limiting example, the lipid nanoparticle comprise 55% of the cationic lipid L319, 10% of the non-cationic lipid DSPC, 2.5% of the PEG lipid PEG-DMG and 32.5% of the structural lipid cholesterol.

In some embodiments, a nanoparticle comprises compounds of Formula (I):

(I)

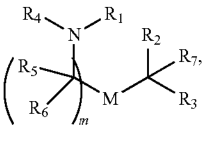

or a salt or isomer thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a carbocycle, heterocycle, —OR, $—O(CH_2)_nN(R)_2$, —C(O)OR, —OC(O)R, $—CX_3$, $—CX_2H$, $—CXH_2$, —CN, $—N(R)_2$, $—C(O)N(R)_2$, —N(R)C(O)R, $—N(R)S(O)_2R$, $—N(R)C(O)N(R)_2$, $—N(R)C(S)N(R)_2$, $—N(R)R_8$, $—O(CH_2)_nOR$, $—N(R)C(=NR_9)N(R)_2$, $—N(R)C(=CHR_9)N(R)_2$, $—OC(O)N(R)_2$, —N(R)C(O)OR, —N(OR)C(O)R, $—N(OR)S(O)_2R$, —N(OR)C(O)OR, $—N(OR)C(O)N(R)_2$, $—N(OR)C(S)N(R)_2$, $—N(OR)C(=NR_9)N(R)_2$, $—N(OR)C(=CHR_9)N(R)_2$, $—C(=NR_9)N(R)_2$, $—C(=NR_9)R$, —C(O)N(R)O R, and $—C(R)N(R)_2C(O)OR$, and each n is independently selected from 1, 2, 3, 4, and 5; each $R_5$ is independently selected from the group consisting of $C_{1-3}$ alkyl, $C_{2-3}$ alkenyl, and H; each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-8}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13.

In some embodiments, a subset of compounds of Formula (I) includes those in which when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, $—(CH_2)_nQ$, $—(CH_2)_nCHQR$, —CHQR, $—CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)$N(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, mono- or di-alkylamino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-8}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_nCHQR$ in which n is 1, or (iii) $R_4$ is —CHQR, and —$CQ(R)_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H; M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_nCHQR$, —CHQR,-$CQ(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —$O(CH_2)_nN(R)_2$, —C(O)OR, —OC(O)R, —$CX_3$, —$CX_2H$, —$CXH_2$, —CN, —$C(O)N(R)_2$, —N(R)C(O)R, —$N(R)S(O)_2R$, —$N(R)C(O)N(R)_2$, —$N(R)C(S)N(R)_2$, —$CRN(R)_2C(O)OR$, —$N(R)R_8$, —$O(CH_2)_nOR$, —N(R)C(=$NR_9$)$N(R)_2$, —N(R)C(=$CHR_9$)$N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=$NR_9$)$N(R)_2$, —N(OR)C(=$CHR_9$)$N(R)_2$, —C(=$NR_9$)R, —C(O)N(R)OR, and —C(=$NR_9$)$N(R)_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{36}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is —$(CH_2)_nQ$ or —$(CH_2)_nCHQR$, where Q is —$N(R)_2$, and n is selected from 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of $C_{1-4}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-2}$ alkyl and $C_{1-2}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or isomers thereof.

In some embodiments, a subset of compounds of Formula (I) includes those of Formula (IA):

(IA)

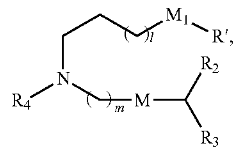

or a salt or isomer thereof, wherein 1 is selected from 1, 2, 3, 4, and 5; m is selected from 5, 6, 7, 8, and 9; $M_1$ is a bond or M'; $R_4$ is unsubstituted $C_{1-3}$ alkyl, or —$(CH_2)_nQ$, in which Q is OH, —$NHC(S)N(R)_2$, —$NHC(O)N(R)_2$, —N(R)C(O)R, —$N(R)S(O)_2R$, —$N(R)R_8$, —$NHC(=NR_9)N(R)_2$, —$NHC(=CHR_9)N(R)_2$, —$OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II):

(II)

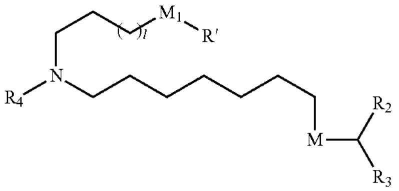

or a salt or isomer thereof, wherein 1 is selected from 1, 2, 3, 4, and 5; $M_1$ is a bond or M'; $R_4$ is unsubstituted $C_{1-3}$ alkyl, or —$(CH_2)_nQ$, in which n is 2, 3, or 4, and Q is OH, —$NHC(S)N(R)_2$, —$NHC(O)N(R)_2$, —N(R)C(O)R, —$N(R)S(O)_2R$, —$N(R)R_8$, —$NHC(=NR_9)N(R)_2$, —$NHC(=CHR_9)N(R)_2$, —$OC(O)N(R)_2$, —N(R)C(O)OR, heteroaryl or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-4}$ alkyl, and $C_{2-14}$ alkenyl.

In some embodiments, a subset of compounds of Formula (I) includes those of Formula (IIa), (IIb), (IIc), or (IIe):

(IIa)

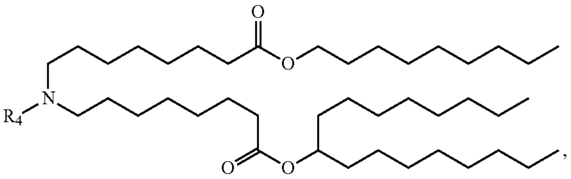

(IIb)

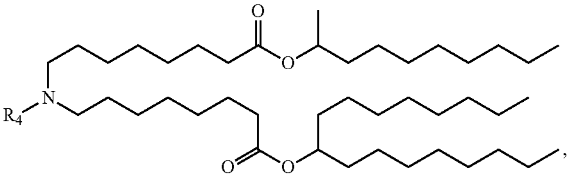

(IIc)

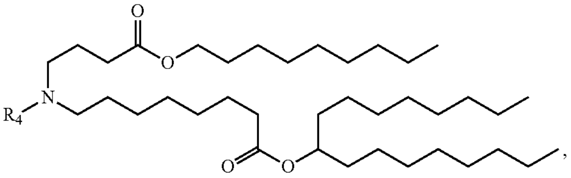

or (IIe)

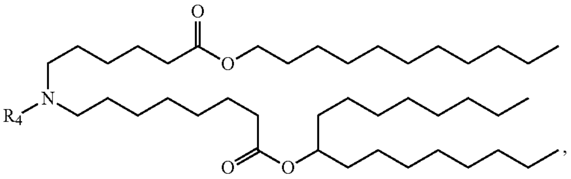

or a salt or isomer thereof, wherein $R_4$ is as described herein.

In some embodiments, a subset of compounds of Formula (I) includes those of Formula (IId):

(IId)

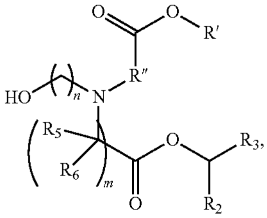

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, a subset of compounds of Formula (I) includes those of Formula (IIa), (IIb), (IIc), or (IIe):

(IIa)

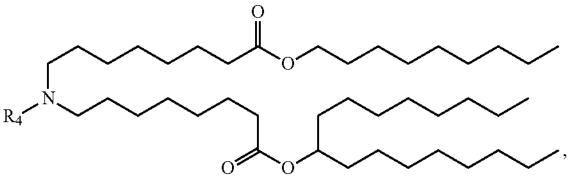

(IIb)

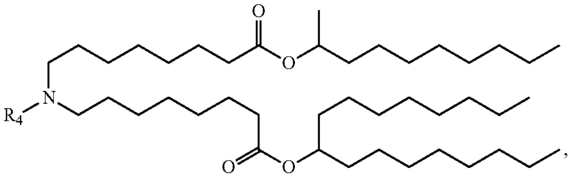

(IIc)

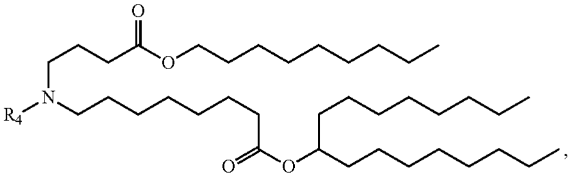

or (IIe)

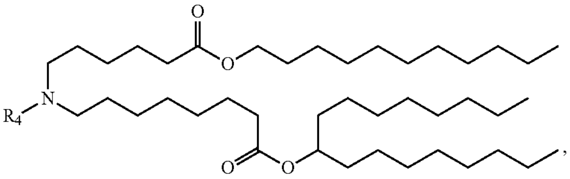

or a salt or isomer thereof, wherein $R_4$ is as described herein.

In some embodiments, a subset of compounds of Formula (I) includes those of Formula (IId):

(IId)

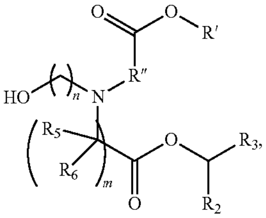

or a salt or isomer thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound of Formula (I) is selected from the group consisting of:

(Compound 1)

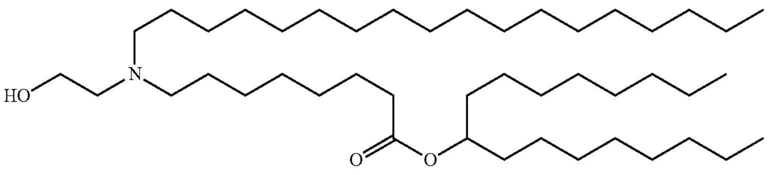

,

-continued
(Compound 2)
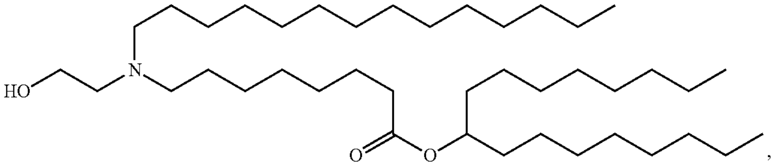
(Compound 3)
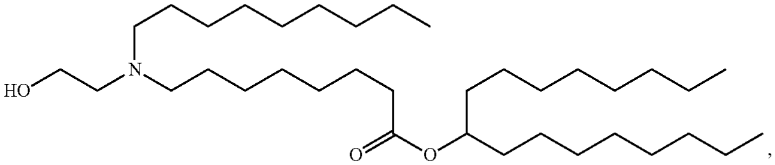
(Compound 4)
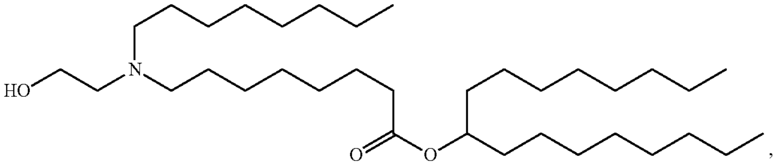
(Compound 5)
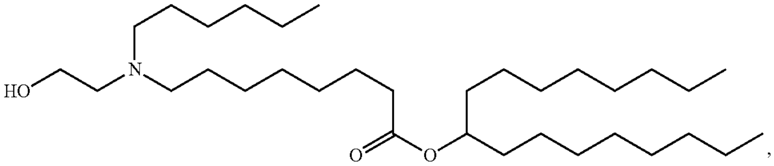
(Compound 6)
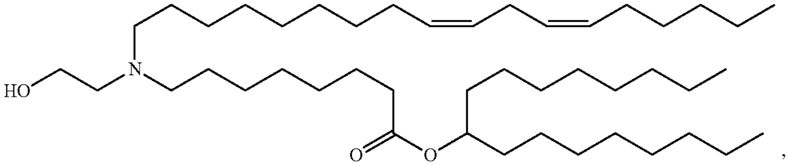
(Compound 7)
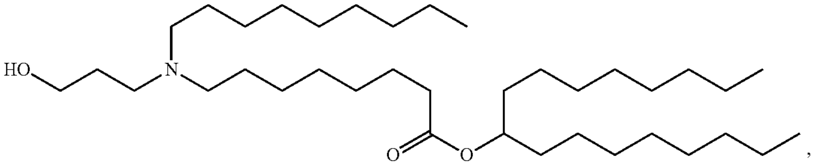
(Compound 8)
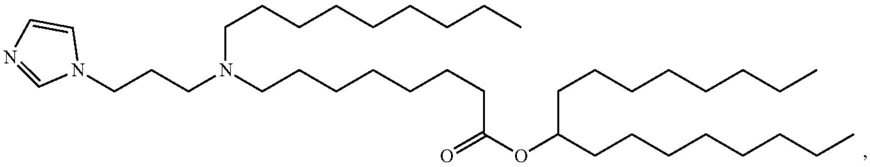
(Compound 9)
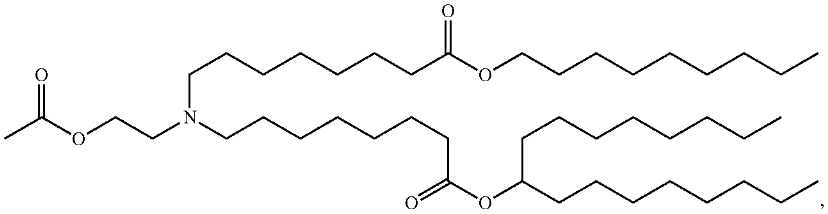

-continued
(Compound 10)
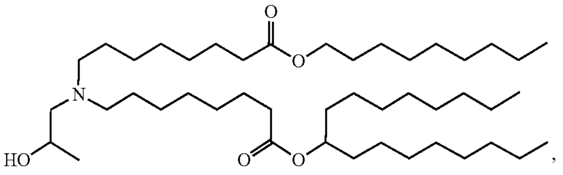
(Compound 11)
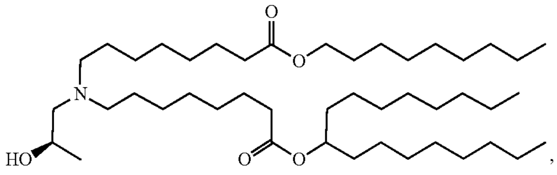
(Compound 12)
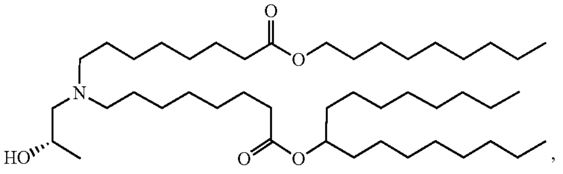
(Compound 13)
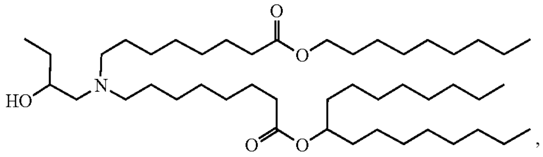
(Compound 14)
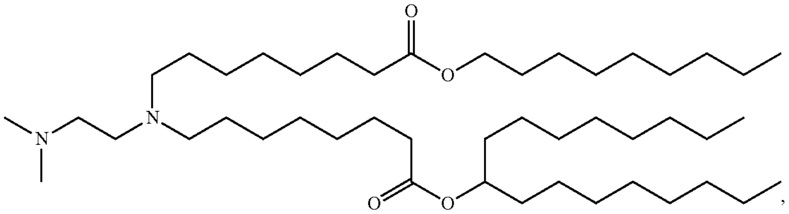
(Compound 15)
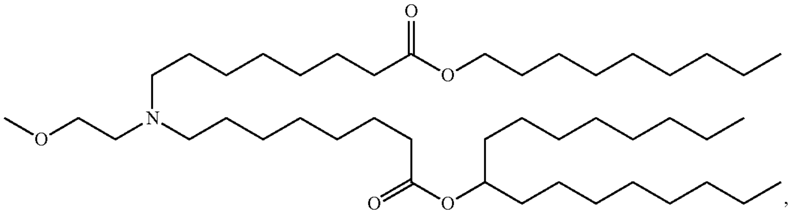
(Compound 16)
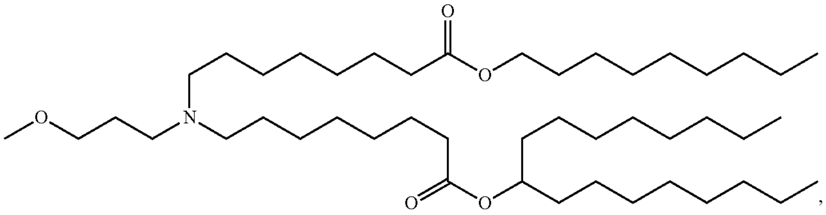
(Compound 17)
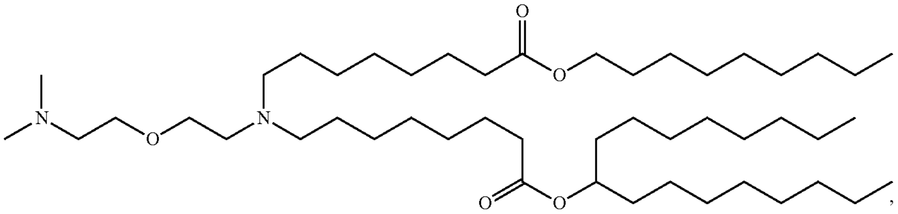
(Compound 18)
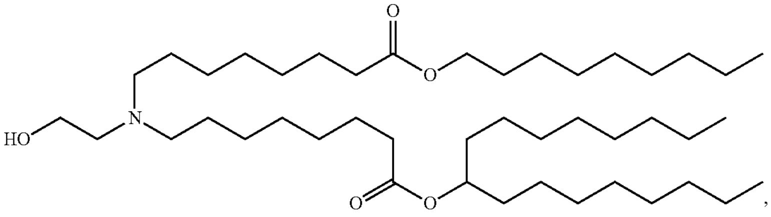

-continued
(Compound 19)
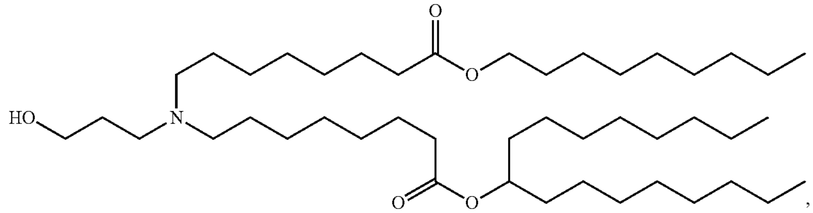
(Compound 20)
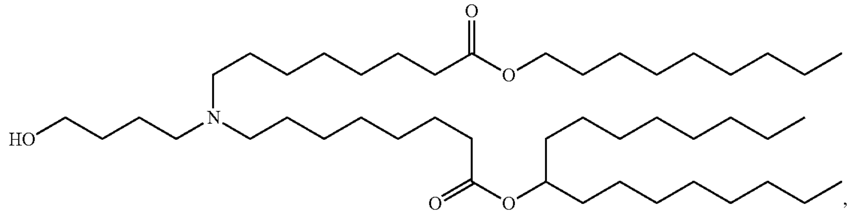
(Compound 21)
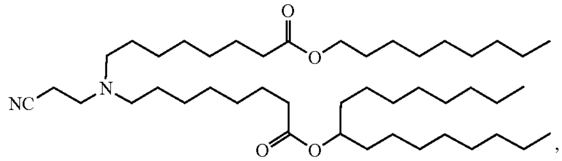
(Compound 22)
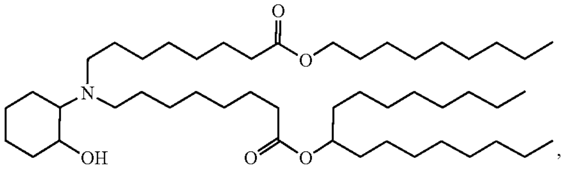
(Compound 23)
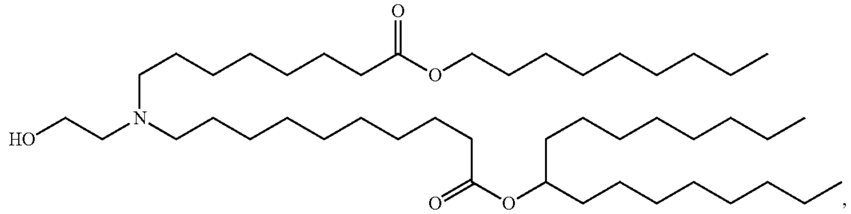
(Compound 24)
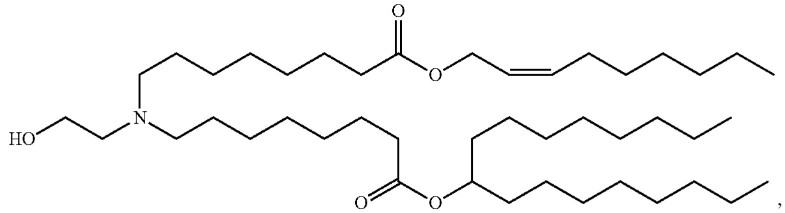
(Compound 25)
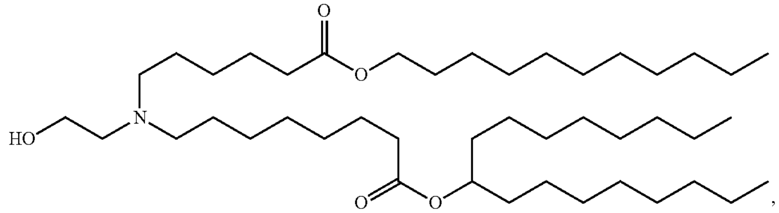
(Compound 26)
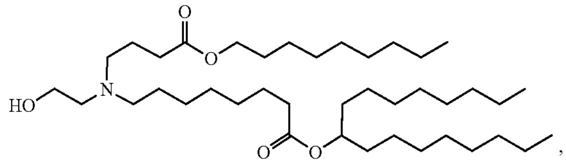
(Compound 27)
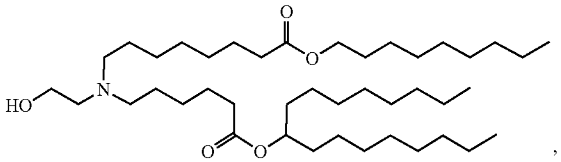

-continued
(Compound 28)
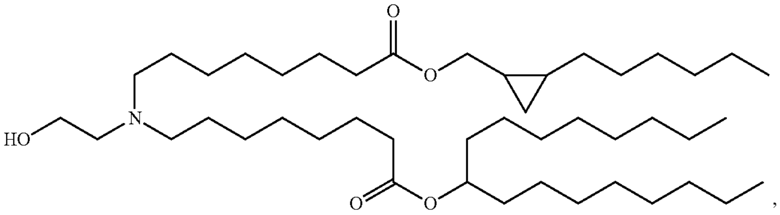
,
(Compound 29)
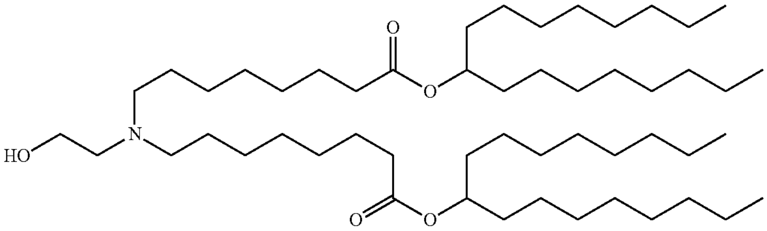
,
(Compound 30)
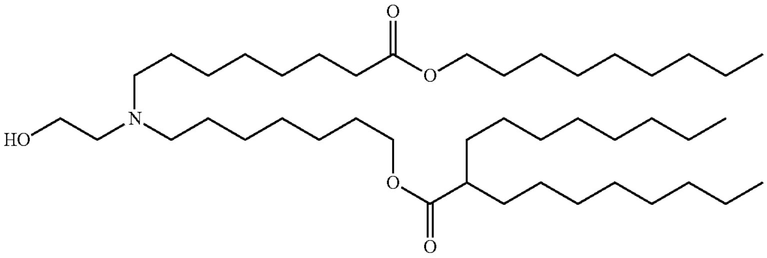
,
(Compound (31)
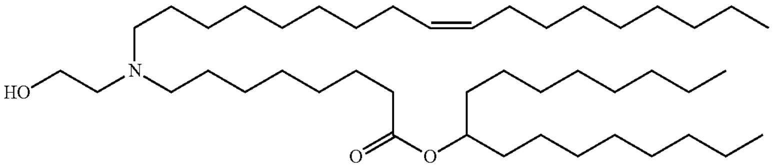
,
(Compound 32)
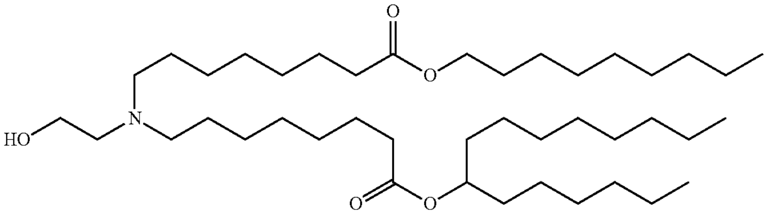
,
(Compound 33)
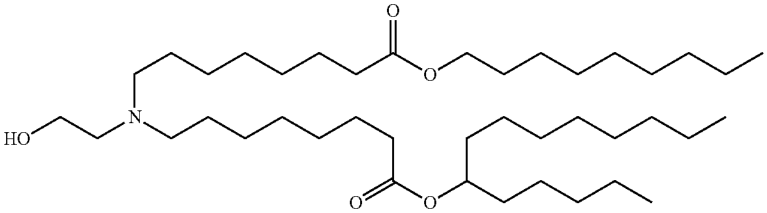
,
(Compound 34)
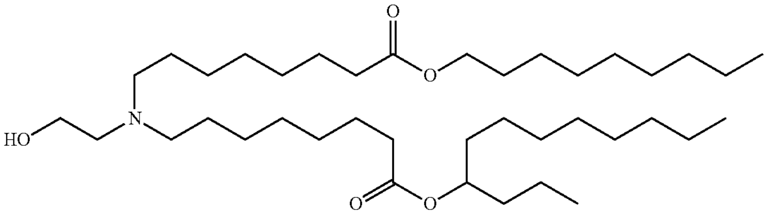
, -continued
(Compound 35)
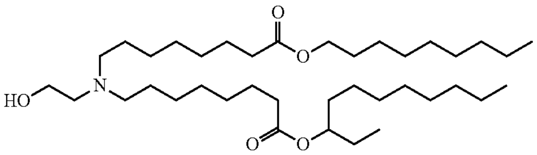
,
(Compound 36)
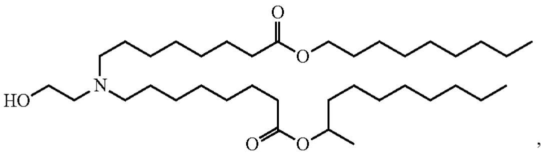
,
(Compound 37)
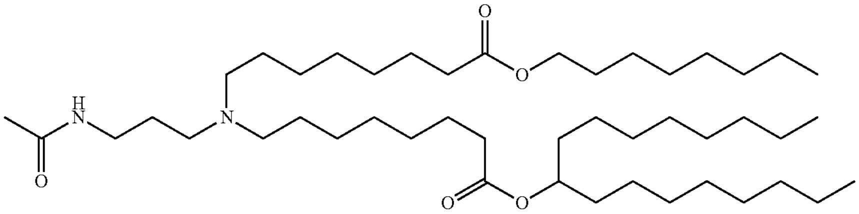
,
(Compound 38)
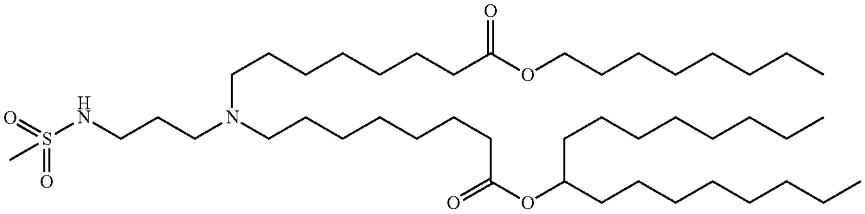
,
(Compound 39)
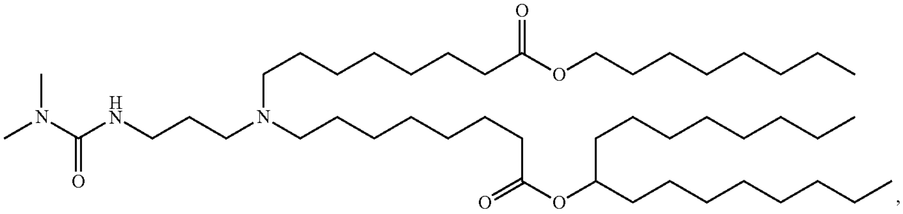
,
(Compound 40)
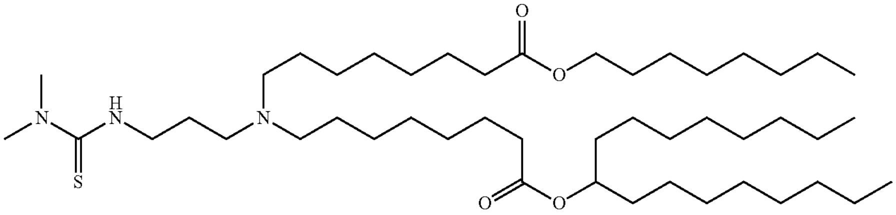
,
(Compound 41)
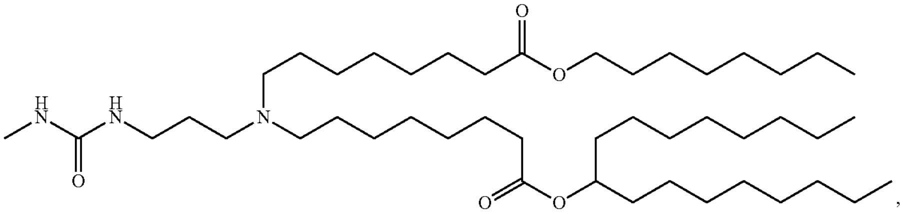
,
(Compound 42)
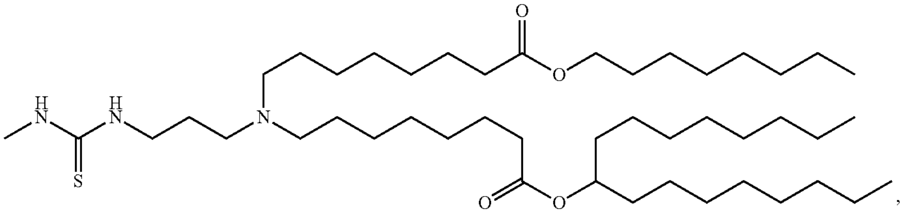
, -continued
(Compound 43)
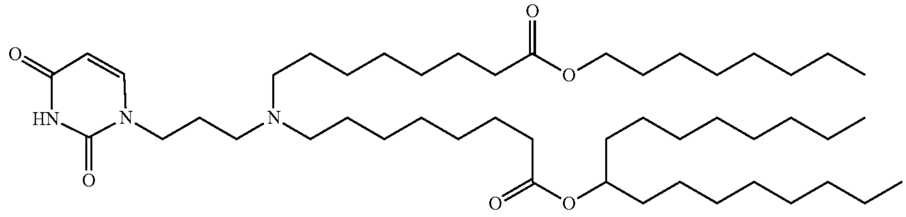
,
(Compound 44)
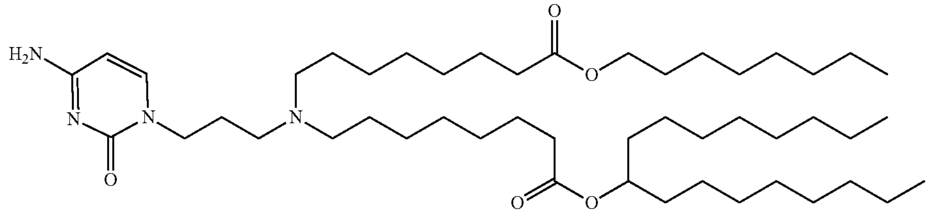
,
(Compound 45)
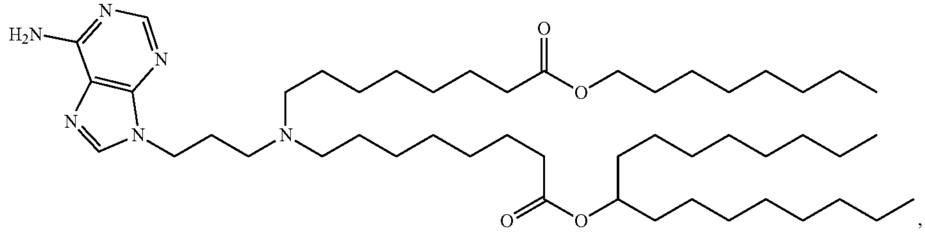
,
(Compound 46)
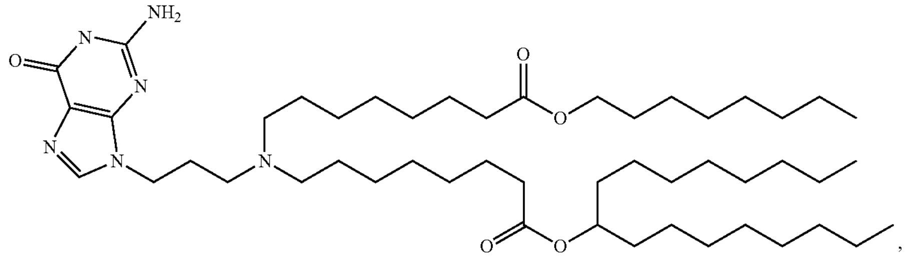
,
(Compound 47)
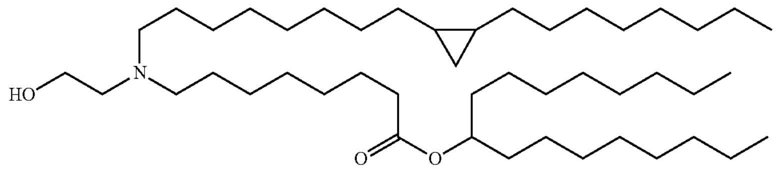
,
(Compound 48)
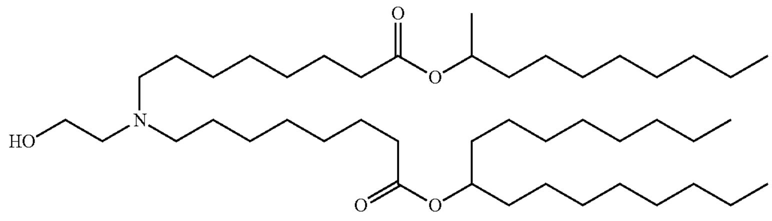
,
(Compound 49)
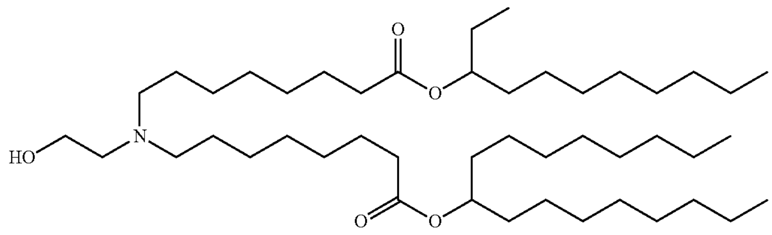
, -continued
(Compound 50)
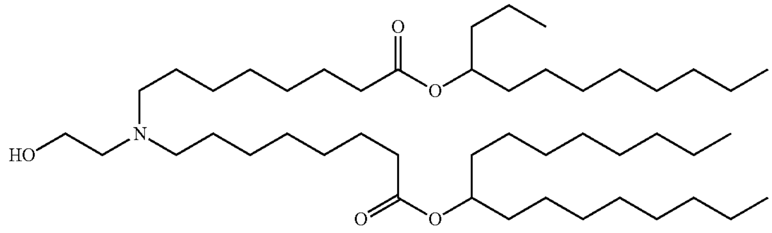
,
(Compound 51)
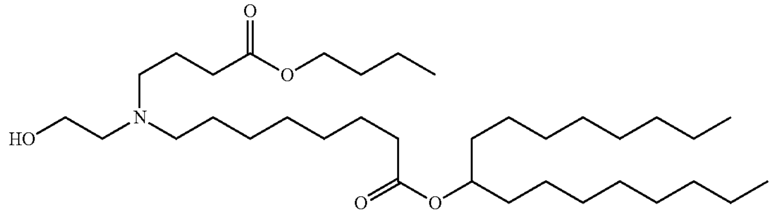
,
(Compound 52)
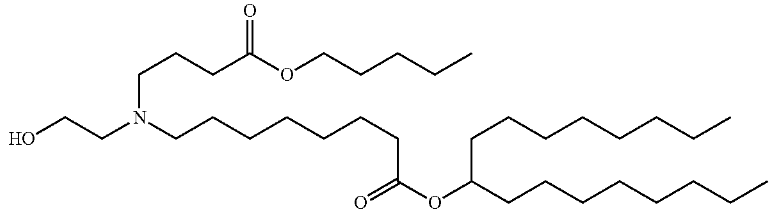
,
(Compound 53)
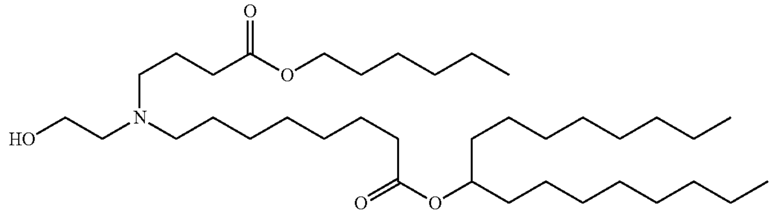
,
(Compound 54)
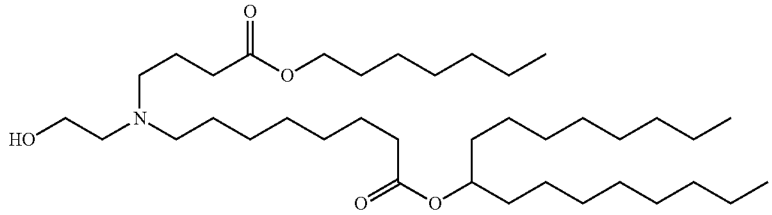
,
(Compound 55)
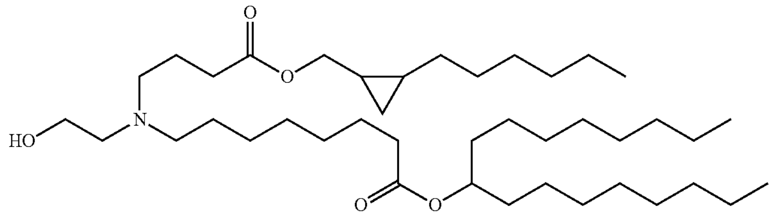
, -continued
(Compound 56)
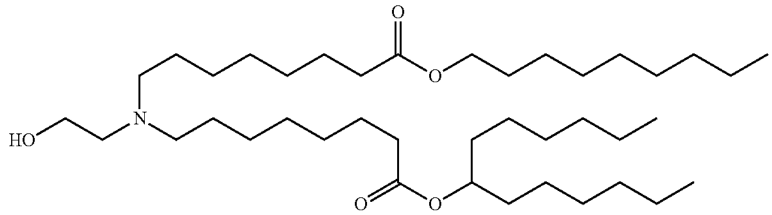
,
(Compound 57)
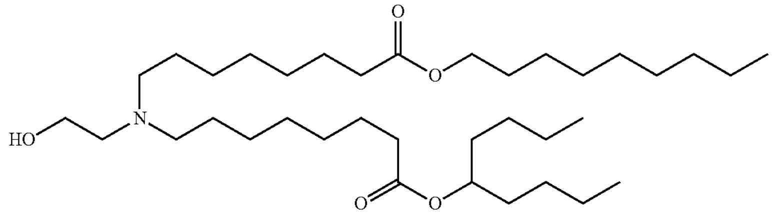
,
(Compound 58)
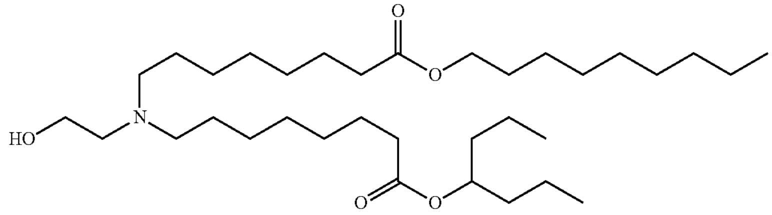
,
(Compound 59)
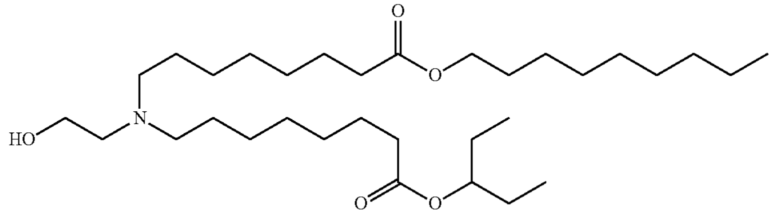
,
(Compound 60)
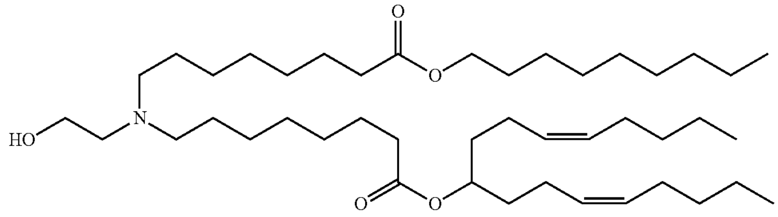
, and
(Compound 61)
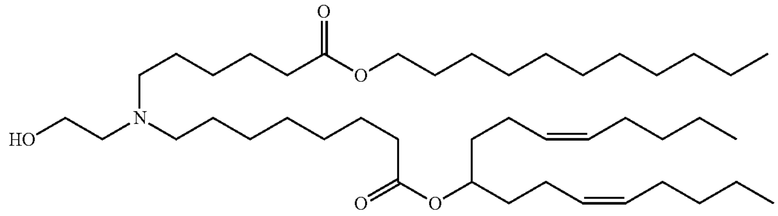
.

In further embodiments, the compound of Formula (I) is selected from the group consisting of:
(Compound 62)
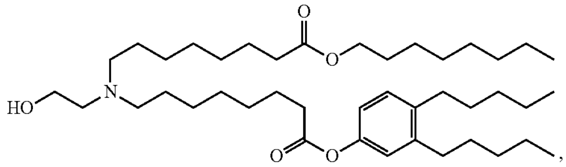
,
-continued
(Compound 63)
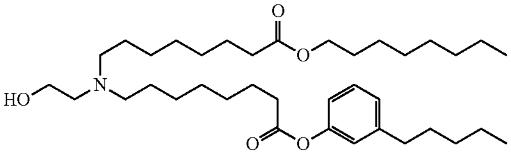
and
(Compound 64)
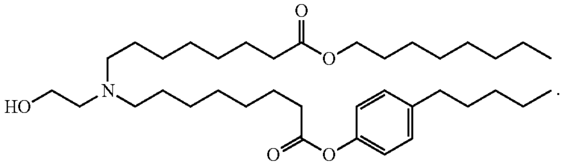
.
In some embodiments, the compound of Formula (I) is selected from the group consisting of:
(Compound 65)
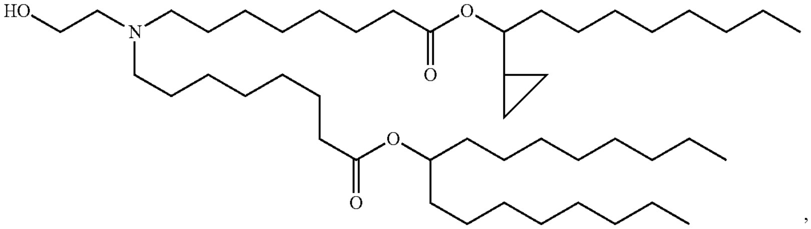
,
(Compound 66)
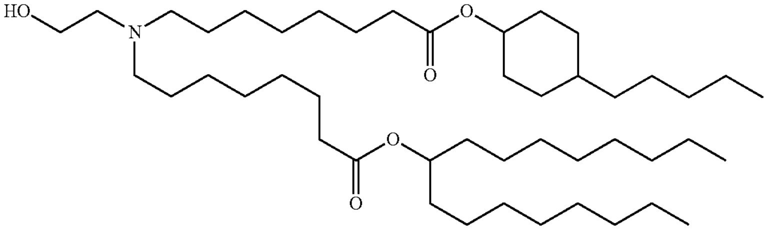
,
(Compound 67)
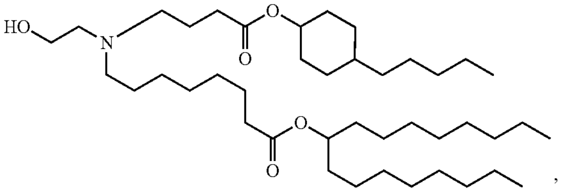
,
(Compound 68)
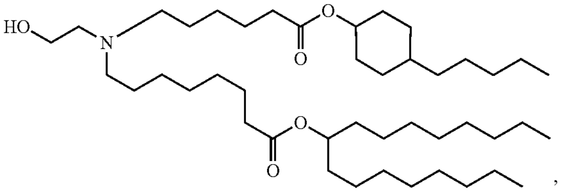
,
(Compound 69)
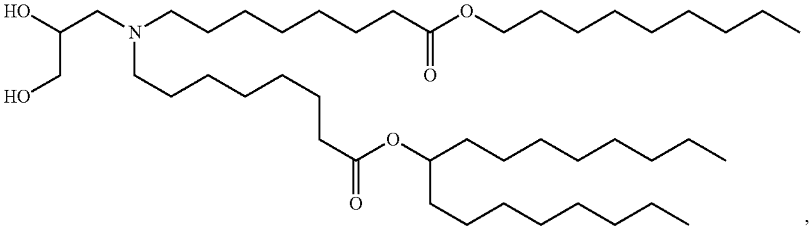
,
(Compound 70)
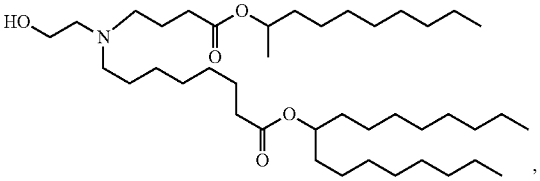
,
(Compound 71)
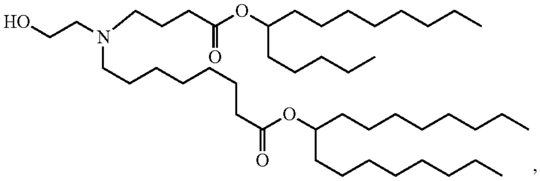
, -continued
(Compound 72)
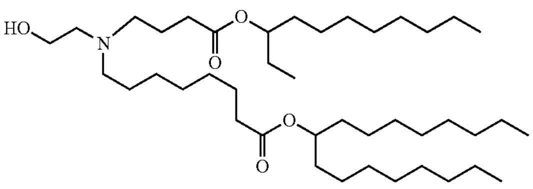
,
(Compound 73)
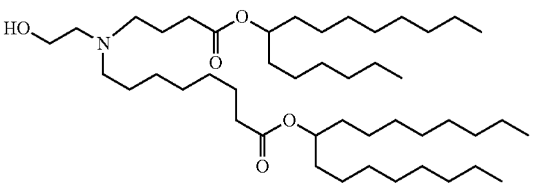
,
(Compound 74)
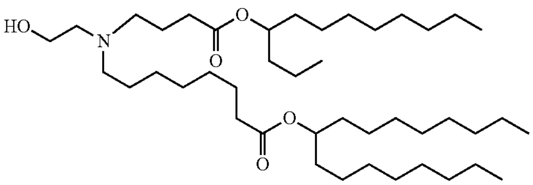
,
(Compound 75)
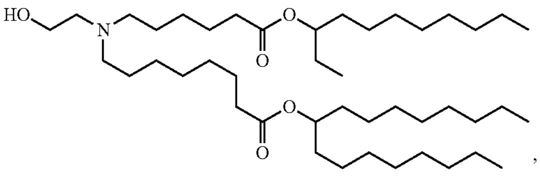
,
(Compound 76)
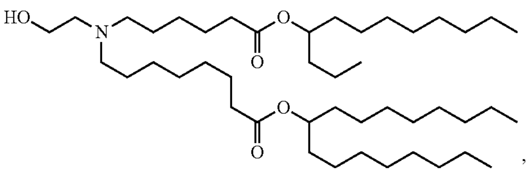
,
(Compound 77)
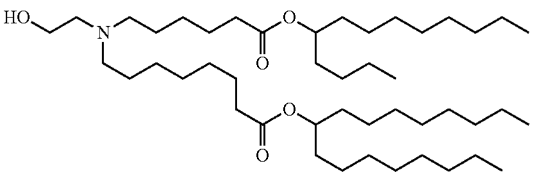
,
(Compound 78)
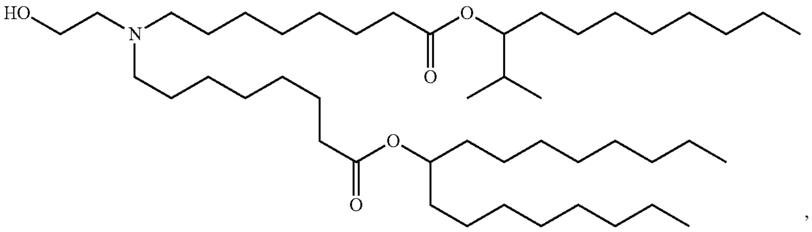
,
(Compound 79)
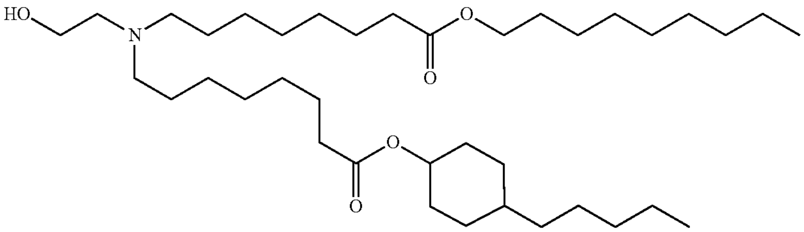
,
(Compound 80)
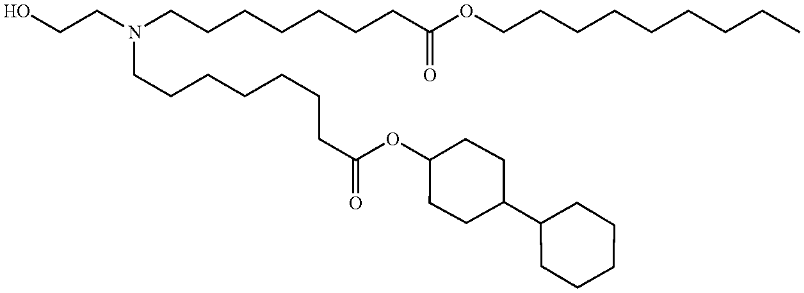
, -continued
(Compound 81)
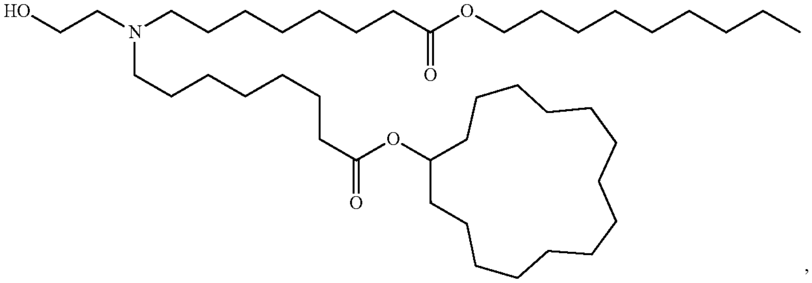
,
(Compound 82)
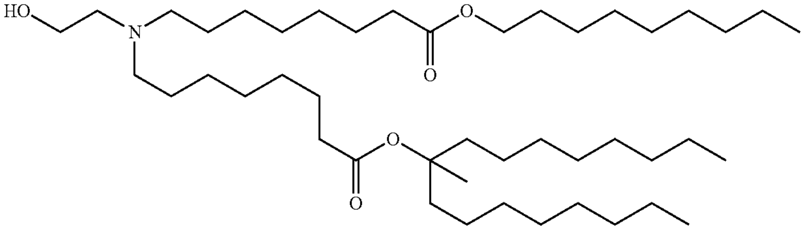
,
(Compound 83)
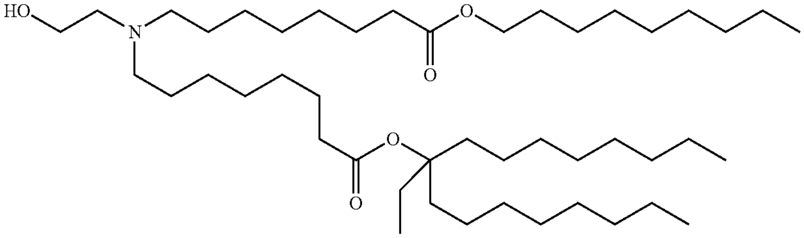
,
(Compound 84)
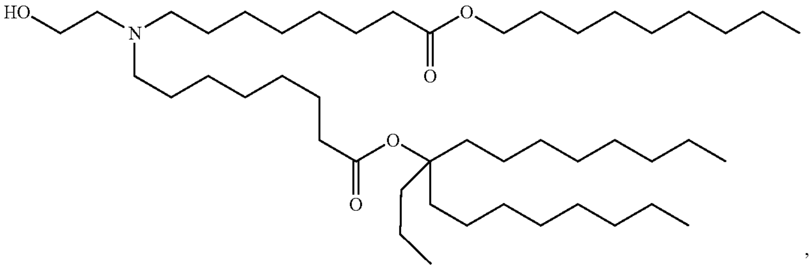
,
(Compound 85)
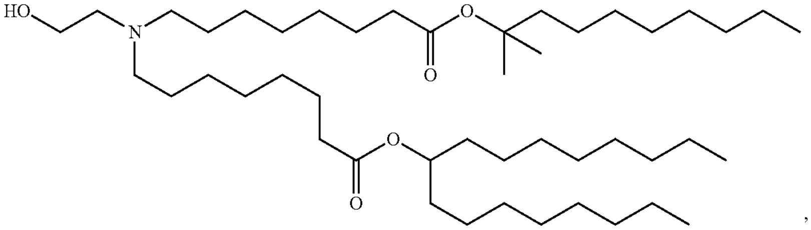
,
(Compound 86)
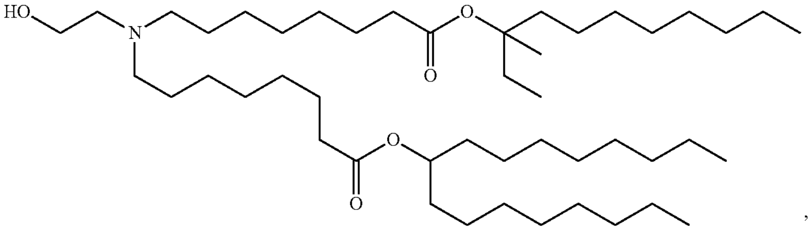
, -continued
(Compound 87)
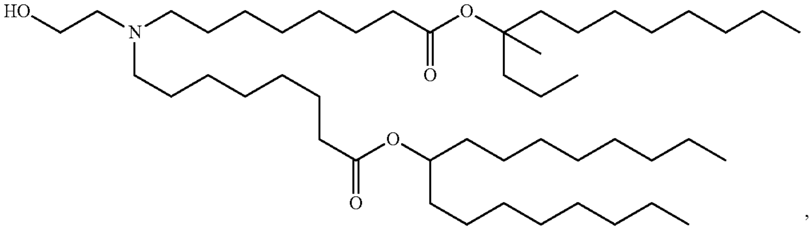
,
(Compound 88)
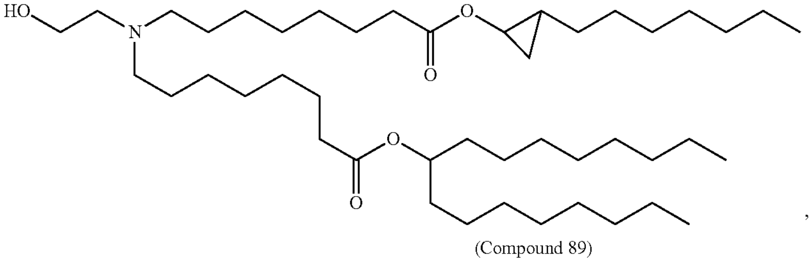
,
(Compound 89)
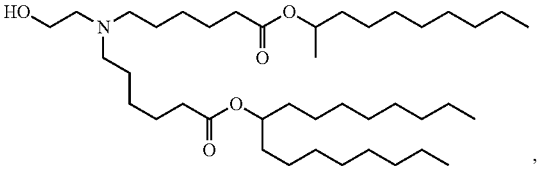
,
(Compound 90)
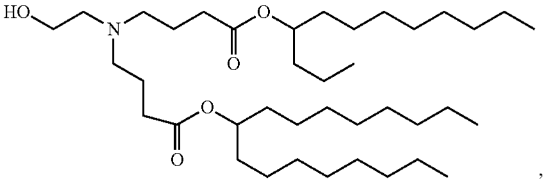
,
(Compound 91)
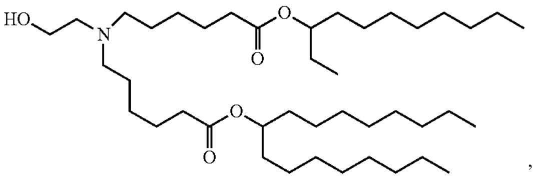
,
(Compound 92)
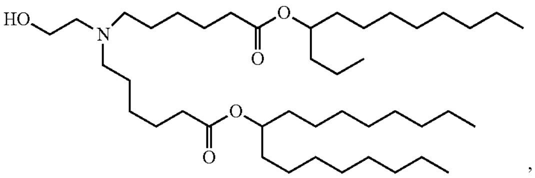
,
(Compound 93)
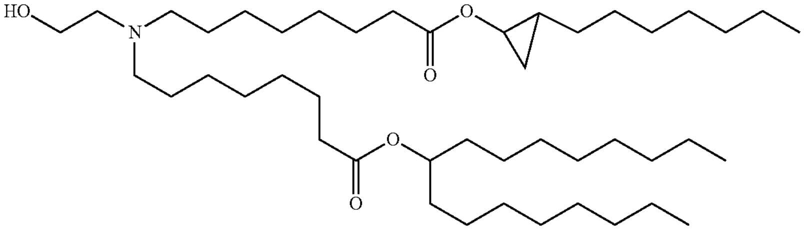
,
(Compound 94)
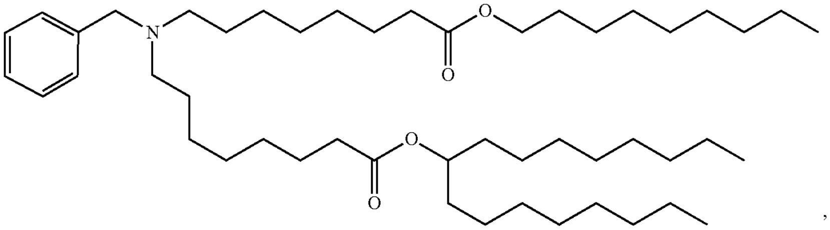
,
(Compound 95)
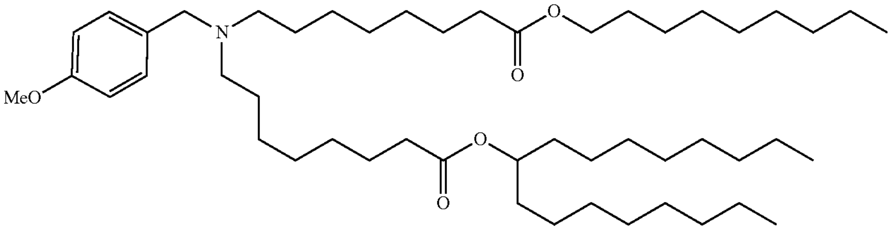
, -continued
(Compound 96)
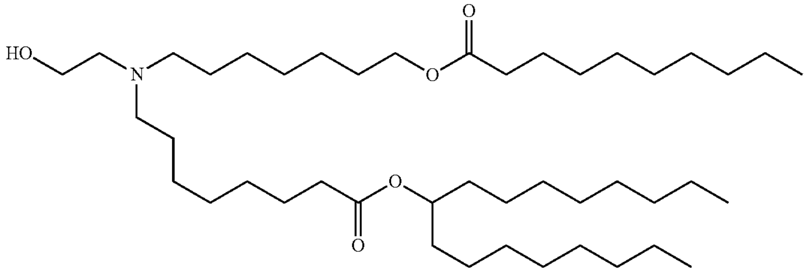
,
(Compound 97)
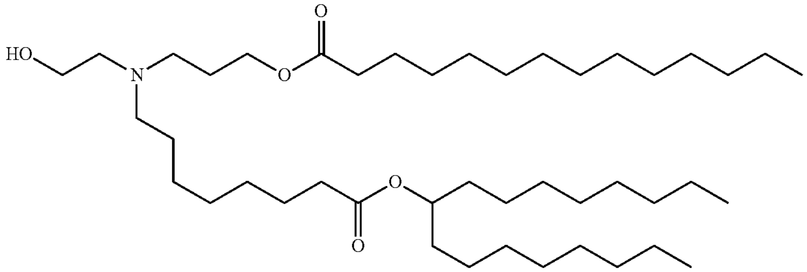
,
(Compound 98)
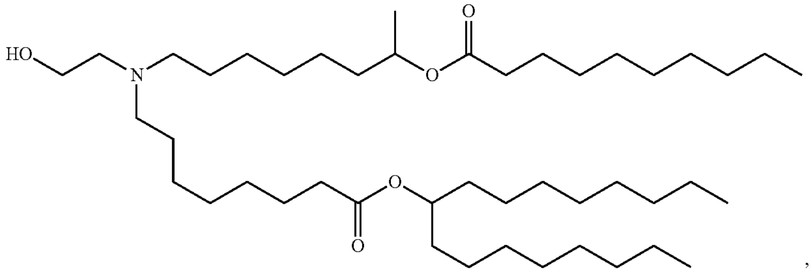
,
(Compound 99)
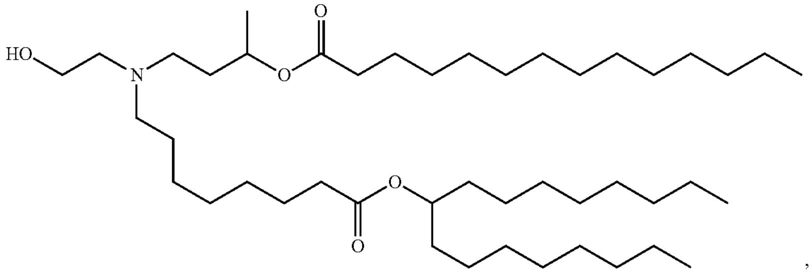
,
(Compound 100)
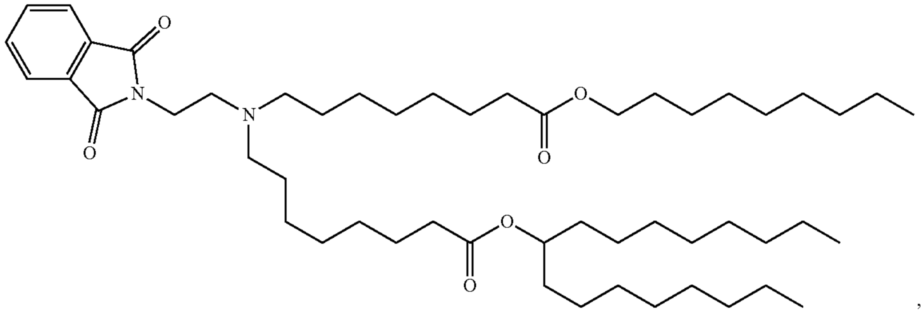
, -continued
(Compound 101)
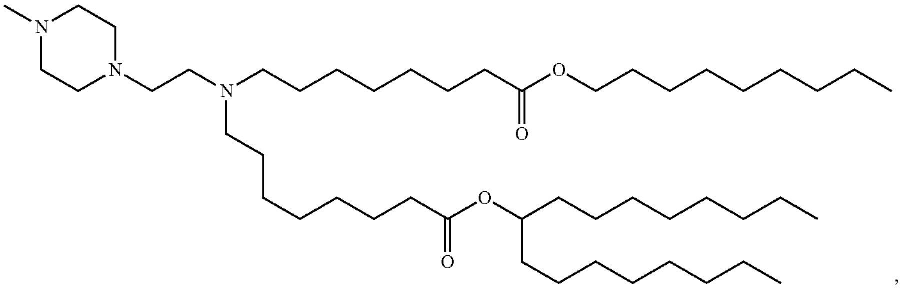
,
(Compound 102)
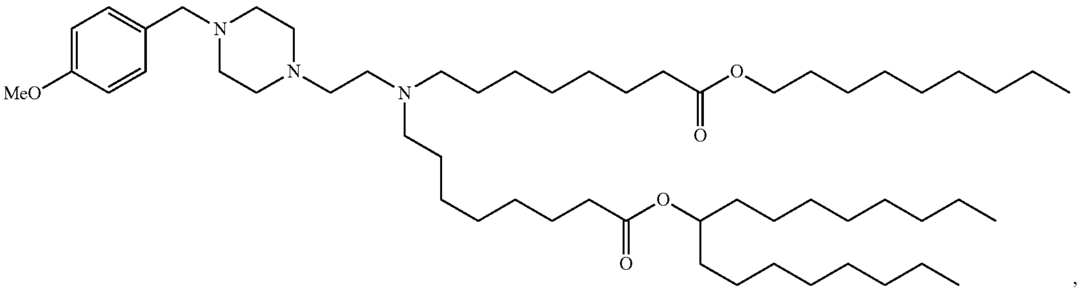
,
(Compound 103)
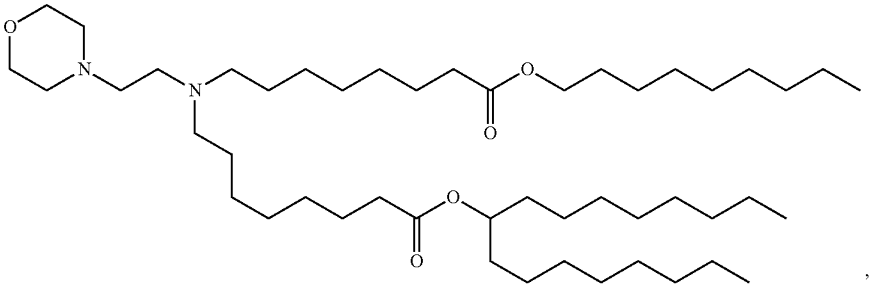
,
(Compound 104)
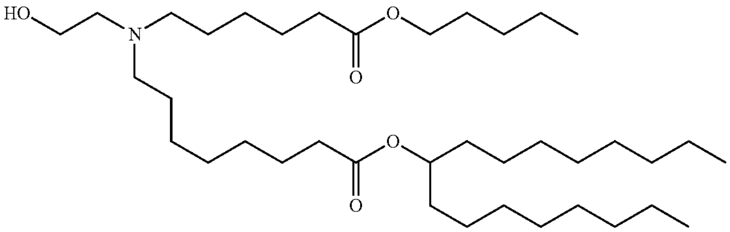
,
(Compound 105)
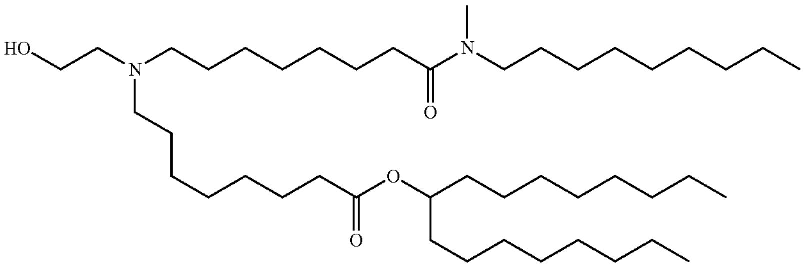
, -continued
(Compound 106)
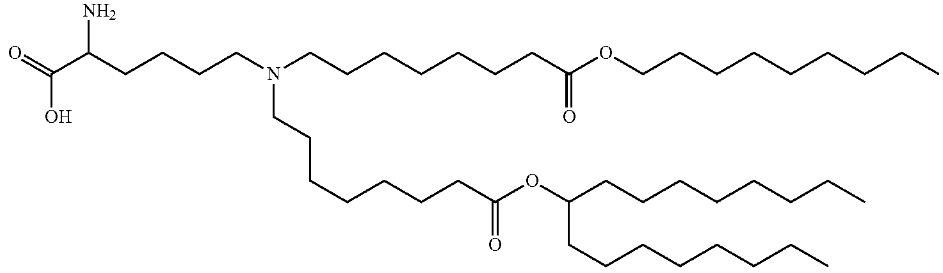
,
(Compound 107)
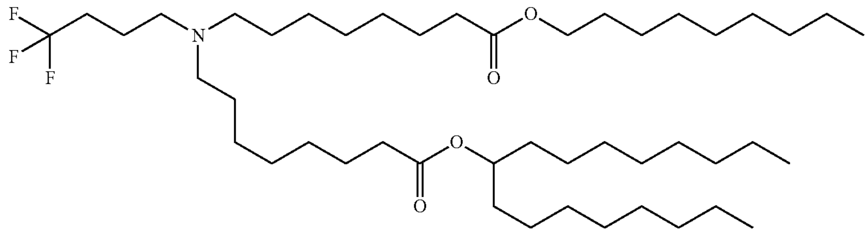
,
(Compound 108)
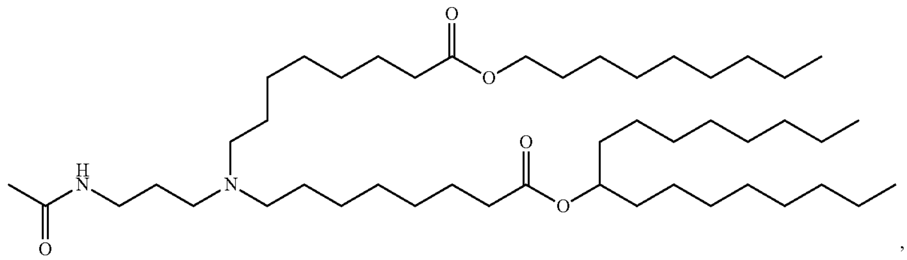
,
(Compound 109)
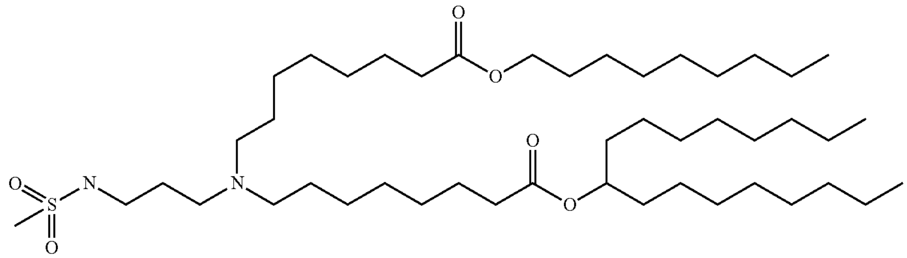
,
(Compound 110)
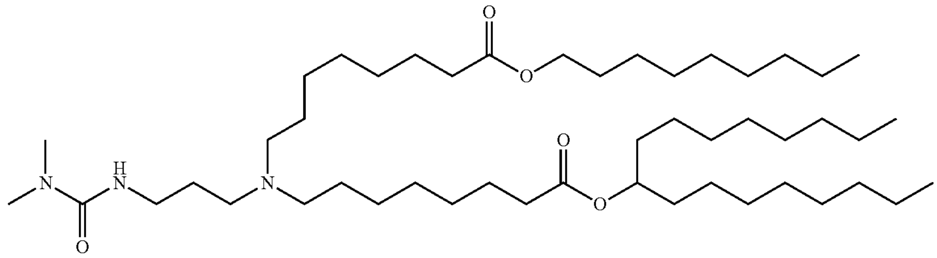
,
(Compound 111)
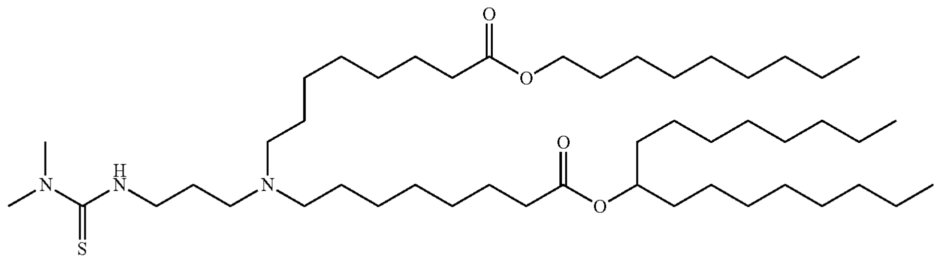
, -continued
(Compound 112)
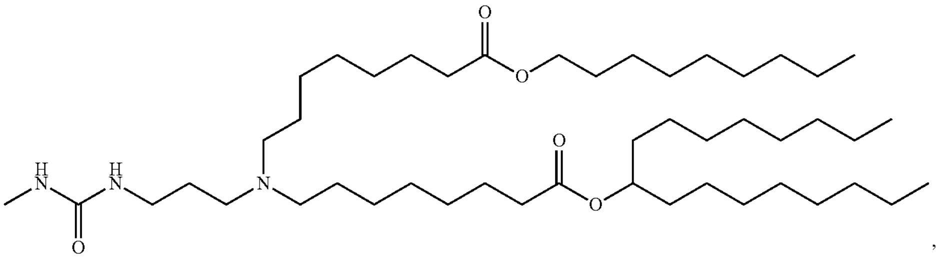
,
(Compound 113)
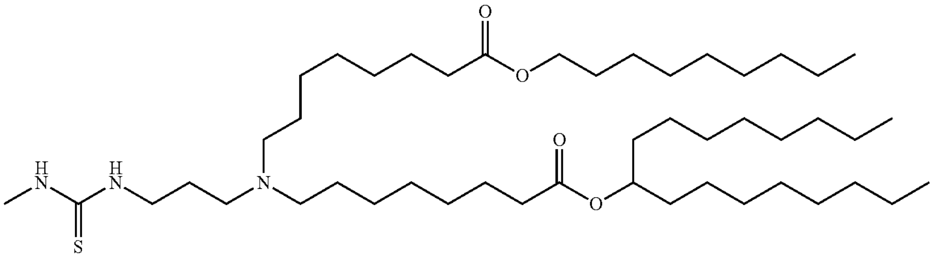
,
(Compound 114)
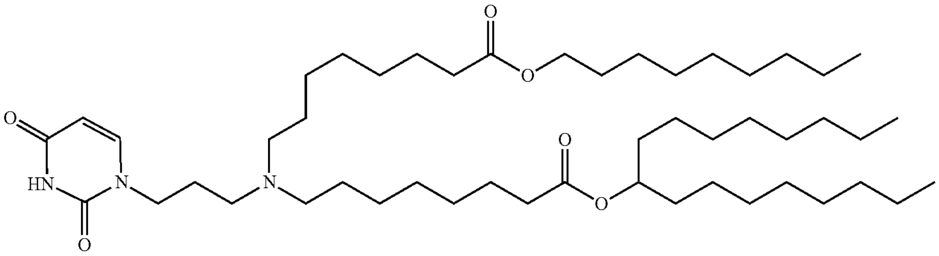
,
(Compound 115)
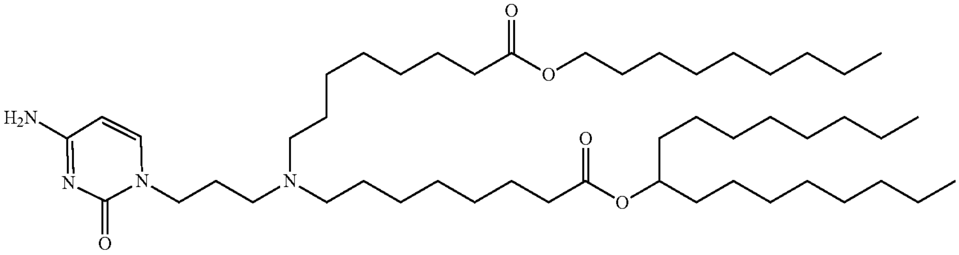
,
(Compound 116)
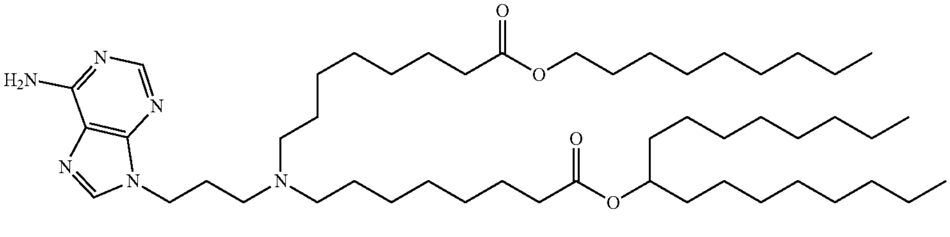
,
(Compound 117)
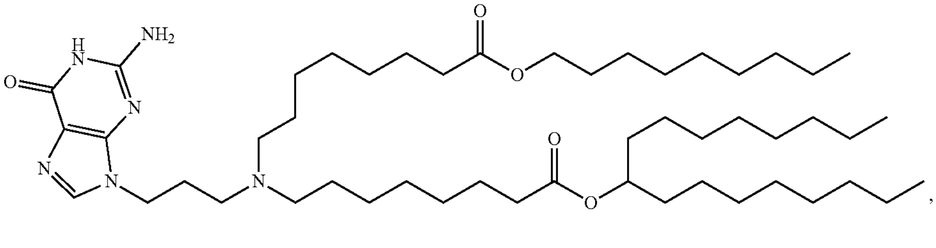
, -continued
(Compound 118)
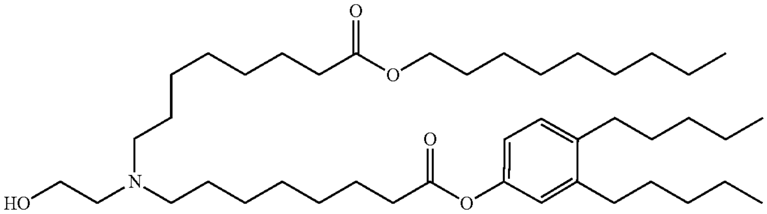
,
(Compound 119)
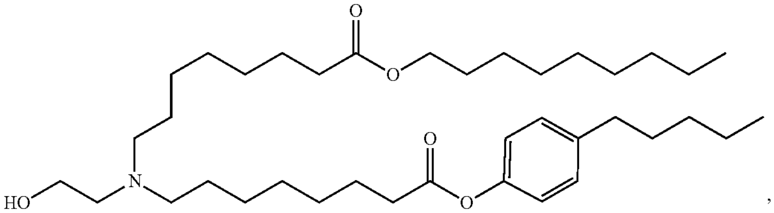
,
(Compound 120)
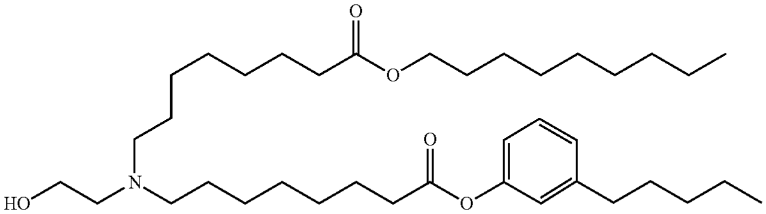
,
(Compound 121)
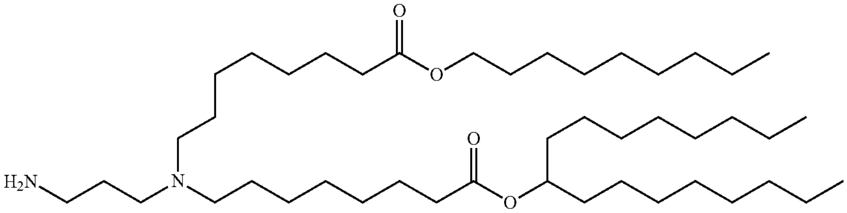
,
(Compound 122)
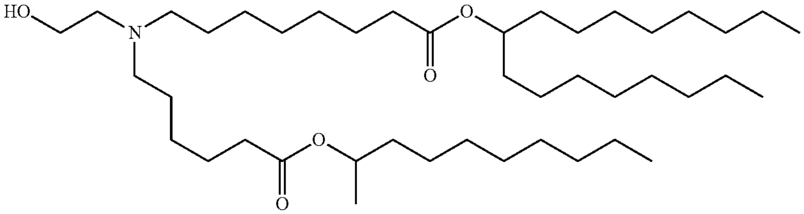
,
(Compound 123)
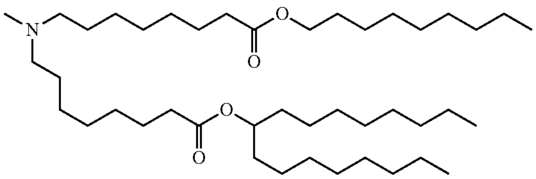
,
(Compound 124)
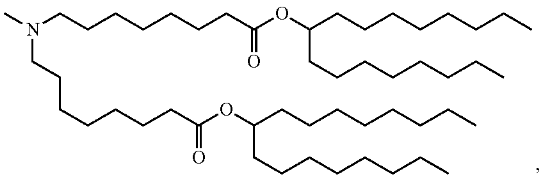
,
(Compound 125)
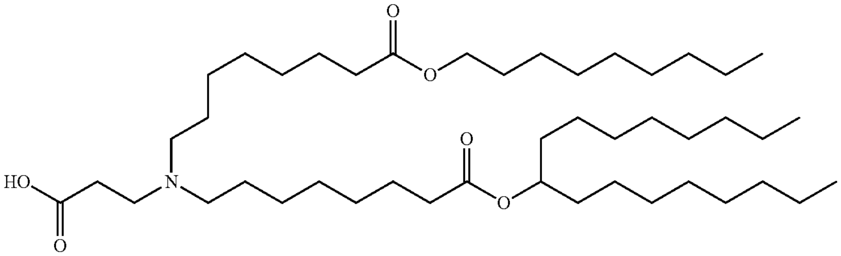
, -continued
(Compound 126)
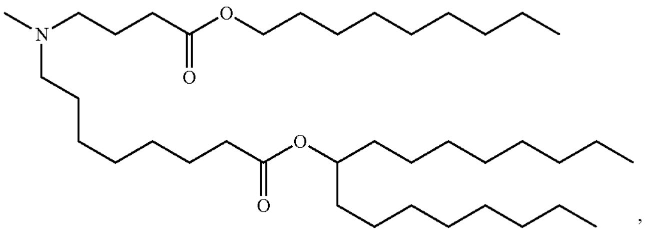
,
(Compound 127)
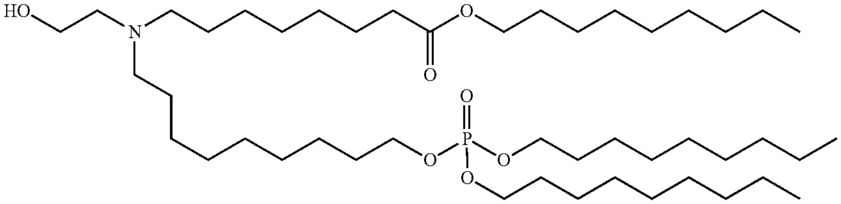
,
(Compound 128)
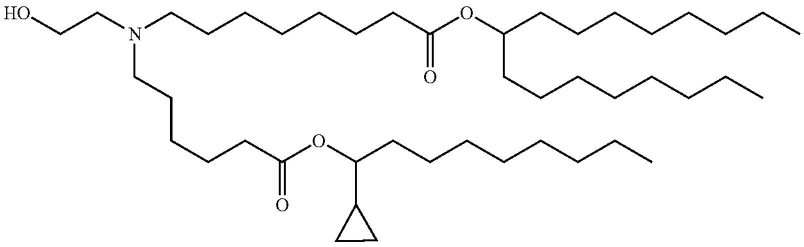
,
(Compound 129)
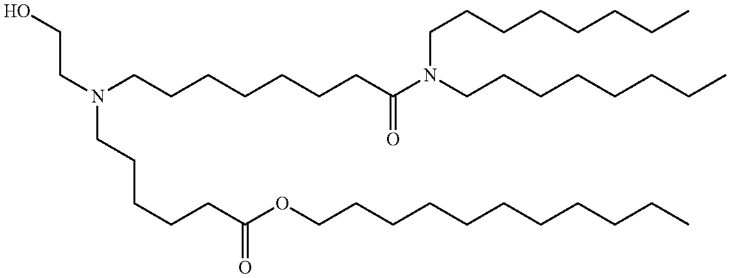
,
(Compound 130)
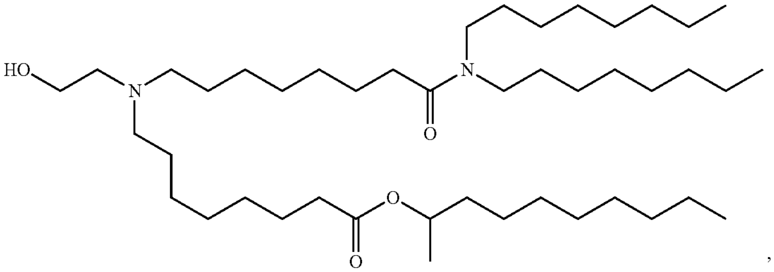
,
(Compound 131)
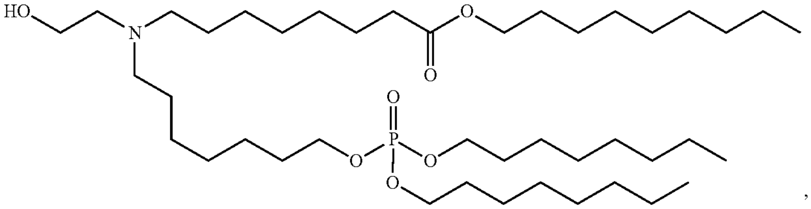
, -continued
(Compound 132)
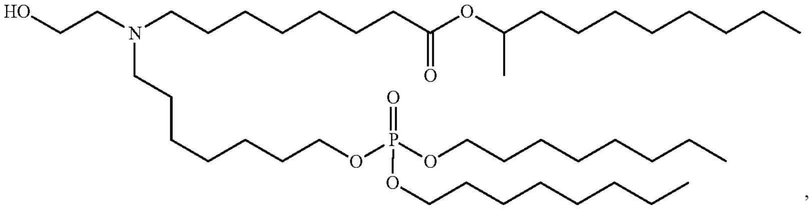
,
(Compound 133)
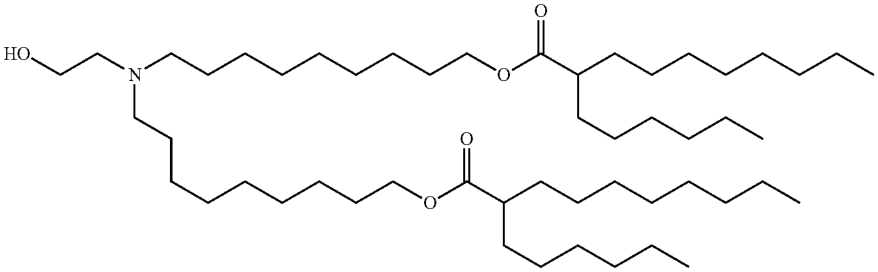
,
(Compound 134)
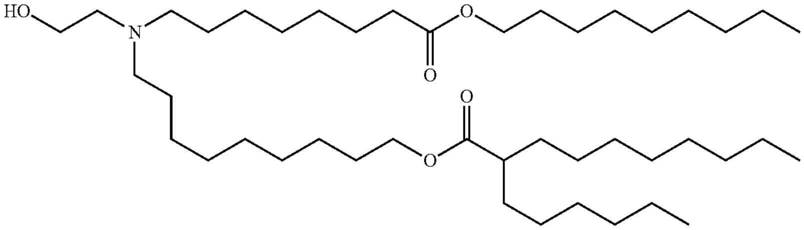
,
(Compound 135)
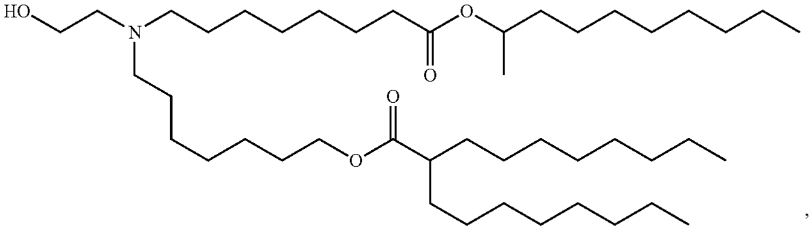
,
(Compound 136)
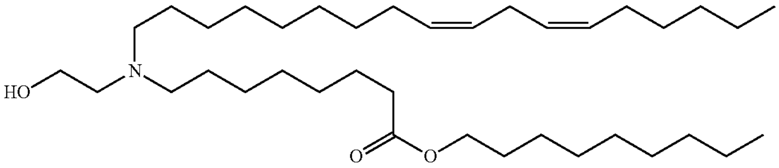
,
(Compound 137)
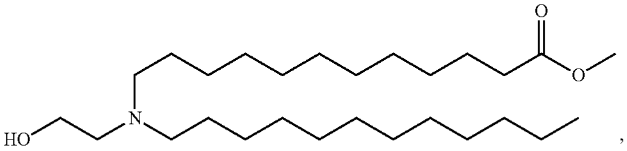
,
(Compound 138)
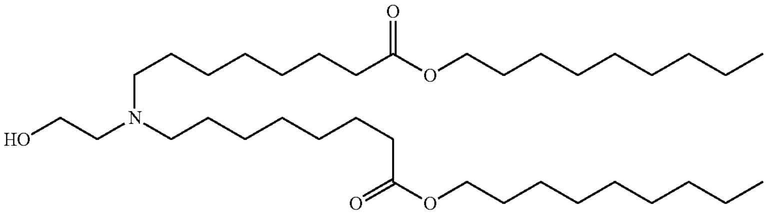
, -continued
(Compound 139)
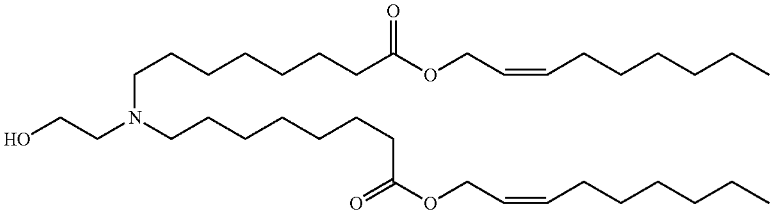
,
(Compound 140)
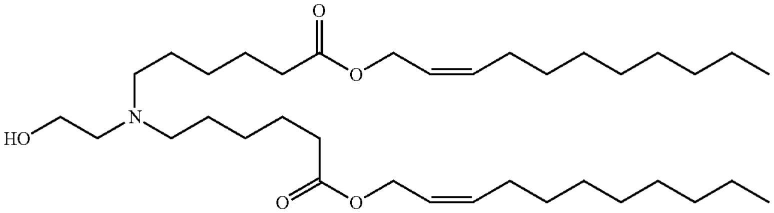
,
(Compound 141)
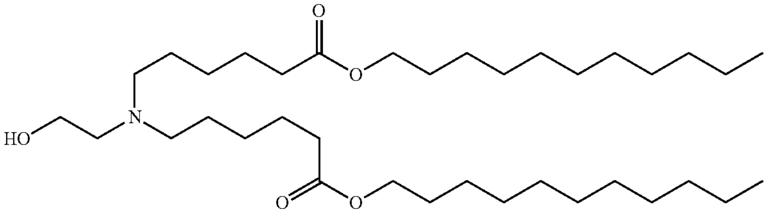
,
(Compound 142)
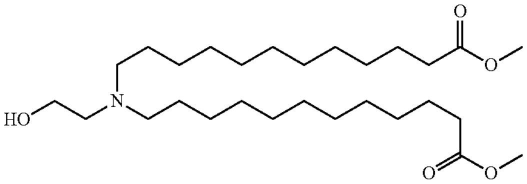
,
(Compound 143)
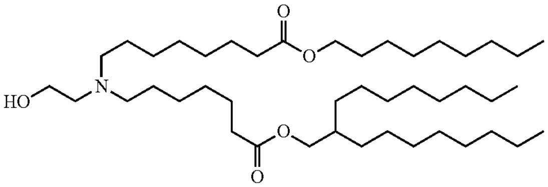
,
(Compound 144)
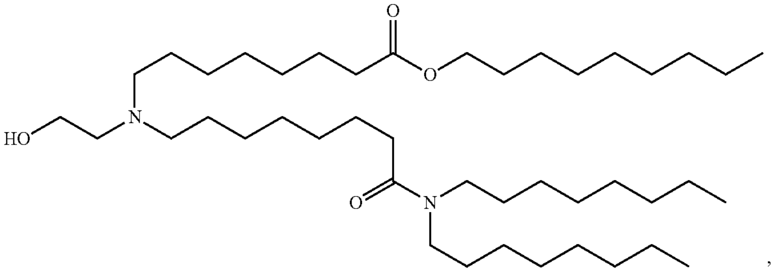
,
(Compound 145)
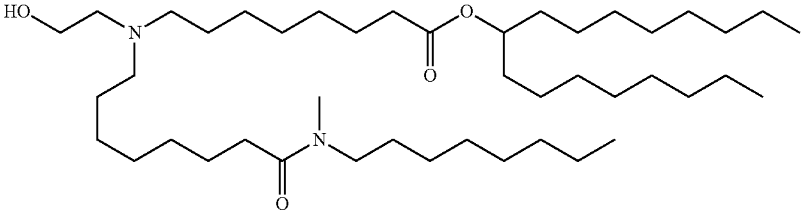
,
(Compound 146)
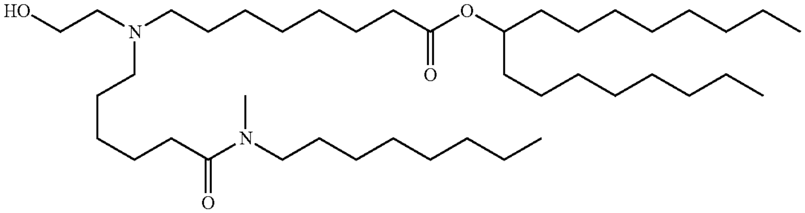
, -continued
(Compound 147)
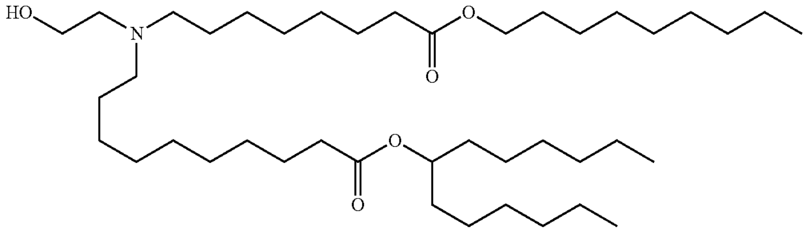
,
(Compound 148)
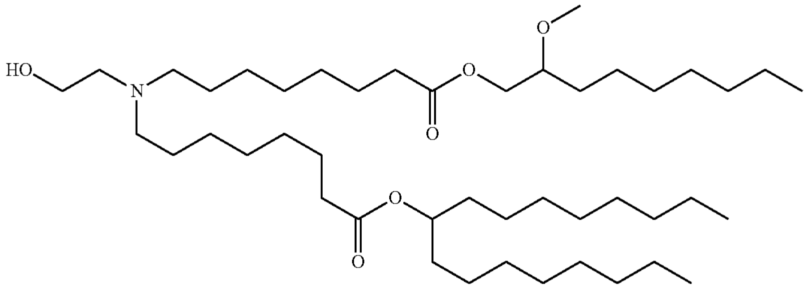
,
(Compound 149)
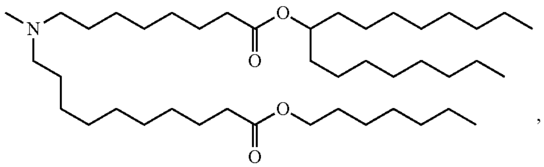
,
(Compound 150)
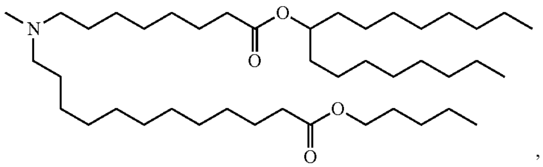
,
(Compoound 151)
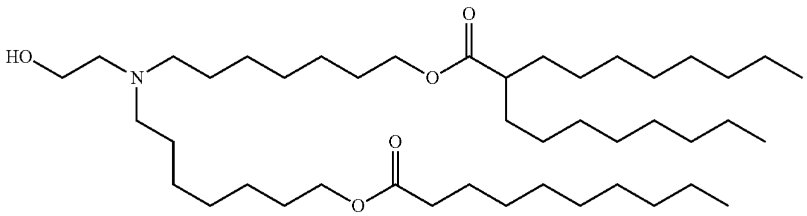
,
(Compound 152)
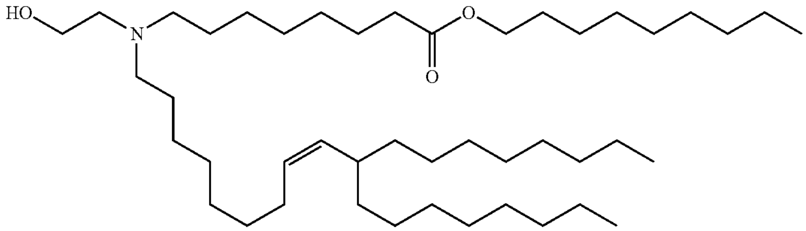
,
(Compound 153)
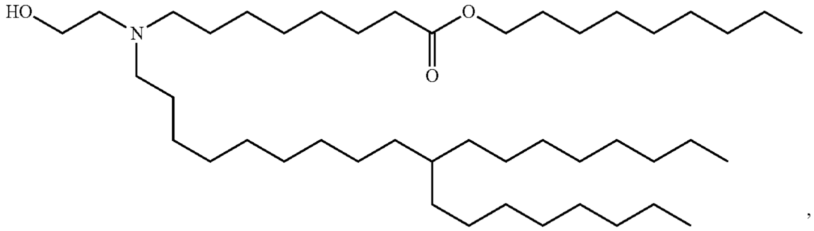
, -continued
(Compound 154)
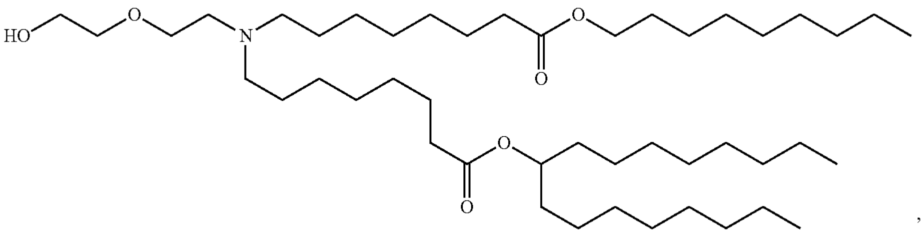
,
(Compound 155)
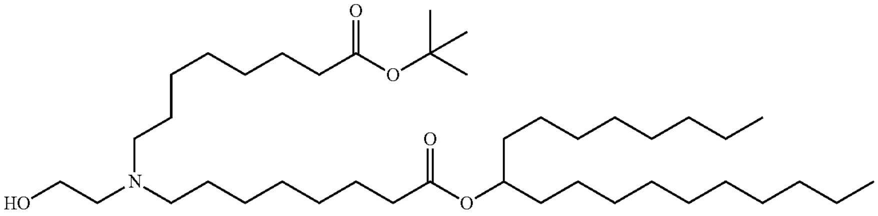
,
(Compound 156)
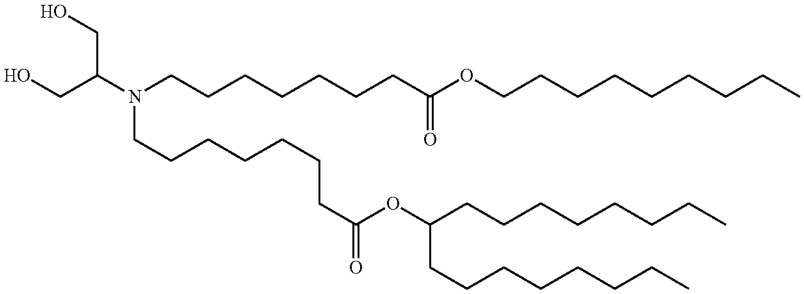
,
(Compound 157)
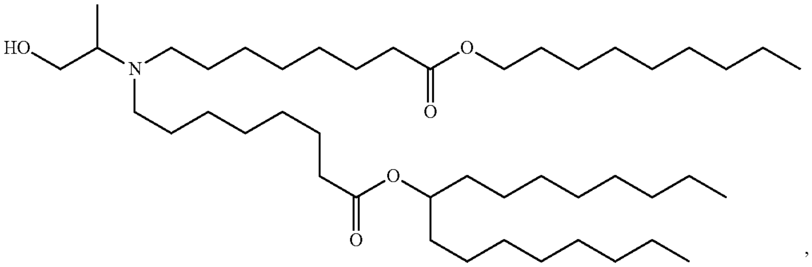
,
(Compound 158)
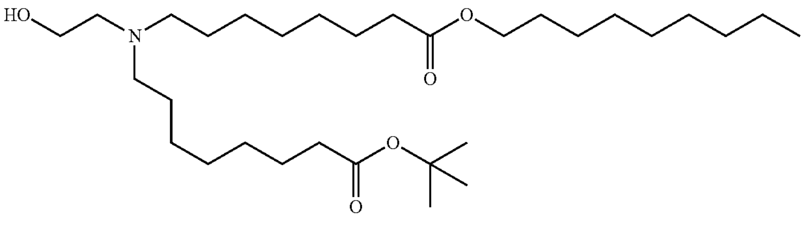
,
(Compound 159)
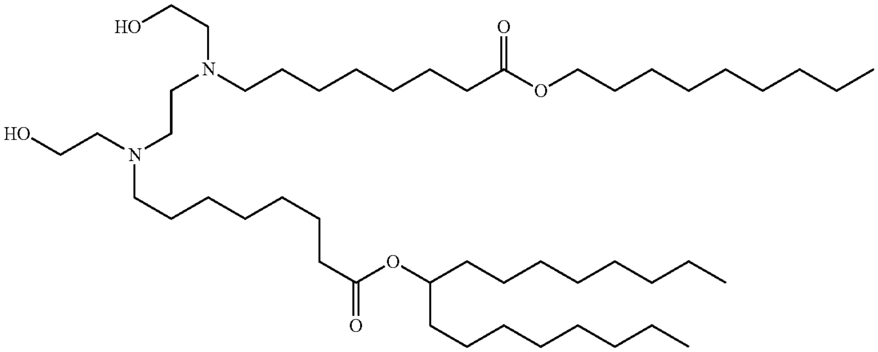
, -continued
(Compound 160)
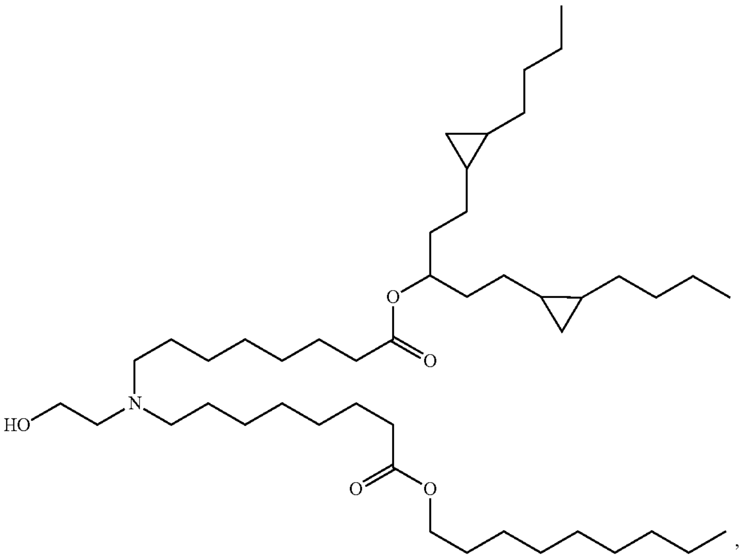
,
(Compound 161)
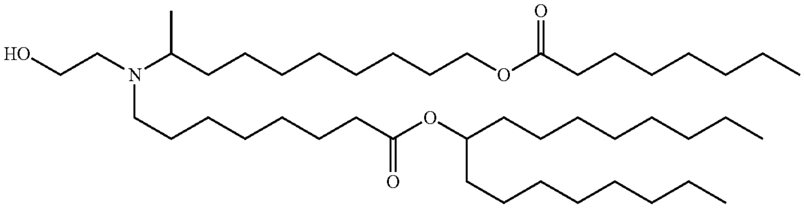
,
(Compound 162)
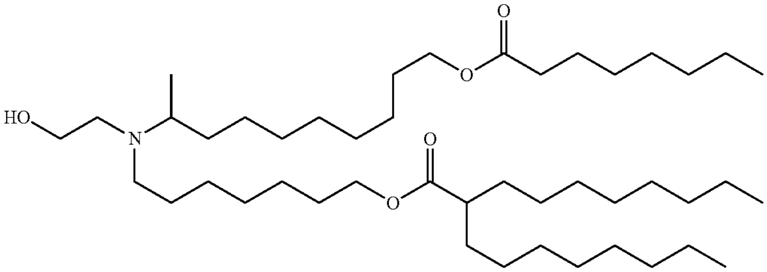
,
(Compound 163)
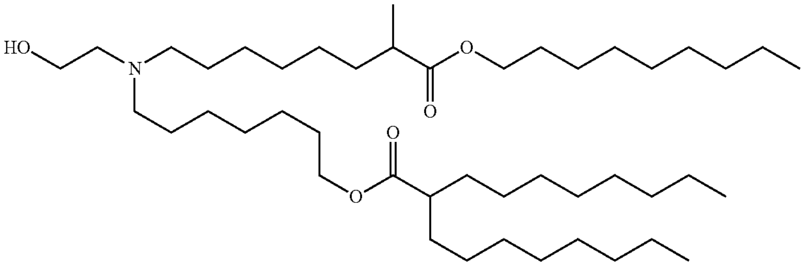
,
(Compound 164)
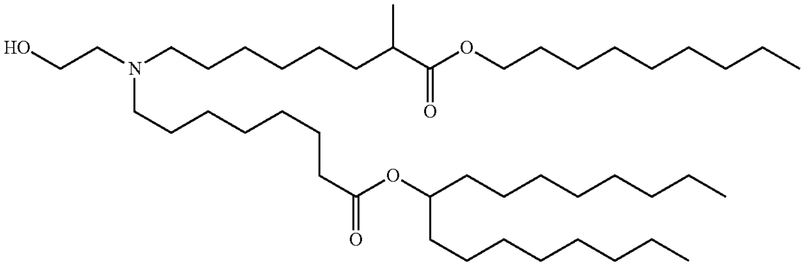
, -continued
(Compound 165)
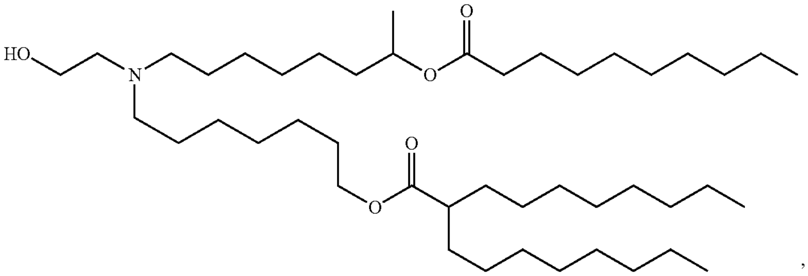
,
(Compound 166)
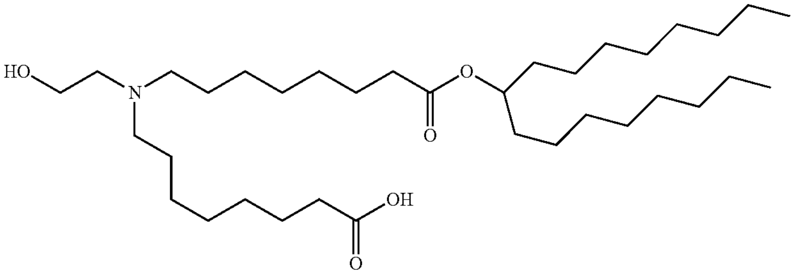
,
(Compound 167)
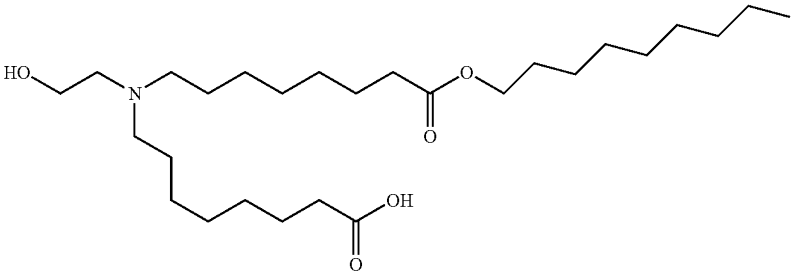
,
(Compound 168)
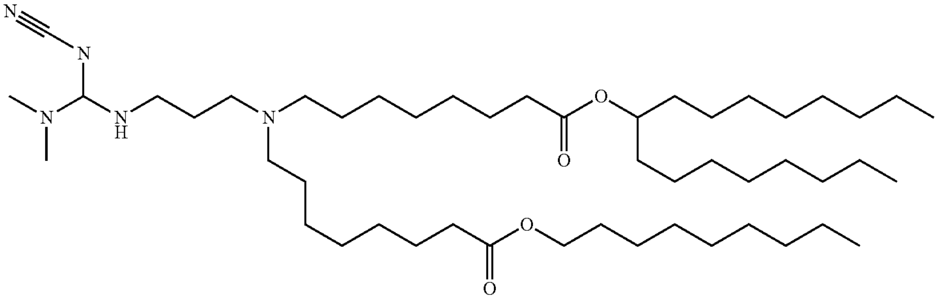
,
(Compound 169)
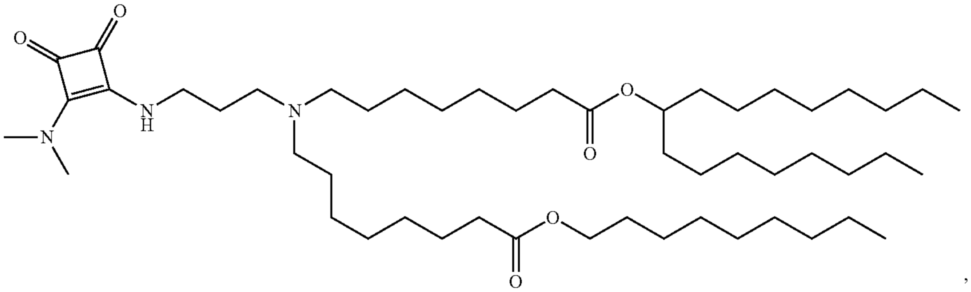
, -continued
(Compound 170)
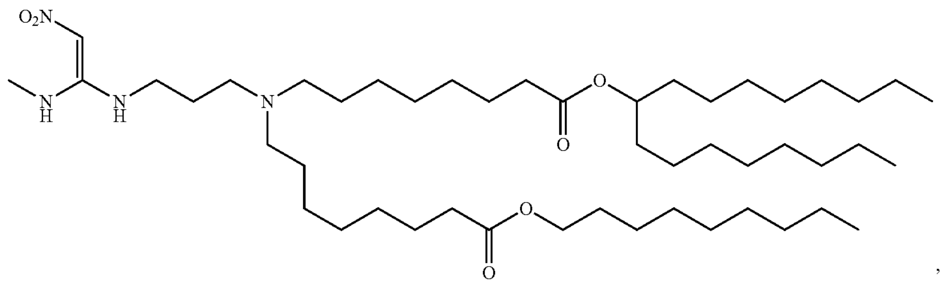
,
(Compound 171)
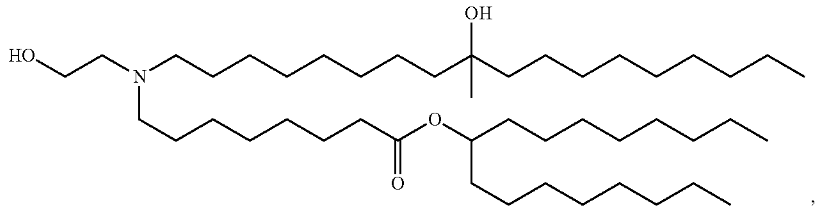
,
(Compound 172)
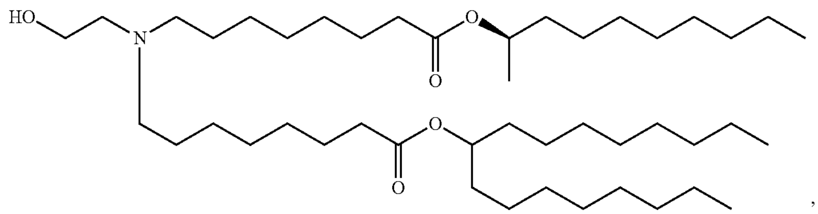
,
(Compound 173)
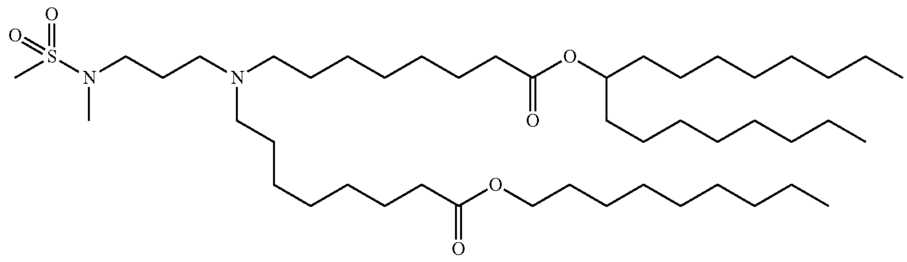
,
(Compound 174)
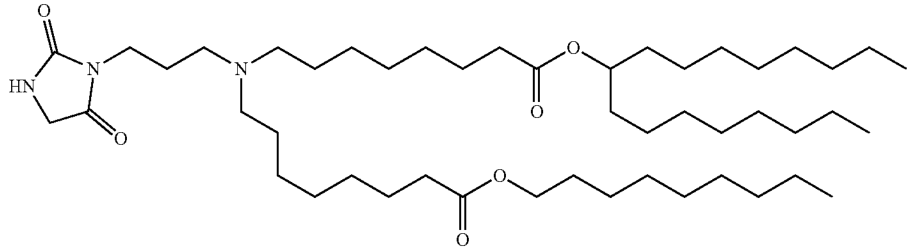
,
(Compound 175)
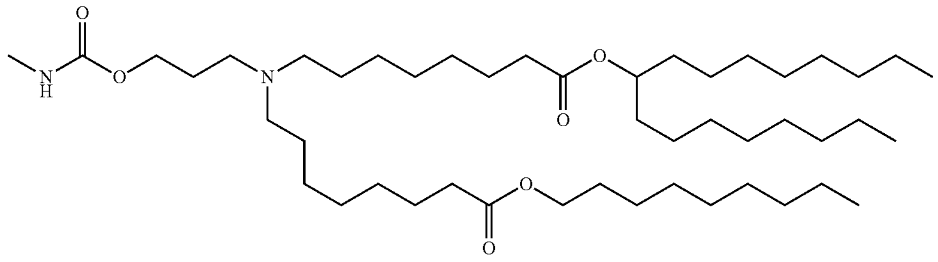
, -continued
(Compound 176)
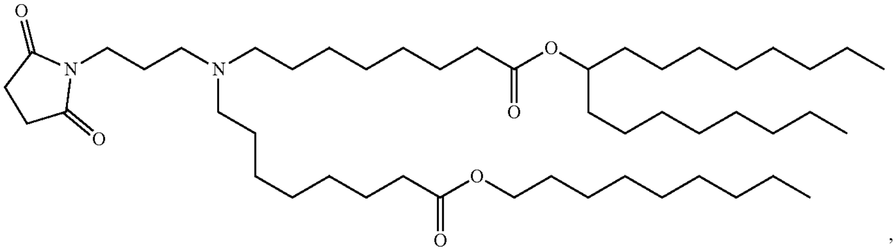
,
(Compound 177)
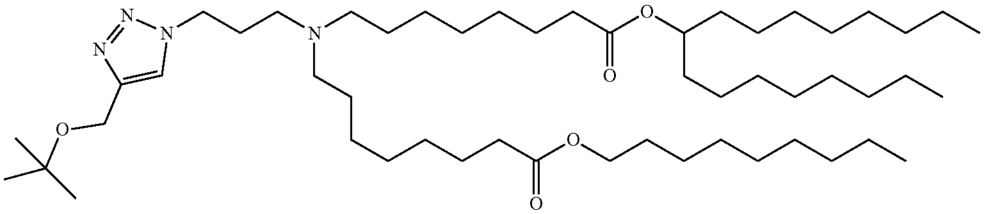
,
(Compound 178)
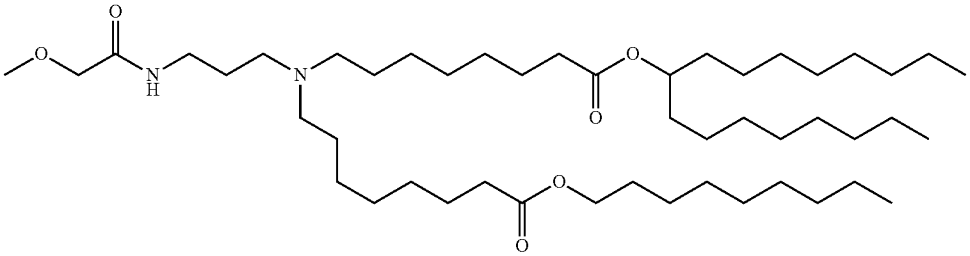
,
(Compound 179)
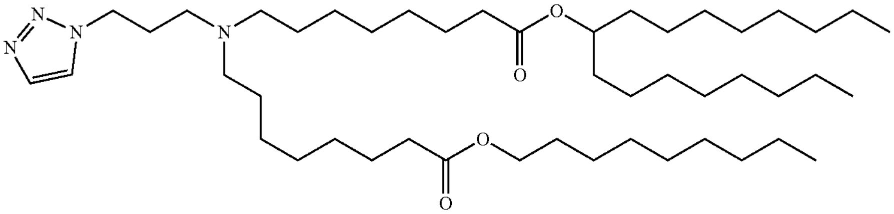
,
(Compound 180)
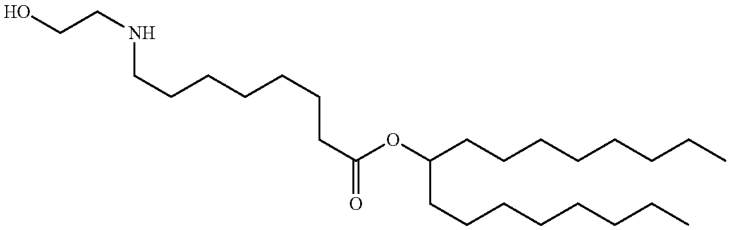
,
(Compound 181)
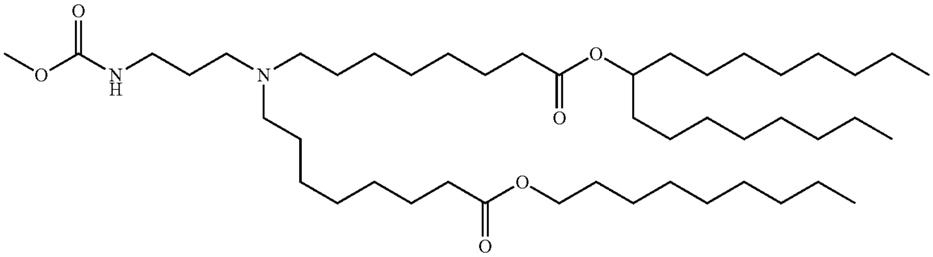
, -continued
(Compound 182)
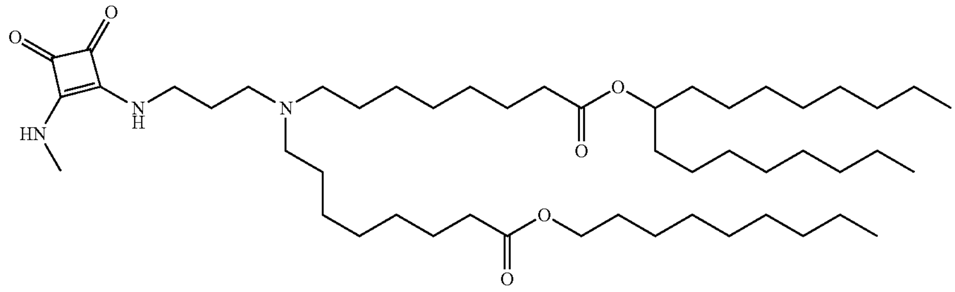
,
(Compound 183)
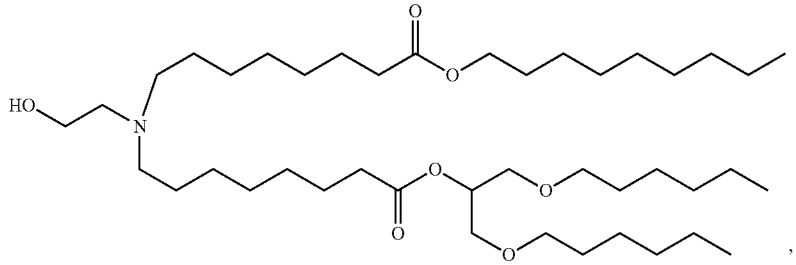
,
(Compound 184)
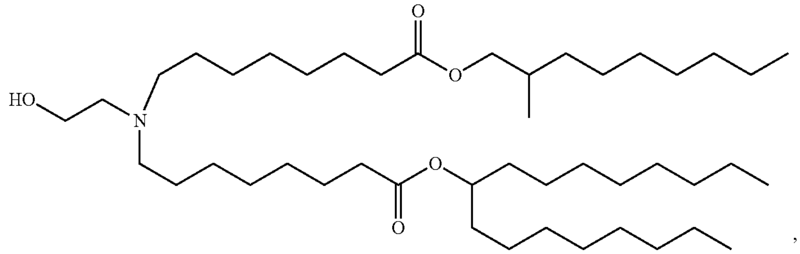
,
(Compound 185)
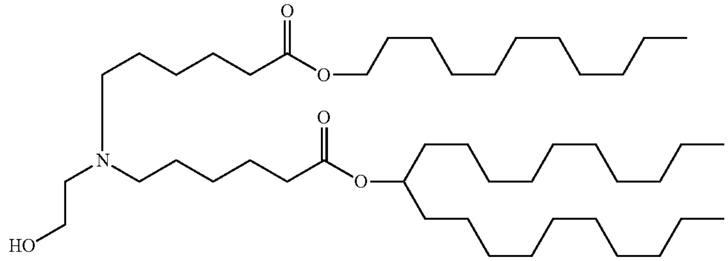
,
(Compound 186)
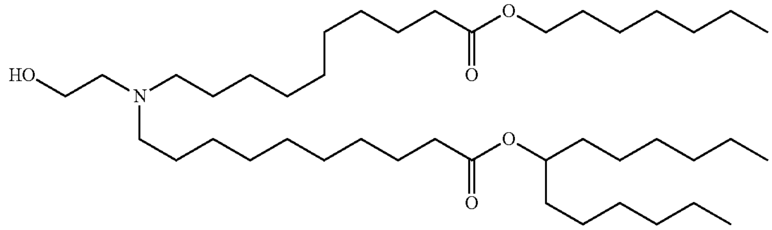
,
(Compound 187)
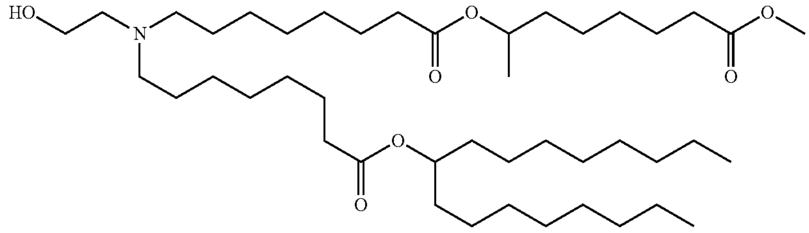
, -continued
(Compound 188)
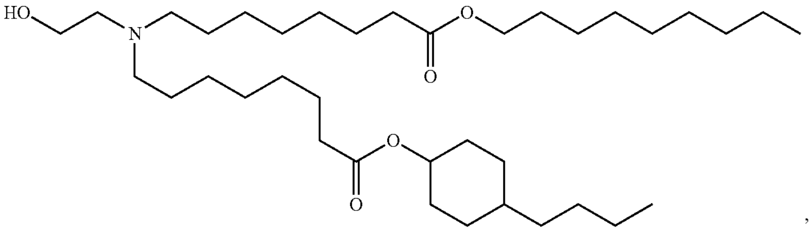
,
(Compound 189)
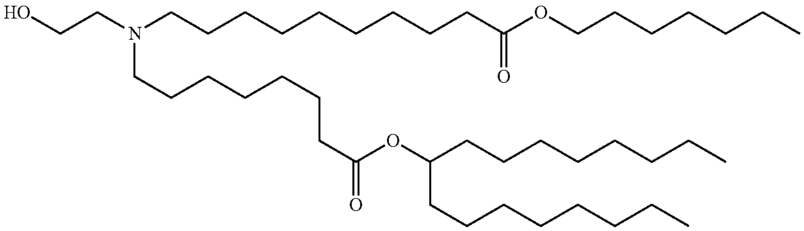
,
(Compound 190)
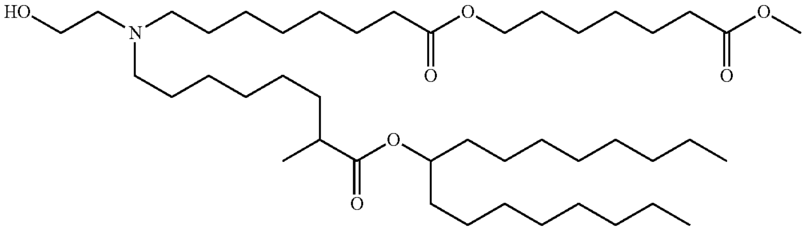
,
(Compound 191)
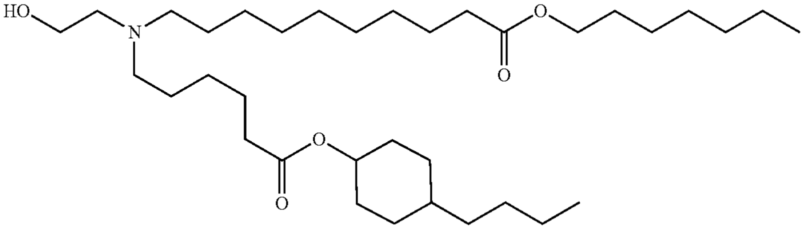
,
(Compound 192)
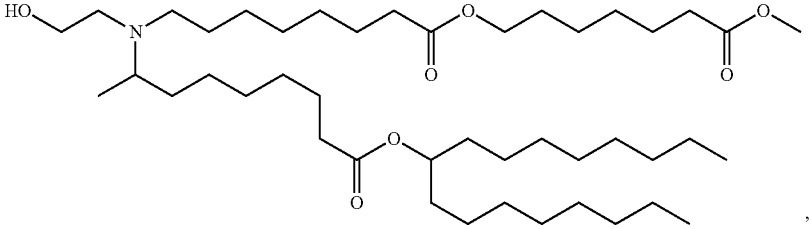
,
(Compound 193)
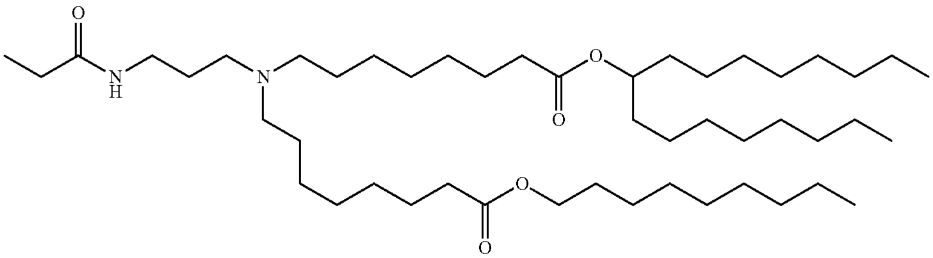
, -continued
(Compound 194)
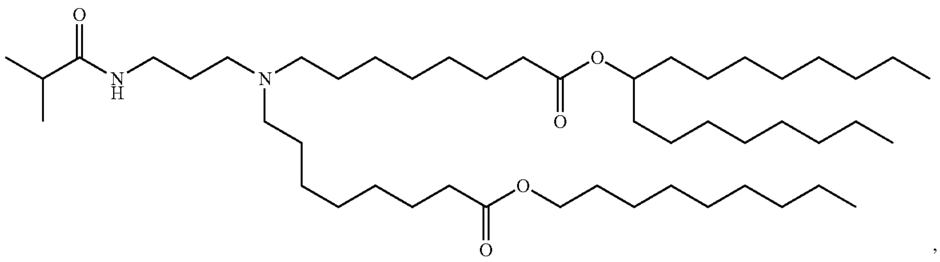
,
(Compound 195)
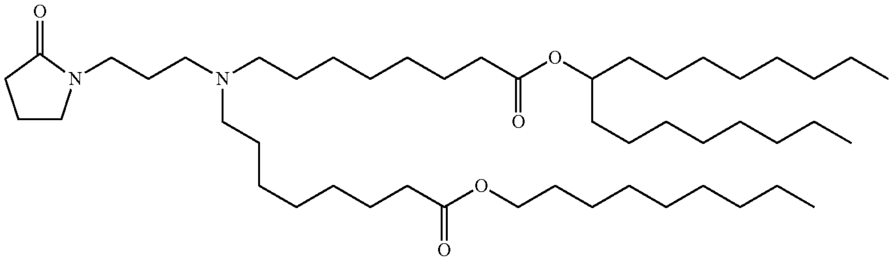
,
(Compound 196)
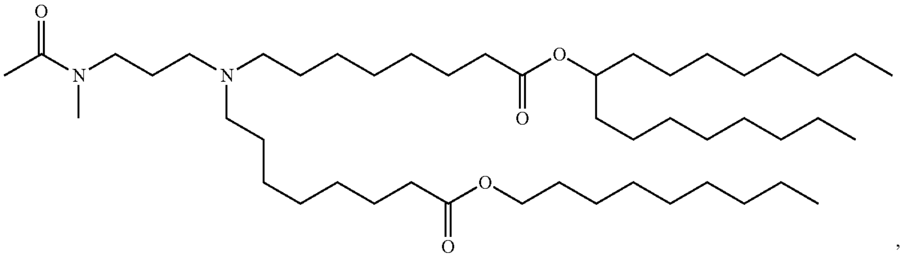
,
(Compound 197)
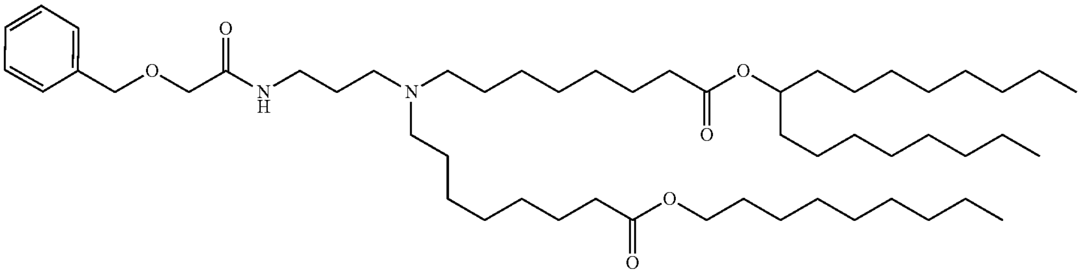
,
(Compound 198)
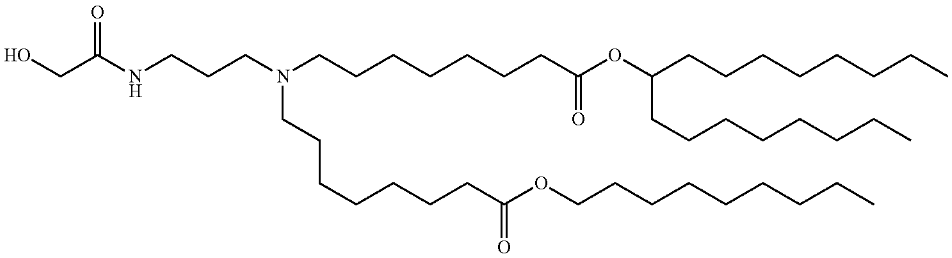
,
(Compound 199)
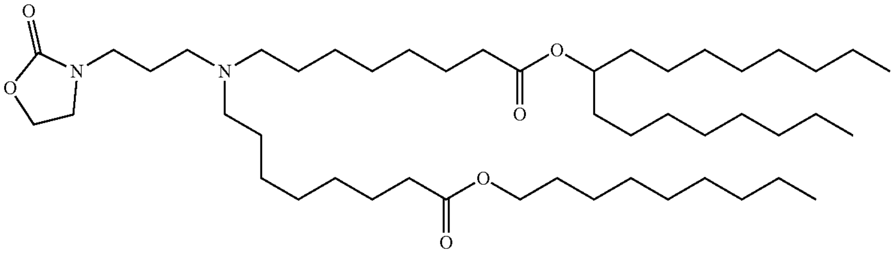
, -continued
(Compound 200)
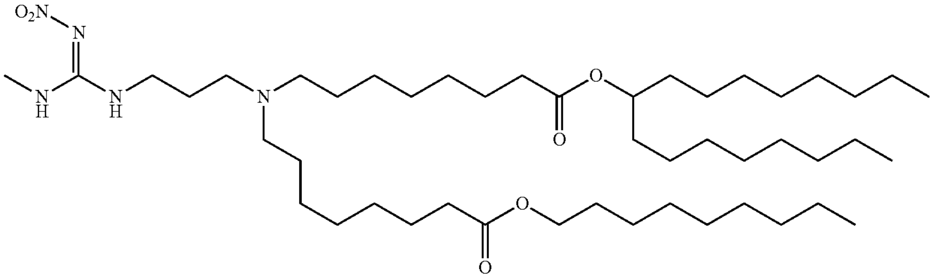
,
(Compound 201)
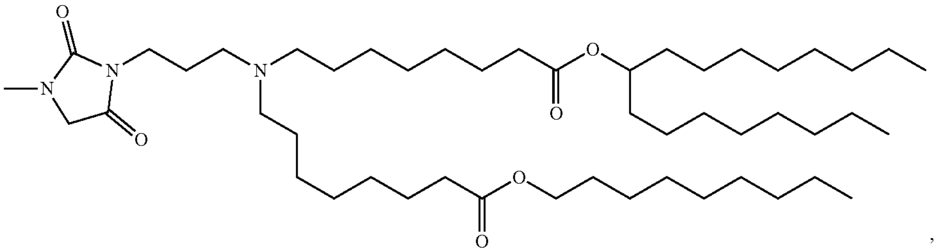
,
(Compound 202)
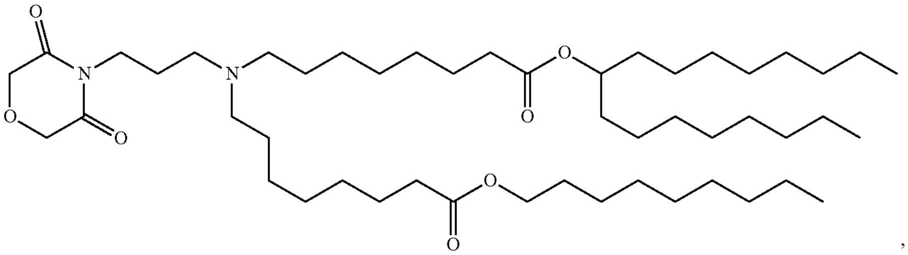
,
(Compound 203)
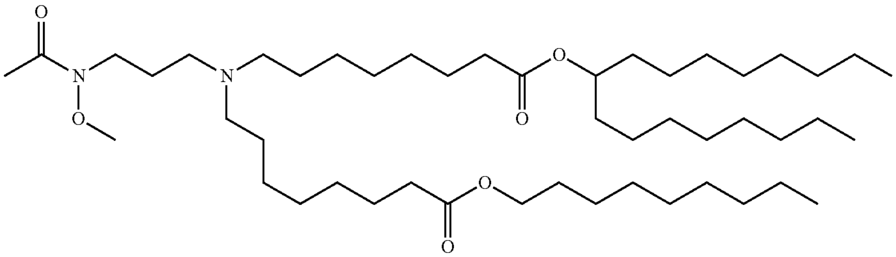
,
(Compound 204)
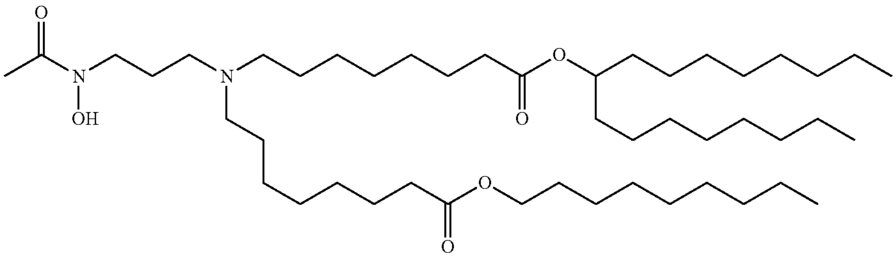
,
(Compound 205)
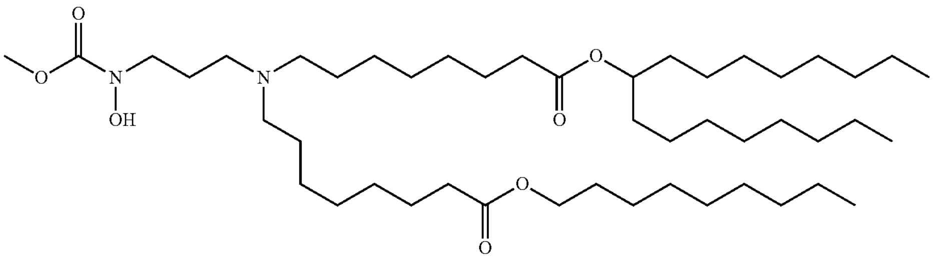
, -continued
(Compound 206)
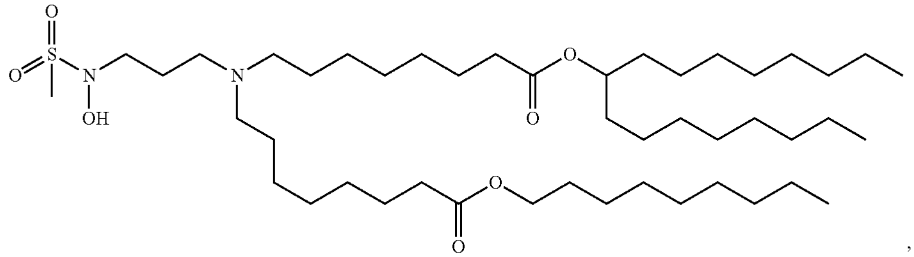
,
(Compound 207)
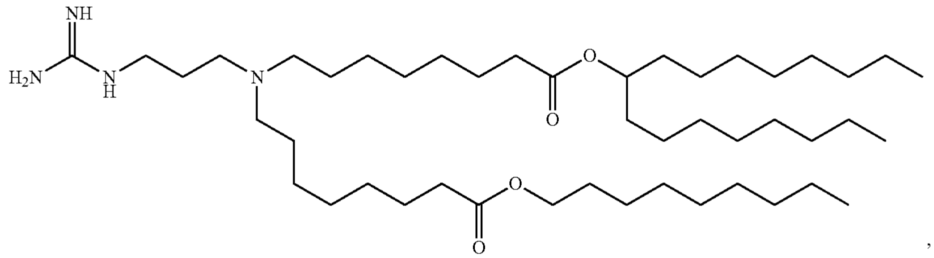
,
(Compound 208)
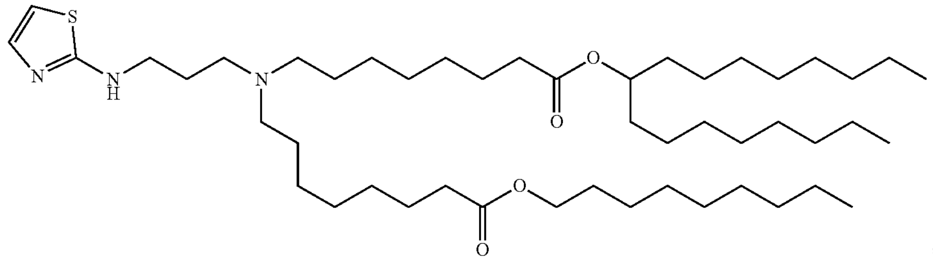
,
(Compound 209)
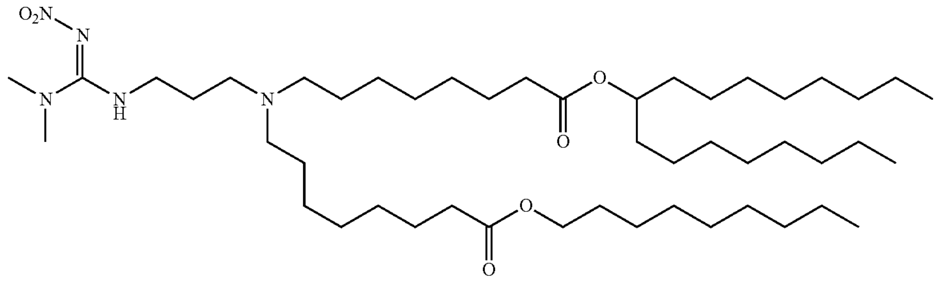
,
(Compound 210)
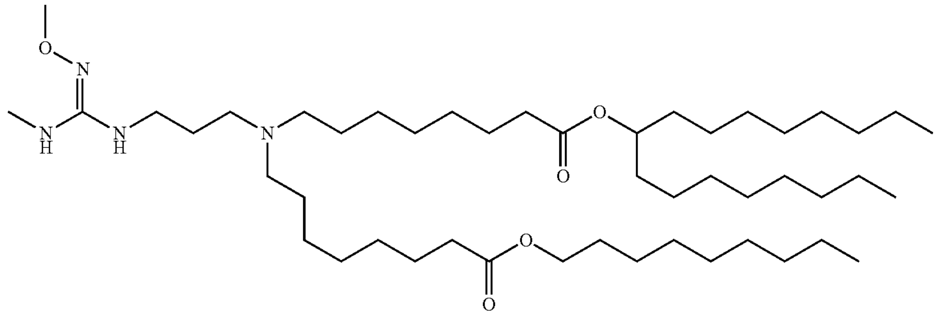
, -continued
(Compound 211)
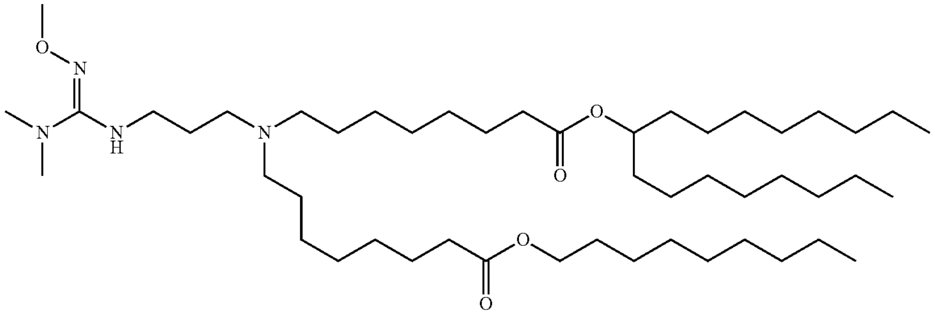
,
(Compound 212)
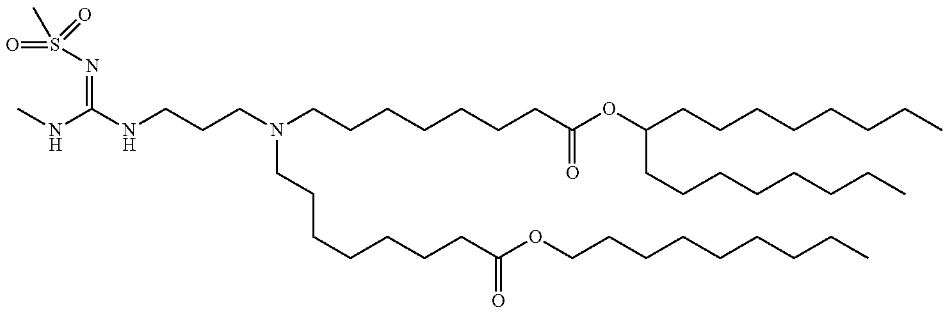
,
(Compound 213)
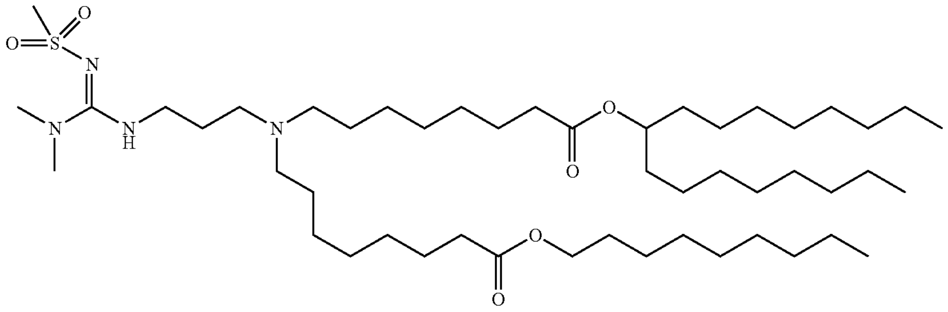
,
(Compound 214)
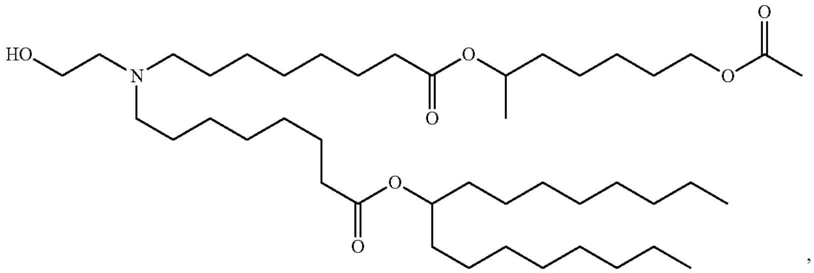
,
(Compound 215)
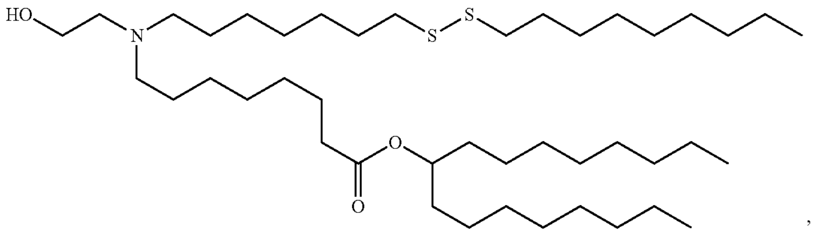
, -continued
(Compound 216)
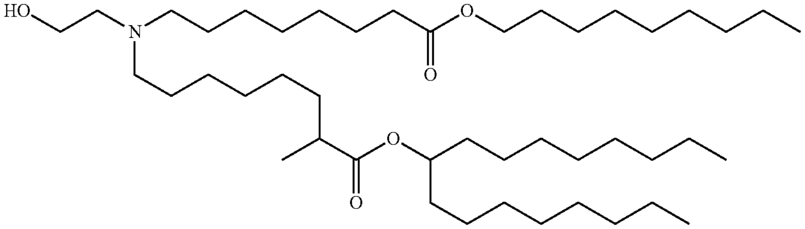
,
(Compound 217)
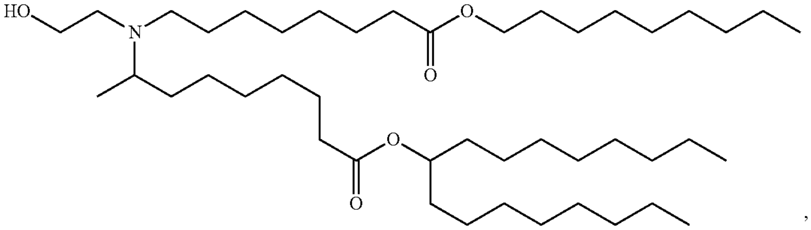
,
(Compound 218)
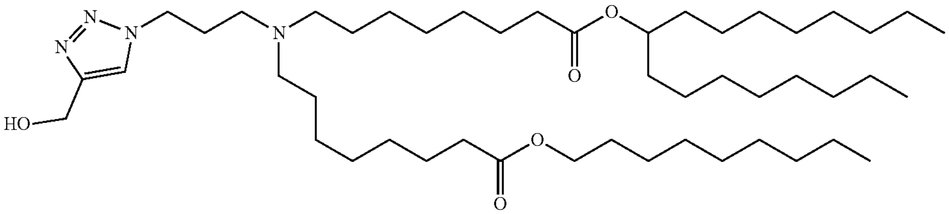
,
(Compound 219)
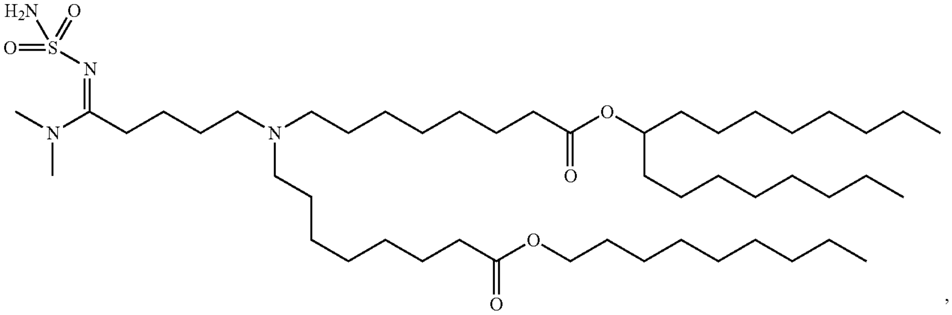
,
(Compound 220)
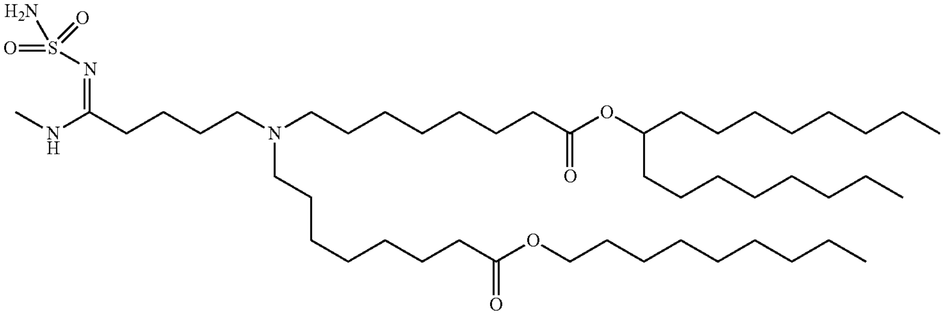
, -continued
(Compound 221)
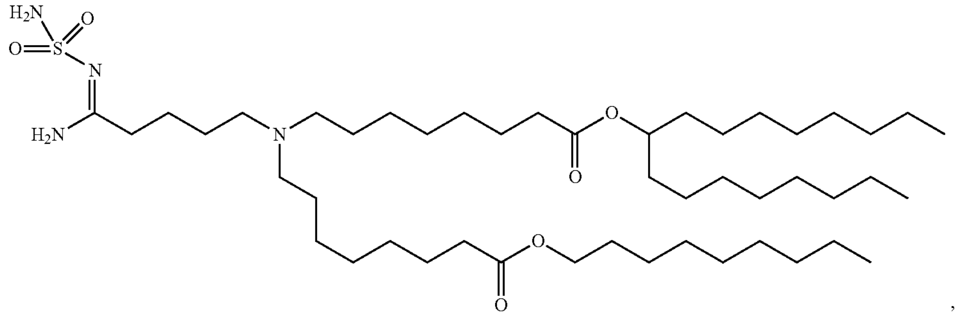
,
(Compoound 222)
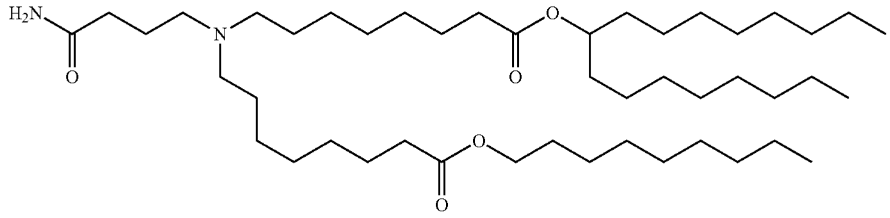
,
(Compound 223)
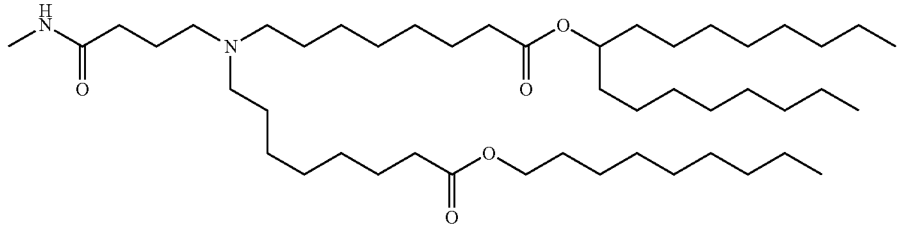
,
(Compound 224)
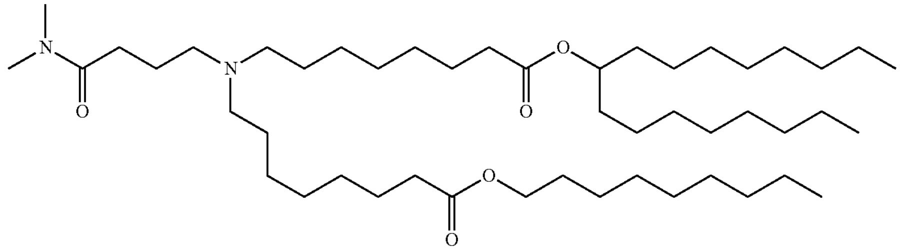
,
(Compound 225)
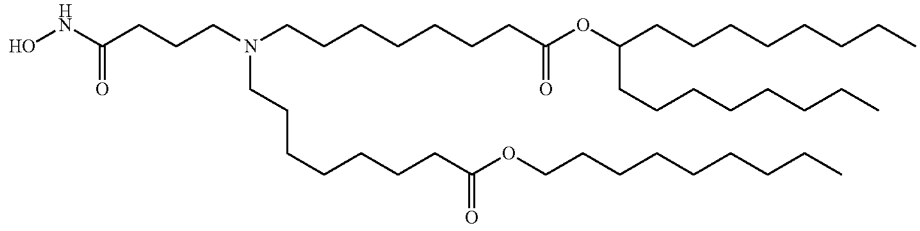
,
(Compound 226)
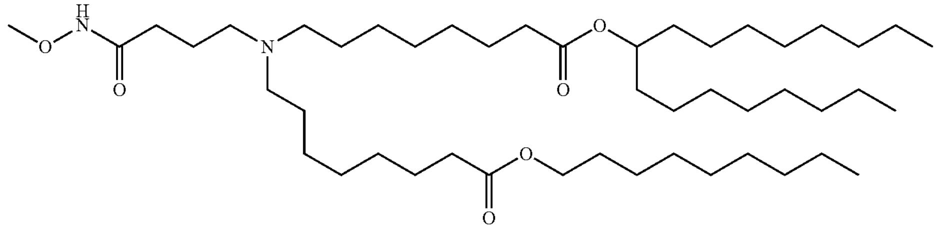
, -continued
(Compound 227)
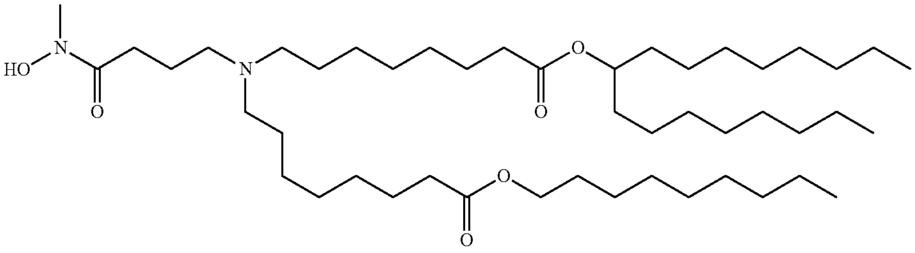
,
(Compound 228)
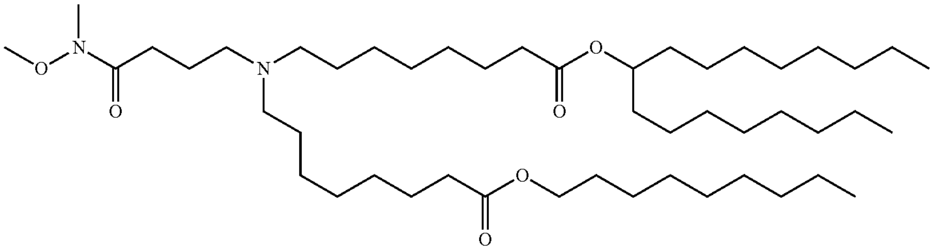
,
(Compound 229)
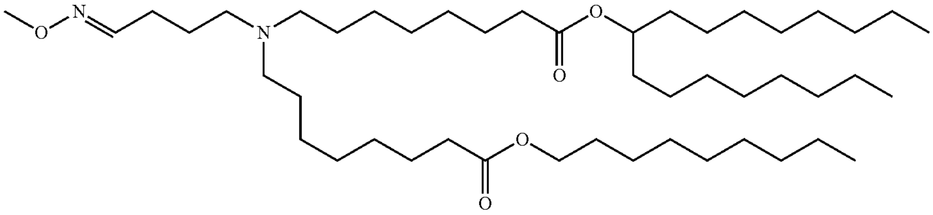
,
(Compound 230)
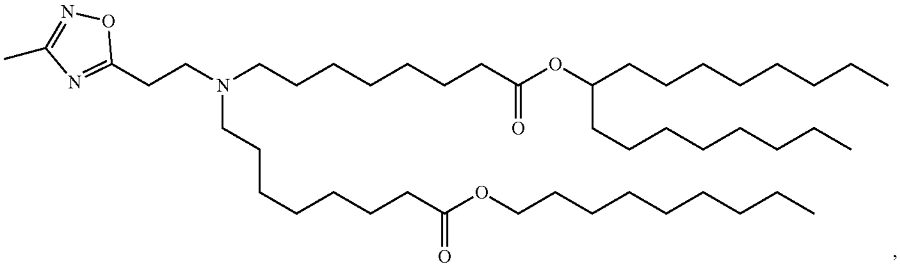
,
(Compound 231)
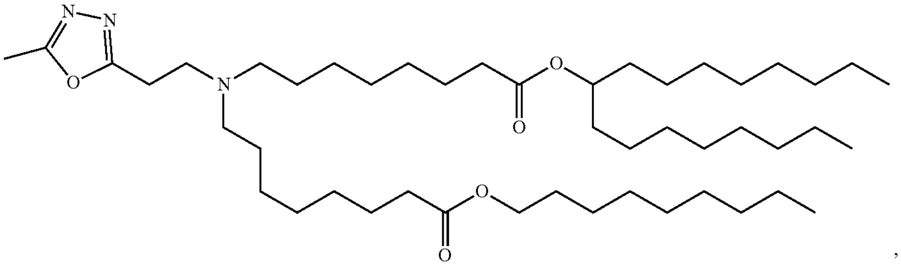
,
(Compound 232)
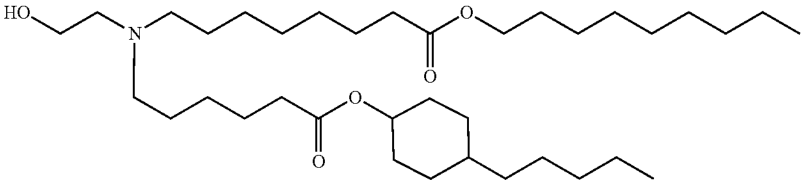
,
and salts and isomers thereof.

In some embodiments, a nanoparticle comprises the following compound:

(Compound 233)

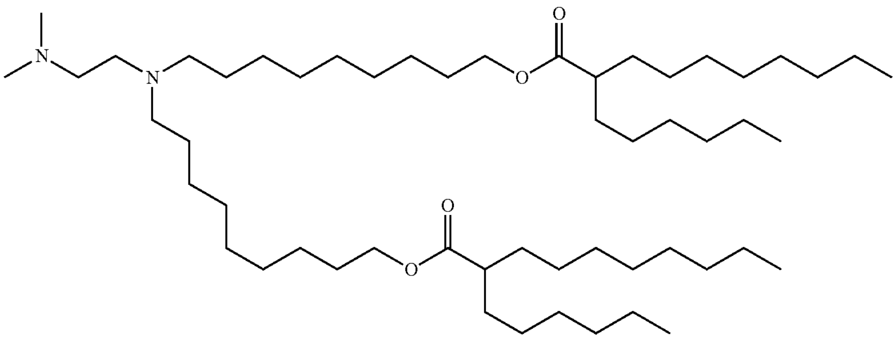

or salts and isomers thereof.

In some embodiments, the disclosure features a nanoparticle composition including a lipid component comprising a compound as described herein (e.g., a compound according to Formula (I), (IA), (II), (IIa), (IIb), (IIc), (IId) or (IIe)).

Relative amounts of the active ingredient, the pharmaceutically acceptable excipient, and/or any additional ingredients in a vaccine composition may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, the RNA vaccine composition may comprise the polynucleotide described herein, formulated in a lipid nanoparticle comprising MC3, Cholesterol, DSPC and PEG2000-DMG, the buffer trisodium citrate, sucrose and water for injection. As a non-limiting example, the composition comprises: 2.0 mg/mL of drug substance (e.g., polynucleotides encoding H10N8 influenza virus), 21.8 mg/mL of MC3, 10.1 mg/mL of cholesterol, 5.4 mg/mL of DSPC, 2.7 mg/mL of PEG2000-DMG, 5.16 mg/mL of trisodium citrate, 71 mg/mL of sucrose and 1.0 mL of water for injection.

In some embodiments, a nanoparticle (e.g., a lipid nanoparticle) has a mean diameter of 10-500 nm, 20-400 nm, 30-300 nm, 40-200 nm. In some embodiments, a nanoparticle (e.g., a lipid nanoparticle) has a mean diameter of 50-150 nm, 50-200 nm, 80-100 nm or 80-200 nm.

Flagellin is an approximately 500 amino acid monomeric protein that polymerizes to form the flagella associated with bacterial motion. Flagellin is expressed by a variety of flagellated bacteria (*Salmonella typhimurium* for example) as well as non-flagellated bacteria (such as *Escherichia coli*). Sensing of flagellin by cells of the innate immune system (dendritic cells, macrophages, etc.) is mediated by the Toll-like receptor 5 (TLR5) as well as by Nod-like receptors (NLRs) Ipaf and Naip5. TLRs and NLRs have been identified as playing a role in the activation of innate immune response and adaptive immune response. As such, flagellin provides an adjuvant effect in a vaccine.

The nucleotide and amino acid sequences encoding known flagellin polypeptides are publicly available in the NCBI GenBank database. The flagellin sequences from *S. Typhimurium, H. Pylori, V. Cholera, S. marcesens, S. flexneri, T. pallidum, L. pneumophila, B. burgdorferei, C. difficile, R. meliloti, A. tumefaciens, R. lupini, B. clarridgeiae, P. Mirabilis, B. subtilus, L. monocytogenes, P. aeruginosa*, and *E. coli*, among others are known.

A flagellin polypeptide, as used herein, refers to a full length flagellin protein, immunogenic fragments thereof, and peptides having at least 50% sequence identity to a flagellin protein or immunogenic fragments thereof. Exemplary flagellin proteins include flagellin from *Salmonella typhi* (UniPro Entry number: Q56086), *Salmonella typhimurium* (A0A0C9DG09), *Salmonella enteritidis* (A0A0C9BAB7), and *Salmonella choleraesuis* (Q6V2X8). In some embodiments, the flagellin polypeptide has at least 60%, 70%, 75%, 80%, 90%, 95%, 97%, 98%, or 99% sequence identity to a flagellin protein or immunogenic fragments thereof.

In some embodiments, the flagellin polypeptide is an immunogenic fragment. An immunogenic fragment is a portion of a flagellin protein that provokes an immune response. In some embodiments, the immune response is a TLR5 immune response. An example of an immunogenic fragment is a flagellin protein in which all or a portion of a hinge region has been deleted or replaced with other amino acids. For example, an antigenic polypeptide may be inserted in the hinge region. Hinge regions are the hypervariable regions of a flagellin. Hinge regions of a flagellin are also referred to as "D3 domain or region," "propeller domain or region," "hypervariable domain or region" and "variable domain or region." "At least a portion of a hinge region," as used herein, refers to any part of the hinge region of the flagellin, or the entirety of the hinge region. In other embodiments an immunogenic fragment of flagellin is a 20, 25, 30, 35, or 40 amino acid C-terminal fragment of flagellin.

The flagellin monomer is formed by domains D0 through D3. D0 and D1, which form the stem, are composed of tandem long alpha helices and are highly conserved among different bacteria. The D1 domain includes several stretches of amino acids that are useful for TLR5 activation. The entire D1 domain or one or more of the active regions within the domain are immunogenic fragments of flagellin. Examples of immunogenic regions within the D1 domain include residues 88-114 and residues 411-431 in *Salmonella typhimurium* FliC flagellin. Within the 13 amino acids in the 88-100 region, at least 6 substitutions are permitted between *Salmonella* flagellin and other flagellins that still preserve TLR5 activation. Thus, immunogenic fragments of flagellin include flagellin like sequences that activate TLR5 and contain a 13 amino acid motif that is 53% or more identical to the *Salmonella* sequence in 88-100 of FliC (LQRVRELAVQSAN; SEQ ID NO: 428).

In some embodiments, the RNA (e.g., mRNA) vaccine includes an RNA that encodes a fusion protein of flagellin and one or more antigenic polypeptides. A "fusion protein" as used herein, refers to a linking of two components of the construct. In some embodiments, a carboxy-terminus of the antigenic polypeptide is fused or linked to an amino terminus of the flagellin polypeptide. In other embodiments, an amino-terminus of the antigenic polypeptide is fused or linked to a carboxy-terminus of the flagellin polypeptide. The fusion protein may include, for example, one, two, three, four, five, six or more flagellin polypeptides linked to one, two, three, four, five, six or more antigenic polypeptides. When two or more flagellin polypeptides and/or two or more antigenic polypeptides are linked such a construct may be referred to as a "multimer."

Each of the components of a fusion protein may be directly linked to one another or they may be connected through a linker. For instance, the linker may be an amino acid linker. The amino acid linker encoded for by the RNA (e.g., mRNA) vaccine to link the components of the fusion protein may include, for instance, at least one member selected from the group consisting of a lysine residue, a glutamic acid residue, a serine residue and an arginine residue. In some embodiments the linker is 1-30, 1-25, 1-25, 5-10, 5, 15, or 5-20 amino acids in length.

In other embodiments the RNA (e.g., mRNA) vaccine includes at least two separate RNA polynucleotides, one encoding one or more antigenic polypeptides and the other encoding the flagellin polypeptide. The at least two RNA polynucleotides may be co-formulated in a carrier such as a lipid nanoparticle.

Liposomes, Lipoplexes, and Lipid Nanoparticles

The RNA vaccines of the invention can be formulated using one or more liposomes, lipoplexes, or lipid nanoparticles. In some embodiments, the RNA vaccine comprises one or more RNA polynucleotides comprising one or more open reading frames encoding one or more of HCMV antigenic polypeptides gB, gH, gL, UL128, UL130 and UL131. In some embodiments, all of the RNA polynucleotide components of the vaccine are formulated in the same liposome, lipoplex or lipid nanoparticle. In other embodiments, one or more of the RNA polynucleotide components of the vaccine are formulated in different liposomes, lipoplexes or lipid nanoparticles. In other embodiments, each of RNA polynucleotide components of the vaccine is formulated in a different liposome, lipoplex or lipid nanoparticle. In some embodiments, an RNA vaccine comprises RNA polynucleotides encoding gB, gH, gL, UL128, UL130 and UL131. The RNA polynucleotides encoding gB, gH, gL, UL128, UL130 and UL131 can be formulated in one or more liposomes, lipoplexes, or lipid nanoparticles. In certain embodiments, RNA polynucleotides encoding gB, gH, gL, UL128, UL130 and UL131 are all included in the same liposome, lipoplexe, or lipid nanoparticle.

In some embodiments, pharmaceutical compositions of RNA vaccines include liposomes. Liposomes are artificially-prepared vesicles which may primarily be composed of a lipid bilayer and may be used as a delivery vehicle for the administration of nutrients and pharmaceutical formulations. Liposomes can be of different sizes such as, but not limited to, a multilamellar vesicle (MLV) which may be hundreds of nanometers in diameter and may contain a series of concentric bilayers separated by narrow aqueous compartments, a small unicellular vesicle (SUV) which may be smaller than 50 nm in diameter, and a large unilamellar vesicle (LUV) which may be between 50 and 500 nm in diameter. Liposome design may include, but is not limited to, opsonins or ligands in order to improve the attachment of liposomes to unhealthy tissue or to activate events such as, but not limited to, endocytosis. Liposomes may contain a low or a high pH in order to improve the delivery of the pharmaceutical formulations.

The formation of liposomes may depend on the physicochemical characteristics such as, but not limited to, the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimization size, polydispersity and the shelf-life of the vesicles for the intended application, and the batch-to-batch reproducibility and possibility of large-scale production of safe and efficient liposomal products.

As a non-limiting example, liposomes such as synthetic membrane vesicles may be prepared by the methods, apparatus and devices described in US Patent Publication No. US20130177638, US20130177637, US20130177636, US20130177635, US20130177634, US20130177633, US20130183375, US20130183373 and US20130183372, the contents of each of which are herein incorporated by reference in its entirety.

In some embodiments, pharmaceutical compositions described herein may include, without limitation, liposomes such as those formed from 1,2-dioleyloxy-N,N-dimethylaminopropane (DODMA) liposomes, DiLa2 liposomes from Marina Biotech (Bothell, Wash.), 1,2-dilinoleyloxy-3-dimethylaminopropane (DLin-DMA), 2,2-dilinoleyl-4-(2-dimethylaminoethyl)-[1,3]-dioxolane (DLin-KC2-DMA), and MC3 (US20100324120; herein incorporated by reference in its entirety) and liposomes which may deliver small molecule drugs such as, but not limited to, DOXIL® from Janssen Biotech, Inc. (Horsham, Pa.).

In some embodiments, pharmaceutical compositions described herein may include, without limitation, liposomes such as those formed from the synthesis of stabilized plasmid-lipid particles (SPLP) or stabilized nucleic acid lipid particle (SNALP) that have been previously described and shown to be suitable for oligonucleotide delivery in vitro and in vivo (see Wheeler et al. Gene Therapy. 1999 6:271-281; Zhang et al. Gene Therapy. 1999 6:1438-1447; Jeffs et al. Pharm Res. 2005 22:362-372; Morrissey et al., Nat Biotechnol. 2005 2:1002-1007; Zimmermann et al., Nature. 2006 441:111-114; Heyes et al. J Contr Rel. 2005 107:276-287; Semple et al. Nature Biotech. 2010 28:172-176; Judge et al. J Clin Invest. 2009 119:661-673; deFougerolles Hum Gene Ther. 2008 19:125-132; U.S. Patent Publication No US20130122104; all of which are incorporated herein in their entireties). The original manufacture method by Wheeler et al. was a detergent dialysis method, which was later improved by Jeffs et al. and is referred to as the spontaneous vesicle formation method. The liposome formulations are composed of 3 to 4 lipid components in addition to the polynucleotide. As an example a liposome can contain, but is not limited to, 55% cholesterol, 20% disteroylphosphatidyl choline (DSPC), 10% PEG-S-DSG, and 15% 1,2-dioleyloxy-N,N-dimethylaminopropane (DODMA), as described by Jeffs et al. As another example, certain liposome formulations may contain, but are not limited to, 48% cholesterol, 20% DSPC, 2% PEG-c-DMA, and 30% cationic lipid, where the cationic lipid can be 1,2-distearloxy-N,N-dimethylaminopropane (DSDMA), DODMA, DLin-DMA, or 1,2-dilinolenyloxy-3-dimethylaminopropane (DLenDMA), as described by Heyes et al.

In some embodiments, liposome formulations may comprise from about about 25.0% cholesterol to about 40.0% cholesterol, from about 30.0% cholesterol to about 45.0% cholesterol, from about 35.0% cholesterol to about 50.0% cholesterol and/or from about 48.5% cholesterol to about 60% cholesterol. In a preferred embodiment, formulations may comprise a percentage of cholesterol selected from the group consisting of 28.5%, 31.5%, 33.5%, 36.5%, 37.0%, 38.5%, 39.0% and 43.5%. In some embodiments, formulations may comprise from about 5.0% to about 10.0% DSPC and/or from about 7.0% to about 15.0% DSPC.

In some embodiments, pharmaceutical compositions may include liposomes which may be formed to deliver polynucleotides which may encode at least one immunogen (antigen) or any other polypeptide of interest. The RNA vaccine may be encapsulated by the liposome and/or it may be contained in an aqueous core which may then be encapsulated by the liposome (see International Pub. Nos. WO2012031046, WO2012031043, WO2012030901 and WO2012006378 and US Patent Publication No. US20130189351, US20130195969 and US20130202684; the contents of each of which are herein incorporated by reference in their entirety).

In another embodiment, liposomes may be formulated for targeted delivery. As a non-limiting example, the liposome may be formulated for targeted delivery to the liver. The liposome used for targeted delivery may include, but is not limited to, the liposomes described in and methods of making liposomes described in US Patent Publication No. US20130195967, the contents of which are herein incorporated by reference in its entirety.

In another embodiment, the polynucleotide which may encode an immunogen (antigen) may be formulated in a cationic oil-in-water emulsion where the emulsion particle comprises an oil core and a cationic lipid which can interact with the polynucleotide anchoring the molecule to the emulsion particle (see International Pub. No. WO2012006380; herein incorporated by reference in its entirety).

In some embodiments, the RNA vaccines may be formulated in a water-in-oil emulsion comprising a continuous hydrophobic phase in which the hydrophilic phase is dispersed. As a non-limiting example, the emulsion may be made by the methods described in International Publication No. WO201087791, the contents of which are herein incorporated by reference in its entirety.

In another embodiment, the lipid formulation may include at least cationic lipid, a lipid which may enhance transfection and a least one lipid which contains a hydrophilic head group linked to a lipid moiety (International Pub. No. WO2011076807 and U.S. Pub. No. 20110200582; the contents of each of which is herein incorporated by reference in their entirety). In another embodiment, the polynucleotides encoding an immunogen may be formulated in a lipid vesicle which may have crosslinks between functionalized lipid bilayers (see U.S. Pub. No. 20120177724, the contents of which is herein incorporated by reference in its entirety).

In some embodiments, the polylnucleotides may be formulated in a lipsome as described in International Patent Publication No. WO2013086526, the contents of which is herein incorporated by reference in its entirety. The RNA vaccines may be encapsulated in a liposome using reverse pH gradients and/or optimized internal buffer compositions as described in International Patent Publication No. WO2013086526, the contents of which is herein incorporated by reference in its entirety.

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the cationic lipid may be a low molecular weight cationic lipid such as those described in US Patent Application No. 20130090372, the contents of which are herein incorporated by reference in its entirety.

In some embodiments, the RNA vaccines may be formulated in a lipid vesicle which may have crosslinks between functionalized lipid bilayers.

In some embodiments, the RNA vaccines may be formulated in a liposome comprising a cationic lipid. The liposome may have a molar ratio of nitrogen atoms in the cationic lipid to the phophates in the RNA (N:P ratio) of between 1:1 and 20:1 as described in International Publication No. WO2013006825, herein incorporated by reference in its entirety. In another embodiment, the liposome may have a N:P ratio of greater than 20:1 or less than 1:1.

In some embodiments, the RNA vaccines may be formulated in a lipid-polycation complex. The formation of the lipid-polycation complex may be accomplished by methods known in the art and/or as described in U.S. Pub. No. 20120178702, herein incorporated by reference in its entirety. As a non-limiting example, the polycation may include a cationic peptide or a polypeptide such as, but not limited to, polylysine, polyornithine and/or polyarginine and the cationic peptides described in International Pub. No. WO2012013326 or US Patent Pub. No. US20130142818; each of which is herein incorporated by reference in its entirety. In another embodiment, the RNA vaccines may be formulated in a lipid-polycation complex which may further include a non-cationic lipid such as, but not limited to, cholesterol or dioleoyl phosphatidylethanolamine (DOPE).

In some embodiments, the RNA vaccines may be formulated in an aminoalcohol lipidoid. Aminoalcohol lipidoids which may be used in the present invention may be prepared by the methods described in U.S. Pat. No. 8,450,298, herein incorporated by reference in its entirety.

The liposome formulation may be influenced by, but not limited to, the selection of the cationic lipid component, the degree of cationic lipid saturation, the nature of the PEGylation, ratio of all components and biophysical parameters such as size. In one example by Semple et al. (Semple et al. Nature Biotech. 2010 28:172-176; herein incorporated by reference in its entirety), the liposome formulation was composed of 57.1% cationic lipid, 7.1% dipalmitoylphosphatidylcholine, 34.3% cholesterol, and 1.4% PEG-c-DMA. As another example, changing the composition of the cationic lipid could more effectively deliver siRNA to various antigen presenting cells (Basha et al. Mol Ther. 2011 19:2186-2200; herein incorporated by reference in its entirety). In some embodiments, liposome formulations may comprise from about 35 to about 45% cationic lipid, from about 40% to about 50% cationic lipid, from about 50% to about 60% cationic lipid and/or from about 55% to about 65% cationic lipid. In some embodiments, the ratio of lipid to mRNA in liposomes may be from about about 5:1 to about 20:1, from about 10:1 to about 25:1, from about 15:1 to about 30:1 and/or at least 30:1.

In some embodiments, the ratio of PEG in the lipid nanoparticle (LNP) formulations may be increased or decreased and/or the carbon chain length of the PEG lipid may be modified from C14 to C18 to alter the pharmacokinetics and/or biodistribution of the LNP formulations. As a non-limiting example, LNP formulations may contain from about 0.5% to about 3.0%, from about 1.0% to about 3.5%, from about 1.5% to about 4.0%, from about 2.0% to about 4.5%, from about 2.5% to about 5.0% and/or from about 3.0% to about 6.0% of the lipid molar ratio of PEG-c-DOMG (R-3-[(ω-methoxy-poly(ethyleneglycol) 2000)carbamoyl)]-1,2-dimyristyloxypropyl-3-amine) (also referred to herein as PEG-DOMG) as compared to the cationic lipid, DSPC and cholesterol. In another embodiment the PEG-c-DOMG may be replaced with a PEG lipid such as, but not limited to, PEG-DSG (1,2-Distearoyl-sn-glycerol, methoxypolyethylene glycol), PEG-DMG (1,2-Dimyristoyl-sn-glycerol) and/or PEG-DPG (1,2-Dipalmitoyl-sn-glycerol, methoxypolyethylene glycol). The cationic lipid may be selected from any lipid known in the art such as, but not limited to, DLin-MC3-DMA, DLin-DMA, C12-200 and DLin-KC2-DMA.

In some embodiments, the RNA vaccines may be formulated in a lipid nanoparticle such as those described in International Publication No. WO2012170930, the contents of which is herein incorporated by reference in its entirety.

In some embodiments, the RNA vaccine formulation comprising the polynucleotide is a nanoparticle which may comprise at least one lipid. The lipid may be selected from, but is not limited to, DLin-DMA, DLin-K-DMA, 98N12-5, C12-200, DLin-MC3-DMA, DLin-KC2-DMA, DODMA, PLGA, PEG, PEG-DMG, PEGylated lipids and amino alcohol lipids. In another aspect, the lipid may be a cationic lipid such as, but not limited to, DLin-DMA, DLin-D-DMA, DLin-MC3-DMA, DLin-KC2-DMA, DODMA and amino alcohol lipids. The amino alcohol cationic lipid may be the lipids described in and/or made by the methods described in US Patent Publication No. US20130150625, herein incorporated by reference in its entirety. As a non-limiting example, the cationic lipid may be 2-amino-3-[(9Z,12Z)-octadeca-9,12-dien-1-yloxy]-2-{[(9Z,2Z)-octadeca-9,12-dien-1-yloxy]methyl}propan-1-ol (Compound 1 in US20130150625); 2-amino-3-[(9Z)-octadec-9-en-1-yloxy]-2-{[(9Z)-octadec-9-en-1-yloxy]methyl}propan-1-ol (Compound 2 in US20130150625); 2-amino-3-[(9Z,12Z)-octadeca-9,12-dien-1-yloxy]-2-[(octyloxy)methyl]propan-1-ol (Compound 3 in US20130150625); and 2-(dimethylamino)-3-[(9Z,12Z)-octadeca-9,12-dien-1-yloxy]-2-{[(9Z,12Z)-octadeca-9,12-dien-1-yloxy]methyl}propan-1-ol (Compound 4 in US20130150625); or any pharmaceutically acceptable salt or stereoisomer thereof.

Lipid nanoparticle formulations typically comprise a lipid, in particular, an ionizable cationic lipid, for example, 2,2-dilinoleyl-4-dimethylaminoethyl-[1,3]-dioxolane (DLin-KC2-DMA), dilinoleyl-methyl-4-dimethylaminobutyrate (DLin-MC3-DMA), or di((Z)-non-2-en-1-yl) 9-((4-(dimethylamino)butanoyl)oxy)heptadecanedioate (L319), and further comprise a neutral lipid, a sterol and a molecule capable of reducing particle aggregation, for example a PEG or PEG-modified lipid.

In some embodiments, the lipid nanoparticle formulation consists essentially of (i) at least one lipid selected from the group consisting of 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy) heptadecanedioate (L319); (ii) a neutral lipid selected from DSPC, DPPC, POPC, DOPE and SM; (iii) a sterol, e.g., cholesterol; and (iv) a PEG-lipid, e.g., PEG-DMG or PEG-cDMA, in a molar ratio of about 20-60% cationic lipid: 5-25% neutral lipid: 25-55% sterol; 0.5-15% PEG-lipid.

In some embodiments, the formulation includes from about 25% to about 75% on a molar basis of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), e.g., from about 35 to about 65%, from about 45 to about 65%, about 60%, about 57.5%, about 50% or about 40% on a molar basis.

In some embodiments, the formulation includes from about 0.5% to about 15% on a molar basis of the neutral lipid e.g., from about 3 to about 12%, from about 5 to about 10% or about 15%, about 10%, or about 7.5% on a molar basis. Exemplary neutral lipids include, but are not limited to, DSPC, POPC, DPPC, DOPE and SM. In some embodiments, the formulation includes from about 5% to about 50% on a molar basis of the sterol (e.g., about 15 to about 45%, about 20 to about 40%, about 40%, about 38.5%, about 35%, or about 31% on a molar basis. An exemplary sterol is cholesterol. In some embodiments, the formulation includes from about 0.5% to about 20% on a molar basis of the PEG or PEG-modified lipid (e.g., about 0.5 to about 10%, about 0.5 to about 5%, about 1.5%, about 0.5%, about 1.5%, about 3.5%, or about 5% on a molar basis. In some embodiments, the PEG or PEG modified lipid comprises a PEG molecule of an average molecular weight of 2,000 Da. In other embodiments, the PEG or PEG modified lipid comprises a PEG molecule of an average molecular weight of less than 2,000, for example around 1,500 Da, around 1,000 Da, or around 500 Da. Exemplary PEG-modified lipids include, but are not limited to, PEG-distearoyl glycerol (PEG-DMG) (also referred herein as PEG-C14 or C14-PEG), PEG-cDMA (further discussed in Reyes et al. J. Controlled Release, 107, 276-287 (2005) the contents of which are herein incorporated by reference in its entirety)

In some embodiments, the formulations of the inventions include 25-75% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 0.5-15% of the neutral lipid, 5-50% of the sterol, and 0.5-20% of the PEG or PEG-modified lipid on a molar basis.

In some embodiments, the formulations of the inventions include 35-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 3-12% of the neutral lipid, 15-45% of the sterol, and 0.5-10% of the PEG or PEG-modified lipid on a molar basis.

In some embodiments, the formulations of the inventions include 45-65% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), 5-10% of the neutral lipid, 25-40% of the sterol, and 0.5-10% of the PEG or PEG-modified lipid on a molar basis.

In some embodiments, the formulations of the inventions include about 60% of a cationic lipid selected from 2,2- dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.5% of the neutral lipid, about 31% of the sterol, and about 1.5% of the PEG or PEG-modified lipid on a molar basis.

In some embodiments, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 38.5% of the sterol, and about 1.5% of the PEG or PEG-modified lipid on a molar basis.

In some embodiments, the formulations of the inventions include about 50% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 10% of the neutral lipid, about 35% of the sterol, about 4.5% or about 5% of the PEG or PEG-modified lipid, and about 0.5% of the targeting lipid on a molar basis.

In some embodiments, the formulations of the inventions include about 40% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 15% of the neutral lipid, about 40% of the sterol, and about 5% of the PEG or PEG-modified lipid on a molar basis.

In some embodiments, the formulations of the inventions include about 57.2% of a cationic lipid selected from 2,2-dilinoleyl-4-dimethylaminoethyl-[1,3]-dioxolane (DLin-KC2-DMA), dilinoleyl-methyl-4-dimethylaminobutyrate (DLin-MC3-DMA), and di((Z)-non-2-en-1-yl) 9-((4-(dimethylamino)butanoyl)oxy)heptadecanedioate (L319), about 7.1% of the neutral lipid, about 34.3% of the sterol, and about 1.4% of the PEG or PEG-modified lipid on a molar basis.

In some embodiments, the formulations of the inventions include about 57.5% of a cationic lipid selected from the PEG lipid is PEG-cDMA (PEG-cDMA is further discussed in Reyes et al. (J. Controlled Release, 107, 276-287 (2005), the contents of which are herein incorporated by reference in its entirety), about 7.5% of the neutral lipid, about 31.5% of the sterol, and about 3.5% of the PEG or PEG-modified lipid on a molar basis.

In preferred embodiments, lipid nanoparticle formulation consists essentially of a lipid mixture in molar ratios of about 20-70% cationic lipid: 5-45% neutral lipid: 20-55% cholesterol: 0.5-15% PEG-modified lipid; more preferably in a molar ratio of about 20-60% cationic lipid: 5-25% neutral lipid: 25-55% cholesterol: 0.5-15% PEG-modified lipid.

In particular embodiments, the molar lipid ratio is approximately 50/10/38.5/1.5 (mol % cationic lipid/neutral lipid, e.g., DSPC/Chol/PEG-modified lipid, e.g., PEG-DMG, PEG-DSG or PEG-DPG), 57.2/7.1134.3/1.4 (mol % cationic lipid/neutral lipid, e.g., DPPC/Chol/PEG-modified lipid, e.g., PEG-cDMA), 40/15/40/5 (mol % cationic lipid/neutral lipid, e.g., DSPC/Chol/PEG-modified lipid, e.g., PEG-DMG), 50/10/35/4.5/0.5 (mol % cationic lipid/neutral lipid, e.g., DSPC/Chol/PEG-modified lipid, e.g., PEG-DSG), 50/10/35/5 (cationic lipid/neutral lipid, e.g., DSPC/Chol/PEG-modified lipid, e.g., PEG-DMG), 40/10/40/10 (mol % cationic lipid/neutral lipid, e.g., DSPC/Chol/PEG-modified lipid, e.g., PEG-DMG or PEG-cDMA), 35/15/40/10 (mol % cationic lipid/neutral lipid, e.g., DSPC/Chol/PEG-modified lipid, e.g., PEG-DMG or PEG-cDMA) or 52/13/30/5 (mol % cationic lipid/neutral lipid, e.g., DSPC/Chol/PEG-modified lipid, e.g., PEG-DMG or PEG-cDMA).

Exemplary lipid nanoparticle compositions and methods of making same are described, for example, in Semple et al. (2010) Nat. Biotechnol. 28:172-176; Jayarama et al. (2012), Angew. Chem. Int. Ed., 51: 8529-8533; and Maier et al. (2013) Molecular Therapy 21, 1570-1578 (the contents of each of which are incorporated herein by reference in their entirety).

In some embodiments, the lipid nanoparticle formulations described herein may comprise a cationic lipid, a PEG lipid and a structural lipid and optionally comprise a non-cationic lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may be 4 component lipid nanoparticles. The lipid nanoparticle may comprise a cationic lipid, a non-cationic lipid, a PEG lipid and a structural lipid. As a non-limiting example, the lipid nanoparticle may comprise about 40-60% of cationic lipid, about 5-15% of a non-cationic lipid, about 1-2% of a PEG lipid and about 30-50% of a structural lipid. As another non-limiting example, the lipid nanoparticle may comprise about 50% cationic lipid, about 10% non-cationic lipid, about 1.5% PEG lipid and about 38.5% structural lipid. As yet another non-limiting example, the lipid nanoparticle may comprise about 55% cationic lipid, about 10% non-cationic lipid, about 2.5% PEG lipid and about 32.5% structural lipid. In some embodiments, the cationic lipid may be any cationic lipid described herein such as, but not limited to, DLin-KC2-DMA, DLin-MC3-DMA and L319.

In some embodiments, the lipid nanoparticle formulations described herein may comprise a cationic lipid, a non-cationic lipid, a PEG lipid and a structural lipid. As a non-limiting example, the lipid nanoparticle comprise about 50% of the cationic lipid DLin-KC2-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DOMG and about 38.5% of the structural lipid cholesterol. As a non-limiting example, the lipid nanoparticle comprise about 50% of the cationic lipid DLin-MC3-DMA, about 10% of the non-cationic lipid DSPC, about 1.5% of the PEG lipid PEG-DMG and about 38.5% of the structural lipid cholesterol. As yet another non-limiting example, the lipid nanoparticle comprise about 55% of the cationic lipid L319, about 10% of the non-cationic lipid DSPC, about 2.5% of the PEG lipid PEG-DMG and about 32.5% of the structural lipid cholesterol.

In some embodiments, the cationic lipid may be selected from, but not limited to, a cationic lipid described in International Publication Nos. WO2012040184, WO2011153120, WO2011149733, WO2011090965, WO2011043913, WO2011022460, WO2012061259, WO2012054365, WO2012044638, WO2010080724, WO201021865, WO2008103276, WO2013086373 and WO2013086354, U.S. Pat. Nos. 7,893,302, 7,404,969, 8,283,333, and 8,466,122 and US Patent Publication No. US20100036115, US20120202871, US20130064894, US20130129785, US20130150625, US20130178541 and US20130225836; the contents of each of which are herein incorporated by reference in their entirety. In another embodiment, the cationic lipid may be selected from, but not limited to, formula A described in International Publication Nos. WO2012040184, WO2011153120, WO2011149733, WO2011090965, WO2011043913, WO2011022460, WO2012061259, WO2012054365, WO2012044638 and WO2013116126 or US Patent Publication No. US20130178541 and US20130225836; the contents of each of which is herein incorporated by reference in their entirety. In yet another embodiment, the cationic lipid may be selected from, but not limited to, formula CLI-CLXXIX of International Publication No. WO2008103276, formula CLI-CLXXIX of U.S. Pat. No. 7,893,302, formula CLI-CLXXXXII of U.S. Pat. No. 7,404,969 and formula I-VI of US Patent Publication No. US20100036115, formula I of US Patent Publication No US20130123338; each of which is herein incorporated by reference in their entirety. As a non-limiting example, the cationic lipid may be selected from (20Z,23Z)—N,N-dimethylnonacosa-20,23-dien-10-amine, (17Z,20Z)—N,N-dimemylhexacosa-17,20-dien-9-amine, (1Z,19Z)—N5N-dimethylpentacosa-1 6, 19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21 Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21 Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl] pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, (13Z,16Z)—N,N-dimethyl-3-nonyldocosa-13,16-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine,N,N-dimethyl-1-[(1S,2S)-2-{[(1R,2R)-2-pentylcyclopropyl] methyl}cyclopropyl]nonadecan-10-amine,N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl] heptyl} dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy) methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl] oxy}-3-(octyloxy)propan-2-amine and (11E,20Z,23Z)—N,N-dimethylnonacosa-11,20,2-trien-10-amine or a pharmaceutically acceptable salt or stereoisomer thereof.

In some embodiments, the lipid may be a cleavable lipid such as those described in International Publication No. WO2012170889, herein incorporated by reference in its entirety.

In another embodiment, the lipid may be a cationic lipid such as, but not limited to, Formula (I) of U.S. Patent Application No. US20130064894, the contents of which are herein incorporated by reference in its entirety.

In some embodiments, the cationic lipid may be synthesized by methods known in the art and/or as described in International Publication Nos. WO2012040184, WO2011153120, WO2011149733, WO2011090965, WO2011043913, WO2011022460, WO2012061259, WO2012054365, WO2012044638, WO2010080724, WO201021865, WO2013086373 and WO2013086354; the contents of each of which are herein incorporated by reference in their entirety.

In another embodiment, the cationic lipid may be a trialkyl cationic lipid. Non-limiting examples of trialkyl cationic lipids and methods of making and using the trialkyl cationic lipids are described in International Patent Publication No. WO2013126803, the contents of which are herein incorporated by reference in its entirety.

In some embodiments, the LNP formulations of the RNA vaccines may contain PEG-c-DOMG at 3% lipid molar ratio. In another embodiment, the LNP formulations RRNA vaccines may contain PEG-c-DOMG at 1.5% lipid molar ratio.

In some embodiments, the pharmaceutical compositions of the RNA vaccines may include at least one of the PEGylated lipids described in International Publication No. WO2012099755, the contents of which is herein incorporated by reference in its entirety.

In some embodiments, the LNP formulation may contain PEG-DMG 2000 (1,2-dimyristoyl-sn-glycero-3-phophoethanolamine-N-[methoxy(polyethylene glycol)-2000). In some embodiments, the LNP formulation may contain PEG-DMG 2000, a cationic lipid known in the art and at least one other component. In another embodiment, the LNP formulation may contain PEG-DMG 2000, a cationic lipid known in the art, DSPC and cholesterol. As a non-limiting example, the LNP formulation may contain PEG-DMG 2000, DLin-DMA, DSPC and cholesterol. As another non-limiting example the LNP formulation may contain PEG-DMG 2000, DLin-DMA, DSPC and cholesterol in a molar ratio of 2:40:10:48 (see e.g., Geall et al., Nonviral delivery of self-amplifying RNA vaccines, PNAS 2012; PMID: 22908294; herein incorporated by reference in its entirety).

In some embodiments, the LNP formulation may be formulated by the methods described in International Publication Nos. WO2011127255 or WO2008103276, the contents of each of which is herein incorporated by reference in their entirety. As a non-limiting example, the RNA vaccines described herein may be encapsulated in LNP formulations as described in WO2011127255 and/or WO2008103276; each of which is herein incorporated by reference in their entirety.

In some embodiments, the RNA vaccines described herein may be formulated in a nanoparticle to be delivered by a parenteral route as described in U.S. Pub. No. US20120207845; the contents of which are herein incorporated by reference in its entirety.

In some embodiments, the RNA vaccines may be formulated in a lipid nanoparticle made by the methods described in US Patent Publication No US20130156845 or International Publication No WO2013093648 or WO2012024526, each of which is herein incorporated by reference in its entirety.

The lipid nanoparticles described herein may be made in a sterile environment by the system and/or methods described in US Patent Publication No. US20130164400, herein incorporated by reference in its entirety.

In some embodiments, the LNP formulation may be formulated in a nanoparticle such as a nucleic acid-lipid particle described in U.S. Pat. No. 8,492,359, the contents of which are herein incorporated by reference in its entirety. As a non-limiting example, the lipid particle may comprise one or more active agents or therapeutic agents; one or more cationic lipids comprising from about 50 mol % to about 85 mol % of the total lipid present in the particle; one or more non-cationic lipids comprising from about 13 mol % to about 49.5 mol % of the total lipid present in the particle; and one or more conjugated lipids that inhibit aggregation of particles comprising from about 0.5 mol % to about 2 mol % of the total lipid present in the particle. The nucleic acid in the nanoparticle may be the polynucleotides described herein and/or are known in the art.

In some embodiments, the LNP formulation may be formulated by the methods described in International Publication Nos. WO2011127255 or WO2008103276, the contents of each of which are herein incorporated by reference in their entirety. As a non-limiting example, modified RNA described herein may be encapsulated in LNP formulations as described in WO2011127255 and/or WO2008103276; the contents of each of which are herein incorporated by reference in their entirety.

In some embodiments, LNP formulations described herein may comprise a polycationic composition. As a non-limiting example, the polycationic composition may be selected from formula 1-60 of US Patent Publication No. US20050222064; the content of which is herein incorporated by reference in its entirety. In another embodiment, the LNP formulations comprising a polycationic composition may be used for the delivery of the modified RNA described herein in vivo and/or in vitro.

In some embodiments, the LNP formulations described herein may additionally comprise a permeability enhancer molecule. Non-limiting permeability enhancer molecules are described in US Patent Publication No. US20050222064; the content of which is herein incorporated by reference in its entirety.

In some embodiments, the RNA vaccine pharmaceutical compositions may be formulated in liposomes such as, but not limited to, DiLa2 liposomes (Marina Biotech, Bothell, Wash.), SMARTICLES® (Marina Biotech, Bothell, Wash.), neutral DOPC (1,2-dioleoyl-sn-glycero-3-phosphocholine) based liposomes (e.g., siRNA delivery for ovarian cancer (Landen et al. Cancer Biology & Therapy 2006 5(12)1708-1713); herein incorporated by reference in its entirety) and hyaluronan-coated liposomes (Quiet Therapeutics, Israel).

In some embodiments, the RNA vaccines may be formulated in a lyophilized gel-phase liposomal composition as described in US Publication No. US2012060293, herein incorporated by reference in its entirety.

The nanoparticle formulations may comprise a phosphate conjugate. The phosphate conjugate may increase in vivo circulation times and/or increase the targeted delivery of the nanoparticle. Phosphate conjugates for use with the present invention may be made by the methods described in International Application No. WO2013033438 or US Patent Publication No. US20130196948, the contents of each of which are herein incorporated by reference in its entirety. As a non-limiting example, the phosphate conjugates may include a compound of any one of the formulas described in International Application No. WO2013033438, herein incorporated by reference in its entirety.

The nanoparticle formulation may comprise a polymer conjugate. The polymer conjugate may be a water soluble conjugate. The polymer conjugate may have a structure as described in U.S. Patent Application No. 20130059360, the contents of which are herein incorporated by reference in its entirety. In one aspect, polymer conjugates with the polynucleotides of the present invention may be made using the methods and/or segmented polymeric reagents described in U.S. Patent Application No. 20130072709, herein incorporated by reference in its entirety. In another aspect, the polymer conjugate may have pendant side groups comprising ring moieties such as, but not limited to, the polymer conjugates described in US Patent Publication No. US20130196948, the contents of which is herein incorporated by reference in its entirety.

The nanoparticle formulations may comprise a conjugate to enhance the delivery of nanoparticles of the present invention in a subject. Further, the conjugate may inhibit phagocytic clearance of the nanoparticles in a subject. In one aspect, the conjugate may be a "self" peptide designed from the human membrane protein CD47 (e.g., the "self" particles described by Rodriguez et al (Science 2013 339, 971-975), herein incorporated by reference in its entirety). As shown by Rodriguez et al. the self peptides delayed macrophage-mediated clearance of nanoparticles which enhanced delivery of the nanoparticles. In another aspect, the conjugate may be the membrane protein CD47 (e.g., see Rodriguez et al. Science 2013 339, 971-975, herein incorporated by reference in its entirety). Rodriguez et al. showed that, similarly to "self" peptides, CD47 can increase the circulating particle ratio in a subject as compared to scrambled peptides and PEG coated nanoparticles.

In some embodiments, the RNA vaccines of the present invention are formulated in nanoparticles which comprise a conjugate to enhance the delivery of the nanoparticles of the present invention in a subject. The conjugate may be the CD47 membrane or the conjugate may be derived from the CD47 membrane protein, such as the "self" peptide described previously. In another aspect the nanoparticle may comprise PEG and a conjugate of CD47 or a derivative thereof. In yet another aspect, the nanoparticle may comprise both the "self" peptide described above and the membrane protein CD47.

In another aspect, a "self" peptide and/or CD47 protein may be conjugated to a virus-like particle or pseudovirion, as described herein for delivery of the RNA vaccines of the present invention.

In another embodiment, RNA vaccine pharmaceutical compositions comprising the polynucleotides of the present invention and a conjugate which may have a degradable linkage. Non-limiting examples of conjugates include an aromatic moiety comprising an ionizable hydrogen atom, a spacer moiety, and a water-soluble polymer. As a non-limiting example, pharmaceutical compositions comprising a conjugate with a degradable linkage and methods for delivering such pharmaceutical compositions are described in US Patent Publication No. US20130184443, the contents of which are herein incorporated by reference in its entirety.

The nanoparticle formulations may be a carbohydrate nanoparticle comprising a carbohydrate carrier and a RNA vaccine. As a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; the contents of which are herein incorporated by reference in its entirety).

Nanoparticle formulations of the present invention may be coated with a surfactant or polymer in order to improve the delivery of the particle. In some embodiments, the nanoparticle may be coated with a hydrophilic coating such as, but not limited to, PEG coatings and/or coatings that have a neutral surface charge. The hydrophilic coatings may help to deliver nanoparticles with larger payloads such as, but not limited to, RNA vaccines within the central nervous system. As a non-limiting example nanoparticles comprising a hydrophilic coating and methods of making such nanoparticles are described in US Patent Publication No. US20130183244, the contents of which are herein incorporated by reference in its entirety.

In some embodiments, the lipid nanoparticles of the present invention may be hydrophilic polymer particles. Non-limiting examples of hydrophilic polymer particles and methods of making hydrophilic polymer particles are described in US Patent Publication No. US20130210991, the contents of which are herein incorporated by reference in its entirety.

In another embodiment, the lipid nanoparticles of the present invention may be hydrophobic polymer particles.

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

In some embodiments, the internal ester linkage may be located on either side of the saturated carbon.

In some embodiments, an immune response may be elicited by delivering a lipid nanoparticle which may include a nanospecies, a polymer and an immunogen. (U.S. Publication No. 20120189700 and International Publication No. WO2012099805; each of which is herein incorporated by reference in their entirety). The polymer may encapsulate the nanospecies or partially encapsulate the nanospecies. The immunogen may be a recombinant protein, a modified RNA and/or a polynucleotide described herein. In some embodiments, the lipid nanoparticle may be formulated for use in a vaccine such as, but not limited to, against a pathogen.

Lipid nanoparticles may be engineered to alter the surface properties of particles so the lipid nanoparticles may penetrate the mucosal barrier. Mucus is located on mucosal tissue such as, but not limited to, oral (e.g., the buccal and esophageal membranes and tonsil tissue), ophthalmic, gastrointestinal (e.g., stomach, small intestine, large intestine, colon, rectum), nasal, respiratory (e.g., nasal, pharyngeal, tracheal and bronchial membranes), genital (e.g., vaginal, cervical and urethral membranes). Nanoparticles larger than 10-200 nm which are preferred for higher drug encapsulation efficiency and the ability to provide the sustained delivery of a wide array of drugs have been thought to be too large to rapidly diffuse through mucosal barriers. Mucus is continuously secreted, shed, discarded or digested and recycled so most of the trapped particles may be removed from the mucosla tissue within seconds or within a few hours. Large polymeric nanoparticles (200 nm-500 nm in diameter) which have been coated densely with a low molecular weight polyethylene glycol (PEG) diffused through mucus only 4 to 6-fold lower than the same particles diffusing in water (Lai et al. PNAS 2007 104(5):1482-487; Lai et al. Adv Drug Deliv Rev. 2009 61(2): 158-171; each of which is herein incorporated by reference in their entirety). The transport of nanoparticles may be determined using rates of permeation and/or fluorescent microscopy techniques including, but not limited to, fluorescence recovery after photobleaching (FRAP) and high resolution multiple particle tracking (MPT). As a non-limiting example, compositions which can penetrate a mucosal barrier may be made as described in U.S. Pat. No. 8,241,670 or International Patent Publication No. WO2013110028, the contents of each of which are herein incorporated by reference in its entirety.

The lipid nanoparticle engineered to penetrate mucus may comprise a polymeric material (i.e. a polymeric core) and/or a polymer-vitamin conjugate and/or a tri-block co-polymer. The polymeric material may include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates. The polymeric material may be biodegradable and/or biocompatible. Non-limiting examples of biocompatible polymers are described in International Patent Publication No. WO2013116804, the contents of which are herein incorporated by reference in its entirety. The polymeric material may additionally be irradiated. As a non-limiting example, the polymeric material may be gamma irradiated (See e.g., International App. No. WO201282165, herein incorporated by reference in its entirety). Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly (lactic acid-co-glycolic acid) (PLGA), poly(L-lactic acid-co-glycolic acid) (PLLGA), poly(D,L-lactide) (PDLA), poly (L-lactide) (PLLA), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and its copolymers, polyhydroxyalkanoates, polypropylene fumarate, polyoxymethylene, poloxamers, poly(ortho)esters, poly(butyric acid), poly(valeric acid), poly(lactide-co-caprolactone), PEG-PLGA-PEG and trimethylene carbonate, polyvinylpyrrolidone. The lipid nanoparticle may be coated or associated with a co-polymer such as, but not limited to, a block co-polymer (such as a branched polyether-polyamide block copolymer described in International Publication No. WO2013012476, herein incorporated by reference in its entirety), and (poly(ethylene glycol))-(poly(propylene oxide))-(poly(ethylene glycol)) triblock copolymer (see e.g., US Publication 20120121718 and US Publication 20100003337 and U.S. Pat. No. 8,263,665; each of which is herein incorporated by reference in their entirety). The co-polymer may be a polymer that is generally regarded as safe (GRAS) and the formation of the lipid nanoparticle may be in such a way that no new chemical entities are created. For example, the lipid nanoparticle may comprise poloxamers coating PLGA nanoparticles without forming new chemical entities which are still able to rapidly penetrate human mucus (Yang et al. Angew. Chem. Int. Ed. 2011 50:2597-2600; the contents of which are herein incorporated by reference in its entirety). A non-limiting scalable method to produce nanoparticles which can penetrate human mucus is described by Xu et al. (See e.g., J Control Release 2013, 170(2):279-86; the contents of which are herein incorporated by reference in its entirety).

The vitamin of the polymer-vitamin conjugate may be vitamin E. The vitamin portion of the conjugate may be substituted with other suitable components such as, but not limited to, vitamin A, vitamin E, other vitamins, cholesterol, a hydrophobic moiety, or a hydrophobic component of other surfactants (e.g., sterol chains, fatty acids, hydrocarbon chains and alkylene oxide chains).

The lipid nanoparticle engineered to penetrate mucus may include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin P4 dornase alfa, neltenexine, erdosteine) and various DNases including rhDNase. The surface altering agent may be embedded or enmeshed in the particle's surface or disposed (e.g., by coating, adsorption, covalent linkage, or other process) on the surface of the lipid nanoparticle. (see e.g., US Publication 20100215580 and US Publication 20080166414 and US20130164343; the contents of each of which is herein incorporated by reference in their entirety).

In some embodiments, the mucus penetrating lipid nanoparticles may comprise at least one polynucleotide described herein. The polynucleotide may be encapsulated in the lipid nanoparticle and/or disposed on the surface of the particle. The polynucleotide may be covalently coupled to the lipid nanoparticle. Formulations of mucus penetrating lipid nanoparticles may comprise a plurality of nanoparticles. Further, the formulations may contain particles which may interact with the mucus and alter the structural and/or adhesive properties of the surrounding mucus to decrease mucoadhesion which may increase the delivery of the mucus penetrating lipid nanoparticles to the mucosal tissue.

In another embodiment, the mucus penetrating lipid nanoparticles may be a hypotonic formulation comprising a mucosal penetration enhancing coating. The formulation may be hypotonice for the epithelium to which it is being delivered. Non-limiting examples of hypotonic formulations may be found in International Patent Publication No. WO2013110028, the contents of which are herein incorporated by reference in its entirety.

In some embodiments, in order to enhance the delivery through the mucosal barrier the RNA vaccine formulation may comprise or be a hypotonic solution. Hypotonic solutions were found to increase the rate at which mucoinert particles such as, but not limited to, mucus-penetrating particles, were able to reach the vaginal epithelial surface (See e.g., Ensign et al. Biomaterials 2013 34(28):6922-9; the contents of which is herein incorporated by reference in its entirety).

In some embodiments, the RNA vaccine is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, Mass.), and polyethylenimine (PEI) or protamine-based targeted and non-targeted delivery of nucleic acids acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments such formulations may also be constructed or compositions altered such that they passively or actively are directed to different cell types in vivo, including but not limited to hepatocytes, immune cells, tumor cells, endothelial cells, antigen presenting cells, and leukocytes (Akinc et al. Mol Ther. 2010 18:1357-1364; Song et al., Nat Biotechnol. 2005 23:709-717; Judge et al., J Clin Invest. 2009 119:661-673; Kaufmann et al., Microvasc Res 2010 80:286-293; Santel et al., Gene Ther 2006 13:1222-1234; Santel et al., Gene Ther 2006 13:1360-1370; Gutbier et al., Pulm Pharmacol. Ther. 2010 23:334-344; Basha et al., Mol. Ther. 2011 19:2186-2200; Fenske and Cullis, Expert Opin Drug Deliv. 2008 5:25-44; Peer et al., Science. 2008 319:627-630; Peer and Lieberman, Gene Ther. 2011 18:1127-1133; all of which are incorporated herein by reference in its entirety). One example of passive targeting of formulations to liver cells includes the DLin-DMA, DLin-KC2-DMA and DLin-MC3-DMA-based lipid nanoparticle formulations which have been shown to bind to apolipoprotein E and promote binding and uptake of these formulations into hepatocytes in vivo (Akinc et al. Mol Ther. 2010 18:1357-1364; herein incorporated by reference in its entirety). Formulations can also be selectively targeted through expression of different ligands on their surface as exemplified by, but not limited by, folate, transferrin, N-acetylgalactosamine (GalNAc), and antibody targeted approaches (Kolhatkar et al., Curr Drug Discov Technol. 2011 8:197-206; Musacchio and Torchilin, Front Biosci. 2011 16:1388-1412; Yu et al., Mol Membr Biol. 2010 27:286-298; Patil et al., Crit Rev Ther Drug Carrier Syst. 2008 25:1-61; Benoit et al., Biomacromolecules. 2011 12:2708-2714; Zhao et al., Expert Opin Drug Deliv. 2008 5:309-319; Akinc et al., Mol Ther. 2010 18:1357-1364; Srinivasan et al., Methods Mol Biol. 2012 820:105-116; Ben-Arie et al., Methods Mol Biol. 2012 757:497-507; Peer 2010 J Control Release. 20:63-68; Peer et al., Proc Natl Acad Sci USA. 2007 104:4095-4100; Kim et al., Methods Mol Biol. 2011 721:339-353; Subramanya et al., Mol Ther. 2010 18:2028-2037; Song et al., Nat Biotechnol. 2005 23:709-717; Peer et al., Science. 2008 319:627-630; Peer and Lieberman, Gene Ther. 2011 18:1127-1133; all of which are incorporated herein by reference in its entirety).

In some embodiments, the RNA vaccine is formulated as a solid lipid nanoparticle. A solid lipid nanoparticle (SLN) may be spherical with an average diameter between 10 to 1000 nm. SLN possess a solid lipid core matrix that can solubilize lipophilic molecules and may be stabilized with surfactants and/or emulsifiers. In a further embodiment, the lipid nanoparticle may be a self-assembly lipid-polymer nanoparticle (see Zhang et al., ACS Nano, 2008, 2 (8), pp 1696-1702; the contents of which are herein incorporated by reference in its entirety). As a non-limiting example, the SLN may be the SLN described in International Patent Publication No. WO2013105101, the contents of which are herein incorporated by reference in its entirety. As another non-limiting example, the SLN may be made by the methods or processes described in International Patent Publication No. WO2013105101, the contents of which are herein incorporated by reference in its entirety.

Liposomes, lipoplexes, or lipid nanoparticles may be used to improve the efficacy of polynucleotides directed protein production as these formulations may be able to increase cell transfection by the RNA vaccine; and/or increase the translation of encoded protein. One such example involves the use of lipid encapsulation to enable the effective systemic delivery of polyplex plasmid DNA (Heyes et al., Mol Ther. 2007 15:713-720; herein incorporated by reference in its entirety). The liposomes, lipoplexes, or lipid nanoparticles may also be used to increase the stability of the polynucleotide.

In some embodiments, the RNA vaccines of the present invention can be formulated for controlled release and/or targeted delivery. As used herein, "controlled release" refers to a pharmaceutical composition or compound release profile that conforms to a particular pattern of release to effect a therapeutic outcome. In some embodiments, the RRNA vaccines may be encapsulated into a delivery agent described herein and/or known in the art for controlled release and/or targeted delivery. As used herein, the term "encapsulate" means to enclose, surround or encase. As it relates to the formulation of the compounds of the invention, encapsulation may be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention may be enclosed, surrounded or encased within the delivery agent. "Partially encapsulation" means that less than 10, 10, 20, 30, 40 50 or less of the pharmaceutical composition or compound of the invention may be enclosed, surrounded or encased within the delivery agent. Advantageously, encapsulation may be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In some embodiments, the controlled release formulation may include, but is not limited to, tri-block co-polymers. As a non-limiting example, the formulation may include two different types of tri-block co-polymers (International Pub. No. WO2012131104 and WO2012131106; the contents of each of which is herein incorporated by reference in its entirety).

In another embodiment, the RNA vaccines may be encapsulated into a lipid nanoparticle or a rapidly eliminated lipid nanoparticle and the lipid nanoparticles or a rapidly eliminated lipid nanoparticle may then be encapsulated into a polymer, hydrogel and/or surgical sealant described herein and/or known in the art. As a non-limiting example, the polymer, hydrogel or surgical sealant may be PLGA, ethylene vinyl acetate (EVAc), poloxamer, GELSITE® (Nanotherapeutics, Inc. Alachua, Fla.), HYLENEX® (Halozyme Therapeutics, San Diego Calif.), surgical sealants such as fibrinogen polymers (Ethicon Inc. Cornelia, Ga.), TIS- SELL® (Baxter International, Inc Deerfield, Ill.), PEG-based sealants, and COSEAL® (Baxter International, Inc Deerfield, Ill.).

In another embodiment, the lipid nanoparticle may be encapsulated into any polymer known in the art which may form a gel when injected into a subject. As another non-limiting example, the lipid nanoparticle may be encapsulated into a polymer matrix which may be biodegradable.

In some embodiments, the the RNA vaccine formulation for controlled release and/or targeted delivery may also include at least one controlled release coating. Controlled release coatings include, but are not limited to, OPADRY®, polyvinylpyrrolidone/vinyl acetate copolymer, polyvinylpyrrolidone, hydroxypropyl methylcellulose, hydroxypropyl cellulose, hydroxyethyl cellulose, EUDRAGIT RL®, EUDRAGIT RS® and cellulose derivatives such as ethylcellulose aqueous dispersions (AQUACOAT® and SURELEASE®).

In some embodiments, the RNA vaccine controlled release and/or targeted delivery formulation may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In some embodiments, the RNA vaccine controlled release and/or targeted delivery formulation comprising at least one polynucleotide may comprise at least one PEG and/or PEG related polymer derivatives as described in U.S. Pat. No. 8,404,222, herein incorporated by reference in its entirety.

In another embodiment, the RNA vaccine controlled release delivery formulation comprising at least one polynucleotide may be the controlled release polymer system described in US20130130348, herein incorporated by reference in its entirety.

In some embodiments, the the RNA vaccines of the present invention may be encapsulated in a therapeutic nanoparticle, referred to herein as "therapeutic nanoparticle RRNA vaccines." Therapeutic nanoparticles may be formulated by methods described herein and known in the art such as, but not limited to, International Pub Nos. WO2010005740, WO2010030763, WO2010005721, WO2010005723, WO2012054923, US Pub. Nos. US20110262491, US20100104645, US20100087337, US20100068285, US20110274759, US20100068286, US20120288541, US20130123351 and US20130230567 and U.S. Pat. Nos. 8,206,747, 8,293,276, 8,318,208 and 8,318,211; the contents of each of which are herein incorporated by reference in their entirety. In another embodiment, therapeutic polymer nanoparticles may be identified by the methods described in US Pub No. US20120140790, the contents of which is herein incorporated by reference in its entirety.

In some embodiments, the therapeutic nanoparticle RNA vaccine may be formulated for sustained release. As used herein, "sustained release" refers to a pharmaceutical composition or compound that conforms to a release rate over a specific period of time. The period of time may include, but is not limited to, hours, days, weeks, months and years. As a non-limiting example, the sustained release nanoparticle may comprise a polymer and a therapeutic agent such as, but not limited to, the the polynucleotides of the present invention (see International Pub No. 2010075072 and US Pub No. US20100216804, US20110217377 and US20120201859, each of which is herein incorporated by reference in their entirety). In another non-limiting example, the sustained release formulation may comprise agents which permit persistent bioavailability such as, but not limited to, crystals, macromolecular gels and/or particulate suspensions (see US Patent Publication No US20130150295, the contents of which is herein incorporated by reference in its entirety).

In some embodiments, the therapeutic nanoparticle RNA vaccines may be formulated to be target specific. As a non-limiting example, the thereapeutic nanoparticles may include a corticosteroid (see International Pub. No. WO2011084518; herein incorporated by reference in its entirety). As a non-limiting example, the therapeutic nanoparticles may be formulated in nanoparticles described in International Pub No. WO2008121949, WO2010005726, WO2010005725, WO2011084521 and US Pub No. US20100069426, US20120004293 and US20100104655, each of which is herein incorporated by reference in their entirety.

In some embodiments, the nanoparticles of the present invention may comprise a polymeric matrix. As a non-limiting example, the nanoparticle may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly(4-hydroxy-L-proline ester) or combinations thereof.

In some embodiments, the therapeutic nanoparticle comprises a diblock copolymer. In some embodiments, the diblock copolymer may include PEG in combination with a polymer such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polylysine, poly(ethylene imine), poly(serine ester), poly(L-lactide-co-L-lysine), poly (4-hydroxy-L-proline ester) or combinations thereof. In another embodiment, the diblock copolymer may comprise the diblock copolymers described in European Patent Publication No. the contents of which are herein incorporated by reference in its entirety. In yet another embodiment, the diblock copolymer may be a high-X diblock copolymer such as those described in International Patent Publication No. WO2013120052, the contents of which are herein incorporated by reference in its entirety.

As a non-limiting example the therapeutic nanoparticle comprises a PLGA-PEG block copolymer (see US Pub. No. US20120004293 and U.S. Pat. No. 8,236,330, each of which is herein incorporated by reference in their entirety). In another non-limiting example, the therapeutic nanoparticle is a stealth nanoparticle comprising a diblock copolymer of PEG and PLA or PEG and PLGA (see U.S. Pat. No. 8,246,968 and International Publication No. WO2012166923, the contents of each of which are herein incorporated by reference in its entirety). In yet another non-limiting example, the therapeutic nanoparticle is a stealth nanoparticle or a target-specific stealth nanoparticle as described in US Patent Publication No. US20130172406, the contents of which are herein incorporated by reference in its entirety.

In some embodiments, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In yet another non-limiting example, the lipid nanoparticle comprises the block copolymer PEG-PLGA-PEG (see e.g., the thermosensitive hydrogel (PEG-PLGA-PEG) was used as a TGF-beta1 gene delivery vehicle in Lee et al. Thermosensitive Hydrogel as a Tgf-β1 Gene Delivery Vehicle Enhances Diabetic Wound Healing. Pharmaceutical Research, 2003 20(12): 1995-2000; as a controlled gene delivery system in Li et al. Controlled Gene Delivery System Based on Thermosensitive Biodegradable Hydrogel. Pharmaceutical Research 2003 20(6):884-888; and Chang et al., Non-ionic amphiphilic biodegradable PEG-PLGA-PEG copolymer enhances gene delivery efficiency in rat skeletal muscle. J Controlled Release. 2007 118:245-253; each of which is herein incorporated by reference in its entirety). The RNA vaccines of the present invention may be formulated in lipid nanoparticles comprising the PEG-PLGA-PEG block copolymer.

In some embodiments, the therapeutic nanoparticle may comprise a multiblock copolymer (See e.g., U.S. Pat. Nos. 8,263,665 and 8,287,910 and US Patent Pub. No. US20130195987; the contents of each of which are herein incorporated by reference in its entirety).

In some embodiments, the block copolymers described herein may be included in a polyion complex comprising a non-polymeric micelle and the block copolymer. (See e.g., U.S. Pub. No. 20120076836; herein incorporated by reference in its entirety).

In some embodiments, the therapeutic nanoparticle may comprise at least one acrylic polymer. Acrylic polymers include but are not limited to, acrylic acid, methacrylic acid, acrylic acid and methacrylic acid copolymers, methyl methacrylate copolymers, ethoxyethyl methacrylates, cyanoethyl methacrylate, amino alkyl methacrylate copolymer, poly (acrylic acid), poly(methacrylic acid), polycyanoacrylates and combinations thereof.

In some embodiments, the therapeutic nanoparticles may comprise at least one poly(vinyl ester) polymer. The poly (vinyl ester) polymer may be a copolymer such as a random copolymer. As a non-limiting example, the random copolymer may have a structure such as those described in International Application No. WO2013032829 or US Patent Publication No US20130121954, the contents of which are herein incorporated by reference in its entirety. In one aspect, the poly(vinyl ester) polymers may be conjugated to the polynucleotides described herein. In another aspect, the poly(vinyl ester) polymer which may be used in the present invention may be those described in, herein incorporated by reference in its entirety.

In some embodiments, the therapeutic nanoparticle may comprise at least one diblock copolymer. The diblock copolymer may be, but it not limited to, a poly(lactic) acid-poly (ethylene)glycol copolymer (see e.g., International Patent Publication No. WO2013044219; herein incorporated by reference in its entirety). As a non-limiting example, the therapeutic nanoparticle may be used to treat cancer (see International publication No. WO2013044219; herein incorporated by reference in its entirety).

In some embodiments, the therapeutic nanoparticles may comprise at least one cationic polymer described herein and/or known in the art.

In some embodiments, the therapeutic nanoparticles may comprise at least one amine-containing polymer such as, but not limited to polylysine, polyethylene imine, poly(amidoamine) dendrimers, poly(beta-amino esters) (See e.g., U.S. Pat. No. 8,287,849; herein incorporated by reference in its entirety) and combinations thereof.

In another embodiment, the nanoparticles described herein may comprise an amine cationic lipid such as those described in International Patent Application No. WO2013059496, the contents of which are herein incorporated by reference in its entirety. In one aspect the cationic lipids may have an amino-amine or an amino-amide moiety.

In some embodiments, the therapeutic nanoparticles may comprise at least one degradable polyester which may contain polycationic side chains. Degradeable polyesters include, but are not limited to, poly(serine ester), poly(L-lactide-co-L-lysine), poly(4-hydroxy-L-proline ester), and combinations thereof. In another embodiment, the degradable polyesters may include a PEG conjugation to form a PEGylated polymer.

In another embodiment, the therapeutic nanoparticle may include a conjugation of at least one targeting ligand. The targeting ligand may be any ligand known in the art such as, but not limited to, a monoclonal antibody. (Kirpotin et al, Cancer Res. 2006 66:6732-6740; herein incorporated by reference in its entirety).

In some embodiments, the therapeutic nanoparticle may be formulated in an aqueous solution which may be used to target cancer (see International Pub No. WO2011084513 and US Pub No. US20110294717, each of which is herein incorporated by reference in their entirety).

In some embodiments, the therapeutic nanoparticle RNA vaccines, e.g., therapeutic nanoparticles comprising at least one RNA vaccine may be formulated using the methods described by Podobinski et al in U.S. Pat. No. 8,404,799, the contents of which are herein incorporated by reference in its entirety.

In some embodiments, the RNA vaccines may be encapsulated in, linked to and/or associated with synthetic nanocarriers. Synthetic nanocarriers include, but are not limited to, those described in International Pub. Nos. WO2010005740, WO2010030763, WO201213501, WO2012149252, WO2012149255, WO2012149259, WO2012149265, WO2012149268, WO2012149282, WO2012149301, WO2012149393, WO2012149405, WO2012149411, WO2012149454 and WO2013019669, and US Pub. Nos. US20110262491, US20100104645, US20100087337 and US20120244222, each of which is herein incorporated by reference in their entirety. The synthetic nanocarriers may be formulated using methods known in the art and/or described herein. As a non-limiting example, the synthetic nanocarriers may be formulated by the methods described in International Pub Nos. WO2010005740, WO2010030763 and WO201213501 and US Pub. Nos. US20110262491, US20100104645, US20100087337 and US2012024422, each of which is herein incorporated by reference in their entirety. In another embodiment, the synthetic nanocarrier formulations may be lyophilized by methods described in International Pub. No. WO2011072218 and U.S. Pat. No. 8,211,473; the content of each of which is herein incorporated by reference in their entirety. In yet another embodiment, formulations of the present invention, including, but not limited to, synthetic nanocarriers, may be lyophilized or reconstituted by the methods described in US Patent Publication No. US20130230568, the contents of which are herein incorporated by reference in its entirety.

In some embodiments, the synthetic nanocarriers may contain reactive groups to release the polynucleotides described herein (see International Pub. No. WO20120952552 and US Pub No. US20120171229, each of which is herein incorporated by reference in their entirety).

In some embodiments, the synthetic nanocarriers may contain an immunostimulatory agent to enhance the immune response from delivery of the synthetic nanocarrier. As a non-limiting example, the synthetic nanocarrier may comprise a Th1 immunostimulatory agent which may enhance a Th1-based response of the immune system (see International Pub No. WO2010123569 and US Pub. No. US20110223201, each of which is herein incorporated by reference in its entirety).

In some embodiments, the synthetic nanocarriers may be formulated for targeted release. In some embodiments, the synthetic nanocarrier is formulated to release the polynucleotides at a specified pH and/or after a desired time interval. As a non-limiting example, the synthetic nanoparticle may be formulated to release the RNA vaccines after 24 hours and/or at a pH of 4.5 (see International Pub. Nos. WO2010138193 and WO2010138194 and US Pub Nos. US20110020388 and US20110027217, each of which is herein incorporated by reference in their entireties).

In some embodiments, the synthetic nanocarriers may be formulated for controlled and/or sustained release of the polynucleotides described herein. As a non-limiting example, the synthetic nanocarriers for sustained release may be formulated by methods known in the art, described herein and/or as described in International Pub No. WO2010138192 and US Pub No. 20100303850, each of which is herein incorporated by reference in their entirety.

In some embodiments, the RNA vaccine may be formulated for controlled and/or sustained release wherein the formulation comprises at least one polymer that is a crystalline side chain (CYSC) polymer. CYSC polymers are described in U.S. Pat. No. 8,399,007, herein incorporated by reference in its entirety.

In some embodiments, the synthetic nanocarrier may be formulated for use as a vaccine. In some embodiments, the synthetic nanocarrier may encapsulate at least one polynucleotide which encode at least one antigen. As a non-limiting example, the synthetic nanocarrier may include at least one antigen and an excipient for a vaccine dosage form (see International Pub No. WO2011150264 and US Pub No. US20110293723, each of which is herein incorporated by reference in their entirety). As another non-limiting example, a vaccine dosage form may include at least two synthetic nanocarriers with the same or different antigens and an excipient (see International Pub No. WO2011150249 and US Pub No. US20110293701, each of which is herein incorporated by reference in their entirety). The vaccine dosage form may be selected by methods described herein, known in the art and/or described in International Pub No. WO2011150258 and US Pub No. US20120027806, each of which is herein incorporated by reference in their entirety).

In some embodiments, the synthetic nanocarrier may comprise at least one polynucleotide which encodes at least one adjuvant. As non-limiting example, the adjuvant may comprise dimethyldioctadecylammonium-bromide, dimethyldioctadecylammonium-chloride, dimethyldioctadecylammonium-phosphate or dimethyldioctadecylammonium-acetate (DDA) and an apolar fraction or part of said apolar fraction of a total lipid extract of a *mycobacterium* (See e.g, U.S. Pat. No. 8,241,610; herein incorporated by reference in its entirety). In another embodiment, the synthetic nanocarrier may comprise at least one polynucleotide and an adjuvant. As a non-limiting example, the synthetic nanocarrier comprising and adjuvant may be formulated by the methods described in International Pub No. WO2011150240 and US Pub No. US20110293700, each of which is herein incorporated by reference in its entirety.

In some embodiments, the synthetic nanocarrier may encapsulate at least one polynucleotide which encodes a peptide, fragment or region from a virus. As a non-limiting example, the synthetic nanocarrier may include, but is not limited to, the nanocarriers described in International Pub No. WO2012024621, WO201202629, WO2012024632 and US Pub No. US20120064110, US20120058153 and US20120058154, each of which is herein incorporated by reference in their entirety.

In some embodiments, the synthetic nanocarrier may be coupled to a polynucleotide which may be able to trigger a humoral and/or cytotoxic T lymphocyte (CTL) response (See e.g., International Publication No. WO2013019669, herein incorporated by reference in its entirety).

In some embodiments, the RNA vaccine may be encapsulated in, linked to and/or associated with zwitterionic lipids. Non-limiting examples of zwitterionic lipids and methods of using zwitterionic lipids are described in US Patent Publication No. US20130216607, the contents of which are herein incorporated by reference in its entirety. In one aspect, the zwitterionic lipids may be used in the liposomes and lipid nanoparticles described herein.

In some embodiments, the RNA vaccine may be formulated in colloid nanocarriers as described in US Patent Publication No. US20130197100, the contents of which are herein incorporated by reference in its entirety.

In some embodiments, the nanoparticle may be optimized for oral administration. The nanoparticle may comprise at least one cationic biopolymer such as, but not limited to, chitosan or a derivative thereof. As a non-limiting example, the nanoparticle may be formulated by the methods described in U.S. Pub. No. 20120282343; herein incorporated by reference in its entirety.

In some embodiments, LNPs comprise the lipid KL52 (an amino-lipid disclosed in U.S. Application Publication No. 2012/0295832 expressly incorporated herein by reference in its entirety). Activity and/or safety (as measured by examining one or more of ALT/AST, white blood cell count and cytokine induction) of LNP administration may be improved by incorporation of such lipids. LNPs comprising KL52 may be administered intravenously and/or in one or more doses. In some embodiments, administration of LNPs comprising KL52 results in equal or improved mRNA and/or protein expression as compared to LNPs comprising MC3.

In some embodiments, RNA vaccine may be delivered using smaller LNPs. Such particles may comprise a diameter from below 0.1 um up to 100 nm such as, but not limited to, less than 0.1 um, less than 1.0 um, less than 5 um, less than 10 um, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, and less than 975 um.

In another embodiment, RNA vaccines may be delivered using smaller LNPs which may comprise a diameter from about 1 nm to about 100 nm, from about 1 nm to about 10 nm, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 50 nM, from about 20 to about 50 nm, from about 30 to about 50 nm, from about 40 to about 50 nm, from about 20 to about 60 nm, from about 30 to about 60 nm, from about 40 to about 60 nm, from about 20 to about 70 nm, from about 30 to about 70 nm, from about 40 to about 70 nm, from about 50 to about 70 nm, from about 60 to about 70 nm, from about 20 to about 80 nm, from about 30 to about 80 nm, from about 40 to about 80 nm, from about 50 to about 80 nm, from about 60 to about 80 nm, from about 20 to about 90 nm, from about 30 to about 90 nm, from about 40 to about 90 nm, from about 50 to about 90 nm, from about 60 to about 90 nm and/or from about 70 to about 90 nm.

In some embodiments, such LNPs are synthesized using methods comprising microfluidic mixers. Exemplary microfluidic mixers may include, but are not limited to a slit interdigitial micromixer including, but not limited to those manufactured by Microinnova (Allerheiligen bei Wildon, Austria) and/or a staggered herringbone micromixer (SHM) (Zhigaltsev, I. V. et al., Bottom-up design and synthesis of limit size lipid nanoparticle systems with aqueous and triglyceride cores using millisecond microfluidic mixing have been published (Langmuir. 2012. 28:3633-40; Belliveau, N. M. et al., Microfluidic synthesis of highly potent limit-size lipid nanoparticles for in vivo delivery of siRNA. Molecular Therapy-Nucleic Acids. 2012. 1:e37; Chen, D. et al., Rapid discovery of potent siRNA-containing lipid nanoparticles enabled by controlled microfluidic formulation. J Am Chem Soc. 2012. 134(16):6948-51; each of which is herein incorporated by reference in its entirety). In some embodiments, methods of LNP generation comprising SHM, further comprise the mixing of at least two input streams wherein mixing occurs by microstructure-induced chaotic advection (MICA). According to this method, fluid streams flow through channels present in a herringbone pattern causing rotational flow and folding the fluids around each other. This method may also comprise a surface for fluid mixing wherein the surface changes orientations during fluid cycling. Methods of generating LNPs using SHM include those disclosed in U.S. Application Publication Nos. 2004/0262223 and 2012/0276209, each of which is expressly incorporated herein by reference in their entirety.

In some embodiments, the RNA vaccine of the present invention may be formulated in lipid nanoparticles created using a micromixer such as, but not limited to, a Slit Interdigital Microstructured Mixer (SIMM-V2) or a Standard Slit Interdigital Micro Mixer (SSIMM) or Caterpillar (CPMM) or Impinging-jet (IJMM) from the Institut für Mikrotechnik Mainz GmbH, Mainz Germany).

In some embodiments, the RNA vaccines of the present invention may be formulated in lipid nanoparticles created using microfluidic technology (see Whitesides, George M. The Origins and the Future of Microfluidics. Nature, 2006 442: 368-373; and Abraham et al. Chaotic Mixer for Microchannels. Science, 2002 295: 647-651; each of which is herein incorporated by reference in its entirety). As a non-limiting example, controlled microfluidic formulation includes a passive method for mixing streams of steady pressure-driven flows in micro channels at a low Reynolds number (See e.g., Abraham et al. Chaotic Mixer for Microchannels. Science, 2002 295: 647-651; which is herein incorporated by reference in its entirety).

In some embodiments, the RNA vaccines of the present invention may be formulated in lipid nanoparticles created using a micromixer chip such as, but not limited to, those from Harvard Apparatus (Holliston, Mass.) or Dolomite Microfluidics (Royston, UK). A micromixer chip can be used for rapid mixing of two or more fluid streams with a split and recombine mechanism.

In some embodiments, the RNA vaccines of the invention may be formulated for delivery using the drug encapsulating microspheres described in International Patent Publication No. WO2013063468 or U.S. Pat. No. 8,440,614, each of which is herein incorporated by reference in its entirety. The microspheres may comprise a compound of the formula (I), (II), (III), (IV), (V) or (VI) as described in International Patent Publication No. WO2013063468, the contents of which are herein incorporated by reference in its entirety. In another aspect, the amino acid, peptide, polypeptide, lipids (APPL) are useful in delivering the RNA vaccines of the invention to cells (see International Patent Publication No. WO2013063468, the contents of which is herein incorporated by reference in its entirety).

In some embodiments, the RNA vaccines of the invention may be formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles may have a diameter from about 10 to 500 nm.

In some embodiments, the lipid nanoparticle may have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In one aspect, the lipid nanoparticle may be a limit size lipid nanoparticle described in International Patent Publication No. WO2013059922, the contents of which are herein incorporated by reference in its entirety. The limit size lipid nanoparticle may comprise a lipid bilayer surrounding an aqueous core or a hydrophobic core; where the lipid bilayer may comprise a phospholipid such as, but not limited to, diacylphosphatidylcholine, a diacylphosphatidylethanolamine, a ceramide, a sphingomyelin, a dihydrosphingomyelin, a cephalin, a cerebroside, a C8-C20 fatty acid diacylphophatidylcholine, and 1-palmitoyl-2-oleoyl phosphatidylcholine (POPC). In another aspect the limit size lipid nanoparticle may comprise a polyethylene glycol-lipid such as, but not limited to, DLPE-PEG, DMPE-PEG, DPPC-PEG and DSPE-PEG.

In some embodiments, the RNA vaccines may be delivered, localized and/or concentrated in a specific location using the delivery methods described in International Patent Publication No. WO2013063530, the contents of which are herein incorporated by reference in its entirety. As a non-limiting example, a subject may be administered an empty polymeric particle prior to, simultaneously with or after delivering the RNA vaccines to the subject. The empty polymeric particle undergoes a change in volume once in contact with the subject and becomes lodged, embedded, immobilized or entrapped at a specific location in the subject.

In some embodiments, the RNA vaccines may be formulated in an active substance release system (See e.g., US Patent Publication No. US20130102545, the contents of which is herein incorporated by reference in its entirety). The active substance release system may comprise 1) at least one nanoparticle bonded to an oligonucleotide inhibitor strand which is hybridized with a catalytically active nucleic acid and 2) a compound bonded to at least one substrate molecule bonded to a therapeutically active substance (e.g., polynucleotides described herein), where the therapeutically active substance is released by the cleavage of the substrate molecule by the catalytically active nucleic acid.

In some embodiments, the RNA vaccines may be formulated in a nanoparticle comprising an inner core comprising a non-cellular material and an outer surface comprising a cellular membrane. The cellular membrane may be derived from a cell or a membrane derived from a virus. As a non-limiting example, the nanoparticle may be made by the methods described in International Patent Publication No. WO2013052167, herein incorporated by reference in its entirety. As another non-limiting example, the nanoparticle described in International Patent Publication No. WO2013052167, herein incorporated by reference in its entirety, may be used to deliver the RNA vaccines described herein.

In some embodiments, the RNA vaccines may be formulated in porous nanoparticle-supported lipid bilayers (protocells). Protocells are described in International Patent Publication No. WO2013056132, the contents of which are herein incorporated by reference in its entirety.

In some embodiments, the RNA vaccines described herein may be formulated in polymeric nanoparticles as described in or made by the methods described in U.S. Pat. Nos. 8,420,123 and 8,518,963 and European Patent No. EP2073848B1, the contents of each of which are herein incorporated by reference in their entirety. As a non-limiting example, the polymeric nanoparticle may have a high glass transition temperature such as the nanoparticles described in or nanoparticles made by the methods described in U.S. Pat. No. 8,518,963, the contents of which are herein incorporated by reference in its entirety. As another non-limiting example, the polymer nanoparticle for oral and parenteral formulations may be made by the methods described in European Patent No. EP2073848B1, the contents of which are herein incorporated by reference in its entirety.

In another embodiment, the RNA vaccines described herein may be formulated in nanoparticles used in imaging. The nanoparticles may be liposome nanoparticles such as those described in US Patent Publication No US20130129636, herein incorporated by reference in its entirety. As a non-limiting example, the liposome may comprise gadolinium(III)2-{4,7-bis-carboxymethyl-10-[(N,N-distearylamidomethyl-N'-amido-methyl]-1,4,7,10-tetra-azacyclododec-1-yl}-acetic acid and a neutral, fully saturated phospholipid component (see e.g., US Patent Publication No US20130129636, the contents of which is herein incorporated by reference in its entirety).

In some embodiments, the nanoparticles which may be used in the present invention are formed by the methods described in U.S. Patent Application No. US20130130348, the contents of which is herein incorporated by reference in its entirety.

The nanoparticles of the present invention may further include nutrients such as, but not limited to, those which deficiencies can lead to health hazards from anemia to neural tube defects (see e.g, the nanoparticles described in International Patent Publication No WO2013072929, the contents of which is herein incorporated by reference in its entirety). As a non-limiting example, the nutrient may be iron in the form of ferrous, ferric salts or elemental iron, iodine, folic acid, vitamins or micronutrients.

In some embodiments, the RNA vaccines of the present invention may be formulated in a swellable nanoparticle. The swellable nanoparticle may be, but is not limited to, those described in U.S. Pat. No. 8,440,231, the contents of which is herein incorporated by reference in its entirety. As a non-limiting embodiment, the swellable nanoparticle may be used for delivery of the RNA vaccines of the present invention to the pulmonary system (see e.g., U.S. Pat. No. 8,440,231, the contents of which is herein incorporated by reference in its entirety).

The RNA vaccines of the present invention may be formulated in polyanhydride nanoparticles such as, but not limited to, those described in U.S. Pat. No. 8,449,916, the contents of which is herein incorporated by reference in its entirety.

The nanoparticles and microparticles of the present invention may be geometrically engineered to modulate macrophage and/or the immune response. In one aspect, the geometrically engineered particles may have varied shapes, sizes and/or surface charges in order to incorporated the polynucleotides of the present invention for targeted delivery such as, but not limited to, pulmonary delivery (see e.g., International Publication No WO2013082111, the contents of which is herein incorporated by reference in its entirety). Other physical features the geometrically engineering particles may have include, but are not limited to, fenestrations, angled arms, asymmetry and surface roughness, charge which can alter the interactions with cells and tissues. As a non-limiting example, nanoparticles of the present invention may be made by the methods described in International Publication No WO2013082111, the contents of which is herein incorporated by reference in its entirety.

In some embodiments, the nanoparticles of the present invention may be water soluble nanoparticles such as, but not limited to, those described in International Publication No. WO2013090601, the contents of which is herein incorporated by reference in its entirety. The nanoparticles may be inorganic nanoparticles which have a compact and zwitterionic ligand in order to exhibit good water solubility. The nanoparticles may also have small hydrodynamic diameters (HD), stability with respect to time, pH, and salinity and a low level of non-specific protein binding.

In some embodiments the nanoparticles of the present invention may be developed by the methods described in US Patent Publication No. US20130172406, the contents of which are herein incorporated by reference in its entirety.

In some embodiments, the nanoparticles of the present invention are stealth nanoparticles or target-specific stealth nanoparticles such as, but not limited to, those described in US Patent Publication No. US20130172406; the contents of which is herein incorporated by reference in its entirety. The nanoparticles of the present invention may be made by the methods described in US Patent Publication No. US20130172406, the contents of which are herein incorporated by reference in its entirety.

In another embodiment, the stealth or target-specific stealth nanoparticles may comprise a polymeric matrix. The polymeric matrix may comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates or combinations thereof.

In some embodiments, the nanoparticle may be a nanoparticle-nucleic acid hybrid structure having a high density nucleic acid layer. As a non-limiting example, the nanoparticle-nucleic acid hybrid structure may made by the methods described in US Patent Publication No. US20130171646, the contents of which are herein incorporated by reference in its entirety. The nanoparticle may comprise a nucleic acid such as, but not limited to, polynucleotides described herein and/or known in the art.

At least one of the nanoparticles of the present invention may be embedded in in the core a nanostructure or coated with a low density porous 3-D structure or coating which is capable of carrying or associating with at least one payload within or on the surface of the nanostructure. Non-limiting examples of the nanostructures comprising at least one nanoparticle are described in International Patent Publication No. WO2013123523, the contents of which are herein incorporated by reference in its entirety.

In some embodiments the RNA (e.g., mRNA) vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, $VP^{22}$ derived or analog peptides, Pestivirus Erns, HSV, $VP^{22}$ (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio)propane, DC-6-14: O,O-ditetradecanoyl-N-.alpha.-trimethylammonioacetyl) diethanolamine chloride, CLIP 1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy)ethyl]-trimethylammo-nium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole), etc.

In other embodiments the RNA (e.g., mRNA) vaccine is not associated with a cationic or polycationic compounds.

Multimeric Complexes

The RNA vaccines described herein can be assembled as multimeric complexes having non-covalent (e.g., hydrogen bonds) linkages between mRNA molecules. These types of multimeric structures allow for uniform distribution of the mRNA in a therapeutic composition. When multiple nucleic acids such as RNA are formulated, for instance, in a lipid based formulation, a relatively uniform distribution of the total nucleic acid through the formulation may be achieved. However, the distribution of a particular nucleic acid with respect to the other nucleic acids in the mixture is not uniform. For instance when the nucleic acid mixture is composed of two distinct mRNA sequences, some of the lipid particles or other formulatory agents will house a single mRNA sequence, while others will house the other mRNA sequence and a few will house both of the mRNA sequences. In a therapeutic context this uneven distribution of mRNA is undesirable because the dosage of the mRNA being delivered to a patient will vary from administration to administration. Quite surprisingly, the multimeric structures described herein have enabled the production of formulations having nucleic acids with a uniform distribution throughout the formulation. It was surprising that a non-covalent interaction between the individual nucleic acids would be capable of producing such a uniform distribution of the nucleic acids in a formulation. Additionally, the multimeric nucleic acid complexes do not interfere with activity such as mRNA expression activity.

In some embodiments the multimeric structures of the RNA polynucleotides making up the vaccine are uniformly distributed throughout a composition such as a lipid nanoparticle. Uniformly distributed, as used herein in the context of multiple nucleic acids (each having a unique nucleotide sequence), refers to the distribution of each of the nucleic acids relative to one another in the formulation. Distribution of the nucleic acids in a formulation may be assessed using methods known in the art. A nucleic acid is uniformly distributed relative to another nucleic acid if the nucleic acid is associated in proximity within a particular area of the formulation to the other nucleic acid at an approximately 1:1 ratio. In some embodiments the nucleic acid is uniformly distributed relative to another nucleic acid if the nucleic acid is positioned within a particular area of the formulation to the other nucleic acid at an approximately 1:1.1, 1:1.2, 1:1.3, 1:1.4, 1:1.5, 1:1.6, 1:1.7, 1:1.8, 1:1.9, or 1:2 ratio.

A multimeric structure as used herein is series of at least nucleic acids linked together to form a multimeric structure. In some embodiments a multimeric structure is composed of 2 or more, 3 or more, 4 or more, 5 or more 6 or more 7 or more, 8 or more, 9 or more nucleic acids. In other embodiments the multimeric structure is composed of 1000 or less, 900 or less, 500 or less, 100 or less, 75 or less, 50 or less, 40 or less, 30 or less, 20 or less or 100 or less nucleic acids. In yet other embodiments a multimeric structure has 3-100, 5-100, 10-100, 15-100, 20-100, 25-100, 30-100, 35-100, 40-100, 45-100, 50-100, 55-100, 60-100, 65-100, 70-100, 75-100, 80-100, 90-100, 5-50, 10-50, 15-50, 20-50, 25-50, 30-50, 35-50, 40-50, 45-50, 100-150, 100-200, 100-300, 100-400, 100-500, 50-500, 50-800, 50-1,000, or 100-1,000 nucleic acids. In preferred embodiments a multimeric structure is composed of 3-5 nucleic acids.

In some embodiments the upper limit on the number of nucleic acids in a multimeric structure depends on the length of dimerizable region. A greater than 20-nucleotide space between mRNAs can provide specificity and enough force to keep the multi-mRNA complex intact for downstream processing and is thus preferred in some embodiments. In some embodiments 4-5 nucleic acids in a multimeric structure may be desirable for vaccines.

The multimeric structures may be self-assembling multimeric mRNA structures composed of a first mRNA having a first linking region comprised of a part A and a part B and a second mRNA having a second linking region comprised of a part C and a part D, wherein at least part A of the first and at least part C of the second linking regions are complementary to one another. Preferably the nucleic acids are linked to one another through a non-covalent bond in the linking regions.

A linking region, as used herein, refers to a nucleic acid sequence having one or more regions or parts that are complementary to one or more regions of other linking regions. A pair of linking regions, each having one complementary region, may be at least 70% complementary to one another. In some embodiments a pair of linking regions are at least 75%, 80%, 85%, 90%, 95%, 96%, 97%, 98%, 99% or 100% complementary to one another. A linking region may be composed of sub-parts, optionally referred to as parts A, B, C, D, . . . , which have shorter regions of complementarity between one another, such that the sub-parts may be complementary with other sub-parts. For instance, a simple multimeric structure of two mRNAs can each have a linking region with a single region of complementarity. The two linking regions are able to form non-covalent interactions with one another through base pairing. More complex multimeric structures are also contemplated wherein a linking region of each nucleic acid has at least two parts, each part having complementarity with a part on another nucleic acid linking region. Linking regions having multiple parts with different complementarity enables the production of larger multimeric complexes of 3, 4, 5 or more nucleic acids.

The linking regions in some embodiments are 5-100 nucleotides in length. In other embodiments the linking regions are 10-25 nucleotides in length.

As used herein, the term "region of complementarity" refers to a region on a first nucleic acid strand that is substantially complementary to a second region on a second nucleic acid strand. Generally, two nucleic acids sharing a region of complementarity are capable, under suitable conditions, of hybridizing (e.g., via nucleic acid base pairing) to form a duplex structure. A region of complementarity can vary in size. In some embodiments, a region of complementarity ranges in length from about 2 base pairs to about 100 base pairs. In some embodiments, a region of complementarity ranges in length from about 5 base pairs to about 75 base pairs. In some embodiments, a region of complementarity ranges in length from about 10 base pairs to about 50 base pairs. In some embodiments, a region of complementarity ranges in length from about 20 base pairs to about 30 base pairs.

The number of nucleic acid bases shared between two nucleic acids across a region of complementarity can vary. In some embodiments, two nucleic acids share 100% complementary base pairs (e.g., no mismatches) across a region of complementarity. In some embodiments, two nucleic acids share at least 99.9%, at least 95%, at least 90%, at least 85%, at least 80%, at least 75% or at least 70% complementary base pairs across a region of complementarity. In some embodiments, a region of complementarity shared between two nucleic acids includes at least 1, at least 2, at least 3, at least 4, at least 5, at least 6, at least 7, at least 8, at least 9, or at least 10 base pair mismatches. In some embodiments, a region of complementarity shared between two nucleic acids includes more than 10 base pair mismatches.

As used herein, the term "non-covalent bond" refers to a chemical interaction (e.g., joining) between molecules that does not involve the sharing of electrons. Generally, non-covalent bonds are formed via electromagnetic interactions between charged molecules. Examples of non-covalent bonds include, but are not limited to, ionic bonds, hydrogen bonds, halogen bonds, Van der Waals forces (e.g., dipole-dipole interactions, London dispersion forces, etc.), π-effects (π-π interactions, cation-π interactions, anion-π interactions), and hydrophobic effect.

In some embodiments, at least one non-covalent bond formed between the nucleic acid molecules (e.g., mRNA molecules) of a multimeric molecule is a result of Watson-Crick base-pairing. The term "Watson-Crick base-pairing", or "base-pairing" refers to the formation of hydrogen bonds between specific pairs of nucleotide bases ("complementary base pairs"). For example, two hydrogen bonds form between adenine (A) and uracil (U), and three hydrogen bonds form between guanine (G) and cytosine (C). One method of assessing the strength of bonding between two polynucleotides is by quantifying the percentage of bonds formed between the guanine and cytosine bases of the two polynucleotides ("GC content"). In some embodiments, the GC content of bonding between two nucleic acids of a multimeric molecule (e.g., a multimeric mRNA molecule) is at least 10%, at least 20%, at least 30%, at least 40%, or at least 50%. In some embodiments, the GC content of bonding between two nucleic acids of a multimeric molecule (e.g., a multimeric mRNA molecule) is between 10% and 70%, about 20% to about 60%, or about 30% to about 60%. The formation of a nucleic acid duplex via bonding of complementary base pairs can also be referred to as "hybridization".

In some embodiments, two nucleic acid molecules (e.g., mRNA molecules) hybridize to form a multimeric molecule. Hybridization can result from the formation of at least 1, at least 2, at least 3, at least 4, at least 5, at least 6, at least 7, at least 8, at least 9, or at least 10 non-covalent bonds between two polynucleotides (e.g., mRNA molecules). In some embodiments, between about 2 non-covalent bonds and about 10 non-covalent bonds are formed between two nucleic acid molecules. In some embodiments, between about 5 and about 15 non-covalent bonds are formed between two nucleic acid molecules. In some embodiments, between about 10 and about 20 non-covalent bonds are formed between two nucleic acid molecules. In some embodiments, between about 15 and about 30 non-covalent bonds are formed between two nucleic acid molecules. In some embodiments, between about 20 and about 50 non-covalent bonds are formed between two nucleic acid molecules. In some embodiments, the number of non-covalent bonds formed between two nucleic acid molecules (e.g., mRNA molecules) is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 non-covalent bonds.

In some embodiments the self-assembling multimeric mRNA structure is comprised of at least 2-100 mRNAs each mRNA having a linking region and a stabilizing nucleic acid, wherein the stabilizing nucleic acid has a nucleotide sequence with regions complementary to each linking region. A stabilizing nucleic acid as used herein is any nucleic acid that has multiple linking regions and is capable of forming non-covalent interactions with at least 2, but more preferably, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 other nucleic acids. For instance the stabilizing nucleic acid may have the following structure: $L_1X_1L_2X_2L_3X_3L_4X_4L_5X_5L_6X_6$ wherein L is a nucleic acid sequence complementary to a linking region and wherein x is any nucleic acid sequence 0-50 nucleotides in length.

In some embodiments, a multimeric mRNA molecule comprises a first mRNA and a second mRNA, wherein the first mRNA and the second mRNA are non-covalently linked to one another through a splint. As used herein, the term "splint" refers to an oligonucleotide having a first region of complementarity with the first nucleic acid and a second region of complementarity with the second nucleic acid. A splint can be a DNA oligonucleotide or an RNA oligonucleotide. In some embodiments, a splint comprises one or more modified oligonucleotides. In some embodiments, a splint is non-covalently linked to a 5'UTR of an mRNA. In some embodiments, a splint is non-covalently linked to a 3'UTR of an mRNA. In some embodiments, non-covalent bonds between nucleic acid molecules (e.g., mRNA molecules) are formed in a non-coding region of each molecule. As used herein, the term "non-coding region" refers to a location of a polynucleotide (e.g., an mRNA) that is not translated into a protein. Examples of non-coding regions include regulatory regions (e.g., DNA binding domains, promoter sequences, enhancer sequences), and untranslated regions (e.g., 5'UTR, 3'UTR). In some embodiments, the non-coding region is an untranslated region (UTR).

By definition, wild type untranslated regions (UTRs) of a gene are transcribed but not translated. In mRNA, the 5'UTR starts at the transcription start site and continues to the start codon but does not include the start codon; whereas, the 3'UTR starts immediately following the stop codon and continues until the transcriptional termination signal.

Natural 5'UTRs bear features which play roles in translation initiation. They harbor signatures like Kozak sequences which are commonly known to be involved in the process by which the ribosome initiates translation of many genes. Kozak sequences have the consensus CCR(A/G) CCAUGG, where R is a purine (adenine or guanine) three bases upstream of the start codon (AUG), which is followed by another 'G'. 5'UTR also have been known to form secondary structures which are involved in elongation factor binding.

It should be understood that any UTR from any gene may be incorporated into the regions of the polynucleotide. Furthermore, multiple wild-type UTRs of any known gene may be utilized. It is also within the scope of the present invention to provide artificial UTRs which are not variants of wild type regions. These UTRs or portions thereof may be placed in the same orientation as in the transcript from which they were selected or may be altered in orientation or location. Hence a 5' or 3' UTR may be inverted, shortened, lengthened, made with one or more other 5' UTRs or 3' UTRs. As used herein, the term "altered" as it relates to a UTR sequence, means that the UTR has been changed in some way in relation to a reference sequence. For example, a 3' or 5' UTR may be altered relative to a wild type or native UTR by the change in orientation or location as taught above or may be altered by the inclusion of additional nucleotides, deletion of nucleotides, swapping or transposition of nucleotides. Any of these changes producing an "altered" UTR (whether 3' or 5') comprise a variant UTR.

In some embodiments, a double, triple or quadruple UTR such as a 5' or 3' UTR may be used. As used herein, a "double" UTR is one in which two copies of the same UTR are encoded either in series or substantially in series.

It is also within the scope of the present invention to have patterned UTRs. As used herein "patterned UTRs" are those UTRs which reflect a repeating or alternating pattern, such as ABABAB or AABBAABBAABB or ABCABCABC or variants thereof repeated once, twice, or more than 3 times. In these patterns, each letter, A, B, or C represent a different UTR at the nucleotide level.

In some embodiments, flanking regions are selected from a family of transcripts whose proteins share a common function, structure, feature of property. For example, polypeptides of interest may belong to a family of proteins which are expressed in a particular cell, tissue or at some time during development. The UTRs from any of these genes may be swapped for any other UTR of the same or different family of proteins to create a new polynucleotide. As used herein, a "family of proteins" is used in the broadest sense to refer to a group of two or more polypeptides of interest which share at least one function, structure, feature, localization, origin, or expression pattern. The untranslated region may also include translation enhancer elements (TEE).

In some embodiments, an UTR of a polynucleotide (e.g., a first nucleic acid) of the present invention is engineered or modified to have regions of complementarity with an UTR of another polynucleotide (a second nucleic acid). For example, UTR nucleotide sequences of two polynucleotides sought to be joined (e.g., in a multimeric molecule) can be modified to include a region of complementarity such that the two UTRs hybridize to form a multimeric molecule.

In some embodiments, the 5'UTR of an RNA polynucleotide encoding an HCMV antigenic polypeptide is modified to allow the formation of a multimeric sequence. In some embodiments, the 5'UTR of an RNA polynucleotide encoding an HCMV protein selected from gH, gL, gB, gO, gM, gM, UL128, UL130, UL131A1 is modified to allow the formation of a multimeric sequence. In some embodiments, the 5'UTR of an RNA polynucleotide encoding an HCMV protein selected from UL128, UL130, UL131A1 is modified to allow the formation of a multimeric sequence. In some embodiments, the 5'UTR of an RNA polynucleotide encoding an HCMV glycoprotein is modified to allow the formation of a multimeric sequence. In some embodiments, the 5'UTR of an RNA polynucleotide encoding an HCMV glycoprotein selected from gH, gL, gB, gO, gM, and gM is modified to allow the formation of a multimeric sequence. In any of these embodiments, the multimer may be a dimer, a trimer, pentamer, hexamer, heptamer, octamer nonamer, or decamer. In any of these embodiments, the multimer may be a homogenous multimer, that is, it may comprise dimers, trimers, pentamers etc having sequence encoding the same HCMV antigenic polypeptide. In any of these embodiments, the multimer may be a heterogeneous multimer comprising dimers, trimers, pentamers etc having sequence encoding different HCMV antigenic polypeptides, for example two different antigenic polypeptides, three different antigenic polypeptides, four different antigenic polypeptide, five different antigenic polypeptides, etc. Exemplary HCMV nucleic acids having modified 5'UTR sequence for the formation of a multimeric molecule (e.g., dimers, trimers, pentamers, etc) comprise SEQ ID Nos: 19-26.

In some embodiments the RNA vaccine may be associated with a cationic or polycationic compounds, including protamine, nucleoline, spermine or spermidine, or other cationic peptides or proteins, such as poly-L-lysine (PLL), polyarginine, basic polypeptides, cell penetrating peptides (CPPs), including HIV-binding peptides, HIV-1 Tat (HIV), Tat-derived peptides, Penetratin, $VP^{22}$ derived or analog peptides, Pestivirus Ems, HSV, $VP^{22}$ (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, histones, cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristooxypropyl dimethyl hydroxyethyl ammonium bromide, DOTAP: dioleoyloxy-3-(trimethylammonio)propane, DC-6-14: O,O-ditetradecanoyl-N-.alpha.-trimethylammonioacetyl) diethanolamine chloride, CLIP 1: rac-[(2,3-dioctadecyloxypropyl)(2-hydroxyethyl)]-dimethylammonium chloride, CLIP6: rac-[2(2,3-dihexadecyloxypropyloxymethyloxy)ethyl]-trimethylammonium, CLIP9: rac-[2(2,3-dihexadecyloxypropyloxysuccinyloxy)ethyl]-trimethylammo-nium, oligofectamine, or cationic or polycationic polymers, e.g. modified polyaminoacids, such as beta-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In other embodiments the RNA vaccine is not associated with a cationic or polycationic compounds.

Modes of Vaccine Administration

HCMV RNA vaccines may be administered by any route which results in a therapeutically effective outcome. These include, but are not limited, to intradermal, intramuscular, and/or subcutaneous administration. The present disclosure provides methods comprising administering RNA vaccines to a subject in need thereof. The exact amount required will vary from subject to subject, depending on the species, age, and general condition of the subject, the severity of the disease, the particular composition, its mode of administration, its mode of activity, and the like. HCMV RNA vaccines compositions are typically formulated in dosage unit form for ease of administration and uniformity of dosage. It will be understood, however, that the total daily usage of HCMV RNA vaccines compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, HCMV RNA vaccines compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, HCMV RNA vaccines compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, HCMV RNA vaccine compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, HCMV RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, a HCMV RNA vaccine composition may be administered three or four times.

In some embodiments, HCMV RNA vaccine compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments the RNA vaccine for use in a method of vaccinating a subject is administered to the subject in a single dosage of between 10 μg/kg and 400 μg/kg of the nucleic acid vaccine in an effective amount to vaccinate the subject. In some embodiments the RNA vaccine for use in a method of vaccinating a subject is administered to the subject in a single dosage of between 10 μg and 400 μg of the nucleic acid vaccine in an effective amount to vaccinate the subject. In some embodiments, an HCMV RNA (e.g., mRNA) vaccine for use in a method of vaccinating a subject is administered to the subject in a single dosage of 10 μg. In some embodiments, an HCMV RNA vaccine for use in a method of vaccinating a subject is administered to the subject in a single dosage of 2 μg. In some embodiments, an HCMV RNA vaccine for use in a method of vaccinating a subject is administered to the subject in two dosages of 10 μg. In some embodiments, an HCMV RNA vaccine for use in a method of vaccinating a subject is administered the subject two dosages of 2 μg.

HCMV vaccines described herein can contain multiple RNA polynucleotides. The RNA polynucleotides can be present in equal or different amounts within the vaccine. For example, a vaccine can comprise: an RNA polynucleotide having an open reading frame encoding HCMV antigenic polypeptide gH, or an antigenic fragment or epitope thereof; an RNA polynucleotide having an open reading frame encoding HCMV antigenic polypeptide gL, or an antigenic fragment or epitope thereof; an RNA polynucleotide having an open reading frame encoding HCMV antigenic polypeptide UL128, or an antigenic fragment or epitope thereof; an RNA polynucleotide having an open reading frame encoding HCMV antigenic polypeptide UL130, or an antigenic fragment or epitope thereof; an RNA polynucleotide having an open reading frame encoding HCMV antigenic polypeptide UL131A, or an antigenic fragment or epitope thereof; and/or an RNA polynucleotide having an open reading frame encoding HCMV antigenic polypeptide gB, or an antigenic fragment or epitope thereof. In some embodiments, the ratio of gH-gL-UL128-UL130-UL131A is approximately 1:1:1:1:1. In other embodiments, the ratio of gH-gL-UL128-UL130-UL131A is approximately 4:2:1:1:1. In some embodiments, the ratio of gB-gH-gL-UL128-UL130-UL131A is approximately 1:1:1:1:1:1. In some embodiments, the vaccine comprises an equimolar concentration of gH, gL, UL128, UL130, and UL131A. In some embodiments, the vaccine comprises an equimolar concentration of gB, gH, gL, UL128, UL130, and UL131A. In some embodiments, the vaccine comprises an equal mass of gH, gL, UL128, UL130, and UL131A. In some embodiments, the vaccine comprises an equal mass of gB, gH, gL, UL128, UL130, and UL131A.

An HCMV RNA vaccine pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

HCMV RNA Vaccine Formulations and Methods of Use

Some aspects of the present disclosure provide formulations of the HCMV RNA (e.g., mRNA) vaccine, wherein the HCMV RNA vaccine is formulated in an effective amount to produce an antigen specific immune response in a subject (e.g., production of antibodies specific to an anti-HCMV antigenic polypeptide). "An effective amount" is a dose of an HCMV RNA (e.g., mRNA) vaccine effective to produce an antigen-specific immune response. Also provided herein are methods of inducing an antigen-specific immune response in a subject.

In some embodiments, the antigen-specific immune response is characterized by measuring an anti-HCMV antigenic polypeptide antibody titer produced in a subject administered an HCMV RNA (e.g., mRNA) vaccine as provided herein. An antibody titer is a measurement of the amount of antibodies within a subject, for example, antibodies that are specific to a particular antigen (e.g., an anti-HCMV antigenic polypeptide) or epitope of an antigen. Antibody titer is typically expressed as the inverse of the greatest dilution that provides a positive result. Enzyme-linked immunosorbent assay (ELISA) is a common assay for determining antibody titers, for example.

In some embodiments, an antibody titer is used to assess whether a subject has had an infection or to determine whether immunizations are required. In some embodiments, an antibody titer is used to determine the strength of an autoimmune response, to determine whether a booster immunization is needed, to determine whether a previous vaccine was effective, and to identify any recent or prior infections. In accordance with the present disclosure, an antibody titer may be used to determine the strength of an immune response induced in a subject by the HCMV RNA vaccine.

In some embodiments, an anti-HCMV antigenic polypeptide antibody titer produced in a subject is increased by at least 1 log relative to a control. For example, anti-HCMV antigenic polypeptide antibody titer produced in a subject may be increased by at least 1.5, at least 2, at least 2.5, or at least 3 log relative to a control. In some embodiments, the anti-HCMV antigenic polypeptide antibody titer produced in the subject is increased by 1, 1.5, 2, 2.5 or 3 log relative to a control. In some embodiments, the anti-HCMV antigenic polypeptide antibody titer produced in the subject is increased by 1-3 log relative to a control. For example, the anti-HCMV antigenic polypeptide antibody titer produced in a subject may be increased by 1-1.5, 1-2, 1-2.5, 1-3, 1.5-2, 1.5-2.5, 1.5-3, 2-2.5, 2-3, or 2.5-3 log relative to a control.

In some embodiments, the anti-HCMV antigenic polypeptide antibody titer produced in a subject is increased at least 2 times relative to a control. For example, the anti-HCMV antigenic polypeptide antibody titer produced in a subject may be increased at least 3 times, at least 4 times, at least 5 times, at least 6 times, at least 7 times, at least 8 times, at least 9 times, or at least 10 times relative to a control. In some embodiments, the anti-HCMV antigenic polypeptide antibody titer produced in the subject is increased 2, 3, 4, 5, 6, 7, 8, 9, or 10 times relative to a control. In some embodiments, the anti-HCMV antigenic polypeptide antibody titer produced in a subject is increased 2-10 times relative to a control. For example, the anti-HCMV antigenic polypeptide antibody titer produced in a subject may be increased 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9, or 9-10 times relative to a control.

A control, in some embodiments, is the anti-HCMV antigenic polypeptide antibody titer produced in a subject who has not been administered an HCMV RNA (e.g., mRNA) vaccine. In some embodiments, a control is an anti-HCMV antigenic polypeptide antibody titer produced in a subject who has been administered a live attenuated HCMV vaccine. An attenuated vaccine is a vaccine produced by reducing the virulence of a viable (live). An attenuated virus is altered in a manner that renders it harmless or less virulent relative to live, unmodified virus. In some embodiments, a control is an anti-HCMV antigenic polypeptide antibody titer produced in a subject administered inactivated HCMV vaccine. In some embodiments, a control is an anti-HCMV antigenic polypeptide antibody titer produced in a subject administered a recombinant or purified HCMV protein vaccine. Recombinant protein vaccines typically include protein antigens that either have been produced in a heterologous expression system (e.g., bacteria or yeast) or purified from large amounts of the pathogenic organism.

In some embodiments, an effective amount of an HCMV RNA (e.g., mRNA) vaccine is a dose that is reduced compared to the standard of care dose of a recombinant HCMV protein vaccine. A "standard of care," as provided herein, refers to a medical or psychological treatment guideline and can be general or specific. "Standard of care" specifies appropriate treatment based on scientific evidence and collaboration between medical professionals involved in the treatment of a given condition. It is the diagnostic and treatment process that a physician/clinician should follow for a certain type of patient, illness or clinical circumstance. A "standard of care dose," as provided herein, refers to the dose of a recombinant or purified HCMV protein vaccine, or a live attenuated or inactivated HCMV vaccine, that a physician/clinician or other medical professional would administer to a subject to treat or prevent HCMV, or an HCMV-related condition, while following the standard of care guideline for treating or preventing HCMV, or an HCMV-related condition.

In some embodiments, the anti-HCMV antigenic polypeptide antibody titer produced in a subject administered an effective amount of an HCMV RNA vaccine is equivalent to an anti-HCMV antigenic polypeptide antibody titer produced in a control subject administered a standard of care dose of a recombinant or purified HCMV protein vaccine or a live attenuated or inactivated HCMV vaccine.

In some embodiments, an effective amount of an HCMV RNA (e.g., mRNA) vaccine is a dose equivalent to an at least 2-fold reduction in a standard of care dose of a recombinant or purified HCMV protein vaccine. For example, an effective amount of an HCMV RNA vaccine may be a dose equivalent to an at least 3-fold, at least 4-fold, at least 5-fold, at least 6-fold, at least 7-fold, at least 8-fold, at least 9-fold, or at least 10-fold reduction in a standard of care dose of a recombinant or purified HCMV protein vaccine. In some embodiments, an effective amount of an HCMV RNA vaccine is a dose equivalent to an at least at least 100-fold, at least 500-fold, or at least 1000-fold reduction in a standard of care dose of a recombinant or purified HCMV protein vaccine. In some embodiments, an effective amount of an HCMV RNA vaccine is a dose equivalent to a 2-, 3-, 4-, 5-, 6-, 7-, 8-, 9-, 10-, 20-, 50-, 100-, 250-, 500-, or 1000-fold reduction in a standard of care dose of a recombinant or purified HCMV protein vaccine. In some embodiments, the anti-HCMV antigenic polypeptide antibody titer produced in a subject administered an effective amount of an HCMV RNA vaccine is equivalent to an anti-HCMV antigenic polypeptide antibody titer produced in a control subject administered the standard of care dose of a recombinant or protein HCMV protein vaccine or a live attenuated or inactivated HCMV vaccine. In some embodiments, an effective amount of an HCMV RNA (e.g., mRNA) vaccine is a dose equivalent to a 2-fold to 1000-fold (e.g., 2-fold to 100-fold, 10-fold to 1000-fold) reduction in the standard of care dose of a recombinant or purified HCMV protein vaccine, wherein the anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount of an HCMV RNA (e.g., mRNA) vaccine is a dose equivalent to a 2 to 1000-, 2 to 900-, 2 to 800-, 2 to 700-, 2 to 600-, 2 to 500-, 2 to 400-, 2 to 300-, 2 to 200-, 2 to 100-, 2 to 90-, 2 to 80-, 2 to 70-, 2 to 60-, 2 to 50-, 2 to 40-, 2 to 30-, 2 to 20-, 2 to 10-, 2 to 9-, 2 to 8-, 2 to 7-, 2 to 6-, 2 to 5-, 2 to 4-, 2 to 3-, 3 to 1000-, 3 to 900-, 3 to 800-, 3 to 700-, 3 to 600-, 3 to 500-, 3 to 400-, 3 to 3 to 00-, 3 to 200-, 3 to 100-, 3 to 90-, 3 to 80-, 3 to 70-, 3 to 60-, 3 to 50-, 3 to 40-, 3 to 30-, 3 to 20-, 3 to 10-, 3 to 9-, 3 to 8-, 3 to 7-, 3 to 6-, 3 to 5-, 3 to 4-, 4 to 1000-, 4 to 900-, 4 to 800-, 4 to 700-, 4 to 600-, 4 to 500-, 4 to 400-, 4 to 4 to 00-, 4 to 200-, 4 to 100-, 4 to 90-, 4 to 80-, 4 to 70-, 4 to 60-, 4 to 50-, 4 to 40-, 4 to 30-, 4 to 20-, 4 to 10-, 4 to 9-, 4 to 8-, 4 to 7-, 4 to 6-, 4 to 5-, 4 to 4-, 5 to 1000-, 5 to 900-, 5 to 800-, 5 to 700-, 5 to 600-, 5 to 500-, 5 to 400-, 5 to 300-, 5 to 200-, 5 to 100-, 5 to 90-, 5 to 80-, 5 to 70-, 5 to 60-, 5 to 50-, 5 to 40-, 5 to 30-, 5 to 20-, 5 to 10-, 5 to 9-, 5 to 8-, 5 to 7-, 5 to 6-, 6 to 1000-, 6 to 900-, 6 to 800-, 6 to 700-, 6 to 600-, 6 to 500-, 6 to 400-, 6 to 300-, 6 to 200-, 6 to 100-, 6 to 90-, 6 to 80-, 6 to 70-, 6 to 60-, 6 to 50-, 6 to 40-, 6 to 30-, 6 to 20-, 6 to 10-, 6 to 9-, 6 to 8-, 6 to 7-, 7 to 1000-, 7 to 900-, 7 to 800-, 7 to 700-, 7 to 600-, 7 to 500-, 7 to 400-, 7 to 300-, 7 to 200-, 7 to 100-, 7 to 90-, 7 to 80-, 7 to 70-, 7 to 60-, 7 to 50-, 7 to 40-, 7 to 30-, 7 to 20-, 7 to 10-, 7 to 9-, 7 to 8-, 8 to 1000-, 8 to 900-, 8 to 800-, 8 to 700-, 8 to 600-, 8 to 500-, 8 to 400-, 8 to 300-, 8 to 200-, 8 to 100-, 8 to 90-, 8 to 80-, 8 to 70-, 8 to 60-, 8 to 50-, 8 to 40-, 8 to 30-, 8 to 20-, 8 to 10-, 8 to 9-, 9 to 1000-, 9 to 900-, 9 to 800-, 9 to 700-, 9 to 600-, 9 to 500-, 9 to 400-, 9 to 300-, 9 to 200-, 9 to 100-, 9 to 90-, 9 to 80-, 9 to 70-, 9 to 60-, 9 to 50-, 9 to 40-, 9 to 30-, 9 to 20-, 9 to 10-, 10 to 1000-, 10 to 900-, 10 to 800-, 10 to 700-, 10 to 600-, 10 to 500-, 10 to 400-, 10 to 300-, 10 to 200-, 10 to 100-, 10 to 90-, 10 to 80-, 10 to 70-, 10 to 60-, 10 to 50-, 10 to 40-, 10 to 30-, 10 to 20-, 20 to 1000-, 20 to 900-, 20 to 800-, 20 to 700-, 20 to 600-, 20 to 500-, 20 to 400-, 20 to 300-, 20 to 200-, 20 to 100-, 20 to 90-, 20 to 80-, 20 to 70-, 20 to 60-, 20 to 50-, 20 to 40-, 20 to 30-, 30 to 1000-, 30 to 900-, 30 to 800-, 30 to 700-, 30 to 600-, 30 to 500-, 30 to 400-, 30 to 300-, 30 to 200-, 30 to 100-, 30 to 90-, 30 to 80-, 30 to 70-, 30 to 60-, 30 to 50-, 30 to 40-, 40 to 1000-, 40 to 900-, 40 to 800-, 40 to 700-, 40 to 600-, 40 to 500-, 40 to 400-, 40 to 300-, 40 to 200-, 40 to 100-, 40 to 90-, 40 to 80-, 40 to 70-, 40 to 60-, 40 to 50-, 50 to 1000-, 50 to 900-, 50 to 800-, 50 to 700-, 50 to 600-, 50 to 500-, 50 to 400-, 50 to 300-, 50 to 200-, 50 to 100-, 50 to 90-, 50 to 80-, 50 to 70-, 50 to 60-, 60 to 1000-, 60 to 900-, 60 to 800-, 60 to 700-, 60 to 600-, 60 to 500-, 60 to 400-, 60 to 300-, 60 to 200-, 60 to 100-, 60 to 90-, 60 to 80-, 60 to 70-, 70 to 1000-, 70 to 900-, 70 to 800-, 70 to 700-, 70 to 600-, 70 to 500-, 70 to 400-, 70 to 300-, 70 to 200-, 70 to 100-, 70 to 90-, 70 to 80-, 80 to 1000-, 80 to 900-, 80 to 800-, 80 to 700-, 80 to 600-, 80 to 500-, 80 to 400-, 80 to 300-, 80 to 200-, 80 to 100-, 80 to 90-, 90 to 1000-, 90 to 900-, 90 to 800-, 90 to 700-, 90 to 600-, 90 to 500-, 90 to 400-, 90 to 300-, 90 to 200-, 90 to 100-, 100 to 1000-, 100 to 900-, 100 to 800-, 100 to 700-, 100 to 600-, 100 to 500-, 100 to 400-, 100 to 300-, 100 to 200-, 200 to 1000-, 200 to 900-, 200 to 800-, 200 to 700-, 200 to 600-, 200 to 500-, 200 to 400-, 200 to 300-, 300 to 1000-, 300 to 900-, 300 to 800-, 300 to 700-, 300 to 600-, 300 to 500-, 300 to 400-, 400 to 1000-, 400 to 900-, 400 to 800-, 400 to 700-, 400 to 600-, 400 to 500-, 500 to 1000-, 500 to 900-, 500 to 800-, 500 to 700-, 500 to 600-, 600 to 1000-, 600 to 900-, 600 to 800-, 600 to 700-, 700 to 1000-, 700 to 900-, 700 to 800-, 800 to 1000-, 800 to 900-, or 900 to 1000-fold reduction in the standard of care dose of a recombinant HCMV protein vaccine. In some embodiments, such as the foregoing, the anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine. In some embodiments, the effective amount is a dose equivalent to (or equivalent to an at least) 2-, 3-, 4-, 5-, 6-, 7-, 8-, 9-, 10-, 20-, 30-, 40-, 50-, 60-, 70-, 80-, 90-, 100-, 110-, 120-, 130-, 140-, 150-, 160-, 170-, 1280-, 190-, 200-, 210-, 220-, 230-, 240-, 250-, 260-, 270-, 280-, 290-, 300-, 310-, 320-, 330-, 340-, 350-, 360-, 370-, 380-, 390-, 400-, 410-, 420-, 430-, 440-, 450-, 4360-, 470-, 480-, 490-, 500-, 510-, 520-, 530-, 540-, 550-, 560-, 5760-, 580-, 590-, 600-, 610-, 620-, 630-, 640-, 650-, 660-, 670-, 680-, 690-, 700-, 710-, 720-, 730-, 740-, 750-, 760-, 770-, 780-, 790-, 800-, 810-, 820-, 830-, 840-, 850-, 860-, 870-, 880-, 890-, 900-, 910-, 920-, 930-, 940-, 950-, 960-, 970-, 980-, 990-, or 1000-fold reduction in the standard of care dose of a recombinant HCMV protein vaccine. In some embodiments, such as the foregoing, an anti-HCMV antigenic polypeptide antibody titer produced in the subject is equivalent to an anti-HCMV antigenic polypeptide antibody titer produced in a control subject administered the standard of care dose of a recombinant or purified HCMV protein vaccine or a live attenuated or inactivated HCMV vaccine.

In some embodiments, the effective amount of an HCMV RNA (e.g., mRNA) vaccine is a total dose of 50-1000 μg. In some embodiments, the effective amount of an HCMV RNA (e.g., mRNA) vaccine is a total dose of 50-1000, 50-900, 50-800, 50-700, 50-600, 50-500, 50-400, 50-300, 50-200, 50-100, 50-90, 50-80, 50-70, 50-60, 60-1000, 60-900, 60-800, 60-700, 60-600, 60-500, 60-400, 60-300, 60-200, 60-100, 60-90, 60-80, 60-70, 70-1000, 70-900, 70-800, 70-700, 70-600, 70-500, 70-400, 70-300, 70-200, 70-100, 70-90, 70-80, 80-1000, 80-900, 80-800, 80-700, 80-600, 80-500, 80-400, 80-300, 80-200, 80-100, 80-90, 90-1000, 90-900, 90-800, 90-700, 90-600, 90-500, 90-400, 90-300, 90-200, 90-100, 100-1000, 100-900, 100-800, 100-700, 100-600, 100-500, 100-400, 100-300, 100-200, 200-1000, 200-900, 200-800, 200-700, 200-600, 200-500, 200-400, 200-300, 300-1000, 300-900, 300-800, 300-700, 300-600, 300-500, 300-400, 400-1000, 400-900, 400-800, 400-700, 400-600, 400-500, 500-1000, 500-900, 500-800, 500-700, 500-600, 600-1000, 600-900, 600-900, 600-700, 700-1000, 700-900, 700-800, 800-1000, 800-900, or 900-1000 μg. In some embodiments, the effective amount of an HCMV RNA (e.g., mRNA) vaccine is a total dose of 50, 100, 150, 200, 250, 300, 350, 400, 450, 500, 550, 600, 650, 700, 750, 800, 850, 900, 950 or 1000 μg. In some embodiments, the effective amount is a dose of 25-500 μg administered to the subject a total of two times. In some embodiments, the effective amount of an HCMV RNA (e.g., mRNA) vaccine is a dose of 25-500, 25-400, 25-300, 25-200, 25-100, 25-50, 50-500, 50-400, 50-300, 50-200, 50-100, 100-500, 100-400, 100-300, 100-200, 150-500, 150-400, 150-300, 150-200, 200-500, 200-400, 200-300, 250-500, 250-400, 250-300, 300-500, 300-400, 350-500, 350-400, 400-500 or 450-500 μg administered to the subject a total of two times. In some embodiments, the effective amount of an HCMV RNA (e.g., mRNA) vaccine is a total dose of 25, 50, 100, 150, 200, 250, 300, 350, 400, 450, or 500 μg administered to the subject a total of two times.

In some embodiments, the antigen specific immune response induced by the HCMV RNA vaccines in a subject is the production of antibodies specific to an anti-HCMV antigenic polypeptide. In some embodiments, such antibodies are capable of neutralizing HCMV in an infected host. In some embodiments, the antigen specific immune response induced by the HCMV RNA vaccines in a subject is antigen-specific T-cell response. Such T-cell response may provide immunity to the immunized animal (e.g., mice or human) against fution HCMV infenctions.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1: Manufacture of Polynucleotides

According to the present disclosure, the manufacture of polynucleotides and or parts or regions thereof may be accomplished utilizing the methods taught in International Application WO2014/152027 entitled "Manufacturing Methods for Production of RNA Transcripts", the contents of which is incorporated herein by reference in its entirety.

Purification methods may include those taught in International Application WO2014/152030 and WO2014/152031, each of which is incorporated herein by reference in its entirety.

Detection and characterization methods of the polynucleotides may be performed as taught in WO2014/144039, which is incorporated herein by reference in its entirety.

Characterization of the polynucleotides of the disclosure may be accomplished using a procedure selected from the group consisting of polynucleotide mapping, reverse transcriptase sequencing, charge distribution analysis, and detection of RNA impurities, wherein characterizing comprises determining the RNA transcript sequence, determining the purity of the RNA transcript, or determining the charge heterogeneity of the RNA transcript. Such methods are taught in, for example, WO2014/144711 and WO2014/144767, the contents of each of which is incorporated herein by reference in its entirety.

Example 2: Chimeric Polynucleotide Synthesis

Introduction

According to the present disclosure, two regions or parts of a chimeric polynucleotide may be joined or ligated using triphosphate chemistry.

According to this method, a first region or part of 100 nucleotides or less is chemically synthesized with a 5' monophosphate and terminal 3'desOH or blocked OH. If the region is longer than 80 nucleotides, it may be synthesized as two strands for ligation.

If the first region or part is synthesized as a non-positionally modified region or part using in vitro transcription (IVT), conversion the 5'monophosphate with subsequent capping of the 3' terminus may follow.

Monophosphate protecting groups may be selected from any of those known in the art.

The second region or part of the chimeric polynucleotide may be synthesized using either chemical synthesis or IVT methods. IVT methods may include an RNA polymerase that can utilize a primer with a modified cap. Alternatively, a cap of up to 130 nucleotides may be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then it is preferable that such region or part comprise a phosphate-sugar backbone.

Ligation is then performed using any known click chemistry, orthoclick chemistry, solulink, or other bioconjugate chemistries known to those in the art.

Synthetic Route

The chimeric polynucleotide is made using a series of starting segments. Such segments include:

(a) Capped and protected 5' segment comprising a normal 3'OH (SEG. 1)

(b) 5' triphosphate segment which may include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) is treated with cordycepin and then with pyrophosphatase to create the 5'monophosphate.

Segment 2 (SEG. 2) is then ligated to SEG. 3 using RNA ligase. The ligated polynucleotide is then purified and treated with pyrophosphatase to cleave the diphosphate. The treated SEG.2-SEG. 3 construct is then purified and SEG. 1 is ligated to the 5' terminus. A further purification step of the chimeric polynucleotide may be performed.

Where the chimeric polynucleotide encodes a polypeptide, the ligated or joined segments may be represented as: 5'UTR (SEG. 1), open reading frame or ORF (SEG. 2) and 3'UTR+PolyA (SEG. 3).

The yields of each step may be as much as 90-95%.

Example 3: PCR for cDNA Production

PCR procedures for the preparation of cDNA are performed using 2× KAPA HIFI™ HotStart ReadyMix by Kapa Biosystems (Woburn, Mass.). This system includes 2× KAPA ReadyMix12.5 μl; Forward Primer (10 μM) 0.75 μl; Reverse Primer (10 μM) 0.75 μl; Template cDNA −100 ng; and $dH_20$ diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reaction is cleaned up using Invitrogen's PURELINK™ PCR Micro Kit (Carlsbad, Calif.) per manufacturer's instructions (up to 5 μg). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 4: In Vitro Transcription (IVT)

The in vitro transcription reaction generates polynucleotides containing uniformly modified polynucleotides. Such uniformly modified polynucleotides may comprise a region or part of the polynucleotides of the disclosure. The input nucleotide triphosphate (NTP) mix is made in-house using natural and un-natural NTPs.

A typical in vitro transcription reaction includes the following:

| | |
|---|---|
| Template cDNA | 1.0 μg |
| 10x transcription buffer (400 mM Tris-HCl pH 8.0, 190 mM $MgCl_2$, 50 mM DTT, 10 mM Spermidine) | 2.0 μl |
| Custom NTPs (25 mM each) | 7.2 μl |
| RNase Inhibitor | 20 U |
| T7 RNA polymerase | 3000 U |
| $dH_20$ | Up to 20.0 μl. and |
| Incubation at 37° C. for 3 hr-5 hrs. | |

Incubation at 37° C. for 3 hr-5 hrs.

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 5: Enzymatic Capping

Capping of a polynucleotide is performed as follows where the mixture includes: IVT RNA 60 μg-180 μg and $dH_2O$ up to 72 μl. The mixture is incubated at 65° C. for 5 minutes to denature RNA, and then is transferred immediately to ice.

The protocol then involves the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The polynucleotide is then purified using Ambion's MEGACLEAR™ Kit (Austin, Tex.) following the manufacturer's instructions. Following the cleanup, the RNA is quantified using the NANODROP™ (ThermoFisher, Waltham, Mass.) and analyzed by agarose gel electrophoresis to confirm the RNA is the proper size and that no degradation of the RNA has occurred. The RNA product may also be sequenced by running a reverse-transcription-PCR to generate the cDNA for sequencing.

Example 6: PolyA Tailing Reaction

Without a poly-T in the cDNA, a poly-A tailing reaction must be performed before cleaning the final product. This is done by mixing Capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubation at 37° C. for 30 min. If the poly-A tail is already in the transcript, then the tailing reaction may be skipped and proceed directly to cleanup with Ambion's MEGACLEAR™ kit (Austin, Tex.) (up to 500 μg). Poly-A Polymerase is preferably a recombinant enzyme expressed in yeast.

It should be understood that the processivity or integrity of the polyA tailing reaction may not always result in an exact size polyA tail. Hence polyA tails of approximately between 40-200 nucleotides, e.g, about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 7: Natural 5' Caps and 5' Cap Analogues

5'-capping of polynucleotides may be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, Mass.). 5'-capping of modified RNA may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate: m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-O methyl-transferase. Enzymes are preferably derived from a recombinant source.

When transfected into mammalian cells, the modified mRNAs have a stability of between 12-18 hours or more than 18 hours, e.g., 24, 36, 48, 60, 72 or greater than 72 hours.

Example 8: Capping Assays

Protein Expression Assay

Polynucleotides encoding a polypeptide, containing any of the caps taught herein can be transfected into cells at equal concentrations. 6, 12, 24 and 36 hours post-transfection the amount of protein secreted into the culture medium can be assayed by ELISA. Synthetic polynucleotides that secrete higher levels of protein into the medium would correspond to a synthetic polynucleotide with a higher translationally-competent Cap structure.

Purity Analysis Synthesis

Polynucleotides encoding a polypeptide, containing any of the caps taught herein can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

Cytokine Analysis

Polynucleotides encoding a polypeptide, containing any of the caps taught herein can be transfected into cells at multiple concentrations. 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to a polynucleotides containing an immune-activating cap structure.

Capping Reaction Efficiency

Polynucleotides encoding a polypeptide, containing any of the caps taught herein can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 9: Agarose Gel Electrophoresis of Modified RNA or RT PCR Products

Individual polynucleotides (200-400 ng in a 20 μl volume) or reverse transcribed PCR products (200-400 ng) are loaded into a well on a non-denaturing 1.2% Agarose E-Gel (Invitrogen, Carlsbad, Calif.) and run for 12-15 minutes according to the manufacturer protocol.

Example 10: Nanodrop Modified RNA Quantification and UV Spectral Data

Modified polynucleotides in TE buffer (1 μl) are used for Nanodrop UV absorbance readings to quantitate the yield of each polynucleotide from an chemical synthesis or in vitro transcription reaction.

Example 11: Formulation of Modified mRNA Using Lipidoids

Polynucleotides are formulated for in vitro experiments by mixing the polynucleotides with the lipidoid at a set ratio prior to addition to cells. In vivo formulation may require the addition of extra ingredients to facilitate circulation throughout the body. To test the ability of these lipidoids to form particles suitable for in vivo work, a standard formulation process used for siRNA-lipidoid formulations may used as a starting point. After formation of the particle, polynucleotide is added and allowed to integrate with the complex. The encapsulation efficiency is determined using a standard dye exclusion assays.

Example 12: hCMV Vaccine—hCMV Glycoprotein Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

Each of the sequences described herein encompasses a chemically modified sequence or an unmodified sequence which includes no nucleotide modifications.

5'UTR is bolded
3'UTR is underlined
hCMV-gH: hCMV, glycoprotein H (Merlin Strain)
(SEQ ID NO: 1)
TCAAGCTTTTGGACCCTCGTACAGAAGCTAATACGACTCACTATAGGGAAATAAGAGAGAAA
AGAAGAGTAAGAAGAAATATAAGAGCCACCATGCGGCCAGGCCTCCCCTCCTACCTCATCAT
CCTCGCCGTCTGTCTCTTCAGCCACCTACTTTCGTCACGATATGGCGCAGAAGCCGTATCCG
AACCGCTGGACAAAGCGTTTCACCTACTGCTCAACACCTACGGGAGACCCATCCGCTTCCTG
CGTGAAAATACCACCCAGTGTACCTACAACAGCAGCCTCCGTAACAGCACGGTCGTCAGGGA
AAACGCCATCAGTTTCAACTTTTTCCAAAGCTATAATCAATACTATGTATTCCATATGCCTC
GATGTCTTTTTGCGGGTCCTCTGGCGGAGCAGTTTCTGAACCAGGTAGATCTGACCGAAACC
CTGGAAAGATACCAACAGAGACTTAACACTTACGCGCTGGTATCCAAAGACCTGGCCAGCTA
CCGATCTTTTTCGCAGCAGCTAAAGGCACAAGACAGCCTAGGTGAACAGCCCACCACTGTGC
CACCGCCCATTGACCTGTCAATACCTCACGTTTGGATGCCACCGCAAACCACTCCACACGGC
TGGACAGAATCACATACCACCTCAGGACTACACCGACCACACTTTAACCAGACCTGTATCCT
CTTTGATGGACACGATCTACTATTCAGCACCGTCACACCTTGTTTGCACCAAGGCTTTTACC
TCATCGACGAACTACGTTACGTTAAAATAACACTGACCGAGGACTTCTTCGTAGTTACGGTG
TCCATAGACGACGACACACCCATGCTGCTTATCTTCGGCCATCTTCCACGCGTACTTTTCAA
AGCGCCCTATCAACGCGACAACTTTATACTACGACAAACTGAAAAACACGAGCTCCTGGTGC
TAGTTAAGAAAGATCAACTGAACCGTCACTCTTATCTCAAAGACCCGGACTTTCTTGACGCC
GCACTTGACTTCAACTACCTAGACCTCAGCGCACTACTACGTAACAGCTTTCACCGTTACGC
CGTGGATGTACTCAAGAGCGGTCGATGTCAGATGCTGGACCGCCGCACGGTAGAAATGGCCT
TCGCCTACGCATTAGCACTGTTCGCAGCAGCCCGACAAGAAGAGGCCGGCGCCCAAGTCTCC
GTCCCACGGGCCCTAGACCGCCAGGCCGCACTCTTACAAATACAAGAATTTATGATCACCTG
CCTCTCACAAACACCACCACGCACCACGTTGCTGCTGTATCCCACGGCCGTGGACCTGGCCA
AACGAGCCCTTTGGACACCGAATCAGATCACCGACATCACCAGCCTCGTACGCCTGGTCTAC
ATACTCTCTAAACAGAATCAGCAACATCTCATCCCCCAATGGGCACTACGACAGATCGCCGA
CTTTGCCCTAAAACTACACAAAACGCACCTGGCCTCTTTTCTTTCAGCCTTCGCACGCCAAG
AACTCTACCTCATGGGCAGCCTCGTCCACTCCATGCTGGTACATACGACGGAGAGACGCGAA
ATCTTCATCGTAGAAACGGGCCTCTGTTCATTGGCCGAGCTATCACACTTTACGCAGTTGTT
AGCTCATCCACACCACGAATACCTCAGCGACCTGTACACACCCTGTTCCAGTAGCGGGCGAC
GCGATCACTCGCTCGAACGCCTCACGCGTCTCTTCCCCGATGCCACCGTCCCCGCTACCGTT
CCCGCCGCCCTCTCCATCCTATCTACCATGCAACCAAGCACGCTGGAAACCTTCCCCGACCT
GTTTTGCTTGCCGCTCGGCGAATCCTTCTCCGCGCTGACCGTCTCCGAACACGTCAGTTATA
TCGTAACAAACCAGTACCTGATCAAAGGTATCTCCTACCCTGTCTCCACCACCGTCGTAGGC
CAGAGCCTCATCATCACCCAGACGGACAGTCAAACTAAATGCGAACTGACGCGCAACATGCA
TACCACACACAGCATCACAGTGGCGCTCAACATTTCGCTAGAAAACTGCGCCTTTTGCCAAA
GCGCCCTGCTAGAATACGACGACACGCAAGGCGTCATCAACATCATGTACATGCACGACTCG
GACGACGTCCTTTTCGCCCTGGATCCCTACAACGAAGTGGTGGTCTCATCTCCGCGAACTCA
CTACCTCATGCTTTTGAAAAACGGTACGGTACTAGAAGTAACTGACGTCGTCGTGGACGCCA
CCGACAGTCGTCTCCTCATGATGTCCGTCTACGCGCTATCGGCCATCATCGGCATCTATCTG
CTCTACCGCATGCTCAAGACATGCTGATAATAGGCTGGAGCCTCGGTGGCCATGCTTCTTGC
CCCTTGGGCCTCCCCCCAGCCCCTCCTCCCCTTCCTGCACCCGTACCCCCGTGGTCTTTGAA
TAAAGTCTGAGTGGGCGGC hCMV-gH: hCMV, glycoprotein H (Merlin Strain)
(SEQ ID NO: 79)
UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCCAGGCCUCCCCUCCUACCUCAUCAU
CCUCGCCGUCUGUCUCUUCAGCCACCUACUUUCGUCACGAUAUGGCGCAGAAGCCGUAUCCG
AACCGCUGGACAAAGCGUUUCACCUACUGCUCAACACCUACGGGAGACCCAUCCGCUUCCUG
CGUGAAAAUACCACCCAGUGUACCUACAACAGCAGCCUCCGUAACAGCACGGUCGUCAGGGA
AAACGCCAUCAGUUUCAACUUUUUCCAAAGCUAUAAUCAAUACUAUGUAUUCCAUAUGCCUC
GAUGUCUUUUUGCGGGUCCUCUGGCGGAGCAGUUUCUGAACCAGGUAGAUCUGACCGAAACC
CUGGAAAGAUACCAACAGAGACUUAACACUUACGCGCUGGUAUCCAAAGACCUGGCCAGCUA
CCGAUCUUUUUCGCAGCAGCUAAAGGCACAAGACAGCCUAGGUGAACAGCCCACCACUGUGC
CACCGCCCAUUGACCUGUCAAUACCUCACGUUUGGAUGCCACCGCAAACCACUCCACACGGC
UGGACAGAAUCACAUACCACCUCAGGACUACACCGACCACACUUUAACCAGACCUGUAUCCU
CUUUGAUGGACACGAUCUACUAUUCAGCACCGUCACACCUUGUUUGCACCAAGGCUUUUACC
UCAUCGACGAACUACGUUACGUUAAAAUAACACUGACCGAGGACUUCUUCGUAGUUACGGUG
UCCAUAGACGACGACACACCCAUGCUGCUUAUCUUCGGCCAUCUUCCACGCGUACUUUUCAA
AGCGCCCUAUCAACGCGACAACUUUAUACUACGACAAACUGAAAAACACGAGCUCCUGGUGC
UAGUUAAGAAAGAUCAACUGAACCGUCACUCUUAUCUCAAAGACCCGGACUUUCUUGACGCC -continued GCACUUGACUUCAACUACCUAGACCUCAGCGCACUACUACGUAACAGCUUUCACCGUUACGC
CGUGGAUGUACUCAAGAGCGGUCGAUGUCAGAUGCUGGACCGCCGCACGGUAGAAAUGGCCU
UCGCCUACGCAUUAGCACUGUUCGCAGCAGCCCGACAAGAAGAGGCCGGCGCCCAAGUCUCC
GUCCCACGGGCCCUAGACCGCCAGGCCGCACUCUUACAAAUACAAGAAUUUAUGAUCACCUG
CCUCUCACAAACACCACCACGCACCACGUUGCUGCUGUAUCCCACGGCCGUGGACCUGGCCA
AACGAGCCCUUUGGACACCGAAUCAGAUCACCGACAUCACCAGCCUCGUACGCCUGGUCUAC
AUACUCUCUAAACAGAAUCAGCAACAUCUCAUCCCCCAAUGGGCACUACGACAGAUCGCCGA
CUUUGCCCUAAAACUACACAAAACGCACCUGGCCUCUUUUCUUUCAGCCUUCGCACGCCAAG
AACUCUACCUCAUGGGCAGCCUCGUCCACUCCAUGCUGGUACAUACGACGGAGAGACGCGAA
AUCUUCAUCGUAGAAACGGGCCUCUGUUCAUUGGCCGAGCUAUCACACUUUACGCAGUUGUU
AGCUCAUCCACACCACGAAUACCUCAGCGACCUGUACACACCCUGUUCCAGUAGCGGGCGAC
GCGAUCACUCGCUCGAACGCCUCACGCGUCUCUUCCCCGAUGCCACCGUCCCCGCUACCGUU
CCCGCCGCCCUCUCCAUCCUAUCUACCAUGCAACCAAGCACGCUGGAAACCUUCCCCGACCU
GUUUUGCUUGCCGCUCGGCGAAUCCUUCUCCGCGCUGACCGUCUCCGAACACGUCAGUUAUA
UCGUAACAAACCAGUACCUGAUCAAAGGUAUCUCCUACCCUGUCUCCACCACCGUCGUAGGC
CAGAGCCUCAUCAUCACCCAGACGGACAGUCAAACUAAAUGCGAACUGACGCGCAACAUGCA
UACCACACACAGCAUCACAGUGGCGCUCAACAUUUCGCUAGAAAACUGCGCCUUUUGCCAAA
GCGCCCUGCUAGAAUACGACGACACGCAAGGCGUCAUCAACAUCAUGUACAUGCACGACUCG
GACGACGUCCUUUUCGCCCUGGAUCCCUACAACGAAGUGGUGGUCUCAUCUCCGCGAACUCA
CUACCUCAUGCUUUUGAAAAACGGUACGGUACUAGAAGUAACUGACGUCGUCGUGGACGCCA
CCGACAGUCGUCUCCUCAUGAUGUCCGUCUACGCGCUAUCGGCCAUCAUCGGCAUCUAUCUG
CUCUACCGCAUGCUCAAGACAUGCUGAUAAUAGGCUGGAGCCUCGGUGGCCAUGCUUCUUGC
CCCUUGGGCCUCCCCCCAGCCCCUCCUCCCCUUCCUGCACCCGUACCCCCGUGGUCUUUGAA
UAAAGUCUGAGUGGGCGGC hCMV-gHFLAG, hCMV glycoproteinH-FLAG tag
(SEQ ID NO: 2)

TCAAGCTTTTGGACCCTCGTAGAGAAGCTAATACGACTCACTATAGGGAAATAAGAGAGAAA
AGAAGAGTAAGAAGAAATATAAGAGCCACCATGCGGCCAGGCCTCCCCTCCTACCTCATCAT
CCTCGCCGTCTGTCTCTTCAGCCACCTACTTTCGTCACGATATGGCGCAGAAGCCGTATCCG
AACCGCTGGACAAAGCGTTTCACCTACTGCTCAACACCTACGGGAGACCCATCCGCTTCCTG
CGTGAAAATACCACCCAGTGTACCTACAACAGCAGCCTCCGTAACAGCACGGTCGTCAGGGA
AAACGCCATCAGTTTCAACTTTTTCCAAAGCTATAATCAATACTATGTATTCCATATGCCTC
GATGTCTTTTTGCGGGTCCTCTGGCGGAGCAGTTTCTGAACCAGGTAGATCTGACCGAAACC
CTGGAAAGATACCAACAGAGACTTAACACTTACGCGCTGGTATCCAAAGACCTGGCCAGCTA
CCGATCTTTTTCGCAGCAGCTAAAGGCACAAGACAGCCTAGGTGAACAGCCCACCACTGTGC
CACCGCCCATTGACCTGTCAATACCTCACGTTTGGATGCCACCGCAAACCACTCCACACGGC
TGGACAGAATCACATACCACCTCAGGACTACACCGACCACACTTTAACCAGACCTGTATCCT
CTTTGATGGACACGATCTACTATTCAGCACCGTCACACCTTGTTTGCACCAAGGCTTTTACC
TCATCGACGAACTACGTTACGTTAAAATAACACTGACCGAGGACTTCTTCGTAGTTACGGTG
TCCATAGACGACGACACACCCATGCTGCTTATCTTCGGCCATCTTCCACGCGTACTTTTCAA
AGCGCCCTATCAACGCGACAACTTTATACTACGACAAACTGAAAAACACGAGCTCCTGGTGC
TAGTTAAGAAAGATCAACTGAACCGTCACTCTTATCTCAAAGACCCGGACTTTCTTGACGCC
GCACTTGACTTCAACTACCTAGACCTCAGCGCACTACTACGTAACAGCTTTCACCGTTACGC
CGTGGATGTACTCAAGAGCGGTCGATGTCAGATGCTGGACCGCCGCACGGTAGAAATGGCCT
TCGCCTACGCATTAGCACTGTTCGCAGCAGCCCGACAAGAAGAGGCCGGCGCCCAAGTCTCC
GTCCCACGGGCCCTAGACCGCCAGGCCGCACTCTTACAAATACAAGAATTTATGATCACCTG
CCTCTCACAAACACCACCACGCACCACGTTGCTGCTGTATCCCACGGCCGTGGACCTGGCCA
AACGAGCCCTTTGGACACCGAATCAGATCACCGACATCACCAGCCTCGTACGCCTGGTCTAC
ATACTCTCTAAACAGAATCAGCAACATCTCATCCCCCAATGGGCACTACGACAGATCGCCGA
CTTTGCCCTAAAACTACACAAAACGCACCTGGCCTCTTTTCTTTCAGCCTTCGCACGCCAAG
AACTCTACCTCATGGGCAGCCTCGTCCACTCCATGCTGGTACATACGACGGAGAGACGCGAA
ATCTTCATCGTAGAAACGGGCCTCTGTTCATTGGCCGAGCTATCACACTTTACGCAGTTGTT
AGCTCATCCACACCACGAATACCTCAGCGACCTGTACACACCCTGTTCCAGTAGCGGGCGAC
GCGATCACTCGCTCGAACGCCTCACGCGTCTCTTCCCCGATGCCACCGTCCCCGCTACCGTT
CCCGCCGCCCTCTCCATCCTATCTACCATGCAACCAAGCACGCTGGAAACCTTCCCCGACCT
GTTTTGCTTGCCGCTCGGCGAATCCTTCTCCGCGCTGACCGTCTCCGAACACGTCAGTTATA
TCGTAACAAACCAGTACCTGATCAAAGGTATCTCCTACCCTGTCTCCACCACCGTCGTAGGC
CAGAGCCTCATCATCACCCAGACGGACAGTCAAACTAAATGCGAACTGACGCGCAACATGCA
TACCACACACAGCATCACAGTGGCGCTCAACATTTCGCTAGAAAACTGCGCCTTTTGCCAAA
GCGCCCTGCTAGAATACGACGACACGCAAGGCGTCATCAACATCATGTACATGCACGACTCG
GACGACGTCCTTTTCGCCCTGGATCCCTACAACGAAGTGGTGGTCTCATCTCCGCGAACTCA
CTACCTCATGCTTTTGAAAAACGGTACGGTACTAGAAGTAACTGACGTCGTCGTGGACGCCA
CCGACAGTCGTCTCCTCATGATGTCCGTCTACGCGCTATCGGCCATCATCGGCATCTATCTG
CTCTACCGCATGCTCAAGACATGCGATTACAAGGACGATGACGATAAGTGATGATAATAGGC
TGGAGCCTCGGTGGCCATGCTTCTTGCCCCTTGGGCCTCCCCCCAGCCCCTCCTCCCCTTCC
TGCACCCGTACCCCCGTGGTCTTTGAATAAAGTCTGAGTGGGCGGC hCMV-gHFLAG, hCMV glycoproteinH-FLAG tag
(SEQ ID NO: 80)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCCAGGCCUCCCCUCCUACCUCAUCAU
CCUCGCCGUCUGUCUCUUCAGCCACCUACUUUCGUCACGAUAUGGCGCAGAAGCCGUAUCCG
AACCGCUGGACAAAGCGUUUCACCUACUGCUCAACACCUACGGGAGACCCAUCCGCUUCCUG
CGUGAAAAUACCACCCAGUGUACCUACAACAGCAGCCUCCGUAACAGCACGGUCGUCAGGGA
AAACGCCAUCAGUUUCAACUUUUUCCAAAGCUAUAAUCAAUACUAUGUAUUCCAUAUGCCUC
GAUGUCUUUUUGCGGGUCCUCUGGCGGAGCAGUUUCUGAACCAGGUAGAUCUGACCGAAACC
CUGGAAAGAUACCAACAGAGACUUAACACUUACGCGCUGGUAUCCAAAGACCUGGCCAGCUA
CCGAUCUUUUUCGCAGCAGCUAAAGGCACAAGACAGCCUAGGUGAACAGCCCACCACUGUGC
CACCGCCCAUUGACCUGUCAAUACCUCACGUUUGGAUGCCACCGCAAACCACUCCACACGGC
UGGACAGAAUCACAUACCACCUCAGGACUACACCGACCACACUUUAACCAGACCUGUAUCCU

-continued

CUUUGAUGGACACGAUCUACUAUUCAGCACCGUCACACCUUGUUUGCACCAAGGCUUUUACC
UCAUCGACGAACUACGUUACGUUAAAAUAACACUGACCGAGGACUUCUUCGUAGUUACGGUG
UCCAUAGACGACGACACACCCAUGCUGCUUAUCUUCGGCCAUCUUCCACGCGUACUUUUCAA
AGCGCCCUAUCAACGCGACAACUUUAUACUACGACAAACUGAAAAACACGAGCUCCUGGUGC
UAGUUAAGAAAGAUCAACUGAACCGUCACUCUUAUCUCAAAGACCCGGACUUUCUUGACGCC
GCACUUGACUUCAACUACCUAGACCUCAGCGCACUACUACGUAACAGCUUUCACCGUUACGC
CGUGGAUGUACUCAAGAGCGGUCGAUGUCAGAUGCUGGACCGCCGCACGGUAGAAAUGGCCU
UCGCCUACGCAUUAGCACUGUUCGCAGCAGCCCGACAAGAAGAGGCCGGCGCCCAAGUCUCC
GUCCCACGGGCCCUAGACCGCCAGGCCGCACUCUUACAAAUACAAGAAUUUAUGAUCACCUG
CCUCUCACAAACACCACCACGCACCACGUUGCUGCUGUAUCCCACGGCCGUGGACCUGGCCA
AACGAGCCCUUUGGACACCGAAUCAGAUCACCGACAUCACCAGCCUCGUACGCCUGGUCUAC
AUACUCUCUAAACAGAAUCAGCAACAUCUCAUCCCCCAAUGGGCACUACGACAGAUCGCCGA
CUUUGCCCUAAAACUACACAAAACGCACCUGGCCUCUUUUCUUUCAGCCUUCGCACGCCAAG
AACUCUACCUCAUGGGCAGCCUCGUCCACUCCAUGCUGGUACAUACGACGGAGAGACGCGAA
AUCUUCAUCGUAGAAACGGGCCUCUGUUCAUUGGCCGAGCUAUCACACUUUACGCAGUUGUU
AGCUCAUCCACACCACGAAUACCUCAGCGACCUGUACACACCCUGUUCCAGUAGCGGGCGAC
GCGAUCACUCGCUCGAACGCCUCACGCGUCUCUUCCCCGAUGCCACCGUCCCCGCUACCGUU
CCCGCCGCCCUCUCCAUCCUAUCUACCAUGCAACCAAGCACGCUGGAAACCUUCCCCGACCU
GUUUUGCUUGCCGCUCGGCGAAUCCUUCUCCGCGCUGACCGUCUCCGAACACGUCAGUUAUA
UCGUAACAAACCAGUACCUGAUCAAAGGUAUCUCCUACCCUGUCUCCACCACCGUCGUAGGC
CAGAGCCUCAUCAUCACCCAGACGGACAGUCAAACUAAAUGCGAACUGACGCGCAACAUGCA
UACCACACACAGCAUCACAGUGGCGCUCAACAUUUCGCUAGAAAACUGCGCCUUUUGCCAAA
GCGCCCUGCUAGAAUACGACGACACGCAAGGCGUCAUCAACAUCAUGUACAUGCACGACUCG
GACGACGUCCUUUUCGCCCUGGAUCCCUACAACGAAGUGGUGGUCUCAUCUCCGCGAACUCA
CUACCUCAUGCUUUUGAAAAACGGUACGGUACUAGAAGUAACUGACGUCGUCGUGGACGCCA
CCGACAGUCGUCUCCUCAUGAUGUCCGUCUACGCGCUAUCGGCCAUCAUCGGCAUCUAUCUG
CUCUACCGCAUGCUCAAGACAUGCGAUUACAAGGACGAUGACGAUAAGUGAUGAUAAUAGGC
UGGAGCCUCGGUGGCCAUGCUUCUUGCCCCUUGGGCCUCCCCCCAGCCCCUCCUCCCCUUCC
UGCACCCGUACCCCCGUGGUCUUUGAAUAAAGUCUGAGUGGGCGGC hCMV-gL, hCMV glycoprotein L (SEQ ID NO: 3)

TCAAGCTTTTGGACCCTCGTACAGAAGCTAATACGACTCACTATAGGGAAATAAGAGAGAAA
AGAAGAGTAAGAAGAAATATAAGAGCCACCATGTGCCGCCGCCCGGATTGCGGCTTCTCTTT
CTCACCTGGACCGGTGATACTGCTGTGGTGTTGCCTTCTGCTGCCCATTGTTTCCTCAGCCG
CCGTCAGCGTCGCTCCTACCGCCGCCGAGAAAGTCCCCGCGGAGTGCCCCGAACTAACGCGC
CGATGCTTGTTGGGTGAGGTGTTTGAGGGTGACAAGTATGAAAGTTGGCTGCGCCCGTTGGT
GAATGTTACCGGGCGCGATGGCCCGCTATCGCAACTTATCCGTTACCGTCCCGTTACGCCGG
AGGCCGCCAACTCCGTGCTGTTGGACGAGGCTTTCCTGGACACTCTGGCCCTGCTGTACAAC
AATCCGGATCAATTGCGGGCCCTGCTGACGCTGTTGAGCTCGGACACAGCGCCGCGCTGGAT
GACGGTGATGCGCGGCTACAGCGAGTGCGGCGATGGCTCGCCGGCCGTGTACACGTGCGTGG
ACGACCTGTGCCGCGGCTACGACCTCACGCGACTGTCATACGGGCGCAGCATCTTCACGGAA
CACGTGTTAGGCTTCGAGCTGGTGCCACCGTCTCTCTTTAACGTGGTGGTGGCCATACGCAA
CGAAGCCACGCGTACCAACCGCGCCGTGCGTCTGCCCGTGAGCACCGCTGCCGCGCCCGAGG
GCATCACGCTCTTTTACGGCCTGTACAACGCAGTGAAGGAATTCTGCCTGCGTCACCAGCTG
GACCCGCCGCTGCTACGCCACCTAGATAAATACTACGCCGGACTGCCGCCCGAGCTGAAGCA
GACGCGCGTCAACCTGCCGGCTCACTCGCGCTATGGCCCTCAAGCAGTGGATGCTCGCTGAT
AATAGGCTGGAGCCTCGGTGGCCATGCTTCTTGCCCCTTGGGCCTCCCCCCAGCCCCTCCTC
CCCTTCCTGCACCCGTACCCCCGTGGTCTTTGAATAAAGTCTGAGTGGGCGGC hCMV-gL, hCMV glycoprotein L (SEQ ID NO: 81)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGUGCCGCCGCCCGGAUUGCGGCUUCUCUUU
CUCACCUGGACCGGUGAUACUGCUGUGGUGUUGCCUUCUGCUGCCCAUUGUUUCCUCAGCCG
CCGUCAGCGUCGCUCCUACCGCCGCCGAGAAAGUCCCCGCGGAGUGCCCCGAACUAACGCGC
CGAUGCUUGUUGGGUGAGGUGUUUGAGGGUGACAAGUAUGAAAGUUGGCUGCGCCCGUUGGU
GAAUGUUACCGGGCGCGAUGGCCCGCUAUCGCAACUUAUCCGUUACCGUCCCGUUACGCCGG
AGGCCGCCAACUCCGUGCUGUUGGACGAGGCUUUCCUGGACACUCUGGCCCUGCUGUACAAC
AAUCCGGAUCAAUUGCGGGCCCUGCUGACGCUGUUGAGCUCGGACACAGCGCCGCGCUGGAU
GACGGUGAUGCGCGGCUACAGCGAGUGCGGCGAUGGCUCGCCGGCCGUGUACACGUGCGUGG
ACGACCUGUGCCGCGGCUACGACCUCACGCGACUGUCAUACGGGCGCAGCAUCUUCACGGAA
CACGUGUUAGGCUUCGAGCUGGUGCCACCGUCUCUCUUUAACGUGGUGGUGGCCAUACGCAA
CGAAGCCACGCGUACCAACCGCGCCGUGCGUCUGCCCGUGAGCACCGCUGCCGCGCCCGAGG
GCAUCACGCUCUUUUACGGCCUGUACAACGCAGUGAAGGAAUUCUGCCUGCGUCACCAGCUG
GACCCGCCGCUGCUACGCCACCUAGAUAAAUACUACGCCGGACUGCCGCCCGAGCUGAAGCA
GACGCGCGUCAACCUGCCGGCUCACUCGCGCUAUGGCCCUCAAGCAGUGGAUGCUCGCUGAU
AAUAGGCUGGAGCCUCGGUGGCCAUGCUUCUUGCCCCUUGGGCCUCCCCCCAGCCCCUCCUC
CCCUUCCUGCACCCGUACCCCCGUGGUCUUUGAAUAAAGUCUGAGUGGGCGGC hCMV-gLFLAG, glycoprotein L-FLAG (SEQ ID NO: 4)

TCAAGCTTTTGGACCCTCGTACAGAAGCTAATACGACTCACTATAGGGAAATAAGAGAGAAA
AGAAGAGTAAGAAGAAATATAAGAGCCACCATGTGCCGCCGCCCGGATTGCGGCTTCTCTTT
CTCACCTGGACCGGTGATACTGCTGTGGTGTTGCCTTCTGCTGCCCATTGTTTCCTCAGCCG
CCGTCAGCGTCGCTCCTACCGCCGCCGAGAAAGTCCCCGCGGAGTGCCCCGAACTAACGCGC
CGATGCTTGTTGGGTGAGGTGTTTGAGGGTGACAAGTATGAAAGTTGGCTGCGCCCGTTGGT
GAATGTTACCGGGCGCGATGGCCCGCTATCGCAACTTATCCGTTACCGTCCCGTTACGCCGG
AGGCCGCCAACTCCGTGCTGTTGGACGAGGCTTTCCTGGACACTCTGGCCCTGCTGTACAAC
AATCCGGATCAATTGCGGGCCCTGCTGACGCTGTTGAGCTCGGACACAGCGCCGCGCTGGAT
GACGGTGATGCGCGGCTACAGCGAGTGCGGCGATGGCTCGCCGGCCGTGTACACGTGCGTGG

-continued

ACGACCTGTGCCGCGGCTACGACCTCACGCGACTGTCATACGGGCGCAGCATCTTCACGGAA
CACGTGTTAGGCTTCGAGCTGGTGCCACCGTCTCTCTTTAACGTGGTGGTGGCCATACGCAA
CGAAGCCACGCGTACCAACCGCGCCGTGCGTCTGCCCGTGAGCACCGCTGCCGCGCCCGAGG
GCATCACGCTCTTTTACGGCCTGTACAACGCAGTGAAGGAATTCTGCCTGCGTCACCAGCTG
GACCCGCCGCTGCTACGCCACCTAGATAAATACTACGCCGGACTGCCGCCCGAGCTGAAGCA
GACGCGCGTCAACCTGCCGGCTCACTCGCGCTATGGCCCTCAAGCAGTGGATGCTCGCGATT
ACAAGGACGATGACGATAAGTGATGATAATAGGCTGGAGCCTCGGTGGCCATGCTTCTTGCC
CCTTGGGCCTCCCCCCAGCCCCTCCTCCCCTTCCTGCACCCGTACCCCCGTGGTCTTTGAAT
AAAGTCTGAGTGGGCGGC hCMV-gLFLAG, glycoprotein L-FLAG (SEQ ID NO: 82)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGUGCCGCCGCCCGGAUUGCGGCUUCUCUUU
CUCACCUGGACCGGUGAUACUGCUGUGGUGUUGCCUUCUGCUGCCCAUUGUUUCCUCAGCCG
CCGUCAGCGUCGCUCCUACCGCCGCCGAGAAAGUCCCCGCGGAGUGCCCCGAACUAACGCGC
CGAUGCUUGUUGGGUGAGGUGUUUGAGGGUGACAAGUAUGAAAGUUGGCUGCGCCCGUUGGU
GAAUGUUACCGGGCGCGAUGGCCCGCUAUCGCAACUUAUCCGUUACCGUCCCGUUACGCCGG
AGGCCGCCAACUCCGUGCUGUUGGACGAGGCUUUCCUGGACACUCUGGCCCUGCUGUACAAC
AAUCCGGAUCAAUUGCGGGCCCUGCUGACGCUGUUGAGCUCGGACACAGCGCCGCGCUGGAU
GACGGUGAUGCGCGGCUACAGCGAGUGCGGCGAUGGCUCGCCGGCCGUGUACACGUGCGUGG
ACGACCUGUGCCGCGGCUACGACCUCACGCGACUGUCAUACGGGCGCAGCAUCUUCACGGAA
CACGUGUUAGGCUUCGAGCUGGUGCCACCGUCUCUCUUUAACGUGGUGGUGGCCAUACGCAA
CGAAGCCACGCGUACCAACCGCGCCGUGCGUCUGCCCGUGAGCACCGCUGCCGCGCCCGAGG
GCAUCACGCUCUUUUACGGCCUGUACAACGCAGUGAAGGAAUUCUGCCUGCGUCACCAGCUG
GACCCGCCGCUGCUACGCCACCUAGAUAAAUACUACGCCGGACUGCCGCCCGAGCUGAAGCA
GACGCGCGUCAACCUGCCGGCUCACUCGCGCUAUGGCCCUCAAGCAGUGGAUGCUCGCGAUU
ACAAGGACGAUGACGAUAAGUGAUGAUAAUAGGCUGGAGCCUCGGUGGCCAUGCUUCUUGCC
CCUUGGGCCUCCCCCCAGCCCCUCCUCCCCUUCCUGCACCCGUACCCCCGUGGUCUUUGAAU
AAAGUCUGAGUGGGCGGC hCMV gB, hCMV glycoprotein B (SEQ ID NO: 5)

TCAAGCTTTTGGACCCTCGTACAGAAGCTAATACGACTCACTATAGGGAAATAAGAGAGAAA
AGAAGAGTAAGAAGAAATATAAGAGCCACCATGGAATCCAGGATCTGGTGCCTGGTAGTCTG
CGTTAACTTGTGTATCGTCTGTCTGGGTGCTGCGGTTTCCTCATCTTCTACTCGTGGAACTT
CTGCTACTCACAGTCACCATTCCTCTCATACGACGTCTGCTGCTCACTCTCGATCCGGTTCA
GTCTCTCAACGCGTAACTTCTTCCCAAACGGTCAGCCATGGTGTTAACGAGACCATCTACAA
CACTACCCTCAAGTACGGAGATGTGGTGGGGGTCAATACCACCAAGTACCCCTATCGCGTGT
GTTCTATGGCCCAGGGTACGGATCTTATTCGCTTTGAACGTAATATCGTCTGCACCTCGATG
AAGCCCATCAATGAAGACCTGGACGAGGGCATCATGGTGGTCTACAAACGCAACATCGTCGC
GCACACCTTTAAGGTACGAGTCTACCAGAAGGTTTTGACGTTTCGTCGTAGCTACGCTTACA
TCCACACCACTTATCTGCTGGGCAGCAACACGGAATACGTGGCGCCTCCTATGTGGGAGATT
CATCATATCAACAGCCACAGTCAGTGCTACAGTTCCTACAGCCGCGTTATAGCAGGCACGGT
TTTCGTGGCTTATCATAGGGACAGCTATGAAAACAAAACCATGCAATTAATGCCCGACGATT
ATTCCAACACCCACAGTACCCGTTACGTGACGGTCAAGGATCAATGGCACAGCCGCGGCAGC
ACCTGGCTCTATCGTGAGACCTGTAATCTGAATTGTATGGTGACCATCACTACTGCGCGCTC
CAAATATCCTTATCATTTTTTCGCCACTTCCACGGGTGACGTGGTTGACATTTCTCCTTTCT
ACAACGGAACCAATCGCAATGCCAGCTACTTTGGAGAAAACGCCGACAAGTTTTTCATTTTT
CCGAACTACACTATCGTCTCCGACTTTGGAAGACCGAATTCTGCGTTAGAGACCCACAGGTT
GGTGGCTTTTCTTGAACGTGCGGACTCGGTGATCTCCTGGGATATACAGGACGAAAAGAATG
TCACTTGTCAACTCACTTTCTGGGAAGCCTCGGAACGCACCATTCGTTCCGAAGCCGAGGAC
TCGTATCACTTTTCTTCTGCCAAAATGACCGCCACTTTCTTATCTAAGAAGCAAGAGGTGAA
CATGTCCGACTCTGCGCTGGACTGCGTACGTGATGAGGCTATAAATAAGTTACAGCAGATTT
TCAATACTTCATACAATCAAACATATGAAAAATATGGAAACGTGTCCGTCTTTGAAACCACT
GGTGGTTTGGTAGTGTTCTGGCAAGGTATCAAGCAAAAATCTCTGGTGGAACTCGAACGTTT
GGCCAACCGCTCCAGTCTGAATCTTACTCATAATAGAACCAAAAGAAGTACAGATGGCAACA
ATGCAACTCATTTATCCAACATGGAATCGGTGCACAATCTGGTCTACGCCCAGCTGCAGTTC
ACCTATGACACGTTGCGCGGTTACATCAACCGGGCGCTGGCGCAAATCGCAGAAGCCTGGTG
TGTGGATCAACGGCGCACCCTAGAGGTCTTCAAGGAACTCAGCAAGATCAACCCGTCAGCCA
TTCTCTCGGCCATTTACAACAAACCGATTGCCGCGCGTTTCATGGGTGATGTCTTGGGCCTG
GCCAGCTGCGTGACCATCAACCAAACCAGCGTCAAGGTGCTGCGTGATATGAACGTGAAGGA
GTCGCCAGGACGCTGCTACTCACGACCCGTGGTCATCTTTAATTTCGCCAACAGCTCGTACG
TGCAGTACGGTCAACTGGGCGAGGACAACGAAATCCTGTTGGGCAACCACCGCACTGAGGAA
TGTCAGCTTCCCAGCCTCAAGATCTTCATCGCCGGGAACTCGGCCTACGAGTACGTGGACTA
CCTCTTCAAACGCATGATTGACCTCAGCAGTATCTCCACCGTCGACAGCATGATCGCCCTGG
ATATCGACCCGCTGGAAAATACCGACTTCAGGGTACTGGAACTTTACTCGCAGAAAGAGCTG
CGTTCCAGCAACGTTTTTGACCTCGAAGAGATCATGCGCGAATTCAACTCGTACAAGCAGCG
GGTAAAGTACGTGGAGGACAAGGTAGTCGACCCGCTACCGCCCTACCTCAAGGGTCTGGACG
ACCTCATGAGCGGCCTGGGCGCCGCGGGAAAGGCCGTTGGCGTAGCCATTGGGGCCGTGGGT
GGCGCGGTGGCCTCCGTGGTCGAAGGCGTTGCCACCTTCCTCAAAAACCCCTTCGGAGCGTT
CACCATCATCCTCGTGGCCATAGCTGTAGTCATTATCACTTATTTGATCTATACTCGACAGC
GGCGTTTGTGCACGCAGCCGCTGCAGAACCTCTTTCCCTATCTGGTGTCCGCCGACGGGACC
ACCGTGACGTCGGGCAGCACCAAAGACACGTCGTTACAGGCTCCGCCTTCCTACGAGGAAAG
TGTTTATAATTCTGGTCGCAAAGGACCGGGACCACCGTCGTCTGATGCATCCACGGCGGCTC
CGCCTTACACCAACGAGCAGGCTTACCAGATGCTTCTGGCCCTGGCCCGTCTGGACGCAGAG
CAGCGAGCGCAGCAGAACGGTACAGATTCTTTGGACGGACGGACTGGCACGCAGGACAAGGG
ACAGAAGCCCAACCTACTAGACCGACTGCGACATCGCAAAAACGGCTACCGACACTTGAAAG
ACTCTGACGAAGAAGAGAACGTCTGATAATAGGCTGGAGCCTCGGTGGCCATGCTTCTTGCC
CCTTGGGCCTCCCCCCAGCCCCTCCTCCCCTTCCTGCACCCGTACCCCCGTGGTCTTTGAAT
AAAGTCTGAGTGGGCGGC

-continued hCMV gB, hCMV glycoprotein B (SEQ ID NO: 83)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGGAAUCCAGGAUCUGGUGCCUGGUAGUCUG
CGUUAACUUGUGUAUCGUCUGUCUGGGUGCUGCGGUUUCCUCAUCUUCUACUCGUGGAACUU
CUGCUACUCACAGUCACCAUUCCUCUCAUACGACGUCUGCUGCUCACUCUCGAUCCGGUUCA
GUCUCUCAACGCGUAACUUCUUCCCAAACGGUCAGCCAUGGUGUUAACGAGACCAUCUACAA
CACUACCCUCAAGUACGGAGAUGUGGUGGGGGUCAAUACCACCAAGUACCCCUAUCGCGUGU
GUUCUAUGGCCCAGGGUACGGAUCUUAUUCGCUUUGAACGUAAUAUCGUCUGCACCUCGAUG
AAGCCCAUCAAUGAAGACCUGGACGAGGGCAUCAUGGUGGUCUACAAACGCAACAUCGUCGC
GCACACCUUUAAGGUACGAGUCUACCAGAAGGUUUUGACGUUUCGUCGUAGCUACGCUUACA
UCCACACCACUUAUCUGCUGGGCAGCAACACGGAAUACGUGGCGCCUCCUAUGUGGGAGAUU
CAUCAUAUCAACAGCCACAGUCAGUGCUACAGUUCCUACAGCCGCGUUAUAGCAGGCACGGU
UUUCGUGGCUUAUCAUAGGGACAGCUAUGAAAACAAAACCAUGCAAUUAAUGCCCGACGAUU
AUUCCAACACCCACAGUACCCGUUACGUGACGGUCAAGGAUCAAUGGCACAGCCGCGGCAGC
ACCUGGCUCUAUCGUGAGACCUGUAAUCUGAAUUGUAUGGUGACCAUCACUACUGCGCGCUC
CAAAUAUCCUUAUCAUUUUUUCGCCACUUCCACGGGUGACGUGGUUGACAUUUCUCCUUUCU
ACAACGGAACCAAUCGCAAUGCCAGCUACUUUGGAGAAAACGCCGACAAGUUUUUCAUUUUU
CCGAACUACACUAUCGUCUCCGACUUUGGAAGACCGAAUUCUGCGUUAGAGACCCACAGGUU
GGUGGCUUUUCUUGAACGUGCGGACUCGGUGAUCUCCUGGGAUAUACAGGACGAAAAGAAUG
UCACUUGUCAACUCACUUUCUGGGAAGCCUCGGAACGCACCAUUCGUUCCGAAGCCGAGGAC
UCGUAUCACUUUUCUUCUGCCAAAAUGACCGCCACUUUCUUAUCUAAGAAGCAAGAGGUGAA
CAUGUCCGACUCUGCGCUGGACUGCGUACGUGAUGAGGCUAUAAAUAAGUUACAGCAGAUUU
UCAAUACUUCAUACAAUCAAACAUAUGAAAAAUAUGGAAACGUGUCCGUCUUUGAAACCACU
GGUGGUUUGGUAGUGUUCUGGCAAGGUAUCAAGCAAAAAUCUCUGGUGGAACUCGAACGUUU
GGCCAACCGCUCCAGUCUGAAUCUUACUCAUAAUAGAACCAAAAGAAGUACAGAUGGCAACA
AUGCAACUCAUUUAUCCAACAUGGAAUCGGUGCACAAUCUGGUCUACGCCCAGCUGCAGUUC
ACCUAUGACACGUUGCGCGGUUACAUCAACCGGGCGCUGGCGCAAAUCGCAGAAGCCUGGUG
UGUGGAUCAACGGCGCACCCUAGAGGUCUUCAAGGAACUCAGCAAGAUCAACCCGUCAGCCA
UUCUCUCGGCCAUUUACAACAAACCGAUUGCCGCGCGUUUCAUGGGUGAUGUCUUGGGCCUG
GCCAGCUGCGUGACCAUCAACCAAACCAGCGUCAAGGUGCUGCGUGAUAUGAACGUGAAGGA
GUCGCCAGGACGCUGCUACUCACGACCCGUGGUCAUCUUUAAUUUCGCCAACAGCUCGUACG
UGCAGUACGGUCAACUGGGCGAGGACAACGAAAUCCUGUUGGGCAACCACCGCACUGAGGAA
UGUCAGCUUCCCAGCCUCAAGAUCUUCAUCGCCGGGAACUCGGCCUACGAGUACGUGGACUA
CCUCUUCAAACGCAUGAUUGACCUCAGCAGUAUCUCCACCGUCGACAGCAUGAUCGCCCUGG
AUAUCGACCCGCUGGAAAAUACCGACUUCAGGGUACUGGAACUUUACUCGCAGAAAGAGCUG
CGUUCCAGCAACGUUUUUGACCUCGAAGAGAUCAUGCGCGAAUUCAACUCGUACAAGCAGCG
GGUAAAGUACGUGGAGGACAAGGUAGUCGACCCGCUACCGCCCUACCUCAAGGGUCUGGACG
ACCUCAUGAGCGGCCUGGGCGCCGCGGGAAAGGCCGUUGGCGUAGCCAUUGGGGCCGUGGGU
GGCGCGGUGGCCUCCGUGGUCGAAGGCGUUGCCACCUUCCUCAAAAACCCCUUCGGAGCGUU
CACCAUCAUCCUCGUGGCCAUAGCUGUAGUCAUUAUCACUUAUUUGAUCUAUACUCGACAGC
GGCGUUUGUGCACGCAGCCGCUGCAGAACCUCUUUCCCUAUCUGGUGUCCGCCGACGGGACC
ACCGUGACGUCGGGCAGCACCAAAGACACGUCGUUACAGGCUCCGCCUUCCUACGAGGAAAG
UGUUUAUAAUUCUGGUCGCAAAGGACCGGGACCACCGUCGUCUGAUGCAUCCACGGCGGCUC
CGCCUUACACCAACGAGCAGGCUUACCAGAUGCUUCUGGCCCUGGCCCGUCUGGACGCAGAG
CAGCGAGCGCAGCAGAACGGUACAGAUUCUUUGGACGGACGGACUGGCACGCAGGACAAGGG
ACAGAAGCCCAACCUACUAGACCGACUGCGACAUCGCAAAAACGGCUACCGACACUUGAAAG
ACUCUGACGAAGAAGAGAACGUCUGAUAAUAGGCUGGAGCCUCGGUGGCCAUGCUUCUUGCC
CCUUGGGCCUCCCCCCAGCCCCUCCUCCCCUUCCUGCACCCGUACCCCCGUGGUCUUUGAAU
AAAGUCUGAGUGGGCGGC hCMV gBFLAG, hCMV glycoproteinB-FLAG (SEQ ID NO: 6)

TCAAGCTTTTGGACCCTCGTAGAGAAGCTAATACGACTCACTATAGGGAAATAAGAGAGAAA
AGAAGAGTAAGAAGAAATATAAGAGCCACCATGGAATCCAGGATCTGGTGCCTGGTAGTCTG
CGTTAACTTGTGTATCGTCTGTCTGGGTGCTGCGGTTTCCTCATCTTCTACTCGTGGAACTT
CTGCTACTCACAGTCACCATTCCTCTCATACGACGTCTGCTGCTCACTCTCGATCCGGTTCA
GTCTCTCAACGCGTAACTTCTTCCCAAACGGTCAGCCATGGTGTTAACGAGACCATCTACAA
CACTACCCTCAAGTACGGAGATGTGGTGGGGGTCAATACCACCAAGTACCCCTATCGCGTGT
GTTCTATGGCCCAGGGTACGGATCTTATTCGCTTTGAACGTAATATCGTCTGCACCTCGATG
AAGCCCATCAATGAAGACCTGGACGAGGGCATCATGGTGGTCTACAAACGCAACATCGTCGC
GCACACCTTTAAGGTACGAGTCTACCAGAAGGTTTTGACGTTTCGTCGTAGCTACGCTTACA
TCCACACCACTTATCTGCTGGGCAGCAACACGGAATACGTGGCGCCTCCTATGTGGGAGATT
CATCATATCAACAGCCACAGTCAGTGCTACAGTTCCTACAGCCGCGTTATAGCAGGCACGGT
TTTCGTGGCTTATCATAGGGACAGCTATGAAAACAAAACCATGCAATTAATGCCCGACGATT
ATTCCAACACCCACAGTACCCGTTACGTGACGGTCAAGGATCAATGGCACAGCCGCGGCAGC
ACCTGGCTCTATCGTGAGACCTGTAATCTGAATTGTATGGTGACCATCACTACTGCGCGCTC
CAAATATCCTTATCATTTTTTCGCCACTTCCACGGGTGACGTGGTTGACATTTCTCCTTTCT
ACAACGGAACCAATCGCAATGCCAGCTACTTTGGAGAAAACGCCGACAAGTTTTTCATTTTT
CCGAACTACACTATCGTCTCCGACTTTGGAAGACCGAATTCTGCGTTAGAGACCCACAGGTT
GGTGGCTTTTCTTGAACGTGCGGACTCGGTGATCTCCTGGGATATACAGGACGAAAAGAATG
TCACTTGTCAACTCACTTTCTGGGAAGCCTCGGAACGCACCATTCGTTCCGAAGCCGAGGAC
TCGTATCACTTTTCTTCTGCCAAAATGACCGCCACTTTCTTATCTAAGAAGCAAGAGGTGAA
CATGTCCGACTCTGCGCTGGACTGCGTACGTGATGAGGCTATAAATAAGTTACAGCAGATTT
TCAATACTTCATACAATCAAACATATGAAAAATATGGAAACGTGTCCGTCTTTGAAACCACT
GGTGGTTTGGTAGTGTTCTGGCAAGGTATCAAGCAAAAATCTCTGGTGGAACTCGAACGTTT
GGCCAACCGCTCCAGTCTGAATCTTACTCATAATAGAACCAAAAGAAGTACAGATGGCAACA
ATGCAACTCATTTATCCAACATGGAATCGGTGCACAATCTGGTCTACGCCCAGCTGCAGTTC

-continued

ACCTATGACACGTTGCGCGGTTACATCAACCGGGCGCTGGCGCAAATCGCAGAAGCCTGGTG
TGTGGATCAACGGCGCACCCTAGAGGTCTTCAAGGAACTCAGCAAGATCAACCCGTCAGCCA
TTCTCTCGGCCATTTACAACAAACCGATTGCCGCGCGTTTCATGGGTGATGTCTTGGGCCTG
GCCAGCTGCGTGACCATCAACCAAACCAGCGTCAAGGTGCTGCGTGATATGAACGTGAAGGA
GTCGCCAGGACGCTGCTACTCACGACCCGTGGTCATCTTTAATTTCGCCAACAGCTCGTACG
TGCAGTACGGTCAACTGGGCGAGGACAACGAAATCCTGTTGGGCAACCACCGCACTGAGGAA
TGTCAGCTTCCCAGCCTCAAGATCTTCATCGCCGGGAACTCGGCCTACGAGTACGTGGACTA
CCTCTTCAAACGCATGATTGACCTCAGCAGTATCTCCACCGTCGACAGCATGATCGCCCTGG
ATATCGACCCGCTGGAAAATACCGACTTCAGGGTACTGGAACTTTACTCGCAGAAAGAGCTG
CGTTCCAGCAACGTTTTTGACCTCGAAGAGATCATGCGCGAATTCAACTCGTACAAGCAGCG
GGTAAAGTACGTGGAGGACAAGGTAGTCGACCCGCTACCGCCCTACCTCAAGGGTCTGGACG
ACCTCATGAGCGGCCTGGGCGCCGCGGGAAAGGCCGTTGGCGTAGCCATTGGGGCCGTGGGT
GGCGCGGTGGCCTCCGTGGTCGAAGGCGTTGCCACCTTCCTCAAAAACCCCTTCGGAGCGTT
CACCATCATCCTCGTGGCCATAGCTGTAGTCATTATCACTTATTTGATCTATACTCGACAGC
GGCGTTTGTGCACGCAGCCGCTGCAGAACCTCTTTCCCTATCTGGTGTCCGCCGACGGGACC
ACCGTGACGTCGGGCAGCACCAAAGACACGTCGTTACAGGCTCCGCCTTCCTACGAGGAAAG
TGTTTATAATTCTGGTCGCAAAGGACCGGGACCACCGTCGTCTGATGCATCCACGGCGGCTC
CGCCTTACACCAACGAGCAGGCTTACCAGATGCTTCTGGCCCTGGCCCGTCTGGACGCAGAG
CAGCGAGCGCAGCAGAACGGTACAGATTCTTTGGACGGACGGACTGGCACGCAGGACAAGGG
ACAGAAGCCCAACCTACTAGACCGACTGCGACATCGCAAAAACGGCTACCGACACTTGAAAG
ACTCTGACGAAGAAGAGAACGTCGATTACAAGGACGATGACGATAAGTGATAATAGGCTGGA
GCCTCGGTGGCCATGCTTCTTGCCCCTTGGGCCTCCCCCCAGCCCCTCCTCCCCTTCCTGCA
CCCGTACCCCCGTGGTCTTTGAATAAAGTCTGAGTGGGCGGC hCMV gBFLAG, hCMV glycoproteinB-FLAG (SEQ ID NO: 84)

TCAAGCUUUUGGACCCUCGUACAGAAGCUAAUACGACUCACUAUAGGGAAAUAAGAGAGAAA
AGAAGAGUAAGAAGAAAUAUAAGAGCCACCAUGGAAUCCAGGAUCUGGUGCCUGGUAGUCUG
CGUUAACUUGUGUAUCGUCUGUCUGGGUGCUGCGGUUUCCUCAUCUUCUACUCGUGGAACUU
CUGCUACUCACAGUCACCAUUCCUCUCAUACGACGUCUGCUGCUCACUCUCGAUCCGGUUCA
GUCUCUCAACGCGUAACUUCUUCCCAAACGGUCAGCCAUGGUGUUAACGAGACCAUCUACAA
CACUACCCUCAAGUACGGAGAUGUGGUGGGGGUCAAUACCACCAAGUACCCCUAUCGCGUGU
GUUCUAUGGCCCAGGGUACGGAUCUUAUUCGCUUUGAACGUAAUAUCGUCUGCACCUCGAUG
AAGCCCAUCAAUGAAGACCUGGACGAGGGCAUCAUGGUGGUCUACAAACGCAACAUCGUCGC
GCACACCUUUAAGGUACGAGUCUACCAGAAGGUUUUGACGUUUCGUCGUAGCUACGCUUACA
UCCACACCACUUAUCUGCUGGGCAGCAACACGGAAUACGUGGCGCCUCCUAUGUGGGAGAUU
CAUCAUAUCAACAGCCACAGUCAGUGCUACAGUUCCUACAGCCGCGUUAUAGCAGGCACGGU
UUUCGUGGCUUAUCAUAGGGACAGCUAUGAAAACAAAACCAUGCAAUUAAUGCCCGACGAUU
AUUCCAACACCCACAGUACCCGUUACGUGACGGUCAAGGAUCAAUGGCACAGCCGCGGCAGC
ACCUGGCUCUAUCGUGAGACCUGUAAUCUGAAUUGUAUGGUGACCAUCACUACUGCGCGCUC
CAAAUAUCCUUAUCAUUUUUUCGCCACUUCCACGGGUGACGUGGUUGACAUUUCUCCUUUCU
ACAACGGAACCAAUCGCAAUGCCAGCUACUUUGGAGAAAACGCCGACAAGUUUUUCAUUUUU
CCGAACUACACUAUCGUCUCCGACUUUGGAAGACCGAAUUCUGCGUUAGAGACCCACAGGUU
GGUGGCUUUUCUUGAACGUGCGGACUCGGUGAUCUCCUGGGAUAUACAGGACGAAAAGAAUG
UCACUUGUCAACUCACUUUCUGGGAAGCCUCGGAACGCACCAUUCGUUCCGAAGCCGAGGAC
UCGUAUCACUUUUCUUCUGCCAAAAUGACCGCCACUUUCUUAUCUAAGAAGCAAGAGGUGAA
CAUGUCCGACUCUGCGCUGGACUGCGUACGUGAUGAGGCUAUAAAUAAGUUACAGCAGAUUU
UCAAUACUUCAUACAAUCAAACAUAUGAAAAAUAUGGAAACGUGUCCGUCUUUGAAACCACU
GGUGGUUUGGUAGUGUUCUGGCAAGGUAUCAAGCAAAAAUCUCUGGUGGAACUCGAACGUUU
GGCCAACCGCUCCAGUCUGAAUCUUACUCAUAAUAGAACCAAAAGAAGUACAGAUGGCAACA
AUGCAACUCAUUUAUCCAACAUGGAAUCGGUGCACAAUCUGGUCUACGCCCAGCUGCAGUUC
ACCUAUGACACGUUGCGCGGUUACAUCAACCGGGCGCUGGCGCAAAUCGCAGAAGCCUGGUG
UGUGGAUCAACGGCGCACCCUAGAGGUCUUCAAGGAACUCAGCAAGAUCAACCCGUCAGCCA
UUCUCUCGGCCAUUUACAACAAACCGAUUGCCGCGCGUUUCAUGGGUGAUGUCUUGGGCCUG
GCCAGCUGCGUGACCAUCAACCAAACCAGCGUCAAGGUGCUGCGUGAUAUGAACGUGAAGGA
GUCGCCAGGACGCUGCUACUCACGACCCGUGGUCAUCUUUAAUUUCGCCAACAGCUCGUACG
UGCAGUACGGUCAACUGGGCGAGGACAACGAAAUCCUGUUGGGCAACCACCGCACUGAGGAA
UGUCAGCUUCCCAGCCUCAAGAUCUUCAUCGCCGGGAACUCGGCCUACGAGUACGUGGACUA
CCUCUUCAAACGCAUGAUUGACCUCAGCAGUAUCUCCACCGUCGACAGCAUGAUCGCCCUGG
AUAUCGACCCGCUGGAAAAUACCGACUUCAGGGUACUGGAACUUUACUCGCAGAAAGAGCUG
CGUUCCAGCAACGUUUUUGACCUCGAAGAGAUCAUGCGCGAAUUCAACUCGUACAAGCAGCG
GGUAAAGUACGUGGAGGACAAGGUAGUCGACCCGCUACCGCCCUACCUCAAGGGUCUGGACG
ACCUCAUGAGCGGCCUGGGCGCCGCGGGAAAGGCCGUUGGCGUAGCCAUUGGGGCCGUGGGU
GGCGCGGUGGCCUCCGUGGUCGAAGGCGUUGCCACCUUCCUCAAAAACCCCUUCGGAGCGUU
CACCAUCAUCCUCGUGGCCAUAGCUGUAGUCAUUAUCACUUAUUUGAUCUAUACUCGACAGC
GGCGUUUGUGCACGCAGCCGCUGCAGAACCUCUUUCCCUAUCUGGUGUCCGCCGACGGGACC
ACCGUGACGUCGGGCAGCACCAAAGACACGUCGUUACAGGCUCCGCCUUCCUACGAGGAAAG
UGUUUAUAAUUCUGGUCGCAAAGGACCGGGACCACCGUCGUCUGAUGCAUCCACGGCGGCUC
CGCCUUACACCAACGAGCAGGCUUACCAGAUGCUUCUGGCCCUGGCCCGUCUGGACGCAGAG
CAGCGAGCGCAGCAGAACGGUACAGAUUCUUUGGACGGACGGACUGGCACGCAGGACAAGGG
ACAGAAGCCCAACCUACUAGACCGACUGCGACAUCGCAAAAACGGCUACCGACACUUGAAAG
ACUCUGACGAAGAAGAGAACGUCGAUUACAAGGACGAUGACGAUAAGUGAUAAUAGGCUGGA
GCCUCGGUGGCCAUGCUUCUUGCCCCUUGGGCCUCCCCCCAGCCCCUCCUCCCCUUCCUGCA
CCCGUACCCCCGUGGUCUUUGAAUAAAGUCUGAGUGGGCGGC

Example 13: hCMV Vaccine—hCMV Variant Glycoprotein Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV-gHtrunc, hCMV glycoproteinH (Ectodomain)

(SEQ ID NO: 7)

TCAAGCTTTTGGACCCTCGTACAGAAGCTAATACGACTCACTATAGGGAAATAAGAGAGAAA
AGAAGAGTAAGAAGAAATATAAGAGCCACCATGCGGCCAGGCCTCCCCTCCTACCTCATCAT
CCTCGCCGTCTGTCTCTTCAGCCACCTACTTTCGTCACGATATGGCGCAGAAGCCGTATCCG
AACCGCTGGACAAAGCGTTTCACCTACTGCTCAACACCTACGGGAGACCCATCCGCTTCCTG
CGTGAAAATACCACCCAGTGTACCTACAACAGCAGCCTCCGTAACAGCACGGTCGTCAGGGA
AAACGCCATCAGTTTCAACTTTTTCCAAAGCTATAATCAATACTATGTATTCCATATGCCTC
GATGTCTTTTTGCGGGTCCTCTGGCGGAGCAGTTTCTGAACCAGGTAGATCTGACCGAAACC
CTGGAAAGATACCAACAGAGACTTAACACTTACGCGCTGGTATCCAAAGACCTGGCCAGCTA
CCGATCTTTTTCGCAGCAGCTAAAGGCACAAGACAGCCTAGGTGAACAGCCCACCACTGTGC
CACCGCCCATTGACCTGTCAATACCTCACGTTTGGATGCCACCGCAAACCACTCCACACGGC
TGGACAGAATCACATACCACCTCAGGACTACACCGACCACACTTTAACCAGACCTGTATCCT
CTTTGATGGACACGATCTACTATTCAGCACCGTCACACCTTGTTTGCACCAAGGCTTTTACC
TCATCGACGAACTACGTTACGTTAAAATAACACTGACCGAGGACTTCTTCGTAGTTACGGTG
TCCATAGACGACGACACACCCATGCTGCTTATCTTCGGCCATCTTCCACGCGTACTTTTCAA
AGCGCCCTATCAACGCGACAACTTTATACTACGACAAACTGAAAAACACGAGCTCCTGGTGC
TAGTTAAGAAAGATCAACTGAACCGTCACTCTTATCTCAAAGACCCGGACTTTCTTGACGCC
GCACTTGACTTCAACTACCTAGACCTCAGCGCACTACTACGTAACAGCTTTCACCGTTACGC
CGTGGATGTACTCAAGAGCGGTCGATGTCAGATGCTGGACCGCCGCACGGTAGAAATGGCCT
TCGCCTACGCATTAGCACTGTTCGCAGCAGCCCGACAAGAAGAGGCCGGCGCCCAAGTCTCC
GTCCCACGGGCCCTAGACCGCCAGGCCGCACTCTTACAAATACAAGAATTTATGATCACCTG
CCTCTCACAAACACCACCACGCACCACGTTGCTGCTGTATCCCACGGCCGTGGACCTGGCCA
AACGAGCCCTTTGGACACCGAATCAGATCACCGACATCACCAGCCTCGTACGCCTGGTCTAC
ATACTCTCTAAACAGAATCAGCAACATCTCATCCCCCAATGGGCACTACGACAGATCGCCGA
CTTTGCCCTAAAACTACACAAAACGCACCTGGCCTCTTTTCTTTCAGCCTTCGCACGCCAAG
AACTCTACCTCATGGGCAGCCTCGTCCACTCCATGCTGGTACATACGACGGAGAGACGCGAA
ATCTTCATCGTAGAAACGGGCCTCTGTTCATTGGCCGAGCTATCACACTTTACGCAGTTGTT
AGCTCATCCACACCACGAATACCTCAGCGACCTGTACACACCCTGTTCCAGTAGCGGGCGAC
GCGATCACTCGCTCGAACGCCTCACGCGTCTCTTCCCCGATGCCACCGTCCCCGCTACCGTT
CCCGCCGCCCTCTCCATCCTATCTACCATGCAACCAAGCACGCTGGAAACCTTCCCCGACCT
GTTTTGCTTGCCGCTCGGCGAATCCTTCTCCGCGCTGACCGTCTCCGAACACGTCAGTTATA
TCGTAACAAACCAGTACCTGATCAAAGGTATCTCCTACCCTGTCTCCACCACCGTCGTAGGC
CAGAGCCTCATCATCACCCAGACGGACAGTCAAACTAAATGCGAACTGACGCGCAACATGCA
TACCACACACAGCATCACAGTGGCGCTCAACATTTCGCTAGAAAACTGCGCCTTTTGCCAAA
GCGCCCTGCTAGAATACGACGACACGCAAGGCGTCATCAACATCATGTACATGCACGACTCG
GACGACGTCCTTTTCGCCCTGGATCCCTACAACGAAGTGGTGGTCTCATCTCCGCGAACTCA
CTACCTCATGCTTTTGAAAAACGGTACGGTACTAGAAGTAACTGACGTCGTCGTGGACGCCA
CCGACTGATAATAGGCTGGAGCCTCGGTGGCCATGCTTCTTGCCCCTTGGGCCTCCCCCCAG
CCCCTCCTCCCCTTCCTGCACCCGTACCCCCGTGGTCTTTGAATAAAGTCTGAGTGGGCGGC hCMV-gHtrunc, hCMV glycoproteinH (Ectodomain)

(SEQ ID NO: 85)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCCAGGCCUCCCCUCCUACCUCAUCAU
CCUCGCCGUCUGUCUCUUCAGCCACCUACUUUCGUCACGAUAUGGCGCAGAAGCCGUAUCCG
AACCGCUGGACAAAGCGUUUCACCUACUGCUCAACACCUACGGGAGACCCAUCCGCUUCCUG
CGUGAAAAUACCACCCAGUGUACCUACAACAGCAGCCUCCGUAACAGCACGGUCGUCAGGGA
AAACGCCAUCAGUUUCAACUUUUUCCAAAGCUAUAAUCAAUACUAUGUAUUCCAUAUGCCUC
GAUGUCUUUUUGCGGGUCCUCUGGCGGAGCAGUUUCUGAACCAGGUAGAUCUGACCGAAACC
CUGGAAAGAUACCAACAGAGACUUAACACUUACGCGCUGGUAUCCAAAGACCUGGCCAGCUA
CCGAUCUUUUUCGCAGCAGCUAAAGGCACAAGACAGCCUAGGUGAACAGCCCACCACUGUGC
CACCGCCCAUUGACCUGUCAAUACCUCACGUUUGGAUGCCACCGCAAACCACUCCACACGGC
UGGACAGAAUCACAUACCACCUCAGGACUACACCGACCACACUUUAACCAGACCUGUAUCCU
CUUUGAUGGACACGAUCUACUAUUCAGCACCGUCACACCUUGUUUGCACCAAGGCUUUUACC
UCAUCGACGAACUACGUUACGUUAAAAUAACACUGACCGAGGACUUCUUCGUAGUUACGGUG
UCCAUAGACGACGACACACCCAUGCUGCUUAUCUUCGGCCAUCUUCCACGCGUACUUUUCAA
AGCGCCCUAUCAACGCGACAACUUUAUACUACGACAAACUGAAAAACACGAGCUCCUGGUGC
UAGUUAAGAAAGAUCAACUGAACCGUCACUCUUAUCUCAAAGACCCGGACUUUCUUGACGCC
GCACUUGACUUCAACUACCUAGACCUCAGCGCACUACUACGUAACAGCUUUCACCGUUACGC
CGUGGAUGUACUCAAGAGCGGUCGAUGUCAGAUGCUGGACCGCCGCACGGUAGAAAUGGCCU
UCGCCUACGCAUUAGCACUGUUCGCAGCAGCCCGACAAGAAGAGGCCGGCGCCCAAGUCUCC
GUCCCACGGGCCCUAGACCGCCAGGCCGCACUCUUACAAAUACAAGAAUUUAUGAUCACCUG
CCUCUCACAAACACCACCACGCACCACGUUGCUGCUGUAUCCCACGGCCGUGGACCUGGCCA
AACGAGCCCUUUGGACACCGAAUCAGAUCACCGACAUCACCAGCCUCGUACGCCUGGUCUAC
AUACUCUCUAAACAGAAUCAGCAACAUCUCAUCCCCCAAUGGGCACUACGACAGAUCGCCGA
CUUUGCCCUAAAACUACACAAAACGCACCUGGCCUCUUUUCUUUCAGCCUUCGCACGCCAAG
AACUCUACCUCAUGGGCAGCCUCGUCCACUCCAUGCUGGUACAUACGACGGAGAGACGCGAA
AUCUUCAUCGUAGAAACGGGCCUCUGUUCAUUGGCCGAGCUAUCACACUUUACGCAGUUGUU
AGCUCAUCCACACCACGAAUACCUCAGCGACCUGUACACACCCUGUUCCAGUAGCGGGCGAC
GCGAUCACUCGCUCGAACGCCUCACGCGUCUCUUCCCCGAUGCCACCGUCCCCGCUACCGUU
CCCGCCGCCCUCUCCAUCCUAUCUACCAUGCAACCAAGCACGCUGGAAACCUUCCCCGACCU
GUUUUGCUUGCCGCUCGGCGAAUCCUUCUCCGCGCUGACCGUCUCCGAACACGUCAGUUAUA
UCGUAACAAACCAGUACCUGAUCAAAGGUAUCUCCUACCCUGUCUCCACCACCGUCGUAGGC
CAGAGCCUCAUCAUCACCCAGACGGACAGUCAAACUAAAUGCGAACUGACGCGCAACAUGCA
UACCACACACAGCAUCACAGUGGCGCUCAACAUUUCGCUAGAAAACUGCGCCUUUUGCCAAA
GCGCCCUGCUAGAAUACGACGACACGCAAGGCGUCAUCAACAUCAUGUACAUGCACGACUCG
GACGACGUCCUUUUCGCCCUGGAUCCCUACAACGAAGUGGUGGUCUCAUCUCCGCGAACUCA
CUACCUCAUGCUUUUGAAAAACGGUACGGUACUAGAAGUAACUGACGUCGUCGUGGACGCCA
CCGACUGAUAAUAGGCUGGAGCCUCGGUGGCCAUGCUUCUUGCCCCUUGGGCCUCCCCCCAG
CCCCUCCUCCCCUUCCUGCACCCGUACCCCCGUGGUCUUUGAAUAAAGUCUGAGUGGGCGGC

-continued hCMV-gHtruncFLAG, glycoprotein H Ectodomain (SEQ ID NO: 8)

TCAAGCTTTTGGACCCTCGTAGAGAAGCTAATACGACTCACTATAGGGAAATAAGAGAGAAA
AGAAGAGTAAGAAGAAATATAAGAGCCACCATGCGGCCAGGCCTCCCCTCCTACCTCATCAT
CCTCGCCGTCTGTCTCTTCAGCCACCTACTTTCGTCACGATATGGCGCAGAAGCCGTATCCG
AACCGCTGGACAAAGCGTTTCACCTACTGCTCAACACCTACGGGAGACCCATCCGCTTCCTG
CGTGAAAATACCACCCAGTGTACCTACAACAGCAGCCTCCGTAACAGCACGGTCGTCAGGGA
AAACGCCATCAGTTTCAACTTTTTCCAAAGCTATAATCAATACTATGTATTCCATATGCCTC
GATGTCTTTTTGCGGGTCCTCTGGCGGAGCAGTTTCTGAACCAGGTAGATCTGACCGAAACC
CTGGAAAGATACCAACAGAGACTTAACACTTACGCGCTGGTATCCAAAGACCTGGCCAGCTA
CCGATCTTTTTCGCAGCAGCTAAAGGCACAAGACAGCCTAGGTGAACAGCCCACCACTGTGC
CACCGCCCATTGACCTGTCAATACCTCACGTTTGGATGCCACCGCAAACCACTCCACACGGC
TGGACAGAATCACATACCACCTCAGGACTACACCGACCACACTTTAACCAGACCTGTATCCT
CTTTGATGGACACGATCTACTATTCAGCACCGTCACACCTTGTTTGCACCAAGGCTTTTACC
TCATCGACGAACTACGTTACGTTAAAATAACACTGACCGAGGACTTCTTCGTAGTTACGGTG
TCCATAGACGACGACACACCCATGCTGCTTATCTTCGGCCATCTTCCACGCGTACTTTTCAA
AGCGCCCTATCAACGCGACAACTTTATACTACGACAAACTGAAAAACACGAGCTCCTGGTGC
TAGTTAAGAAAGATCAACTGAACCGTCACTCTTATCTCAAAGACCCGGACTTTCTTGACGCC
GCACTTGACTTCAACTACCTAGACCTCAGCGCACTACTACGTAACAGCTTTCACCGTTACGC
CGTGGATGTACTCAAGAGCGGTCGATGTCAGATGCTGGACCGCCGCACGGTAGAAATGGCCT
TCGCCTACGCATTAGCACTGTTCGCAGCAGCCCGACAAGAAGAGGCCGGCGCCCAAGTCTCC
GTCCCACGGGCCCTAGACCGCCAGGCCGCACTCTTACAAATACAAGAATTTATGATCACCTG
CCTCTCACAAACACCACCACGCACCACGTTGCTGCTGTATCCCACGGCCGTGGACCTGGCCA
AACGAGCCCTTTGGACACCGAATCAGATCACCGACATCACCAGCCTCGTACGCCTGGTCTAC
ATACTCTCTAAACAGAATCAGCAACATCTCATCCCCCAATGGGCACTACGACAGATCGCCGA
CTTTGCCCTAAAACTACACAAAACGCACCTGGCCTCTTTTCTTTCAGCCTTCGCACGCCAAG
AACTCTACCTCATGGGCAGCCTCGTCCACTCCATGCTGGTACATACGACGGAGAGACGCGAA
ATCTTCATCGTAGAAACGGGCCTCTGTTCATTGGCCGAGCTATCACACTTTACGCAGTTGTT
AGCTCATCCACACCACGAATACCTCAGCGACCTGTACACACCCTGTTCCAGTAGCGGGCGAC
GCGATCACTCGCTCGAACGCCTCACGCGTCTCTTCCCCGATGCCACCGTCCCCGCTACCGTT
CCCGCCGCCCTCTCCATCCTATCTACCATGCAACCAAGCACGCTGGAAACCTTCCCCGACCT
GTTTTGCTTGCCGCTCGGCGAATCCTTCTCCGCGCTGACCGTCTCCGAACACGTCAGTTATA
TCGTAACAAACCAGTACCTGATCAAAGGTATCTCCTACCCTGTCTCCACCACCGTCGTAGGC
CAGAGCCTCATCATCACCCAGACGGACAGTCAAACTAAATGCGAACTGACGCGCAACATGCA
TACCACACACAGCATCACAGTGGCGCTCAACATTTCGCTAGAAAACTGCGCCTTTTGCCAAA
GCGCCCTGCTAGAATACGACGACACGCAAGGCGTCATCAACATCATGTACATGCACGACTCG
GACGACGTCCTTTTCGCCCTGGATCCCTACAACGAAGTGGTGGTCTCATCTCCGCGAACTCA
CTACCTCATGCTTTTGAAAAACGGTACGGTACTAGAAGTAACTGACGTCGTCGTGGACGCCA
CCGACGATTACAAGGACGATGACGATAAGTGATGATAATAGGCTGGAGCCTCGGTGGCCATG
CTTCTTGCCCCTTGGGCCTCCCCCCAGCCCCTCCTCCCCTTCCTGCACCCGTACCCCCGTGG
TCTTTGAATAAAGTCTGAGTGGGCGGC hCMV-gHtruncFLAG, glycoprotein H Ectodomain (SEQ ID NO: 86)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCCAGGCCUCCCCUCCUACCUCAUCAU
CCUCGCCGUCUGUCUCUUCAGCCACCUACUUUCGUCACGAUAUGGCGCAGAAGCCGUAUCCG
AACCGCUGGACAAAGCGUUUCACCUACUGCUCAACACCUACGGGAGACCCAUCCGCUUCCUG
CGUGAAAAUACCACCCAGUGUACCUACAACAGCAGCCUCCGUAACAGCACGGUCGUCAGGGA
AAACGCCAUCAGUUUCAACUUUUUCCAAAGCUAUAAUCAAUACUAUGUAUUCCAUAUGCCUC
GAUGUCUUUUUGCGGGUCCUCUGGCGGAGCAGUUUCUGAACCAGGUAGAUCUGACCGAAACC
CUGGAAAGAUACCAACAGAGACUUAACACUUACGCGCUGGUAUCCAAAGACCUGGCCAGCUA
CCGAUCUUUUUCGCAGCAGCUAAAGGCACAAGACAGCCUAGGUGAACAGCCCACCACUGUGC
CACCGCCCAUUGACCUGUCAAUACCUCACGUUUGGAUGCCACCGCAAACCACUCCACACGGC
UGGACAGAAUCACAUACCACCUCAGGACUACACCGACCACACUUUAACCAGACCUGUAUCCU
CUUUGAUGGACACGAUCUACUAUUCAGCACCGUCACACCUUGUUUGCACCAAGGCUUUUACC
UCAUCGACGAACUACGUUACGUUAAAAUAACACUGACCGAGGACUUCUUCGUAGUUACGGUG
UCCAUAGACGACGACACACCCAUGCUGCUUAUCUUCGGCCAUCUUCCACGCGUACUUUUCAA
AGCGCCCUAUCAACGCGACAACUUUAUACUACGACAAACUGAAAAACACGAGCUCCUGGUGC
UAGUUAAGAAAGAUCAACUGAACCGUCACUCUUAUCUCAAAGACCCGGACUUUCUUGACGCC
GCACUUGACUUCAACUACCUAGACCUCAGCGCACUACUACGUAACAGCUUUCACCGUUACGC
CGUGGAUGUACUCAAGAGCGGUCGAUGUCAGAUGCUGGACCGCCGCACGGUAGAAAUGGCCU
UCGCCUACGCAUUAGCACUGUUCGCAGCAGCCCGACAAGAAGAGGCCGGCGCCCAAGUCUCC
GUCCCACGGGCCCUAGACCGCCAGGCCGCACUCUUACAAAUACAAGAAUUUAUGAUCACCUG
CCUCUCACAAACACCACCACGCACCACGUUGCUGCUGUAUCCCACGGCCGUGGACCUGGCCA
AACGAGCCCUUUGGACACCGAAUCAGAUCACCGACAUCACCAGCCUCGUACGCCUGGUCUAC
AUACUCUCUAAACAGAAUCAGCAACAUCUCAUCCCCCAAUGGGCACUACGACAGAUCGCCGA
CUUUGCCCUAAAACUACACAAAACGCACCUGGCCUCUUUUCUUUCAGCCUUCGCACGCCAAG
AACUCUACCUCAUGGGCAGCCUCGUCCACUCCAUGCUGGUACAUACGACGGAGAGACGCGAA
AUCUUCAUCGUAGAAACGGGCCUCUGUUCAUUGGCCGAGCUAUCACACUUUACGCAGUUGUU
AGCUCAUCCACACCACGAAUACCUCAGCGACCUGUACACACCCUGUUCCAGUAGCGGGCGAC
GCGAUCACUCGCUCGAACGCCUCACGCGUCUCUUCCCCGAUGCCACCGUCCCCGCUACCGUU
CCCGCCGCCCUCUCCAUCCUAUCUACCAUGCAACCAAGCACGCUGGAAACCUUCCCCGACCU
GUUUUGCUUGCCGCUCGGCGAAUCCUUCUCCGCGCUGACCGUCUCCGAACACGUCAGUUAUA
UCGUAACAAACCAGUACCUGAUCAAAGGUAUCUCCUACCCUGUCUCCACCACCGUCGUAGGC
CAGAGCCUCAUCAUCACCCAGACGGACAGUCAAACUAAAUGCGAACUGACGCGCAACAUGCA
UACCACACACAGCAUCACAGUGGCGCUCAACAUUUCGCUAGAAAACUGCGCCUUUUGCCAAA
GCGCCCUGCUAGAAUACGACGACACGCAAGGCGUCAUCAACAUCAUGUACAUGCACGACUCG
GACGACGUCCUUUUCGCCCUGGAUCCCUACAACGAAGUGGUGGUCUCAUCUCCGCGAACUCA
CUACCUCAUGCUUUUGAAAAACGGUACGGUACUAGAAGUAACUGACGUCGUCGUGGACGCCA
CCGACGAUUACAAGGACGAUGACGAUAAGUGAUGAUAAUAGGCUGGAGCCUCGGUGGCCAUG

-continued

CUUCUUGCCCCUUGGGCCUCCCCCCAGCCCCUCCUCCCCUUCCUGCACCCGUACCCCCGUGG
UCUUUGAAUAAAGUCUGAGUGGGCGGC hCMVgHtrunc6XHis, glycoprotein H Ectodomain-6XHis tag
(SEQ ID NO: 9)

TCAAGCTTTTGGACCCTCGTACAGAAGCTAATACGACTCACTATAGGGAAATAAGAGAGAAA
AGAAGAGTAAGAAGAAATATAAGAGCCACCATGCGGCCAGGCCTCCCCTCCTACCTCATCAT
CCTCGCCGTCTGTCTCTTCAGCCACCTACTTTCGTCACGATATGGCGCAGAAGCCGTATCCG
AACCGCTGGACAAAGCGTTTCACCTACTGCTCAACACCTACGGGAGACCCATCCGCTTCCTG
CGTGAAAATACCACCCAGTGTACCTACAACAGCAGCCTCCGTAACAGCACGGTCGTCAGGGA
AAACGCCATCAGTTTCAACTTTTTCCAAAGCTATAATCAATACTATGTATTCCATATGCCTC
GATGTCTTTTTGCGGGTCCTCTGGCGGAGCAGTTTCTGAACCAGGTAGATCTGACCGAAACC
CTGGAAAGATACCAACAGAGACTTAACACTTACGCGCTGGTATCCAAAGACCTGGCCAGCTA
CCGATCTTTTTCGCAGCAGCTAAAGGCACAAGACAGCCTAGGTGAACAGCCCACCACTGTGC
CACCGCCCATTGACCTGTCAATACCTCACGTTTGGATGCCACCGCAAACCACTCCACACGGC
TGGACAGAATCACATACCACCTCAGGACTACACCGACCACACTTTAACCAGACCTGTATCCT
CTTTGATGGACACGATCTACTATTCAGCACCGTCACACCTTGTTTGCACCAAGGCTTTTACC
TCATCGACGAACTACGTTACGTTAAAATAACACTGACCGAGGACTTCTTCGTAGTTACGGTG
TCCATAGACGACGACACACCCATGCTGCTTATCTTCGGCCATCTTCCACGCGTACTTTTCAA
AGCGCCCTATCAACGCGACAACTTTATACTACGACAAACTGAAAAACACGAGCTCCTGGTGC
TAGTTAAGAAAGATCAACTGAACCGTCACTCTTATCTCAAAGACCCGGACTTTCTTGACGCC
GCACTTGACTTCAACTACCTAGACCTCAGCGCACTACTACGTAACAGCTTTCACCGTTACGC
CGTGGATGTACTCAAGAGCGGTCGATGTCAGATGCTGGACCGCCGCACGGTAGAAATGGCCT
TCGCCTACGCATTAGCACTGTTCGCAGCAGCCCGACAAGAAGAGGCCGGCGCCCAAGTCTCC
GTCCCACGGGCCCTAGACCGCCAGGCCGCACTCTTACAAATACAAGAATTTATGATCACCTG
CCTCTCACAAACACCACCACGCACCACGTTGCTGCTGTATCCCACGGCCGTGGACCTGGCCA
AACGAGCCCTTTGGACACCGAATCAGATCACCGACATCACCAGCCTCGTACGCCTGGTCTAC
ATACTCTCTAAACAGAATCAGCAACATCTCATCCCCCAATGGGCACTACGACAGATCGCCGA
CTTTGCCCTAAAACTACACAAAACGCACCTGGCCTCTTTTCTTTCAGCCTTCGCACGCCAAG
AACTCTACCTCATGGGCAGCCTCGTCCACTCCATGCTGGTACATACGACGGAGAGACGCGAA
ATCTTCATCGTAGAAACGGGCCTCTGTTCATTGGCCGAGCTATCACACTTTACGCAGTTGTT
AGCTCATCCACACCACGAATACCTCAGCGACCTGTACACACCCTGTTCCAGTAGCGGGCGAC
GCGATCACTCGCTCGAACGCCTCACGCGTCTCTTCCCCGATGCCACCGTCCCCGCTACCGTT
CCCGCCGCCCTCTCCATCCTATCTACCATGCAACCAAGCACGCTGGAAACCTTCCCCGACCT
GTTTTGCTTGCCGCTCGGCGAATCCTTCTCCGCGCTGACCGTCTCCGAACACGTCAGTTATA
TCGTAACAAACCAGTACCTGATCAAAGGTATCTCCTACCCTGTCTCCACCACCGTCGTAGGC
CAGAGCCTCATCATCACCCAGACGGACAGTCAAACTAAATGCGAACTGACGCGCAACATGCA
TACCACACACAGCATCACAGTGGCGCTCAACATTTCGCTAGAAAACTGCGCCTTTTGCCAAA
GCGCCCTGCTAGAATACGACGACACGCAAGGCGTCATCAACATCATGTACATGCACGACTCG
GACGACGTCCTTTTCGCCCTGGATCCCTACAACGAAGTGGTGGTCTCATCTCCGCGAACTCA
CTACCTCATGCTTTTGAAAAACGGTACGGTACTAGAAGTAACTGACGTCGTCGTGGACGCCA
CCGACCACCATCACCACCATCACTGATGATAATAGGCTGGAGCCTCGGTGGCCATGCTTCTT
GCCCCTTGGGCCTCCCCCCAGCCCCTCCTCCCCTTCCTGCACCCGTACCCCCGTGGTCTTTG
AATAAAGTCTGAGTGGGCGGC hCMVgHtrunc6XHis, glycoprotein H Ectodomain-6XHis tag
(SEQ ID NO: 87)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCCAGGCCUCCCCUCCUACCUCAUCAU
CCUCGCCGUCUGUCUCUUCAGCCACCUACUUUCGUCACGAUAUGGCGCAGAAGCCGUAUCCG
AACCGCUGGACAAAGCGUUUCACCUACUGCUCAACACCUACGGGAGACCCAUCCGCUUCCUG
CGUGAAAAUACCACCCAGUGUACCUACAACAGCAGCCUCCGUAACAGCACGGUCGUCAGGGA
AAACGCCAUCAGUUUCAACUUUUUCCAAAGCUAUAAUCAAUACUAUGUAUUCCAUAUGCCUC
GAUGUCUUUUUGCGGGUCCUCUGGCGGAGCAGUUUCUGAACCAGGUAGAUCUGACCGAAACC
CUGGAAAGAUACCAACAGAGACUUAACACUUACGCGCUGGUAUCCAAAGACCUGGCCAGCUA
CCGAUCUUUUUCGCAGCAGCUAAAGGCACAAGACAGCCUAGGUGAACAGCCCACCACUGUGC
CACCGCCCAUUGACCUGUCAAUACCUCACGUUUGGAUGCCACCGCAAACCACUCCACACGGC
UGGACAGAAUCACAUACCACCUCAGGACUACACCGACCACACUUUAACCAGACCUGUAUCCU
CUUUGAUGGACACGAUCUACUAUUCAGCACCGUCACACCUUGUUUGCACCAAGGCUUUUACC
UCAUCGACGAACUACGUUACGUUAAAAUAACACUGACCGAGGACUUCUUCGUAGUUACGGUG
UCCAUAGACGACGACACACCCAUGCUGCUUAUCUUCGGCCAUCUUCCACGCGUACUUUUCAA
AGCGCCCUAUCAACGCGACAACUUUAUACUACGACAAACUGAAAAACACGAGCUCCUGGUGC
UAGUUAAGAAAGAUCAACUGAACCGUCACUCUUAUCUCAAAGACCCGGACUUUCUUGACGCC
GCACUUGACUUCAACUACCUAGACCUCAGCGCACUACUACGUAACAGCUUUCACCGUUACGC
CGUGGAUGUACUCAAGAGCGGUCGAUGUCAGAUGCUGGACCGCCGCACGGUAGAAAUGGCCU
UCGCCUACGCAUUAGCACUGUUCGCAGCAGCCCGACAAGAAGAGGCCGGCGCCCAAGUCUCC
GUCCCACGGGCCCUAGACCGCCAGGCCGCACUCUUACAAAUACAAGAAUUUAUGAUCACCUG
CCUCUCACAAACACCACCACGCACCACGUUGCUGCUGUAUCCCACGGCCGUGGACCUGGCCA
AACGAGCCCUUUGGACACCGAAUCAGAUCACCGACAUCACCAGCCUCGUACGCCUGGUCUAC
AUACUCUCUAAACAGAAUCAGCAACAUCUCAUCCCCCAAUGGGCACUACGACAGAUCGCCGA
CUUUGCCCUAAAACUACACAAAACGCACCUGGCCUCUUUUCUUUCAGCCUUCGCACGCCAAG
AACUCUACCUCAUGGGCAGCCUCGUCCACUCCAUGCUGGUACAUACGACGGAGAGACGCGAA
AUCUUCAUCGUAGAAACGGGCCUCUGUUCAUUGGCCGAGCUAUCACACUUUACGCAGUUGUU
AGCUCAUCCACACCACGAAUACCUCAGCGACCUGUACACACCCUGUUCCAGUAGCGGGCGAC
GCGAUCACUCGCUCGAACGCCUCACGCGUCUCUUCCCCGAUGCCACCGUCCCCGCUACCGUU
CCCGCCGCCCUCUCCAUCCUAUCUACCAUGCAACCAAGCACGCUGGAAACCUUCCCCGACCU
GUUUUGCUUGCCGCUCGGCGAAUCCUUCUCCGCGCUGACCGUCUCCGAACACGUCAGUUAUA
UCGUAACAAACCAGUACCUGAUCAAAGGUAUCUCCUACCCUGUCUCCACCACCGUCGUAGGC
CAGAGCCUCAUCAUCACCCAGACGGACAGUCAAACUAAAUGCGAACUGACGCGCAACAUGCA
UACCACACACAGCAUCACAGUGGCGCUCAACAUUUCGCUAGAAAACUGCGCCUUUUGCCAAA
GCGCCCUGCUAGAAUACGACGACACGCAAGGCGUCAUCAACAUCAUGUACAUGCACGACUCG

-continued

GACGACGUCCUUUUCGCCCUGGAUCCCUACAACGAAGUGGUGGUCUCAUCUCCGCGAACUCA
CUACCUCAUGCUUUUGAAAAACGGUACGGUACUAGAAGUAACUGACGUCGUCGUGGACGCCA
CCGACCACCAUCACCACCAUCACUGAUGAUAAUAGGCUGGAGCCUCGGUGGCCAUGCUUCUU
GCCCCUUGGGCCUCCCCCCAGCCCCUCCUCCCCUUCCUGCACCCGUACCCCCGUGGUCUUUG
AAUAAAGUCUGAGUGGGCGGC hCMV TrgB, glycoprotein B (ectodomain)

(SEQ ID NO: 10)

TCAAGCTTTTGGACCCTCGTACAGAAGCTAATACGACTCACTATAGGGAAATAAGAGAGAAA
AGAAGAGTAAGAAGAAATATAAGAGCCACCATGGAATCCAGGATCTGGTGCCTGGTAGTCTG
CGTTAACTTGTGTATCGTCTGTCTGGGTGCTGCGGTTTCCTCATCTTCTACTCGTGGAACTT
CTGCTACTCACAGTCACCATTCCTCTCATACGACGTCTGCTGCTCACTCTCGATCCGGTTCA
GTCTCTCAACGCGTAACTTCTTCCCAAACGGTCAGCCATGGTGTTAACGAGACCATCTACAA
CACTACCCTCAAGTACGGAGATGTGGTGGGGGTCAATACCACCAAGTACCCCTATCGCGTGT
GTTCTATGGCCCAGGGTACGGATCTTATTCGCTTTGAACGTAATATCGTCTGCACCTCGATG
AAGCCCATCAATGAAGACCTGGACGAGGGCATCATGGTGGTCTACAAACGCAACATCGTCGC
GCACACCTTTAAGGTACGAGTCTACCAGAAGGTTTTGACGTTTCGTCGTAGCTACGCTTACA
TCCACACCACTTATCTGCTGGGCAGCAACACGGAATACGTGGCGCCTCCTATGTGGGAGATT
CATCATATCAACAGCCACAGTCAGTGCTACAGTTCCTACAGCCGCGTTATAGCAGGCACGGT
TTTCGTGGCTTATCATAGGGACAGCTATGAAAACAAAACCATGCAATTAATGCCCGACGATT
ATTCCAACACCCACAGTACCCGTTACGTGACGGTCAAGGATCAATGGCACAGCCGCGGCAGC
ACCTGGCTCTATCGTGAGACCTGTAATCTGAATTGTATGGTGACCATCACTACTGCGCGCTC
CAAATATCCTTATCATTTTTCGCCACTTCCACGGGTGACGTGGTTGACATTTCTCCTTTCT
ACAACGGAACCAATCGCAATGCCAGCTACTTTGGAGAAAACGCCGACAAGTTTTTCATTTTT
CCGAACTACACTATCGTCTCCGACTTTGGAAGACCGAATTCTGCGTTAGAGACCCACAGGTT
GGTGGCTTTTCTTGAACGTGCGGACTCGGTGATCTCCTGGGATATACAGGACGAAAAGAATG
TCACTTGTCAACTCACTTTCTGGGAAGCCTCGGAACGCACCATTCGTTCCGAAGCCGAGGAC
TCGTATCACTTTTCTTCTGCCAAAATGACCGCCACTTTCTTATCTAAGAAGCAAGAGGTGAA
CATGTCCGACTCTGCGCTGGACTGCGTACGTGATGAGGCTATAAATAAGTTACAGCAGATTT
TCAATACTTCATACAATCAAACATATGAAAAATATGGAAACGTGTCCGTCTTTGAAACCACT
GGTGGTTTGGTAGTGTTCTGGCAAGGTATCAAGCAAAAATCTCTGGTGGAACTCGAACGTTT
GGCCAACCGCTCCAGTCTGAATCTTACTCATAATAGAACCAAAAGAAGTACAGATGGCAACA
ATGCAACTCATTTATCCAACATGGAATCGGTGCACAATCTGGTCTACGCCCAGCTGCAGTTC
ACCTATGACACGTTGCGCGGTTACATCAACCGGGCGCTGGCGCAAATCGCAGAAGCCTGGTG
TGTGGATCAACGGCGCACCCTAGAGGTCTTCAAGGAACTCAGCAAGATCAACCCGTCAGCCA
TTCTCTCGGCCATTTACAACAAACCGATTGCCGCGCGTTTCATGGGTGATGTCTTGGGCCTG
GCCAGCTGCGTGACCATCAACCAAACCAGCGTCAAGGTGCTGCGTGATATGAACGTGAAGGA
GTCGCCAGGACGCTGCTACTCACGACCCGTGGTCATCTTTAATTTCGCCAACAGCTCGTACG
TGCAGTACGGTCAACTGGGCGAGGACAACGAAATCCTGTTGGGCAACCACCGCACTGAGGAA
TGTCAGCTTCCCAGCCTCAAGATCTTCATCGCCGGGAACTCGGCCTACGAGTACGTGGACTA
CCTCTTCAAACGCATGATTGACCTCAGCAGTATCTCCACCGTCGACAGCATGATCGCCCTGG
ATATCGACCCGCTGGAAAATACCGACTTCAGGGTACTGGAACTTTACTCGCAGAAAGAGCTG
CGTTCCAGCAACGTTTTTGACCTCGAAGAGATCATGCGCGAATTCAACTCGTACAAGCAGTG
ATAATAGGCTGGAGCCTCGGTGGCCATGCTTCTTGCCCCTTGGGCCTCCCCCCAGCCCCTCC
TCCCCTTCCTGCACCCGTACCCCCGTGGTCTTTGAATAAAGTCTGAGTGGGCGGC hCMV TrgB, glycoprotein B (ectodomain)

(SEQ ID NO: 88)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGGAAUCCAGGAUCUGGUGCCUGGUAGUCUG
CGUUAACUUGUGUAUCGUCUGUCUGGGUGCUGCGGUUUCCUCAUCUUCUACUCGUGGAACUU
CUGCUACUCACAGUCACCAUUCCUCUCAUACGACGUCUGCUGCUCACUCUCGAUCCGGUUCA
GUCUCUCAACGCGUAACUUCUUCCCAAACGGUCAGCCAUGGUGUUAACGAGACCAUCUACAA
CACUACCCUCAAGUACGGAGAUGUGGUGGGGGUCAAUACCACCAAGUACCCCUAUCGCGUGU
GUUCUAUGGCCCAGGGUACGGAUCUUAUUCGCUUUGAACGUAAUAUCGUCUGCACCUCGAUG
AAGCCCAUCAAUGAAGACCUGGACGAGGGCAUCAUGGUGGUCUACAAACGCAACAUCGUCGC
GCACACCUUUAAGGUACGAGUCUACCAGAAGGUUUUGACGUUUCGUCGUAGCUACGCUUACA
UCCACACCACUUAUCUGCUGGGCAGCAACACGGAAUACGUGGCGCCUCCUAUGUGGGAGAUU
CAUCAUAUCAACAGCCACAGUCAGUGCUACAGUUCCUACAGCCGCGUUAUAGCAGGCACGGU
UUUCGUGGCUUAUCAUAGGGACAGCUAUGAAAACAAAACCAUGCAAUUAAUGCCCGACGAUU
AUUCCAACACCCACAGUACCCGUUACGUGACGGUCAAGGAUCAAUGGCACAGCCGCGGCAGC
ACCUGGCUCUAUCGUGAGACCUGUAAUCUGAAUUGUAUGGUGACCAUCACUACUGCGCGCUC
CAAAUAUCCUUAUCAUUUUUCGCCACUUCCACGGGUGACGUGGUUGACAUUUCUCCUUUCU
ACAACGGAACCAAUCGCAAUGCCAGCUACUUUGGAGAAAACGCCGACAAGUUUUUCAUUUUU
CCGAACUACACUAUCGUCUCCGACUUUGGAAGACCGAAUUCUGCGUUAGAGACCCACAGGUU
GGUGGCUUUUCUUGAACGUGCGGACUCGGUGAUCUCCUGGGAUAUACAGGACGAAAAGAAUG
UCACUUGUCAACUCACUUUCUGGGAAGCCUCGGAACGCACCAUUCGUUCCGAAGCCGAGGAC
UCGUAUCACUUUUCUUCUGCCAAAAUGACCGCCACUUUCUUAUCUAAGAAGCAAGAGGUGAA
CAUGUCCGACUCUGCGCUGGACUGCGUACGUGAUGAGGCUAUAAAUAAGUUACAGCAGAUUU
UCAAUACUUCAUACAAUCAAACAUAUGAAAAAUAUGGAAACGUGUCCGUCUUUGAAACCACU
GGUGGUUUGGUAGUGUUCUGGCAAGGUAUCAAGCAAAAAUCUCUGGUGGAACUCGAACGUUU
GGCCAACCGCUCCAGUCUGAAUCUUACUCAUAAUAGAACCAAAAGAAGUACAGAUGGCAACA
AUGCAACUCAUUUAUCCAACAUGGAAUCGGUGCACAAUCUGGUCUACGCCCAGCUGCAGUUC
ACCUAUGACACGUUGCGCGGUUACAUCAACCGGGCGCUGGCGCAAAUCGCAGAAGCCUGGUG
UGUGGAUCAACGGCGCACCCUAGAGGUCUUCAAGGAACUCAGCAAGAUCAACCCGUCAGCCA
UUCUCUCGGCCAUUUACAACAAACCGAUUGCCGCGCGUUUCAUGGGUGAUGUCUUGGGCCUG
GCCAGCUGCGUGACCAUCAACCAAACCAGCGUCAAGGUGCUGCGUGAUAUGAACGUGAAGGA
GUCGCCAGGACGCUGCUACUCACGACCCGUGGUCAUCUUUAAUUUCGCCAACAGCUCGUACG
UGCAGUACGGUCAACUGGGCGAGGACAACGAAAUCCUGUUGGGCAACCACCGCACUGAGGAA
UGUCAGCUUCCCAGCCUCAAGAUCUUCAUCGCCGGGAACUCGGCCUACGAGUACGUGGACUA
CCUCUUCAAACGCAUGAUUGACCUCAGCAGUAUCUCCACCGUCGACAGCAUGAUCGCCCUGG

-continued

AUAUCGACCCGCUGGAAAAUACCGACUUCAGGGUACUGGAACUUUACUCGCAGAAAGAGCUG
CGUUCCAGCAACGUUUUUGACCUCGAAGAGAUCAUGCGCGAAUUCAACUCGUACAAGCAGUG
AUAAUAGGCUGGAGCCUCGGUGGCCAUGCUUCUUGCCCCUUGGGCCUCCCCCCAGCCCCUCC
UCCCCUUCCUGCACCCGUACCCCCGUGGUCUUUGAAUAAAGUCUGAGUGGGCGGC hCMV TrgBFLAG, hCMV glycoproteinB ectodomain-FLAG (SEQ ID NO: 11)

TCAAGCTTTTGGACCCTCGTACAGAAGCTAATACGACTCACTATAGGGAAATAAGAGAGAAA
AGAAGAGTAAGAAGAAATATAAGAGCCACCATGGAATCCAGGATCTGGTGCCTGGTAGTCTG
CGTTAACTTGTGTATCGTCTGTCTGGGTGCTGCGGTTTCCTCATCTTCTACTCGTGGAACTT
CTGCTACTCACAGTCACCATTCCTCTCATACGACGTCTGCTGCTCACTCTCGATCCGGTTCA
GTCTCTCAACGCGTAACTTCTTCCCAAACGGTCAGCCATGGTGTTAACGAGACCATCTACAA
CACTACCCTCAAGTACGGAGATGTGGTGGGGGTCAATACCACCAAGTACCCCTATCGCGTGT
GTTCTATGGCCCAGGGTACGGATCTTATTCGCTTTGAACGTAATATCGTCTGCACCTCGATG
AAGCCCATCAATGAAGACCTGGACGAGGGCATCATGGTGGTCTACAAACGCAACATCGTCGC
GCACACCTTTAAGGTACGAGTCTACCAGAAGGTTTTGACGTTTCGTCGTAGCTACGCTTACA
TCCACACCACTTATCTGCTGGGCAGCAACACGGAATACGTGGCGCCTCCTATGTGGGAGATT
CATCATATCAACAGCCACAGTCAGTGCTACAGTTCCTACAGCCGCGTTATAGCAGGCACGGT
TTTCGTGGCTTATCATAGGGACAGCTATGAAAACAAAACCATGCAATTAATGCCCGACGATT
ATTCCAACACCCACAGTACCCGTTACGTGACGGTCAAGGATCAATGGCACAGCCGCGGCAGC
ACCTGGCTCTATCGTGAGACCTGTAATCTGAATTGTATGGTGACCATCACTACTGCGCGCTC
CAAATATCCTTATCATTTTTTCGCCACTTCCACGGGTGACGTGGTTGACATTTCTCCTTTCT
ACAACGGAACCAATCGCAATGCCAGCTACTTTGGAGAAAACGCCGACAAGTTTTTCATTTTT
CCGAACTACACTATCGTCTCCGACTTTGGAAGACCGAATTCTGCGTTAGAGACCCACAGGTT
GGTGGCTTTTCTTGAACGTGCGGACTCGGTGATCTCCTGGGATATACAGGACGAAAAGAATG
TCACTTGTCAACTCACTTTCTGGGAAGCCTCGGAACGCACCATTCGTTCCGAAGCCGAGGAC
TCGTATCACTTTTCTTCTGCCAAAATGACCGCCACTTTCTTATCTAAGAAGCAAGAGGTGAA
CATGTCCGACTCTGCGCTGGACTGCGTACGTGATGAGGCTATAAATAAGTTACAGCAGATTT
TCAATACTTCATACAATCAAACATATGAAAAATATGGAAACGTGTCCGTCTTTGAAACCACT
GGTGGTTTGGTAGTGTTCTGGCAAGGTATCAAGCAAAAATCTCTGGTGGAACTCGAACGTTT
GGCCAACCGCTCCAGTCTGAATCTTACTCATAATAGAACCAAAAGAAGTACAGATGGCAACA
ATGCAACTCATTTATCCAACATGGAATCGGTGCACAATCTGGTCTACGCCCAGCTGCAGTTC
ACCTATGACACGTTGCGCGGTTACATCAACCGGGCGCTGGCGCAAATCGCAGAAGCCTGGTG
TGTGGATCAACGGCGCACCCTAGAGGTCTTCAAGGAACTCAGCAAGATCAACCCGTCAGCCA
TTCTCTCGGCCATTTACAACAAACCGATTGCCGCGCGTTTCATGGGTGATGTCTTGGGCCTG
GCCAGCTGCGTGACCATCAACCAAACCAGCGTCAAGGTGCTGCGTGATATGAACGTGAAGGA
GTCGCCAGGACGCTGCTACTCACGACCCGTGGTCATCTTTAATTTCGCCAACAGCTCGTACG
TGCAGTACGGTCAACTGGGCGAGGACAACGAAATCCTGTTGGGCAACCACCGCACTGAGGAA
TGTCAGCTTCCCAGCCTCAAGATCTTCATCGCCGGGAACTCGGCCTACGAGTACGTGGACTA
CCTCTTCAAACGCATGATTGACCTCAGCAGTATCTCCACCGTCGACAGCATGATCGCCCTGG
ATATCGACCCGCTGGAAAATACCGACTTCAGGGTACTGGAACTTTACTCGCAGAAAGAGCTG
CGTTCCAGCAACGTTTTTGACCTCGAAGAGATCATGCGCGAATTCAACTCGTACAAGCAGGA
TTACAAGGACGATGACGATAAGTGATAATAGGCTGGAGCCTCGGTGGCCATGCTTCTTGCCC
CTTGGGCCTCCCCCCAGCCCCTCCTCCCCTTCCTGCACCCGTACCCCCGTGGTCTTTGAATA
AAGTCTGAGTGGGCGGC hCMV TrgBFLAG, hCMV glycoproteinB ectodomain-FLAG (SEQ ID NO: 89)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGGAAUCCAGGAUCUGGUGCCUGGUAGUCUG
CGUUAACUUGUGUAUCGUCUGUCUGGGUGCUGCGGUUUCCUCAUCUUCUACUCGUGGAACUU
CUGCUACUCACAGUCACCAUUCCUCUCAUACGACGUCUGCUGCUCACUCUCGAUCCGGUUCA
GUCUCUCAACGCGUAACUUCUUCCCAAACGGUCAGCCAUGGUGUUAACGAGACCAUCUACAA
CACUACCCUCAAGUACGGAGAUGUGGUGGGGGUCAAUACCACCAAGUACCCCUAUCGCGUGU
GUUCUAUGGCCCAGGGUACGGAUCUUAUUCGCUUUGAACGUAAUAUCGUCUGCACCUCGAUG
AAGCCCAUCAAUGAAGACCUGGACGAGGGCAUCAUGGUGGUCUACAAACGCAACAUCGUCGC
GCACACCUUUAAGGUACGAGUCUACCAGAAGGUUUUGACGUUUCGUCGUAGCUACGCUUACA
UCCACACCACUUAUCUGCUGGGCAGCAACACGGAAUACGUGGCGCCUCCUAUGUGGGAGAUU
CAUCAUAUCAACAGCCACAGUCAGUGCUACAGUUCCUACAGCCGCGUUAUAGCAGGCACGGU
UUUCGUGGCUUAUCAUAGGGACAGCUAUGAAAACAAAACCAUGCAAUUAAUGCCCGACGAUU
AUUCCAACACCCACAGUACCCGUUACGUGACGGUCAAGGAUCAAUGGCACAGCCGCGGCAGC
ACCUGGCUCUAUCGUGAGACCUGUAAUCUGAAUUGUAUGGUGACCAUCACUACUGCGCGCUC
CAAAUAUCCUUAUCAUUUUUUCGCCACUUCCACGGGUGACGUGGUUGACAUUUCUCCUUUCU
ACAACGGAACCAAUCGCAAUGCCAGCUACUUUGGAGAAAACGCCGACAAGUUUUUCAUUUUU
CCGAACUACACUAUCGUCUCCGACUUUGGAAGACCGAAUUCUGCGUUAGAGACCCACAGGUU
GGUGGCUUUUCUUGAACGUGCGGACUCGGUGAUCUCCUGGGAUAUACAGGACGAAAAGAAUG
UCACUUGUCAACUCACUUUCUGGGAAGCCUCGGAACGCACCAUUCGUUCCGAAGCCGAGGAC
UCGUAUCACUUUUCUUCUGCCAAAAUGACCGCCACUUUCUUAUCUAAGAAGCAAGAGGUGAA
CAUGUCCGACUCUGCGCUGGACUGCGUACGUGAUGAGGCUAUAAAUAAGUUACAGCAGAUUU
UCAAUACUUCAUACAAUCAAACAUAUGAAAAAUAUGGAAACGUGUCCGUCUUUGAAACCACU
GGUGGUUUGGUAGUGUUCUGGCAAGGUAUCAAGCAAAAAUCUCUGGUGGAACUCGAACGUUU
GGCCAACCGCUCCAGUCUGAAUCUUACUCAUAAUAGAACCAAAAGAAGUACAGAUGGCAACA
AUGCAACUCAUUUAUCCAACAUGGAAUCGGUGCACAAUCUGGUCUACGCCCAGCUGCAGUUC
ACCUAUGACACGUUGCGCGGUUACAUCAACCGGGCGCUGGCGCAAAUCGCAGAAGCCUGGUG
UGUGGAUCAACGGCGCACCCUAGAGGUCUUCAAGGAACUCAGCAAGAUCAACCCGUCAGCCA
UUCUCUCGGCCAUUUACAACAAACCGAUUGCCGCGCGUUUCAUGGGUGAUGUCUUGGGCCUG
GCCAGCUGCGUGACCAUCAACCAAACCAGCGUCAAGGUGCUGCGUGAUAUGAACGUGAAGGA
GUCGCCAGGACGCUGCUACUCACGACCCGUGGUCAUCUUUAAUUUCGCCAACAGCUCGUACG
UGCAGUACGGUCAACUGGGCGAGGACAACGAAAUCCUGUUGGGCAACCACCGCACUGAGGAA
UGUCAGCUUCCCAGCCUCAAGAUCUUCAUCGCCGGGAACUCGGCCUACGAGUACGUGGACUA
CCUCUUCAAACGCAUGAUUGACCUCAGCAGUAUCUCCACCGUCGACAGCAUGAUCGCCCUGG

-continued

AUAUCGACCCGCUGGAAAAUACCGACUUCAGGGUACUGGAACUUUACUCGCAGAAAGAGCUG
CGUUCCAGCAACGUUUUUGACCUCGAAGAGAUCAUGCGCGAAUUCAACUCGUACAAGCAGGA
UUACAAGGACGAUGACGAUAAGUGAUAAUAGGCUGGAGCCUCGGUGGCCAUGCUUCUUGCCC
CUUGGGCCUCCCCCCAGCCCCUCCUCCCCUUCCUGCACCCGUACCCCCGUGGUCUUUGAAUA
AAGUCUGAGUGGGCGGC hCMV-TrgB6XHis, hCMV glycoprotein ectodomain-6XHis tag
(SEQ ID NO: 12)

TCAAGCTTTTGGACCCTCGTAGAGAAGCTAATACGACTCACTATAGGGAAATAAGAGAGAAA
AGAAGAGTAAGAAGAAATATAAGAGCCACCATGGAATCCAGGATCTGGTGCCTGGTAGTCTG
CGTTAACTTGTGTATCGTCTGTCTGGGTGCTGCGGTTTCCTCATCTTCTACTCGTGGAACTT
CTGCTACTCACAGTCACCATTCCTCTCATACGACGTCTGCTGCTCACTCTCGATCCGGTTCA
GTCTCTCAACGCGTAACTTCTTCCCAAACGGTCAGCCATGGTGTTAACGAGACCATCTACAA
CACTACCCTCAAGTACGGAGATGTGGTGGGGGTCAATACCACCAAGTACCCCTATCGCGTGT
GTTCTATGGCCCAGGGTACGGATCTTATTCGCTTTGAACGTAATATCGTCTGCACCTCGATG
AAGCCCATCAATGAAGACCTGGACGAGGGCATCATGGTGGTCTACAAACGCAACATCGTCGC
GCACACCTTTAAGGTACGAGTCTACCAGAAGGTTTTGACGTTTCGTCGTAGCTACGCTTACA
TCCACACCACTTATCTGCTGGGCAGCAACACGGAATACGTGGCGCCTCCTATGTGGGAGATT
CATCATATCAACAGCCACAGTCAGTGCTACAGTTCCTACAGCCGCGTTATAGCAGGCACGGT
TTTCGTGGCTTATCATAGGGACAGCTATGAAAACAAAACCATGCAATTAATGCCCGACGATT
ATTCCAACACCCACAGTACCCGTTACGTGACGGTCAAGGATCAATGGCACAGCCGCGGCAGC
ACCTGGCTCTATCGTGAGACCTGTAATCTGAATTGTATGGTGACCATCACTACTGCGCGCTC
CAAATATCCTTATCATTTTTTCGCCACTTCCACGGGTGACGTGGTTGACATTTCTCCTTTCT
ACAACGGAACCAATCGCAATGCCAGCTACTTTGGAGAAAACGCCGACAAGTTTTTCATTTTT
CCGAACTACACTATCGTCTCCGACTTTGGAAGACCGAATTCTGCGTTAGAGACCCACAGGTT
GGTGGCTTTTCTTGAACGTGCGGACTCGGTGATCTCCTGGGATATACAGGACGAAAAGAATG
TCACTTGTCAACTCACTTTCTGGGAAGCCTCGGAACGCACCATTCGTTCCGAAGCCGAGGAC
TCGTATCACTTTTCTTCTGCCAAAATGACCGCCACTTTCTTATCTAAGAAGCAAGAGGTGAA
CATGTCCGACTCTGCGCTGGACTGCGTACGTGATGAGGCTATAAATAAGTTACAGCAGATTT
TCAATACTTCATACAATCAAACATATGAAAAATATGGAAACGTGTCCGTCTTTGAAACCACT
GGTGGTTTGGTAGTGTTCTGGCAAGGTATCAAGCAAAAATCTCTGGTGGAACTCGAACGTTT
GGCCAACCGCTCCAGTCTGAATCTTACTCATAATAGAACCAAAAGAAGTACAGATGGCAACA
ATGCAACTCATTTATCCAACATGGAATCGGTGCACAATCTGGTCTACGCCCAGCTGCAGTTC
ACCTATGACACGTTGCGCGGTTACATCAACCGGGCGCTGGCGCAAATCGCAGAAGCCTGGTG
TGTGGATCAACGGCGCACCCTAGAGGTCTTCAAGGAACTCAGCAAGATCAACCCGTCAGCCA
TTCTCTCGGCCATTTACAACAAACCGATTGCCGCGCGTTTCATGGGTGATGTCTTGGGCCTG
GCCAGCTGCGTGACCATCAACCAAACCAGCGTCAAGGTGCTGCGTGATATGAACGTGAAGGA
GTCGCCAGGACGCTGCTACTCACGACCCGTGGTCATCTTTAATTTCGCCAACAGCTCGTACG
TGCAGTACGGTCAACTGGGCGAGGACAACGAAATCCTGTTGGGCAACCACCGCACTGAGGAA
TGTCAGCTTCCCAGCCTCAAGATCTTCATCGCCGGGAACTCGGCCTACGAGTACGTGGACTA
CCTCTTCAAACGCATGATTGACCTCAGCAGTATCTCCACCGTCGACAGCATGATCGCCCTGG
ATATCGACCCGCTGGAAAATACCGACTTCAGGGTACTGGAACTTTACTCGCAGAAAGAGCTG
CGTTCCAGCAACGTTTTTGACCTCGAAGAGATCATGCGCGAATTCAACTCGTACAAGCAGCA
CCATCACCACCATCACTGATAATAGGCTGGAGCCTCGGTGGCCATGCTTCTTGCCCCTTGGG
CCTCCCCCCAGCCCCTCCTCCCCTTCCTGCACCCGTACCCCCGTGGTCTTTGAATAAAGTCT
GAGTGGGCGGC hCMV-TrgB6XHis, hCMV glycoprotein ectodomain-6XHis tag
(SEQ ID NO: 90)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGGAAUCCAGGAUCUGGUGCCUGGUAGUCUG
CGUUAACUUGUGUAUCGUCUGUCUGGGUGCUGCGGUUUCCUCAUCUUCUACUCGUGGAACUU
CUGCUACUCACAGUCACCAUUCCUCUCAUACGACGUCUGCUGCUCACUCUCGAUCCGGUUCA
GUCUCUCAACGCGUAACUUCUUCCCAAACGGUCAGCCAUGGUGUUAACGAGACCAUCUACAA
CACUACCCUCAAGUACGGAGAUGUGGUGGGGGUCAAUACCACCAAGUACCCCUAUCGCGUGU
GUUCUAUGGCCCAGGGUACGGAUCUUAUUCGCUUUGAACGUAAUAUCGUCUGCACCUCGAUG
AAGCCCAUCAAUGAAGACCUGGACGAGGGCAUCAUGGUGGUCUACAAACGCAACAUCGUCGC
GCACACCUUUAAGGUACGAGUCUACCAGAAGGUUUUGACGUUUCGUCGUAGCUACGCUUACA
UCCACACCACUUAUCUGCUGGGCAGCAACACGGAAUACGUGGCGCCUCCUAUGUGGGAGAUU
CAUCAUAUCAACAGCCACAGUCAGUGCUACAGUUCCUACAGCCGCGUUAUAGCAGGCACGGU
UUUCGUGGCUUAUCAUAGGGACAGCUAUGAAAACAAAACCAUGCAAUUAAUGCCCGACGAUU
AUUCCAACACCCACAGUACCCGUUACGUGACGGUCAAGGAUCAAUGGCACAGCCGCGGCAGC
ACCUGGCUCUAUCGUGAGACCUGUAAUCUGAAUUGUAUGGUGACCAUCACUACUGCGCGCUC
CAAAUAUCCUUAUCAUUUUUUCGCCACUUCCACGGGUGACGUGGUUGACAUUUCUCCUUUCU
ACAACGGAACCAAUCGCAAUGCCAGCUACUUUGGAGAAAACGCCGACAAGUUUUUCAUUUUU
CCGAACUACACUAUCGUCUCCGACUUUGGAAGACCGAAUUCUGCGUUAGAGACCCACAGGUU
GGUGGCUUUUCUUGAACGUGCGGACUCGGUGAUCUCCUGGGAUAUACAGGACGAAAAGAAUG
UCACUUGUCAACUCACUUUCUGGGAAGCCUCGGAACGCACCAUUCGUUCCGAAGCCGAGGAC
UCGUAUCACUUUUCUUCUGCCAAAAUGACCGCCACUUUCUUAUCUAAGAAGCAAGAGGUGAA
CAUGUCCGACUCUGCGCUGGACUGCGUACGUGAUGAGGCUAUAAAUAAGUUACAGCAGAUUU
UCAAUACUUCAUACAAUCAAACAUAUGAAAAAUAUGGAAACGUGUCCGUCUUUGAAACCACU
GGUGGUUUGGUAGUGUUCUGGCAAGGUAUCAAGCAAAAAUCUCUGGUGGAACUCGAACGUUU
GGCCAACCGCUCCAGUCUGAAUCUUACUCAUAAUAGAACCAAAAGAAGUACAGAUGGCAACA
AUGCAACUCAUUUAUCCAACAUGGAAUCGGUGCACAAUCUGGUCUACGCCCAGCUGCAGUUC
ACCUAUGACACGUUGCGCGGUUACAUCAACCGGGCGCUGGCGCAAAUCGCAGAAGCCUGGUG
UGUGGAUCAACGGCGCACCCUAGAGGUCUUCAAGGAACUCAGCAAGAUCAACCCGUCAGCCA
UUCUCUCGGCCAUUUACAACAAACCGAUUGCCGCGCGUUUCAUGGGUGAUGUCUUGGGCCUG
GCCAGCUGCGUGACCAUCAACCAAACCAGCGUCAAGGUGCUGCGUGAUAUGAACGUGAAGGA
GUCGCCAGGACGCUGCUACUCACGACCCGUGGUCAUCUUUAAUUUCGCCAACAGCUCGUACG
UGCAGUACGGUCAACUGGGCGAGGACAACGAAAUCCUGUUGGGCAACCACCGCACUGAGGAA
UGUCAGCUUCCCAGCCUCAAGAUCUUCAUCGCCGGGAACUCGGCCUACGAGUACGUGGACUA

-continued

CCUCUUCAAACGCAUGAUUGACCUCAGCAGUAUCUCCACCGUCGACAGCAUGAUCGCCCUGG
AUAUCGACCCGCUGGAAAAUACCGACUUCAGGGUACUGGAACUUUACUCGCAGAAAGAGCUG
CGUUCCAGCAACGUUUUUGACCUCGAAGAGAUCAUGCGCGAAUUCAACUCGUACAAGCAGCA
CCAUCACCACCAUCACUGAUAAUAGGCUGGAGCCUCGGUGGCCAUGCUUCUUGCCCCUUGGG
CCUCCCCCCAGCCCCUCCUCCCCUUCCUGCACCCGUACCCCCGUGGUCUUUGAAUAAAGUCU
GAGUGGGCGGC

Example 14: hCMV Vaccine—hCMV UL Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV_UL128

(SEQ ID NO: 13)

TCAAGCTTTTGGACCCTCGTACAGAAGCTAATACGACTCACTATAGGGAAATAAGAGAGAAA
AGAAGAGTAAGAAGAAATATAAGAGCCACCATGAGTCCCAAAGATCTGACGCCGTTCTTGAC
GGCGTTGTGGCTGCTATTGGGTCACAGCCGCGTGCCGCGGGTGCGCGCAGAAGAATGTTGCG
AATTCATAAACGTCAACCACCCGCCGGAACGCTGTTACGATTTCAAAATGTGCAATCGCTTC
ACCGTCGCGCTGCGGTGTCCGGACGGCGAAGTCTGCTACAGTCCCGAGAAAACGGCTGAGAT
TCGCGGGATCGTCACCACCATGACCCATTCATTGACACGCCAGGTCGTACACAACAAACTGA
CGAGCTGCAACTACAATCCGTTATACCTCGAAGCTGACGGGCGAATACGCTGCGGCAAAGTA
AACGACAAGGCGCAGTACCTGCTGGGCGCCGCTGGCAGCGTTCCCTATCGATGGATCAATCT
GGAATACGACAAGATAACCCGGATCGTGGGCCTGGATCAGTACCTGGAGAGCGTTAAGAAAC
ACAAACGGCTGGATGTGTGCCGCGCTAAAATGGGCTATATGCTGCAGTGATAATAGGCTGGA
GCCTCGGTGGCCATGCTTCTTGCCCCTTGGGCCTCCCCCCAGCCCCTCCTCCCCTTCCTGCA
CCCGTACCCCCGTGGTCTTTGAATAAAGTCTGAGTGGGCGGC hCMV_UL128

(SEQ ID NO: 91)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGAGUCCCAAAGAUCUGACGCCGUUCUUGAC
GGCGUUGUGGCUGCUAUUGGGUCACAGCCGCGUGCCGCGGGUGCGCGCAGAAGAAUGUUGCG
AAUUCAUAAACGUCAACCACCCGCCGGAACGCUGUUACGAUUUCAAAAUGUGCAAUCGCUUC
ACCGUCGCGCUGCGGUGUCCGGACGGCGAAGUCUGCUACAGUCCCGAGAAAACGGCUGAGAU
UCGCGGGAUCGUCACCACCAUGACCCAUUCAUUGACACGCCAGGUCGUACACAACAAACUGA
CGAGCUGCAACUACAAUCCGUUAUACCUCGAAGCUGACGGGCGAAUACGCUGCGGCAAAGUA
AACGACAAGGCGCAGUACCUGCUGGGCGCCGCUGGCAGCGUUCCCUAUCGAUGGAUCAAUCU
GGAAUACGACAAGAUAACCCGGAUCGUGGGCCUGGAUCAGUACCUGGAGAGCGUUAAGAAAC
ACAAACGGCUGGAUGUGUGCCGCGCUAAAAUGGGCUAUAUGCUGCAGUGAUAAUAGGCUGGA
GCCUCGGUGGCCAUGCUUCUUGCCCCUUGGGCCUCCCCCCAGCCCCUCCUCCCCUUCCUGCA
CCCGUACCCCCGUGGUCUUUGAAUAAAGUCUGAGUGGGCGGC hCMV-128FLAG, UL128-FLAG tag (SEQ ID NO: 14)

TCAAGCTTTTGGACCCTCGTACAGAAGCTAATACGACTCACTATAGGGAAATAAGAGAGAAA
AGAAGAGTAAGAAGAAATATAAGAGCCACCATGAGTCCCAAAGATCTGACGCCGTTCTTGAC
GGCGTTGTGGCTGCTATTGGGTCACAGCCGCGTGCCGCGGGTGCGCGCAGAAGAATGTTGCG
AATTCATAAACGTCAACCACCCGCCGGAACGCTGTTACGATTTCAAAATGTGCAATCGCTTC
ACCGTCGCGCTGCGGTGTCCGGACGGCGAAGTCTGCTACAGTCCCGAGAAAACGGCTGAGAT
TCGCGGGATCGTCACCACCATGACCCATTCATTGACACGCCAGGTCGTACACAACAAACTGA

-continued

CGAGCTGCAACTACAATCCGTTATACCTCGAAGCTGACGGGCGAATACGCTGCGGCAAAGTA

AACGACAAGGCGCAGTACCTGCTGGGCGCCGCTGGCAGCGTTCCCTATCGATGGATCAATCT

GGAATACGACAAGATAACCCGGATCGTGGGCCTGGATCAGTACCTGGAGAGCGTTAAGAAAC

ACAAACGGCTGGATGTGTGCCGCGCTAAAATGGGCTATATGCTGCAGGATTACAAGGACGAT

GACGATAAGTGATAATAGGCTGGAGCCTCGGTGGCCATGCTTCTTGCCCCTTGGGCCTCCCC

CCAGCCCCTCCTCCCCTTCCTGCACCCGTACCCCCGTGGTCTTTGAATAAAGTCTGAGTGGG

CGGC hCMV-128FLAG, UL128-FLAG tag (SEQ ID NO: 92)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGAGUCCCAAAGAUCUGACGCCGUUCUUGAC

GGCGUUGUGGCUGCUAUUGGGUCACAGCCGCGUGCCGCGGGUGCGCGCAGAAGAAUGUUGCG

AAUUCAUAAACGUCAACCACCCGCCGGAACGCUGUUACGAUUUCAAAAUGUGCAAUCGCUUC

ACCGUCGCGCUGCGGUGUCCGGACGGCGAAGUCUGCUACAGUCCCGAGAAAACGGCUGAGAU

UCGCGGGAUCGUCACCACCAUGACCCAUUCAUUGACACGCCAGGUCGUACACAACAAACUGA

CGAGCUGCAACUACAAUCCGUUAUACCUCGAAGCUGACGGGCGAAUACGCUGCGGCAAAGUA

AACGACAAGGCGCAGUACCUGCUGGGCGCCGCUGGCAGCGUUCCCUAUCGAUGGAUCAAUCU

GGAAUACGACAAGAUAACCCGGAUCGUGGGCCUGGAUCAGUACCUGGAGAGCGUUAAGAAAC

ACAAACGGCUGGAUGUGUGCCGCGCUAAAAUGGGCUAUAUGCUGCAGGAUUACAAGGACGAU

GACGAUAAGUGAUAAUAGGCUGGAGCCUCGGUGGCCAUGCUUCUUGCCCCUUGGGCCUCCCC

CCAGCCCCUCCUCCCCUUCCUGCACCCGUACCCCCGUGGUCUUUGAAUAAAGUCUGAGUGGG

CGGC hCMV-UL130

(SEQ ID NO: 15)

TCAAGCTTTTGGACCCTCGTACAGAAGCTAATACGACTCACTATAGGGAAATAAGAGAGAAA

AGAAGAGTAAGAAGAAATATAAGAGCCACCATGCTGCGGCTTCTGCTTCGTCACCACTTTCA

CTGCCTGCTTCTGTGCGCGGTTTGGGCAACGCCCTGTCTGGCGTCTCCGTGGTCGACGCTAA

CAGCAAACCAGAATCCGTCCCCGCCATGGTCTAAACTGACGTATTCCAAACCGCATGACGCG

GCGACGTTTTACTGTCCTTTTCTCTATCCCTCGCCCCCACGATCCCCCTTGCAATTCTCGGG

GTTCCAGCGGGTATCAACGGGTCCCGAGTGTCGCAACGAGACCCTGTATCTGCTGTACAACC

GGGAAGGCCAGACCTTGGTGGAGAGAAGCTCCACCTGGGTGAAAAAGGTGATCTGGTACCTG

AGCGGTCGGAACCAAACCATCCTCCAACGGATGCCCCGAACGGCTTCGAAACCGAGCGACGG

AAACGTGCAGATCAGCGTGGAAGACGCCAAGATTTTTGGAGCGCACATGGTGCCCAAGCAGA

CCAAGCTGCTACGCTTCGTCGTCAACGATGGCACACGTTATCAGATGTGTGTGATGAAGCTG

GAGAGCTGGGCTCACGTCTTCCGGGACTACAGCGTGTCTTTTCAGGTGCGATTGACGTTCAC

CGAGGCCAATAACCAGACTTACACCTTCTGCACCCATCCCAATCTCATCGTTTGATAATAGG

CTGGAGCCTCGGTGGCCATGCTTCTTGCCCCTTGGGCCTCCCCCCAGCCCCTCCTCCCCTTC

CTGCACCCGTACCCCCGTGGTCTTTGAATAAAGTCTGAGTGGGCGGC hCMV-UL130

(SEQ ID NO: 93)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCUGCGGCUUCUGCUUCGUCACCACUUUCA

CUGCCUGCUUCUGUGCGCGGUUUGGGCAACGCCCUGUCUGGCGUCUCCGUGGUCGACGCUAA

CAGCAAACCAGAAUCCGUCCCCGCCAUGGUCUAAACUGACGUAUUCCAAACCGCAUGACGCG

-continued

GCGACGUUUUACUGUCCUUUUCUCUAUCCCUCGCCCCCACGAUCCCCCUUGCAAUUCUCGGG

GUUCCAGCGGGUAUCAACGGGUCCCGAGUGUCGCAACGAGACCCUGUAUCUGCUGUACAACC

GGGAAGGCCAGACCUUGGUGGAGAGAAGCUCCACCUGGGUGAAAAAGGUGAUCUGGUACCUG

AGCGGUCGGAACCAAACCAUCCUCCAACGGAUGCCCCGAACGGCUUCGAAACCGAGCGACGG

AAACGUGCAGAUCAGCGUGGAAGACGCCAAGAUUUUUGGAGCGCACAUGGUGCCCAAGCAGA

CCAAGCUGCUACGCUUCGUCGUCAACGAUGGCACACGUUAUCAGAUGUGUGUGAUGAAGCUG

GAGAGCUGGGCUCACGUCUUCCGGGACUACAGCGUGUCUUUUCAGGUGCGAUUGACGUUCAC

CGAGGCCAAUAACCAGACUUACACCUUCUGCACCCAUCCCAAUCUCAUCGUUUGAUAAUAGG

CUGGAGCCUCGGUGGCCAUGCUUCUUGCCCCUUGGGCCUCCCCCCAGCCCCUCCUCCCCUUC

CUGCACCCGUACCCCCGUGGUCUUUGAAUAAAGUCUGAGUGGGCGGC hCMV-UL130FLAG, UL130-FLAG tag (SEQ ID NO: 16)

TCAAGCTTTTGGACCCTCGTACAGAAGCTAATACGACTCACTATAGGGAAATAAGAGAGAAA

AGAAGAGTAAGAAGAAATATAAGAGCCACCATGCTGCGGCTTCTGCTTCGTCACCACTTTCA

CTGCCTGCTTCTGTGCGCGGTTTGGGCAACGCCCTGTCTGGCGTCTCCGTGGTCGACGCTAA

CAGCAAACCAGAATCCGTCCCCGCCATGGTCTAAACTGACGTATTCCAAACCGCATGACGCG

GCGACGTTTTACTGTCCTTTTCTCTATCCCTCGCCCCCACGATCCCCCTTGCAATTCTCGGG

GTTCCAGCGGGTATCAACGGGTCCCGAGTGTCGCAACGAGACCCTGTATCTGCTGTACAACC

GGGAAGGCCAGACCTTGGTGGAGAGAAGCTCCACCTGGGTGAAAAAGGTGATCTGGTACCTG

AGCGGTCGGAACCAAACCATCCTCCAACGGATGCCCCGAACGGCTTCGAAACCGAGCGACGG

AAACGTGCAGATCAGCGTGGAAGACGCCAAGATTTTTGGAGCGCACATGGTGCCCAAGCAGA

CCAAGCTGCTACGCTTCGTCGTCAACGATGGCACACGTTATCAGATGTGTGTGATGAAGCTG

GAGAGCTGGGCTCACGTCTTCCGGGACTACAGCGTGTCTTTTCAGGTGCGATTGACGTTCAC

CGAGGCCAATAACCAGACTTACACCTTCTGCACCCATCCCAATCTCATCGTTGATTACAAGG

ACGATGACGATAAGTGATGATAATAGGCTGGAGCCTCGGTGGCCATGCTTCTTGCCCCTTGG

GCCTCCCCCCAGCCCCTCCTCCCCTTCCTGCACCCGTACCCCCGTGGTCTTTGAATAAAGTC

TGAGTGGGCGGC hCMV-UL130FLAG, UL130-FLAG tag (SEQ ID NO: 94)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGCUGCGGCUUCUGCUUCGUCACCACUUUCA

CUGCCUGCUUCUGUGCGCGGUUUGGGCAACGCCCUGUCUGGCGUCUCCGUGGUCGACGCUAA

CAGCAAACCAGAAUCCGUCCCCGCCAUGGUCUAAACUGACGUAUUCCAAACCGCAUGACGCG

GCGACGUUUUACUGUCCUUUUCUCUAUCCCUCGCCCCCACGAUCCCCCUUGCAAUUCUCGGG

GUUCCAGCGGGUAUCAACGGGUCCCGAGUGUCGCAACGAGACCCUGUAUCUGCUGUACAACC

GGGAAGGCCAGACCUUGGUGGAGAGAAGCUCCACCUGGGUGAAAAAGGUGAUCUGGUACCUG

AGCGGUCGGAACCAAACCAUCCUCCAACGGAUGCCCCGAACGGCUUCGAAACCGAGCGACGG

AAACGUGCAGAUCAGCGUGGAAGACGCCAAGAUUUUUGGAGCGCACAUGGUGCCCAAGCAGA

CCAAGCUGCUACGCUUCGUCGUCAACGAUGGCACACGUUAUCAGAUGUGUGUGAUGAAGCUG

GAGAGCUGGGCUCACGUCUUCCGGGACUACAGCGUGUCUUUUCAGGUGCGAUUGACGUUCAC

CGAGGCCAAUAACCAGACUUACACCUUCUGCACCCAUCCCAAUCUCAUCGUUGAUUACAAGG

ACGAUGACGAUAAGUGAUGAUAAUAGGCUGGAGCCUCGGUGGCCAUGCUUCUUGCCCCUUGG

-continued

GCCUCCCCCCAGCCCCUCCUCCCCUUCCUGCACCCGUACCCCCGUGGUCUUUGAAUAAAGUC
UGAGUGGGCGGC hCMV-UL131A (SEQ ID NO: 17)

TCAAGCTTTTGGACCCTCGTACAGAAGCTAATACGACTCACTATAGGGAAATAAGAGAGAAA
AGAAGAGTAAGAAGAAATATAAGAGCCACCATGCGGCTGTGTCGGGTGTGGCTGTCTGTTTG
TCTGTGCGCCGTGGTGCTGGGTCAGTGCCAGCGGGAAACCGCGGAAAAAAACGATTATTACC
GAGTACCGCATTACTGGGACGCGTGCTCTCGCGCGCTGCCCGACCAAACCCGTTACAAGTAT
GTGGAACAGCTCGTGGACCTCACGTTGAACTACCACTACGATGCGAGCCACGGCTTGGACAA
CTTTGACGTGCTCAAGAGAATCAACGTGACCGAGGTGTCGTTGCTCATCAGCGACTTTAGAC
GTCAGAACCGTCGCGGCGGCACCAACAAAAGGACCACGTTCAACGCCGCCGGTTCGCTGGCG
CCACACGCCCGGAGCCTCGAGTTCAGCGTGCGGCTCTTTGCCAACTGATAATAGGCTGGAGC
CTCGGTGGCCATGCTTCTTGCCCCTTGGGCCTCCCCCCAGCCCCTCCTCCCCTTCCTGCACC
CGTACCCCCGTGGTCTTTGAATAAAGTCTGAGTGGGCGGC hCMV-UL131A (SEQ ID NO: 95)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCUGUGUCGGGUGUGGCUGUCUGUUUG
UCUGUGCGCCGUGGUGCUGGGUCAGUGCCAGCGGGAAACCGCGGAAAAAAACGAUUAUUACC
GAGUACCGCAUUACUGGGACGCGUGCUCUCGCGCGCUGCCCGACCAAACCCGUUACAAGUAU
GUGGAACAGCUCGUGGACCUCACGUUGAACUACCACUACGAUGCGAGCCACGGCUUGGACAA
CUUUGACGUGCUCAAGAGAAUCAACGUGACCGAGGUGUCGUUGCUCAUCAGCGACUUUAGAC
GUCAGAACCGUCGCGGCGGCACCAACAAAAGGACCACGUUCAACGCCGCCGGUUCGCUGGCG
CCACACGCCCGGAGCCUCGAGUUCAGCGUGCGGCUCUUUGCCAACUGAUAAUAGGCUGGAGC
CUCGGUGGCCAUGCUUCUUGCCCCUUGGGCCUCCCCCCAGCCCCUCCUCCCCUUCCUGCACC
CGUACCCCCGUGGUCUUUGAAUAAAGUCUGAGUGGGCGGC hCMV-UL131AFLAG, UL131A-FLAG (SEQ ID NO: 18)

TCAAGCTTTTGGACCCTCGTACAGAAGCTAATACGACTCACTATAGGGAAATAAGAGAGAAA
AGAAGAGTAAGAAGAAATATAAGAGCCACCATGCGGCTGTGTCGGGTGTGGCTGTCTGTTTG
TCTGTGCGCCGTGGTGCTGGGTCAGTGCCAGCGGGAAACCGCGGAAAAAAACGATTATTACC
GAGTACCGCATTACTGGGACGCGTGCTCTCGCGCGCTGCCCGACCAAACCCGTTACAAGTAT
GTGGAACAGCTCGTGGACCTCACGTTGAACTACCACTACGATGCGAGCCACGGCTTGGACAA
CTTTGACGTGCTCAAGAGAATCAACGTGACCGAGGTGTCGTTGCTCATCAGCGACTTTAGAC
GTCAGAACCGTCGCGGCGGCACCAACAAAAGGACCACGTTCAACGCCGCCGGTTCGCTGGCG
CCACACGCCCGGAGCCTCGAGTTCAGCGTGCGGCTCTTTGCCAACGATTACAAGGACGATGA
CGATAAGTGATGATAATAGGCTGGAGCCTCGGTGGCCATGCTTCTTGCCCCTTGGGCCTCCC
CCCAGCCCCTCCTCCCCTTCCTGCACCCGTACCCCCGTGGTCTTTGAATAAAGTCTGAGTGG
GCGGC hCMV-UL131AFLAG, UL131A-FLAG (SEQ ID NO: 96)

UCAAGCUUUUGGACCCUCGUACAGAAGCUAAUACGACUCACUAUAGGGAAAUAAGAGAGAAA
AGAAGAGUAAGAAGAAAUAUAAGAGCCACCAUGCGGCUGUGUCGGGUGUGGCUGUCUGUUUG
UCUGUGCGCCGUGGUGCUGGGUCAGUGCCAGCGGGAAACCGCGGAAAAAAACGAUUAUUACC
GAGUACCGCAUUACUGGGACGCGUGCUCUCGCGCGCUGCCCGACCAAACCCGUUACAAGUAU

-continued

GUGGAACAGCUCGUGGACCUCACGUUGAACUACCACUACGAUGCGAGCCACGGCUUGGACAA

CUUUGACGUGCUCAAGAGAAUCAACGUGACCGAGGUGUCGUUGCUCAUCAGCGACUUUAGAC

GUCAGAACCGUCGCGGCGGCACCAACAAAAGGACCACGUUCAACGCCGCCGGUUCGCUGGCG

CCACACGCCCGGAGCCUCGAGUUCAGCGUGCGGCUCUUUGCCAACGAUUACAAGGACGAUGA

CGAUAAGUGAUGAUAAUAGGCUGGAGCCUCGGUGGCCAUGCUUCUUGCCCCUUGGGCCUCCC

CCCAGCCCCUCCUCCCCUUCCUGCACCCGUACCCCCGUGGUCUUUGAAUAAAGUCUGAGUGG

GCGGC

Example 15: hCMV Vaccine—hCMV UL Multimeric Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV gH penta (SEQ ID NO: 19)

TCAAGCTTTTGGACCCTCGTACAGAAGCTAATACGACTCACTATAGGGACAGACGAGAGAGA

AGCACGCCAATTCTGCCTGCTTAAGCCATGCGGCCAGGCCTCCCCTCCTACCTCATCATCCT

CGCCGTCTGTCTCTTCAGCCACCTACTTTCGTCACGATATGGCGCAGAAGCCGTATCCGAAC

CGCTGGACAAAGCGTTTCACCTACTGCTCAACACCTACGGGAGACCCATCCGCTTCCTGCGT

GAAAATACCACCCAGTGTACCTACAACAGCAGCCTCCGTAACAGCACGGTCGTCAGGGAAAA

CGCCATCAGTTTCAACTTTTTCCAAAGCTATAATCAATACTATGTATTCCATATGCCTCGAT

GTCTTTTTGCGGGTCCTCTGGCGGAGCAGTTTCTGAACCAGGTAGATCTGACCGAAACCCTG

GAAAGATACCAACAGAGACTTAACACTTACGCGCTGGTATCCAAAGACCTGGCCAGCTACCG

ATCTTTTTCGCAGCAGCTAAAGGCACAAGACAGCCTAGGTGAACAGCCCACCACTGTGCCAC

CGCCCATTGACCTGTCAATACCTCACGTTTGGATGCCACCGCAAACCACTCCACACGGCTGG

ACAGAATCACATACCACCTCAGGACTACACCGACCACACTTTAACCAGACCTGTATCCTCTT

TGATGGACACGATCTACTATTCAGCACCGTCACACCTTGTTTGCACCAAGGCTTTTACCTCA

TCGACGAACTACGTTACGTTAAAATAACACTGACCGAGGACTTCTTCGTAGTTACGGTGTCC

ATAGACGACGACACACCCATGCTGCTTATCTTCGGCCATCTTCCACGCGTACTTTTCAAAGC

GCCCTATCAACGCGACAACTTTATACTACGACAAACTGAAAAACACGAGCTCCTGGTGCTAG

TTAAGAAAGATCAACTGAACCGTCACTCTTATCTCAAAGACCCGGACTTTCTTGACGCCGCA

CTTGACTTCAACTACCTAGACCTCAGCGCACTACTACGTAACAGCTTTCACCGTTACGCCGT

GGATGTACTCAAGAGCGGTCGATGTCAGATGCTGGACCGCCGCACGGTAGAAATGGCCTTCG

CCTACGCATTAGCACTGTTCGCAGCAGCCCGACAAGAAGAGGCCGGCGCCCAAGTCTCCGTC

CCACGGGCCCTAGACCGCCAGGCCGCACTCTTACAAATACAAGAATTTATGATCACCTGCCT

CTCACAAACACCACCACGCACCACGTTGCTGCTGTATCCCACGGCCGTGGACCTGGCCAAAC

GAGCCCTTTGGACACCGAATCAGATCACCGACATCACCAGCCTCGTACGCCTGGTCTACATA

CTCTCTAAACAGAATCAGCAACATCTCATCCCCCAATGGGCACTACGACAGATCGCCGACTT

TGCCCTAAAACTACACAAAACGCACCTGGCCTCTTTTCTTTCAGCCTTCGCACGCCAAGAAC

TCTACCTCATGGGCAGCCTCGTCCACTCCATGCTGGTACATACGACGGAGAGACGCGAAATC

TTCATCGTAGAAACGGGCCTCTGTTCATTGGCCGAGCTATCACACTTTACGCAGTTGTTAGC

TCATCCACACCACGAATACCTCAGCGACCTGTACACACCCTGTTCCAGTAGCGGGCGACGCG

ATCACTCGCTCGAACGCCTCACGCGTCTCTTCCCCGATGCCACCGTCCCCGCTACCGTTCCC

-continued

GCCGCCCTCTCCATCCTATCTACCATGCAACCAAGCACGCTGGAAACCTTCCCCGACCTGTT

TTGCTTGCCGCTCGGCGAATCCTTCTCCGCGCTGACCGTCTCCGAACACGTCAGTTATATCG

TAACAAACCAGTACCTGATCAAAGGTATCTCCTACCCTGTCTCCACCACCGTCGTAGGCCAG

AGCCTCATCATCACCCAGACGGACAGTCAAACTAAATGCGAACTGACGCGCAACATGCATAC

CACACACAGCATCACAGTGGCGCTCAACATTTCGCTAGAAAACTGCGCCTTTTGCCAAAGCG

CCCTGCTAGAATACGACGACACGCAAGGCGTCATCAACATCATGTACATGCACGACTCGGAC

GACGTCCTTTTCGCCCTGGATCCCTACAACGAAGTGGTGGTCTCATCTCCGCGAACTCACTA

CCTCATGCTTTTGAAAAACGGTACGGTACTAGAAGTAACTGACGTCGTCGTGGACGCCACCG

ACAGTCGTCTCCTCATGATGTCCGTCTACGCGCTATCGGCCATCATCGGCATCTATCTGCTC

TACCGCATGCTCAAGACATGCTGATAATAGGCTGGAGCCTCGGTGGCCATGCTTCTTGCCCC

TTGGGCCTCCCCCCAGCCCCTCCTCCCCTTCCTGCACCCGTACCCCCGTGGTCTTTGAATAA

AGTCTGAGTGGGCGGC hCMV gH penta (SEQ ID NO: 97)

UCAAGCUUUUGGACCCUCGUACAGAAGCUAAUACGACUCACUAUAGGGACAGACGAGAGAGA

AGCACGCCAAUUCUGCCUGCUUAAGCCAUGCGGCCAGGCCUCCCCUCCUACCUCAUCAUCCU

CGCCGUCUGUCUCUUCAGCCACCUACUUUCGUCACGAUAUGGCGCAGAAGCCGUAUCCGAAC

CGCUGGACAAAGCGUUUCACCUACUGCUCAACACCUACGGGAGACCCAUCCGCUUCCUGCGU

GAAAAUACCACCCAGUGUACCUACAACAGCAGCCUCCGUAACAGCACGGUCGUCAGGGAAAA

CGCCAUCAGUUUCAACUUUUUCCAAAGCUAUAAUCAAUACUAUGUAUUCCAUAUGCCUCGAU

GUCUUUUUGCGGGUCCUCUGGCGGAGCAGUUUCUGAACCAGGUAGAUCUGACCGAAACCCUG

GAAAGAUACCAACAGAGACUUAACACUUACGCGCUGGUAUCCAAAGACCUGGCCAGCUACCG

AUCUUUUUCGCAGCAGCUAAAGGCACAAGACAGCCUAGGUGAACAGCCCACCACUGUGCCAC

CGCCCAUUGACCUGUCAAUACCUCACGUUUGGAUGCCACCGCAAACCACUCCACACGGCUGG

ACAGAAUCACAUACCACCUCAGGACUACACCGACCACACUUUAACCAGACCUGUAUCCUCUU

UGAUGGACACGAUCUACUAUUCAGCACCGUCACACCUUGUUUGCACCAAGGCUUUUACCUCA

UCGACGAACUACGUUACGUUAAAAUAACACUGACCGAGGACUUCUUCGUAGUUACGGUGUCC

AUAGACGACGACACACCCAUGCUGCUUAUCUUCGGCCAUCUUCCACGCGUACUUUUCAAAGC

GCCCUAUCAACGCGACAACUUUAUACUACGACAAACUGAAAAACACGAGCUCCUGGUGCUAG

UUAAGAAAGAUCAACUGAACCGUCACUCUUAUCUCAAAGACCCGGACUUUCUUGACGCCGCA

CUUGACUUCAACUACCUAGACCUCAGCGCACUACUACGUAACAGCUUUCACCGUUACGCCGU

GGAUGUACUCAAGAGCGGUCGAUGUCAGAUGCUGGACCGCCGCACGGUAGAAAUGGCCUUCG

CCUACGCAUUAGCACUGUUCGCAGCAGCCCGACAAGAAGAGGCCGGCGCCCAAGUCUCCGUC

CCACGGGCCCUAGACCGCCAGGCCGCACUCUUACAAAUACAAGAAUUUAUGAUCACCUGCCU

CUCACAAACACCACCACGCACCACGUUGCUGCUGUAUCCCACGGCCGUGGACCUGGCCAAAC

GAGCCCUUUGGACACCGAAUCAGAUCACCGACAUCACCAGCCUCGUACGCCUGGUCUACAUA

CUCUCUAAACAGAAUCAGCAACAUCUCAUCCCCCAAUGGGCACUACGACAGAUCGCCGACUU

UGCCCUAAAACUACACAAAACGCACCUGGCCUCUUUUCUUUCAGCCUUCGCACGCCAAGAAC

UCUACCUCAUGGGCAGCCUCGUCCACUCCAUGCUGGUACAUACGACGGAGAGACGCGAAAUC

UUCAUCGUAGAAACGGGCCUCUGUUCAUUGGCCGAGCUAUCACACUUUACGCAGUUGUUAGC

UCAUCCACACCACGAAUACCUCAGCGACCUGUACACACCCUGUUCCAGUAGCGGGCGACGCG

AUCACUCGCUCGAACGCCUCACGCGUCUCUUCCCCGAUGCCACCGUCCCCGCUACCGUUCCC

-continued

GCCGCCCUCUCCAUCCUAUCUACCAUGCAACCAAGCACGCUGGAAACCUUCCCCGACCUGUU

UUGCUUGCCGCUCGGCGAAUCCUUCUCCGCGCUGACCGUCUCCGAACACGUCAGUUAUAUCG

UAACAAACCAGUACCUGAUCAAAGGUAUCUCCUACCCUGUCUCCACCACCGUCGUAGGCCAG

AGCCUCAUCAUCACCCAGACGGACAGUCAAACUAAAUGCGAACUGACGCGCAACAUGCAUAC

CACACACAGCAUCACAGUGGCGCUCAACAUUUCGCUAGAAAACUGCGCCUUUUGCCAAAGCG

CCCUGCUAGAAUACGACGACACGCAAGGCGUCAUCAACAUCAUGUACAUGCACGACUCGGAC

GACGUCCUUUUCGCCCUGGAUCCCUACAACGAAGUGGUGGUCUCAUCUCCGCGAACUCACUA

CCUCAUGCUUUUGAAAAACGGUACGGUACUAGAAGUAACUGACGUCGUCGUGGACGCCACCG

ACAGUCGUCUCCUCAUGAUGUCCGUCUACGCGCUAUCGGCCAUCAUCGGCAUCUAUCUGCUC

UACCGCAUGCUCAAGACAUGCUGAUAAUAGGCUGGAGCCUCGGUGGCCAUGCUUCUUGCCCC

UUGGGCCUCCCCCCAGCCCCUCCUCCCCUUCCUGCACCCGUACCCCCGUGGUCUUUGAAUAA

AGUCUGAGUGGGCGGC hCMV gL penta (SEQ ID NO: 20)

TCAAGCTTTTGGACCCTCGTACAGAAGCTAATACGACTCACTATAGGGCTTAAGCAGGCAGA

ATTGGCCCTTAGCCTGTACCAGCCGAACCATGTGCCGCCGCCCGGATTGCGGCTTCTCTTTC

TCACCTGGACCGGTGATACTGCTGTGGTGTTGCCTTCTGCTGCCCATTGTTTCCTCAGCCGC

CGTCAGCGTCGCTCCTACCGCCGCCGAGAAAGTCCCCGCGGAGTGCCCCGAACTAACGCGCC

GATGCTTGTTGGGTGAGGTGTTTGAGGGTGACAAGTATGAAAGTTGGCTGCGCCCGTTGGTG

AATGTTACCGGGCGCGATGGCCCGCTATCGCAACTTATCCGTTACCGTCCCGTTACGCCGGA

GGCCGCCAACTCCGTGCTGTTGGACGAGGCTTTCCTGGACACTCTGGCCCTGCTGTACAACA

ATCCGGATCAATTGCGGGCCCTGCTGACGCTGTTGAGCTCGGACACAGCGCCGCGCTGGATG

ACGGTGATGCGCGGCTACAGCGAGTGCGGCGATGGCTCGCCGGCCGTGTACACGTGCGTGGA

CGACCTGTGCCGCGGCTACGACCTCACGCGACTGTCATACGGGCGCAGCATCTTCACGGAAC

ACGTGTTAGGCTTCGAGCTGGTGCCACCGTCTCTCTTTAACGTGGTGGTGGCCATACGCAAC

GAAGCCACGCGTACCAACCGCGCCGTGCGTCTGCCCGTGAGCACCGCTGCCGCGCCCGAGGG

CATCACGCTCTTTTACGGCCTGTACAACGCAGTGAAGGAATTCTGCCTGCGTCACCAGCTGG

ACCCGCCGGTGCTACGCCACCTAGATAAATACTACGCCGGACTGCCGCCCGAGCTGAAGCAG

ACGCGCGTCAACCTGCCGGCTCACTCGCGCTATGGCCCTCAAGCAGTGGATGCTCGCTGATA

ATAGGCTGGAGCCTCGGTGGCCATGCTTCTTGCCCCTTGGGCCTCCCCCCAGCCCCTCCTCC

CCTTCCTGCACCCGTACCCCCGTGGTCTTTGAATAAAGTCTGAGTGGGCGGC hCMV gL penta (SEQ ID NO: 98)

UCAAGCUUUUGGACCCUCGUACAGAAGCUAAUACGACUCACUAUAGGGCUUAAGCAGGCAGA

AUUGGCCCUUAGCCUGUACCAGCCGAACCAUGUGCCGCCGCCCGGAUUGCGGCUUCUCUUUC

UCACCUGGACCGGUGAUACUGCUGUGGUGUUGCCUUCUGCUGCCCAUUGUUUCCUCAGCCGC

CGUCAGCGUCGCUCCUACCGCCGCCGAGAAAGUCCCCGCGGAGUGCCCCGAACUAACGCGCC

GAUGCUUGUUGGGUGAGGUGUUUGAGGGUGACAAGUAUGAAAGUUGGCUGCGCCCGUUGGUG

AAUGUUACCGGGCGCGAUGGCCCGCUAUCGCAACUUAUCCGUUACCGUCCCGUUACGCCGGA

GGCCGCCAACUCCGUGCUGUUGGACGAGGCUUUCCUGGACACUCUGGCCCUGCUGUACAACA

AUCCGGAUCAAUUGCGGGCCCUGCUGACGCUGUUGAGCUCGGACACAGCGCCGCGCUGGAUG

ACGGUGAUGCGCGGCUACAGCGAGUGCGGCGAUGGCUCGCCGGCCGUGUACACGUGCGUGGA

CGACCUGUGCCGCGGCUACGACCUCACGCGACUGUCAUACGGGCGCAGCAUCUUCACGGAAC

-continued

ACGUGUUAGGCUUCGAGCUGGUGCCACCGUCUCUCUUUAACGUGGUGGUGGCCAUACGCAAC
GAAGCCACGCGUACCAACCGCGCCGUGCGUCUGCCCGUGAGCACCGCUGCCGCGCCCGAGGG
CAUCACGCUCUUUUACGGCCUGUACAACGCAGUGAAGGAAUUCUGCCUGCGUCACCAGCUGG
ACCCGCCGCUGCUACGCCACCUAGAUAAAUACUACGCCGGACUGCCGCCCGAGCUGAAGCAG
ACGCGCGUCAACCUGCCGGCUCACUCGCGCUAUGGCCCUCAAGCAGUGGAUGCUCGCUGAUA
AUAGGCUGGAGCCUCGGUGGCCAUGCUUCUUGCCCCUUGGGCCUCCCCCCAGCCCCUCCUCC
CCUUCCUGCACCCGUACCCCCGUGGUCUUUGAAUAAAGUCUGAGUGGGCGGC hCMV gL dimer (SEQ ID NO: 21)

TCAAGCTTTTGGACCCTCGTACAGAAGCTAATACGACTCACTATAGGGTGGCTCTTATATTT
CTTCTTACTCTTCTTTTCTCTCTTATTTCCATGTGCCGCCGCCCGGATTGCGGCTTCTCTTT
CTCACCTGGACCGGTGATACTGCTGTGGTGTTGCCTTCTGCTGCCCATTGTTTCCTCAGCCG
CCGTCAGCGTCGCTCCTACCGCCGCCGAGAAAGTCCCCGCGGAGTGCCCCGAACTAACGCGC
CGATGCTTGTTGGGTGAGGTGTTTGAGGGTGACAAGTATGAAAGTTGGCTGCGCCCGTTGGT
GAATGTTACCGGGCGCGATGGCCCGCTATCGCAACTTATCCGTTACCGTCCCGTTACGCCGG
AGGCCGCCAACTCCGTGCTGTTGGACGAGGCTTTCCTGGACACTCTGGCCCTGCTGTACAAC
AATCCGGATCAATTGCGGGCCCTGCTGACGCTGTTGAGCTCGGACACAGCGCCGCGCTGGAT
GACGGTGATGCGCGGCTACAGCGAGTGCGGCGATGGCTCGCCGGCCGTGTACACGTGCGTGG
ACGACCTGTGCCGCGGCTACGACCTCACGCGACTGTCATACGGGCGCAGCATCTTCACGGAA
CACGTGTTAGGCTTCGAGCTGGTGCCACCGTCTCTCTTTAACGTGGTGGTGGCCATACGCAA
CGAAGCCACGCGTACCAACCGCGCCGTGCGTCTGCCCGTGAGCACCGCTGCCGCGCCCGAGG
GCATCACGCTCTTTTACGGCCTGTACAACGCAGTGAAGGAATTCTGCCTGCGTCACCAGCTG
GACCCGCCGCTGCTACGCCACCTAGATAAATACTACGCCGGACTGCCGCCCGAGCTGAAGCA
GACGCGCGTCAACCTGCCGGCTCACTCGCGCTATGGCCCTCAAGCAGTGGATGCTCGCTGAT
AATAGGCTGGAGCCTCGGTGGCCATGCTTCTTGCCCCTTGGGCCTCCCCCCAGCCCCTCCTC
CCCTTCCTGCACCCGTACCCCCGTGGTCTTTGAATAAAGTCTGAGTGGGCGGC hCMV gL dimer (SEQ ID NO: 114)

UCAAGCUUUUGGACCCUCGUACAGAAGCUAAUACGACUCACUAUAGGGUGGCUCUUAUAUUU
CUUCUUACUCUUCUUUUCUCUCUUAUUUCCAUGUGCCGCCGCCCGGAUUGCGGCUUCUCUUU
CUCACCUGGACCGGUGAUACUGCUGUGGUGUUGCCUUCUGCUGCCCAUUGUUUCCUCAGCCG
CCGUGAGCGUCGCUCCUACCGCCGCCGAGAAAGUCCCCGCGGAGUGCCCCGAACUAACGCGC
CGAUGCUUGUUGGGUGAGGUGUUUGAGGGUGACAAGUAUGAAAGUUGGCUGCGCCCGUUGGU
GAAUGUUACCGGGCGCGAUGGCCCGCUAUCGCAACUUAUCCGUUACCGUCCCGUUACGCCGG
AGGCCGCCAACUCCGUGCUGUUGGACGAGGCUUUCCUGGACACUCUGGCCCUGCUGUACAAC
AAUCCGGAUCAAUUGCGGGCCCUGCUGACGCUGUUGAGCUCGGACACAGCGCCGCGCUGGAU
GACGGUGAUGCGCGGCUACAGCGAGUGCGGCGAUGGCUCGCCGGCCGUGUACACGUGCGUGG
ACGACCUGUGCCGCGGCUACGACCUCACGCGACUGUCAUACGGGCGCAGCAUCUUCACGGAA
CACGUGUUAGGCUUCGAGCUGGUGCCACCGUCUCUCUUUAACGUGGUGGUGGCCAUACGCAA
CGAAGCCACGCGUACCAACCGCGCCGUGCGUCUGCCCGUGAGCACCGCUGCCGCGCCCGAGG
GCAUCACGCUCUUUUACGGCCUGUACAACGCAGUGAAGGAAUUCUGCCUGCGUCACCAGCUG
GACCCGCCGCUGCUACGCCACCUAGAUAAAUACUACGCCGGACUGCCGCCCGAGCUGAAGCA
GACGCGCGUCAACCUGCCGGCUCACUCGCGCUAUGGCCCUCAAGCAGUGGAUGCUCGCUGAU

-continued

AAUAGGCUGGAGCCUCGGUGGCCAUGCUUCUUGCCCCUUGGGCCUCCCCCCAGCCCCUCCUC

CCCUUCCUGCACCCGUACCCCCGUGGUCUUUGAAUAAAGUCUGAGUGGGCGGC hCMV UL128 penta (SEQ ID NO: 22)

TCAAGCTTTTGGACCCTCGTACAGAAGCTAATACGACTCACTATAGGGTTCGGCTGGTACAG

GCTAACCAGAAGACAGATAAGAGCCTCCATGAGTCCCAAAGATCTGACGCCGTTCTTGACGG

CGTTGTGGCTGCTATTGGGTCACAGCCGCGTGCCGCGGGTGCGCGCAGAAGAATGTTGCGAA

TTCATAAACGTCAACCACCCGCCGGAACGCTGTTACGATTTCAAAATGTGCAATCGCTTCAC

CGTCGCGCTGCGGTGTCCGGACGGCGAAGTCTGCTACAGTCCCGAGAAAACGGCTGAGATTC

GCGGGATCGTCACCACCATGACCCATTCATTGACACGCCAGGTCGTACACAACAAACTGACG

AGCTGCAACTACAATCCGTTATACCTCGAAGCTGACGGGCGAATACGCTGCGGCAAAGTAAA

CGACAAGGCGCAGTACCTGCTGGGCGCCGCTGGCAGCGTTCCCTATCGATGGATCAATCTGG

AATACGACAAGATAACCCGGATCGTGGGCCTGGATCAGTACCTGGAGAGCGTTAAGAAACAC

AAACGGCTGGATGTGTGCCGCGCTAAAATGGGCTATATGCTGCAGTGATAATAGGCTGGAGC

CTCGGTGGCCATGCTTCTTGCCCCTTGGGCCTCCCCCCAGCCCCTCCTCCCCTTCCTGCACC

CGTACCCCCGTGGTCTTTGAATAAAGTCTGAGTGGGCGGC hCMV UL128 penta (SEQ ID NO: 99)

UCAAGCUUUUGGACCCUCGUACAGAAGCUAAUACGACUCACUAUAGGGUUCGGCUGGUACAG

GCUAACCAGAAGACAGAUAAGAGCCUCCAUGAGUCCCAAAGAUCUGACGCCGUUCUUGACGG

CGUUGUGGCUGCUAUUGGGUCACAGCCGCGUGCCGCGGGUGCGCGCAGAAGAAUGUUGCGAA

UUCAUAAACGUCAACCACCCGCCGGAACGCUGUUACGAUUUCAAAAUGUGCAAUCGCUUCAC

CGUCGCGCUGCGGUGUCCGGACGGCGAAGUCUGCUACAGUCCCGAGAAAACGGCUGAGAUUC

GCGGGAUCGUCACCACCAUGACCCAUUCAUUGACACGCCAGGUCGUACACAACAAACUGACG

AGCUGCAACUACAAUCCGUUAUACCUCGAAGCUGACGGGCGAAUACGCUGCGGCAAAGUAAA

CGACAAGGCGCAGUACCUGCUGGGCGCCGCUGGCAGCGUUCCCUAUCGAUGGAUCAAUCUGG

AAUACGACAAGAUAACCCGGAUCGUGGGCCUGGAUCAGUACCUGGAGAGCGUUAAGAAACAC

AAACGGCUGGAUGUGUGCCGCGCUAAAAUGGGCUAUAUGCUGCAGUGAUAAUAGGCUGGAGC

CUCGGUGGCCAUGCUUCUUGCCCCUUGGGCCUCCCCCCAGCCCCUCCUCCCCUUCCUGCACC

CGUACCCCCGUGGUCUUUGAAUAAAGUCUGAGUGGGCGGC hCMV-UL130 penta (SEQ ID NO: 23)

TCAAGCTTTTGGACCCTCGTACAGAAGCTAATACGACTCACTATAGGGAGGCTCTTATCTGT

CTTCTCAGTCCGAATTCGAAGTACGGCTACCATGCTGCGGCTTCTGCTTCGTCACCACTTTC

ACTGCCTGCTTCTGTGCGCGGTTTGGGCAACGCCCTGTCTGGCGTCTCCGTGGTCGACGCTA

ACAGCAAACCAGAATCCGTCCCCGCCATGGTCTAAACTGACGTATTCCAAACCGCATGACGC

GGCGACGTTTTACTGTCCTTTTCTCTATCCCTCGCCCCCACGATCCCCCTTGCAATTCTCGG

GGTTCCAGCGGGTATCAACGGGTCCCGAGTGTCGCAACGAGACCCTGTATCTGCTGTACAAC

CGGGAAGGCCAGACCTTGGTGGAGAGAAGCTCCACCTGGGTGAAAAAGGTGATCTGGTACCT

GAGCGGTCGGAACCAAACCATCCTCCAACGGATGCCCCGAACGGCTTCGAAACCGAGCGACG

GAAACGTGCAGATCAGCGTGGAAGACGCCAAGATTTTTGGAGCGCACATGGTGCCCAAGCAG

ACCAAGCTGCTACGCTTCGTCGTCAACGATGGCACACGTTATCAGATGTGTGTGATGAAGCT

GGAGAGCTGGGCTCACGTCTTCCGGGACTACAGCGTGTCTTTTCAGGTGCGATTGACGTTCA

CCGAGGCCAATAACCAGACTTACACCTTCTGCACCCATCCCAATCTCATCGTTTGATAATAG

-continued

GCTGGAGCCTCGGTGGCCATGCTTCTTGCCCCTTGGGCCTCCCCCCAGCCCCTCCTCCCCTT

CCTGCACCCGTACCCCCGTGGTCTTTGAATAAAGTCTGAGTGGGCGGC hCMV-UL130 penta (SEQ ID NO: 100)

UCAAGCUUUUGGACCCUCGUACAGAAGCUAAUACGACUCACUAUAGGGAGGCUCUUAUCUGU

CUUCUCAGUCCGAAUUCGAAGUACGGCUACCAUGCUGCGGCUUCUGCUUCGUCACCACUUUC

ACUGCCUGCUUCUGUGCGCGGUUUGGGCAACGCCCUGUCUGGCGUCUCCGUGGUCGACGCUA

ACAGCAAACCAGAAUCCGUCCCCGCCAUGGUCUAAACUGACGUAUUCCAAACCGCAUGACGC

GGCGACGUUUUACUGUCCUUUUCUCUAUCCCUCGCCCCCACGAUCCCCCUUGCAAUUCUCGG

GGUUCCAGCGGGUAUCAACGGGUCCCGAGUGUCGCAACGAGACCCUGUAUCUGCUGUACAAC

CGGGAAGGCCAGACCUUGGUGGAGAGAAGCUCCACCUGGGUGAAAAAGGUGAUCUGGUACCU

GAGCGGUCGGAACCAAACCAUCCUCCAACGGAUGCCCCGAACGGCUUCGAAACCGAGCGACG

GAAACGUGCAGAUCAGCGUGGAAGACGCCAAGAUUUUUGGAGCGCACAUGGUGCCCAAGCAG

ACCAAGCUGCUACGCUUCGUCGUCAACGAUGGCACACGUUAUCAGAUGUGUGUGAUGAAGCU

GGAGAGCUGGGCUCACGUCUUCCGGGACUACAGCGUGUCUUUUCAGGUGCGAUUGACGUUCA

CCGAGGCCAAUAACCAGACUUACACCUUCUGCACCCAUCCCAAUCUCAUCGUUUGAUAAUAG

GCUGGAGCCUCGGUGGCCAUGCUUCUUGCCCCUUGGGCCUCCCCCCAGCCCCUCCUCCCCUU

CCUGCACCCGUACCCCCGUGGUCUUUGAAUAAAGUCUGAGUGGGCGGC hCMVUL130 trimer (SEQ ID NO: 24)

TCAAGCTTTTGGACCCTCGTACAGAAGCTAATACGACTCACTATAGGGTGGCTCTTATATTT

CTTCTTAGTCCGAATTCGAAGTACGGCTACATGCTGCGGCTTCTGCTTCGTCACCACTTTCA

CTGCCTGCTTCTGTGCGCGGTTTGGGCAACGCCGTGTCTGGCGTCTCCGTGGTCGACGCTAA

CAGCAAACCAGAATCCGTCCCCGCCATGGTCTAAACTGACGTATTCCAAACCGCATGACGCG

GCGACGTTTTACTGTCCTTTTCTCTATCCCTCGCCCCCACGATCCCCCTTGCAATTCTCGGG

GTTCCAGCGGGTATCAACGGGTCCCGAGTGTCGCAACGAGACCCTGTATCTGCTGTACAACC

GGGAAGGCCAGACCTTGGTGGAGAGAAGCTCCACCTGGGTGAAAAAGGTGATCTGGTACCTG

AGCGGTCGGAACCAAACCATCCTCCAACGGATGCCCCGAACGGCTTCGAAACCGAGCGACGG

AAACGTGCAGATCAGCGTGGAAGACGCCAAGATTTTTGGAGCGCACATGGTGCCCAAGCAGA

CCAAGCTGCTACGCTTCGTCGTCAACGATGGCACACGTTATCAGATGTGTGTGATGAAGCTG

GAGAGCTGGGCTCACGTCTTCCGGGACTACAGCGTGTCTTTTCAGGTGCGATTGACGTTCAC

CGAGGCCAATAACCAGACTTACACCTTCTGCACCCATCCCAATCTCATCGTTTGATAATAGG

CTGGAGCCTCGGTGGCCATGCTTCTTGCCCCTTGGGCCTCCCCCCAGCCCCTCCTCCCCTTC

CTGCACCCGTACCCCCGTGGTCTTTGAATAAAGTCTGAGTGGGCGGC hCMVUL130 trimer (SEQ ID NO: 115)

UCAAGCUUUUGGACCCUCGUACAGAAGCUAAUACGACUCACUAUAGGGUGGCUCUUAUAUUU

CUUCUUAGUCCGAAUUCGAAGUACGGCUACAUGCUGCGGCUUCUGCUUCGUCACCACUUUCA

CUGCCUGCUUCUGUGCGCGGUUUGGGCAACGCCCUGUCUGGCGUCUCCGUGGUCGACGCUAA

CAGCAAACCAGAAUCCGUCCCCGCCAUGGUCUAAACUGACGUAUUCCAAACCGCAUGACGCG

GCGACGUUUUACUGUCCUUUUCUCUAUCCCUCGCCCCCACGAUCCCCCUUGCAAUUCUCGGG

GUUCCAGCGGGUAUCAACGGGUCCCGAGUGUCGCAACGAGACCCUGUAUCUGCUGUACAACC

GGGAAGGCCAGACCUUGGUGGAGAGAAGCUCCACCUGGGUGAAAAAGGUGAUCUGGUACCUG

-continued

AGCGGUCGGAACCAAACCAUCCUCCAACGGAUGCCCCGAACGGCUUCGAAACCGAGCGACGG

AAACGUGCAGAUCAGCGUGGAAGACGCCAAGAUUUUUGGAGCGCACAUGGUGCCCAAGCAGA

CCAAGCUGCUACGCUUCGUCGUCAACGAUGGCACACGUUAUCAGAUGUGUGUGAUGAAGCUG

GAGAGCUGGGCUCACGUCUUCCGGGACUACAGCGUGUCUUUUCAGGUGCGAUUGACGUUCAC

CGAGGCCAAUAACCAGACUUACACCUUCUGCACCCAUCCCAAUCUCAUCGUUUGAUAAUAGG

CUGGAGCCUCGGUGGCCAUGCUUCUUGCCCCUUGGGCCUCCCCCCAGCCCCUCCUCCCCUUC

CUGCACCCGUACCCCCGUGGUCUUUGAAUAAAGUCUGAGUGGGCGGC hCMV-UL131A penta (SEQ ID NO: 25)

TCAAGCTTTTGGACCCTCGTACAGAAGCTAATACGACTCACTATAGGGTAGCCGTACTTCGA

ATTCGGACAAGCTTCTCTCTCGTCTGTCCATGCGGCTGTGTCGGGTGTGGCTGTCTGTTTGT

CTGTGCGCCGTGGTGCTGGGTCAGTGCCAGCGGGAAACCGCGGAAAAAAACGATTATTACCG

AGTACCGCATTACTGGGACGCGTGCTCTCGCGCGCTGGCCGACCAAACCCGTTACAAGTATG

TGGAACAGCTCGTGGACCTCACGTTGAACTACCACTACGATGCGAGCCACGGCTTGGACAAC

TTTGACGTGCTCAAGAGAATCAACGTGACCGAGGTGTCGTTGCTCATCAGCGACTTTAGACG

TCAGAACCGTCGCGGCGGCACCAACAAAAGGACCACGTTCAACGCCGCCGGTTCGCTGGCGC

CACACGCCCGGAGCCTCGAGTTCAGCGTGCGGCTCTTTGCCAACTGATAATAGGCTGGAGCC

TCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC hCMV-UL131A penta (SEQ ID NO: 101)

UCAAGCUUUUGGACCCUCGUACAGAAGCUAAUACGACUCACUAUAGGGUAGCCGUACUUCGA

AUUCGGACAAGCUUCUCUCUCGUCUGUCCAUGCGGCUGUGUCGGGUGUGGCUGUCUGUUUGU

CUGUGCGCCGUGGUGCUGGGUCAGUGCCAGCGGGAAACCGCGGAAAAAAACGAUUAUUACCG

AGUACCGCAUUACUGGGACGCGUGCUCUCGCGCGCUGCCCGACCAAACCCGUUACAAGUAUG

UGGAACAGCUCGUGGACCUCACGUUGAACUACCACUACGAUGCGAGCCACGGCUUGGACAAC

UUUGACGUGCUCAAGAGAAUCAACGUGACCGAGGUGUCGUUGCUCAUCAGCGACUUUAGACG

UCAGAACCGUCGCGGCGGCACCAACAAAAGGACCACGUUCAACGCCGCCGGUUCGCUGGCGC

CACACGCCCGGAGCCUCGAGUUCAGCGUGCGGCUCUUUGCCAACUGAUAAUAGGCUGGAGCC

UCGGUGGCCAUGCUUCUUGCCCCUUGGGCCUCCCCCCAGCCCCUCCUCCCCUUCCUGCACCC

GUACCCCCGUGGUCUUUGAAUAAAGUCUGAGUGGGCGGC hCMVUL131A trimer (SEQ ID NO: 26)

TCAAGCTTTTGGACCCTCGTACAGAAGCTAATACGACTCACTATAGGGTAGCCGTACTTCGA

ATTCGGACTTTCTTTTCTCTCTTATTTCCATGCGGCTGTGTCGGGTGTGGCTGTCTGTTTGT

CTGTGCGCCGTGGTGCTGGGTCAGTGCCAGCGGGAAACCGCGGAAAAAAACGATTATTACCG

AGTACCGCATTACTGGGACGCGTGCTCTCGCGCGCTGCCCGACCAAACCCGTTACAAGTATG

TGGAACAGCTCGTGGACCTCACGTTGAACTACCACTACGATGCGAGCCACGGCTTGGACAAC

TTTGACGTGCTCAAGAGAATCAACGTGACCGAGGTGTCGTTGCTCATCAGCGACTTTAGACG

TCAGAACCGTCGCGGCGGCACCAACAAAAGGACCACGTTCAACGCCGCCGGTTCGCTGGCGC

CACACGCCCGGAGCCTCGAGTTCAGCGTGCGGCTCTTTGCCAACTGATAATAGGCTGGAGCC

TCGGTGGCCATGCTTCTTGCCCCTTGGGCCTCCCCCCAGCCCCTCCTCCCCTTCCTGCACCC

GTACCCCCGTGGTCTTTGAATAAAGTCTGAGTGGGCGGC

-continued hCMVUL131A trimer (SEQ ID NO: 102)

UCAAGCUUUUGGACCCUCGUACAGAAGCUAAUACGACUCACUAUAGGGUAGCCGUACUUCGA

AUUCGGACUUUCUUUUCUCUCUUAUUUCCAUGCGGCUGUGUCGGGUGUGGCUGUCUGUUUGU

CUGUGCGCCGUGGUGCUGGGUCAGUGCCAGCGGGAAACCGCGGAAAAAAACGAUUAUUACCG

AGUACCGCAUUACUGGGACGCGUGCUCUCGCGCGCUGCCCGACCAAACCCGUUACAAGUAUG

UGGAACAGCUCGUGGACCUCACGUUGAACUACCACUACGAUGCGAGCCACGGCUUGGACAAC

UUUGACGUGCUCAAGAGAAUCAACGUGACCGAGGUGUCGUUGCUCAUCAGCGACUUUAGACG

UCAGAACCGUCGCGGCGGCACCAACAAAAGGACCACGUUCAACGCCGCCGGUUCGCUGGCGC

CACACGCCCGGAGCCUCGAGUUCAGCGUGCGGCUCUUUGCCAACUGAUAAUAGGCUGGAGCC

UCGGUGGCCAUGCUUCUUGCCCCUUGGGCCUCCCCCCAGCCCCUCCUCCCCUUCCUGCACCC

GUACCCCCGUGGUCUUUGAAUAAAGUCUGAGUGGGCGGC

Example 16: hCMV Vaccine—hCMV UL Fusion Sequences

A hCMV vaccine may comprise, for example, at least one RNA polynucleotide encoded by at least one of the following sequences or by at least one fragment or epitope of the following sequences. In some embodiments, a hCMV vaccine may comprise at least one RNA polynucleotide comprising at least one of the mRNA sequences listed below or at least one fragment of the mRNA sequences listed below.

hCMV pp65-IE1, hCMV UL83-UL123 fusion (SEQ ID NO: 27)

TCAAGCTTTTGGACCCTCGTACAGAAGCTAATACGACTCACTATAGGGAAATAAGAGAGAAA

AGAAGAGTAAGAAGAAATATAAGAGCCACCATGGAGTCGCGCGGTCGCCGTTGTCCCGAAAT

GATATCCGTACTGGGTCCCATTTCGGGGCACGTGCTGAAAGCCGTGTTTAGTCGCGGCGATA

CGCCGGTGCTGCCGCACGAGACGCGACTCCTGCAGACGGGTATCCACGTACGCGTGAGCCAG

CCCTCGCTGATCCTGGTGTCGCAGTACACGCCCGACTCGACGCCATGCCACCGCGGCGACAA

TCAGCTGCAGGTGCAGCACACGTACTTTACGGGCAGCGAGGTGGAGAACGTGTCGGTCAACG

TGCACAACCCCACGGGCCGAAGCATCTGCCCCAGCCAAGAGCCCATGTCGATCTATGTGTAC

GCGCTGCCGCTCAAGATGCTGAACATCCCCAGCATCAACGTGCACCACTACCCGTCGGCGGC

CGAGCGCAAACACCGACACCTGCCCGTAGCCGACGCTGTTATTCACGCGTCGGGCAAGCAGA

TGTGGCAGGCGCGTCTCACGGTCTCGGGACTGGCCTGGACGCGTCAGCAGAACCAGTGGAAA

GAGCCCGACGTCTACTACACGTCAGCGTTCGTGTTTCCCACCAAGGACGTGGCACTGCGGCA

CGTGGTGTGCGCGCACGAGCTGGTTTGCTCCATGGAGAACACGCGCGCAACCAAGATGCAGG

TGATAGGTGACCAGTACGTCAAGGTGTACCTGGAGTCCTTCTGCGAGGACGTGCCCTCCGGC

AAGCTCTTTATGCACGTCACGCTGGGCTCTGACGTGGAAGAGGACCTAACGATGACCCGCAA

CCCGCAACCCTTCATGCGCCCCCACGAGCGCAACGGCTTTACGGTGTTGTGTCCCAAAAATA

TGATAATCAAACCGGGCAAGATCTCGCACATCATGCTGGATGTGGCTTTTACCTCACACGAG

CATTTTGGGCTGCTGTGTCCCAAGAGCATCCCGGGCCTGAGCATCTCAGGTAACCTGTTGAT

GAACGGGCAGCAAATCTTCCTGGAGGTACAAGCGATACGCGAGACCGTGGAACTGCGTCAGT

ACGATCCCGTGGCTGCGCTCTTCTTTTTCGATATCGACTTGTTGCTGCAGCGCGGGCCTCAG

TACAGCGAGCACCCCACCTTCACCAGCCAGTATCGCATCCAGGGCAAGCTTGAGTACCGACA

CACCTGGGACCGGCACGACGAGGGTGCCGCCCAGGGCGACGACGACGTCTGGACCAGCGGAT

CGGACTCCGACGAAGAACTCGTAACCACCGAGCGTAAGACGCCCCGCGTCACCGGCGGCGGC

GCCATGGCGAGCGCCTCCACTTCCGCGGGCCGCAAACGCAAATCAGCATCCTCGGCGACGGC

GTGCACGGCGGGCGTTATGACACGCGGCCGCCTTAAGGCCGAGTCCACCGTCGCGCCCGAAG

-continued

AGGACACCGACGAGGATTCCGACAACGAAATCCACAATCCGGCCGTGTTCACCTGGCCGCCC

TGGCAGGCCGGCATCCTGGCCCGCAACCTGGTGCCCATGGTGGCTACGGTTCAGGGTCAGAA

TCTGAAGTACCAGGAGTTCTTCTGGGACGCCAACGACATCTACCGCATCTTCGCCGAATTGG

AAGGCGTATGGCAGCCCGCTGCGCAACCCAAACGTCGCCGCCACCGGCAAGACGCCTTGCCC

GGGCCATGCATCGCCTCGACGCCCAAAAAGCACCGAGGTGAGTCCTCTGCCAAGAGAAAGAT

GGACCCTGATAATCCTGACGAGGGCCCTTCCTCCAAGGTGCCACGGCCCGAGACACCCGTGA

CCAAGGCCACGACGTTCCTGCAGACTATGTTAAGGAAGGAGGTTAACAGTCAGCTGAGCCTG

GGAGACCCGCTGTTCCCAGAATTGGCCGAAGAATCCCTCAAAACCTTTGAACAAGTGACCGA

GGATTGCAACGAGAACCCCGAAAAAGATGTCCTGACAGAACTCGTCAAACAGATTAAGGTTC

GAGTGGACATGGTGCGGCATAGAATCAAGGAGCACATGCTGAAAAAATATACCCAGACGGAA

GAAAAATTCACTGGCGCCTTTAATATGATGGGAGGATGTTTGCAGAATGCCTTAGATATCTT

AGATAAGGTTCATGAGCCTTTCGAGGACATGAAGTGTATTGGGCTAACTATGCAGAGCATGT

ATGAGAACTACATTGTACCTGAGGATAAGCGGGAGATGTGGATGGCTTGTATTAAGGAGCTG

CATGATGTGAGCAAGGGCGCCGCTAACAAGTTGGGGGGTGCACTGCAGGCTAAGGCCCGTGC

TAAAAAGGATGAACTTAGGAGAAAGATGATGTATATGTGCTACAGGAATATAGAGTTCTTTA

CCAAGAACTCAGCCTTCCCTAAGACCACCAATGGCTGCAGTCAGGCCATGGCGGCATTGCAG

AACTTGCCTCAGTGCTCTCCTGATGAGATTATGTCTTATGCCCAGAAAATCTTTAAGATTTT

GGATGAGGAGAGAGACAAGGTGCTCACGCACATTGATCACATATTTATGGATATCCTCACTA

CATGTGTGGAAACAATGTGTAATGAGTACAAGGTCACTAGTGACGCTTGTATGATGACCATG

TACGGGGGCATCTCTCTCTTAAGTGAGTTCTGTCGGGTGCTGTGCTGCTATGTCTTAGAGGA

GACTAGTGTGATGCTGGCCAAGCGGCCTCTGATAACCAAGCCTGAGGTTATCAGTGTAATGA

AGCGCCGCATTGAGGAGATCTGCATGAAGGTCTTTGCCCAGTACATTCTGGGGGCCGATCCT

TTGAGAGTCTGCTCTCCTAGTGTGGATGACCTACGGGCCATCGCCGAGGAGTCAGATGAGGA

AGAGGCTATTGTAGCCTACACTTTGGCCACCGCTGGTGCCAGCTCCTCTGATTCTCTGGTGT

CACCTCCAGAGTCCCCTGTACCCGCGACTATCCCTCTGTCCTCAGTAATTGTGGCTGAGAAC

AGTGATCAGGAAGAAAGTGAACAGAGTGATGAGGAACAGGAGGAGGGTGCTCAGGAGGAGCG

GGAGGACACTGTGTCTGTCAAGTCTGAGCCAGTGTCTGAGATAGAGGAAGTTGCCTCAGAGG

AAGAGGAGGATGGTGCTGAGGAACCCACCGCCTCTGGAGGCAAGAGCACCCACCCTATGGTG

ACTAGAAGCAAGGCTGACCAGTGATAATAGGCTGGAGCCTCGGTGGCCATGCTTCTTGCCCC

TTGGGCCTCCCCCCAGCCCCTCCTCCCCTTCCTGCACCCGTACCCCCGTGGTCTTTGAATAA

AGTCTGAGTGGGCGGC hCMV pp65-IE1, hCMV UL83-UL123 fusion (SEQ ID NO: 103)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAGUCGCGCGGUCGCCGUUGUCCCGAAAU

GAUAUCCGUACUGGGUCCCAUUUCGGGGCACGUGCUGAAAGCCGUGUUUAGUCGCGGCGAUA

CGCCGGUGCUGCCGCACGAGACGCGACUCCUGCAGACGGGUAUCCACGUACGCGUGAGCCAG

CCCUCGCUGAUCCUGGUGUCGCAGUACACGCCCGACUCGACGCCAUGCCACCGCGGCGACAA

UCAGCUGCAGGUGCAGCACACGUACUUUACGGGCAGCGAGGUGGAGAACGUGUCGGUCAACG

UGCACAACCCCACGGGCCGAAGCAUCUGCCCCAGCCAAGAGCCCAUGUCGAUCUAUGUGUAC

GCGCUGCCGCUCAAGAUGCUGAACAUCCCCAGCAUCAACGUGCACCACUACCCGUCGGCGGC

CGAGCGCAAACACCGACACCUGCCCGUAGCCGACGCUGUUAUUCACGCGUCGGGCAAGCAGA

-continued

UGUGGCAGGCGCGUCUCACGGUCUCGGGACUGGCCUGGACGCGUCAGCAGAACCAGUGGAAA

GAGCCCGACGUCUACUACACGUCAGCGUUCGUGUUUCCCACCAAGGACGUGGCACUGCGGCA

CGUGGUGUGCGCGCACGAGCUGGUUUGCUCCAUGGAGAACACGCGCGCAACCAAGAUGCAGG

UGAUAGGUGACCAGUACGUCAAGGUGUACCUGGAGUCCUUCUGCGAGGACGUGCCCUCCGGC

AAGCUCUUUAUGCACGUCACGCUGGGCUCUGACGUGGAAGAGGACCUAACGAUGACCCGCAA

CCCGCAACCCUUCAUGCGCCCCCACGAGCGCAACGGCUUUACGGUGUUGUGUCCCAAAAAUA

UGAUAAUCAAACCGGGCAAGAUCUCGCACAUCAUGCUGGAUGUGGCUUUUACCUCACACGAG

CAUUUUGGGCUGCUGUGUCCCAAGAGCAUCCCGGGCCUGAGCAUCUCAGGUAACCUGUUGAU

GAACGGGCAGCAAAUCUUCCUGGAGGUACAAGCGAUACGCGAGACCGUGGAACUGCGUCAGU

ACGAUCCCGUGGCUGCGCUCUUCUUUUUCGAUAUCGACUUGUUGCUGCAGCGCGGGCCUCAG

UACAGCGAGCACCCCACCUUCACCAGCCAGUAUCGCAUCCAGGGCAAGCUUGAGUACCGACA

CACCUGGGACCGGCACGACGAGGGUGCCGCCCAGGGCGACGACGACGUCUGGACCAGCGGAU

CGGACUCCGACGAAGAACUCGUAACCACCGAGCGUAAGACGCCCCGCGUCACCGGCGGCGGC

GCCAUGGCGAGCGCCUCCACUUCCGCGGGCCGCAAACGCAAAUCAGCAUCCUCGGCGACGGC

GUGCACGGCGGGCGUUAUGACACGCGGCCGCCUUAAGGCCGAGUCCACCGUCGCGCCCGAAG

AGGACACCGACGAGGAUUCCGACAACGAAAUCCACAAUCCGGCCGUGUUCACCUGGCCGCCC

UGGCAGGCCGGCAUCCUGGCCCGCAACCUGGUGCCCAUGGUGGCUACGGUUCAGGGUCAGAA

UCUGAAGUACCAGGAGUUCUUCUGGGACGCCAACGACAUCUACCGCAUCUUCGCCGAAUUGG

AAGGCGUAUGGCAGCCCGCUGCGCAACCCAAACGUCGCCGCCACCGGCAAGACGCCUUGCCC

GGGCCAUGCAUCGCCUCGACGCCCAAAAAGCACCGAGGUGAGUCCUCUGCCAAGAGAAAGAU

GGACCCUGAUAAUCCUGACGAGGGCCCUUCCUCCAAGGUGCCACGGCCCGAGACACCCGUGA

CCAAGGCCACGACGUUCCUGCAGACUAUGUUAAGGAAGGAGGUUAACAGUCAGCUGAGCCUG

GGAGACCCGCUGUUCCCAGAAUUGGCCGAAGAAUCCCUCAAAACCUUUGAACAAGUGACCGA

GGAUUGCAACGAGAACCCCGAAAAAGAUGUCCUGACAGAACUCGUCAAACAGAUUAAGGUUC

GAGUGGACAUGGUGCGGCAUAGAAUCAAGGAGCACAUGCUGAAAAAAUAUACCCAGACGGAA

GAAAAAUUCACUGGCGCCUUUAAUAUGAUGGGAGGAUGUUUGCAGAAUGCCUUAGAUAUCUU

AGAUAAGGUUCAUGAGCCUUUCGAGGACAUGAAGUGUAUUGGGCUAACUAUGCAGAGCAUGU

AUGAGAACUACAUUGUACCUGAGGAUAAGCGGGAGAUGUGGAUGGCUUGUAUUAAGGAGCUG

CAUGAUGUGAGCAAGGGCGCCGCUAACAAGUUGGGGGGUGCACUGCAGGCUAAGGCCCGUGC

UAAAAAGGAUGAACUUAGGAGAAAGAUGAUGUAUAUGUGCUACAGGAAUAUAGAGUUCUUUA

CCAAGAACUCAGCCUUCCCUAAGACCACCAAUGGCUGCAGUCAGGCCAUGGCGGCAUUGCAG

AACUUGCCUCAGUGCUCUCCUGAUGAGAUUAUGUCUUAUGCCCAGAAAAUCUUUAAGAUUUU

GGAUGAGGAGAGAGACAAGGUGCUCACGCACAUUGAUCACAUAUUUAUGGAUAUCCUCACUA

CAUGUGUGGAAACAAUGUGUAAUGAGUACAAGGUCACUAGUGACGCUUGUAUGAUGACCAUG

UACGGGGGCAUCUCUCUCUUAAGUGAGUUCUGUCGGGUGCUGUGCUGCUAUGUCUUAGAGGA

GACUAGUGUGAUGCUGGCCAAGCGGCCUCUGAUAACCAAGCCUGAGGUUAUCAGUGUAAUGA

AGCGCCGCAUUGAGGAGAUCUGCAUGAAGGUCUUUGCCCAGUACAUUCUGGGGGCCGAUCCU

UUGAGAGUCUGCUCUCCUAGUGUGGAUGACCUACGGGCCAUCGCCGAGGAGUCAGAUGAGGA

AGAGGCUAUUGUAGCCUACACUUUGGCCACCGCUGGUGCCAGCUCCUCUGAUUCUCUGGUGU

CACCUCCAGAGUCCCCUGUACCCGCGACUAUCCCUCUGUCCUCAGUAAUUGUGGCUGAGAAC

-continued

AGUGAUCAGGAAGAAAGUGAACAGAGUGAUGAGGAACAGGAGGAGGGUGCUCAGGAGGAGCG

GGAGGACACUGUGUCUGUCAAGUCUGAGCCAGUGUCUGAGAUAGAGGAAGUUGCCUCAGAGG

AAGAGGAGGAUGGUGCUGAGGAACCCACCGCCUCUGGAGGCAAGAGCACCCACCCUAUGGUG

ACUAGAAGCAAGGCUGACCAGUGAUAAUAGGCUGGAGCCUCGGUGGCCAUGCUUCUUGCCCC

UUGGGCCUCCCCCCAGCCCCUCCUCCCCUUCCUGCACCCGUACCCCCGUGGUCUUUGAAUAA

AGUCUGAGUGGGCGGC hCMV pp65-IE1FLAG, hCMV UL83-UL123 FLAG tag (SEQ ID NO: 28)

TCAAGCTTTTGGACCCTCGTAGAGAAGCTAATACGACTCACTATAGGGAAATAAGAGAGAAA

AGAAGAGTAAGAAGAAATATAAGAGCCACCATGGAGTCGCGCGGTCGCCGTTGTCCCGAAAT

GATATCCGTACTGGGTCCCATTTCGGGGCACGTGCTGAAAGCCGTGTTTAGTCGCGGCGATA

CGCCGGTGCTGCCGCACGAGACGCGACTCCTGCAGACGGGTATCCACGTACGCGTGAGCCAG

CCCTCGCTGATCCTGGTGTCGCAGTACACGCCCGACTCGACGCCATGCCACCGCGGCGACAA

TCAGCTGCAGGTGCAGCACACGTACTTTACGGGCAGCGAGGTGGAGAACGTGTCGGTCAACG

TGCACAACCCCACGGGCCGAAGCATCTGCCCCAGCCAAGAGCCCATGTCGATCTATGTGTAC

GCGCTGCCGCTCAAGATGCTGAACATCCCCAGCATCAACGTGCACCACTACCCGTCGGCGGC

CGAGCGCAAACACCGACACCTGCCCGTAGCCGACGCTGTTATTCACGCGTCGGGCAAGCAGA

TGTGGCAGGCGCGTCTCACGGTCTCGGGACTGGCCTGGACGCGTCAGCAGAACCAGTGGAAA

GAGCCCGACGTCTACTACACGTCAGCGTTCGTGTTTCCCACCAAGGACGTGGCACTGCGGCA

CGTGGTGTGCGCGCACGAGCTGGTTTGCTCCATGGAGAACACGCGCGCAACCAAGATGCAGG

TGATAGGTGACCAGTACGTCAAGGTGTACCTGGAGTCCTTCTGCGAGGACGTGCCCTCCGGC

AAGCTCTTTATGCACGTCACGCTGGGCTCTGACGTGGAAGAGGACCTAACGATGACCCGCAA

CCCGCAACCCTTCATGCGCCCCCACGAGCGCAACGGCTTTACGGTGTTGTGTCCCAAAAATA

TGATAATCAAACCGGGCAAGATCTCGCACATCATGCTGGATGTGGCTTTTACCTCACACGAG

CATTTTGGGCTGCTGTGTCCCAAGAGCATCCCGGGCCTGAGCATCTCAGGTAACCTGTTGAT

GAACGGGCAGCAAATCTTCCTGGAGGTACAAGCGATACGCGAGACCGTGGAACTGCGTCAGT

ACGATCCCGTGGCTGCGCTCTTCTTTTTCGATATCGACTTGTTGCTGCAGCGCGGGCCTCAG

TACAGCGAGCACCCCACCTTCACCAGCCAGTATCGCATCCAGGGCAAGCTTGAGTACCGACA

CACCTGGGACCGGCACGACGAGGGTGCCGCCCAGGGCGACGACGACGTCTGGACCAGCGGAT

CGGACTCCGACGAAGAACTCGTAACCACCGAGCGTAAGACGCCCCGCGTCACCGGCGGCGGC

GCCATGGCGAGCGCCTCCACTTCCGCGGGCCGCAAACGCAAATCAGCATCCTCGGCGACGGC

GTGCACGGCGGGCGTTATGACACGCGGCCGCCTTAAGGCCGAGTCCACCGTCGCGCCCGAAG

AGGACACCGACGAGGATTCCGACAACGAAATCCACAATCCGGCCGTGTTCACCTGGCCGCCC

TGGCAGGCCGGCATCCTGGCCCGCAACCTGGTGCCCATGGTGGCTACGGTTCAGGGTCAGAA

TCTGAAGTACCAGGAGTTCTTCTGGGACGCCAACGACATCTACCGCATCTTCGCCGAATTGG

AAGGCGTATGGCAGCCCGCTGCGCAACCCAAACGTCGCCGCCACCGGCAAGACGCCTTGCCC

GGGCCATGCATCGCCTCGACGCCCAAAAAGCACCGAGGTGAGTCCTCTGCCAAGAGAAAGAT

GGACCCTGATAATCCTGACGAGGGCCCTTCCTCCAAGGTGCCACGGCCCGAGACACCCGTGA

CCAAGGCCACGACGTTCCTGCAGACTATGTTAAGGAAGGAGGTTAACAGTCAGCTGAGCCTG

GGAGACCCGCTGTTCCCAGAATTGGCCGAAGAATCCCTCAAAACCTTTGAACAAGTGACCGA

GGATTGCAACGAGAACCCCGAAAAAGATGTCCTGACAGAACTCGTCAAACAGATTAAGGTTC

GAGTGGACATGGTGCGGCATAGAATCAAGGAGCACATGCTGAAAAAATATACCCAGACGGAA

-continued
GAAAAATTCACTGGCGCCTTTAATATGATGGGAGGATGTTTGCAGAATGCCTTAGATATCTT

AGATAAGGTTCATGAGCCTTTCGAGGACATGAAGTGTATTGGGCTAACTATGCAGAGCATGT

ATGAGAACTACATTGTACCTGAGGATAAGCGGGAGATGTGGATGGCTTGTATTAAGGAGCTG

CATGATGTGAGCAAGGGCGCCGCTAACAAGTTGGGGGGTGCACTGCAGGCTAAGGCCCGTGC

TAAAAAGGATGAACTTAGGAGAAAGATGATGTATATGTGCTACAGGAATATAGAGTTCTTTA

CCAAGAACTCAGCCTTCCCTAAGACCACCAATGGCTGCAGTCAGGCCATGGCGGCATTGCAG

AACTTGCCTCAGTGCTCTCCTGATGAGATTATGTCTTATGCCCAGAAAATCTTTAAGATTTT

GGATGAGGAGAGAGACAAGGTGCTCACGCACATTGATCACATATTTATGGATATCCTCACTA

CATGTGTGGAAACAATGTGTAATGAGTACAAGGTCACTAGTGACGCTTGTATGATGACCATG

TACGGGGGCATCTCTCTCTTAAGTGAGTTCTGTCGGGTGCTGTGCTGCTATGTCTTAGAGGA

GACTAGTGTGATGCTGGCCAAGCGGCCTCTGATAACCAAGCCTGAGGTTATCAGTGTAATGA

AGCGCCGCATTGAGGAGATCTGCATGAAGGTCTTTGCCCAGTACATTCTGGGGGCCGATCCT

TTGAGAGTCTGCTCTCCTAGTGTGGATGACCTACGGGCCATCGCCGAGGAGTCAGATGAGGA

AGAGGCTATTGTAGCCTACACTTTGGCCACCGCTGGTGCCAGCTCCTCTGATTCTCTGGTGT

CACCTCCAGAGTCCCCTGTACCCGCGACTATCCCTCTGTCCTCAGTAATTGTGGCTGAGAAC

AGTGATCAGGAAGAAAGTGAACAGAGTGATGAGGAACAGGAGGAGGGTGCTCAGGAGGAGCG

GGAGGACACTGTGTCTGTCAAGTCTGAGCCAGTGTCTGAGATAGAGGAAGTTGCCTCAGAGG

AAGAGGAGGATGGTGCTGAGGAACCCACCGCCTCTGGAGGCAAGAGCACCCACCCTATGGTG

ACTAGAAGCAAGGCTGACCAGGATTACAAGGACGATGACGATAAGTGATAATAGGCTGGAGC

CTCGGTGGCCATGCTTCTTGCCCCTTGGGCCTCCCCCCAGCCCCTCCTCCCCTTCCTGCACC

CGTACCCCCGTGGTCTTTGAATAAAGTCTGAGTGGGCGGC hCMV pp65-IE1, hCMV UL83-UL123 fusion (SEQ ID NO: 104)

UCAAGCUUUUGGACCCUCGUACAGAAGCUAAUACGACUCACUAUAGGGAAAUAAGAGAGAAA

AGAAGAGUAAGAAGAAAUAUAAGAGCCACCAUGGAGUCGCGCGGUCGCCGUUGUCCCGAAAU

GAUAUCCGUACUGGGUCCCAUUUCGGGGCACGUGCUGAAAGCCGUGUUUAGUCGCGGCGAUA

CGCCGGUGCUGCCGCACGAGACGCGACUCCUGCAGACGGGUAUCCACGUACGCGUGAGCCAG

CCCUCGCUGAUCCUGGUGUCGCAGUACACGCCCGACUCGACGCCAUGCCACCGCGGCGACAA

UCAGCUGCAGGUGCAGCACACGUACUUUACGGGCAGCGAGGUGGAGAACGUGUCGGUCAACG

UGCACAACCCCACGGGCCGAAGCAUCUGCCCCAGCCAAGAGCCCAUGUCGAUCUAUGUGUAC

GCGCUGCCGCUCAAGAUGCUGAACAUCCCCAGCAUCAACGUGCACCACUACCCGUCGGCGGC

CGAGCGCAAACACCGACACCUGCCCGUAGCCGACGCUGUUAUUCACGCGUCGGGCAAGCAGA

UGUGGCAGGCGCGUCUCACGGUCUCGGGACUGGCCUGGACGCGUCAGCAGAACCAGUGGAAA

GAGCCCGACGUCUACUACACGUCAGCGUUCGUGUUUCCCACCAAGGACGUGGCACUGCGGCA

CGUGGUGUGCGCGCACGAGCUGGUUUGCUCCAUGGAGAACACGCGCGCAACCAAGAUGCAGG

UGAUAGGUGACCAGUACGUCAAGGUGUACCUGGAGUCCUUCUGCGAGGACGUGCCCUCCGGC

AAGCUCUUUAUGCACGUCACGCUGGGCUCUGACGUGGAAGAGGACCUAACGAUGACCCGCAA

CCCGCAACCCUUCAUGCGCCCCCACGAGCGCAACGGCUUUACGGUGUUGUGUCCCAAAAAUA

UGAUAAUCAAACCGGGCAAGAUCUCGCACAUCAUGCUGGAUGUGGCUUUUACCUCACACGAG

CAUUUUGGGCUGCUGUGUCCCAAGAGCAUCCCGGGCCUGAGCAUCUCAGGUAACCUGUUGAU

GAACGGGCAGCAAAUCUUCCUGGAGGUACAAGCGAUACGCGAGACCGUGGAACUGCGUCAGU

-continued

ACGAUCCCGUGGCUGCGCUCUUCUUUUUCGAUAUCGACUUGUUGCUGCAGCGCGGGCCUCAG
UACAGCGAGCACCCCACCUUCACCAGCCAGUAUCGCAUCCAGGGCAAGCUUGAGUACCGACA
CACCUGGGACCGGCACGACGAGGGUGCCGCCCAGGGCGACGACGACGUCUGGACCAGCGGAU
CGGACUCCGACGAAGAACUCGUAACCACCGAGCGUAAGACGCCCCGCGUCACCGGCGGCGGC
GCCAUGGCGAGCGCCUCCACUUCCGCGGGCCGCAAACGCAAAUCAGCAUCCUCGGCGACGGC
GUGCACGGCGGGCGUUAUGACACGCGGCCGCCUUAAGGCCGAGUCCACCGUCGCGCCCGAAG
AGGACACCGACGAGGAUUCCGACAACGAAAUCCACAAUCCGGCCGUGUUCACCUGGCCGCCC
UGGCAGGCCGGCAUCCUGGCCCGCAACCUGGUGCCCAUGGUGGCUACGGUUCAGGGUCAGAA
UCUGAAGUACCAGGAGUUCUUCUGGGACGCCAACGACAUCUACCGCAUCUUCGCCGAAUUGG
AAGGCGUAUGGCAGCCCGCUGCGCAACCCAAACGUCGCCGCCACCGGCAAGACGCCUUGCCC
GGGCCAUGCAUCGCCUCGACGCCCAAAAAGCACCGAGGUGAGUCCUCUGCCAAGAGAAAGAU
GGACCCUGAUAAUCCUGACGAGGGCCCUUCCUCCAAGGUGCCACGGCCCGAGACACCCGUGA
CCAAGGCCACGACGUUCCUGCAGACUAUGUUAAGGAAGGAGGUUAACAGUCAGCUGAGCCUG
GGAGACCCGCUGUUCCCAGAAUUGGCCGAAGAAUCCCUCAAAACCUUUGAACAAGUGACCGA
GGAUUGCAACGAGAACCCCGAAAAAGAUGUCCUGACAGAACUCGUCAAACAGAUUAAGGUUC
GAGUGGACAUGGUGCGGCAUAGAAUCAAGGAGCACAUGCUGAAAAAAUAUACCCAGACGGAA
GAAAAAUUCACUGGCGCCUUUAAUAUGAUGGGAGGAUGUUUGCAGAAUGCCUUAGAUAUCUU
AGAUAAGGUUCAUGAGCCUUUCGAGGACAUGAAGUGUAUUGGGCUAACUAUGCAGAGCAUGU
AUGAGAACUACAUUGUACCUGAGGAUAAGCGGGAGAUGUGGAUGGCUUGUAUUAAGGAGCUG
CAUGAUGUGAGCAAGGGCGCCGCUAACAAGUUGGGGGGUGCACUGCAGGCUAAGGCCCGUGC
UAAAAAGGAUGAACUUAGGAGAAAGAUGAUGUAUAUGUGCUACAGGAAUAUAGAGUUCUUUA
CCAAGAACUCAGCCUUCCCUAAGACCACCAAUGGCUGCAGUCAGGCCAUGGCGGCAUUGCAG
AACUUGCCUCAGUGCUCUCCUGAUGAGAUUAUGUCUUAUGCCCAGAAAAUCUUUAAGAUUUU
GGAUGAGGAGAGAGACAAGGUGCUCACGCACAUUGAUCACAUAUUUAUGGAUAUCCUCACUA
CAUGUGUGGAAACAAUGUGUAAUGAGUACAAGGUCACUAGUGACGCUUGUAUGAUGACCAUG
UACGGGGGCAUCUCUCUCUUAAGUGAGUUCUGUCGGGUGCUGUGCUGCUAUGUCUUAGAGGA
GACUAGUGUGAUGCUGGCCAAGCGGCCUCUGAUAACCAAGCCUGAGGUUAUCAGUGUAAUGA
AGCGCCGCAUUGAGGAGAUCUGCAUGAAGGUCUUUGCCCAGUACAUUCUGGGGGCCGAUCCU
UUGAGAGUCUGCUCUCCUAGUGUGGAUGACCUACGGGCCAUCGCCGAGGAGUCAGAUGAGGA
AGAGGCUAUUGUAGCCUACACUUUGGCCACCGCUGGUGCCAGCUCCUCUGAUUCUCUGGUGU
CACCUCCAGAGUCCCCUGUACCCGCGACUAUCCCUCUGUCCUCAGUAAUUGUGGCUGAGAAC
AGUGAUCAGGAAGAAAGUGAACAGAGUGAUGAGGAACAGGAGGAGGGUGCUCAGGAGGAGCG
GGAGGACACUGUGUCUGUCAAGUCUGAGCCAGUGUCUGAGAUAGAGGAAGUUGCCUCAGAGG
AAGAGGAGGAUGGUGCUGAGGAACCCACCGCCUCUGGAGGCAAGAGCACCCACCCUAUGGUG
ACUAGAAGCAAGGCUGACCAGUGAUAAUAGGCUGGAGCCUCGGUGGCCAUGCUUCUUGCCCC
UUGGGCCUCCCCCCAGCCCCUCCUCCCCUUCCUGCACCCGUACCCCCGUGGUCUUUGAAUAA
AGUCUGAGUGGGCGGC

Example 17: hCMV Vaccine—hCMV Concatameric Sequences

A hCMV vaccine may comprise, for example, at least one RNA polynucleotide encoded by at least one of the sequences in FIGS. 25A-25H or by at least one fragment or epitope of the sequences in FIGS. 25A-25H. In some embodiments, a hCMV vaccine may comprise at least one RNA polynucleotide comprising at least one of the mRNA sequences listed in FIGS. 25A-25H or at least one fragment of the mRNA sequences listed in FIGS. 25A-25H.

Example 18: Immunogenicity Study

The instant study is designed to test the immunogenicity in mice of candidate CMV vaccines comprising an mRNA polynucleotide encoding the gH and gL glycoproteins or the UL128, UL130, and UL131A polypeptides obtained from MCMV.

Mice are vaccinated on week 0 and 4 via intramuscular (IM) or intradermal (ID) routes. One group remains unvaccinated and one is administered inactivated MCMV. Serum is collected from each mouse on weeks 1, 3 (pre-dose) and 5. Individual bleeds are tested for anti-gH and anti-gL activity or anti-UL128, anti-UL130, and anti-UL131A via ELISA assay from all three time points, and pooled samples from week 5 only are tested by Western blot using inactivated MCMV.

ELISA Immunoassays

Antibody production is measured in a sample by ELISA. Appropriately diluted samples were placed in 96-well plates precoated with a capture antibody directed against an epitope of the antibody. Serum samples typically were diluted 1:100 for the assay. Incubation and washing protocols were performed using routine methods. Data is read at 450 nm with wavelength. Data is reported and plotted.

Example 19: MCMV Challenge

The instant study is designed to test the efficacy in mice of candidate CMV vaccines against a lethal challenge using a mouse CMV vaccine comprising mRNAs encoding gH and gL or UL128, UL130, and UL131A. Due to the strict species specificity of CMV infection, there is no animal model available for study of HCMV infection and immunity. Murine cytomegalovirus (MCMV) infection is the most widely used mouse model simulating HCMV infection. In the current study, the immunogenicity and protective efficacy of MCMV gH, gL, UL128, UL130, UL131A antigens are investigated.

BALB/c mice are randomly divided into groups. The groups are respectively immunized with (1) 10 μg gB (positive control), (2) 10 μg gH and gL mRNAs (combination of separate sequences), (3) 10 μg gH-gL concatamer mRNA (single sequence), (4) 10 μg UL128, UL130, UL131A mRNAs (combination of separate sequences), (5) 10 μg UL128-UL130-UL131A concatamer mRNA (single sequence), (6) 10 μg gH-gL-UL128-UL130-UL131A concatamer mRNA (single sequence) and (7) PBS. Mice are immunized two times (second dose at day 28) by injection into the right quadriceps muscle (IM) or by intradermal administration (ID), and are challenged with a lethal dose (5×LD50, 200 μl/mouse) of SG-MCMV (Smith strain, 105 PFU) by intraperitoneal injection. This infection causes systemic virus replication in mice and death of all unvaccinated mice within one week after the challenge.

Endpoint is day 5 post infection, death or euthanasia. Animals displaying severe illness as determined by >30% weight loss, extreme lethargy or paralysis are euthanized. The protective effects of the DNA vaccines are evaluated comprehensively using infection symptoms of body temperature, weight loss, and survival. The mice are weighed and assessed daily in order to monitor weight loss, apparent physical condition (bristled hair and wounded skin), body temperature, and behaviour. The mice are humanely euthanized via cervical dislocation after chloroform (inhalation excess) in all cases in order to minimize or avoid animal suffering.

Example 20: MCMV Neutralization Assay

Mice are immunized according to the methods in Example 18. Mouse serum samples are collected 3 weeks after the second immunization. Serum samples are stored at −20° C. until use. Neutralizing antibody directed against MCMV are determined by a plaque reduction assay, for example, as described in Geoffroy F, et al., Murine cytomegalovirus inactivated by sodium periodate is innocuous and immunogenic in mice and protects them against death and infection. Vaccine. 1996; 14:1686-1694. Decomplemented sera (30 μl) are serially diluted 2-fold with MEM. Each dilution is mixed with 100 PFU MCMV in 30 μl of MEM and then incubated 1 hour at 4° C. and 1 hour at 37° C. The mixture is layered onto 3T3 monolayers and PFU are calculated by the standard plaque assay. A neutralization titer is expressed as the highest serum dilution required to achieve a 50% reduction in the number of plaques.

Example 21: IFN-γ ELISPOT Assay

Mice are immunized with gH or gL, or co-immunized with gH/gL mRNAs twice (day 0 and day 28) at a dosage of 10 μg by IM. Two weeks after the second immunization, splenocytes are isolated for ELISPOT assays. Immunospot are coated with rat anti-mouse IFN-γ mAb in accordance with manufacturer instructions, incubated at 4° C. overnight and then blocked with 200 μl of blocking solution. Subsequently, $2\times10^5$ lymphocytes are added to the wells in triplicate, stimulated with 10 μg/ml of corresponding gH or gL peptides or a gH/gL polypeptide mixture (for co-immunization group). After 18 hours, the lymphocytes are discarded and biotin-labeled anti-mouse IFN-γ Ab antibody is added to each well and incubated at 37° C. for 1 h. Next, diluted Streptavidin-HRP conjugate solution is added and incubated at room temperature for 2 hours. Finally, the plates are treated with 100 μl of AEC substrate solution and incubated at room temperature for 20 min in the dark. The reaction is stopped by washing with dematerialized water. Spots are quantified by an ELISPOT reader.

TABLE 2

| Human Cytomegalovirus Sequences | | | |
|---|---|---|---|
| SEQ ID NO: | Protein Name | Protein Sequence | Nucleotide Sequence (SEQ ID NO:) |
| 32 | gi\|52139248\|ref\|YP_081523.1\| envelope glycoprotein H [Human herpesvirus 5] | MRPGLPSYLIILAVCLFSHLLSSRYGAEAVSE PLDKAFHLLLNTYGRPIRFLRENTTQCTYNSS LRNSTVVRENAISFNFFQSYNQYYVFHMPRC LFAGPLAEQFLNQVDLTETLERYQQRLNTYA LVSKDLASYRSFSQQLKAQDSLGEQPTTVPP PIDLSIPHVWMPPQTTPHGWTESHTTSGLHR PHFNQTCILFDGHDLLFSTVTPCLHQGFYLID ELRYVKITLTEDFFVVTVSIDDDTPMLLIFGH LPRVLFKAPYQRDNFILRQTEKHELLVLVKK DQLNRHSYLKDPDFLDAALDFNYLDLSALL RNSFHRYAVDVLKSGRCQMLDRRTVEMAF AYALALFAAARQEEAGAQVSVPRALDRQAA LLQIQEFMITCLSQTPPRTTLLLYPTAVDLAK RALWTPNQITDITSLVRLVYILSKQNQQHLIP QWALRQIADFALKLHKTHLASFLSAFARQEL YLMGSLVHSMLVHTTERREIFIVETGLCSLA ELSHFTQLLAHPHHEYLSDLYTPCSSSGRRD HSLERLTRLFPDATVPATVPAALSILSTMQPS TLETFPDLFCLPLGESFSALTVSEHVSYIVTN QYLIKGISYPVSTTVVGQSLIITQTDSQTKCEL TRNMHTTHSITVALNISLENCAFCQSALLEY DDTQGVINIMYMHDSDDVLFALDPYNEVVV SSPRTHYLMLLKNGTVLEVTDVVVDATDSR LLMMSVYALSAIIGIYLLYRMLKTC | 1 |
| 33 | gi\|822887470\|gb\|AKI08892.1\| RL1 protein [Human herpesvirus 5] | MPATDTNSTHTTPLHPENQHTLPLHHSTTQP HVQTSDKHADKQHRTQMELDAADYAACAQ ARQHLYGQTQPQPHAYPNANPQESAHFCTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 3 |
| 34 | gi\|822888315\|gb\|AKI09732.1\| RL1 protein [Human herpesvirus 5] | MPATDTNSTHTTPLHPEDQHTLPLQHNTTQP HVQTSDKPADKQHRTQMELDAADYAACAQ ARQHLYGQTQ PQLHAYPNANPQESAHFCTDNQHRLTNLLH NIGEGAALGYPVPRAEIRRGGGDWADSASD FDADCWCMWG RFGTMGRQPVVTLLLARQRDGLADWNVVR CRGTGFRAHDSEDGVSVWRQHLVFLLGGHG RRVQLERPSAGEAQARGLLPRIRITPVSTSPR PKAPQPTTSTASHPHATARPDHTLFPVPSTPS ATVHNPRNYAVQLHAETTRTWRWARRGER GAWMPAETFTCPKDKRPW | 6 |
| 35 | gi\|136968\|sp\|P16750.1\| GO_HCMVA RecName: Full = Glycoprotein O; Short = gO; Flags: Precursor | MGRKEMMVRDVPKMVFLISISFLLVSFINCK VMSKALYNRPWRGLVLSKIGKYKLDQLKLE ILRQLETTISTKYNVSKQPVKNLTMNMTEFP QYYILAGPIQNYSITYLWFDFYSTQLRKPAK YVYSQYNHTAKTITFRPPPCGTVPSMTCLSE MLNVSKRNDTGEQGCGNFTTFNPMFFNVPR WNTKLYVGPTKVNVDSQTIYFLGLTALLLR YAQRNCTHSFYLVNAMSRNLFRVPKYINGT KLKNTMRKLKRKQAPVKEQFEKKAKKTQST TTPYFSYTTSAALNVTTNVTYSITTAARRVST STIAYRPDSSFMKSIMATQLRDLATWVYTTL RYRQNPFCEPSRNRTAVSEFMKNTHVLIRNE TPYTIYGTLDMSSLYYNETMFVENKTASDSN KTTPTSPSMGFQRTFIDPLWDYLDSLLFLDEI RNFSLRSPTYVNLTPPEHRRAVNLSTLNSLW WWLQ | |
| 36 | gi\|583844649\|gb\|AHI58989.1\| envelope glycoprotein N [Human herpesvirus 5] | MECNTLVLGLLVLSVVASSNNTSTASTPRPS SSTHASTTVKATTVATTSTTTATSTSSTTSAK PGFTTHDPNVMRPHAHNDFYNAHCTSHMYE LSLSSFAAWWTMLNALILMGAFCIVLRHCCF QNFTATTTKGY | |

TABLE 2-continued

Human Cytomegalovirus Sequences

| SEQ ID NO: | Protein Name | Protein Sequence | Nucleotide Sequence (SEQ ID NO:) |
|---|---|---|---|
| 37 | gi\|136994\|sp\| P16733.1\| GM_HCMVA RecName: Full = Envelope glycoprotein M; Short = gM | MAPSHVDKVNTRTWSASIVFMVLTFVNVSV HLVLSNFPHLGYPCVYYHVVDFERLNMSAY NVMHLHTPMLFLDSVQLVCYAVFMQLVFL AVTIYYLVCWIKISMRKDKGMSLNQSTRDIS YMGDSLTAFLFILSMDTFQLFTLTMSFRLPS MIAFMAAVHFFCLTIFNVSMVTQYRSYKRSL FFFSRLHPKLKGTVQFRTLIVNLVEVALGFNT TVVAMALCYGFGNNFFVRTGHMVLAVFVV YAIISIIYFLLIEAVFFQYVKVQFGYHLGAFFG LCGLIYPIVQYDTFLSNEYRTGISWSFGMLFFI WAMFTTCRAVRYFRGRGSGSVKYQALATA SGEEVAVLSHHDSLESRRLREEEDDDDDEDF EDA | |
| 38 | gi\|77455773\|gb\| ABA86616.1\| UL128 [Human herpesvirus 5] | MSPKDLTPFLTALWLLLGHSRVLRVRAEECC EFINVNHPPERCYDFKMCNRFTVALRCPDGE VCYSPEKTAEIRGIVTTMTHSLTRQVVHNKL TSCNYNPLYLEADGRIRCGKVNDKAQYLLG AAGSVPYRWINLEYDKITRIVGLDQYLESVK KHKRLDVCRAKMGYMLQ | 13 |
| 39 | gi\|77455773\|gb\| ABA86616.1\| UL128 [Human herpesvirus 5] | MSPKDLTPFLTALWLLLGHSRVLRVRAEECC EFINVNHPPERCYDFKMCNRFTVALRCPDGE VCYSPEKTAEIRGIVTTMTHSLTRQVVHNKL TSCNYNPLYLEADGRIRCGKVNDKAQYLLG AAGSVPYRWINLEYDKITRIVGLDQYLESVK KHKRLDVCRAKMGYMLQ | 14 |
| 40 | gi\|822891002\|gb\| AKI12403.1\| RL1 protein [Human herpesvirus 5] | MPATDTNSTHTTPLHPEHHHSTTQPHAQTSD KHADKQHRTQMELDAADYAACAQARQHL YGQTQPQLHAYPNANPQESAHFCTENQHQL TNLLHNIGEGAALGYPVPRAEIRRGGGDWA DSASDFDADCWCMWGRFGTMGRQPVVTLL LARQRDGLADWNVVRCRGTGFRAHDSEDG VSVWRQHLVFLLGGHGRRVQLERPSAGEAQ ARGLLPRIRITPISTSPRPKPPQPTTSTASHPHA TARPDHTLFPVPSTPSATVHNPRNYAVQLHA ETTRTWRWARRGERGAWMPAETFTCPKDK RPW | 15 |
| 41 | gi\|52139182\|ref\| YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 16 |
| 42 | gi\|52139291\|ref\| YP_081566.1\| envelope protein UL131A [Human herpesvirus 5] | MRLCRVWLSVCLCAVVLGQCQRETAEKND YYRVPHYWDACSRALPDQTRYKYVEQLVD LTLNYHYDASHGLDNFDVLKRINVTEVSLLI SDFRRQNRRGGTNKRTTFNAAGSLAPHARS LEFSVRLFAN | 17 |
| 43 | gi\|52139291\|ref\| YP_081566.1\| envelope protein UL131A [Human herpesvirus 5] | MRLCRVWLSVCLCAVVLGQCQRETAEKND YYRVPHYWDACSRALPDQTRYKYVEQLVD LTLNYHYDASHGLDNFDVLKRINVTEVSLLI SDFRRQNRRGGTNKRTTFNAAGSLAPHARS LEFSVRLFAN | 18 |
| 44 | gi\|52139182\|ref\| YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST | 2 |

TABLE 2-continued

| SEQ ID NO: | Protein Name | Protein Sequence | Nucleotide Sequence (SEQ ID NO:) |
|---|---|---|---|
| Human Cytomegalovirus Sequences | | | |
| | | ASHPHATARPDHTLFPVPSTPSATVHNPRNY AVQLHAETTRTWRWARRGERGAWMPAETF TCPKDKRPW | |
| 45 | gi\|52139182\|ref\|YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 4 |
| 46 | gi\|822888315\|gb\|AKI09732.1\| RL1 protein [Human herpesvirus 5] | MPATDTNSTHTTPLHPEDQHTLPLQHNTTQP HVQTSDKPADKQHRTQMELDAADYAACAQ ARQHLYGQTQPQLHAYPNANPQESAHFCTD NQHRLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPVSTSPRPKAPQPTTST ASHPHATARPDHTLFPVPSTPSATVHNPRNY AVQLHAETTRTWRWARRGERGAWMPAETF TCPKDKRPW | 6 |
| 47 | gi\|52139182\|ref\|YP_081455.1\| protein RL1 [Human herpesvirus 5] | MPATDTNSTHTTPLHPEDQHTLPLHHSTTQP HVQTSDKHADKQHRTQMELDAADYAACAQ ARQHLYGQTQPQLHAYPNANPQESAHFRTE NQHQLTNLLHNIGEGAALGYPVPRAEIRRGG GDWADSASDFDADCWCMWGRFGTMGRQP VVTLLLARQRDGLADWNVVRCRGTGFRAH DSEDGVSVWRQHLVFLLGGHGRRVQLERPS AGEAQARGLLPRIRITPISTSPRPKPPQPTTST ASHPHATARPDHTLFPVPSTPSATVHNPRNY AVQLHAETTRTWRWARRGERGAWMPAETF TCPKDKRPW | 7 |
| 48 | hCMV-gHtruncFLAG, glycoprotein H Ectodomain | SSFWTLVQKLIRLTIGK-ERKEE-EEI- EPPCGQASPPTSSSSPSVSSATYFRHDMAQKP YPNRWTKRFTYCSTPTGDPSASCVKIPPSVPT TAASVTARSSGKTPSVSTFSKAIINTMY SICLDVFLRVLWRSSF-TR-I- PKPWKDTNRDLTLTRWYPKTWPATDLFRSS- RHKTA-V NSPPLCHRPLTCQYLTFGCHRKPLHTAGQNH IPPQDYTDHTLTRPVSSLMDTIYYSAPSHLVC TKAFTSSTNYVTLK-H-PRTSS-LRCP TTTHPCCLSSAIFHAYFSKRPINATTLYYDKL KNTSSWC-LRKIN-VTLISKTRTFLTPHLTSTT- TSAHYYVTAFTVTPWMYSRAVDVRCWTAA R-KWPSPTH-HCSQQPDKKRPAPKSPSHGP- TARPHSYKYKNL-SPASHKHHH APRCCCIPRPWTWPNEPFGHRIRSPTSPASYA WSTYSLNRISNISSPNGHYDRSPTLP-N YTKRTWPLFFQPSHAKNSTSWAASSTPCWYI RRRDAKSSS-KRASVHWPSYHTLRSC-LI HTTNTSATCTHPVPVAGDAITRSNASRVSSP MPPSPLPFPPPSPSYLPCNQARWKPSPTC FACRSANPSPR-PSPNTSVIS-QTST- SKVSPTLSPPPS-ARASSSPRRTVKLNAN-RAT CIPHTASQWRSTFR-KTAPFAKAPC- NTTTRKASSTSCTCTTRTTSFSPWIPTTKWWS HLRELTTSCF-KTVRY-K- LTSSWTPPTITRTMTISDDNRLEPRWPCFLPL GPPPSPSSPSCTRTPVVFE-SLSGR | 8 |
| 49 | hCMVgHtrunc6XHis, glycoprotein H Ectodomain-6XHis tag | SSFWTLVQKLIRLTIGK-ERKEE-EEI- EPPCGQASPPTSSSSPSVSSATYFRHDMAQKP YPNRWTKRFTYCSTPTGDPSASCVKIPPSVPT TAASVTARSSGKTPSVSTFSKAIINTMY SICLDVFLRVLWRSSF-TR-I- | 9 |

TABLE 2-continued

Human Cytomegalovirus Sequences

| SEQ ID NO: | Protein Name | Protein Sequence | Nucleotide Sequence (SEQ ID NO:) |
|---|---|---|---|
| | | PKPWKDTNRDLTLTRWYPKTWPATDLFRSS-<br>RHKTA-VNSPPLCHRPLTCQYLTFG<br>CHRKPLHTAGQNHIPPQDYTDHTLTRPVSSL<br>MDTIYYSAPSHLVCTKAFTSSTNYVTLK-H-<br>PRTSS-LRCP-TTTHPCCLSSAIFHAYFSKR<br>PINATTLYYDKLKNTSSWC-LRKIN-<br>TVTLISKTRTFLTPHLTSTT-<br>TSAHYYVTAFTVTPWMYSRAVD<br>VRCWTAAR-KWPSPTH-<br>HCSQQPDKKRPAPKSPSHGP-<br>TARPHSYKYKNL-SPASHKHHH<br>APRCCCIPRPWTWPNEPFGHRIRSPTSPASYA<br>WSTYSLNRISNISSPNGHYDRSPTLP-N<br>YTKRTWPLFFQPSHAKNSTSWAASSTPCWYI<br>RRRDAKSSS-KRASVHWPSYHTLRSC-LI<br>HTTNTSATCTHPVPVAGDAITRSNASRVSSP<br>MPPSPLPFPPPSPSYLPCNQARWKPSPTC<br>FACRSANPSPR-PSPNTSVIS-QTST-<br>SKVSPTLSPPPS-ARASSSPRRTVKLNAN-RAT<br>CIPHTASQWRSTFR-KTAPFAKAPC-<br>NTTTRKASSTSCTCTTRTTSFSPWIPTTKWWS<br>HLRELTTSCF-KTVRY-K-LTSSWTPPTTITTIT<br>DDNRLEPRWPCFLPLGPPPSPSSPSCTR<br>TPVVFE-SLSGR | |
| 50 | hCMV_TrgB, glycoprotein B (ectodomain) | SSFWTLVQKLIRLTIGK-ERKEE-EEI-<br>EPPWNPGSGAW-ALTCVSSVWVLRFPHLLLV<br>ELLLLTVTIPLIRRLLLTLDPVQSLNA-<br>LLPKRSAMVLTRPSTTLPSSTEMWWGSIPPST<br>PIACVLWPRVRILFALNVISSAPR-<br>SPSMKTWTRASWWSTNATSSRTPLRYESTR<br>RF-RFVVATLTSTPLICWAATRNTW<br>RLLCGRFIISTATVSATVPTAAL-QARFS<br>WLIIGTAMKTKPCN-CPTIIPTPTVPVT-<br>RSRINGTAAAAPGSIVRPVI-IVW-<br>PSLLRAPNILIIFSPLPRVTWLTFLLSTTEPIA<br>MPATLEKTPTSFSFFRTTLSSPTLEDRILR-<br>RPTGWWLFLNVRTR-SPGIYRTKR<br>MSLVNSLSGKPRNAPFVPKPRTRITFLLPK-<br>PPLSYLRSKR-TCPTLRWTAYVMRL-<br>ISYSRFSILHTIKHMKNMETCPSLKPLVVW-<br>CSGKVSSKNLWWNSNVWPTAPV-<br>ILLIIEPKEVQMATMQLIYPTWNRCTIWSTPS<br>CSSPMTRCAVTSTGRWRKSQKPGVWI<br>NGAP-RSSRNSARSTRQPFSRP FTTN<br>RLPRVSWVMSWAWPAA-PSTKPASRCCVI-T-<br>RSRQDAATHDPWSSLISPTARTCSTVNWART<br>TKSCWATTALRNVSFPASRSSSPGTRPTSTW<br>TTSSNA-LTSAVSPPSTA-SPWISTRW<br>KIPTSGYWNFTRRKSCVPATFLTSKRSCANS<br>TRTSSDNRLEPRWPCFLPLGPPPSPSSPSCTRT<br>PVVFE-SLSGR | 10 |
| 51 | hCMV_TrgBFLAG, hCMV glycoproteinB ectodomain-FLAG | SSFWTLVQKLIRLTIGK-ERKEE-EEI-<br>EPPWNPGSGAW-SALTCVSSVWVLR<br>FPHLLLVELLLLTVTIPLIRRLLLTLDPVQSLN<br>A-LLPKRSAMVLTRPSTTLPSSTEMWWG<br>SIPPSTPIACVLWPRVRILFALNVISSAPR-<br>SPSMKTWTRASWWSTNATSSRTPLRYESTR<br>RF-RFVVATLTSTPLICWAATRNTWRLLCGR<br>FIISTATVSATVPTAAL-QARFSWLII<br>GTAMKTKPCN-CPTIIPTPTVPVT-<br>RSRINGTAAAAPGSIVRPVI-IVW-PSLLRAPN<br>ILIIFSPLPRVTWLTFLLSTTEPIAMPATLEKTP<br>TSFSFFRTTLSSPTLEDRILR-RPTGWWLF<br>LNVRTR-SPGIYRTKRMSLVNS<br>LSGKPRNAPFVPKPRTRITFLLPK-<br>PPLSYLRSKR-TCPTLRWTAYVMRL-<br>ISYSRFSILHTIKHMKNMETCPSLKPLVVW-<br>CSGKVSSKNLWWNSNVWPTAP<br>V-ILLIIEPKEVQMATMQLIYPTWNRCTI<br>WSTPSCSSPMTRCAVTSTGRWRKSQKPGVW<br>INGAP-RSSRNSARSTRQPFSRPFTTNRL<br>PRVSWVMSWAWPAA-PSTKPASRCCVI-T-RS | 11 |

TABLE 2-continued

| Human Cytomegalovirus Sequences | | | |
|---|---|---|---|
| SEQ ID NO: | Protein Name | Protein Sequence | Nucleotide Sequence (SEQ ID NO:) |
| | | RQDAATHDPWSSLISPTARTCSTVNWARTTK SCWATTALRNVSFPASRSSSPGTRPTSTW TTSSNA-LTSAVSPPSTA-SPWISTRW KIPTSGYWNFTRRKSCVPATFLTSKRSCANS TRTSRITRTMTISDNRLEPRWPCFLPLGPPPSP SSPSCTRTPVVFE-SLSGR | |
| 52 | hCMV-TrgB6XHis, hCMV glycoprotein ectodomain-6XHis tag | SSFWTLVQKLIRLTIGK-ERKEE-EEI-EPPWNPGSGAW-SALTCVSSVWVLR FPHLLLVELLLLTVTIPLIRRLLLTLDPVQSLN A-LLPKRSAMVLTRPSTTLPSSTEMWWGSIP PSTPIACVLWPRVRILFALNVISSAPR-SPSMKTWTRASWWSTNATSSRTPLRYESTR RF-RFVVATLTSTPLICWAATRNTWRLLCGR FIISTATVSATVPTAAL-QARFSWLIIG TAMKTKPCN-CPTIIPTPTVPVT-RSRINGTAAAAPGSIVRPVI-IVW-PSLLRA PNILIIFSPLPRVTWLTFLLSTTEPIAMPATLEK TPTSFSFFRTTLSSPTLEDRILR-RPTGWWLF LNVRTR-SPGIYRTKRMSLVNSLSGKPRN APFVPKPRTRITFLLPK-PPLSYLRSKR-TCPTLRWTAYVMRL-ISYSRFSIL HTIKHMKNMETCPSLKPLVVW-CSGKVSSKNLWWNSNVWPTAP V-ILLIIEPKEVQMATMQLIYPTWNRCTIWST PSCSSPMTRCAVTSTGRWRKSQKPGVWI NGAP-RSSRNSARSTRQPFSRPFTTNRLPRVS WVMSWAWPAA-PSTKPASRCCVI-T-RS RQDAATHDPWSSLISPTARTCSTVNWARTTK SCWATTALRNVSFPASRSSSPGTRPTSTW TTSSNA-LTSAVSPPSTA-SPWISTRWKIP TSGYWNFTRRKSCVPATFLTSKRSCANSTR TSSTITTITDNRLEPRWPCFLPLGPPPSPSSPSC TRTPVVFE-SLSGR | 12 |
| 55 | hCMV glycoprotein L | MCRRPDCGFSFSPGPVILLWCCLLLPIVSSAA VSVAPTAAEKVPAECPELTRRCLLGEVFEGD KYESWLRPLVNVTGRDGPLSQLIRYRPVTPE AANSVLLDEAFLDTLALLYNNPDQLRALLTL LSSDTAPRWMTVMRGYSECGDGSPAVYTCV DDLCRGYDLTRLSYGRSIFTEHVLGFELVPPS LFNVVVAIRNEATRTNRAVRLPVSTAAAPEG ITLFYGLYNAVKEFCLRHQLDPPLLRHLDKY YAGLPPELKQTRVNLPAHSRYGPQAVDAR | 3 |
| 56 | hCMV glycoprotein B | MESRIWCLVVCVNLCIVCLGAAVSSSSTRGT SATHSHHSSHTTSAAHSRSGSVSQRVTSSQT VSHGVNETIYNTTLKYGDVVGVNTTKYPYR VCSMAQGTDLIRFERNIVCTSMKPINEDLDE GIMVVYKRNIVAHTFKVRVYQKVLTFRRSY AYIHTTYLLGSNTEYVAPPMWEIHHINSHSQ CYSSYSRVIAGTVFVAYHRDSYENKTMQLM PDDYSNTHSTRYVTVKDQWHSRGSTWLYRE TCNLNCMVTITTARSKYPYHFFATSTGDVVD ISPFYNGTNRNASYFGENADKFFIFPNYTIVS DFGRPNSALETHRLVAFLERADSVISWDIQD EKNVTCQLTFWEASERTIRSEAEDSYHFSSA KMTATFLSKKQEVNMSDSALDCVRDEAINK LQQIFNTSYNQTYEKYGNVSVFETTGGLVVF WQGIKQKSLVELERLANRSSLNLTHNRTKRS TDGNNATHLSNMESVHNLVYAQLQFTYDTL RGYINRALAQIAEAWCVDQRRTLEVFKELSK INPSAILSAIYNKPIAARFMGDVLGLASCVTI NQTSVKVLRDMNVKESPGRCYSRPVVIFNFA NSSYVQYGQLGEDNEILLGNHRTEECQLPSL KIFIAGNSAYEYVDYLFKRMIDLSSISTVDSM IALDIDPLENTDFRVLELYSQKELRSSNVFDL EEIMREFNSYKQRVKYVEDKVVDPLPPYLK GLDDLMSGLGAAGKAVGVAIGAVGGAVAS VVEGVATFLKNPFGAFTIILVAIAVVIITYLIY TRQRRLCTQPLQNLFPYLVSADGTTVTSGST KDTSLQAPPSYEESVYNSGRKGPGPPSSDAS | 5 |

TABLE 2-continued

| Human Cytomegalovirus Sequences | | | |
|---|---|---|---|
| SEQ ID NO: | Protein Name | Protein Sequence | Nucleotide Sequence (SEQ ID NO:) |
| | | TAAPPYTNEQAYQMLLALARLDAEQRAQQ NGTDSLDGRTGTQDKGQKPNLLDRLRHRKN GYRHLKDSDEEENV | |
| 57 | hCMV UL130 | MLRLLLRHHFHCLLLCAVWATPCLASPWST LTANQNPSPPWSKLTYSKPHDAATFYCPFLY PSPPRSPLQFSGFQRVSTGPECRNETLYLLYN REGQTLVERSSTWVKKVIWYLSGRNQTILQR MPRTASKPSDGNVQISVEDAKIFGAHMVPK QTKLLRFVVNDGTRYQMCVMKLESWAHVF RDYSVSFQVRLTFTEANNQTYTFCTHPNLIV | 15 |
| 53 | Ig heavy chain epsilon-1 signal peptide (IgE HC SP) | MDWTWILFLVAAATRVHS | |
| 54 | IgGk chain V-III region HAH signal peptide (IgGk SP) | METPAQLLFLLLLWLPDTTG | |

Represents a stop sequence

TABLE 3

| CMV (Human herpesvirus 5) Amino Acid Sequences | | |
|---|---|---|
| Protein | Name | GenBank Accession |
| Glycoprotein H | envelope glycoprotein H [Human herpesvirus 5] | ACZ79986.1 |
| Glycoprotein H | envelope glycoprotein H [Human herpesvirus 5] | AAA45918.1 |
| Glycoprotein H | envelope glycoprotein H [Human herpesvirus 5] | ACS93310.2 |
| Glycoprotein H | envelope glycoprotein H [Human herpesvirus 5] | AAA45911.1 |
| Glycoprotein H | envelope glycoprotein H [Human herpesvirus 5] | AAA98521.1 |
| Glycoprotein H | glycoprotein H [Human herpesvirus 5] | BAF44184.1 |
| Glycoprotein H | envelope glycoprotein H [Human herpesvirus 5] | AAA45912.1 |
| Glycoprotein H | envelope glycoprotein H [Human herpesvirus 5] | AKI21335.1 |
| Glycoprotein H | envelope glycoprotein H [Human herpesvirus 5] | AIC80661.1 |
| Glycoprotein H | envelope glycoprotein H [Human herpesvirus 5] | AKI11476.1 |
| Glycoprotein H | envelope glycoprotein H [Human herpesvirus 5] | ACZ80151.1 |
| Glycoprotein H | envelope glycoprotein H [Human herpesvirus 5] | AHV84023.1 |
| Glycoprotein H | envelope glycoprotein H [Human herpesvirus 5] | AAA45917.1 |
| Glycoprotein H | envelope glycoprotein H [Human herpesvirus 5] | AAA45915.1 |
| Glycoprotein H | envelope glycoprotein H [Human herpesvirus 5] | AFR55394.1 |
| Glycoprotein H | envelope glycoprotein H [Human herpesvirus 5] | AKI14309.1 |
| Glycoprotein H | envelope glycoprotein H [Human herpesvirus 5] | AKI11640.1 |
| Glycoprotein H | glycoprotein H [Human herpesvirus 5] | BAF44187.1 |
| Glycoprotein H | envelope glycoprotein H [Human herpesvirus 5] | AKI18318.1 |
| Glycoprotein H | envelope glycoprotein H [Human herpesvirus 5] | AHB20043.1 |
| Glycoprotein H | envelope glycoprotein H [Human herpesvirus 5] | AAA45909.1 |
| Glycoprotein H | glycoprotein H [Human herpesvirus 5] | BAF44190.1 |
| Glycoprotein H | RecName: Full = Envelope glycoprotein H; Short = gH; Flags: Precursor | P12824.1 |
| Glycoprotein H | envelope glycoprotein H [Human herpesvirus 5] | AKI07789.1 |
| Glycoprotein H | glycoprotein H [Human herpesvirus 5] | BAF44183.1 |
| Glycoprotein H | envelope glycoprotein H [Human herpesvirus 5] | AGL96664.1 |
| Glycoprotein H | glycoprotein H [Human herpesvirus 5] | BAF44189.1 |
| Glycoprotein H | envelope glycoprotein H [Human herpesvirus 5] | AKI08793.1 |
| Glycoprotein H | glycoprotein H [Human herpesvirus 5] | BAF44185.1 |
| Glycoprotein H | envelope glycoprotein H [Human herpesvirus 5] | ADV04392.1 |
| Glycoprotein H | envelope glycoprotein H [Human herpesvirus 5] | AFR56062.1 |
| Glycoprotein H | envelope glycoprotein H [Human herpesvirus 5] | ACS92000.1 |
| Glycoprotein H | envelope glycoprotein H [Human herpesvirus 5] | AKI15316.1 |
| Glycoprotein H | envelope glycoprotein H [Human herpesvirus 5] | AFR54893.1 |
| Glycoprotein H | envelope glycoprotein H [Human herpesvirus 5] | AHJ86162.1 |
| Glycoprotein H | envelope glycoprotein H [Human herpesvirus 5] | ACS92165.1 |
| Glycoprotein H | envelope glycoprotein H [Human herpesvirus 5] | ACT81746.1 |
| Glycoprotein H | envelope glycoprotein H [Human herpesvirus 5] | AKI12305.1 |
| Glycoprotein H | envelope glycoprotein H [Human herpesvirus 5] | AKI09634.1 |
| Glycoprotein H | glycoprotein H [Human herpesvirus 5] | BAF44191.1 |

TABLE 3-continued

CMV (Human herpesvirus 5) Amino Acid Sequences

| Protein | Name | GenBank Accession |
|---|---|---|
| Glycoprotein H | RecName: Full = Envelope glycoprotein H; Short = gH; AltName: Full = Glycoprotein P86; Flags: Precursor [Human herpesvirus 5 strain Towne] | P17176.1 |
| Glycoprotein H | envelope glycoprotein H [Human herpesvirus 5] | AKI13641.1 |
| Glycoprotein H | envelope glycoprotein H [Human herpesvirus 5] | AKI20832.1 |
| Glycoprotein H | envelope glycoprotein H [Human herpesvirus 5] | AKI09465.1 |
| Glycoprotein H | envelope glycoprotein H [Human herpesvirus 5] | ACS93407.1 |
| Glycoprotein H | envelope glycoprotein H [Human herpesvirus 5] | AKI07621.1 |
| Glycoprotein H | glycoprotein H [Human herpesvirus 5] | BAF44186.1 |
| Glycoprotein H | envelope glycoprotein H [Human herpesvirus 5] | AKI22834.1 |
| Glycoprotein H | envelope glycoprotein H [Human herpesvirus 5] | AKI14981.1 |
| Glycoprotein H | envelope glycoprotein H [Human herpesvirus 5] | AKI10139.1 |
| Glycoprotein H | envelope glycoprotein H [Human herpesvirus 5] | ACZ79822.1 |
| Glycoprotein H | envelope glycoprotein H [Human herpesvirus 5] | AAA45910.1 |
| Glycoprotein H | envelope glycoprotein H [Human herpesvirus 5] | AAA45913.1 |
| Glycoprotein H | glycoprotein H [Human herpesvirus 5] | BAF44188.1 |
| Glycoprotein H | envelope glycoprotein H [Human herpesvirus 5] | AKI18822.1 |
| Glycoprotein H | envelope glycoprotein H [Human herpesvirus 5] | AFR56229.1 |
| Glycoprotein H | envelope glycoprotein H [Human herpesvirus 5] | YP_081523.1 |
| Glycoprotein H | envelope glycoprotein H [Human herpesvirus 5] | AKI19826.1 |
| Glycoprotein H | envelope glycoprotein H [Human herpesvirus 5] | AAA45914.1 |
| Glycoprotein H | envelope glycoprotein H [Human herpesvirus 5] | AKI23334.1 |
| Glycoprotein H | envelope glycoprotein H [Human herpesvirus 5] | AKI14141.1 |
| Glycoprotein H | envelope glycoprotein H [Human herpesvirus 5] | AHB19545.1 |
| Glycoprotein H | envelope glycoprotein H [Human herpesvirus 5] | ACU83725.1 |
| Glycoprotein H | envelope glycoprotein H [Human herpesvirus 5] | AKI17318.1 |
| Glycoprotein H | envelope glycoprotein H [Human herpesvirus 5] | AKI13975.1 |
| Glycoprotein L | RecName: Full = Envelope glycoprotein L; Flags: Precursor [Human herpesvirus 5 (strain 5040)] | Q68672.1 |
| Glycoprotein L | RecName: Full = Envelope glycoprotein L; Flags: Precursor [Human herpesvirus 5 (strain 2387)] | Q68669.1 |
| Glycoprotein L | envelope glycoprotein L [Human herpesvirus 5] | AKI08825.1 |
| Glycoprotein L | envelope glycoprotein L [Human herpesvirus 5] | ACS92032.1 |
| Glycoprotein L | envelope glycoprotein L [Human herpesvirus 5] | AHJ86194.1 |
| Glycoprotein L | RecName: Full = Envelope glycoprotein L; Flags: Precursor | P16832.2 |
| Glycoprotein L | RecName: Full = Envelope glycoprotein L; Flags: Precursor [Human herpesvirus 5 (strain 5035)] | Q68671.1 |
| Glycoprotein L | envelope glycoprotein L [Human herpesvirus 5] | AHB20074.1 |
| Glycoprotein L | envelope glycoprotein L [Human herpesvirus 5] | AKI12337.1 |
| Glycoprotein L | RecName: Full = Envelope glycoprotein L; Flags: Precursor [Human herpesvirus 5 (strain 1042)] | Q68668.1 |
| Glycoprotein L | envelope glycoprotein L [Human herpesvirus 5] | AKI23365.1 |
| Glycoprotein L | envelope glycoprotein L [Human herpesvirus 5] | AKI21032.1 |
| Glycoprotein L | envelope glycoprotein L [Human herpesvirus 5] | YP_081555.1 |
| Glycoprotein L | RecName: Full = Envelope glycoprotein L; Flags: Precursor [Human herpesvirus 5 (strain 4654)] | Q68670.1 |
| Glycoprotein L | envelope glycoprotein L [Human herpesvirus 5] | AKI17850.1 |
| Glycoprotein L | envelope glycoprotein L [Human herpesvirus 5] | ACZ80183.1 |
| Glycoprotein L | envelope glycoprotein L [Human herpesvirus 5] | AKI11508.1 |
| Glycoprotein L | envelope glycoprotein L [Human herpesvirus 5] | AKI10171.1 |
| Glycoprotein L | RecName: Full = Envelope glycoprotein L; Flags: Precursor [Human herpesvirus 5 (strain 5160)] | Q68673.1 |
| Glycoprotein L | RecName: Full = Envelope glycoprotein L; Flags: Precursor [Human herpesvirus 5 strain PT] | Q68666.1 |
| Glycoprotein L | envelope glycoprotein L [Human herpesvirus 5] | AKI18350.1 |
| Glycoprotein L | envelope glycoprotein L [Human herpesvirus 5] | AIC80693.1 |
| Glycoprotein L | envelope glycoprotein L [Human herpesvirus 5] | AKI12003.1 |
| Glycoprotein L | envelope glycoprotein L [Human herpesvirus 5] | AKI15849.1 |
| Glycoprotein L | envelope glycoprotein L [Human herpesvirus 5] | AKI13336.1 |
| Glycoprotein L | envelope glycoprotein L [Human herpesvirus 5] | AKI10840.1 |
| Glycoprotein L | RecName: Full = Envelope glycoprotein L; Flags: Precursor | Q68667.1 |
| Glycoprotein L | envelope glycoprotein L [Human herpesvirus 5] | AHV84055.1 |
| Glycoprotein L | envelope glycoprotein L [Human herpesvirus 5] | AKI07653.1 |
| Glycoprotein L | envelope glycoprotein L [Human herpesvirus 5] | AFR55425.1 |
| Glycoprotein L | envelope glycoprotein L [Human herpesvirus 5] | AKI15013.1 |
| Glycoprotein L | envelope glycoprotein L [Human herpesvirus 5] | ACT81943.1 |
| Glycoprotein L | envelope glycoprotein L [Human herpesvirus 5] | AKI21367.1 |
| Glycoprotein L | envelope glycoprotein L [Panine herpesvirus 2] | NP_612739.1 |
| pp150 | tegument protein pp150 [Human herpesvirus 5] | ACZ79954.1 |
| pp150 | tegument protein pp150 [Human herpesvirus 5] | AFR56030.1 |
| pp150 | tegument protein pp150 [Human herpesvirus 5] | ACU83693.1 |
| pp150 | tegument protein pp150 [Human herpesvirus 5] | AKI12106.1 |
| pp150 | tegument protein pp150 [Human herpesvirus 5] | AKI19625.1 |
| pp150 | tegument protein pp150 [Human herpesvirus 5] | AFR55362.1 |
| pp150 | tegument protein pp150 [Human herpesvirus 5] | AKI14613.1 |

TABLE 3-continued

CMV (Human herpesvirus 5) Amino Acid Sequences

| Protein | Name | GenBank Accession |
|---|---|---|
| pp150 | tegument protein pp150 [Human herpesvirus 5] | AKI07924.1 |
| pp150 | tegument protein pp150 [Human herpesvirus 5] | AIC80127.1 |
| pp150 | tegument protein pp150 [Human herpesvirus 5] | AHB19512.1 |
| pp150 | tegument protein pp150 [Human herpesvirus 5] | YP_081491.1 |
| pp150 | tegument protein pp150 [Human herpesvirus 5] | AKI16116.1 |
| pp150 | extended tegument protein pp150 [Human herpesvirus 5] | AII79810.1 |
| pp150 | tegument protein pp150 [Human herpesvirus 5] | AIC80629.1 |
| pp150 | tegument protein pp150 [Human herpesvirus 5] | AFR55862.1 |
| pp150 | tegument protein pp150 [Human herpesvirus 5] | AKI10942.1 |
| pp150 | tegument protein pp150 [Human herpesvirus 5] | ACS91968.1 |
| pp150 | tegument protein pp150 [Human herpesvirus 5] | AKI15451.1 |
| pp150 | tegument protein pp150 [Human herpesvirus 5] | ACS92133.1 |
| pp150 | tegument protein pp150 [Human herpesvirus 5] | AFR56364.1 |
| pp150 | tegument protein pp150 [Human herpesvirus 5] | AFR54694.1 |
| pp150 | tegument protein pp150 [Human herpesvirus 5] | AKI23468.1 |
| pp150 | tegument protein pp150 [Human herpesvirus 5] | AKI17619.1 |
| pp150 | tegument protein pp150 [Human herpesvirus 5] | AFR55527.1 |
| pp150 | tegument protein pp150 [Human herpesvirus 5] | AFR55193.1 |
| pp150 | tegument protein pp150 [Human herpesvirus 5] | AFR54534.1 |
| pp150 | tegument protein pp150 [Human herpesvirus 5] | AKI18789.1 |
| pp150 | tegument protein pp150 [Human herpesvirus 5] | AKI07588.1 |
| pp150 | tegument protein pp150 [Human herpesvirus 5] | AKI22466.1 |
| pp150 | tegument protein pp150 [Human herpesvirus 5] | AKI20463.1 |
| pp150 | tegument protein pp150 [Human herpesvirus 5] | AKI14780.1 |
| pp150 | tegument protein pp150 [Human herpesvirus 5] | AKI15116.1 |
| pp150 | tegument protein pp150 [Human herpesvirus 5] | AKI14445.1 |
| pp150 | tegument protein pp150 [Human herpesvirus 5] | AKI22633.1 |
| pp150 | tegument protein pp150 [Human herpesvirus 5] | AKI09096.1 |
| pp150 | tegument protein pp150 [Human herpesvirus 5] | AKI13271.1 |
| pp150 | tegument protein pp150 [Human herpesvirus 5] | AKI08760.1 |
| pp150 | tegument protein pp150 [Human herpesvirus 5] | AFR56197.1 |
| pp150 | tegument protein pp150 [Human herpesvirus 5] | AFR54861.1 |
| pp150 | tegument protein pp150 [Human herpesvirus 5] | ACZ80119.1 |
| pp150 | tegument protein pp150 [Human herpesvirus 5] | AKI19960.1 |
| pp150 | tegument protein pp150 [Human herpesvirus 5] | AKI21134.1 |
| pp150 | tegument protein pp150 [Human herpesvirus 5] | AKI11938.1 |
| pp150 | tegument protein pp150 [Human herpesvirus 5] | AKI20128.1 |
| pp150 | tegument protein pp150 [Human herpesvirus 5] | AKI08928.1 |
| pp150 | tegument protein pp150 [Human herpesvirus 5] | ACZ80284.1 |
| pp150 | tegument protein pp150 [Human herpesvirus 5] | AKI21302.1 |
| pp150 | tegument protein pp150 [Human herpesvirus 5] | AKI12272.1 |
| pp150 | tegument protein pp150 [Human herpesvirus 5] | AKI20967.1 |
| pp150 | tegument protein pp150 [Human herpesvirus 5] | AKI19793.1 |
| pp150 | tegument protein pp150 [Human herpesvirus 5] | AKI23136.1 |
| pp150 | tegument protein pp150 [Human herpesvirus 5] | AKI10106.1 |
| pp150 | tegument protein pp150 [Human herpesvirus 5] | AKI11772.1 |
| pp150 | tegument protein pp150 [Human herpesvirus 5] | AKI08591.1 |
| pp150 | tegument protein pp150 [Human herpesvirus 5] | AKI11443.1 |
| pp150 | tegument protein pp150 [Human herpesvirus 5] | AKI14948.1 |
| pp150 | tegument protein pp150 [Human herpesvirus 5] | ADE88040.1 |
| pp150 | tegument protein pp150 [Human herpesvirus 5] | AKI22969.1 |
| pp150 | tegument protein pp150 [Human herpesvirus 5] | AHJ86130.1 |
| pp150 | tegument protein pp150 [Human herpesvirus 5] | ACT81879.1 |
| pp150 | tegument protein pp150 [Human herpesvirus 5] | AKI15950.1 |
| pp150 | tegument protein pp150 [Human herpesvirus 5] | AKI15617.1 |
| pp150 | tegument protein pp150 [Human herpesvirus 5] | AHB19679.1 |
| pp150 | tegument protein pp150 [Human herpesvirus 5] | AHB19344.1 |
| pp150 | tegument protein pp150 [Human herpesvirus 5] | ACT81714.1 |
| pp150 | tegument protein pp150 [Human herpesvirus 5] | AKI07756.1 |
| pp150 | tegument protein pp150 [Human herpesvirus 5] | AKI11607.1 |
| pp150 | tegument protein pp150 [Human herpesvirus 5] | AIC80295.1 |
| pp150 | tegument protein pp150 [Human herpesvirus 5] | AKI11275.1 |
| pp150 | tegument protein pp150 [Human herpesvirus 5] | AHB20010.1 |
| pp150 | tegument protein pp150 [Human herpesvirus 5] | AIC80463.1 |
| pp150 | tegument protein pp150 [Human herpesvirus 5] | AKI17952.1 |
| pp150 | tegument protein pp150 [Human herpesvirus 5] | ACM48022.1 |
| pp150 | tegument protein pp150 [Human herpesvirus 5] | AKI16285.1 |
| pp150 | tegument protein pp150 [Human herpesvirus 5] | AKI09601.1 |
| pp150 | tegument protein pp150 [Human herpesvirus 5] | AKI22299.1 |
| pp150 | tegument protein pp150 [Human herpesvirus 5] | AHV83990.1 |
| pp150 | tegument protein pp150 [Human herpesvirus 5] | AKI23301.1 |
| pp150 | tegument protein pp150 [Human herpesvirus 5] | AGL96632.1 |
| pp150 | tegument protein pp150 [Human herpesvirus 5] | AKI18285.1 |
| pp150 | tegument protein pp150 [Human herpesvirus 5] | ADV04360.1 |
| pp65 | tegument protein pp65 [Human herpesvirus 5] | ACZ79994.1 |

TABLE 3-continued

CMV (Human herpesvirus 5) Amino Acid Sequences

| Protein | Name | GenBank Accession |
|---|---|---|
| pp65 | tegument protein pp65 [Human herpesvirus 5] | ACS92173.1 |
| pp65 | tegument protein pp65 [Human herpesvirus 5] | AKI09642.1 |
| pp65 | tegument protein pp65 [Human herpesvirus 5] | AKI16326.1 |
| pp65 | tegument protein pp65 [Human herpesvirus 5] | ADD39129.1 |
| pp65 | tegument protein pp65 [Human herpesvirus 5] | ACM48061.1 |
| pp65 | tegument protein pp65 [Human herpesvirus 5] | AKI20001.1 |
| pp65 | tegument protein pp65 [Human herpesvirus 5] | AKI14149.1 |
| pp65 | tegument protein pp65 [Human herpesvirus 5] | AHB19720.1 |
| pp65 | tegument protein pp65 [Human herpesvirus 5] | ADV04400.1 |
| pp65 | tegument protein pp65 [Human herpesvirus 5] | AKI21507.1 |
| pp65 | tegument protein pp65 [Human herpesvirus 5] | AKI15825.1 |
| pp65 | tegument protein pp65 [Human herpesvirus 5] | AKI08299.1 |
| pp65 | tegument protein pp65 [Human herpesvirus 5] | AKI07965.1 |
| pp65 | tegument protein pp65 [Human herpesvirus 5] | AKI22339.1 |
| pp65 | tegument protein pp65 [Human herpesvirus 5] | AKI12978.1 |
| pp65 | tegument protein pp65 [Human herpesvirus 5] | AKI11979.1 |
| pp65 | tegument protein pp65 [Human herpesvirus 5] | AHB19886.1 |
| pp65 | tegument protein pp65 [Human herpesvirus 5] | YP_081531.1 |
| pp65 | tegument protein pp65 [Human herpesvirus 5] | AKI23010.1 |
| pp65 | tegument protein pp65 [Human herpesvirus 5] | AKI10983.1 |
| pp65 | tegument protein pp65 [Human herpesvirus 5] | AKI10314.1 |
| pp65 | tegument protein pp65 [Human herpesvirus 5] | AFR56070.1 |
| pp65 | 65K lower matrix phosphoprotein - human cytomegalovirus (strain Towne) | WMBETW |
| pp65 | mutant UL83 [Human herpesvirus 5] | AAP59842.1 |
| pp65 | tegument protein pp65 [Human herpesvirus 5] | AKI14317.1 |
| pp65 | tegument protein pp65 [Human herpesvirus 5] | AFR54574.1 |
| pp65 | tegument protein pp65 [Human herpesvirus 5] | AFR56237.1 |
| pp65 | tegument protein pp65 [Human herpesvirus 5] | AKI18326.1 |
| pp65 | tegument protein pp65 [Human herpesvirus 5] | AKI22842.1 |
| pp65 | tegument protein PP65 [Human herpesvirus 5] | AHV84031.1 |
| pp65 | tegument protein [synthetic construct] | AAT68258.1 |
| pp65 | phosphorylated matrix protein (pp65) [Human herpesvirus 5] | AAA45996.1 |
| pp65 | tegument protein pp65 [Panine herpesvirus 2] | NP_612716.1 |
| pp65 | tegument protein pp65 [Human herpesvirus 5] | ADJ68256.1 |
| pp65 | tegument protein pp65 [Human herpesvirus 5] | ADJ68266.1 |
| UL100 (gM) | envelope glycoprotein M [Human herpesvirus 5] | ACT81935.1 |
| UL100 (gM) | envelope glycoprotein M [Human herpesvirus 5] | YP_081547.1 |
| UL100 (gM) | envelope glycoprotein M [Human herpesvirus 5] | ACM48077.1 |
| UL100 (gM) | RecName: Full = Envelope glycoprotein M; Short = gM | P16733.1 |
| UL100 (gM) | envelope glycoprotein M [Human herpesvirus 5] | AKI18175.1 |
| UL100 (gM) | envelope glycoprotein M [Human herpesvirus 5] | AFR54590.1 |
| UL100 (gM) | envelope glycoprotein M [Human herpesvirus 5] | AKI20017.1 |
| UL100 (gM) | envelope glycoprotein M [Human herpesvirus 5] | AKI09994.1 |
| UL100 (gM) | UL100 [Human herpesvirus 5] | AAS48986.1 |
| UL100 (gM) | envelope glycoprotein M [Human herpesvirus 5] | AKI20856.1 |
| UL100 (gM) | envelope glycoprotein M [Human herpesvirus 5] | AKI14333.1 |
| UL100 (gM) | envelope glycoprotein M [Human herpesvirus 5] | AHB19736.1 |
| UL100 (gM) | envelope glycoprotein M [Human herpesvirus 5] | AGT36389.1 |
| UL100 (gM) | envelope glycoprotein M [Human herpesvirus 5] | ACZ80175.1 |
| UL100 (gM) | envelope glycoprotein M [Human herpesvirus 5] | AKI18009.1 |
| UL100 (gM) | envelope glycoprotein M [Human herpesvirus 5] | AKI23358.1 |
| UL100 (gM) | envelope glycoprotein M [Human herpesvirus 5] | AHV84047.1 |
| UL100 (gM) | envelope glycoprotein M [Human herpesvirus 5] | ACS92024.1 |
| UL100 (gM) | envelope glycoprotein M [Human herpesvirus 5] | AKI10999.1 |
| UL100 (gM) | envelope glycoprotein M [Human herpesvirus 5] | AKI16173.1 |
| UL100 (gM) | envelope glycoprotein M [Human herpesvirus 5] | AFR54917.1 |
| UL100 (gM) | UL100 [Human herpesvirus 5] | ABV71622.1 |
| UL100 (gM) | envelope glycoprotein M [Human herpesvirus 5] | AKI13999.1 |
| UL100 (gM) | envelope glycoprotein M [Human herpesvirus 5] | AKI12329.1 |
| UL100 (gM) | envelope glycoprotein M [Human herpesvirus 5] | AKI21523.1 |
| UL100 (gM) | envelope glycoprotein M [Human herpesvirus 5] | AKI18342.1 |
| UL100 (gM) | envelope glycoprotein M [Human herpesvirus 5] | AKI09658.1 |
| UL100 (gM) | envelope glycoprotein M [Human herpesvirus 5] | AKI07813.1 |
| UL100 (gM) | envelope glycoprotein M [Human herpesvirus 5] | AKI18846.1 |
| UL100 (gM) | envelope glycoprotein M [Human herpesvirus 5] | AFR55081.1 |
| UL100 (gM) | envelope glycoprotein M [Human herpesvirus 5] | AKI17342.1 |
| UL123 | regulatory protein IE1 [Human herpesvirus 5] | ACT81950.1 |
| UL123 | regulatory protein IE1 [Human herpesvirus 5] | AKI07996.1 |
| UL123 | regulatory protein IE1 [Human herpesvirus 5] | AAR31361.1 |
| UL123 | regulatory protein IE1 [Human herpesvirus 5] | AKI09840.1 |
| UL123 | regulatory protein IE1 [Human herpesvirus 5] | AKI12010.1 |
| UL123 | regulatory protein IE1 [Human herpesvirus 5] | AAR31390.1 |
| UL123 | regulatory protein IE1 [Human herpesvirus 5] | AFR55598.1 |
| UL123 | regulatory protein IE1 [Human herpesvirus 5] | AKI08832.1 |

TABLE 3-continued

| CMV (Human herpesvirus 5) Amino Acid Sequences | | |
|---|---|---|
| Protein | Name | GenBank Accession |
| UL123 | immediate early transcriptional regulator [Human herpesvirus 5] | ACL27071.1 |
| UL123 | regulatory protein IE1 [Human herpesvirus 5] | AHB19584.1 |
| UL123 | regulatory protein IE1 [Human herpesvirus 5] | AKI18861.1 |
| UL123 | regulatory protein IE1 [Human herpesvirus 5] | AAR31419.1 |
| UL123 | regulatory protein IE1 [Human herpesvirus 5] | AKI23372.1 |
| UL123 | regulatory protein IE1 [Human herpesvirus 5] | AKI16357.1 |
| UL123 | regulatory protein IE1 [Human herpesvirus 5] | AKI10512.1 |
| UL123 | regulatory protein IE1 [Human herpesvirus 5] | AKI19028.1 |
| UL123 | regulatory protein IE1 [Human herpesvirus 5] | AKI11347.1 |
| UL123 | 72 kDa immediate-early 1 protein [Human herpesvirus 5] | ACT34667.1 |
| UL123 | regulatory protein IE1 [Human herpesvirus 5] | ADB84698.1 |
| UL123 | immediate early transcriptional regulator [Human herpesvirus 5] | ACL27072.1 |
| UL123 | regulatory protein IE1 [Human herpesvirus 5] | AKI22873.1 |
| UL123 | regulatory protein IE1 [Human herpesvirus 5] | AKI20200.1 |
| UL123 | regulatory protein IE1 [Human herpesvirus 5] | AKI12677.1 |
| UL123 | regulatory protein IE1 [Human herpesvirus 5] | AHV84062.1 |
| UL123 | regulatory protein IE1 [Human herpesvirus 5] | AFR55096.1 |
| UL123 | regulatory protein IE1 [Human herpesvirus 5] | AFR54932.1 |
| UL123 | regulatory protein IE1 [Human herpesvirus 5] | AKI22205.1 |
| UL123 | regulatory protein IE1 [Human herpesvirus 5] | AFR55264.1 |
| UL123 | regulatory protein IE1 [Human herpesvirus 5] | AKI18357.1 |
| UL123 | regulatory protein IE1 [Human herpesvirus 5] | AKI17188.1 |
| UL123 | regulatory protein IE1 [Human herpesvirus 5] | AKI12841.1 |
| UL123 | regulatory protein IE1 [Human herpesvirus 5] | AKI09673.1 |
| UL123 | regulatory protein IE1 [Human herpesvirus 5] | AKI21537.1 |
| UL123 | regulatory protein IE1 [Human herpesvirus 5] | AKI20871.1 |
| UL123 | regulatory protein IE1 [Human herpesvirus 5] | AGL96703.1 |
| UL123 | regulatory protein IE1 [Human herpesvirus 5] | AAR31477.1 |
| UL123 | regulatory protein IE1 [Human herpesvirus 5] | AKI21374.1 |
| UL123 | regulatory protein IE1 [Human herpesvirus 5] | ACZ80025.1 |
| UL123 | 72 kDa immediate-early 1 protein [Human herpesvirus 5] | ACT34666.1 |
| UL123 | regulatory protein IE1 [Human herpesvirus 5] | AKI20032.1 |
| UL123 | regulatory protein IE1 [Human herpesvirus 5] | AAR31303.1 |
| UL123 | regulatory protein IE1 [Human herpesvirus 5] | AIC80700.1 |
| UL123 | regulatory protein IE1 [Human herpesvirus 5] | ADB84746.1 |
| UL123 | immediate early transcriptional regulator [Human herpesvirus 5] | ACL27084.1 |
| UL123 | regulatory protein IE1 [Human herpesvirus 5] | ADV04431.1 |
| UL123 | regulatory protein IE1 [Human herpesvirus 5] | AKI11515.1 |
| UL123 | regulatory protein IE1 [Human herpesvirus 5] | AFR56435.1 |
| UL123 | immediate early transcriptional regulator [Human herpesvirus 5] | ACL27074.1 |
| UL123 | regulatory protein IE1 [Human herpesvirus 5] | AKI14180.1 |
| UL123 | regulatory protein IE1 [Human herpesvirus 5] | AKI07828.1 |
| UL123 | regulatory protein IE1 [Human herpesvirus 5] | AHB19751.1 |
| UL123 | regulatory protein IE1 [Human herpesvirus 5] | ADB84818.1 |
| UL123 | regulatory protein IE1 [Human herpesvirus 5] | AKI18526.1 |
| UL123 | regulatory protein IE1 [Human herpesvirus 5] | AKI14014.1 |
| UL123 | regulatory protein IE1 [Human herpesvirus 5] | ACT81785.1 |
| UL123 | regulatory protein IE1 [Human herpesvirus 5] | ADB44102.1 |
| UL123 | regulatory protein IE1 [Human herpesvirus 5] | AKI15187.1 |
| UL123 | immediate early transcriptional regulator [Human herpesvirus 5] | ACL27092.1 |
| UL123 | immediate early transcriptional regulator [Human herpesvirus 5] | ACL27056.1 |
| UL123 | regulatory protein IE1 [Human herpesvirus 5] | AKI18024.1 |
| UL123 | regulatory protein IE1 [Human herpesvirus 5] | AKI14517.1 |
| UL123 | regulatory protein IE1 [Human herpesvirus 5] | ADE88106.1 |
| UL123 | regulatory protein IE1 [Human herpesvirus 5] | AKI15355.1 |
| UL123 | regulatory protein IE1 [Human herpesvirus 5] | AKI10178.1 |
| UL123 | regulatory protein IE1 [Human herpesvirus 5] | ADB84722.1 |
| UL123 | regulatory protein IE1 [Human herpesvirus 5] | ADB84650.1 |
| UL123 | regulatory protein IE1 [Human herpesvirus 5] | AFR56268.1 |
| UL123 | regulatory protein IE1 [Human herpesvirus 5] | YP_081562.1 |
| UL123 | regulatory protein IE1 [Human herpesvirus 5] | AKI22538.1 |
| UL123 | regulatory protein IE1 [Human herpesvirus 5] | AHB19917.1 |
| UL123 | regulatory protein IE1 [Human herpesvirus 5] | AAR31332.1 |
| UL123 | RecName: Full = 55 kDa immediate-early protein 1; Short = IE1 | P13202.1 |
| UL123 | regulatory protein IE1 [Human herpesvirus 5] | AAR31448.1 |
| UL123 | regulatory protein IE1 [Human herpesvirus 5] | AKI14852.1 |
| UL123 | regulatory protein IE1 [Human herpesvirus 5] | AKI14348.1 |
| UL123 | immediate early transcriptional regulator [Human herpesvirus 5] | ACL27066.1 |
| UL123 | immediate early transcriptional regulator [Human herpesvirus 5] | ACL27058.1 |
| UL123 | immediate early transcriptional regulator [Human herpesvirus 5] | ACL27086.1 |
| UL123 | regulatory protein IE1 [Human herpesvirus 5] | AKI16022.1 |
| UL123 | regulatory protein IE1 [Human herpesvirus 5] | AIC80534.1 |
| UL123 | immediate early transcriptional regulator [Human herpesvirus 5] | ACL27094.1 |
| UL123 | immediate early transcriptional regulator [Human herpesvirus 5] | ACL27093.1 |
| UL123 | immediate early transcriptional regulator [Human herpesvirus 5] | ACL27073.1 |

TABLE 3-continued

| CMV (Human herpesvirus 5) Amino Acid Sequences | | |
|---|---|---|
| Protein | Name | GenBank Accession |
| UL123 | pp65/IE1 fusion protein [synthetic construct] | ABQ23593.1 |
| UL123 | regulatory protein IE1 [Human herpesvirus 5] | ACS92204.1 |
| UL123 | RecName: Full = 55 kDa immediate-early protein 1; Short = IE1 [Human herpesvirus 5 strain Towne] | P03169.1 |
| UL123 | regulatory protein IE1 [Human herpesvirus 5] | ADB84794.1 |
| UL123 | major immediate-early protein [Human herpesvirus 5] | AAA45979.1 |
| UL123 | immediate early transcriptional regulator [Human herpesvirus 5] | ACL27059.1 |
| UL123 | regulatory protein IE1 [Human herpesvirus 5] | AKI21039.1 |
| UL123 | immediate early transcriptional regulator [Human herpesvirus 5] | ACL27065.1 |
| UL123 | immediate early transcriptional regulator [Human herpesvirus 5] | ACL27087.1 |
| UL123 | regulatory protein IE1 [Human herpesvirus 5] | AAR31504.1 |
| UL123 | immediate early transcriptional regulator [Human herpesvirus 5] | ACL27082.1 |
| UL123 | immediate early transcriptional regulator [Human herpesvirus 5] | ACL27055.1 |
| UL123 | immediate early transcriptional regulator [Human herpesvirus 5] | ACL27081.1 |
| UL123 | regulatory protein IE1 [Human herpesvirus 5] | AKI12344.1 |
| UL123 | immediate early transcriptional regulator [Human herpesvirus 5] | ACL27089.1 |
| UL123 | immediate early transcriptional regulator [Human herpesvirus 5] | ACL27062.1 |
| UL123 | immediate early transcriptional regulator [Human herpesvirus 5] | ACL27057.1 |
| UL128 | envelope protein UL128 [Human herpesvirus 5] | AAR31451.1 |
| UL128 | UL128 [Human herpesvirus 5] | ABA86617.1 |
| UL128 | envelope protein UL128 [Human herpesvirus 5] | AAR31335.1 |
| UL128 | envelope protein UL128 [Human herpesvirus 5] | ADV04433.1 |
| UL128 | UL128 [Human herpesvirus 5] | ADF30829.1 |
| UL128 | envelope protein UL128 [Human herpesvirus 5] | ACS92206.1 |
| UL128 | envelope protein UL128 [Human herpesvirus 5] | ADB84652.1 |
| UL128 | envelope protein UL128 [Human herpesvirus 5] | AHJ86203.1 |
| UL128 | envelope protein UL128 [Human herpesvirus 5] | AAO11759.2 |
| UL128 | envelope protein UL128 [Human herpesvirus 5] | AKI07662.1 |
| UL128 | UL128 [Human herpesvirus 5] | ABA86608.1 |
| UL128 | envelope protein UL128 [Human herpesvirus 5] | AKI12512.1 |
| UL128 | envelope protein UL128 [Human herpesvirus 5] | AKI21705.1 |
| UL128 | envelope protein UL128 [Human herpesvirus 5] | AKI20034.1 |
| UL128 | RecName: Full = Uncharacterized protein UL128 | P16837.2 |
| UL128 | UL128 [Human herpesvirus 5] | ABA86623.1 |
| UL128 | envelope protein UL128 [Human herpesvirus 5] | AKI16857.1 |
| UL128 | envelope protein UL128 [Human herpesvirus 5] | AKI18528.1 |
| UL128 | envelope protein UL128 [Human herpesvirus 5] | ADB84820.1 |
| UL128 | envelope protein UL128 [Human herpesvirus 5] | AAR31422.1 |
| UL128 | envelope protein UL128 [Human herpesvirus 5] | AGL96705.1 |
| UL128 | envelope protein UL128 [Human herpesvirus 5] | ACT81952.1 |
| UL128 | envelope protein UL128 [Human herpesvirus 5] | AKI18359.1 |
| UL128 | UL128 [Human herpesvirus 5] | AAO11775.2 |
| UL128 | UL128 [Human herpesvirus 5] | ABA86605.1 |
| UL128 | UL128 [Human herpesvirus 5] | ADF30833.1 |
| UL128 | envelope protein UL128 [Human herpesvirus 5] | AKI11182.1 |
| UL128 | envelope protein UL128 [Human herpesvirus 5] | AKI15691.1 |
| UL128 | UL128 [Human herpesvirus 5] | ABA86622.1 |
| UL128 | UL128 [Human herpesvirus 5] | ADF30832.1 |
| UL128 | UL128 [Human herpesvirus 5] | ABA86616.1 |
| UL128 | envelope protein UL128 [Human herpesvirus 5] | AAO11755.2 |
| UL128 | envelope protein UL128 [Human herpesvirus 5] | AFR55266.1 |
| UL128 | UL128 [Human herpesvirus 5] | ABA86618.1 |
| UL128 | envelope protein UL128 [Human herpesvirus 5] | ADB84700.1 |
| UL128 | UL128 [Human herpesvirus 5] | ADE62337.1 |
| UL128 | UL128 [Human herpesvirus 5] | ADF30837.1 |
| UL128 | UL128 [Human herpesvirus 5] | ABA86604.1 |
| UL128 | envelope protein UL128 [Human herpesvirus 5] | AKI21208.1 |
| UL128 | UL128 [Human herpesvirus 5] | ABA86609.1 |
| UL128 | envelope protein UL128 [Human herpesvirus 5] | AKI10514.1 |
| UL128 | truncated UL128 protein [Human herpesvirus 5] | ADG36331.1 |
| UL128 | HCMVUL128 [Human herpesvirus 5] | CAA35330.1 |
| UL130 | UL130 [Human herpesvirus 5] | ABA86653.1 |
| UL130 | UL130 [Human herpesvirus 5] | ABA86666.1 |
| UL130 | UL130 [Human herpesvirus 5] | ABA86652.1 |
| UL130 | envelope glycoprotein UL130 [Human herpesvirus 5] | YP_081565.1 |
| UL130 | envelope glycoprotein UL130 [Human herpesvirus 5] | AKI08835.1 |
| UL130 | UL130 [Human herpesvirus 5] | AAY33781.1 |
| UL130 | envelope glycoprotein UL130 [Human herpesvirus 5] | ACS92042.1 |
| UL130 | envelope glycoprotein UL130 [Human herpesvirus 5] | AKI10515.1 |
| UL130 | envelope glycoprotein UL130 [Human herpesvirus 5] | AKI07663.1 |
| UL130 | envelope glycoprotein UL130 [Human herpesvirus 5] | AHB19754.1 |
| UL130 | envelope glycoprotein UL130 [Human herpesvirus 5] | AFR55435.1 |
| UL130 | UL130 [Human herpesvirus 5] | AAY33778.1 |
| UL130 | envelope glycoprotein UL130 [Human herpesvirus 5] | AKI18864.1 |
| UL130 | envelope glycoprotein UL130 [Human herpesvirus 5] | AIC80537.1 |

TABLE 3-continued

CMV (Human herpesvirus 5) Amino Acid Sequences

| Protein | Name | GenBank Accession |
|---|---|---|
| UL130 | envelope glycoprotein UL130 [Human herpesvirus 5] | ADB44105.1 |
| UL130 | envelope glycoprotein UL130 [Human herpesvirus 5] | ADB84797.1 |
| UL130 | envelope glycoprotein UL130 [Human herpesvirus 5] | AKI22373.1 |
| UL130 | envelope glycoprotein UL130 [Human herpesvirus 5] | AGL96706.1 |
| UL130 | envelope glycoprotein UL130 [Human herpesvirus 5] | AKI22042.1 |
| UL130 | envelope glycoprotein UL130 [Human herpesvirus 5] | AHJ86204.1 |
| UL130 | RecName: Full = Uncharacterized protein UL130 | P16772.1 |
| UL130 | envelope glycoprotein UL130 [Human herpesvirus 5] | AKI20706.1 |
| UL130 | UL130 [Human herpesvirus 5] | ABA86662.1 |
| UL130 | UL130 [Human herpesvirus 5] | ABA86665.1 |
| UL130 | UL130 [Human herpesvirus 5] | ABA86659.1 |
| UL130 | UL130 [Human herpesvirus 5] | ADF30831.1 |
| UL130 | orf UL130 [Human herpesvirus 5] | AAA85889.1 |
| UL130 | envelope glycoprotein UL130 [Human herpesvirus 5] | AKI11183.1 |
| UL130 | envelope glycoprotein UL130 [Human herpesvirus 5] | AKI19031.1 |
| UL130 | UL130 [Human herpesvirus 5] | ADE62342.1 |
| UL130 | envelope glycoprotein UL130 [Human herpesvirus 5] | AFR55099.1 |
| UL130 | envelope glycoprotein UL130 [Human herpesvirus 5] | AAR31336.1 |
| UL130 | UL130 [Human herpesvirus 5] | ABA86654.1 |
| UL130 | envelope glycoprotein UL130 [Human herpesvirus 5] | AKI17191.1 |
| UL130 | envelope glycoprotein UL130 [Human herpesvirus 5] | ADB84701.1 |
| UL130 | UL130 [Human herpesvirus 5] | ADF30838.1 |
| UL130 | envelope glycoprotein UL130 [Human herpesvirus 5] | AKI15859.1 |
| UL130 | UL130 [Human herpesvirus 5] | ABA86651.1 |
| UL130 | envelope glycoprotein UL130 [Human herpesvirus 5] | AFR55267.1 |
| UL130 | envelope glycoprotein UL130 [Human herpesvirus 5] | ACS92207.1 |
| UL130 | envelope glycoprotein UL130 [Human herpesvirus 5] | AAR31307.1 |
| UL130 | envelope glycoprotein UL130 [Human herpesvirus 5] | AKI15358.1 |
| UL130 | envelope glycoprotein UL130 [Human herpesvirus 5] | AKI21042.1 |
| UL130 | envelope glycoprotein UL130 [Human herpesvirus 5] | AKI16360.1 |
| UL130 | UL130 [Human herpesvirus 5] | ABA86661.1 |
| UL130 | envelope glycoprotein UL130 [Human herpesvirus 5] | AHB19920.1 |
| UL130 | UL130 [Human herpesvirus 5] | ABV71640.1 |
| UL130 | envelope glycoprotein UL130 [Human herpesvirus 5] | AKI23375.1 |
| UL130 | envelope glycoprotein UL130 [Human herpesvirus 5] | AKI08333.1 |
| UL130 | envelope glycoprotein UL130 [Human herpesvirus 5] | AKI21377.1 |
| UL130 | envelope glycoprotein UL130 [Human herpesvirus 5] | AKI16526.1 |
| UL130 | UL130 [Human herpesvirus 5] | ADE62336.1 |
| UL130 | envelope glycoprotein UL130 [Human herpesvirus 5] | AKI14017.1 |
| UL130 | envelope glycoprotein UL130 [Human herpesvirus 5] | AKI09843.1 |
| UL130 | mutant fusion protein [Human herpesvirus 5] | ADE62322.1 |
| UL130 | envelope glycoprotein UL130 [Human herpesvirus 5] | AKI12013.1 |
| UL130 | envelope glycoprotein UL130 [Human herpesvirus 5] | AKI20371.1 |
| UL130 | envelope glycoprotein UL130 [Human herpesvirus 5] | ACZ81666.1 |
| UL130 | envelope glycoprotein UL130 [Human herpesvirus 5] | AAR31365.1 |
| UL130 | envelope glycoprotein UL130 [Human herpesvirus 5] | AAO11754.1 |
| UL131A | envelope protein UL131A [Human herpesvirus 5] | YP_081566.1 |
| UL131A | envelope protein UL131A [Human herpesvirus 5] | AKI12514.1 |
| UL131A | envelope protein UL131A [Human herpesvirus 5] | AKI11683.1 |
| UL131A | envelope protein UL131A [Human herpesvirus 5] | AAO11766.1 |
| UL131A | UL131A [Human herpesvirus 5] | ABA86643.1 |
| UL131A | UL131A [Human herpesvirus 5] | ADE62341.1 |
| UL131A | truncated envelope protein UL131A [Human herpesvirus 5] | ADV04435.1 |
| UL131A | envelope protein UL131A [Human herpesvirus 5] | AFR56272.1 |
| UL131A | envelope protein UL131A [Human herpesvirus 5] | AKI11018.1 |
| UL131A | envelope protein UL131A [Human herpesvirus 5] | AHB19755.1 |
| UL131A | envelope protein UL131A [Human herpesvirus 5] | AKI12348.1 |
| UL131A | UL131a protein [Human herpesvirus 5] | ADG36333.1 |
| UL131A | UL131A [Human herpesvirus 5] | ABA86640.1 |
| UL131A | envelope protein UL131A [Human herpesvirus 5] | AKI08836.1 |
| UL131A | UL131A [Human herpesvirus 5] | ABA86639.1 |
| UL131A | envelope protein UL131A [Human herpesvirus 5] | AKI10182.1 |
| UL131A | envelope protein UL131A [Human herpesvirus 5] | ADB84774.1 |
| UL131A | envelope protein UL131A [Human herpesvirus 5] | ADB84822.1 |
| UL131A | UL131A [Human herpesvirus 5] | ADF30839.1 |
| UL131A | UL131A [Human herpesvirus 5] | ABA86648.1 |
| UL131A | UL131A [Human herpesvirus 5] | ABA86635.1 |
| UL131A | envelope protein UL131A [Human herpesvirus 5] | AFR55436.1 |
| UL131A | UL131A [Human herpesvirus 5] | ABA86637.1 |
| UL131A | UL131A [Human herpesvirus 5] | ABA86644.1 |
| UL131A | UL131A [Human herpesvirus 5] | ABA86647.1 |
| UL131A | UL131A [Human herpesvirus 5] | ABA86629.1 |
| UL131A | UL131A [Human herpesvirus 5] | ABA86630.1 |
| UL131A | UL131A [Human herpesvirus 5] | ABA86646.1 |
| UL55 (gB) | envelope glycoprotein B [Human herpesvirus 5] | ACS91991.1 |

TABLE 3-continued

CMV (Human herpesvirus 5) Amino Acid Sequences

| Protein | Name | GenBank Accession |
|---|---|---|
| UL55 (gB) | envelope glycoprotein B [Human herpesvirus 5] | AKI12129.1 |
| UL55 (gB) | envelope glycoprotein B [Human herpesvirus 5] | ACZ79977.1 |
| UL55 (gB) | envelope glycoprotein B [Human herpesvirus 5] | AFR55216.1 |
| UL55 (gB) | envelope glycoprotein B [Human herpesvirus 5] | AKI22656.1 |
| UL55 (gB) | glycoprotein B [Human herpesvirus 5] | AAA45934.1 |
| UL55 (gB) | envelope glycoprotein B [Human herpesvirus 5] | AFR54884.1 |
| UL55 (gB) | envelope glycoprotein B [Human herpesvirus 5] | AKI22156.1 |
| UL55 (gB) | envelope glycoprotein B [Human herpesvirus 5] | AKI14299.1 |
| UL55 (gB) | envelope glycoprotein B [Human herpesvirus 5] | ADV04383.1 |
| UL55 (gB) | envelope glycoprotein B [Human herpesvirus 5] | AKI20990.1 |
| UL55 (gB) | envelope glycoprotein B [Human herpesvirus 5] | AKI09624.1 |
| UL55 (gB) | envelope glycoprotein B [Human herpesvirus 5] | ADD39116.1 |
| UL55 (gB) | envelope glycoprotein B [Human herpesvirus 5] | ACT81737.1 |
| UL55 (gB) | envelope glycoprotein B [Human herpesvirus 5] | AKI11131.1 |
| UL55 (gB) | envelope glycoprotein B [Human herpesvirus 5] | AKI17642.1 |
| UL55 (gB) | envelope glycoprotein B [Human herpesvirus 5] | AIC80652.1 |
| UL55 (gB) | envelope glycoprotein B [Human herpesvirus 5] | AFR55719.1 |
| UL55 (gB) | envelope glycoprotein B [Human herpesvirus 5] | AKI09288.1 |
| UL55 (gB) | glycoprotein B [Human herpesvirus 5] | AAA45930.1 |
| UL55 (gB) | envelope glycoprotein B [Human herpesvirus 5] | AKI12960.1 |
| UL55 (gB) | glycoprotein B [Human herpesvirus 5] | AAA45926.1 |
| UL55 (gB) | glycoprotein B [Human herpesvirus 5] | AAA45925.1 |
| UL55 (gB) | envelope glycoprotein B [Human herpesvirus 5] | AII80437.1 |
| UL55 (gB) | envelope glycoprotein B [Human herpesvirus 5] | AKI22824.1 |
| UL55 (gB) | envelope glycoprotein B [Human herpesvirus 5] | AHV84013.1 |
| UL55 (gB) | envelope glycoprotein B [Human herpesvirus 5] | AKI07947.1 |
| UL55 (gB) | envelope glycoprotein B [Human herpesvirus 5] | AFR54557.1 |
| UL55 (gB) | envelope glycoprotein B [Human herpesvirus 5] | AHB19702.1 |
| UL55 (gB) | RecName: Full = Envelope glycoprotein B; Short = gB; Flags: Precursor | P06473.1 |
| UL55 (gB) | glycoprotein B [Human herpesvirus 5] | ADB92600.1 |
| UL55 (gB) | envelope glycoprotein B [Human herpesvirus 5] | ADE88063.1 |
| UL55 (gB) | envelope glycoprotein B [Human herpesvirus 5] | AHJ86153.1 |
| UL55 (gB) | envelope glycoprotein B [Human herpesvirus 5] | AFR55885.1 |
| UL55 (gB) | UL55 [Human herpesvirus 5] | ABV71586.1 |
| UL55 (gB) | envelope glycoprotein B [Human herpesvirus 5] | ACS92156.1 |
| UL55 (gB) | envelope glycoprotein B [Human herpesvirus 5] | AKI23491.1 |
| UL55 (gB) | RecName: Full = Envelope glycoprotein B; Short = gB; Contains: RecName: Full = Glycoprotein GP55; Flags: Precursor | P13201.1 |
| UL55 (gB) | glycoprotein B [Human herpesvirus 5] | ABQ23592.1 |
| UL55 (gB) | glycoprotein B [Human herpesvirus 5] | AAB07485.1 |
| UL55 (gB) | envelope glycoprotein B [Human herpesvirus 5] | ACM48044.1 |
| UL55 (gB) | glycoprotein B [Human herpesvirus 5] | AAA45928.1 |
| UL55 (gB) | envelope glycoprotein B [Human herpesvirus 5] | ACS32370.1 |
| UL55 (gB) | envelope glycoprotein B [Human herpesvirus 5] | AKI19983.1 |
| UL55 (gB) | envelope glycoprotein B [Human herpesvirus 5] | AKI13294.1 |
| UL55 (gB) | envelope glycoprotein B [Human herpesvirus 5] | AFR55048.1 |
| UL55 (gB) | envelope glycoprotein B [Human herpesvirus 5] | AKI19483.1 |
| UL55 (gB) | envelope glycoprotein B [Human herpesvirus 5] | YP_081514.1 |
| UL55 (gB) | envelope glycoprotein B [Human herpesvirus 5] | AKI20319.1 |
| UL55 (gB) | envelope glycoprotein B [Human herpesvirus 5] | AHB20033.1 |
| UL55 (gB) | envelope glycoprotein B [Human herpesvirus 5] | AKI23324.1 |
| UL55 (gB) | envelope glycoprotein B [Human herpesvirus 5] | AKI13965.1 |
| UL55 (gB) | envelope glycoprotein B [Human herpesvirus 5] | ACS93398.1 |
| UL55 (gB) | envelope glycoprotein B [Human herpesvirus 5] | AKI08783.1 |
| UL55 (gB) | envelope glycoprotein B [Human herpesvirus 5] | AFR55550.1 |
| UL55 (gB) | envelope glycoprotein B [Human herpesvirus 5] | AKI19648.1 |
| UL55 (gB) | envelope glycoprotein B [Human herpesvirus 5] | AGL96655.1 |
| UL55 (gB) | glycoprotein B [Human herpesvirus 5] | AAA45932.1 |
| UL55 (gB) | glycoprotein B [Human herpesvirus 5] | AAA45933.1 |
| UL55 (gB) | glycoprotein B [*Gorilla gorilla* cytomegalovirus 2.1] | ACT68391.2 |
| UL55 (gB) | glycoprotein B [Human herpesvirus 5] | AAA45931.1 |
| UL55 (gB) | glycoprotein B [Human herpesvirus 5] | AAA45923.1 |
| UL55 (gB) | glycoprotein gB precursor [synthetic construct] | AAT68257.1 |
| UL55 (gB) | glycoprotein B [Human herpesvirus 5] | AAA45924.1 |
| UL55 (gB) | glycoprotein B [Human herpesvirus 5] | AAA45935.1 |
| UL73 (gN) | structural glycoprotein gpUL73 [Human herpesvirus 5] | AAM82374.1 |
| UL73 (gN) | structural glycoprotein gpUL73 [Human herpesvirus 5] | AAG23509.1 |
| UL73 (gN) | structural glycoprotein gpUL73 [Human herpesvirus 5] | AAM82416.1 |
| UL73 (gN) | envelope glycoprotein gpUL73 [Human herpesvirus 5] | AAO24877.1 |
| UL73 (gN) | envelope glycoprotein N [Human herpesvirus 5] | ADE20136.1 |
| UL73 (gN) | envelope glycoprotein N [Human herpesvirus 5] | YP_081521.1 |
| UL73 (gN) | glycoprotein N [Human herpesvirus 5] | ACI45834.1 |
| UL73 (gN) | envelope glycoprotein gpUL73 [Human herpesvirus 5] | AAO27562.1 |
| UL73 (gN) | glycoprotein N [Human herpesvirus 5] | ACI45816.1 |
| UL73 (gN) | envelope glycoprotein N [Human herpesvirus 5] | ACS93313.1 |

TABLE 3-continued

CMV (Human herpesvirus 5) Amino Acid Sequences

| Protein | Name | GenBank Accession |
|---|---|---|
| UL73 (gN) | envelope glycoprotein N [Human herpesvirus 5] | AKI07618.1 |
| UL73 (gN) | glycoprotein N [Human herpesvirus 5] | ADC32373.1 |
| UL73 (gN) | structural glycoprotein gpUL73 [Human herpesvirus 5] | AAG23521.1 |
| UL73 (gN) | glycoprotein N [Human herpesvirus 5] | ADH42929.1 |
| UL73 (gN) | glycoprotein N [Human herpesvirus 5] | ADC32376.1 |
| UL73 (gN) | glycoprotein N [Human herpesvirus 5] | ADH42919.1 |
| UL73 (gN) | glycoprotein N [Human herpesvirus 5] | ACI45808.1 |
| UL73 (gN) | envelope glycoprotein gpUL73 [Human herpesvirus 5] | AAO24851.1 |
| UL73 (gN) | glycoprotein N [Human herpesvirus 5] | ABY48941.1 |
| UL73 (gN) | structural glycoprotein gpUL73 [Human herpesvirus 5] | AAG23512.1 |
| UL73 (gN) | structural glycoprotein gpUL73 [Human herpesvirus 5] | AAM82399.1 |
| UL73 (gN) | UL73 [Human herpesvirus 5] | ABZ04151.1 |
| UL73 (gN) | envelope glycoprotein gpUL73 [Human herpesvirus 5] | AAO24895.1 |
| UL73 (gN) | structural glycoprotein gpUL73 [Human herpesvirus 5] | AAM82420.1 |
| UL73 (gN) | structural glycoprotein UL73 [Human herpesvirus 5] | AAL77782.1 |
| UL73 (gN) | glycoprotein N [Human herpesvirus 5] | ADH42921.1 |
| UL73 (gN) | structural glycoprotein gpUL73 [Human herpesvirus 5] | AAM82396.1 |
| UL73 (gN) | envelope glycoprotein gpUL73 [Human herpesvirus 5] | AAO24881.1 |
| UL73 (gN) | envelope glycoprotein gpUL73 [Human herpesvirus 5] | AAO24889.1 |
| UL73 (gN) | envelope glycoprotein gpUL73 [Human herpesvirus 5] | AAO24892.1 |
| UL73 (gN) | glycoprotein N [Human herpesvirus 5] | ABY48942.1 |
| UL73 (gN) | glycoprotein N [Human herpesvirus 5] | ACI45800.1 |
| UL73 (gN) | envelope glycoprotein gpUL73 [Human herpesvirus 5] | AAO27565.1 |
| UL73 (gN) | glycoprotein N [Human herpesvirus 5] | ABY48936.1 |
| UL73 (gN) | glycoprotein N [Human herpesvirus 5] | ABY48935.1 |
| UL73 (gN) | structural glycoprotein gpUL73 [Human herpesvirus 5] | AAM82375.1 |
| UL73 (gN) | structural glycoprotein gpUL73 [Human herpesvirus 5] | AAM82403.1 |
| UL73 (gN) | envelope glycoprotein N [Human herpesvirus 5] | AHB19542.1 |
| UL73 (gN) | envelope glycoprotein N [Human herpesvirus 5] | AKI23166.1 |
| UL73 (gN) | structural glycoprotein gpUL73 [Human herpesvirus 5] | AAM82412.1 |
| UL73 (gN) | envelope glycoprotein gpUL73 [Human herpesvirus 5] | AAO24836.1 |
| UL73 (gN) | UL73 [Human herpesvirus 5] | ABZ04148.1 |
| UL73 (gN) | envelope glycoprotein N [Human herpesvirus 5] | ACS93153.1 |
| UL73 (gN) | envelope glycoprotein N [Human herpesvirus 5] | AGT36363.1 |
| UL73 (gN) | structural glycoprotein gpUL73 [Human herpesvirus 5] | AAG23511.1 |
| UL73 (gN) | glycoprotein N [Human herpesvirus 5] | ADH42925.1 |
| UL73 (gN) | glycoprotein N [Human herpesvirus 5] | ACI45830.1 |
| UL73 (gN) | structural glycoprotein gpUL73 [Human herpesvirus 5] | AAG23510.1 |
| UL73 (gN) | glycoprotein N [Human herpesvirus 5] | ACI45798.1 |
| UL73 (gN) | structural glycoprotein UL73 [Human herpesvirus 5] | AAL77762.1 |
| UL73 (gN) | glycoprotein N [Human herpesvirus 5] | ADH42926.1 |
| UL73 (gN) | structural glycoprotein UL73 [Human herpesvirus 5] | AAL77766.1 |
| UL73 (gN) | glycoprotein N [Human herpesvirus 5] | ACI45823.1 |
| UL73 (gN) | structural glycoprotein gpUL73 [Human herpesvirus 5] | AAM82378.1 |
| UL73 (gN) | structural glycoprotein gpUL73 [Human herpesvirus 5] | AAM82379.1 |
| UL73 (gN) | UL73 [Human herpesvirus 5] | ABZ04149.1 |
| UL73 (gN) | structural glycoprotein UL73 [Human herpesvirus 5] | AAL77764.1 |
| UL73 (gN) | glycoprotein N [Human herpesvirus 5] | ACI45835.1 |
| UL73 (gN) | glycoprotein N [Human herpesvirus 5] | ACI45825.1 |
| UL73 (gN) | glycoprotein N [Human herpesvirus 5] | ADH42931.1 |
| UL73 (gN) | envelope glycoprotein N [Human herpesvirus 5] | ACS93218.1 |
| UL73 (gN) | structural glycoprotein gpUL73 [Human herpesvirus 5] | AAM82408.1 |
| UL73 (gN) | glycoprotein N [Human herpesvirus 5] | ACI45831.1 |
| UL73 (gN) | envelope glycoprotein gpUL73 [Human herpesvirus 5] | AAO27561.1 |
| UL73 (gN) | glycoprotein N [Human herpesvirus 5] | ACI45826.1 |
| UL74 (gO) | UL74 protein [Human herpesvirus 5] | AAN40064.1 |
| UL74 (gO) | envelope glycoprotein O [Human herpesvirus 5] | AKI16316.1 |
| UL74 (gO) | envelope glycoprotein O [Human herpesvirus 5] | ACS93259.1 |
| UL74 (gO) | UL74 protein [Human herpesvirus 5] | AAN40079.1 |
| UL74 (gO) | envelope glycoprotein O [Human herpesvirus 5] | AKI18316.1 |
| UL74 (gO) | glycoprotein O [Human herpesvirus 5] | ABY48961.1 |
| UL74 (gO) | glycoprotein O [Human herpesvirus 5] | ABY48960.1 |
| UL74 (gO) | glycoprotein O [Human herpesvirus 5] | ABY48959.1 |
| UL74 (gO) | envelope glycoprotein O [Human herpesvirus 5] | ACS93169.1 |
| UL74 (gO) | UL74 protein [Human herpesvirus 5] | AAN40044.1 |
| UL74 (gO) | envelope glycoprotein O [Human herpesvirus 5] | ACS93340.1 |
| UL74 (gO) | RecName: Full = Glycoprotein O; Short = gO; Flags: Precursor | P16750.1 |
| UL74 (gO) | UL74 protein [Human herpesvirus 5] | AAN40046.1 |
| UL74 (gO) | UL74 protein [Human herpesvirus 5] | AAN40054.1 |
| UL74 (gO) | envelope glycoprotein O [Human herpesvirus 5] | AKI08959.1 |
| UL74 (gO) | envelope glycoprotein O [Human herpesvirus 5] | AKI20327.1 |
| UL74 (gO) | UL74 protein [Human herpesvirus 5] | AAN40071.1 |

TABLE 3-continued

CMV (Human herpesvirus 5) Amino Acid Sequences

| Protein | Name | GenBank Accession |
|---|---|---|
| UL74 (gO) | envelope glycoprotein O [Human herpesvirus 5] | AHB19710.1 |
| UL74 (gO) | envelope glycoprotein O [Human herpesvirus 5] | AKI07787.1 |
| UL74 (gO) | UL74 protein [Human herpesvirus 5] | AAN40043.1 |
| UL74 (gO) | UL74 protein [Human herpesvirus 5] | AAN40078.1 |
| UL74 (gO) | envelope glycoprotein O [Human herpesvirus 5] | ACS93309.1 |
| UL74 (gO) | envelope glycoprotein O [Human herpesvirus 5] | ACS93234.1 |
| UL74 (gO) | UL74 protein [Human herpesvirus 5] | AAN40040.1 |
| UL74 (gO) | envelope glycoprotein O [Human herpesvirus 5] | AKI19491.1 |
| UL74 (gO) | envelope glycoprotein O [Human herpesvirus 5] | AKI16979.1 |
| UL74 (gO) | envelope glycoprotein O [Human herpesvirus 5] | AKI20998.1 |
| UL74 (gO) | envelope glycoprotein O [Human herpesvirus 5] | AKI23000.1 |
| UL74 (gO) | envelope glycoprotein O [Human herpesvirus 5] | AKI10806.1 |
| UL74 (gO) | UL74 protein [Human herpesvirus 5] | AAN40073.1 |
| UL74 (gO) | UL74 protein [Human herpesvirus 5] | AAN40057.1 |
| UL74 (gO) | UL74 protein [Human herpesvirus 5] | AAN40050.1 |
| UL74 (gO) | glycoprotein O [Human herpesvirus 5] | ABY48952.1 |
| UL74 (gO) | envelope glycoprotein O [Human herpesvirus 5] | AKI09296.1 |
| UL74 (gO) | envelope glycoprotein O [Human herpesvirus 5] | ACS93149.1 |
| UL74 (gO) | envelope glycoprotein O [Human herpesvirus 5] | AKI14979.1 |
| UL74 (gO) | UL74 protein [Human herpesvirus 5] | AAN40060.1 |
| UL74 (gO) | glycoprotein O [Human herpesvirus 5] | ABY48954.1 |
| UL74 (gO) | glycoprotein O [Human herpesvirus 5] | ABY48955.1 |
| UL74 (gO) | envelope glycoprotein O [Human herpesvirus 5] | ACS93219.1 |
| UL74 (gO) | envelope glycoprotein O [Human herpesvirus 5] | ACS93164.1 |
| UL74 (gO) | envelope glycoprotein O [Human herpesvirus 5] | YP_081522.1 |
| UL74 (gO) | glycoprotein O [Human herpesvirus 5] | ABY48956.1 |
| UL74 (gO) | envelope glycoprotein O [Human herpesvirus 5] | AKI11474.1 |
| UL74 (gO) | UL74 protein [Human herpesvirus 5] | AAN40039.1 |
| UL74 (gO) | UL74 protein [Human herpesvirus 5] | AAN40041.1 |
| UL74 (gO) | envelope glycoprotein O [Human herpesvirus 5] | ACS93154.1 |
| UL74 (gO) | envelope glycoprotein O [Human herpesvirus 5] | ACT81745.1 |
| UL74 (gO) | envelope glycoprotein O [Human herpesvirus 5] | ACS92164.1 |
| UL74 (gO) | UL74 protein [Human herpesvirus 5] | AAN40052.1 |
| UL74 (gO) | envelope glycoprotein O [Human herpesvirus 5] | AHJ86161.1 |
| UL74 (gO) | envelope glycoprotein O [Human herpesvirus 5] | ACS93204.1 |
| UL74 (gO) | envelope glycoprotein O [Human herpesvirus 5] | AKI15314.1 |
| UL74 (gO) | envelope glycoprotein O [Human herpesvirus 5] | ACZ80315.1 |
| UL74 (gO) | envelope glycoprotein O [Human herpesvirus 5] | AKI23332.1 |
| UL74 (gO) | envelope glycoprotein O [Human herpesvirus 5] | ACU83724.1 |
| UL74 (gO) | UL74 protein [Human herpesvirus 5] | AAN40047.1 |
| UL74 (gO) | envelope glycoprotein O [Human herpesvirus 5] | AHV84021.1 |
| UL74 (gO) | UL74 protein [Human herpesvirus 5] | AAN40056.1 |
| UL74 (gO) | envelope glycoprotein O [Human herpesvirus 5] | AKI22164.1 |
| UL74 (gO) | envelope glycoprotein O [Human herpesvirus 5] | ACS93189.1 |
| UL74 (gO) | UL74 protein [Human herpesvirus 5] | AAN40074.1 |
| UL74 (gO) | envelope glycoprotein O [Human herpesvirus 5] | AKI18820.1 |
| UL74 (gO) | envelope glycoprotein O [Human herpesvirus 5] | AKI07619.1 |
| UL74 (gO) | UL74 protein [Human herpesvirus 5] | AAN40072.1 |
| UL74 (gO) | envelope glycoprotein O [Human herpesvirus 5] | AKI19991.1 |
| UL74 (gO) | UL74 protein [Human herpesvirus 5] | AAN40062.1 |
| UL74 (gO) | envelope glycoprotein O [Human herpesvirus 5] | AKI10471.1 |
| UL74 (gO) | UL74 protein [Human herpesvirus 5] | AAN40042.1 |
| UL74 (gO) | glycoprotein O [Human herpesvirus 5] | AAT91377.1 |
| UL74 (gO) | glycoprotein O [Human herpesvirus 5] | ACI45857.1 |
| UL74 (gO) | UL74 protein [Human herpesvirus 5] | AAP88253.1 |
| | RecName: Full = Large structural phosphoprotein; AltName: Full = 150 kDa matrix phosphoprotein; AltName: Full = 150 kDa phosphoprotein; Short = pp150; AltName: Full = Basic phosphoprotein; Short = BPP; AltName: Full = Phosphoprotein UL32; AltName: Full = Tegument protein UL32 | P08318.1 |
| | UL32 [Human herpesvirus 5] | ABV71562.1 |
| | UL32 [Human herpesvirus 5] | AAG31644.1 |
| | UL32 [Human herpesvirus 5] | AAS48942.1 |
| | UL83 [Human herpesvirus 5] | ABV71605.1 |
| | RecName: Full = 65 kDa phosphoprotein; Short = pp65; AltName: Full = 65 kDa matrix phosphoprotein; AltName: Full = Phosphoprotein UL83; AltName: Full = Tegument protein UL83 | P06725.2 |
| | RecName: Full = 65 kDa phosphoprotein; Short = pp65; AltName: Full = 64 kDa matrix phosphoprotein; Short = pp64; AltName: Full = GP64; AltName: Full = Phosphoprotein UL83; AltName: Full = Tegument protein UL83 [Human herpesvirus 5 strain Towne] | P18139.2 |
| | HCMVUL115 [Human herpesvirus 5] | CAA35317.1 |
| | truncated UL115 protein [Human herpesvirus 5] | ADG34192.1 |

Figure 1B:
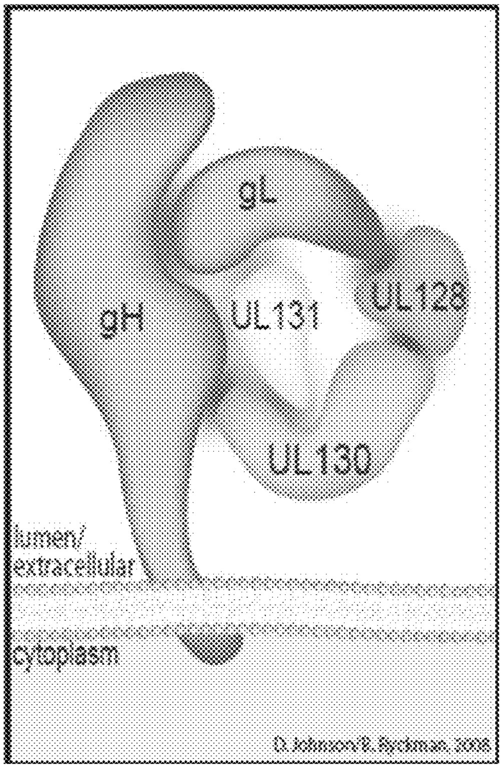
Figure 1C:
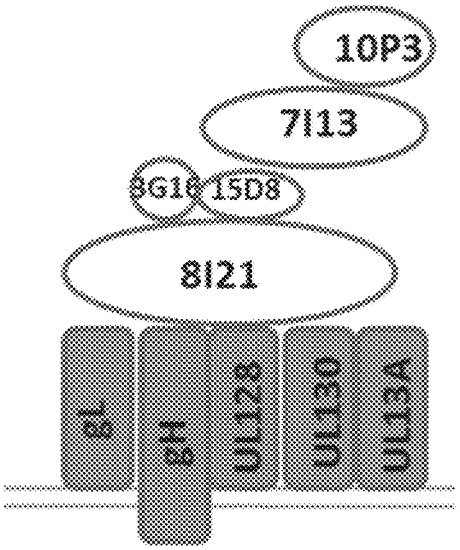
Figure 2A:
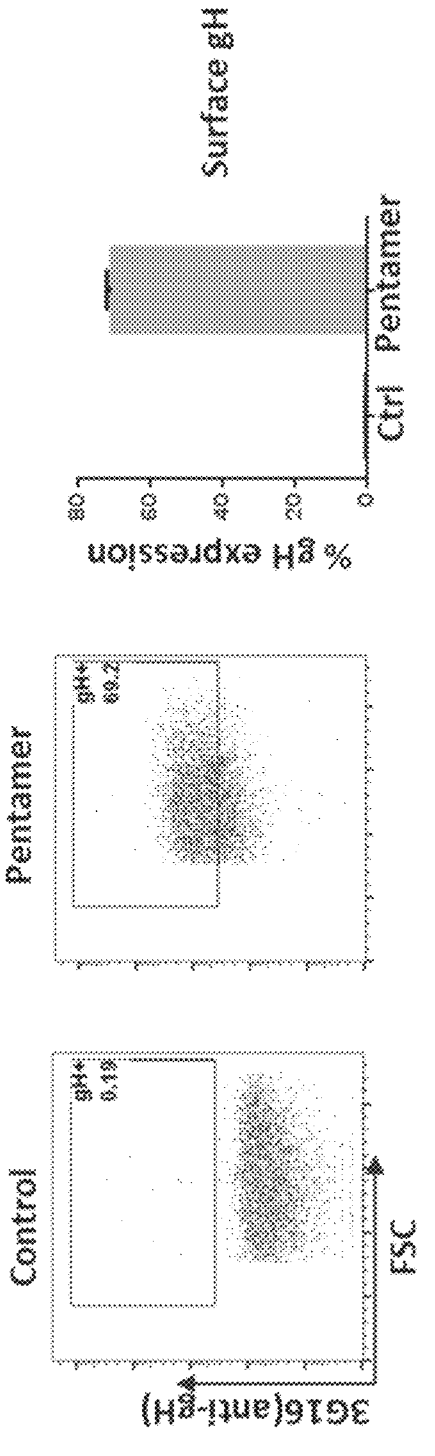
FIGS. 2A-2D show that delivery of pre-mixed mRNAs encoding the various subunits of hCMV pentamer leads to surface expression of the pentameric complex in HeLa cells.
Figure 2B:
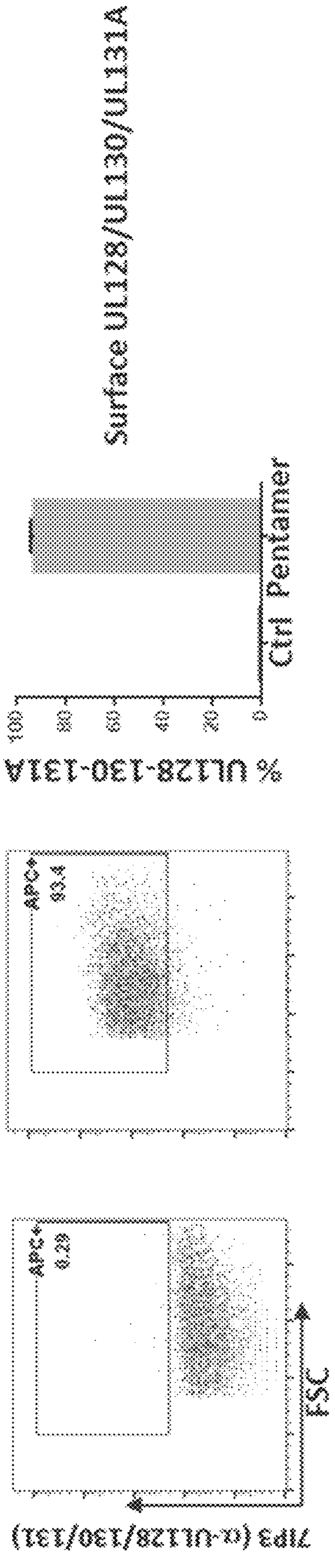
Figure 2C:
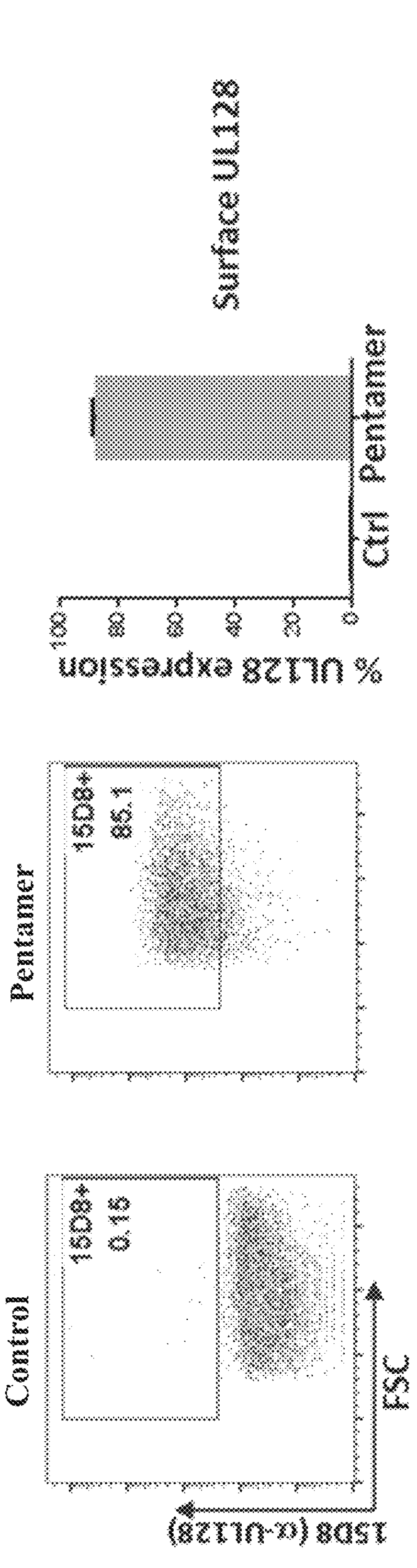
Figure 2D:
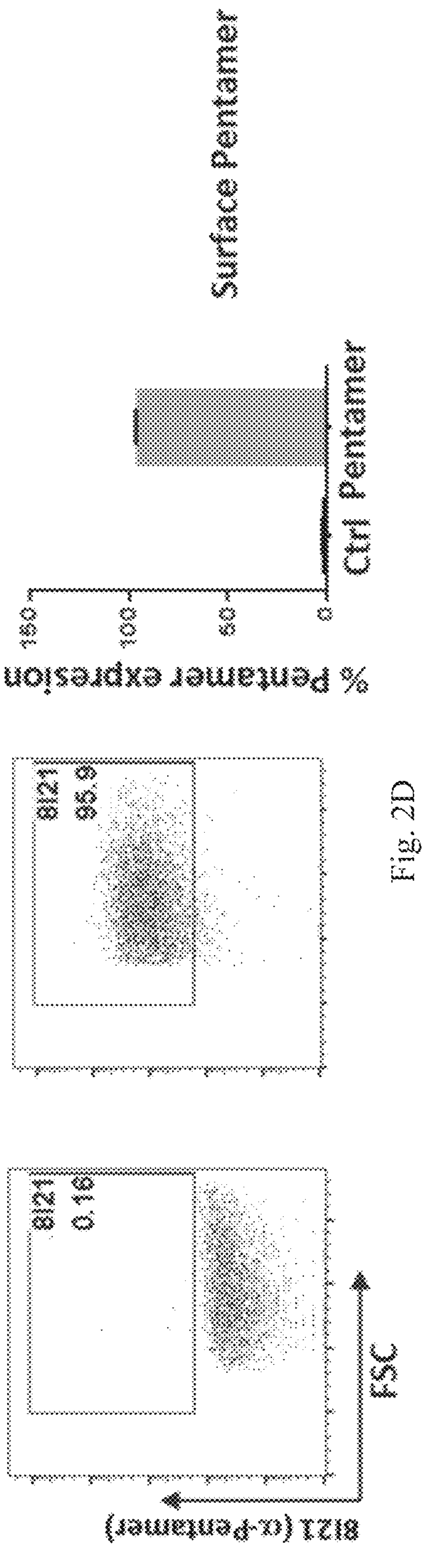

Example 22: Expression of mRNA Vaccine Constructs Encoding the hICMV Pentameric Complex in HeLa Cells Expression of mRNA vaccine constructs encoding the subunits of the hCMV pentameric complex, including gH, gL, UL128, UL130, and UL131A was tested (FIG. 1B). mRNAs encoding each subunit were mixed at a gH:gL: UL128:UL130:UL131A ratio of 4:2:1:1:1. The total amount of mRNA used for transfecting HeLa cells was 2 μg. The transfected HeLa cells were incubated for 24 hours before they were analyzed using fluorescence-activated cell sorting (FACS) on a flow cytometer for the surface expression of the pentameric complex subunits as well as the complete pentamer (FIGS. 2A-2D). Antibodies specific for gH, UL128, the UL128/130/131A complex, or the complete pentamer were used for the detection of surface expression of the proteins. Surface expression of gH, UL128, the UL128/130/131A complex, and the complete pentameric complex were detected in HeLa cells (FIGS. 2A-2D).

Figure 3A:
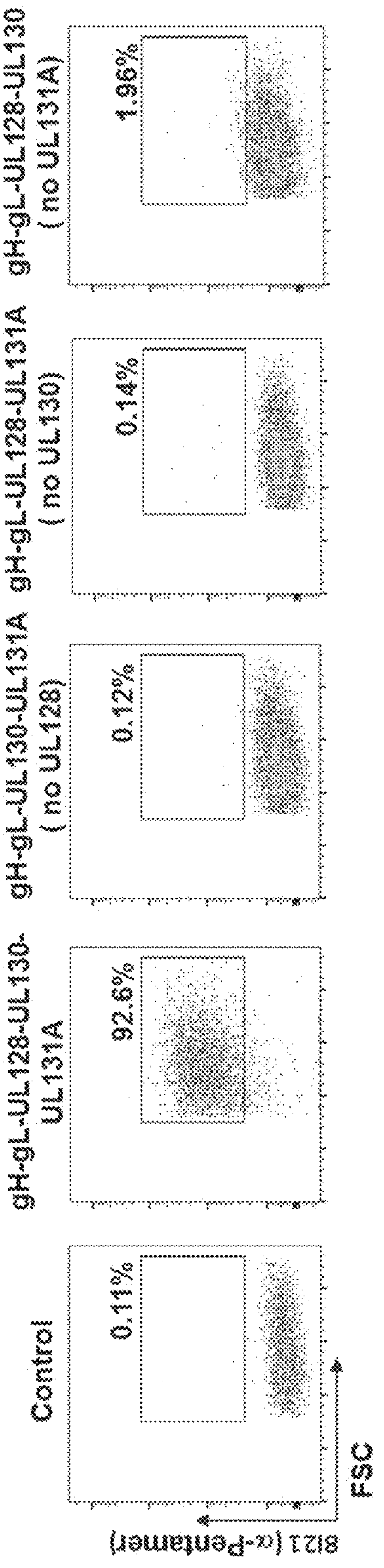
FIGS. 3A-3B show that the hCMV pentameric complex does not express on the cell surface in the absence of one of the core subunits. mRNAs encoding all or some of the subunits in the pentamer were expressed in HeLa cells and the surface expression of the pentamer was detected by an anti-pentamer antibody (8I21). Surface expression of the pentamer was only detected at high levels when all the core subunits were expressed.
Figure 3B:
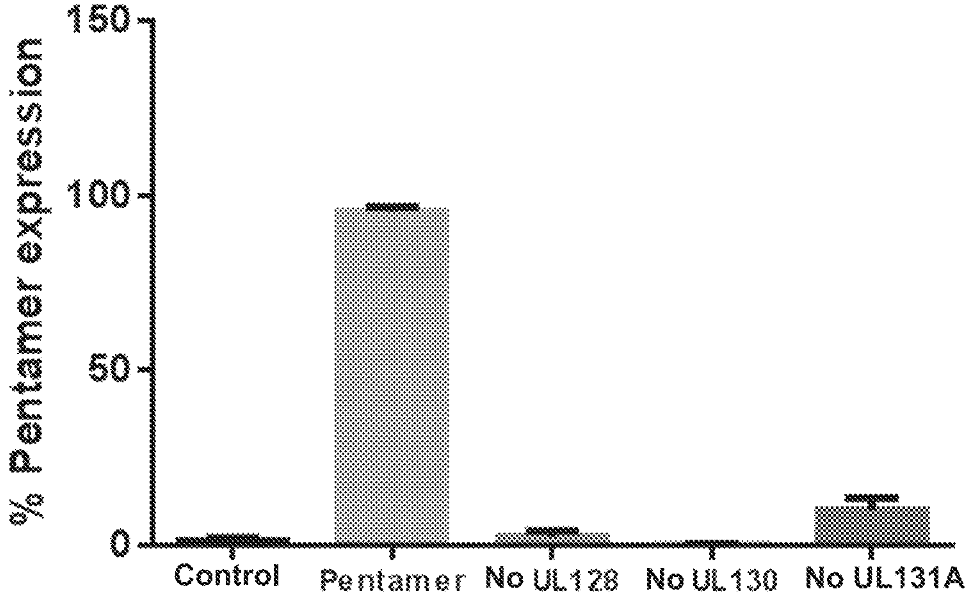

Different combinations of the mRNAs encoding the pentameric subunits were also tested to determine whether all of the core subunits were need for the surface expression of the complete pentameric complex (FIGS. 3A-3B). The experiments were carried out as described above with the indicated mRNA combinations. An antibody specific for the complete pentameric complex was used (8I21). The results show that the pentameric complex does not express on the cell surface in the absence of any of UL128, UL130, or UL131A.

Figure 4A:
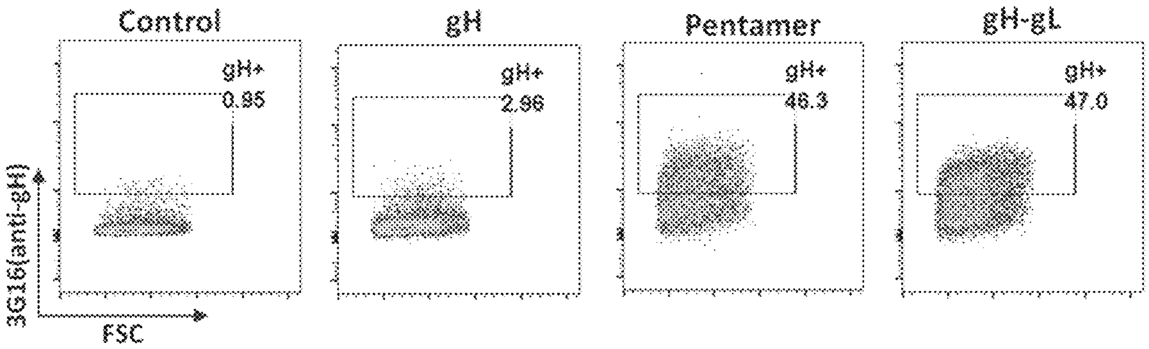
FIGS. 4A-B shows the dimerization of gH-gL is sufficient to lead to surface expression of gH. The anti-gH antibody (3G16) was used for the detection of gH on the cell surface. When gH and gL were co-expressed, a similar level of gH was detected on the surface of HeLa cells as when all subunits in the pentameric complex were expressed. When gH was expressed alone, very little gH was detected on the surface of the transfected HeLa cells.
Figure 4B:
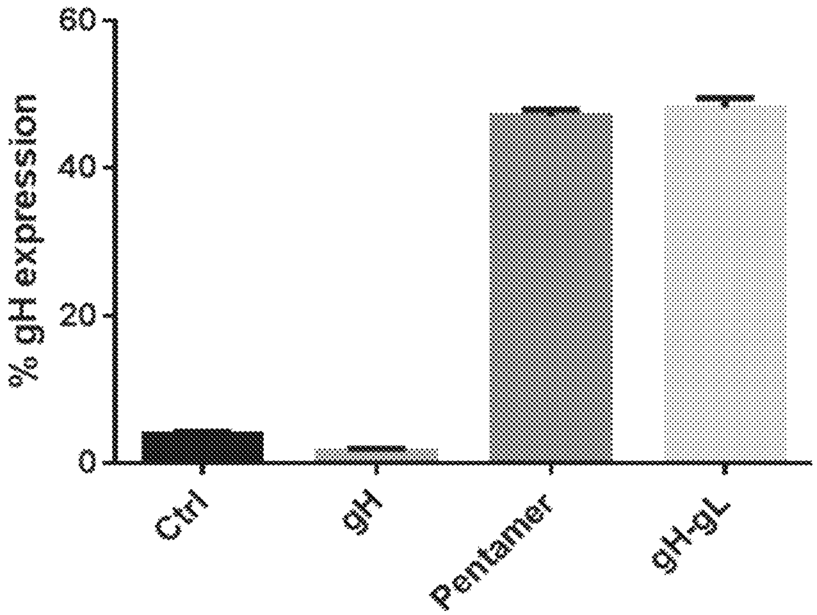

Next, the surface expression of the gH glycoprotein with or without gL was tested. The experiments were carried out as described above using mRNA constructs encoding gH, gH and gL, or constructs encoding the pentameric complex. An antibody specific for gH (3G16) was used. The results showed that expression of gH alone does not lead to gH expression on the cell surface. However, when gH was complexed with gL, a similar level of gH was detected on the surface of the HeLa cells as when all subunits in the pentameric complex were expressed (FIGS. 4A-4B).

Figure 5B:
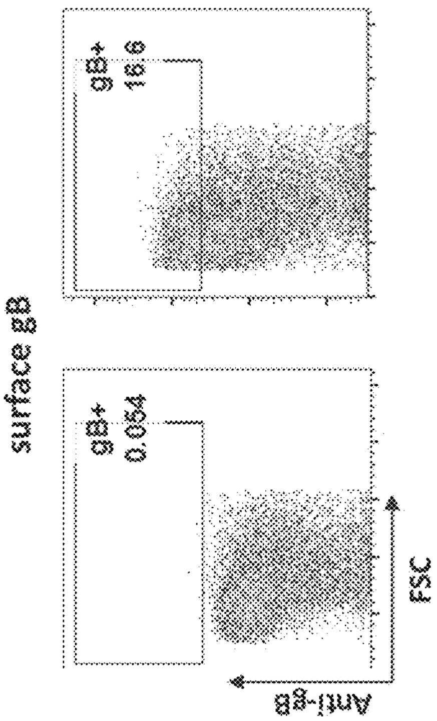
FIGS. 5A-5D show the intracellular and surface expression of hCMV antigen gB. The mRNA encoding gB was expressed both intracellularly and on the cell surface (FIGS. 5A-5C). Both gB precursor and the proteolytically processed, mature gB, were detected by anti-gB antibodies in an immunoblot (FIG. 5D). "*" indicates that the lane was overloaded.
Figure 5A:
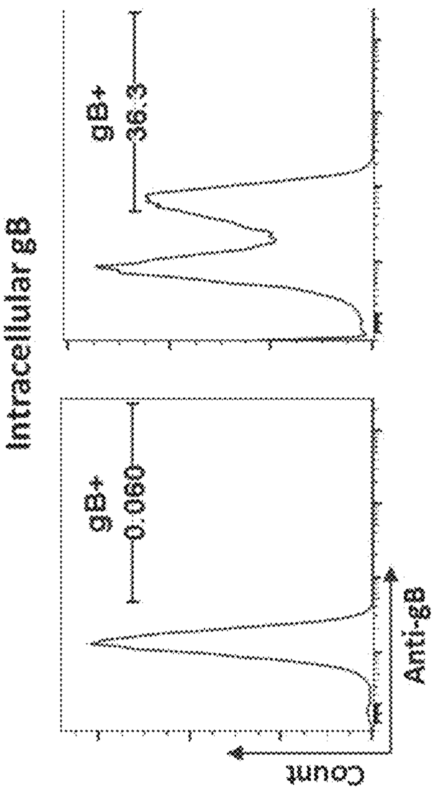
Figure 5D:
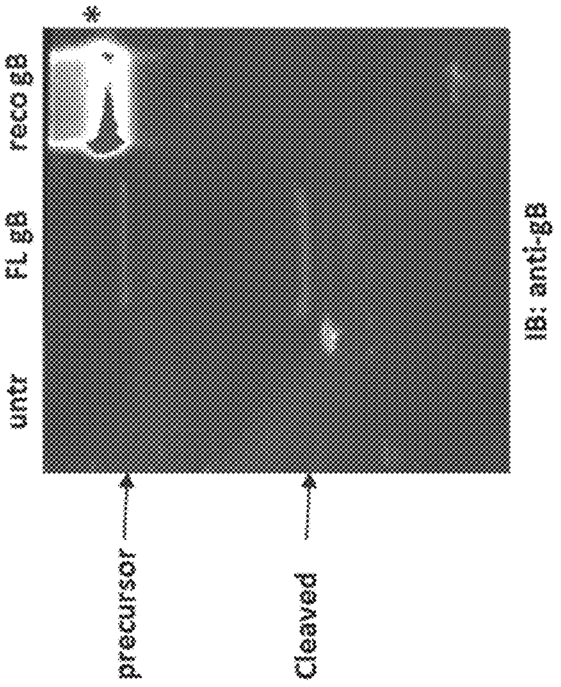
Figure 5C:
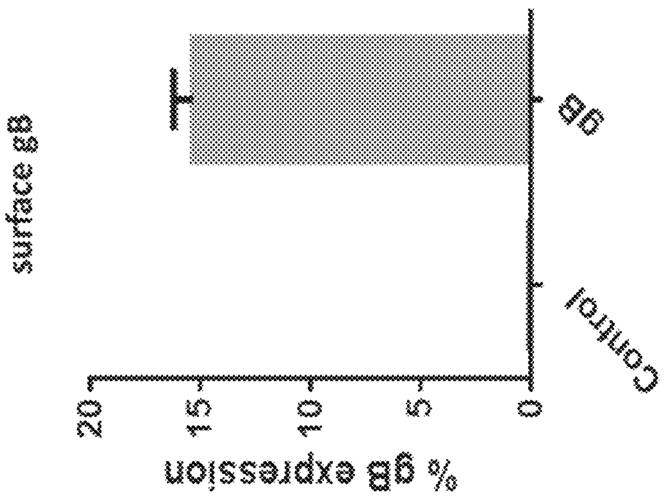

The intracellular and surface expression of gB was also tested using antibodies specific for gB. FIG. 5A shows intracellular gB expression. The surface expression of gB was measured by FACS on a flow cytometer and surface expression of gB was detected (FIG. 5B). The quantification of gB surface expression is shown in FIG. 5C. Further, an immunoblot conducted on cell lysates from HeLa cells transfected with mRNA constructs encoding gB is shown in FIG. 5D. Untransfected HeLa cell lysates were used as a negative control and reconstituted full-length gB protein was used as a positive control. As shown in FIG. 5D, middle lane, both full-length gB (the precursor) and the mature gB after proteolytic cleavage were detected.

Example 23: High Titers of Anti-Pentameric Antibodies Following Immunization with hCMV Pentameric Complex mRNA Vaccine Constructs The immunogenicity of candidate hCMV mRNA vaccine constructs encoding the pentameric complex subunits and/or the gB antigen was tested in mice. The immunization schedule and mRNA fomulations ares shown in Table 4 below.

Mice were divided into groups (5 mice per group) and vaccinated on day 0, 21, and 42 via intramuscular (IM) routes. One group of mice was vaccinated with empty lipid nanoparticles (LNP) as a control. Other groups of mice received hCMV mRNA vaccine constructs encoding the pentameric complex, the gB antigen, both the pentameric complex and gB antigen, or either the pentameric protein complex or the gB protein antigen combined with MF59. When mRNA vaccine constructions were given, different preparation procedures were used. The "pre-mix" mRNAs were pre-mixed and then formulated, while the "post-mix" mRNAs were individually formulated and then mixed. The mRNAs encoding all the subunits of the pentameric complex were formulated with different ratios as shown in Table 4: gH-gL-UL128-UL130-UL131A was 4:2:1:1:1 or 1:1:1:1:1. gB+pentamer was formulated at 1:1:1:1:1:1. The dose schedules used are indicated in Table 4.

Mice sera were collected from each mouse on days −1 (pre-dos), 20, 41, 62, and 84.

Figure 6:
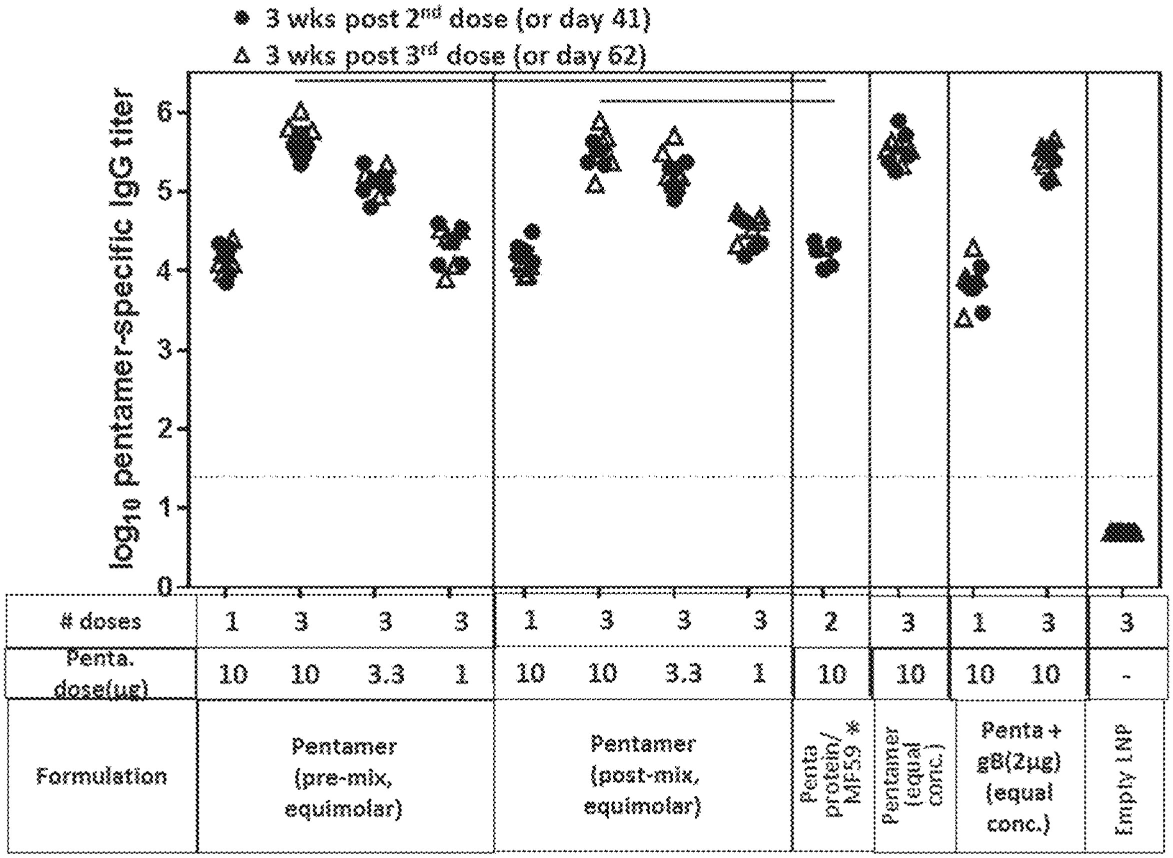
FIG. 6 shows an immunogenicity study of the hCMV pentameric complex mRNA vaccine constructs. Mice were vaccinated according to the vaccination schedule with indicated dosages of the mRNAs. High titers of anti-pentamer antibodies were detected in mice serum following the immunization. Different formulations of the pentamer mRNAs produced comparable levels of antibodies. A third immunization did not lead to boosting of antibody production.
Figure 7:
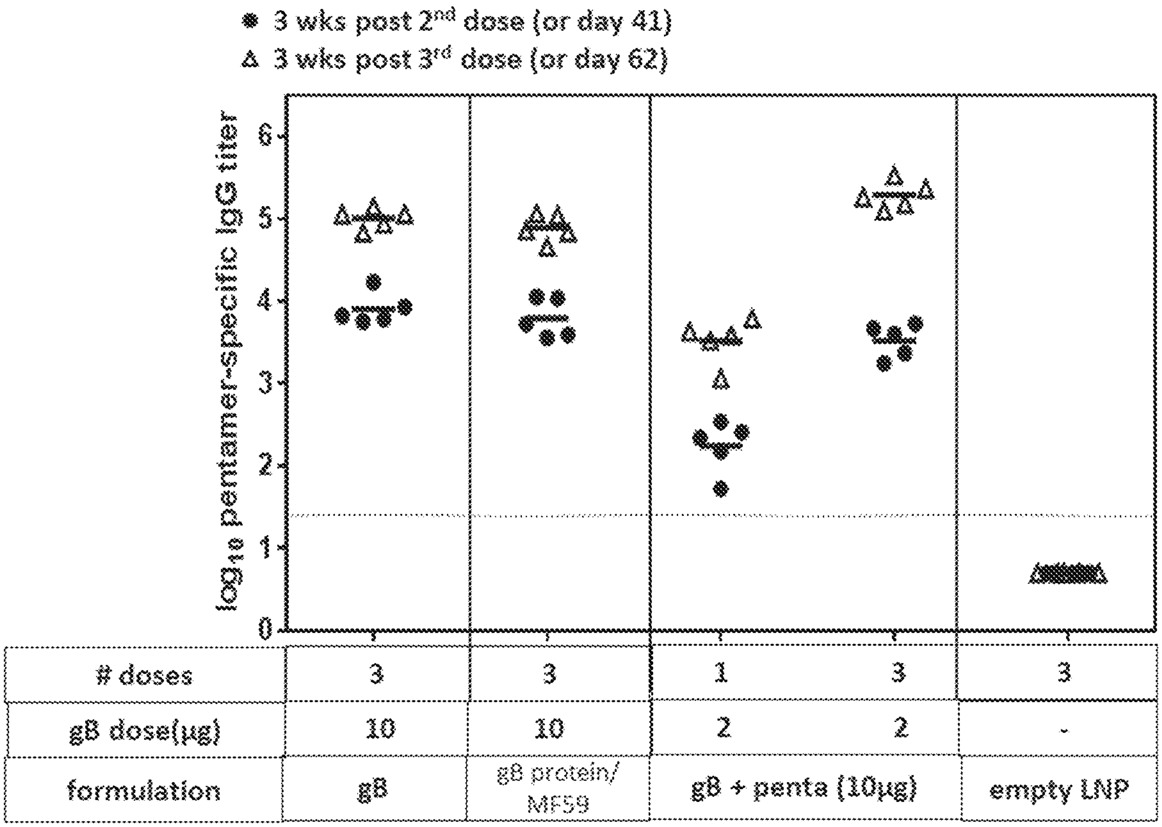
FIG. 7 shows an immunogenicity study of the hCMV gB mRNA vaccine construct, with or without the pentameric complex mRNA constructs. gB mRNA constructs produced similar IgG titers as the gB protein/MF59 antigens after 3 immunizations. A boost in IgG production was observed after the third immunization. Addition of pentameric mRNA constructs did not interefere with the induction of anti-gB IgG.

Individual bleeds from all time points were tested via ELISA assay carried out on plates coated with hCMV pentamers. Serum samples typically were diluted 1:100 for the assay. Incubation and washing protocols were performed using routine methods. Data was read at 450 nm wavelength. Data was reported and plotted (FIGS. 6 and 7). FIG. 6 shows that anti-pentamer-specific IgG were induced by hCMV mRNA vaccine constructs. However, little or no boosting was observed after the $3^{rd}$ immunization. IgG response was maintained from 6-9 weeks following a single immunization. Adding mRNAs encoding gB to mRNAs encoding the pentameric complex subunits did not interefere with anti-pentameric IgG production. Different molar ratios of the mRNAs encoding different pentameric complex subunits did not lead to different IgG induction levels. FIG. 7 shows that the mRNA vaccine constructs encoding gB induced anti-gB IgG response. IgG titers were similar for gB mRNA compared to gB protein/MF59 at 10 μg dose after three immunizations. A boost response was observed after the 3′d immunization of gB mRNAs or antigens. Adding mRNAs encoding the pentameric complex subunits to mRNAs encoding gB did not interefere with anti-gB IgG production.

Figure 8:
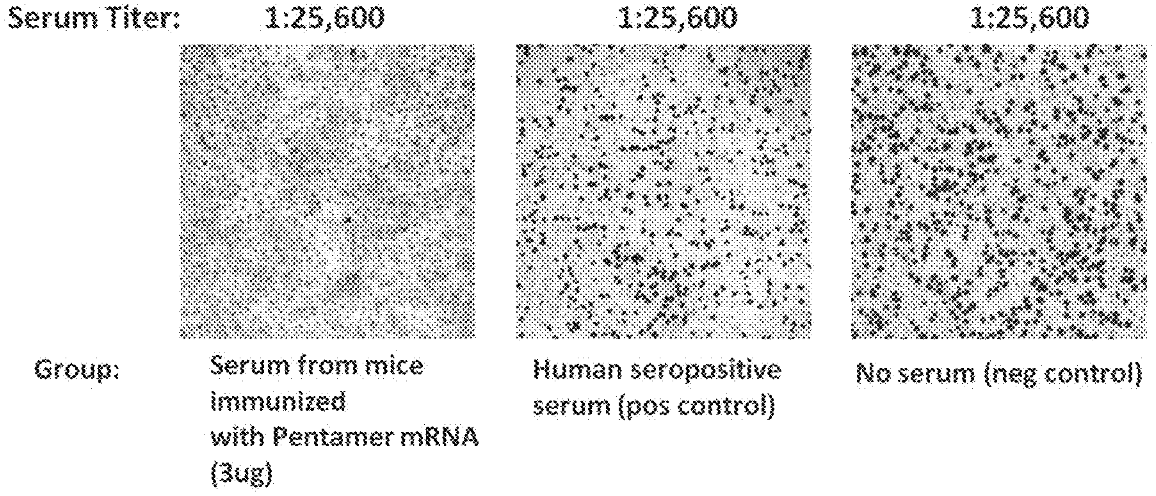
FIG. 8 shows a neutralization study of the hCMV pentameric complex mRNA vaccine constructs in the epithelial cell line ARPE-19. IE1 staining in infected ARPE-19 cells is demonstrated. Immunization with hCMV pentameric complex mRNA vaccine constructs elicits highly potent neutralizing antibodies in mice. Neutralizing antiboey titer (1:25600) in mice serum at day 41 (3 weeks post second immunization) was able to neutrzalize the hCMV clinical isolate VR1814 in ARPE-19 cells.

Example 24: Immunization with hCMV Pentameric Complex mRNA Elicits Highly Potent Neutralizing Antibodies in Mice Neutralization assays were conducted in epithelial cell line ARPE-19 infected with hCMV clinical isolate VR1814 were conducted. Mice were immunized according to the methods in Example 23. Mouse serum samples were collected 3 weeks after the second immunization (on day 41). Mice sera collected from mice immunized with 3 μg of hCMV mRNA pentameric vaccine constructs were diluted (1:25600) and added to the infected cells. The cells were stained for hCMV IE1 protein (as an indication of the presence of hCMV in the cells). Results showed that serum from mice immunized with 3 μg of hCMV pentameric mRNA vaccine constructs were able to neutralize the hCMV in ARPE-19 cells, while the controls of human seropositive serum or no serum did not neutralize the hCMV in ARPE-19 cells (FIG. 8).

Figure 9:
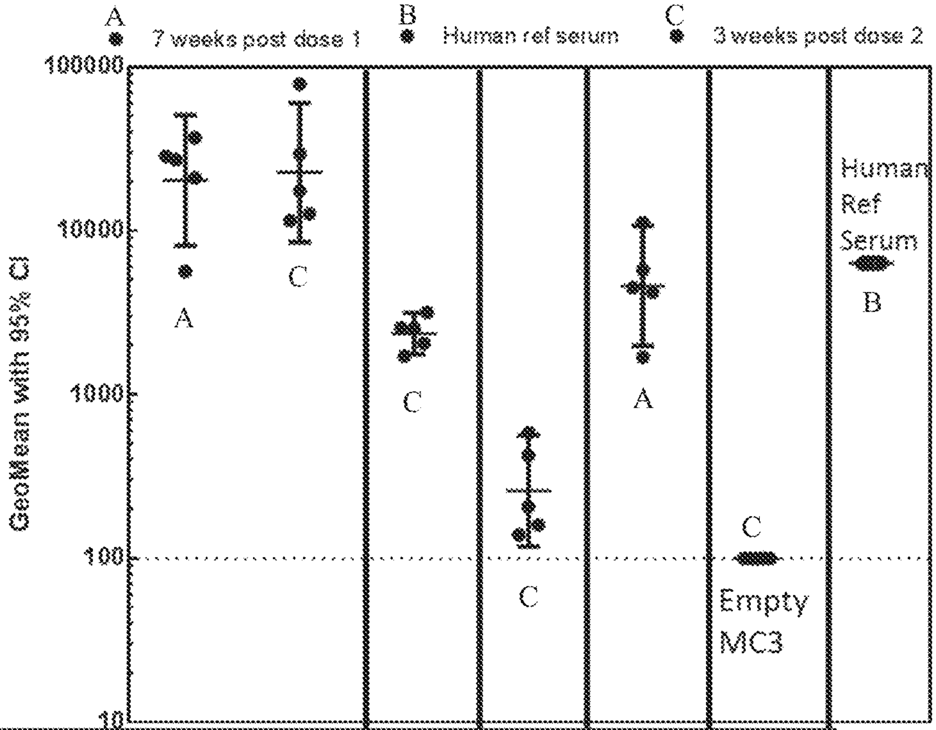
FIG. 9 shows a measurement of hCMV neutralization IgG tiers in ARPE-19 cells infected with the hCMV clinical isolate strain VR1814. See also Table 5.
Figure 10A:
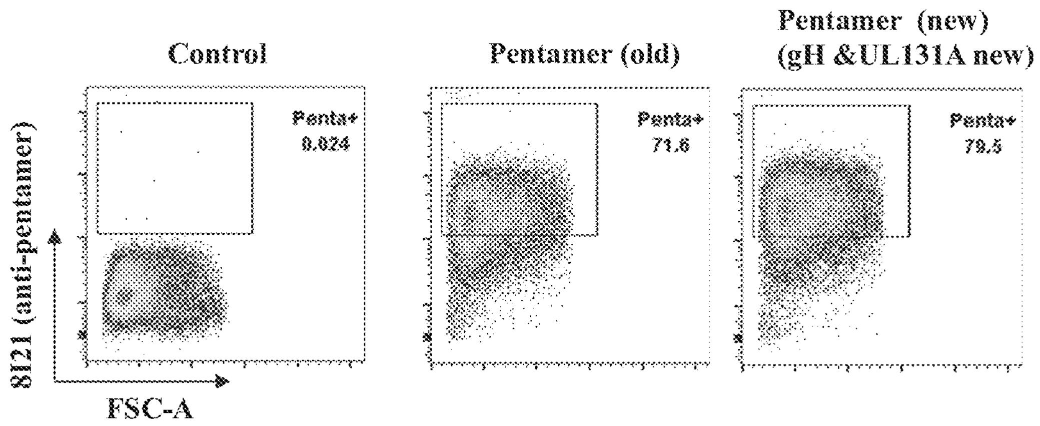
FIGS. 10A-10B show the surface expression in HeLa cells of the hCMV pentameric complex (gH-gL-UL128-UL130-UL131A) encoded by the first-generation pentameric constructs described herein (referred to as "old") and second-generation pentameric constructs also described herein (referred to as "new"). The sequences of the mRNAs within the second generation constructs are provided in Table 6, corresponding to SEQ ID NOs: 58-69.
Figure 10B:
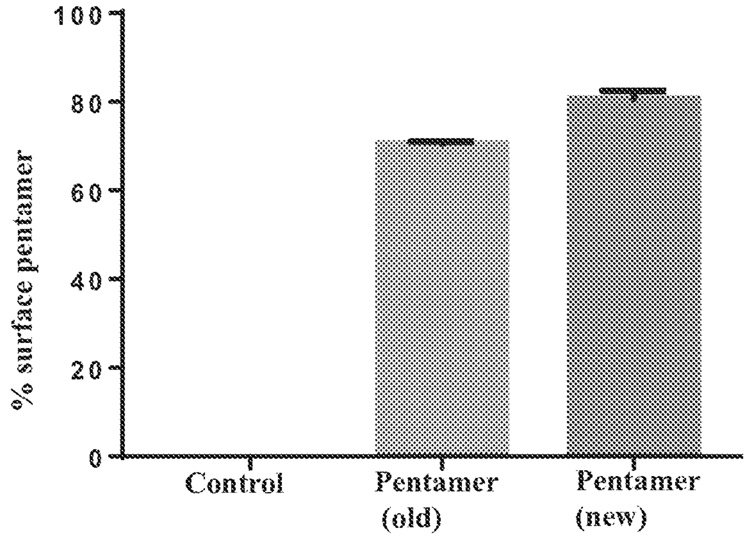
Figure 10C:
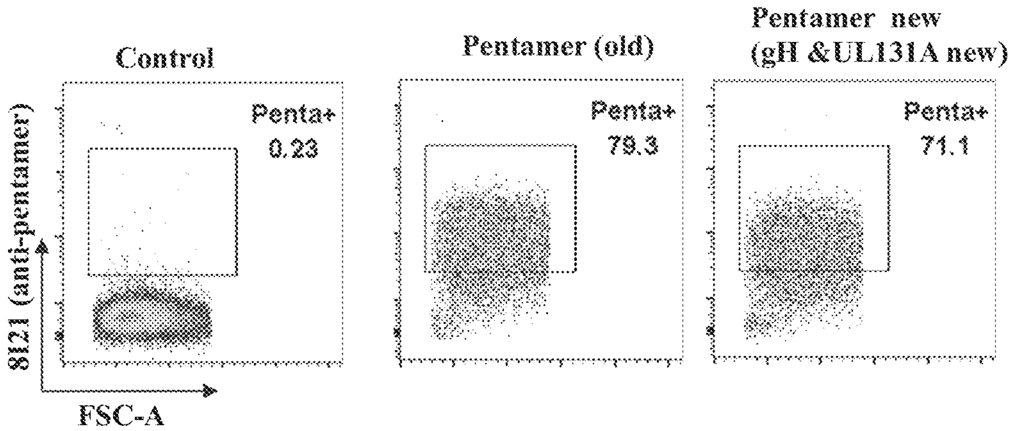
Figure 10D:
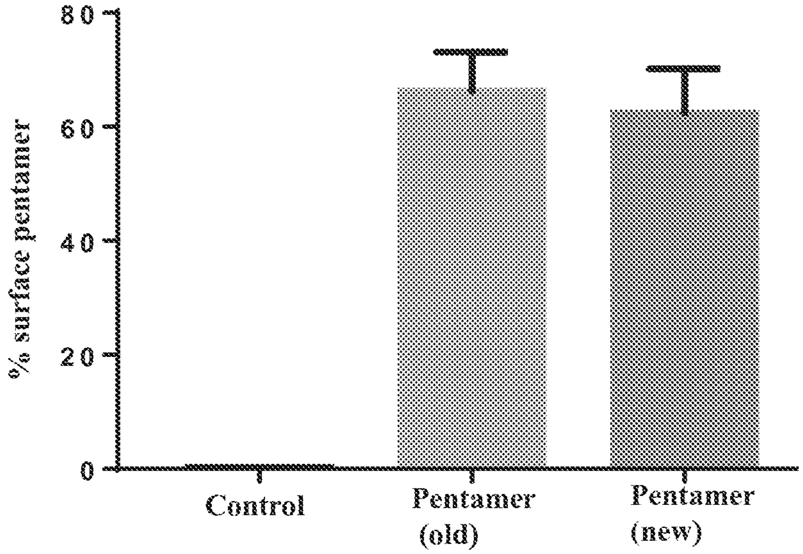
Figure 11A:
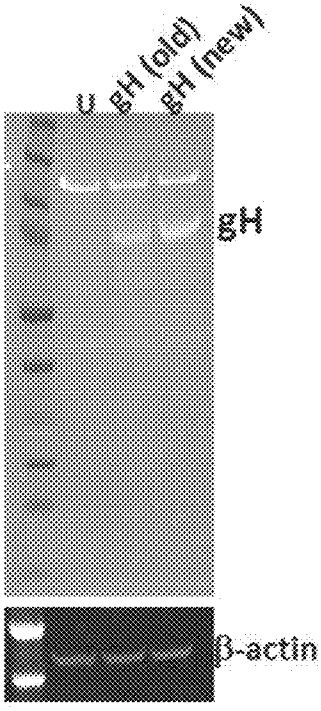
FIGS. 11A-11E depicts Western blots showing the expression of the subunits of the hCMV pentameric complex (gH, gL, UL128, UL130, and UL131A) encoded by the first generation pentameric constructs described herein (referred to as "old") and second-generation pentameric constructs also described herein (referred to as "new").
Figure 11B:
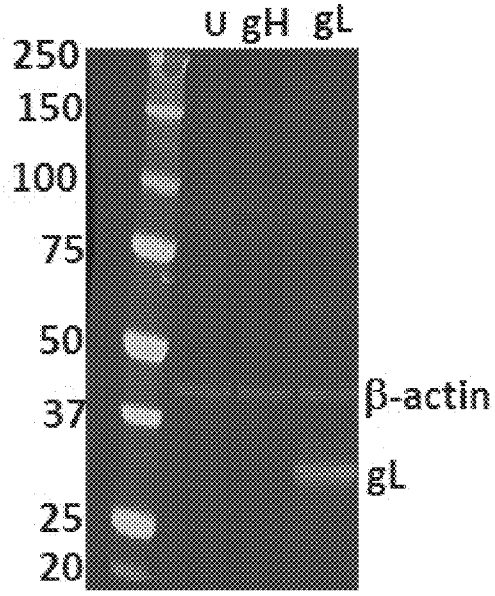
Figure 11C:
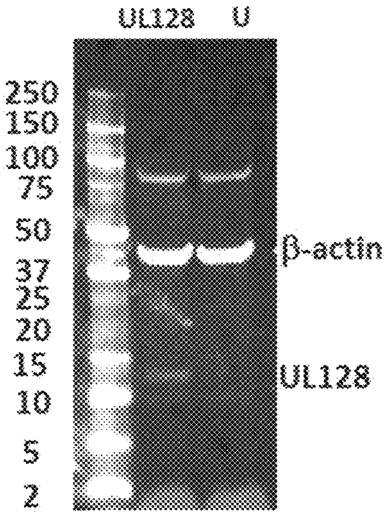
Figure 11D:
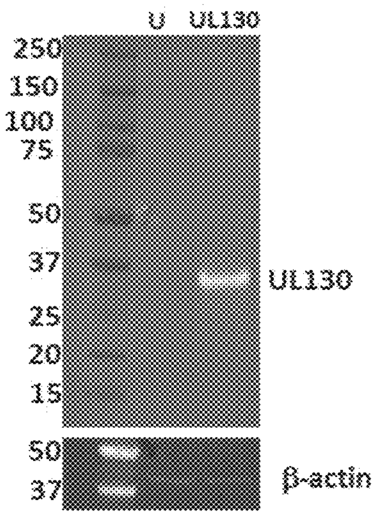
Figure 11E:
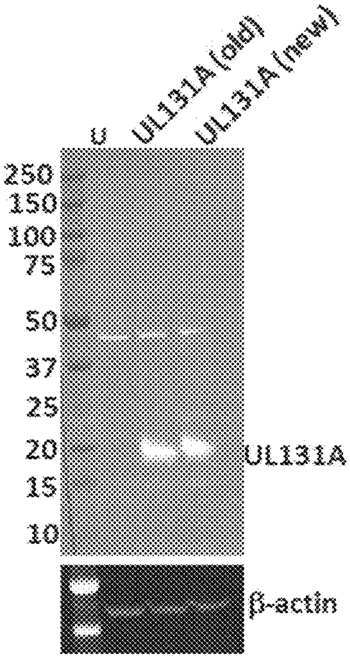
Figure 12:
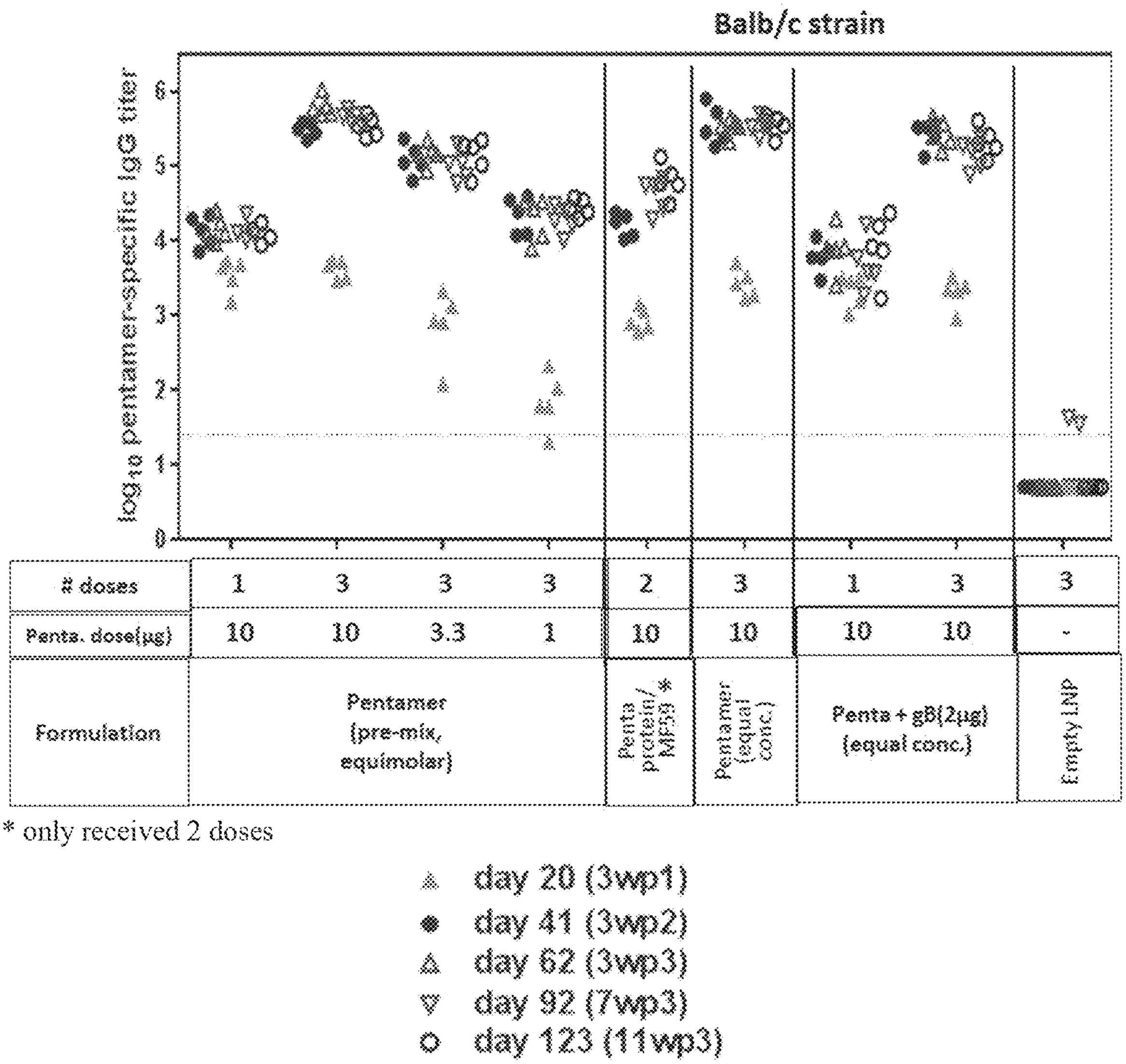
FIG. 12 shows that immunization with the pentameric mRNA complex elicits high titers of antibodies that are maintained up to several months. An immunogenicity study of the hCMV pentameric complex mRNA vaccine constructs is shown. Balb/c mice were vaccinated according to the vaccination schedule with indicated dosages of the mRNAs (lower panel). Mice serum IgG titers were measured at days 20, 41, 62, 92, and 123 post immunization. hCMV pentamer coated plates were used to measure the serum IgG titer. High titers of anti-pentamer antibodies were detected in the serum of the immunized mice.
Figure 13:
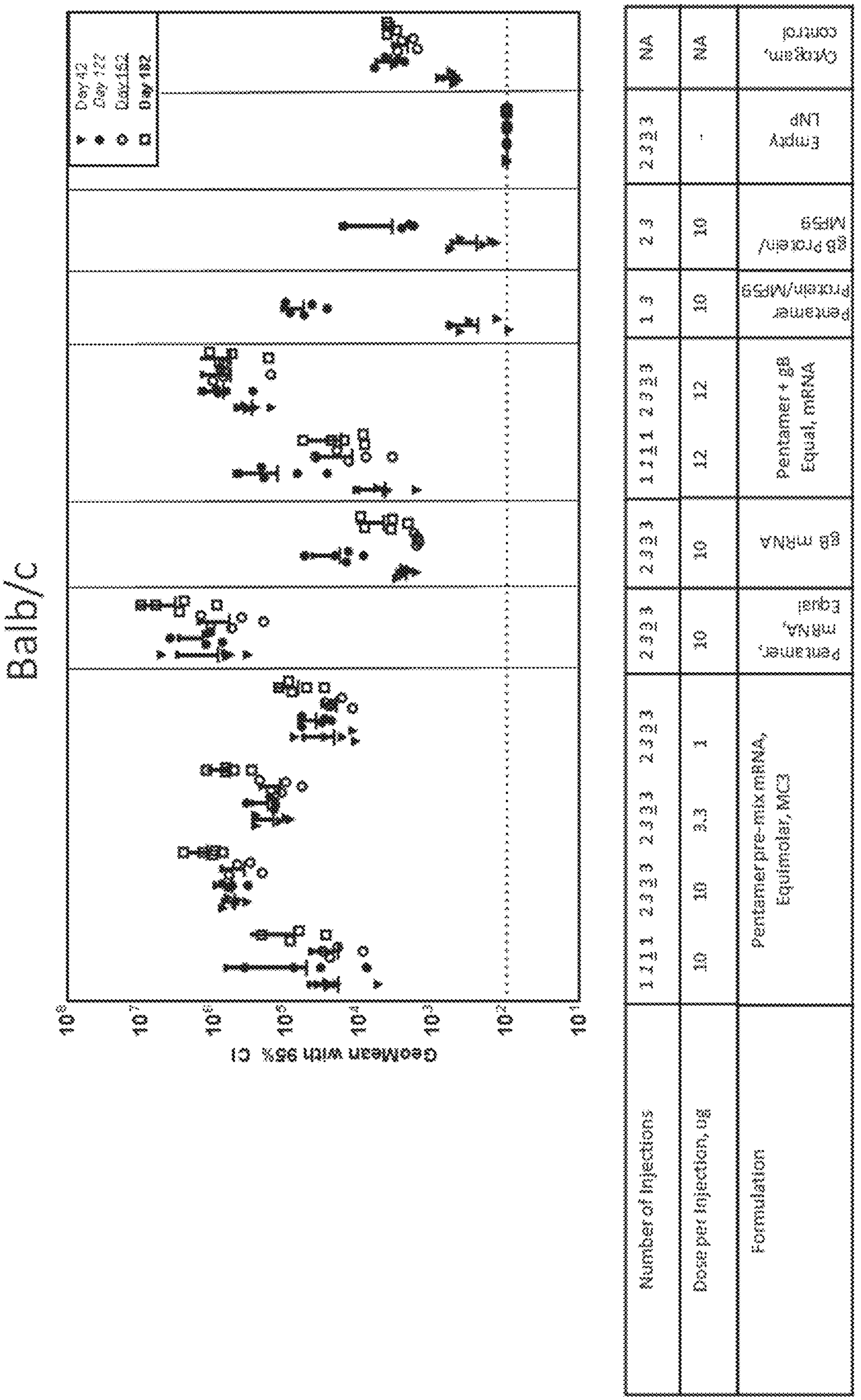
FIG. 13 shows that hCMV mRNA vaccine constructs elicited higher neutralizing antibody titers in mice than CytoGam®, a hyperimmune serum used clinically for prophylaxis of hCMV. Balb/c mice were vaccinated according to the vaccination schedule with indicated dosages of the mRNAs (lower panel). Neutralizing antibody titers in mice serum were measured at days 42, 122, 152, and 182 post immunization, with ARPE-19 epithelial cells infected with the hCMV clinical isolate VR1814. High titers of neutralizing antibodies induced by the hCMV pentameric complex mRNA vaccine were maintained up to 6 months.
Figure 14:
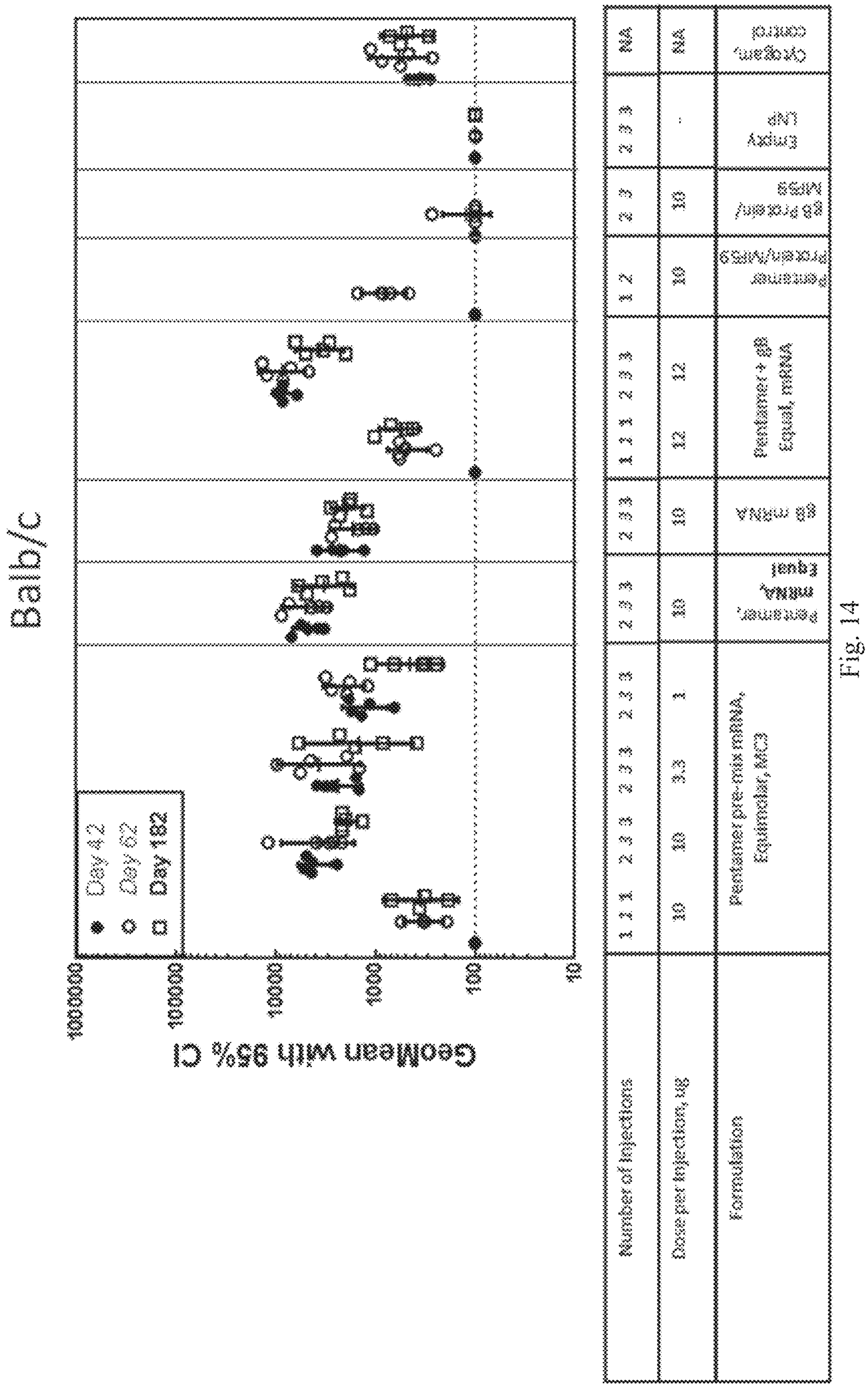
FIG. 14 is a graph showing the neutralizing antibody titers induced in mice by hCMV pentameric complex mRNA vaccine constructs. Balb/c mice were vaccinated according to the vaccination schedule with indicated dosages of the mRNAs (lower panel). Neutralizing antibody titers in mice serum were measured at days 42, 62, and 182 post immunization, with HEL299 fibroblast cells infected with 500-2000 pfu of hCMV AD169 strain.

The hCMV neutralization titers of mouse serum measured in ARPE-19 cells infected with clinical hCMV isolate strain VR1814 are shown in FIG. 9 and Table 5.

TABLE 4

Immunization schedule

| Group | Vaccine | Route | Dose schedule | N |
|---|---|---|---|---|
| 1 | Pentamer (*4:2:1:1:1, pre-mix), Equimolar | IM | d 0 (10 ug) | 5 |

TABLE 4-continued

| Immunization schedule | | | | |
|---|---|---|---|---|
| Group | Vaccine | Route | Dose schedule | N |
| 2 | Pentamer (4:2:1:1:1, pre-mix) | IM | d 0, d 21, d 42 (10 ug, 3 ug, 1 ug) | 5 |
| 3 | Pentamer (4:2:1:1:1), post-mix) | IM | d 0 (10 ug) | 5 |
| 4 | Pentamer (4:2:1:1:1, post-mix) | IM | d 0, d 21, d 42 (10 ug, 3 ug, 1 ug) | 5 |
| 5 | Pentamer (1:1:1:1:1, pre-mex), Equal conc | IM | d 0, d 21, d 42 (10 ug) | 5 |
| 6 | gB | IM | d 0, d 21, d 42 (10 ug) | 5 |
| 7 | gB + Pentamer (1:1:1:1:1:1, pre-mix) | IM | d 0 (12 ug) | 5 |
| 8 | gB + Pentamer (1:1:1:1:1:1, pre-mix) | IM | d 0, d 21, d 42 (12 ug) | 5 |
| 9 | Pentamer protein/MF59 | IM | d 21, d 42 (10 ug) | 5 |
| 10 | gB protein/MF59 | IM | d 0, d 21, d 42 (10 ug) | 5 |
| 11 | Empty LNP | IM | d 0, d 21, d 42 | 5 |

TABLE 5

| hCMV neutralization titers of mouse serum measured in ARPE-19 cells infected with clinical isolate VR1814 | | | |
|---|---|---|---|
| Formulation | # of doses | Dose (ug) | NT50 Titer |
| Pentamer, Pre-mix (Equimolar) | 2 | 10 | >2E4 |
| Pentamer, Pre-mix (Equimolar) | 2 | 3 | >2E4 |
| Pentamer, Post-mix (Equimolar) | 2 | 10 | >2E4 |

TABLE 5-continued

| hCMV neutralization titers of mouse serum measured in ARPE-19 cells infected with clinical isolate VR1814 | | | |
|---|---|---|---|
| Formulation | # of doses | Dose (ug) | NT50 Titer |
| Pentamer, Post-mix (Equimolar) | 7 | 3 | >2E4 |
| Pentamer + gB (Equal conc) | 2 | 12 | >2E4 |

Example 25: Second Generation hCMV Pentameric Complex mRNA Vaccine Constructs HCMV pentameric complex mRNA vaccine constructs were modified to produce second generation mRNA constructs. The nucleotide sequences of the second generation mRNA constructs and the encoded amino acid sequences are provided in Table 6. The expression of the second generation hCMV mRNA vaccine constructs was validated by Western blot (FIGS. 11A-11E). Further, to test the surface expression of the hCMV pentamer using the second generation mRNA vaccine constructs, HeLa cells were transfected with 1.25 μg of each of the mRNA vaccine constructs (gH-gL-U1128-UL130-UL131A at 1:1:1:1:1). The transfected HeLa cells were then stained with pentamer-specific antibodies and analyzed with Fluorescence-activated cell sorting (FACS). The fluorescent cell population indicates surface expression of the hCMV pentamer (FIG. 10).

Figure 20A:
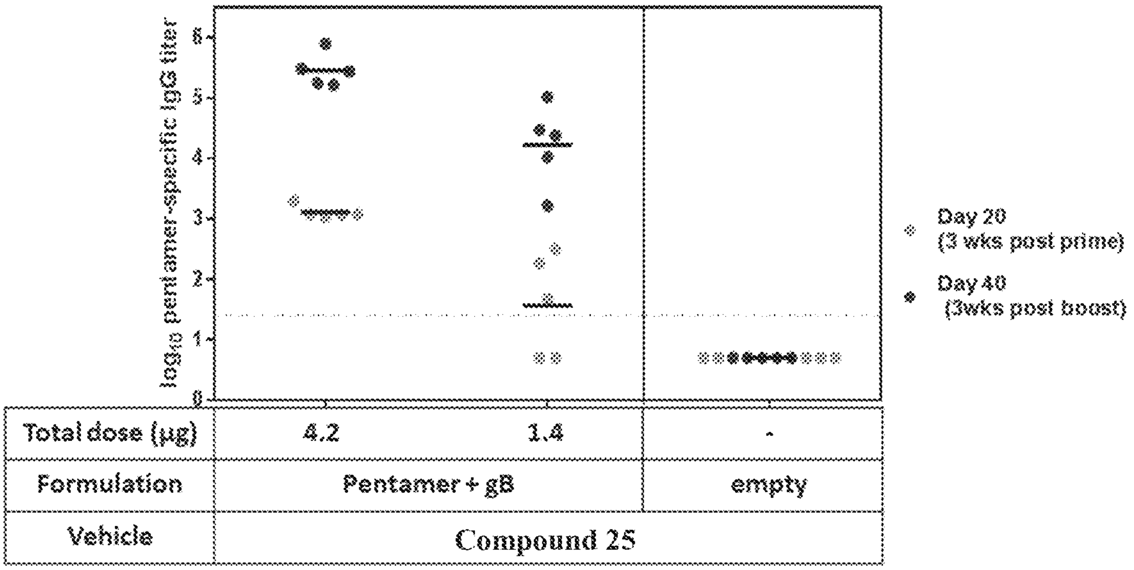
FIGS. 20A-20B are graphs showing the immunogenicity of second generation hCMV mRNA vaccine constructs formulated with Compound 25 lipids. The second generation mRNA constructs encoding the pentamer and gB induced pentamer-specific antibodies (FIG. 20A) and gB-specific antibodies (FIG. 20B) as early as 20 days post first immunization. The pentamer-specific and gB-specific antibody titers continue to increase in mice after the boost dose.
Figure 20B:
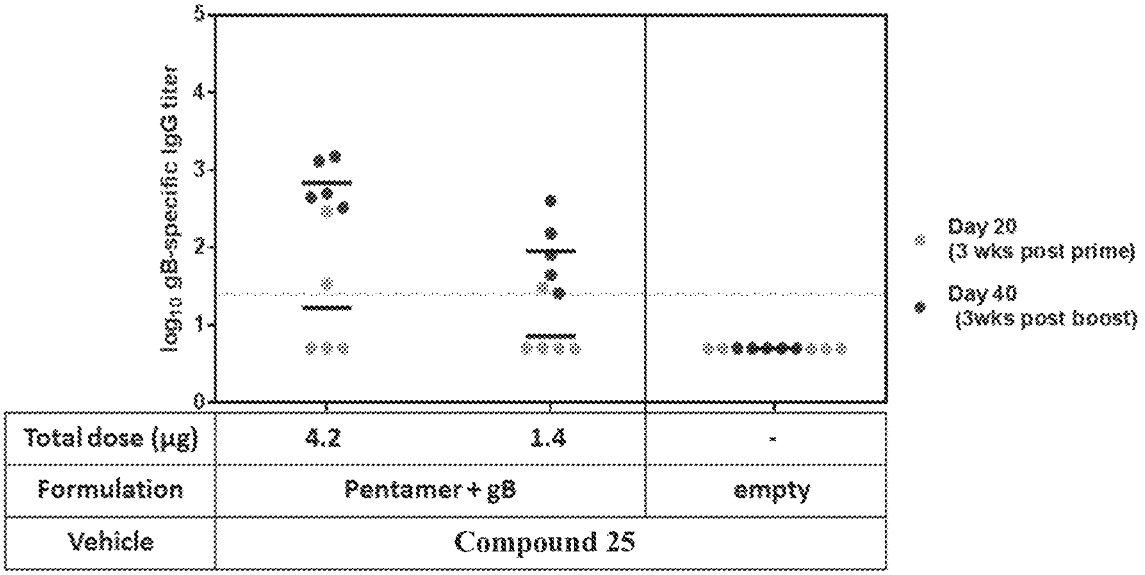
Figure 21:
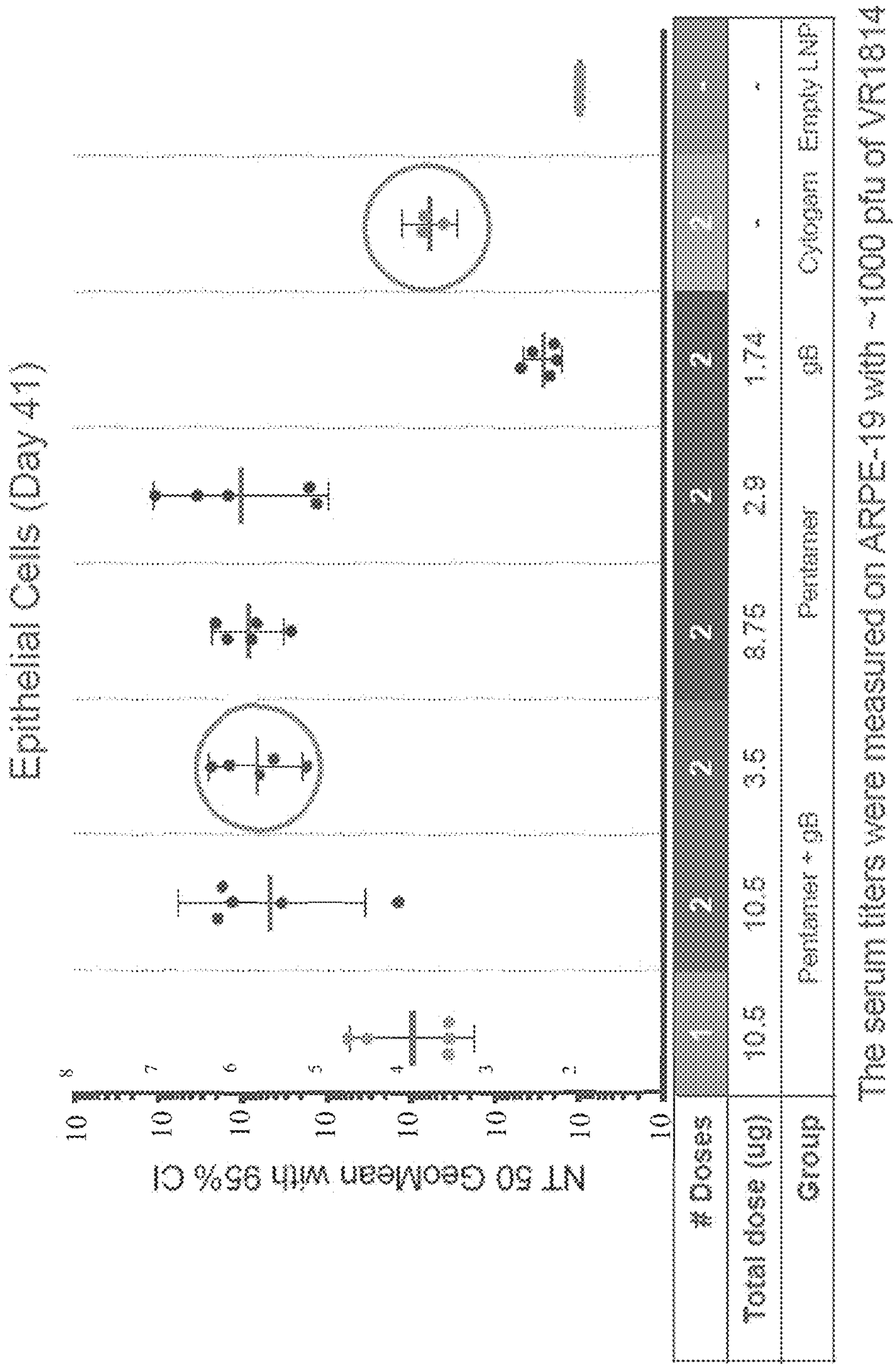
FIG. 21 is a graph showing that a 3 μg total dose of HCMV mRNA vaccine constructs encoding the pentameric complex elicited higher neutralization antibody titers than CytoGam®, a hyperimmune serum used clinically for prophylaxis of hCMV.
Figure 22:
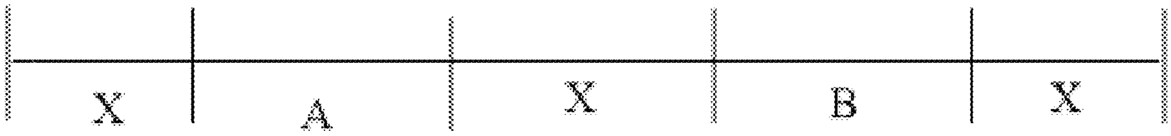
FIG. 22 is a schematic showing an exemplary linking region, wherein X is any nucleic acid sequence of 0-100 nucleotides and A and B are complementary parts, which are complementary to one or more other nucleic acids.
Figure 23:
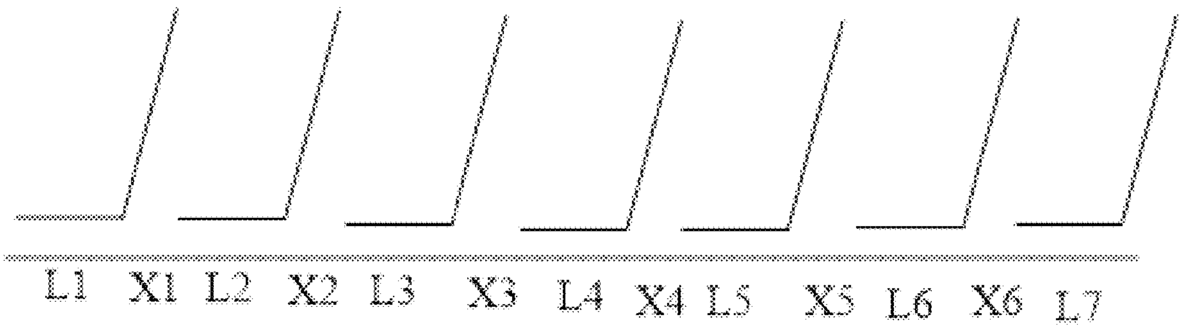
FIG. 23 shows an example of a stabilizing nucleic acid with the following structure: $L_1X_1L_2X_2L_3X_3L_4X_4L_5X_5L_6X_6L_7$, wherein L is a nucleic acid sequence complementary to a linking region and wherein x is any nucleic acid sequence 0-50 nucleotides in length.
Figure 24:
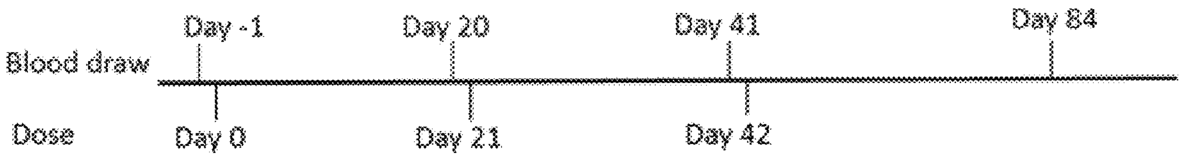
FIG. 24 shows the immunization and bleed schedule corresponding to Table 4.

The second generation hCMV mRNA vaccines encoding the pentamer and gB were also formulated with Compound 25 lipids and the immunogenicity of the formulation was tested (FIGS. 20A-20B). Mice were immunized with a total dose of 4.2 μg or 1.4 μg of the mRNA vaccine. Mice serum samples were taken on day 20 and day 40 post immunization and the serum IgG titers were assessed on pentamer coated plates or gB coated plates. The second generation hCMV mRNA vaccines induced high levels of pentamer-specific (FIG. 20A) and gB-specific (FIG. 20B) antibodies.

An HCMV vaccine may comprise, for example, at least one RNA polynucleotide encoded by at least one of the following sequences or by at least one fragment or epitope of the following sequences:

TABLE 6

| Second Generation hCMV mRNA Vaccine Construct Sequences | | |
|---|---|---|
| Name of mRNA Construct | Sequence | SEQ ID NO |
| hCMV_gH dimer, nucleotide sequence | TCAAGCTTTTGGACCCTCGTACAGAAGCTAATACGACTCACTATAGGGAAATA<br>AGAGAGAAAAGAAGAGTAAGAAGAAATATAAGAGCCACCATGCGGCCAGGCC<br>TCCCCTCCTACCTCATCATCCTCGCCGTCTGTCTCTTCAGCCACCTACTTTCGTC<br>ACGATATGGCGCAGAAGCCGTATCCGAACCGCTGGACAAAGCGTTTCACCTAC<br>TGCTCAACACCTACGGGAGACCCATCCGCTTCCTGCGTGAAAATACCACCCAG<br>TGTACCTACAACAGCAGCCTCCGTAACAGCACGGTCGTCAGGGAAAACGCCAT<br>CAGTTTCAACTTCTTCCAAAGCTATAATCAATACTATGTATTCCATATGCCTCG<br>ATGTCTCTTTGCGGGTCCTCTGGCGGAGCAGTTTCTGAACCAGGTAGATCTGAC<br>CGAAACCCTGGAAAGATACCAACAGAGACTTAACACTTACGCGCTGGTATCCA<br>AAGACCTGGCCAGCTACCGATCTTTCTCGCAGCAGCTAAAGGCACAAGACAGC<br>CTAGGTGAACAGCCCACCACTGTGCCACCGCCCATTGACCTGTCAATACCTCAC<br>GTTTGGATGCCACCGCAAACCACTCCACACGGCTGGACAGAATCACATACCAC<br>CTCAGGACTACACCGACCACACTTTAACCAGACCTGTATCCTCTTTGATGGACA<br>CGATCTACTATTCAGCACCGTCACACCTTGTTTGCACCAAGGCTTTTACCTCAT<br>CGACGAACTACGTTACGTTAAAATAACACTGACCGAGGACTTCTTCGTAGTTA<br>CGGTGTCCATAGACGACGACACACCCATGCTGCTTATCTTCGGCCATCTTCCAC<br>GCGTACTTTTCAAAGCGCCCTATCAACGCGACAACTTTATACTACGACAAACTG<br>AGAAACACGAGCTCCTGGTGCTAGTTAAGAAAGATCAACTGAACCGTCACTCT<br>TATCTCAAAGACCCGGACTTTCTTGACGCCGCACTTGACTTCAACTACCTAGAC | 58 |

TABLE 6-continued

Second Generation hCMV mRNA Vaccine Construct Sequences

| Name of mRNA Construct | Sequence | SEQ ID NO |
|---|---|---|
| | CTCAGCGCACTACTACGTAACAGCTTTCACCGTTACGCCGTGGATGTACTCAAG<br>AGCGGTCGATGTCAGATGCTGGACCGCCGCACGGTAGAAATGGCCTTCGCCTA<br>CGCATTAGCACTGTTCGCAGCAGCCCGACAAGAAGAGGCCGGCGCCCAAGTCT<br>CCGTCCCACGGGCCCTAGACCGCCAGGCCGCACTCTTACAAATACAAGAATTT<br>ATGATCACCTGCCTCTCACAAACACCACCACGCACCACGTTGCTGCTGTATCCC<br>ACGGCCGTGGACCTGGCCAAACGAGCCCTTTGGACACCGAATCAGATCACCGA<br>CATCACCAGCCTCGTACGCCTGGTCTACATACTCTCTAAACAGAATCAGCAAC<br>ATCTCATCCCCCAATGGGCACTACGACAGATCGCCGACTTTGCCCTAAAACTAC<br>ACAAAACGCACCTGGCCTCTTTTCTTTCAGCCTTCGCACGCCAAGAACTCTACC<br>TCATGGGCAGCCTCGTCCACTCCATGCTGGTACATACGACGGAGAGACGCGAA<br>ATCTTCATCGTAGAAACGGGCCTCTGTTCATTGGCCGAGCTATCACACTTTACG<br>CAGTTGTTAGCTCATCCACACCACGAATACCTCAGCGACCTGTACACACCCTGT<br>TCCAGTAGCGGGCGACGCGATCACTCGCTCGAACGCCTCACGCGTCTCTTCCCC<br>GATGCCACCGTCCCCGCTACCGTTCCCGCCGCCCTCTCCATCCTATCTACCATG<br>CAACCAAGCACGCTGGAAACCTTCCCCGACCTGTTTTGCTTGCCGCTCGGCGAA<br>TCCTTCTCCGCGCTGACCGTCTCCGAACACGTCAGTTATATCGTAACAAACCAG<br>TACCTGATCAAAGGTATCTCCTACCCTGTCTCCACCACCGTCGTAGGCCAGAGC<br>CTCATCATCACCCAGACGGACAGTCAAACTAAATGCGAACTGACGCGCAACAT<br>GCATACCACACACAGCATCACAGTGGCGCTCAACATTTCGCTAGAAAACTGCG<br>CCTTTTGCCAAAGCGCCCTGCTAGAATACGACGACACGCAAGGCGTCATCAAC<br>ATCATGTACATGCACGACTCGGACGACGTCCTTTTCGCCCTGGATCCCTACAAC<br>GAAGTGGTGGTCTCATCTCCGCGAACTCACTACCTCATGCTTTTGAAGAACGGT<br>ACGGTACTAGAAGTAACTGACGTCGTCGTGGACGCCACCGACAGTCGTCTCCT<br>CATGATGTCCGTCTACGCGCTATCGGCCATCATCGGCATCTATCTGCTCTACCG<br>CATGCTCAAGACATGCTGATAATAGGCTGGAGCCTCGGTGGCCATGCTTCTTGC<br>CCCTTGGGCCTCCCCCCAGCCCCTCCTCCCCTTCCTGCACCCGTACCCCCGTGG<br>TCTTTGAATAAAGTCTGAGTGGGCGGC | |
| hCMV_gH dimer, nucleotide sequence | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGCGGCCAG<br>GCCUCCCCUCCUACCUCAUCAUCCUCGCCGUCUGUCUCUUCAGCCACCUACU<br>UUCGUCACGAUAUGGCGCAGAAGCCGUAUCCGAACCGCUGGACAAAGCGUU<br>UCACCUACUGCUCAACACCUACGGGAGACCCAUCCGCUUCCUGCGUGAAAAU<br>ACCACCCAGUGUACCUACAACAGCAGCCUCCGUAACAGCACGGUCGUCAGGG<br>AAAACGCCAUCAGUUUCAACUUCUUCCAAAGCUAUAAUCAAUACUAUGUAU<br>UCCAUAUGCCUCGAUGUCUCUUUGCGGGUCCUCUGGCGGAGCAGUUUCUGA<br>ACCAGGUAGAUCUGACCGAAACCCUGGAAAGAUACCAACAGAGACUUAACA<br>CUUACGCGCUGGUAUCCAAAGACCUGGCCAGCUACCGAUCUUUCUCGCAGCA<br>GCUAAAGGCACAAGACAGCCUAGGUGAACAGCCCACCACUGUGCCACCGCCC<br>AUUGACCUGUCAAUACCUCACGUUUGGAUGCCACCGCAAACCACUCCACACG<br>GCUGGACAGAAUCACAUACCACCUCAGGACUACACCGACCACACUUUAACCA<br>GACCUGUAUCCUCUUUGAUGGACACGAUCUACUAUUCAGCACCGUCACACCU<br>UGUUUGCACCAAGGCUUUUACCUCAUCGACGAACUACGUUACGUUAAAAUA<br>ACACUGACCGAGGACUUCUUCGUAGUUACGGUGUCCAUAGACGACGACACA<br>CCCAUGCUGCUUAUCUUCGGCCAUCUUCCACGCGUACUUUUCAAAGCGCCCU<br>AUCAACGCGACAACUUUAUACUACGACAAACUGAGAAACACGAGCUCCUGG<br>UGCUAGUUAAGAAAGAUCAACUGAACCGUCACUCUUAUCUCAAAGACCCGG<br>ACUUUCUUGACGCCGCACUUGACUUCAACUACCUAGACCUCAGCGCACUACU<br>ACGUAACAGCUUUCACCGUUACGCCGUGGAUGUACUCAAGAGCGGUCGAUG<br>UCAGAUGCUGGACCGCCGCACGGUAGAAAUGGCCUUCGCCUACGCAUUAGCA<br>CUGUUCGCAGCAGCCCGACAAGAAGAGGCCGGCGCCCAAGUCUCCGUCCCAC<br>GGGCCCUAGACCGCCAGGCCGCACUCUUACAAAUACAAGAAUUUAUGAUCAC<br>CUGCCUCUCACAAACACCACCACGCACCACGUUGCUGCUGUAUCCCACGGCC<br>GUGGACCUGGCCAAACGAGCCCUUUGGACACCGAAUCAGAUCACCGACAUCA<br>CCAGCCUCGUACGCCUGGUCUACAUACUCUCUAAACAGAAUCAGCAACAUCU<br>CAUCCCCCAAUGGGCACUACGACAGAUCGCCGACUUUGCCCUAAAACUACAC<br>AAAACGCACCUGGCCUCUUUUCUUUCAGCCUUCGCACGCCAAGAACUCUACC<br>UCAUGGGCAGCCUCGUCCACUCCAUGCUGGUACAUACGACGGAGAGACGCGA<br>AAUCUUCAUCGUAGAAACGGGCCUCUGUUCAUUGGCCGAGCUAUCACACUU<br>UACGCAGUUGUUAGCUCAUCCACACCACGAAUACCUCAGCGACCUGUACACA<br>CCCUGUUCCAGUAGCGGGCGACGCGAUCACUCGCUCGAACGCCUCACGCGUC<br>UCUUCCCCGAUGCCACCGUCCCCGCUACCGUUCCCGCCGCCCUCUCCAUCCUA<br>UCUACCAUGCAACCAAGCACGCUGGAAACCUUCCCCGACCUGUUUUGCUUGC<br>CGCUCGGCGAAUCCUUCUCCGCGCUGACCGUCUCCGAACACGUCAGUUAUAU<br>CGUAACAAACCAGUACCUGAUCAAAGGUAUCUCCUACCCUGUCUCCACCACC<br>GUCGUAGGCCAGAGCCUCAUCAUCACCCAGACGGACAGUCAAACUAAAUGCG<br>AACUGACGCGCAACAUGCAUACCACACACAGCAUCACAGUGGCGCUCAACAU<br>UUCGCUAGAAAACUGCGCCUUUUGCCAAAGCGCCCUGCUAGAAUACGACGAC<br>ACGCAAGGCGUCAUCAACAUCAUGUACAUGCACGACUCGGACGACGUCCUUU<br>UCGCCCUGGAUCCCUACAACGAAGUGGUGGUCUCAUCUCCGCGAACUCACUA<br>CCUCAUGCUUUUGAAGAACGGUACGGUACUAGAAGUAACUGACGUCGUCGU<br>GGACGCCACCGACAGUCGUCUCCUCAUGAUGUCCGUCUACGCGCUAUCGGCC<br>AUCAUCGGCAUCUAUCUGCUCUACCGCAUGCUCAAGACAUGCUGAUAAUAG<br>GCUGGAGCCUCGGUGGCCAUGCUUCUUGCCCCUUGGGCCUCCCCCCAGCCCC | 108 |

TABLE 6-continued

Second Generation hCMV mRNA Vaccine Construct Sequences

| Name of mRNA Construct | Sequence | SEQ ID NO |
|---|---|---|
| | UCCUCCCCUUCCUGCACCCGUACCCCCGUGGUCUUUGAAUAAAGUCUGAGUG GGCGGC | |
| hCMV_gH dimer, amino acid sequence | MRPGLPSYLIILAVCLFSHLLSSRYGAEAVSEPLDKAFHLLLNTYGRPIRFLRENTTQ CTYNSSLRNSTVVRENAISFNFFQSYNQYYVFHMPRCLFAGPLAEQFLNQVDLTET LERYQQRLNTYALVSKDLASYRSFSQQLKAQDSLGEQPTTVPPPIDLSIPHVWMPP QTTPHGWTESHTTSGLHRPHFNQTCILFDGHDLLFSTVTPCLHQGFYLIDELRYVKI TLTEDFFVVTVSIDDDTPMLLIFGHLPRVLFKAPYQRDNFILRQTEKHELLVLVKKD QLNRHSYLKDPDFLDAALDFNYLDLSALLRNSFHRYAVDVLKSGRCQMLDRRTV EMAFAYALALFAAARQEEAGAQVSVPRALDRQAALLQIQEFMITCLSQTPPRTTLL LYPTAVDLAKRALWTPNQITDITSLVRLVYILSKQNQQHLIPQWALRQIADFALKL HKTHLASFLSAFARQELYLMGSLVHSMLVHTTERREIFIVETGLCSLAELSHFTQLL AHPHHEYLSDLYTPCSSSGRRDHSLERLTRLFPDATVPATVPAALSILSTMQPSTLE TFPDLFCLPLGESFSALTVSEHVSYIVTNQYLIKGISYPVSTTVVGQSLIITQTDSQTK CELTRNMHTTHSITVALNISLENCAFCQSALLEYDDTQGVINIMYMHDSDDVLFAL DPYNEVVVSSPRTHYLMLLKNGTVLEVTDVVVDATDSRLLMMSVYALSAIIGIYL LYRMLKTC | 59 |
| hCMV-gL, nucleotide sequence | TCAAGCTTTTGGACCCTCGTACAGAAGCTAATACGACTCACTATAGGGAAATA AGAGAGAAAAGAAGAGTAAGAAGAAATATAAGAGCCACCATGTGCCGCCGCC CGGATTGCGGCTTCTCTTTCTCACCTGGACCGGTGATACTGCTGTGGTGTTGCC TTCTGCTGCCCATTGTTTCCTCAGCCGCCGTCAGCGTCGCTCCTACCGCCGCCG AGAAAGTCCCCGCGGAGTGCCCCGAACTAACGCGCCGATGCTTGTTGGGTGAG GTGTTTGAGGGTGACAAGTATGAAAGTTGGCTGCGCCCGTTGGTGAATGTTAC CGGGCGCGATGGCCCGCTATCGCAACTTATCCGTTACCGTCCCGTTACGCCGGA GGCCGCCAACTCCGTGCTGTTGGACGAGGCTTTCCTGGACACTCTGGCCCTGCT GTACAACAATCCGGATCAATTGCGGGCCCTGCTGACGCTGTTGAGCTCGGACA CAGCGCCGCGCTGGATGACGGTGATGCGCGGCTACAGCGAGTGCGGCGATGGC TCGCCGGCCGTGTACACGTGCGTGGACGACCTGTGCCGCGGCTACGACCTCAC GCGACTGTCATACGGGCGCAGCATCTTCACGGAACACGTGTTAGGCTTCGAGC TGGTGCCACCGTCTCTCTTTAACGTGGTGGTGGCCATACGCAACGAAGCCACG CGTACCAACCGCGCCGTGCGTCTGCCCGTGAGCACCGCTGCCGCGCCCGAGGG CATCACGCTCTTTTACGGCCTGTACAACGCAGTGAAGGAATTCTGCCTGCGTCA CCAGCTGGACCCGCCGCTGCTACGCCACCTAGATAAATACTACGCCGGACTGC CGCCCGAGCTGAAGCAGACGCGCGTCAACCTGCCGGCTCACTCGCGCTATGGC CCTCAAGCAGTGGATGCTCGCTGATAATAGGCTGGAGCCTCGGTGGCCATGCT TCTTGCCCCTTGGGCCTCCCCCCAGCCCCTCCTCCCCTTCCTGCACCCGTACCCC CGTGGTCTTTGAATAAAGTCTGAGTGGGCGGC | 60 |
| hCMV-gL, nucleotide sequence | UCAAGCUUUUGGACCCUCGUACAGAAGCUAAUACGACUCACUAUAGGGAAA UAAGAGAGAAAAGAAGAGUAAGAAGAAAUAUAAGAGCCACCAUGUGCCGCC GCCCGGAUUGCGGCUUCUCUUUCUCACCUGGACCGGUGAUACUGCUGUGGU GUUGCCUUCUGCUGCCCAUUGUUUCCUCAGCCGCCGUCAGCGUCGCUCCUAC CGCCGCCGAGAAAGUCCCCGCGGAGUGCCCCGAACUAACGCGCCGAUGCUUG UUGGGUGAGGUGUUUGAGGGUGACAAGUAUGAAAGUUGGCUGCGCCCGUUG GUGAAUGUUACCGGGCGCGAUGGCCCGCUAUCGCAACUUAUCCGUUACCGUC CCGUUACGCCGGAGGCCGCCAACUCCGUGCUGUUGGACGAGGCUUUCCUGGA CACUCUGGCCCUGCUGUACAACAAUCCGGAUCAAUUGCGGGCCCUGCUGACG CUGUUGAGCUCGGACACAGCGCCGCGCUGGAUGACGGUGAUGCGCGGCUAC AGCGAGUGCGGCGAUGGCUCGCCGGCCGUGUACACGUGCGUGGACGACCUG UGCCGCGGCUACGACCUCACGCGACUGUCAUACGGGCGCAGCAUCUUCACGG AACACGUGUUAGGCUUCGAGCUGGUGCCACCGUCUCUCUUUAACGUGGUGG UGGCCAUACGCAACGAAGCCACGCGUACCAACCGCGCCGUGCGUCUGCCCGU GAGCACCGCUGCCGCGCCCGAGGGCAUCACGCUCUUUUACGGCCUGUACAAC GCAGUGAAGGAAUUCUGCCUGCGUCACCAGCUGGACCCGCCGCUGCUACGCC ACCUAGAUAAAUACUACGCCGGACUGCCGCCCGAGCUGAAGCAGACGCGCGU CAACCUGCCGGCUCACUCGCGCUAUGGCCCUCAAGCAGUGGAUGCUCGCUGA UAAUAGGCUGGAGCCUCGGUGGCCAUGCUUCUUGCCCCUUGGGCCUCCCCCC AGCCCCUCCUCCCCUUCCUGCACCCGUACCCCCGUGGUCUUUGAAUAAAGUC UGAGUGGGCGGC | 109 |
| hCMV-gL, amino acid sequence | MCRRPDCGFSFSPGPVILLWCCLLLPIVSSAAVSVAPTAAEKVPAECPELTRRCLLG EVFEGDKYESWLRPLVNVTGRDGPLSQLIRYRPVTPEAANSVLLDEAFLDTLALLY NNPDQLRALLTLLSSDTAPRWMTVMRGYSECGDGSPAVYTCVDDLCRGYDLTRL SYGRSIFTEHVLGFELVPPSLFNVVVAIRNEATRTNRAVRLPVSTAAAPEGITLFYG LYNAVKEFCLRHQLDPPLLRHLDKYYAGLPPELKQTRVNLPAHSRYGPQAVDAR | 61 |
| hCMV_UL128, nucleotide sequence | TCAAGCTTTTGGACCCTCGTACAGAAGCTAATACGACTCACTATAGGGAAATA AGAGAGAAAAGAAGAGTAAGAAGAAATATAAGAGCCACCATGAGTCCCAAAG ATCTGACGCCGTTCTTGACGGCGTTGTGGCTGCTATTGGGTCACAGCCGCGTGC CGCGGGTGCGCGCAGAAGAATGTTGCGAATTCATAAACGTCAACCACCCGCCG GAACGCTGTTACGATTTCAAAATGTGCAATCGCTTCACCGTCGCGCTGCGGTGT CCGGACGGCGAAGTCTGCTACAGTCCCGAGAAAACGGCTGAGATTCGCGGGAT CGTCACCACCATGACCCATTCATTGACACGCCAGGTCGTACACAACAAACTGA | 62 |

TABLE 6-continued

Second Generation hCMV mRNA Vaccine Construct Sequences

| Name of mRNA Construct | Sequence | SEQ ID NO |
|---|---|---|
| | CGAGCTGCAACTACAATCCGTTATACCTCGAAGCTGACGGGCGAATACGCTGC GGCAAAGTAAACGACAAGGCGCAGTACCTGCTGGGCGCCGCTGGCAGCGTTCC CTATCGATGGATCAATCTGGAATACGACAAGATAACCCGGATCGTGGGCCTGG ATCAGTACCTGGAGAGCGTTAAGAAACACAAACGGCTGGATGTGTGCCGCGCT AAAATGGGCTATATGCTGCAGTGATAATAGGCTGGAGCCTCGGTGGCCATGCT TCTTGCCCCTTGGGCCTCCCCCCAGCCCCTCCTCCCCTTCCTGCACCCGTACCCC CGTGGTCTTTGAATAAAGTCTGAGTGGGCGGC | |
| hCMV_UL128, nucleotide sequence | UCAAGCUUUUGGACCCUCGUACAGAAGCUAAUACGACUCACUAUAGGGAAA UAAGAGAGAAAAGAAGAGUAAGAAGAAAUAUAAGAGCCACCAUGAGUCCCA AAGAUCUGACGCCGUUCUUGACGGCGUUGUGGCUGCUAUUGGGUCACAGCC GCGUGCCGCGGGUGCGCGCAGAAGAAUGUUGCGAAUUCAUAAACGUCAACC ACCCGCCGGAACGCUGUUACGAUUUCAAAAUGUGCAAUCGCUUCACCGUCGC GCUGCGGUGUCCGGACGGCGAAGUCUGCUACAGUCCCGAGAAAACGGCUGA GAUUCGCGGGAUCGUCACCACCAUGACCCAUUCAUUGACACGCCAGGUCGUA CACAACAAACUGACGAGCUGCAACUACAAUCCGUUAUACCUCGAAGCUGACG GGCGAAUACGCUGCGGCAAAGUAAACGACAAGGCGCAGUACCUGCUGGGCG CCGCUGGCAGCGUUCCCUAUCGAUGGAUCAAUCUGGAAUACGACAAGAUAA CCCGGAUCGUGGGCCUGGAUCAGUACCUGGAGAGCGUUAAGAAACACAAAC GGCUGGAUGUGUGCCGCGCUAAAAUGGGCUAUAUGCUGCAGUGAUAAUAGG CUGGAGCCUCGGUGGCCAUGCUUCUUGCCCCUUGGGCCUCCCCCCAGCCCCU CCUCCCCUUCCUGCACCCGUACCCCCGUGGUCUUUGAAUAAAGUCUGAGUGG GCGGC | 110 |
| hCMV_UL128, amino acid sequence | MSPKDLTPFLTALWLLLGHSRVPRVRAEECCEFINVNHPPERCYDFKMCNRFTVA LRCPDGEVCYSPEKTAEIRGIVITMTHSLTRQVVHNKLTSCNYNPLYLEADGRIRC GKVNDKAQYLLGAAGSVPYRWINLEYDKITRIVGLDQYLESVKKHKRLDVCRAK MGYMLQ | 63 |
| hCMV-UL130, nucleotide sequence | TCAAGCTTTTGGACCCTCGTACAGAAGCTAATACGACTCACTATAGGGAAATA AGAGAGAAAAGAAGAGTAAGAAGAAATATAAGAGCCACCATGCTGCGGCTTC TGCTTCGTCACCACTTTCACTGCCTGCTTCTGTGCGCGGTTTGGGCAACGCCCT GTCTGGCGTCTCCGTGGTCGACGCTAACAGCAAACCAGAATCCGTCCCCGCCA TGGTCTAAACTGACGTATTCCAAACCGCATGACGCGGCGACGTTTTACTGTCCT TTTCTCTATCCCTCGCCCCCACGATCCCCCTTGCAATTCTCGGGGTTCCAGCGG GTATCAACGGGTCCCGAGTGTCGCAACGAGACCCTGTATCTGCTGTACAACCG GGAAGGCCAGACCTTGGTGGAGAGAAGCTCCACCTGGGTGAAAAAGGTGATC TGGTACCTGAGCGGTCGGAACCAAACCATCCTCCAACGGATGCCCCGAACGGC TTCGAAACCGAGCGACGGAAACGTGCAGATCAGCGTGGAAGACGCCAAGATT TTTGGAGCGCACATGGTGCCCAAGCGCTGCTACGCTTCGTCGTCAACGATGGC ACACGTTATCAGATGTGTGTGATGAAGCTGGAGAGCTGGGCTCACGTCTTCCG GGACTACAGCGTGTCTTTTCAGGTGCGATTGACGTTCACCGAGGCCAATAACC AGACTTACACCTTCTGCACCCATCCCAATCTCATCGTTTGATAATAGGCTGGAG CCTCGGTGGCCATGCTTCTTGCCCCTTGGGCCTCCCCCCAGCCCCTCCTCCCCTT CCTGCACCCGTACCCCCGTGGTCTTTGAATAAAGTCTGAGTGGGCGGC | 64 |
| hCMV-UL130, nucleotide sequence | UCAAGCUUUUGGACCCUCGUACAGAAGCUAAUACGACUCACUAUAGGGAAA UAAGAGAGAAAAGAAGAGUAAGAAGAAAUAUAAGAGCCACCAUGCUGCGGC UUCUGCUUCGUCACCACUUUCACUGCCUGCUUCUGUGCGCGGUUUGGGCAAC GCCCUGUCUGGCGUCUCCGUGGUCGACGCUAACAGCAAACCAGAAUCCGUCC CCGCCAUGGUCUAAACUGACGUAUUCCAAACCGCAUGACGCGGCGACGUUUU ACUGUCCUUUUCUCUAUCCCUCGCCCCCACGAUCCCCCUUGCAAUUCUCGGG GUUCCAGCGGGUAUCAACGGGUCCCGAGUGUCGCAACGAGACCCUGUAUCU GCUGUACAACCGGGAAGGCCAGACCUUGGUGGAGAGAAGCUCCACCUGGGU GAAAAAGGUGAUCUGGUACCUGAGCGGUCGGAACCAAACCAUCCUCCAACG GAUGCCCCGAACGGCUUCGAAACCGAGCGACGGAAACGUGCAGAUCAGCGU GGAAGACGCCAAGAUUUUUGGAGCGCACAUGGUGCCCAAGCGCUGCUACGC UUCGUCGUCAACGAUGGCACACGUUAUCAGAUGUGUGUGAUGAAGCUGGAG AGCUGGGCUCACGUCUUCCGGGACUACAGCGUGUCUUUUCAGGUGCGAUUG ACGUUCACCGAGGCCAAUAACCAGACUUACACCUUCUGCACCCAUCCCAAUC UCAUCGUUUGAUAAUAGGCUGGAGCCUCGGUGGCCAUGCUUCUUGCCCCUU GGGCCUCCCCCCAGCCCCUCCUCCCCUUCCUGCACCCGUACCCCCGUGGUCUU UGAAUAAAGUCUGAGUGGGCGGC | 111 |
| hCMV-UL130, amino acid sequence | MLRLLLRHHFHCLLLCAVWATPCLASPWSTLTANQNPSPPWSKLTYSKPHDAATF YCPFLYPSPPRSPLQFSGFQRVSTGPECRNETLYLLYNREGQTLVERSSTWVKKVI WYLSGRNQTILQRMPRTASKPSDGNVQISVEDAKIFGAHMVPKQTKLLRFVVNDG TRYQMCVMKLESWAHVFRDYSVSFQVRLTFTEANNQTYTFCTHPNLIV | 65 |
| hCMV UL131A, nucleotide sequence | TCAAGCTTTTGGACCCTCGTACAGAAGCTAATACGACTCACTATAGGGAAATA AGAGAGAAAAGAAGAGTAAGAAGAAATATAAGAGCCACCATGCGGCTGTGTC GGGTGTGGCTGTCTGTTTGTCTGTGCGCCGTGGTGCTGGGTCAGTGCCAGCGGG AAACCGCGGAAAAGAACGATTATTACCGAGTACCGCATTACTGGGACGCGTGC TCTCGCGCGCTGCCCGACCAAACCCGTTACAAGTATGTGGAACAGCTCGTGGA | 66 |

TABLE 6-continued

Second Generation hCMV mRNA Vaccine Construct Sequences

| Name of mRNA Construct | Sequence | SEQ ID NO |
|---|---|---|
| | CCTCACGTTGAACTACCACTACGATGCGAGCCACGGCTTGGACAACTTTGACG<br>TGCTCAAGAGAATCAACGTGACCGAGGTGTCGTTGCTCATCAGCGACTTTAGA<br>CGTCAGAACCGTCGCGGCGGCACCAACAAAAGGACCACGTTCAACGCCGCCG<br>GTTCGCTGGCGCCACACGCCCGGAGCCTCGAGTTCAGCGTGCGGCTCTTTGCCA<br>ACTGATAATAGGCTGGAGCCTCGGTGGCCATGCTTCTTGCCCCTTGGGCCTCCC<br>CCCAGCCCCTCCTCCCCTTCCTGCACCCGTACCCCCGTGGTCTTTGAATAAAGT<br>CTGAGTGGGCGGC | |
| hCMV UL131A, nucleotide sequence | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGCGGCUGU<br>GUCGGGUGUGGCUGUCUGUUUGUCUGUGCGCCGUGGUGCUGGGUCAGUGCC<br>AGCGGGAAACCGCGGAAAAGAACGAUUAUUACCGAGUACCGCAUUACUGGG<br>ACGCGUGCUCUCGCGCGCUGCCCGACCAAACCCGUUACAAGUAUGUGGAACA<br>GCUCGUGGACCUCACGUUGAACUACCACUACGAUGCGAGCCACGGCUUGGAC<br>AACUUUGACGUGCUCAAGAGAAUCAACGUGACCGAGGUGUCGUUGCUCAUC<br>AGCGACUUUAGACGUCAGAACCGUCGCGGCGGCACCAACAAAAGGACCACGU<br>UCAACGCCGCCGGUUCGCUGGCGCCACACGCCCGGAGCCUCGAGUUCAGCGU<br>GCGGCUCUUUGCCAACUGAUAAUAGGCUGGAGCCUCGGUGGCCAUGCUUCU<br>UGCCCCUUGGGCCUCCCCCCAGCCCCUCCUCCCCUUCCUGCACCCGUACCCCC<br>GUGGUCUUUGAAUAAAGUCUGAGUGGGCGGC | 112 |
| hCMV UL131A, amino acid sequence | MRLCRVWLSVCLCAVVLGQCQRETAEKNDYYRVPHYWDACSRALPDQTRYKYV<br>EQLVDLTLNYHYDASHGLDNFDVLKRINVTEVSLLISDFRRQNRRGGTNKRTTFN<br>AAGSLAPHARSLEFSVRLFAN | 67 |
| hCMV_gB, nucleotide sequence | TCAAGCTTTTGGACCCTCGTACAGAAGCTAATACGACTCACTATAGGGAAATA<br>AGAGAGAAAAGAAGAGTAAGAAGAAATATAAGAGCCACCATGGAATCCAGGA<br>TCTGGTGCCTGGTAGTCTGCGTTAACTTGTGTATCGTCTGTCTGGGTGCTGCGG<br>TTTCCTCATCTTCTACTCGTGGAACTTCTGCTACTCACAGTCACCATTCCTCTCA<br>TACGACGTCTGCTGCTCACTCTCGATCCGGTTCAGTCTCTCAACGCGTAACTTC<br>TTCCCAAACGGTCAGCCATGGTGTTAACGAGACCATCTACAACACTACCCTCA<br>AGTACGGAGATGTGGTGGGGGTCAATACCACCAAGTACCCCTATCGCGTGTGT<br>TCTATGGCCCAGGGTACGGATCTTATTCGCTTTGAACGTAATATCGTCTGCACC<br>TCGATGAAGCCCATCAATGAAGACCTGGACGAGGGCATCATGGTGGTCTACAA<br>ACGCAACATCGTCGCGCACACCTTTAAGGTACGAGTCTACCAGAAGGTTTTGA<br>CGTTTCGTCGTAGCTACGCTTACATCCACACCACTTATCTGCTGGGCAGCAACA<br>CGGAATACGTGGCGCCTCCTATGTGGGAGATTCATCATATCAACAGCCACAGT<br>CAGTGCTACAGTTCCTACAGCCGCGTTATAGCAGGCACGGTTTTCGTGGCTTAT<br>CATAGGGACAGCTATGAAAACAAAACCATGCAATTAATGCCCGACGATTATTC<br>CAACACCCACAGTACCCGTTACGTGACGGTCAAGGATCAATGGCACAGCCGCG<br>GCAGCACCTGGCTCTATCGTGAGACCTGTAATCTGAATTGTATGGTGACCATCA<br>CTACTGCGCGCTCCAAATATCCTTATCATTTTTTCGCCACTTCCACGGGTGACG<br>TGGTTGACATTTCTCCTTTCTACAACGGAACCAATCGCAATGCCAGCTACTTTG<br>GAGAAAACGCCGACAAGTTTTTCATTTTTCCGAACTACACTATCGTCTCCGACT<br>TTGGAAGACCGAATTCTGCGTTAGAGACCCACAGGTTGGTGGCTTTTCTTGAAC<br>GTGCGGACTCGGTGATCTCCTGGGATATACAGGACGAAAAGAATGTCACTTGT<br>CAACTCACTTTCTGGGAAGCCTCGGAACGCACCATTCGTTCCGAAGCCGAGGA<br>CTCGTATCACTTTTCTTCTGCCAAAATGACCGCCACTTTCTTATCTAAGAAGCA<br>AGAGGTGAACATGTCCGACTCTGCGCTGGACTGCGTACGTGATGAGGCTATAA<br>ATAAGTTACAGCAGATTTTCAATACTTCATACAATCAAACATATGAAAAATAT<br>GGAAACGTGTCCGTCTTTGAAACCACTGGTGGTTTGGTAGTGTTCTGGCAAGGT<br>ATCAAGCAAAAATCTCTGGTGGAACTCGAACGTTTGGCCAACCGCTCCAGTCT<br>GAATCTTACTCATAATAGAACCAAAAGAAGTACAGATGGCAACAATGCAACTC<br>ATTTATCCAACATGGAATCGGTGCACAATCTGGTCTACGCCCAGCTGCAGTTCA<br>CCTATGACACGTTGCGCGGTTACATCAACCGGGCGCTGGCGCAAATCGCAGAA<br>GCCTGGTGTGTGGATCAACGGCGCACCCTAGAGGTCTTCAAGGAACTCAGCAA<br>GATCAACCCGTCAGCCATTCTCTCGGCCATTTACAACAAACCGATTGCCGCGCG<br>TTTCATGGGTGATGTCTTGGGCCTGGCCAGCTGCGTGACCATCAACCAAACCA<br>GCGTCAAGGTGCTGCGTGATATGAACGTGAAGGAGTCGCCAGGACGCTGCTAC<br>TCACGACCCGTGGTCATCTTTAATTTCGCCAACAGCTCGTACGTGCAGTACGGT<br>CAACTGGGCGAGGACAACGAAATCCTGTTGGGCAACCACCGCACTGAGGAAT<br>GTCAGCTTCCCAGCCTCAAGATCTTCATCGCCGGGAACTCGGCCTACGAGTAC<br>GTGGACTACCTCTTCAAACGCATGATTGACCTCAGCAGTATCTCCACCGTCGAC<br>AGCATGATCGCCCTGGATATCGACCCGCTGGAAAATACCGACTTCAGGGTACT<br>GGAACTTTACTCGCAGAAAGAGCTGCGTTCCAGCAACGTTTTTGACCTCGAAG<br>AGATCATGCGCGAATTCAACTCGTACAAGCAGCGGGTAAAGTACGTGGAGGAC<br>AAGGTAGTCGACCCGCTACCGCCCTACCTCAAGGGTCTGGACGACCTCATGAG<br>CGGCCTGGGCGCCGCGGGAAAGGCCGTTGGCGTAGCCATTGGGGCCGTGGGTG<br>GCGCGGTGGCCTCCGTGGTCGAAGGCGTTGCCACCTTCCTCAAAAACCCCTTCG<br>GAGCGTTCACCATCATCCTCGTGGCCATAGCTGTAGTCATTATCACTTATTTGA<br>TCTATACTCGACAGCGGCGTTTGTGCACGCAGCCGCTGCAGAACCTCTTTCCCT<br>ATCTGGTGTCCGCCGACGGGACCACCGTGACGTCGGGCAGCACCAAAGACACG<br>TCGTTACAGGCTCCGCCTTCCTACGAGGAAAGTGTTTATAATTCTGGTCGCAAA | 68 |

TABLE 6-continued

Second Generation hCMV mRNA Vaccine Construct Sequences

| Name of mRNA Construct | Sequence | SEQ ID NO |
|---|---|---|
| | GGACCGGGACCACCGTCGTCTGATGCATCCACGGCGGCTCCGCCTTACACCAA<br>CGAGCAGGCTTACCAGATGCTTCTGGCCCTGGCCCGTCTGGACGCAGAGCAGC<br>GAGCGCAGCAGAACGGTACAGATTCTTTGGACGGACGGACTGGCACGCAGGA<br>CAAGGGACAGAAGCCCAACCTACTAGACCGACTGCGACATCGCAAAAACGGC<br>TACCGACACTTGAAAGACTCTGACGAAGAAGAGAACGTCTTGATAATAGGCTG<br>GAGCCTCGGTGGCCATGCTTCTTGCCCCTTGGGCCTCCCCCCAGCCCCTCCTCC<br>CCTTCCTGCACCCGTACCCCCGTGGTCTTTGAATAAAGTCTGAGTGGGCGGC | |
| hCMV_gB, nucleotide sequence | UCAAGCUUUUGGACCCUCGUACAGAAGCUAAUACGACUCACUAUAGGGAAA<br>UAAGAGAGAAAAGAAGAGUAAGAAGAAAUAUAAGAGCCACCAUGGAAUCCA<br>GGAUCUGGUGCCUGGUAGUCUGCGUUAACUUGUGUAUCGUCUGUCUGGGUG<br>CUGCGGUUUCCUCAUCUUCUACUCGUGGAACUUCUGCUACUCACAGUCACCA<br>UUCCUCUCAUACGACGUCUGCUGCUCACUCUCGAUCCGGUUCAGUCUCUCAA<br>CGCGUAACUUCUUCCCAAACGGUCAGCCAUGGUGUUAACGAGACCAUCUACA<br>ACACUACCCUCAAGUACGGAGAUGUGGUGGGGGUCAAUACCACCAAGUACC<br>CCUAUCGCGUGUGUUCUAUGGCCCAGGGUACGGAUCUUAUUCGCUUUGAAC<br>GUAAUAUCGUCUGCACCUCGAUGAAGCCCAUCAAUGAAGACCUGGACGAGG<br>GCAUCAUGGUGGUCUACAAACGCAACAUCGUCGCGCACACCUUUAAGGUAC<br>GAGUCUACCAGAAGGUUUUGACGUUUCGUCGUAGCUACGCUUACAUCCACA<br>CCACUUAUCUGCUGGGCAGCAACACGGAAUACGUGGCGCCUCCUAUGUGGG<br>AGAUUCAUCAUAUCAACAGCCACAGUCAGUGCUACAGUUCCUACAGCCGCGU<br>UAUAGCAGGCACGGUUUUCGUGGCUUAUCAUAGGGACAGCUAUGAAAACAA<br>AACCAUGCAAUUAAUGCCCGACGAUUAUUCCAACACCCACAGUACCCGUUAC<br>GUGACGGUCAAGGAUCAAUGGCACAGCCGCGGCAGCACCUGGCUCUAUCGU<br>GAGACCUGUAAUCUGAAUUGUAUGGUGACCAUCACUACUGCGCGCUCCAAA<br>UAUCCUUAUCAUUUUUUCGCCACUUCCACGGGUGACGUGGUUGACAUUUCU<br>CCUUUCUACAACGGAACCAAUCGCAAUGCCAGCUACUUUGGAGAAAACGCCG<br>ACAAGUUUUUCAUUUUUCCGAACUACACUAUCGUCUCCGACUUUGGAAGAC<br>CGAAUUCUGCGUUAGAGACCCACAGGUUGGUGGCUUUUCUUGAACGUGCGG<br>ACUCGGUGAUCUCCUGGGAUAUACAGGACGAAAAGAAUGUCACUUGUCAAC<br>UCACUUUCUGGGAAGCCUCGGAACGCACCAUUCGUUCCGAAGCCGAGGACUC<br>GUAUCACUUUUCUUCUGCCAAAAUGACCGCCACUUUCUUAUCUAAGAAGCA<br>AGAGGUGAACAUGUCCGACUCUGCGCUGGACUGCGUACGUGAUGAGGCUAU<br>AAAUAAGUUACAGCAGAUUUUCAAUACUUCAUACAAUCAAACAUAUGAAAA<br>AUAUGGAAACGUGUCCGUCUUUGAAACCACUGGUGGUUUGGUAGUGUUCUG<br>GCAAGGUAUCAAGCAAAAAUCUCUGGUGGAACUCGAACGUUUGGCCAACCG<br>CUCCAGUCUGAAUCUUACUCAUAAUAGAACCAAAAGAAGUACAGAUGGCAA<br>CAAUGCAACUCAUUUAUCCAACAUGGAAUCGGUGCACAAUCUGGUCUACGC<br>CCAGCUGCAGUUCACCUAUGACACGUUGCGCGGUUACAUCAACCGGGCGCUG<br>GCGCAAAUCGCAGAAGCCUGGUGUGUGGAUCAACGGCGCACCCUAGAGGUC<br>UUCAAGGAACUCAGCAAGAUCAACCCGUCAGCCAUUCUCUCGGCCAUUUACA<br>ACAAACCGAUUGCCGCGCGUUUCAUGGGUGAUGUCUUGGGCCUGGCCAGCU<br>GCGUGACCAUCAACCAAACCAGCGUCAAGGUGCUGCGUGAUAUGAACGUGA<br>AGGAGUCGCCAGGACGCUGCUACUCACGACCCGUGGUCAUCUUUAAUUUCGC<br>CAACAGCUCGUACGUGCAGUACGGUCAACUGGGCGAGGACAACGAAAUCCU<br>GUUGGGCAACCACCGCACUGAGGAAUGUCAGCUUCCCAGCCUCAAGAUCUUC<br>AUCGCCGGGAACUCGGCCUACGAGUACGUGGACUACCUCUUCAAACGCAUGA<br>UUGACCUCAGCAGUAUCUCCACCGUCGACAGCAUGAUCGCCCUGGAUAUCGA<br>CCCGCUGGAAAAUACCGACUUCAGGGUACUGGAACUUUACUCGCAGAAAGA<br>GCUGCGUUCCAGCAACGUUUUUGACCUCGAAGAGAUCAUGCGCGAAUUCAA<br>CUCGUACAAGCAGCGGGUAAAGUACGUGGAGGACAAGGUAGUCGACCCGCU<br>ACCGCCCUACCUCAAGGGUCUGGACGACCUCAUGAGCGGCCUGGGCGCCGCG<br>GGAAAGGCCGUUGGCGUAGCCAUUGGGGCCGUGGGUGGCGCGGUGGCCUCC<br>GUGGUCGAAGGCGUUGCCACCUUCCUCAAAAACCCCUUCGGAGCGUUCACCA<br>UCAUCCUCGUGGCCAUAGCUGUAGUCAUUAUCACUUAUUUGAUCUAUACUC<br>GACAGCGGCGUUUGUGCACGCAGCCGCUGCAGAACCUCUUUCCCUAUCUGGU<br>GUCCGCCGACGGGACCACCGUGACGUCGGGCAGCACCAAAGACACGUCGUUA<br>CAGGCUCCGCCUUCCUACGAGGAAAGUGUUUAUAAUUCUGGUCGCAAAGGA<br>CCGGGACCACCGUCGUCUGAUGCAUCCACGGCGGCUCCGCCUUACACCAACG<br>AGCAGGCUUACCAGAUGCUUCUGGCCCUGGCCCGUCUGGACGCAGAGCAGCG<br>AGCGCAGCAGAACGGUACAGAUUCUUUGGACGGACGGACUGGCACGCAGGA<br>CAAGGGACAGAAGCCCAACCUACUAGACCGACUGCGACAUCGCAAAAACGGC<br>UACCGACACUUGAAAGACUCUGACGAAGAAGAGAACGUCUUGAUAAUAGGC<br>UGGAGCCUCGGUGGCCAUGCUUCUUGCCCCUUGGGCCUCCCCCCAGCCCCUC<br>CUCCCCUUCCUGCACCCGUACCCCCGUGGUCUUUGAAUAAAGUCUGAGUGGG<br>CGGC | 113 |
| hCMV_gB, amino acid sequence | MESRIWCLVVCVNLCIVCLGAAVSSSSTRGTSATHSHHSSHTTSAAHSRSGSVSQR<br>VTSSQTVSHGVNETIYNTTLKYGDVVGVNTTKYPYRVCSMAQGTDLIRFERNIVC<br>TSMKPINEDLDEGIMVVYKRNIVAHTFKVRVYQKVLTFRRSYAYIHTTYLLGSNTE<br>YVAPPMWEIHHINSHSQCYSSYSRVIAGTVFVAYHRDSYENKTMQLMPDDYSNTH<br>STRYVTVKDQWHSRGSTWLYRETCNLNCMVTITTARSKYPYHFFATSTGDVVDIS<br>PFYNGTNRNASYFGENADKFFIFPNYTIVSDFGRPNSALETHRLVAFLERADSVISW<br>DIQDEKNVTCQLTFWEASERTIRSEAEDSYHFSSAKMTATFLSKKQEVNMSDSALD | 69 |

TABLE 6-continued

Second Generation hCMV mRNA Vaccine Construct Sequences

| Name of mRNA Construct | Sequence | SEQ ID NO |
|---|---|---|
| | CVRDEAINKLQQIFNTSYNQTYEKYGNVSVFETTGGLVVFWQGIKQKSLVELERL<br>ANRSSLNLTHNRTKRSTDGNNATHLSNMESVHNLVYAQLQFTYDTLRGYINRALA<br>QIAEAWCVDQRRTLEVFKELSKINPSAILSAIYNKPIAARFMGDVLGLASCVTINQT<br>SVKVLRDMNVKESPGRCYSRPVVIFNFANSSYVQYGQLGEDNEILLGNHRTEECQ<br>LPSLKIFIAGNSAYEYVDYLFKRMIDLSSISTVDSMIALDIDPLENTDFRVLELYSQK<br>ELRSSNVFDLEEIMREFNSYKQRVKYVEDKVVDPLPPYLKGLDDLMSGLGAAGKA<br>VGVAIGAVGGAVASVVEGVATFLKNPFGAFTIILVAIAVVIITYLIYTRQRRLCTQP<br>LQNLFPYLVSADGTTVTSGSTKDTSLQAPPSYEESVYNSGRKGPGPPSSDASTAAPP<br>YTNEQAYQMLLALARLDAEQRAQQNGTDSLDGRTGTQDKGQKPNLLDRLRHRK<br>NGYRHLKDSDEEENV | |

Example 26: 2A Peptide Linked Pentameric Subunits

Figure 15:
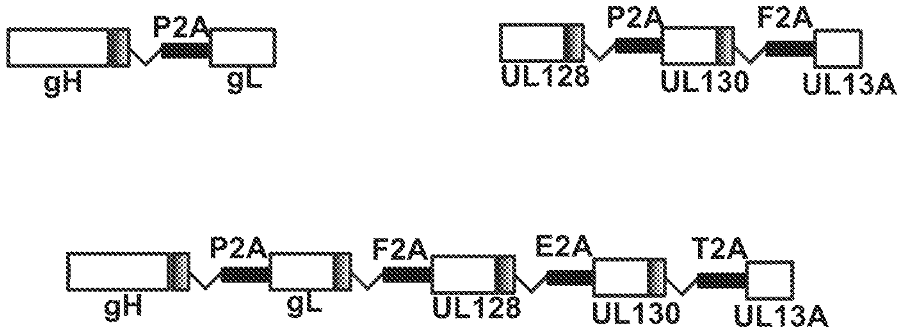
FIG. 15 is a schematic representation of pentametic subunits linked by a self-cleaving 2A peptide (e.g., as described in Kim et al., *PLoS ONE* 6(4): e18556, 2011).
Figure 16:
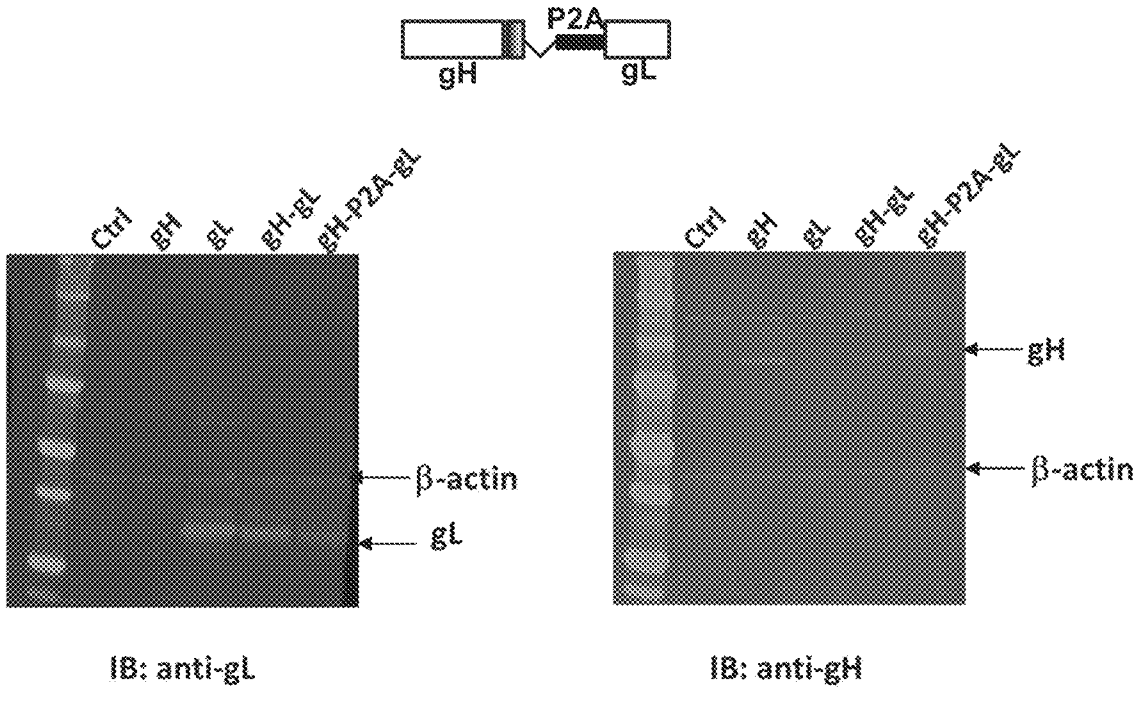
FIG. 16 is a Western blot showing that gH and gL linked by the 2A peptide underwent efficient self-cleavage to generate individual gH and gL subunits.
Figure 17:
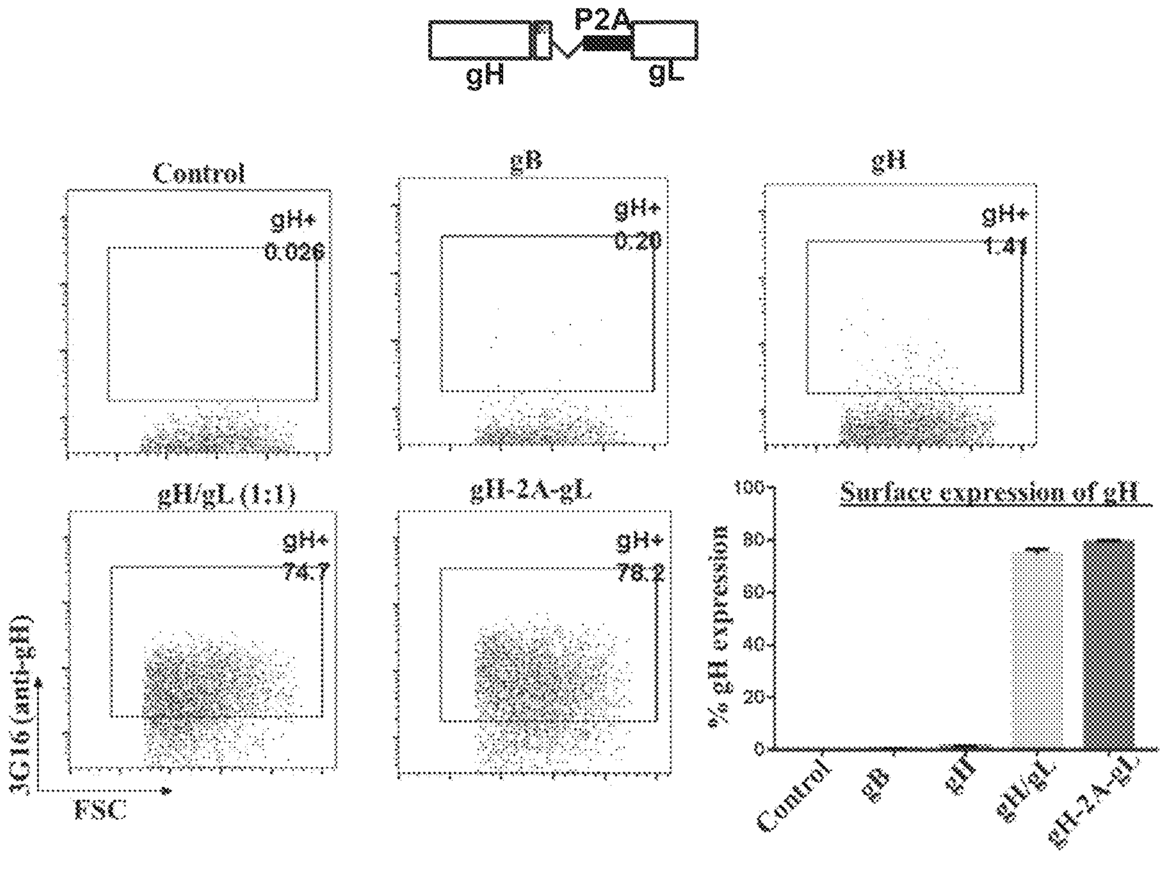
FIG. 17 is a graph showing that the individual gH and gL subunits generated from self-cleavage of the 2A peptide linked were able to dimerize and translocate to the cell surface.

Multivalent mRNA vaccine constructs encoding the subunits of the hCMV pentamer (gH, gL, UL128, UL130, and Ul131A) were designed. The multivalent mRNA encoded pentamer subunits were linked with 2A self-cleaving peptides (FIG. 15), which allows the linked subunits to process into individual subunits. 1 μg of the mRNA vaccine constructs encoding a 2A peptide linked gH-gL were transfected into 293T cells. The cells were harvested 24 hours post transfection and the cleavage of the 2A peptide were analyzed by detecting individual gH or gL subunits using Western blotting. Individual gH and gL were detected, indicating successful expression of the construct and cleavage of the 2A peptide (FIG. 16). Further, processed gH or gL when expressed in HeLa cells, dimerized, and translocated to the cell surface 24 hours after the Hela cells were transfected with 0.5 μg of mRNA encoding the 2A linked gH-gL (FIG. 17).

Example 27: Comparison of Equimolar Vs Equal Mass of Pentamer

Figure 18A:
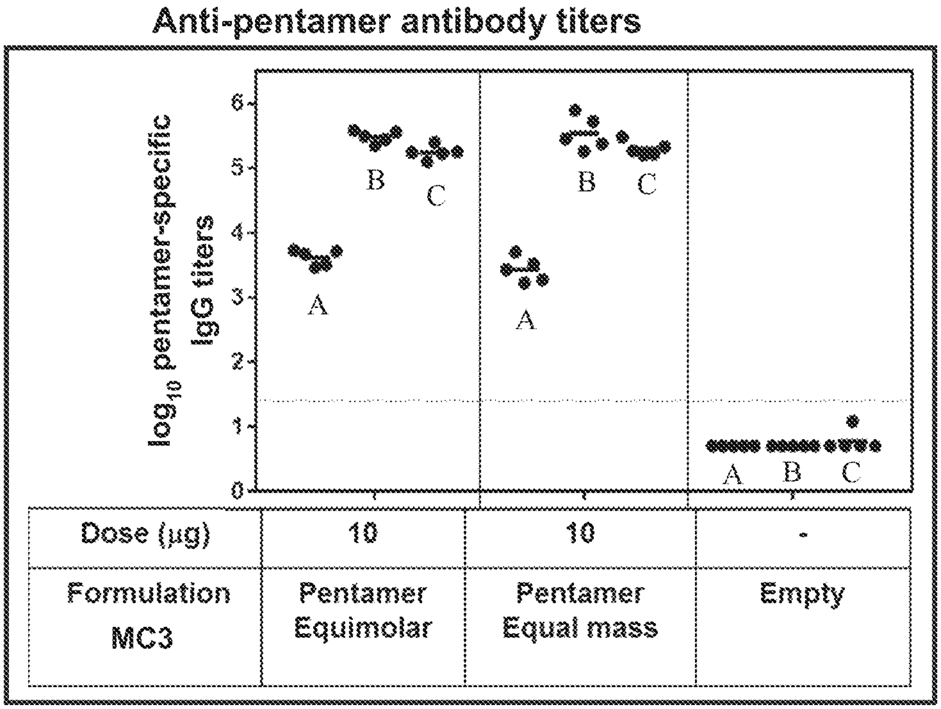
FIGS. 18A-B demonstrates high and sustained titers of anti-pentamer binding and neutralizing antibodies in mice.
Figure 18B:
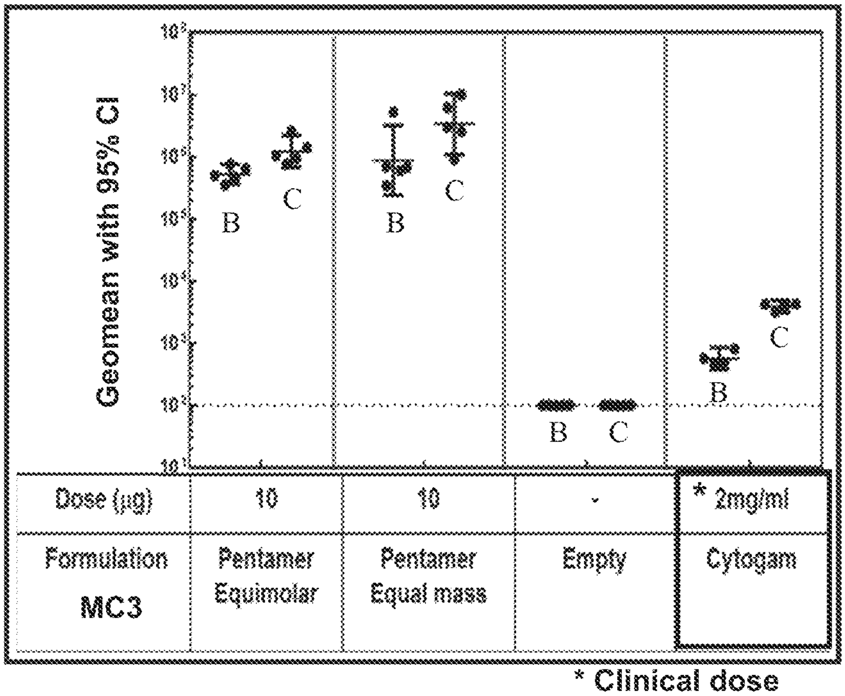

Pentameric formulations containing the pentameric subunit mRNAs at equimolar concentrations were compared to pentameric formulations containing the pentameric subunit mRNAs in equal mass. FIG. 18 demonstrates high and sustained titers of anti-pentamer binding and neutralizing antibodies in mice. FIG. 18A depicts a graph showing anti-pentamer antibody titers. Equimolar and equal mass formulations of the pentameric mRNAs were found to be equally effective. FIG. 18B depicts a graph showing neutralizing titers measured on ARPE19 epithelial cells infected with hCMV strain VR1814. Equimolar and equal mass formulations of the pentameric mRNAs were compared and were found to be equally effective. Neutralizing titers were found to be approximately 25 fold higher than CytoGam®.

Example 28: Neutralization Activity is Dependent on Anti-Pentamer Antibodies

Figure 19A:
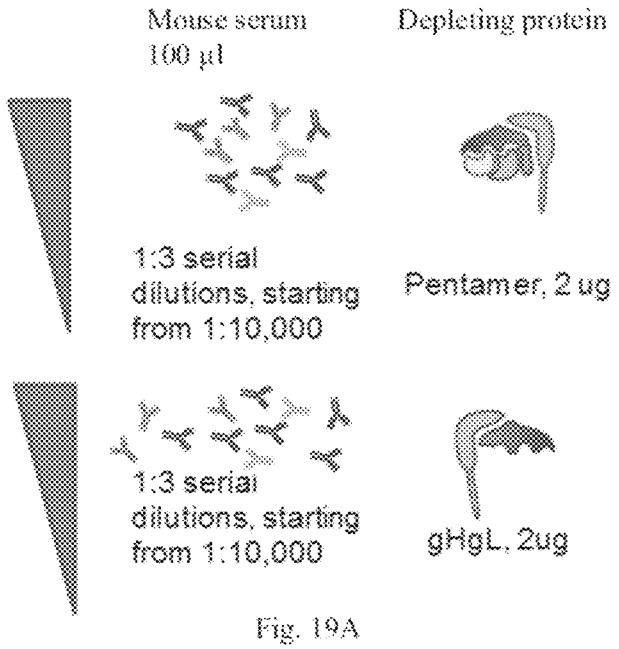
FIGS. 19A-C demonstrates that neutralization activity against epithelial cell infection is dependent on anti-pentamer antibodies.
Figure 19B:
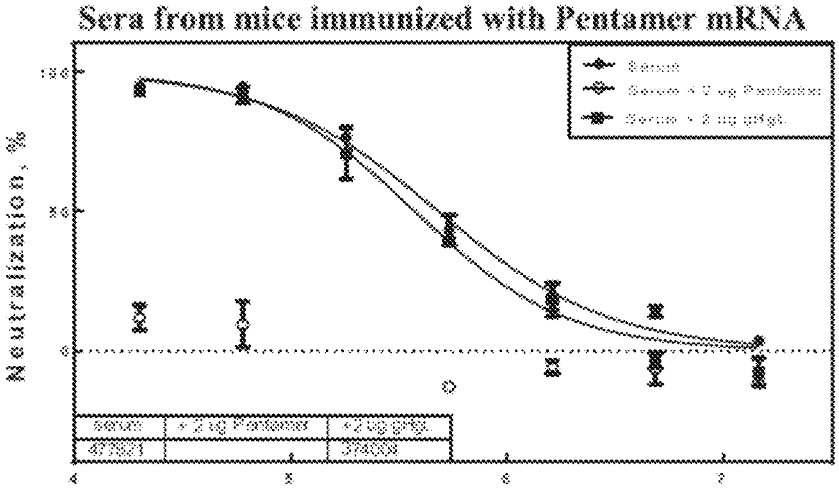
Figure 19C:
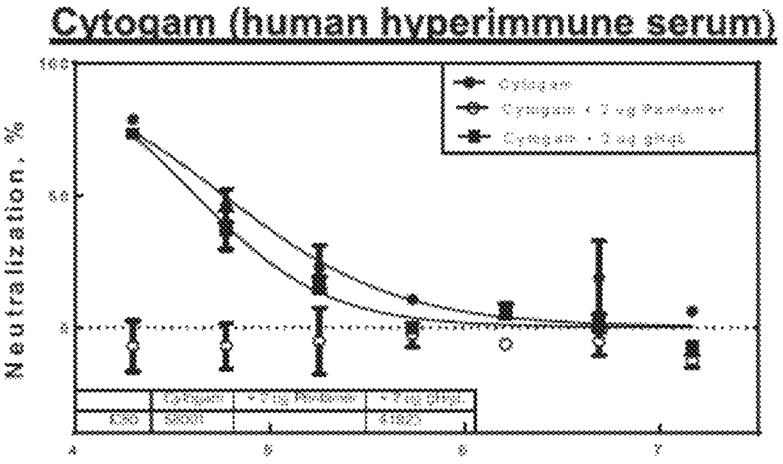

Neutralization data was assessed and compared against CytoGam®. FIG. 19 demonstrates that neutralization activity against epithelial cell infection is dependent on anti-pentamer antibodies. FIG. 19A shows that the depleting protein was either the pentamer or a gH/gL dimer. FIG. 19B and FIG. 19C depict graphs showing neutralization. FIG. 19B shows neutralization by sera from mice immunized with the pentamer or with a gH/gL dimer. FIG. 19C shows neutralization by CytoGam® combined with the pentamer or with a gH/gL.

Example 28:Phase 1 Clinical Trial for Prevention of Mother-to-Child (Congenital) Transmission A phase 1 clinical trial is conducted to assess the safety of the chemically modified or unmodified hCMV mRNA vaccine encoding the pentameric complex (gH, gL, UL128, UL130, and UL131A)+gB in humans and to evaluate the ability of the hCMV mRNA vaccines to induce an immune response. One hundred and twenty (120) volunteers (both females and males) between ages 18-49 are enrolled in the clinical trial. The volunteers are tested for CMV prior to the start of the clinical trial. Sixty (60) of the healthy volunteers are $CMV^+$, while the other sixty (60) are $CMV^-$.

The healthy volunteers are divided into three dosage groups, each dosage group receiving a different dose of the hCMV mRNA vaccine (e.g., low, medium, or high). For each dosage group (n=40), the hCMV mRNA vaccine is administered intramuscularly (IM, n=20) or intravenously (IV, n=20). Thus, the 120 volunteers are placed into 6 groups (referred to as a "dose arm"): low dose-IM (n=20), low dose-IV (n=20), medium dose-IM (n=20), medium dose-IV (n=20), high dose-IM (n=20), high dose-IV (n=20). In each dose arm, the volunteers are separated into two cohorts: the safety cohort (n=4, 2 receiving vaccines and 2 receiving placebos); and the expansion cohort (n=16, 13 receiving vaccines and 3 receiving placebos). The immunization of the volunteers in the expansion cohort starts 7 days after the last healthy volunteer in the safety cohort has been immunized.

hCMV vaccines or placebos are given to the volunteers in the 6 dose arms on day 1, day 31, and day 61. It is a double blind clinical trial. The volunteers are followed up to a year. Blood samples are taken on day 1, day 8, day 22, day 30, day 44, 6 months, and 1 year after the first immunization.

Neutralizing hCMV antibody titers in the blood samples are measured using an Enzyme-linked ImmunoSpot (ELISPOT) assay or using a low cytometric intracellular cytokine staining (ICS) assay. Sustained neutralization antibody titers and strong anamnestic responses are expected in volunteers who received the hCMV mRNA vaccines by 12 months. The level of IgG induced by the hCMV mRNA vaccines are expected to be at least 4 times above the baseline (a clinical endpoint). The neutralization antibody titer in the blood samples of volunteers who received the hCMV mRNA vaccine, measured in a plaque reduction neutralization test (PRNT50) in both epithelial and fibroblast cells, is expected to be higher than that of Cytogam® (a clinical end point).

Early signal of efficacy (ESOE) can also be indicated by measuring the viral load in urine and saliva of the volunteers by PCR on day 1, 6 months, and 12 months.

Parameters indicating safety of the vaccine are measured. Immunized volunteers are evaluated for clinical signs of hCMV infection (a clinical endpoint). Biochemical assays are performed to assess the coagulation parameters and the blood level of C-reactive proteins (CRP). The hCMV mRNA vaccine is expected to be safe.

Once safety and immunogenicity have been demonstrated, trials are conducted among target populations in phase 2 clinical trials. In some embodiments, suitable dose levels chosen from phase 1 trials will be used in phase 2 trials.

Example 29: Phase 2 Clinical Trial—Day Care Personnel

A phase 2 clinical trial is conducted to evaluate the chemically modified or unmodified hCMV mRNA vaccine encoding the pentameric complex (gH, gL, UL128, UL130, and UL131A)+gB in humans in the following populations: seronegative and seropositive (safety cohort) day care personnel; seronegative and seropositive (safety cohort) parents who have a child in daycare; and seronegative toddlers.

Three hundred (300) subjects are enrolled in the phase 2 clinical trial and are grouped as in the phase 1 clinical trial described in Example 26. All subjects are immunized with the same dose of hCMV mRNA vaccine. In some embodiments a dose-response trial is conducted. Subjects receive the first dose of the vaccine on day 1, which is 2-4 weeks prior to the initiation of immunosuppressive therapy, and receive boosts at approximately 1, 3, and 6 months. It is a double blind clinical trial. The subjects are followed up to a year. Blood samples are taken on approximately day 1, day 8, day 22, day 30, day 44, 6 months, and 1 year after the first immunization.

The safety and immunogenicity of the vaccines are assessed using methods described in the phase 1 trial described in Example 28. A vaccine efficacy of at least 70% is expected. Clinical endpoints for this trial include infection in urine and/or saliva, as detected by PCR. The hCMV mRNA vaccine is expected to induce immune response and generate neutralizing antibodies. The safety profile is also expected to be high.

Example 30: Phase 3 Clinical Trial—Adolescent Boys and Girls

A phase 3 clinical trial is conducted in adolescent boys and girls. Optionally, a phase 3 clinical trial is also conducted in toddlers. No CMV screening is performed prior to enrollment.

EQUIVALENTS

Those skilled in the art will recognize, or be able to ascertain using no more than routine experimentation, many equivalents to the specific embodiments of the disclosure described herein. Such equivalents are intended to be encompassed by the following claims.

All references, including patent documents, disclosed herein are incorporated by reference in their entirety.

What is claimed is:

1. A human cytomegalovirus (hCMV) immunogenic composition comprising: (a) at least one messenger ribonucleic acid (mRNA) polynucleotide comprising an open reading frame encoding a hCMV gH polypeptide; (b) at least one mRNA polynucleotide comprising an open reading frame encoding a hCMV gL polypeptide; (c) at least one mRNA polynucleotide comprising an open reading frame encoding a hCMV UL128 polypeptide; (d) at least one mRNA polynucleotide comprising an open reading frame encoding a hCMV UL130 polypeptide; (e) at least one mRNA polynucleotide comprising an open reading frame encoding a hCMV UL131A polypeptide; and (f) at least one mRNA polynucleotide comprising an open reading frame encoding a hCMV gB polypeptide, wherein the mRNA polynucleotides of (a)-(f) are formulated in at least one lipid nanoparticle comprising 20-60 mole percent ionizable cationic lipid of Compound 25:

(Compound 25)

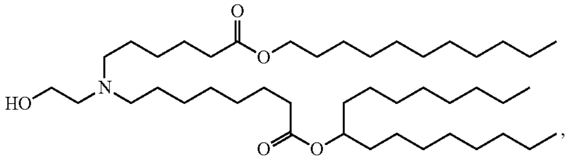

0.5-15 mole percent PEG-modified lipid, 25-55 mole percent sterol, and 5-25 mole percent non-cationic lipid that is not a sterol, and wherein the mRNA polynucleotides of (a)-(f) are not self-replicating RNA.

2. The hCMV immunogenic composition of claim 1, wherein the lipid nanoparticle comprises 40-50 mole percent ionizable cationic lipid of Compound 25.

3. The hCMV immunogenic composition of claim 2, wherein the lipid nanoparticle comprises 50 mole percent ionizable cationic lipid of Compound 25.

4. The hCMV immunogenic composition of claim 2, wherein the lipid nanoparticle comprises 49 mole percent ionizable cationic lipid of Compound 25.

5. The hCMV immunogenic composition of claim 2, wherein the lipid nanoparticle comprises 48 mole percent ionizable cationic lipid of Compound 25.

6. The hCMV immunogenic composition of claim 2, wherein the lipid nanoparticle comprises 47 mole percent ionizable cationic lipid of Compound 25.

7. The hCMV immunogenic composition of claim 2, wherein the lipid nanoparticle comprises 46 mole percent ionizable cationic lipid of Compound 25.

8. The hCMV immunogenic composition of claim 2, wherein the lipid nanoparticle comprises 45 mole percent ionizable cationic lipid of Compound 25.

9. The hCMV immunogenic composition of claim 1, wherein the non-cationic lipid that is not a sterol is a neutral lipid.

10. The hCMV immunogenic composition of claim 1, wherein at least one mRNA polynucleotide comprises at least one chemical modification.

11. The hCMV immunogenic composition of claim 10, wherein the chemical modification is selected from pseudouridine, 1-methylpseudouridine, 1-ethylpseudouridine, 2-thiouridine, 4'-thiouridine, 5-methylcytosine, 5-methyluridine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methyl-pseudouridine, 4-thio-pseudouridine, 5-aza-uridine, dihydropseudouridine, 5-methoxyuridine, and 2'-O-methyl uridine.

12. The hCMV immunogenic composition of claim 11, wherein the chemical modification is a 1-methylpseudouridine or 1-ethylpseudouridine.

13. The hCMV immunogenic composition of claim 10, wherein the chemical modification is in the carbon 5-position of the uracil.

14. The hCMV immunogenic composition of claim 1, wherein at least one mRNA polynucleotide further includes a 5' terminal cap.

15. The hCMV immunogenic composition of claim 14, wherein the 5' terminal cap is 7mG(5')ppp(5')NlmpNp.

16. The hCMV immunogenic composition of claim 1, wherein the open reading frame is codon-optimized.

17. A method of inducing an antigen-specific immune response in a subject, the method comprising administering to the subject the immunogenic composition of claim 1 in an amount effective to produce an antigen-specific immune response in the subject.

18. A method comprising administering to a woman of child-bearing age a therapeutically effective amount of the immunogenic composition of claim 1.

19. The method of claim 18, wherein the hCMV gH polypeptide comprises an amino acid sequence that has at least 90% identity to the amino acid sequence of SEQ ID NO: 59, the hCMV gL polypeptide comprises an amino acid sequence that has at least 90% identity to the amino acid sequence of SEQ ID NO: 61, the hCMV UL128 polypeptide comprises an amino acid sequence that has at least 90% identity to the amino acid sequence of SEQ ID NO: 63, the hCMV UL130 polypeptide comprises an amino acid sequence that has at least 90% identity to the amino acid sequence of SEQ ID NO: 65, the hCMV UL131A polypeptide comprises an amino acid sequence that has at least 90% identity to the amino acid sequence of SEQ ID NO: 67, and/or the hCMV gB protein comprises an amino acid sequence that has at least 90% identity to the amino acid sequence of SEQ ID NO: 69.

20. The method of claim 19, wherein the hCMV gH polypeptide comprises the amino acid sequence of SEQ ID NO: 59, the hCMV gL polypeptide comprises the amino acid sequence of SEQ ID NO: 61, the hCMV UL128 polypeptide comprises the amino acid sequence of SEQ ID NO: 63, the hCMV UL130 polypeptide comprises the amino acid sequence of SEQ ID NO: 65, the hCMV UL131A polypeptide comprises the amino acid sequence of SEQ ID NO: 67, and/or the hCMV gB protein comprises the amino acid sequence of SEQ ID NO: 69.

21. The method of claim 18, wherein the mRNA polynucleotide of (a) comprises a sequence that has at least 90% identity to the nucleotide sequence of SEQ ID NO: 108, the mRNA polynucleotide of (b) comprises a sequence that has at least 90% identity to the nucleotide sequence of SEQ ID NO: 109, the mRNA polynucleotide of (c) comprises a sequence that has at least 90% identity to the nucleotide sequence of SEQ ID NO: 110, the mRNA polynucleotide of (d) comprises a sequence that has at least 90% identity to the nucleotide sequence of SEQ ID NO: 93, the mRNA polynucleotide of (e) comprises a sequence that has at least 90% identity to the nucleotide sequence of SEQ ID NO: 112, and/or the mRNA polynucleotide of (f) comprises a sequence that has at least 90% identity to the nucleotide sequence of SEQ ID NO: 83.

22. The method of claim 18, wherein the hCMV vaccine comprises (a) a mRNA polynucleotide comprising nucleotides 46-2437 of SEQ ID NO: 108, (b) a mRNA polynucleotide comprising nucleotides 46-1045 of SEQ ID NO: 109, (c) a mRNA polynucleotide comprising nucleotides 46-724 of SEQ ID NO: 110, (d) a mRNA polynucleotide comprising nucleotides 46-853 of SEQ ID NO: 93, (e) a mRNA polynucleotide comprising nucleotides 46-598 of SEQ ID NO: 112, and (f) a mRNA polynucleotide comprising nucleotides 46-2932 of SEQ ID NO: 83.

23. The method of claim 18, wherein the mRNA polynucleotides further comprise polyA tails.

24. The hCMV immunogenic composition of claim 1, wherein the sterol is cholesterol.

* * * * *